US007022488B2

(12) United States Patent
Servant et al.

(10) Patent No.: US 7,022,488 B2
(45) Date of Patent: Apr. 4, 2006

(54) FUNCTIONAL COUPLING OF T1RS AND T2RS BY GI PROTEINS, AND CELLS-BASED ASSAYS FOR THE IDENTIFICATION OF T1R AND T2R MODULATORS

(75) Inventors: Guy Servant, San Diego, CA (US); Mark Ozeck, San Diego, CA (US); Paul Brust, San Diego, CA (US); Hong Xu, San Diego, CA (US)

(73) Assignee: Senomyx, Inc., LaJolla, CA (US)

( * ) Notice: Subject to any disclaimer, the term of this patent is extended or adjusted under 35 U.S.C. 154(b) by 109 days.

(21) Appl. No.: 10/770,127

(22) Filed: Feb. 3, 2004

(65) Prior Publication Data

US 2004/0214239 A1 Oct. 28, 2004

Related U.S. Application Data

(60) Provisional application No. 60/457,318, filed on Mar. 26, 2003, and provisional application No. 60/444,172, filed on Feb. 3, 2003.

(51) Int. Cl.

| | |
|---|---|
| ***G01N 33/53*** | (2006.01) |
| ***G01N 33/567*** | (2006.01) |
| ***C12P 21/06*** | (2006.01) |
| ***C12N 1/20*** | (2006.01) |

(52) U.S. Cl. ........................ 435/7.1; 435/7.2; 435/69.1; 435/320.1

(58) Field of Classification Search ................ 435/69.1, 435/320.1, 7.1; 530/350
See application file for complete search history.

(56) References Cited

U.S. PATENT DOCUMENTS

| | | | | |
|---|---|---|---|---|
| 6,558,910 B1 * | 5/2003 | Zuker et al. | ................. | 435/7.2 |
| 2002/0051997 A1 * | 5/2002 | Zuker et al. | ................. | 435/7.1 |
| 2002/0160424 A1 | 10/2002 | Adler et al. | | |
| 2004/0191862 A1 * | 9/2004 | Zoller et al. | ............... | 435/69.1 |

OTHER PUBLICATIONS

McDonald et al., Analytical Biochemistry, 1999, 268, 318–329.*

Naor et al., Trends in Endorcinology Metabolism, 2000, 11(3), 91–99.*

Wu et al., Proceedings of the National Academies of Science, 2002, 99(4), 2392–2397.*

Margolskee, The Journal of Biological Chemistry, 2002, 277(1), 1–4.*

Li et al., Proceedings of the National Academies of Science, 2002, 99(7), 4692–4696.*

Li X, et al., "Human Receptors for Sweet and Umami Taste", Proc. Natl. Acad. Sci. Apr. 2, 2002, vol. 99, No. 7, pp 4692–4696.

Hoon et al. "Putative Mammalian Taste Recetprs: A Class of Taste Specific GPCRs with distinct Topographic Selectivity", Cell, Feb. 19, 2004, vol. 96, pp 541–551.

Wu et al; "Expression of Bitter Taste Receptors of the T2R family in Gastrointestinal Tract and Enteroendocrine STC–1 Cells", Proc. Natl. Acad. Sci., Feb. 19, 2002, vol. 99 No. 4, pp 2392–2397.

Noar et al. "Activation of MAPK Cascades by G–Protein Coupled Receptors: The Case of Gonadotropin–Releasing Hormone Receptor", Trends in Endocrinology Metabolism, 200, vol. 11, No. 3, pp 91–99.

McDonald et al, "A Scintallation Proximity Assay for the Raf–MEK/ERK Kinase Cascade: High–Throughput Screening and Identification of Selective Enzyme Inhibitors", Analytical Biochemistry, 199, 268 pp 318–329.

* cited by examiner

*Primary Examiner*—Robert A. Wax
*Assistant Examiner*—Suzanne M. Mayer
(74) *Attorney, Agent, or Firm*—Robin L. Teskin; Duane Morris, LLP

(57) ABSTRACT

The invention resides in part in the discovery that G proteins other than $G\alpha_{15}$ couples to T1R and T2R taste receptors, particularly $G_i$ proteins such as $G_{\alpha i}$. Related to this discovery, the invention provides cell-based assay methods for identifying compounds that modulate the activity of specific T1R or T2R taste receptors or which modulate the effect of other T1R or T2R modulators on T1R or T2R activity. These assay methods preferably detect the effect of a putative T1R or T2R modulator compound on MAPK activation, cAMP accumulation, or adenylyl cyclase activity or another signaling pathway regulated by $G_i$ proteins. The level of MAPK activation, cAMP accumulation or adenylyl cyclase is preferably determined by immunoassay methods that use ligands (monoclonal or polyclonal antibodies) that specifically bind an activated (phosphorylated) MAPK, cAMP, or adenylyl cyclase.

56 Claims, 8 Drawing Sheets

Figure 1:
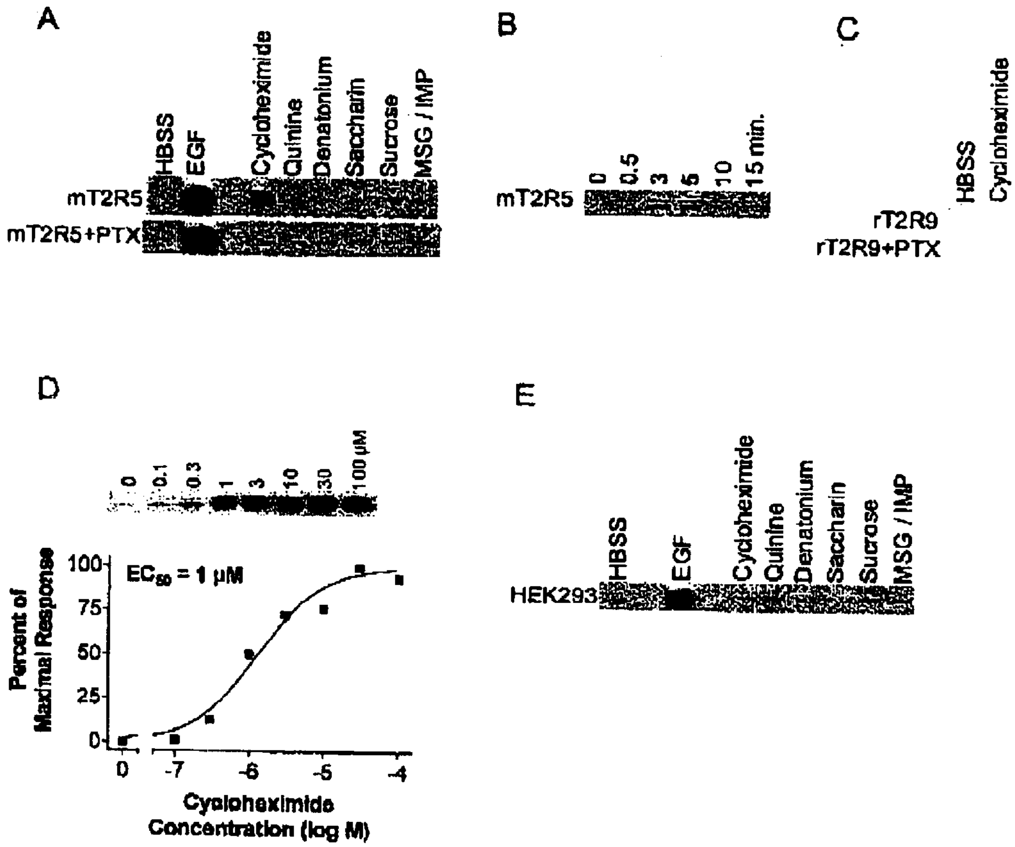

SEQUENCE LISTING

```
<160> NUMBER OF SEQ ID NOS: 210

<210> SEQ ID NO 1
<211> LENGTH: 299
<212> TYPE: PRT
<213> ORGANISM: Homo sapiens

<400> SEQUENCE: 1

Met Leu Glu Ser His Leu Ile Ile Tyr Phe Leu Leu Ala Val Ile Gln
1               5                   10                  15

Phe Leu Leu Gly Ile Phe Thr Asn Gly Ile Ile Val Val Val Asn Gly
            20                  25                  30

Ile Asp Leu Ile Lys His Arg Lys Met Ala Pro Leu Asp Leu Leu Leu
        35                  40                  45

Ser Cys Leu Ala Val Ser Arg Ile Phe Leu Gln Leu Phe Ile Phe Tyr
    50                  55                  60

Val Asn Val Ile Val Ile Phe Phe Ile Glu Phe Ile Met Cys Ser Ala
65                  70                  75                  80

Asn Cys Ala Ile Leu Leu Phe Ile Asn Glu Leu Glu Leu Trp Leu Ala
                85                  90                  95

Thr Trp Leu Gly Val Phe Tyr Cys Ala Lys Val Ala Ser Val Arg His
            100                 105                 110

Pro Leu Phe Ile Trp Leu Lys Met Arg Ile Ser Lys Leu Val Pro Trp
        115                 120                 125

Met Ile Leu Gly Ser Leu Leu Tyr Val Ser Met Ile Cys Val Phe His
```

-continued

```
    130                 135                 140

Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Val Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
    210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Ser Leu Lys Phe His Ile Arg Arg
                245                 250                 255

Phe Ile Phe Leu Phe Phe Ile Leu Val Ile Gly Ile Tyr Pro Ser Gly
            260                 265                 270

His Ser Leu Ile Leu Ile Leu Gly Asn Pro Lys Leu Lys Gln Asn Ala
        275                 280                 285

Lys Lys Phe Leu Leu His Ser Lys Cys Cys Gln
    290                 295
```

<210> SEQ ID NO 2
<211> LENGTH: 900
<212> TYPE: DNA
<213> ORGANISM: Homo sapiens

<400> SEQUENCE: 2

```
atgctagagt ctcacctcat tatctatttt cttcttgcag tgatacaatt tcttcttggg     60

attttcacaa atggcatcat tgtggtggtg aatggcattg acttgatcaa gcacagaaaa    120

atggctccgc tggatctcct tctttcttgt ctggcagttt ctagaatttt tctgcagttg    180

ttcatcttct acgttaatgt gattgttatc ttcttcatag aattcatcat gtgttctgcg    240

aattgtgcaa ttctcttatt tataaatgaa ttggaacttt ggcttgccac atggctcggc    300

gttttctatt gtgccaaggt tgccagcgtc cgtcacccac tcttcatctg gttgaagatg    360

aggatatcca agctggtccc atggatgatc ctggggtctc tgctatatgt atctatgatt    420

tgtgttttcc atagcaaata tgcagggttt atggtcccat acttcctaag gaaatttttc    480

tcccaaaatg ccacaattca aaaagaagat acactggcta tacagatttt ctcttttgtt    540

gctgagttct cagtgccatt gcttatcttc ctttttgctg ttttgctctt gattttctct    600

ctggggaggc acacccggca aatgagaaac acagtggccg gcagcagggt tcctggcagg    660

ggtgcaccca tcagcgcgtt gctgtctatc ctgtccttcc tgatcctcta cttctcccac    720

tgcatgataa aagtttttct ctcttctcta aagtttcaca tcagaaggtt catctttctg    780

ttcttcatcc ttgtgattgg tatataccct tctggacact ctctcatctt aattttagga    840

aatcctaaat tgaaacaaaa tgcaaaaaag ttcctcctcc acagtaagtg ctgtcagtga    900
```

<210> SEQ ID NO 3
<211> LENGTH: 301
<212> TYPE: PRT
<213> ORGANISM: Homo sapiens

<400> SEQUENCE: 3

```
Met Ala Leu Ser Phe Ser Ala Ile Leu His Ile Ile Met Met Ser Ala
```

-continued

```
1               5                   10                  15

Glu Phe Phe Thr Gly Ile Thr Val Asn Gly Phe Leu Ile Ile Val Asn
            20                  25                  30

Cys Asn Glu Leu Ile Lys His Arg Lys Leu Met Pro Ile Gln Ile Leu
        35                  40                  45

Leu Met Cys Ile Gly Met Ser Arg Phe Gly Leu Gln Met Val Leu Met
    50                  55                  60

Val Gln Ser Phe Phe Ser Val Phe Phe Pro Leu Leu Tyr Val Lys Ile
65                  70                  75                  80

Ile Tyr Gly Ala Ala Met Met Phe Leu Trp Met Phe Phe Ser Ser Ile
                85                  90                  95

Ser Leu Trp Phe Ala Thr Cys Leu Ser Val Phe Tyr Cys Leu Lys Ile
            100                 105                 110

Ser Gly Phe Thr Gln Ser Cys Phe Leu Trp Leu Lys Phe Arg Ile Pro
        115                 120                 125

Lys Leu Ile Pro Trp Leu Phe Trp Glu Ala Phe Trp Pro Leu Ala Leu
    130                 135                 140

His Leu Cys Val Glu Val Asp Tyr Ala Lys Asn Val Glu Glu Asp Ala
145                 150                 155                 160

Leu Arg Asn Thr Thr Leu Lys Lys Ser Lys Thr Lys Ile Lys Lys Ile
                165                 170                 175

Ser Glu Val Leu Leu Val Asn Leu Ala Leu Ile Phe Pro Leu Ala Ile
            180                 185                 190

Phe Val Met Cys Thr Ser Met Leu Leu Ile Ser Leu Tyr Lys His Thr
        195                 200                 205

His Arg Met Gln His Gly Ser His Gly Phe Arg Asn Ala Asn Thr Glu
    210                 215                 220

Ala His Ile Asn Ala Leu Lys Thr Val Ile Thr Phe Phe Cys Phe Phe
225                 230                 235                 240

Ile Ser Tyr Phe Ala Ala Phe Met Thr Asn Met Thr Phe Ser Leu Pro
                245                 250                 255

Tyr Arg Ser His Gln Phe Phe Met Leu Lys Asp Ile Met Ala Ala Tyr
            260                 265                 270

Pro Ser Gly His Ser Val Ile Ile Ile Leu Ser Asn Ser Lys Phe Gln
        275                 280                 285

Gln Ser Phe Arg Arg Ile Leu Cys Leu Lys Lys Lys Leu
    290                 295                 300


<210> SEQ ID NO 4
<211> LENGTH: 910
<212> TYPE: DNA
<213> ORGANISM: Homo sapiens

<400> SEQUENCE: 4

atggccttgt ctttttcagc tattcttcat attatcatga tgtcagcaga attcttcaca      60

gggatcacag taaatggatt tcttatcatt gttaactgta atgaattgat caaacataga     120

aagctaatgc caattcaaat cctcttaatg tgcataggga tgtctagatt tggtctgcag     180

atggtgttaa tggtacaaag ttttttctct gtgttctttc cactccttta cgtcaaaata     240

atttatggtg cagcaatgat gttcctttgg atgtttttta gctctatcag cctatggttt     300

gccacttgcc tttctgtatt ttactgcctc aagatttcag gcttcactca gtcctgtttt     360

ctttggttga aattcaggat cccaaagtta ataccttggc tgcttctggg aagcgttctg     420

gcctctgtga gcattgcatc tgtgtgtcga ggtagattac gctaaaaatg tggaagagga     480
```

-continued

```
tgccctcaga aacaccacac taaaaaagag taaaacaaag ataaagaaaa ttagtgaagt    540

gcttcttgtc aacttggcat taatatttcc tctagccata tttgtgatgt gcacttctat    600

gttactcatc tctctttaca agcacactca tcggatgcaa catggatctc atggctttag    660

aaatgccaac acagaagccc atataaatgc attaaaaaca gtgataacat tcttttgctt    720

ctttatttct tattttgctg ccttcatgac aaatatgaca tttagtttac cttacagaag    780

tcaccagttc tttatgctga aggacataat ggcagcatat ccctctggcc actcggttat    840

aataatcttg agtaattcta agttccaaca atcatttaga agaattctct gcctcaaaaa    900

gaaactatga                                                           910
```

```
<210> SEQ ID NO 5
<211> LENGTH: 316
<212> TYPE: PRT
<213> ORGANISM: Homo sapiens

<400> SEQUENCE: 5

Met Met Gly Leu Thr Glu Gly Val Phe Leu Ile Leu Ser Gly Thr Gln
1               5                   10                  15

Phe Thr Leu Gly Ile Leu Val Asn Cys Phe Ile Glu Leu Val Asn Gly
            20                  25                  30

Ser Ser Trp Phe Lys Thr Lys Arg Met Ser Leu Ser Asp Phe Ile Ile
        35                  40                  45

Thr Thr Leu Ala Leu Leu Arg Ile Ile Leu Leu Cys Ile Ile Leu Thr
    50                  55                  60

Asp Ser Phe Leu Ile Glu Phe Ser Pro Asn Thr His Asp Ser Gly Ile
65                  70                  75                  80

Ile Met Gln Ile Ile Asp Val Ser Trp Thr Phe Thr Asn His Leu Ser
                85                  90                  95

Ile Trp Leu Ala Thr Cys Leu Gly Val Leu Tyr Cys Leu Lys Ile Ala
            100                 105                 110

Ser Phe Ser His Pro Thr Phe Leu Trp Leu Lys Trp Arg Val Ser Arg
        115                 120                 125

Val Met Val Trp Met Leu Leu Gly Ala Leu Leu Leu Ser Cys Gly Ser
    130                 135                 140

Thr Ala Ser Leu Ile Asn Glu Phe Lys Leu Tyr Ser Val Phe Arg Gly
145                 150                 155                 160

Ile Glu Ala Thr Arg Asn Val Thr Glu His Phe Arg Lys Lys Arg Ser
                165                 170                 175

Glu Tyr Tyr Leu Ile His Val Leu Gly Thr Leu Trp Tyr Leu Pro Pro
            180                 185                 190

Leu Ile Val Ser Leu Ala Ser Tyr Ser Leu Leu Ile Phe Ser Leu Gly
        195                 200                 205

Arg His Thr Arg Gln Met Leu Gln Asn Gly Thr Ser Ser Arg Asp Pro
    210                 215                 220

Thr Thr Glu Ala His Lys Arg Ala Ile Arg Ile Ile Leu Ser Phe Phe
225                 230                 235                 240

Phe Leu Phe Leu Leu Tyr Phe Leu Ala Phe Leu Ile Ala Ser Phe Gly
                245                 250                 255

Asn Phe Leu Pro Lys Thr Lys Met Ala Lys Met Ile Gly Glu Val Met
            260                 265                 270

Thr Met Phe Tyr Pro Ala Gly His Ser Phe Ile Leu Ile Leu Gly Asn
        275                 280                 285
```

-continued

```
Ser Lys Leu Lys Gln Thr Phe Val Val Met Leu Arg Cys Glu Ser Gly
    290                 295                 300

His Leu Lys Pro Gly Ser Lys Gly Pro Ile Phe Ser
305                 310                 315


<210> SEQ ID NO 6
<211> LENGTH: 951
<212> TYPE: DNA
<213> ORGANISM: Homo sapiens

<400> SEQUENCE: 6

atgatgggac tcaccgaggg ggtgttcctg attctgtctg gcactcagtt cacactggga      60

attctggtca attgtttcat tgagttggtc aatggtagca gctggttcaa gaccaagaga     120

atgtctttgt ctgacttcat catcaccacc ctggcactct tgaggatcat tctgctgtgt     180

attatcttga ctgatagttt tttaatagaa ttctctccca acacacatga ttcagggata     240

ataatgcaaa ttattgatgt ttcctggaca tttacaaacc atctgagcat ttggcttgcc     300

acctgtcttg gtgtcctcta ctgcctgaaa atcgccagtt tctctcaccc cacattcctc     360

tggctcaagt ggagagtttc tagggtgatg gtatggatgc tgttgggtgc actgctctta     420

tcctgtggta gtaccgcatc tctgatcaat gagtttaagc tctattctgt ctttagggga     480

attgaggcca ccaggaatgt gactgaacac ttcagaaaga agaggagtga gtattatctg     540

atccatgttc ttgggactct gtggtacctg cctcccttaa ttgtgtccct ggcctcctac     600

tctttgctca tcttctccct ggggaggcac acacggcaga tgctgcaaaa tgggacaagc     660

tccagagatc caaccactga ggcccacaag agggccatca gaatcatcct ttccttcttc     720

tttctcttct tactttactt tcttgctttc ttaattgcat catttggtaa tttcctacca     780

aaaaccaaga tggctaagat gattggcgaa gtaatgacaa tgttttatcc tgctggccac     840

tcatttattc tcattctggg gaacagtaag ctgaagcaga catttgtagt gatgctccgg     900

tgtgagtctg gtcatctgaa gcctggatcc aagggaccca ttttctctta g              951


<210> SEQ ID NO 7
<211> LENGTH: 299
<212> TYPE: PRT
<213> ORGANISM: Homo sapiens

<400> SEQUENCE: 7

Met Leu Arg Leu Phe Tyr Phe Ser Ala Ile Ile Ala Ser Val Ile Leu
1               5                   10                  15

Asn Phe Val Gly Ile Ile Met Asn Leu Phe Ile Thr Val Val Asn Cys
            20                  25                  30

Lys Thr Trp Val Lys Ser His Arg Ile Ser Ser Ser Asp Arg Ile Leu
        35                  40                  45

Phe Ser Leu Gly Ile Thr Arg Phe Leu Met Leu Gly Leu Phe Leu Val
    50                  55                  60

Asn Thr Ile Tyr Phe Val Ser Ser Asn Thr Glu Arg Ser Val Tyr Leu
65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
            100                 105                 110

Phe Gln His Ser Val Phe Leu Leu Leu Lys Arg Asn Ile Ser Pro Lys
        115                 120                 125

Ile Pro Arg Leu Leu Leu Ala Cys Val Leu Ile Ser Ala Phe Thr Thr
```

-continued

```
    130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Ser Leu Gln Phe Ile Ile Asn
            180                 185                 190

Val Thr Ser Ala Ser Leu Leu Ile His Ser Leu Arg Arg His Ile Gln
        195                 200                 205

Lys Met Gln Lys Asn Ala Thr Gly Phe Trp Asn Pro Gln Thr Glu Ala
    210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                245                 250                 255

Met Asp Met Gly Thr Lys Ser Ile Cys Leu Ile Phe Ala Thr Leu Tyr
            260                 265                 270

Ser Pro Gly His Ser Val Leu Ile Ile Ile Thr His Pro Lys Leu Lys
        275                 280                 285

Thr Thr Ala Lys Lys Ile Leu Cys Phe Lys Lys
    290                 295


<210> SEQ ID NO 8
<211> LENGTH: 900
<212> TYPE: DNA
<213> ORGANISM: Homo sapiens

<400> SEQUENCE: 8

atgcttcggt tattctattt ctctgctatt attgcctcag ttattttaaa ttttgtagga     60

atcattatga atctgtttat tacagtggtc aattgcaaaa cttgggtcaa aagccataga    120

atctcctctt ctgataggat tctgttcagc ctgggcatca ccaggtttct tatgctggga    180

ctatttctgg tgaacaccat ctacttcgtc tcttcaaata cggaaaggtc agtctacctg    240

tctgcttttt ttgtgttgtg tttcatgttt ttggactcga gcagtgtctg gtttgtgacc    300

ttgctcaata tcttgtactg tgtgaagatt actaacttcc aacactcagt gtttctcctg    360

ctgaagcgga atatctcccc aaagatcccc aggctgctgc tggcctgtgt gctgatttct    420

gctttcacca cttgcctgta catcacgctt agccaggcat cacctttccc tgaacttgtg    480

actacgagaa ataacacatc atttaatatc agtgagggca tcttgtcttt agtggtttct    540

ttggtcttga gctcatctct ccagttcatc attaatgtga cttctgcttc cttgctaata    600

cactccttga ggagacatat acagaagatg cagaaaaatg ccactggttt ctggaatccc    660

cagacggaag ctcatgtagg tgctatgaag ctgatggtct atttcctcat cctctacatt    720

ccatattcag ttgctaccct ggtccagtat ctccccttt atgcagggat ggatatgggg    780

accaaatcca tttgtctgat tttgccacc ctttactctc caggacattc tgttctcatt    840

attatcacac atcctaaact gaaaacaaca gcaaagaaga ttctttgttt caaaaaatag    900


<210> SEQ ID NO 9
<211> LENGTH: 299
<212> TYPE: PRT
<213> ORGANISM: Homo sapiens

<400> SEQUENCE: 9

Met Leu Ser Ala Gly Leu Gly Leu Leu Met Leu Val Ala Val Val Glu
```

-continued

```
1               5                   10                  15

Phe Leu Ile Gly Leu Ile Gly Asn Gly Ser Leu Val Val Trp Ser Phe
            20                  25                  30

Arg Glu Trp Ile Arg Lys Phe Asn Trp Ser Ser Tyr Asn Leu Ile Ile
        35                  40                  45

Leu Gly Leu Ala Gly Cys Arg Phe Leu Leu Gln Trp Leu Ile Ile Leu
    50                  55                  60

Asp Leu Ser Leu Phe Pro Leu Phe Gln Ser Ser Arg Trp Leu Arg Tyr
65                  70                  75                  80

Leu Ser Ile Phe Trp Val Leu Val Ser Gln Ala Ser Leu Trp Phe Ala
                85                  90                  95

Thr Phe Leu Ser Val Phe Tyr Cys Lys Lys Ile Thr Thr Phe Asp Arg
            100                 105                 110

Pro Ala Tyr Leu Trp Leu Lys Gln Arg Ala Tyr Asn Leu Ser Leu Trp
        115                 120                 125

Cys Leu Leu Gly Tyr Phe Ile Ile Asn Leu Leu Leu Thr Val Gln Ile
    130                 135                 140

Gly Leu Thr Phe Tyr His Pro Pro Gln Gly Asn Ser Ser Ile Arg Tyr
145                 150                 155                 160

Pro Phe Glu Ser Trp Gln Tyr Leu Tyr Ala Phe Gln Leu Asn Ser Gly
                165                 170                 175

Ser Tyr Leu Pro Leu Val Val Phe Leu Val Ser Ser Gly Met Leu Ile
            180                 185                 190

Val Ser Leu Tyr Thr His His Lys Lys Met Lys Val His Ser Ala Gly
        195                 200                 205

Arg Arg Asp Val Arg Ala Lys Ala His Ile Thr Ala Leu Lys Ser Leu
    210                 215                 220

Gly Cys Phe Leu Leu Leu His Leu Val Tyr Ile Met Ala Ser Pro Phe
225                 230                 235                 240

Ser Ile Thr Ser Lys Thr Tyr Pro Pro Asp Leu Thr Ser Val Phe Ile
                245                 250                 255

Trp Glu Thr Leu Met Ala Ala Tyr Pro Ser Leu His Ser Leu Ile Leu
            260                 265                 270

Ile Met Gly Ile Pro Arg Val Lys Gln Thr Cys Gln Lys Ile Leu Trp
        275                 280                 285

Lys Thr Val Cys Ala Arg Arg Cys Trp Gly Pro
    290                 295


<210> SEQ ID NO 10
<211> LENGTH: 900
<212> TYPE: DNA
<213> ORGANISM: Homo sapiens

<400> SEQUENCE: 10

atgctgagcg ctggcctagg actgctgatg ctggtggcag tggttgaatt tctcatcggt      60

ttaattggaa atggaagcct ggtggtctgg agttttagag aatggatcag aaaattcaac     120

tggtcctcat ataacctcat tatcctgggc ctggctggct gccgatttct cctgcagtgg     180

ctgatcattt tggacttaag cttgtttcca cttttccaga gcagccgttg gcttcgctat     240

cttagtatct tctgggtcct ggtaagccag gccagcttat ggtttgccac cttcctcagt     300

gtcttctatt gcaagaagat cacgaccttc gatcgcccgg cctacttgtg gctgaagcag     360

agggcctata acctgagtct ctggtgcctt ctgggctact ttataatcaa tttgttactt     420

acagtccaaa ttggcttaac attctatcat cctccccaag gaaacagcag cattcggtat     480
```

-continued

```
ccctttgaaa gctggcagta cctgtatgca tttcagctca attcaggaag ttatttgcct    540

ttagtggtgt ttcttgtttc ctctgggatg ctgattgtct ctttgtatac acaccacaag    600

aagatgaagg tccattcagc tggtaggagg gatgtccggg ccaaggctca catcactgcg    660

ctgaagtcct tgggctgctt cctcttactt cacctggttt atatcatggc cagccccttc    720

tccatcacct ccaagactta tcctcctgat ctcaccagtg tcttcatctg ggagacactc    780

atggcagcct atccttctct tcattctctc atattgatca tggggattcc tagggtgaag    840

cagacttgtc agaagatcct gtggaagaca gtgtgtgctc ggagatgctg ggcccatga     900
```

```
<210> SEQ ID NO 11
<211> LENGTH: 277
<212> TYPE: PRT
<213> ORGANISM: Homo sapiens
<220> FEATURE:
<221> NAME/KEY: MOD_RES
<222> LOCATION: (106)..(125)
<223> OTHER INFORMATION: Variable amino acid
<220> FEATURE:
<221> NAME/KEY: MOD_RES
<222> LOCATION: (203)..(217)
<223> OTHER INFORMATION: Variable amino acid

<400> SEQUENCE: 11

Met Leu Ala Ala Ala Leu Gly Leu Leu Met Pro Ile Ala Gly Ala Glu
1               5                   10                  15

Phe Leu Ile Gly Leu Val Gly Asn Gly Val Pro Val Val Cys Ser Phe
            20                  25                  30

Arg Gly Trp Val Lys Lys Met Gly Val Pro Ile Asn Ser His Asp Ser
        35                  40                  45

Gly Lys Pro Leu Ser Pro Thr Gln Ala Asp His Val Gly His Lys Ser
    50                  55                  60

Val Ser Thr Phe Pro Glu Gln Trp Leu Ala Leu Leu Ser Cys Leu Arg
65                  70                  75                  80

Val Leu Val Ser Gln Ala Asn Met Phe Ala Thr Phe Phe Ser Gly Phe
                85                  90                  95

Cys Cys Met Glu Ile Met Thr Phe Val Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Leu Leu Val
        115                 120                 125

Ser Phe Lys Ile Thr Phe Tyr Phe Ser Ala Leu Val Gly Trp Thr Leu
    130                 135                 140

Lys Pro Leu Thr Gly Asn Ser Asn Ile Leu His Pro Ile Leu Asn Leu
145                 150                 155                 160

Leu Phe Leu Ile Ala Val Gln Arg Arg Leu Ile Ala Ile Cys Asp Val
                165                 170                 175

Ser Val Pro Leu Val Phe Leu Arg His His Arg Lys Met Glu Asp His
            180                 185                 190

Thr Ala Val Arg Arg Arg Leu Lys Pro Arg Xaa Xaa Xaa Xaa Xaa Xaa
        195                 200                 205

Xaa Xaa Xaa Xaa Xaa Xaa Xaa Xaa Xaa Leu Tyr Met Val Ser Ala Leu
    210                 215                 220

Ala Arg His Phe Ser Met Thr Phe Ser Pro Ser Asp Leu Thr Ile Leu
225                 230                 235                 240

Ala Ile Ser Ala Thr Leu Met Ala Val Tyr Thr Ser Phe Pro Ser Ile
                245                 250                 255
```

-continued

```
Val Met Val Met Arg Asn Gln Thr Cys Gln Arg Ile Leu Glu Met Ile
            260                 265                 270

Cys Thr Trp Lys Ser
        275


<210> SEQ ID NO 12
<211> LENGTH: 823
<212> TYPE: DNA
<213> ORGANISM: Homo sapiens

<400> SEQUENCE: 12

atgttggcgg ctgccctagg attgctgatg cccattgcag ggctgaatt tctcattggc      60

ctggttggaa atggagtccc tgtggtctgc agttttagag gatgggtcaa aaaaatgtaa     120

ggagtcccta taaattctca tgattctggt aagtagccac tttctcctac tcaggccgat     180

catgttggac ataagtctgt ttccactttc ccagagcagt ggttggcttt actatcttaa     240

tgtcttcgag tcctggtaag ccaggccaac atgtagtttg ccactttctt cagtggcttc     300

tgctgcatgg agatcatgac ctttgtcccg ctgacttctt gtagctgaaa agactgggtt     360

tttgtttttt gctagtgtct ttcaagatca ctttttattt ctcagctctt gttggctgga     420

ccctttaaaa acccttaaca ggaaacagca acatcctgca tcccatttta aatctgttat     480

ttttatagat tgctgtccag tgaaggagac tgattgctat ttgtgatgtt tctgttccac     540

ttgtcttttt gtaaagacat cacaggaaga tggaggacca cacagctgtc aggaggaggc     600

tcaaaccaag gtgctcatcg ctctgaactt ccccctttac atggtttctg ccttggccag     660

acacttttcc atgaccttct aatctccctc tgatctcacc attcttgcca tctctgcaac     720

actcatggct gtttatactt catttccgtc tattgtaatg gttatgagga atcagacttg     780

tcagagaatt ctgtaggaga tgatatgtac atggaaatcc tag                       823


<210> SEQ ID NO 13
<211> LENGTH: 318
<212> TYPE: PRT
<213> ORGANISM: Homo sapiens

<400> SEQUENCE: 13

Met Ala Asp Lys Val Gln Thr Thr Leu Leu Phe Leu Ala Val Gly Glu
1               5                   10                  15

Phe Ser Val Gly Ile Leu Gly Asn Ala Phe Ile Gly Leu Val Asn Cys
            20                  25                  30

Met Asp Trp Val Lys Lys Arg Lys Ile Ala Ser Ile Asp Leu Ile Leu
        35                  40                  45

Thr Ser Leu Ala Ile Ser Arg Ile Cys Leu Leu Cys Val Ile Leu Leu
    50                  55                  60

Asp Cys Phe Ile Leu Val Leu Tyr Pro Asp Val Tyr Ala Thr Gly Lys
65                  70                  75                  80

Glu Met Arg Ile Ile Asp Phe Phe Trp Thr Leu Thr Asn His Leu Ser
                85                  90                  95

Ile Trp Phe Ala Thr Cys Leu Ser Ile Tyr Tyr Phe Phe Lys Ile Gly
            100                 105                 110

Asn Phe Phe His Pro Leu Phe Leu Trp Met Lys Trp Arg Ile Asp Arg
        115                 120                 125

Val Ile Ser Trp Ile Leu Leu Gly Cys Val Val Leu Ser Val Phe Ile
    130                 135                 140

Ser Leu Pro Ala Thr Glu Asn Leu Asn Ala Asp Phe Arg Phe Cys Val
145                 150                 155                 160
```

-continued

```
Lys Ala Lys Arg Lys Thr Asn Leu Thr Trp Ser Cys Arg Val Asn Lys
                165                 170                 175

Thr Gln His Ala Ser Thr Lys Leu Phe Leu Asn Leu Ala Thr Leu Leu
            180                 185                 190

Pro Phe Cys Val Cys Leu Met Ser Phe Phe Leu Leu Ile Leu Ser Leu
        195                 200                 205

Arg Arg His Ile Arg Arg Met Gln Leu Ser Ala Thr Gly Cys Arg Asp
    210                 215                 220

Pro Ser Thr Glu Ala His Val Arg Ala Leu Lys Ala Val Ile Ser Phe
225                 230                 235                 240

Leu Leu Leu Phe Ile Ala Tyr Tyr Leu Ser Phe Leu Ile Ala Thr Ser
                245                 250                 255

Ser Tyr Phe Met Pro Glu Thr Glu Leu Ala Val Ile Phe Gly Glu Ser
            260                 265                 270

Ile Ala Leu Ile Tyr Pro Ser Ser His Ser Phe Ile Leu Ile Leu Gly
        275                 280                 285

Asn Asn Lys Leu Arg His Ala Ser Leu Lys Val Ile Trp Lys Val Met
    290                 295                 300

Ser Ile Leu Lys Gly Arg Lys Phe Gln Gln His Lys Gln Ile
305                 310                 315
```

<210> SEQ ID NO 14
<211> LENGTH: 957
<212> TYPE: DNA
<213> ORGANISM: Homo sapiens

<400> SEQUENCE: 14

```
atggcagata aagtgcagac tactttattg ttcttagcag ttggagagtt ttcagtgggg     60

atcttaggga atgcattcat tggattggta aactgcatgg actgggtcaa gaagaggaaa    120

attgcctcca ttgatttaat cctcacaagt ctggccatat ccagaatttg tctattgtgc    180

gtaatactat tagattgttt tatattggtg ctatatccag atgtctatgc cactggtaaa    240

gaaatgagaa tcattgactt cttctggaca ctaaccaatc atttaagtat ctggtttgca    300

acctgcctca gcatttacta tttcttcaag ataggtaatt tctttcaccc acttttcctc    360

tggatgaagt ggagaattga cagggtgatt tcctggattc tactggggtg cgtggttctc    420

tctgtgttta ttagccttcc agccactgag aatttgaacg ctgatttcag gttttgtgtg    480

aaggcaaaga ggaaaacaaa cttaacttgg agttgcagag taaataaaac tcaacatgct    540

tctaccaagt tatttctcaa cctggcaacg ctgctcccct tttgtgtgtg cctaatgtcc    600

tttttcctct tgatcctctc cctgcggaga catatcaggc gaatgcagct cagtgccaca    660

gggtgcagag accccagcac agaagcccat gtgagagccc tgaaagctgt catttccttc    720

cttctcctct ttattgccta ctatttgtcc tttctcattg ccacctccag ctactttatg    780

ccagagacgg aattagctgt gatttttggt gagtccatag ctctaatcta cccctcaagt    840

cattcattta tcctaatact ggggaacaat aaattaagac atgcatctct aaaggtgatt    900

tggaaagtaa tgtctattct aaaaggaaga aaattccaac aacataaaca aatctga       957
```

<210> SEQ ID NO 15
<211> LENGTH: 309
<212> TYPE: PRT
<213> ORGANISM: Homo sapiens

<400> SEQUENCE: 15

-continued

```
Met Phe Ser Pro Ala Asp Asn Ile Phe Ile Ile Leu Ile Thr Gly Glu
1               5                   10                  15

Phe Ile Leu Gly Ile Leu Gly Asn Gly Tyr Ile Ala Leu Val Asn Trp
            20                  25                  30

Ile Asp Trp Ile Lys Lys Lys Lys Ile Ser Thr Val Asp Tyr Ile Leu
        35                  40                  45

Thr Asn Leu Val Ile Ala Arg Ile Cys Leu Ile Ser Val Met Val Val
    50                  55                  60

Asn Gly Ile Val Ile Val Leu Asn Pro Asp Val Tyr Thr Lys Asn Lys
65                  70                  75                  80

Gln Gln Ile Val Ile Phe Thr Phe Trp Thr Phe Ala Asn Tyr Leu Asn
                85                  90                  95

Met Trp Ile Thr Thr Cys Leu Asn Val Phe Tyr Phe Leu Lys Ile Ala
            100                 105                 110

Ser Ser Ser His Pro Leu Phe Leu Trp Leu Lys Trp Lys Ile Asp Met
        115                 120                 125

Val Val His Trp Ile Leu Leu Gly Cys Phe Ala Ile Ser Leu Leu Val
    130                 135                 140

Ser Leu Ile Ala Ala Ile Val Leu Ser Cys Asp Tyr Arg Phe His Ala
145                 150                 155                 160

Ile Ala Lys His Lys Arg Asn Ile Thr Glu Met Phe His Val Ser Lys
                165                 170                 175

Ile Pro Tyr Phe Glu Pro Leu Thr Leu Phe Asn Leu Phe Ala Ile Val
            180                 185                 190

Pro Phe Ile Val Ser Leu Ile Ser Phe Phe Leu Leu Val Arg Ser Leu
        195                 200                 205

Trp Arg His Thr Lys Gln Ile Lys Leu Tyr Ala Thr Gly Ser Arg Asp
    210                 215                 220

Pro Ser Thr Glu Val His Val Arg Ala Ile Lys Thr Met Thr Ser Phe
225                 230                 235                 240

Ile Phe Phe Phe Phe Leu Tyr Tyr Ile Ser Ser Ile Leu Met Thr Phe
                245                 250                 255

Ser Tyr Leu Met Thr Lys Tyr Lys Leu Ala Val Glu Phe Gly Glu Ile
            260                 265                 270

Ala Ala Ile Leu Tyr Pro Leu Gly His Ser Leu Ile Leu Ile Val Leu
        275                 280                 285

Asn Asn Lys Leu Arg Gln Thr Phe Val Arg Met Leu Thr Cys Arg Lys
    290                 295                 300

Ile Ala Cys Met Ile
305
```

<210> SEQ ID NO 16
<211> LENGTH: 930
<212> TYPE: DNA
<213> ORGANISM: Homo sapiens

<400> SEQUENCE: 16

```
atgttcagtc ctgcagataa catctttata atcctaataa ctggagaatt catactagga      60

atattgggga atggatacat tgcactagtc aactggattg actggattaa gaagaaaaag     120

atttccacag ttgactacat ccttaccaat ttagttatcg ccagaatttg tttgatcagt     180

gtaatggttg taaatggcat tgtaatagta ctgaacccag atgtttatac aaaaaataaa     240

caacagatag tcatttttac cttctggaca tttgccaact acttaaatat gtggattacc     300

acctgcctta atgtcttcta ttttctgaag atagccagtt cctctcatcc actttttctc     360
```

-continued

```
tggctgaagt ggaaaattga tatggtggtg cactggatcc tgctgggatg ctttgccatt    420

tccttgttgg tcagccttat agcagcaata gtactgagtt gtgattatag gtttcatgca    480

attgccaaac ataaaagaaa cattactgaa atgttccatg tgagtaaaat accatacttt    540

gaacccttga ctctctttaa cctgtttgca attgtcccat ttattgtgtc actgatatca    600

tttttccttt tagtaagatc tttatggaga cataccaagc aaataaaact ctatgctacc    660

ggcagtagag accccagcac agaagttcat gtgagagcca ttaaaactat gacttcattt    720

atcttctttt ttttcctata ctatatttct tctattttga tgacctttag ctatcttatg    780

acaaaataca agttagctgt ggagtttgga gagattgcag caattctcta ccccttgggt    840

cactcactta ttttaattgt tttaaataat aaactgaggc agacatttgt cagaatgctg    900

acatgtagaa aaattgcctg catgatatga                                      930


<210> SEQ ID NO 17
<211> LENGTH: 312
<212> TYPE: PRT
<213> ORGANISM: Homo sapiens

<400> SEQUENCE: 17

Met Pro Ser Ala Ile Glu Ala Ile Tyr Ile Ile Leu Ile Ala Gly Glu
1               5                   10                  15

Leu Thr Ile Gly Ile Trp Gly Asn Gly Phe Ile Val Leu Val Asn Cys
            20                  25                  30

Ile Asp Trp Leu Lys Arg Arg Asp Ile Ser Leu Ile Asp Ile Ile Leu
        35                  40                  45

Ile Ser Leu Ala Ile Ser Arg Ile Cys Leu Leu Cys Val Ile Ser Leu
    50                  55                  60

Asp Gly Phe Phe Met Leu Leu Phe Pro Gly Thr Tyr Gly Asn Ser Val
65                  70                  75                  80

Leu Val Ser Ile Val Asn Val Val Trp Thr Phe Ala Asn Asn Ser Ser
                85                  90                  95

Leu Trp Phe Thr Ser Cys Leu Ser Ile Phe Tyr Leu Leu Lys Ile Ala
            100                 105                 110

Asn Ile Ser His Pro Phe Phe Phe Trp Leu Lys Leu Lys Ile Asn Lys
        115                 120                 125

Val Met Leu Ala Ile Leu Leu Gly Ser Phe Leu Ile Ser Leu Ile Ile
    130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
                165                 170                 175

Thr Phe Lys Gln Leu Thr Leu Asn Leu Gly Val Met Val Pro Phe Ile
            180                 185                 190

Leu Cys Leu Ile Ser Phe Phe Leu Leu Leu Phe Ser Leu Val Arg His
        195                 200                 205

Thr Lys Gln Ile Arg Leu His Ala Thr Gly Phe Arg Asp Pro Ser Thr
    210                 215                 220

Glu Ala His Met Arg Ala Ile Lys Ala Val Ile Ile Phe Leu Leu Leu
225                 230                 235                 240

Leu Ile Val Tyr Tyr Pro Val Phe Leu Val Met Thr Ser Ser Ala Leu
                245                 250                 255

Ile Pro Gln Gly Lys Leu Val Leu Met Ile Gly Asp Ile Val Thr Val
            260                 265                 270
```

-continued

```
Ile Phe Pro Ser Ser His Ser Phe Ile Leu Ile Met Gly Asn Ser Lys
        275                 280                 285

Leu Arg Glu Ala Phe Leu Lys Met Leu Arg Phe Val Lys Cys Phe Leu
    290                 295                 300

Arg Arg Arg Lys Pro Phe Val Pro
305                 310


<210> SEQ ID NO 18
<211> LENGTH: 939
<212> TYPE: DNA
<213> ORGANISM: Homo sapiens

<400> SEQUENCE: 18

atgccaagtg caatagaggc aatatatatt attttaattg ctggtgaatt gaccataggg     60

atttggggaa atggattcat tgtactagtt aactgcattg actggctcaa aagaagagat    120

atttccttga ttgacatcat cctgatcagc ttggccatct ccagaatctg tctgctgtgt    180

gtaatatcat tagatggctt ctttatgctg ctctttccag gtacatatgg caatagcgtg    240

ctagtaagca ttgtgaatgt tgtctggaca tttgccaata attcaagtct ctggtttact    300

tcttgcctca gtatcttcta tttactcaag atagccaata tatcgcaccc atttttcttc    360

tggctgaagc taaagatcaa caaggtcatg cttgcgattc ttctggggtc ctttcttatc    420

tctttaatta ttagtgttcc aaagaatgat gatatgtggt atcacctttt caaagtcagt    480

catgaagaaa acattacttg gaaattcaaa ctgagtaaaa ttccaggtac tttcaaacag    540

ttaaccctga acctgggggt gatggttccc tttatccttt gcctgatctc attttttcttg    600

ttacttttct ccctagttag acacaccaag cagattcgac tgcatgctac agggttcaga    660

gaccccagta cagaggccca catgagggcc ataaaggcag tgatcatctt tctgctcctc    720

ctcatcgtgt actacccagt ctttcttgtt atgacctcta gcgctctgat tcctcaggga    780

aaattagtgt tgatgattgg tgacatagta actgtcattt tcccatcaag ccattcattc    840

attctaatta tgggaaatag caagttgagg gaagcttttc tgaagatgtt aagatttgtg    900

aagtgtttcc ttagaagaag aaagcctttt gttccatag                           939


<210> SEQ ID NO 19
<211> LENGTH: 307
<212> TYPE: PRT
<213> ORGANISM: Homo sapiens

<400> SEQUENCE: 19

Met Leu Arg Val Val Glu Gly Ile Phe Ile Phe Val Val Val Ser Glu
1               5                   10                  15

Ser Val Phe Gly Val Leu Gly Asn Gly Phe Ile Gly Leu Val Asn Cys
            20                  25                  30

Ile Asp Cys Ala Lys Asn Lys Leu Ser Thr Ile Gly Phe Ile Leu Thr
        35                  40                  45

Gly Leu Ala Ile Ser Arg Ile Phe Leu Ile Trp Ile Ile Ile Thr Asp
    50                  55                  60

Gly Phe Ile Gln Ile Phe Ser Pro Asn Ile Tyr Ala Ser Gly Asn Leu
65                  70                  75                  80

Ile Glu Tyr Ile Ser Tyr Phe Trp Val Ile Gly Asn Gln Ser Ser Met
                85                  90                  95

Trp Phe Ala Thr Ser Leu Ser Ile Phe Tyr Phe Leu Lys Ile Ala Asn
            100                 105                 110
```

-continued

```
Phe Ser Asn Tyr Ile Phe Leu Trp Leu Lys Ser Arg Thr Asn Met Val
        115                 120                 125

Leu Pro Phe Met Ile Val Phe Leu Leu Ile Ser Ser Leu Leu Asn Phe
    130                 135                 140

Ala Tyr Ile Ala Lys Ile Leu Asn Asp Tyr Lys Thr Lys Asn Asp Thr
145                 150                 155                 160

Val Trp Asp Leu Asn Met Tyr Lys Ser Glu Tyr Phe Ile Lys Gln Ile
                165                 170                 175

Leu Leu Asn Leu Gly Val Ile Phe Phe Phe Thr Leu Ser Leu Ile Thr
            180                 185                 190

Cys Ile Phe Leu Ile Ile Ser Leu Trp Arg His Asn Arg Gln Met Gln
        195                 200                 205

Ser Asn Val Thr Gly Leu Arg Asp Ser Asn Thr Glu Ala His Val Lys
    210                 215                 220

Ala Met Lys Val Leu Ile Ser Phe Ile Ile Leu Phe Ile Leu Tyr Phe
225                 230                 235                 240

Ile Gly Met Ala Ile Glu Ile Ser Cys Phe Thr Val Arg Glu Asn Lys
                245                 250                 255

Leu Leu Leu Met Phe Gly Met Thr Thr Thr Ala Ile Tyr Pro Trp Gly
            260                 265                 270

His Ser Phe Ile Leu Ile Leu Gly Asn Ser Lys Leu Lys Gln Ala Ser
        275                 280                 285

Leu Arg Val Leu Gln Gln Leu Lys Cys Cys Glu Lys Arg Lys Asn Leu
    290                 295                 300

Arg Val Thr
305
```

<210> SEQ ID NO 20
<211> LENGTH: 924
<212> TYPE: DNA
<213> ORGANISM: Homo sapiens

<400> SEQUENCE: 20

```
atgctacgtg tagtggaagg catcttcatt tttgttgtag ttagtgagtc agtgtttggg     60

gttttgggga atggatttat tggacttgta aactgcattg actgtgccaa gaataagtta    120

tctacgattg gctttattct caccggctta gctatttcaa gaatttttct gatatggata    180

ataattacag atggatttat acagatattc tctccaaata tatatgcctc cggtaaccta    240

attgaatata ttagttactt ttgggtaatt ggtaatcaat caagtatgtg gtttgccacc    300

agcctcagca tcttctattt cctgaagata gcaaattttt ccaactacat atttctctgg    360

ttgaagagca gaacaaatat ggttcttccc ttcatgatag tattcttact tatttcatcg    420

ttacttaatt ttgcatacat tgcgaagatt cttaatgatt ataaaacgaa gaatgacaca    480

gtctgggatc tcaacatgta taaaagtgaa tactttatta aacagatttt gctaaatctg    540

ggagtcattt tcttctttac actatcccta attacatgta ttttttttaat catttccctt    600

tggagacaca acaggcagat gcaatcgaat gtgacaggat tgagagactc caacacagaa    660

gctcatgtga aggcaatgaa agttttgata tctttcatca tcctctttat cttgtatttt    720

ataggcatgg ccatagaaat atcatgtttt actgtgcgag aaaacaaact gctgcttatg    780

tttggaatga caaccacagc catctatccc tggggtcact catttatctt aattctagga    840

aacagcaagc taaagcaagc ctctttgagg gtactgcagc aattgaagtg ctgtgagaaa    900

aggaaaaatc tcagagtcac atag                                           924
```

-continued

<210> SEQ ID NO 21
<211> LENGTH: 242
<212> TYPE: PRT
<213> ORGANISM: Homo sapiens
<220> FEATURE:
<221> NAME/KEY: MOD_RES
<222> LOCATION: (58)..(89)
<223> OTHER INFORMATION: Variable amino acid

<400> SEQUENCE: 21

```
Met Ala Asn Met Leu Lys Asn Met Leu Thr Met Ile Ser Ala Ile Asp
1               5                   10                  15

Phe Ile Met Gly Ile Gln Arg Ser Arg Val Met Val Leu Val His Cys
            20                  25                  30

Ile Asp Trp Ile Arg Arg Trp Lys Leu Ser Leu Ile Asp Phe Ile Leu
        35                  40                  45

Thr Cys Trp Ala Ile Ser Arg Ile Phe Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Asn His Leu Cys Thr Phe Ala
                85                  90                  95

Thr Cys Leu Ala Val Phe Tyr Phe Leu Lys Ile Val Asn Phe Ser Tyr
            100                 105                 110

Leu Phe Tyr Phe Trp Leu Lys Trp Arg Ile Asn Lys Val Ala Phe Ile
        115                 120                 125

Leu Pro Leu Val Ser Ala Phe Ser Val Tyr Gln Leu Ser Phe Asp Val
    130                 135                 140

His Phe Cys Leu Leu Val Ser Cys Pro Lys Lys Tyr Glu Arg His Met
145                 150                 155                 160

Thr Gly Leu Leu Asn Val Ser Asn Asn Lys Asn Val Asn Asn Ile Ile
                165                 170                 175

Ile Phe Phe Ile Gly Ser Leu Ser Ser Phe Ser Ile Ser Ser Ile Phe
            180                 185                 190

Phe Leu Leu Leu Leu Leu Ser Ser Arg His Met Lys His Ile Arg Phe
        195                 200                 205

Asn Phe Arg Asp Cys Arg Thr Pro Val Tyr Gly Pro Ile Ser Glu Pro
    210                 215                 220

Arg Lys Arg Phe Ser Phe Phe Val Leu Leu Leu Tyr Lys Asn Leu Pro
225                 230                 235                 240

Phe Ser
```

<210> SEQ ID NO 22
<211> LENGTH: 309
<212> TYPE: PRT
<213> ORGANISM: Homo sapiens

<400> SEQUENCE: 22

```
Met Ser Ser Ile Trp Glu Thr Leu Phe Ile Arg Ile Leu Val Val Phe
1               5                   10                  15

Ile Met Gly Thr Val Gly Asn Phe Ile Val Leu Val Asn Ile Ile Asp
            20                  25                  30

Ile Arg Asn Lys Val Ser Leu Ile Asp Phe Ile Leu Asn Cys Leu Ala
        35                  40                  45

Ile Ser Arg Ile Cys Phe Leu Ile Thr Ile Leu Ala Thr Ser Phe Asn
    50                  55                  60
```

-continued

```
Ile Gly Tyr Glu Lys Met Pro Asp Ser Lys Asn Leu Ala Val Ser Phe
65                  70                  75                  80

Asp Ile Leu Trp Thr Gly Ser Ser Tyr Phe Cys Leu Ser Cys Thr Thr
                85                  90                  95

Cys Leu Ser Val Phe Tyr Phe Leu Lys Val Ala Asn Phe Ser Asn Pro
            100                 105                 110

Ile Phe Leu Trp Met Lys Trp Lys Ile His Lys Val Leu Leu Phe Ile
        115                 120                 125

Val Leu Glu Ala Thr Ile Ser Phe Cys Thr Thr Ser Ile Leu Lys Glu
    130                 135                 140

Ile Ile Ile Asn Ser Leu Ile Glu Arg Val Thr Ile Lys Gly Asn Leu
145                 150                 155                 160

Thr Phe Asn Tyr Met Asp Thr Met His Asp Phe Thr Ser Leu Phe Leu
                165                 170                 175

Leu Gln Met Met Phe Ile Leu Pro Phe Val Glu Thr Leu Ala Ser Ile
            180                 185                 190

Leu Leu Leu Ile Leu Ser Leu Trp Ser His Thr Arg Gln Met Lys Leu
        195                 200                 205

His Gly Ile Tyr Ser Arg Asp Pro Ser Thr Glu Ala His Val Lys Pro
    210                 215                 220

Ile Lys Ala Ile Ile Ser Phe Leu Leu Leu Phe Ile Val His Tyr Phe
225                 230                 235                 240

Ile Ser Ile Ile Leu Thr Leu Ala Cys Pro Leu Leu Asp Phe Val Ala
                245                 250                 255

Ala Arg Thr Phe Ser Ser Val Leu Val Phe Phe His Pro Ser Gly His
            260                 265                 270

Ser Phe Leu Leu Ile Leu Arg Asp Ser Lys Leu Lys Gln Ala Ser Leu
        275                 280                 285

Cys Val Leu Lys Lys Met Lys Tyr Ala Lys Lys Asp Ile Ile Ser His
    290                 295                 300

Phe Tyr Lys His Ala
305
```

<210> SEQ ID NO 23
<211> LENGTH: 948
<212> TYPE: DNA
<213> ORGANISM: Homo sapiens

<400> SEQUENCE: 23

```
atgtcaagca tttgggagac actgtttata agaattcttg tagtgtaatt cataatgggg     60

actgtgggaa attgattcat tgtattggtt aatatcattg actgaatcag gaactgaaag    120

gtctccctga ttgattttat tctcaactgc ttggccatct ccaggatatg tttcctgtag    180

ataacaattt tagctacctc tttcaatata ggctatgaga aaatgcctga ttctaagaat    240

cttgcagtaa gttttgacat tctctggaca ggatccagct atttctgcct gtcctgtacc    300

acttgcctca gtgtcttcta tttcctcaag gtagccaact tctccaatcc cattttcctc    360

tggatgaaat ggaaaattca caaggtgctt ctctttattg tactagaggc aacgatctct    420

ttctgcacaa cttccattct gaaggaaata ataattaata gtttaatcta agaacgggta    480

acaataaaag gcaacttgac atttaattat atggatacca tgcatgattt cacttctctg    540

tttctccttc agatgatgtt catccttcct tttgtggaaa cactggcttc cattcttctc    600

ttaatcctct ccttatggag ccacaccagg cagatgaagc tacatggtat ttattccagg    660

gatcccagca cagaagccca tgtaaaacct ataaaagcta taatttcatt tctactcctc    720
```

-continued

```
tttattgtgc attatttcat cagtatcata ctaacattgg cctgtcctct tctagacttc    780

gttgcggcaa ggacttttag tagtgtgctg gtatttttcc atccatctgg ccattcattt    840

cttctaattt tacgggacag caaactgaag caagcttctc tctgtgtcct gaagaagatg    900

aagtatgcca aaaaggacat aatctctcat ttttataaac atgcctga                 948
```

<210> SEQ ID NO 24
<211> LENGTH: 303
<212> TYPE: PRT
<213> ORGANISM: Homo sapiens

<400> SEQUENCE: 24

```
Met Glu Ser Ala Leu Pro Ser Ile Phe Thr Leu Val Ile Ile Ala Glu
1               5                   10                  15

Phe Ile Ile Gly Asn Leu Ser Asn Gly Phe Ile Val Leu Ile Asn Cys
            20                  25                  30

Ile Asp Trp Val Ser Lys Arg Glu Leu Ser Ser Val Asp Lys Leu Leu
        35                  40                  45

Ile Ile Leu Ala Ile Ser Arg Ile Gly Leu Ile Trp Glu Ile Leu Val
    50                  55                  60

Ser Trp Phe Leu Ala Leu His Tyr Leu Ala Ile Phe Val Ser Gly Thr
65                  70                  75                  80

Gly Leu Arg Ile Met Ile Phe Ser Trp Ile Val Ser Asn His Phe Asn
                85                  90                  95

Leu Trp Leu Ala Thr Ile Phe Ser Ile Phe Tyr Leu Leu Lys Ile Ala
            100                 105                 110

Ser Phe Ser Ser Pro Ala Phe Leu Tyr Leu Lys Trp Arg Val Asn Lys
        115                 120                 125

Val Ile Leu Met Ile Leu Leu Gly Thr Leu Val Phe Leu Phe Leu Asn
    130                 135                 140

Leu Ile Gln Ile Asn Met His Ile Lys Asp Trp Leu Asp Arg Tyr Glu
145                 150                 155                 160

Arg Asn Thr Thr Trp Asn Phe Ser Met Ser Asp Phe Glu Thr Phe Ser
                165                 170                 175

Val Ser Val Lys Phe Thr Met Thr Met Phe Ser Leu Thr Pro Phe Thr
            180                 185                 190

Val Ala Phe Ile Ser Phe Leu Leu Leu Ile Phe Ser Leu Gln Lys His
        195                 200                 205

Leu Gln Lys Met Gln Leu Asn Tyr Lys Gly His Arg Asp Pro Arg Thr
    210                 215                 220

Lys Val His Thr Asn Ala Leu Lys Ile Val Ile Ser Phe Leu Leu Phe
225                 230                 235                 240

Tyr Ala Ser Phe Phe Leu Cys Val Leu Ile Ser Trp Ile Ser Glu Leu
                245                 250                 255

Tyr Gln Asn Thr Val Ile Tyr Met Leu Cys Glu Thr Ile Gly Val Phe
            260                 265                 270

Ser Pro Ser Ser His Ser Phe Leu Leu Ile Leu Gly Asn Ala Lys Leu
        275                 280                 285

Arg Gln Ala Phe Leu Leu Val Ala Ala Lys Val Trp Ala Lys Arg
    290                 295                 300
```

<210> SEQ ID NO 25
<211> LENGTH: 912
<212> TYPE: DNA
<213> ORGANISM: Homo sapiens -continued

<400> SEQUENCE: 25

```
atggaaagtg ccctgccgag tatcttcact cttgtaataa ttgcagaatt cataattggg      60
aatttgagca atggatttat agtactgatc aactgcattg actgggtcag taaaagagag     120
ctgtcctcag tcgataaact cctcattatc ttggcaatct ccagaattgg gctgatctgg     180
gaaatattag taagttggtt tttagctctg cattatctag ccatatttgt gtctggaaca     240
ggattaagaa ttatgatttt tagctggata gtttctaatc acttcaatct ctggcttgct     300
acaatcttca gcatctttta tttgctcaaa atagcgagtt tctctagccc tgcttttctc     360
tatttgaagt ggagagtaaa caaagtgatt ctgatgatac tgctaggaac cttggtcttc     420
ttatttttaa atctgataca aataaacatg catataaaag actggctgga ccgatatgaa     480
agaaacacaa cttggaattt cagtatgagt gactttgaaa cattttcagt gtcggtcaaa     540
ttcactatga ctatgttcag tctaacacca tttactgtgg ccttcatctc ttttctcctg     600
ttaattttct ccctgcagaa acatctccag aaaatgcaac tcaattacaa aggacacaga     660
gaccccagga ccaaggtcca tacaaatgcc ttgaaaattg tgatctcatt ccttttattc     720
tatgctagtt tctttctatg tgttctcata tcatggattt ctgagctgta tcagaacaca     780
gtgatctaca tgctttgtga gacgattgga gtcttctctc cttcaagcca ctcctttctt     840
ctgattctag gaaacgctaa gttaagacag gcctttcttt tggtggcagc taaggtatgg     900
gctaaacgat ga                                                         912
```

<210> SEQ ID NO 26
<211> LENGTH: 317
<212> TYPE: PRT
<213> ORGANISM: Homo sapiens

<400> SEQUENCE: 26

```
Met Gly Gly Val Ile Lys Ser Ile Phe Thr Phe Val Leu Ile Val Glu
1               5                   10                  15

Phe Ile Ile Gly Asn Leu Gly Asn Ser Phe Ile Ala Leu Val Asn Cys
            20                  25                  30

Ile Asp Trp Val Lys Gly Arg Lys Ile Ser Ser Val Asp Arg Ile Leu
        35                  40                  45

Thr Ala Leu Ala Ile Ser Arg Ile Ser Leu Val Trp Leu Ile Phe Gly
    50                  55                  60

Ser Trp Cys Val Ser Val Phe Phe Pro Ala Leu Phe Ala Thr Glu Lys
65                  70                  75                  80

Met Phe Arg Met Leu Thr Asn Ile Trp Thr Val Ile Asn His Phe Ser
                85                  90                  95

Val Trp Leu Ala Thr Gly Leu Gly Thr Phe Tyr Phe Leu Lys Ile Ala
            100                 105                 110

Asn Phe Ser Asn Ser Ile Phe Leu Tyr Leu Lys Trp Arg Val Lys Lys
        115                 120                 125

Val Val Leu Val Leu Leu Leu Val Thr Ser Val Phe Leu Phe Leu Asn
    130                 135                 140

Ile Ala Leu Ile Asn Ile His Ile Asn Ala Ser Ile Asn Gly Tyr Arg
145                 150                 155                 160

Arg Asn Lys Thr Cys Ser Ser Asp Ser Ser Asn Phe Thr Arg Phe Ser
                165                 170                 175

Ser Leu Ile Val Leu Thr Ser Thr Val Phe Ile Phe Ile Pro Phe Thr
            180                 185                 190
```

-continued

```
Leu Ser Leu Ala Met Phe Leu Leu Leu Ile Phe Ser Met Trp Lys His
        195                 200                 205

Arg Lys Lys Met Gln His Thr Val Lys Ile Ser Gly Asp Ala Ser Thr
    210                 215                 220

Lys Ala His Arg Gly Val Lys Ser Val Ile Thr Phe Phe Leu Leu Tyr
225                 230                 235                 240

Ala Ile Phe Ser Leu Ser Phe Phe Ile Ser Val Trp Thr Ser Glu Arg
                245                 250                 255

Leu Glu Glu Asn Leu Ile Ile Leu Ser Gln Val Met Gly Met Ala Tyr
            260                 265                 270

Pro Ser Cys His Ser Cys Val Leu Ile Leu Gly Asn Lys Lys Leu Arg
        275                 280                 285

Gln Ala Ser Leu Ser Val Leu Leu Trp Leu Arg Tyr Met Phe Lys Asp
    290                 295                 300

Gly Glu Pro Ser Gly His Lys Glu Phe Arg Glu Ser Ser
305                 310                 315
```

<210> SEQ ID NO 27
<211> LENGTH: 954
<212> TYPE: DNA
<213> ORGANISM: Homo sapiens

<400> SEQUENCE: 27

```
atgggtggtg tcataaagag catatttaca ttcgttttaa ttgtggaatt tataattgga     60

aatttaggaa atagtttcat agcactggtg aactgtattg actgggtcaa gggaagaaag    120

atctcttcgg ttgatcggat cctcactgct ttggcaatct ctcgaattag cctggtttgg    180

ttaatattcg gaagctggtg tgtgtctgtg tttttcccag ctttatttgc cactgaaaaa    240

atgttcagaa tgcttactaa tatctggaca gtgatcaatc attttagtgt ctggttagct    300

acaggcctcg gtacttttta ttttctcaag atagccaatt tttctaactc tatttttctc    360

tacctaaagt ggagggttaa aaaggtggtt ttggtgctgc ttcttgtgac ttcggtcttc    420

ttgtttttaa atattgcact gataaacatc catataaatg ccagtatcaa tggatacaga    480

agaaacaaga cttgcagttc tgattcaagt aactttacac gattttccag tcttattgta    540

ttaaccagca ctgtgttcat tttcataccc tttactttgt ccctggcaat gtttcttctc    600

ctcatcttct ccatgtggaa acatcgcaag aagatgcagc acactgtcaa aatatccgga    660

gacgccagca ccaaagccca cagaggagtt aaaagtgtga tcactttctt cctactctat    720

gccattttct ctctgtcttt tttcatatca gtttggacct ctgaaaggtt ggaggaaaat    780

ctaattattc tttcccaggt gatgggaatg gcttatcctt catgtcactc atgtgttctg    840

attcttggaa acaagaagct gagacaggcc tctctgtcag tgctactgtg gctgaggtac    900

atgttcaaag atggggagcc ctcaggtcac aaagaattta gagaatcatc ttga          954
```

<210> SEQ ID NO 28
<211> LENGTH: 299
<212> TYPE: PRT
<213> ORGANISM: Homo sapiens

<400> SEQUENCE: 28

```
Met Ile Thr Phe Leu Pro Ile Ile Phe Ser Ile Leu Val Val Val Thr
1               5                   10                  15

Phe Val Leu Gly Asn Phe Ala Asn Gly Phe Ile Val Leu Val Asn Ser
            20                  25                  30

Ile Glu Trp Val Lys Arg Gln Lys Ile Ser Phe Ala Asp Gln Ile Leu
```

-continued

```
        35                  40                  45

Thr Ala Leu Ala Val Ser Arg Val Gly Leu Leu Trp Val Ile Leu Leu
    50                  55                  60

His Trp Tyr Ala Thr Val Leu Asn Pro Gly Ser Tyr Ser Leu Gly Val
65                  70                  75                  80

Arg Ile Thr Thr Ile Asn Ala Trp Ala Val Thr Asn His Phe Ser Ile
                85                  90                  95

Trp Val Ala Thr Ser Leu Ser Ile Phe Tyr Phe Leu Lys Ile Ala Asn
            100                 105                 110

Phe Ser Asn Phe Ile Phe Leu His Leu Lys Arg Arg Ile Lys Ser Val
        115                 120                 125

Ile Pro Val Ile Leu Leu Gly Ser Leu Leu Phe Leu Val Cys His Leu
    130                 135                 140

Val Val Val Asn Met Asp Glu Ser Met Trp Thr Lys Glu Tyr Glu Gly
145                 150                 155                 160

Asn Val Ser Trp Glu Ile Lys Leu Ser Asp Pro Thr His Leu Ser Asp
                165                 170                 175

Met Thr Val Thr Thr Leu Ala Asn Leu Ile Pro Phe Thr Leu Ser Leu
            180                 185                 190

Leu Ser Phe Leu Leu Leu Ile Cys Ser Leu Cys Lys His Leu Lys Lys
        195                 200                 205

Met Gln Phe His Gly Lys Gly Ser Pro Asp Ser Asn Thr Lys Val His
    210                 215                 220

Ile Lys Ala Leu Gln Thr Val Thr Ser Phe Leu Leu Leu Phe Ala Val
225                 230                 235                 240

Tyr Phe Leu Ser Leu Ile Thr Ser Ile Trp Asn Phe Arg Arg Arg Leu
                245                 250                 255

Asn Glu Pro Val Leu Met Leu Ser Gln Thr Thr Ala Ile Ile Tyr Pro
            260                 265                 270

Ser Phe His Ser Phe Ile Leu Ile Trp Gly Ser Lys Lys Leu Lys Gln
        275                 280                 285

Thr Phe Leu Leu Ile Leu Cys Gln Ile Lys Cys
    290                 295

<210> SEQ ID NO 29
<211> LENGTH: 903
<212> TYPE: DNA
<213> ORGANISM: Homo sapiens

<400> SEQUENCE: 29

atgataactt ttctacccat catttttttcc attctagtag tggttacatt tgttcttggg     60

aattttgcta atggcttcat agtgttggta aattccattg agtgggtcaa gagacaaaag    120

atctcctttg ctgaccaaat tctcactgct ctggcagtct ccagagttgg tttgctctgg    180

gtaatattat tacattggta tgcaactgtt ttgaatccag gttcatatag tttaggagta    240

agaattacta ctattaatgc ctgggctgta accaaccatt tcagcatctg ggttgctact    300

agcctcagca tattttattt cctcaagatt gccaatttct ccaactttat ttttcttcac    360

ttaaaaagga gaattaagag tgtcattcca gtgatactat tggggtcttt gttatttttg    420

gtttgtcatc ttgttgtggt aaacatggat gagagtatgt ggacaaaaga atatgaagga    480

aacgtgagtt gggagatcaa attgagtgat ccgacgcacc tttcagatat gactgtaacc    540

acgcttgcaa acttaatacc ctttactctg tccctgttat cttttctgct cttaatctgt    600

tctttgtgta aacatctcaa gaagatgcag ttccatggca aaggatctcc agattccaac    660
```

-continued

```
accaaggtcc acataaaagc tttgcaaacg gtgacctcct tcctcttgtt atttgctgtt    720

tactttctgt ccctaatcac atcgatttgg aattttagga ggaggctgta gaacgaacct    780

gtcctcatgc tcagccaaac tactgcaatt atataccctt catttcattc attcatccta    840

atttggggaa gcaagaagct gaaacagacc tttcttttga ttttgtgtca gattaagtgc    900

tga                                                                   903


<210> SEQ ID NO 30
<211> LENGTH: 291
<212> TYPE: PRT
<213> ORGANISM: Homo sapiens

<400> SEQUENCE: 30

Met Ile Pro Ile Gln Leu Thr Val Phe Phe Met Ile Ile Tyr Val Leu
1               5                   10                  15

Glu Ser Leu Thr Ile Ile Val Gln Ser Ser Leu Ile Val Ala Val Leu
            20                  25                  30

Gly Arg Glu Trp Leu Gln Val Arg Arg Leu Met Pro Val Asp Met Ile
        35                  40                  45

Leu Ile Ser Leu Gly Ile Ser Arg Phe Cys Leu Gln Trp Ala Ser Met
    50                  55                  60

Leu Asn Asn Phe Cys Ser Tyr Phe Asn Leu Asn Tyr Val Leu Cys Asn
65                  70                  75                  80

Leu Thr Ile Thr Trp Glu Phe Phe Asn Ile Leu Thr Phe Trp Leu Asn
                85                  90                  95

Ser Leu Leu Thr Val Phe Tyr Cys Ile Lys Val Ser Ser Phe Thr His
            100                 105                 110

His Ile Phe Leu Trp Leu Arg Trp Arg Ile Leu Arg Leu Phe Pro Trp
        115                 120                 125

Ile Leu Leu Gly Ser Leu Met Ile Thr Cys Val Thr Ile Ile Pro Ser
    130                 135                 140

Ala Ile Gly Asn Tyr Ile Gln Ile Gln Leu Leu Thr Met Glu His Leu
145                 150                 155                 160

Pro Arg Asn Ser Thr Val Thr Asp Lys Leu Glu Asn Phe His Gln Tyr
                165                 170                 175

Gln Phe Gln Ala His Thr Val Ala Leu Val Ile Pro Phe Ile Leu Phe
            180                 185                 190

Leu Ala Ser Thr Ile Phe Leu Met Ala Ser Leu Thr Lys Gln Ile Gln
        195                 200                 205

His His Ser Thr Gly His Cys Asn Pro Ser Met Lys Ala Arg Phe Thr
    210                 215                 220

Ala Leu Arg Ser Leu Ala Val Leu Phe Ile Val Phe Thr Ser Tyr Phe
225                 230                 235                 240

Leu Thr Ile Leu Ile Thr Ile Ile Gly Thr Leu Phe Asp Lys Arg Cys
                245                 250                 255

Trp Leu Trp Val Trp Glu Ala Phe Val Tyr Ala Phe Ile Leu Met His
            260                 265                 270

Ser Thr Ser Leu Met Leu Ser Ser Pro Thr Leu Lys Arg Ile Leu Lys
        275                 280                 285

Gly Lys Cys
    290


<210> SEQ ID NO 31
<211> LENGTH: 876
```

-continued

```
<212> TYPE: DNA
<213> ORGANISM: Homo sapiens

<400> SEQUENCE: 31

atgataccca tccaactcac tgtcttcttc atgatcatct atgtgcttga gtccttgaca     60

attattgtgc agagcagcct aattgttgca gtgctgggca gagaatggct gcaagtcaga    120

aggctgatgc ctgtggacat gattctcatc agcctgggca tctctcgctt ctgtctacag    180

tgggcatcaa tgctgaacaa tttttgctcc tattttaatt tgaattatgt actttgcaac    240

ttaacaatca cctgggaatt ttttaatatc cttacattct ggttaaacag cttgcttacc    300

gtgttctact gcatcaaggt ctcttctttc acccatcaca tctttctctg gctgaggtgg    360

agaattttga ggttgtttcc ctggatatta ctgggttctc tgatgattac ttgtgtaaca    420

atcatccctt cagctattgg gaattacatt caaattcagt tactcaccat ggagcatcta    480

ccaagaaaca gcactgtaac tgacaaactt gaaaattttc atcagtatca gttccaggct    540

catacagttg cattggttat tcctttcatc ctgttcctgg cctccaccat ctttctcatg    600

gcatcactga ccaagcagat acaacatcat agcactggtc actgcaatcc aagcatgaaa    660

gcgcgcttca ctgccctgag gtcccttgcc gtcttattta ttgtgtttac ctcttacttt    720

ctaaccatac tcatcaccat tataggtact ctatttgata agagatgttg gttatgggtc    780

tgggaagctt ttgtctatgc tttcatctta atgcattcca cttcactgat gctgagcagc    840

cctacgttga aaaggattct aaagggaaag tgctag                              876


<210> SEQ ID NO 32
<211> LENGTH: 330
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (61)..(61)
<223> OTHER INFORMATION: Variable amino acid
<220> FEATURE:
<221> NAME/KEY: MOD_RES
<222> LOCATION: (207)..(207)
<223> OTHER INFORMATION: Variable amino acid

<400> SEQUENCE: 32

Met Cys Ser Ala Xaa Leu Leu Ile Ile Leu Ser Ile Leu Val Val Phe
1               5                   10                  15

Ala Phe Val Leu Gly Asn Val Ala Asn Gly Phe Ile Ala Leu Ile Asn
            20                  25                  30

Val Asn Asp Trp Val Lys Thr Gln Lys Ile Ser Ser Thr Asp Gln Ile
        35                  40                  45

Val Thr Ala Leu Ala Phe Ser Arg Ile Gly Leu Leu Xaa Thr Leu Ile
    50                  55                  60

Ile Leu Leu His Trp Tyr Ala Thr Val Phe Asn Ser Ala Leu Tyr Ser
65                  70                  75                  80

Leu Glu Val Arg Ile Val Pro Ser Asn Val Ser Ala Ile Ile Asn His
                85                  90                  95

Phe Ser Ile Trp Leu Ala Thr Ser Leu Ser Ile Phe Tyr Leu Phe Lys
            100                 105                 110

Ile Ala Asn Phe Ser Asn Phe Ile Phe Leu His Leu Lys Lys Arg Ile
        115                 120                 125
```

-continued

```
Lys Ser Val Leu Leu Val Ile Leu Leu Gly Ser Leu Val Phe Leu Ile
    130                 135                 140

Cys Asn Leu Ala Val Val Thr Met Asp Asp Ser Val Trp Thr Lys Glu
145                 150                 155                 160

Phe Glu Gly Asn Val Thr Trp Lys Ile Glu Leu Arg Asn Ala Ile His
                165                 170                 175

Leu Ser Asn Met Thr Ile Thr Asn His Ala Ser Lys Leu His Thr Val
            180                 185                 190

His Ser Asp Ser Asn Ile Phe Ser Ala Val Ser Leu Phe Ser Xaa Thr
        195                 200                 205

Met Leu Ala Asn Phe Thr Leu Phe Ile Leu Thr Leu Ile Ser Phe Leu
    210                 215                 220

Leu Leu Val Cys Ser Pro Cys Lys His Leu Lys Met Met Gln Leu His
225                 230                 235                 240

Gly Lys Gly Ser Gln Asp Leu Ser Thr Lys Val His Ile Lys Pro Leu
                245                 250                 255

Gln Thr Val Ile Ser Phe Arg Met Leu Phe Ala Ile Tyr Phe Leu Cys
            260                 265                 270

Ile Ile Thr Ser Thr Trp Asn Pro Arg Thr Gln Gln Ser Asn Leu Val
        275                 280                 285

Phe Leu Leu Tyr Gln Thr Leu Ala Ile Met Tyr Pro Ser Phe His Ser
    290                 295                 300

Phe Ile Leu Ile Met Arg Ser Arg Lys Leu Lys Gln Thr Ser Leu Ser
305                 310                 315                 320

Val Leu Cys Gln Val Thr Cys Trp Val Lys
                325                 330


<210> SEQ ID NO 33
<211> LENGTH: 313
<212> TYPE: PRT
<213> ORGANISM: Homo sapiens

<400> SEQUENCE: 33

Met Phe Val Gly Ile Asn Ile Phe Phe Leu Val Val Ala Thr Arg Gly
1               5                   10                  15

Leu Val Leu Gly Met Leu Gly Asn Gly Leu Ile Gly Leu Val Asn Cys
            20                  25                  30

Ile Glu Trp Ala Lys Ser Trp Lys Val Ser Ser Ala Asp Phe Ile Leu
        35                  40                  45

Thr Ser Leu Ala Ile Val Arg Ile Ile Arg Leu Tyr Leu Ile Leu Phe
    50                  55                  60

Asp Ser Phe Ile Met Val Leu Ser Pro His Leu Tyr Thr Ile Arg Lys
65                  70                  75                  80

Leu Val Lys Leu Phe Thr Ile Leu Trp Ala Leu Ile Asn Gln Leu Ser
                85                  90                  95

Ile Phe Ala Thr Cys Leu Ser Ile Phe Tyr Leu Leu Lys Ile Ala Asn
            100                 105                 110

Phe Ser His Ser Leu Phe Leu Trp Leu Lys Trp Arg Met Asn Gly Met
        115                 120                 125

Ile Val Met Leu Leu Ile Leu Ser Leu Phe Leu Leu Ile Phe Asp Ser
    130                 135                 140

Leu Val Leu Glu Ile Phe Ile Asp Ile Ser Leu Asn Ile Ile Asp Lys
145                 150                 155                 160

Ser Asn Leu Thr Leu Tyr Leu Asp Glu Ser Lys Thr Leu Tyr Asp Lys
                165                 170                 175
```

-continued

```
Leu Ser Ile Leu Lys Thr Leu Leu Ser Leu Thr Tyr Val Ile Pro Phe
            180                 185                 190

Leu Leu Thr Leu Thr Ser Leu Leu Leu Leu Phe Ile Ser Leu Val Arg
        195                 200                 205

His Thr Lys Asn Leu Gln Leu Asn Ser Leu Gly Ser Arg Asp Ser Ser
    210                 215                 220

Thr Glu Ala His Lys Arg Ala Met Lys Met Val Ile Ala Phe Leu Leu
225                 230                 235                 240

Leu Phe Ile Ile Asn Phe Ile Ser Thr Leu Ile Gly Asp Trp Ile Phe
                245                 250                 255

Leu Glu Val Glu Asn Tyr Gln Val Met Met Phe Ile Met Met Ile Leu
            260                 265                 270

Leu Ala Phe Pro Ser Gly His Ser Phe Ile Ile Ile Leu Gly Asn Asn
        275                 280                 285

Lys Leu Arg Gln Ser Ser Leu Arg Leu Leu Trp His Leu Lys Phe Ser
    290                 295                 300

Leu Lys Lys Ala Lys Pro Leu Thr Ser
305                 310
```

<210> SEQ ID NO 34
<211> LENGTH: 945
<212> TYPE: DNA
<213> ORGANISM: Homo sapiens

<400> SEQUENCE: 34

```
atgttcgttg gaattaatat ttctttctg gtggtggcaa caagaggact tgtcttagga     60

atgctgggaa acgggctcat tggactggta aactgcattg agtgggccaa gagttggaag    120

gtctcatcag ctgatttcat cctcaccagc ttggctatag tcagaatcat tcgactgtat    180

ttaatactat ttgattcatt tataatggta ttgtcccctc atctatatac catccgtaaa    240

ctagtaaaac tgtttactat tctttgggca ttaattaatc agttaagtat ctagtttgcc    300

acctgcctaa gcattttcta cttgcttaag atagccaatt tctcccactc ccttttcctc    360

tggctgaagt ggagaatgaa cggaatgatt gttatgcttc ttatattgtc tttgttctta    420

ctgatttttg acagtttagt gctagaaata tttattgata tctcactcaa tataatagat    480

aaaagtaatc tgactttata tttagatgaa agtaaaactc tctatgataa actctctatt    540

ttaaaaactc ttctcagctt gacatacgtt attccctttc ttctgactct gacctctttg    600

ctccttttat ttatatcctt agtgagacac accaagaatt tgcagctcaa ctctctgggc    660

tcaagggact ccagcacaga ggcccataaa agggccatga aaatggtgat agccttcctc    720

ctcctttta ttattaactt tatttccact ttaataggag attggatctt ccttgaggta    780

gagaattatc aggtcatgat gtttattatg atgattttac ttgcctttcc ctcaggccac    840

tcatttatta taattttggg aaacaacaag ctaagacaga gctccttgag actactgtgg    900

catcttaaat tctctctgaa aaaagcaaaa cctttaactt catag                    945
```

<210> SEQ ID NO 35
<211> LENGTH: 121
<212> TYPE: PRT
<213> ORGANISM: Homo sapiens

<400> SEQUENCE: 35

```
Val Thr Thr Leu Ala Asn Leu Ile Pro Phe Thr Leu Ser Leu Ile Cys
1               5                   10                  15
```

-continued

```
Phe Leu Leu Leu Ile Cys Ser Leu Cys Lys His Leu Lys Lys Met Arg
            20                  25                  30

Leu His Ser Lys Gly Ser Gln Asp Pro Ser Thr Lys Val His Ile Lys
        35                  40                  45

Ala Leu Gln Thr Val Thr Ser Phe Leu Met Leu Phe Ala Ile Tyr Phe
    50                  55                  60

Leu Cys Ile Ile Thr Ser Thr Trp Asn Leu Arg Thr Gln Gln Ser Lys
65                  70                  75                  80

Leu Val Leu Leu Leu Cys Gln Thr Val Ala Ile Met Tyr Pro Ser Phe
                85                  90                  95

His Ser Phe Ile Leu Ile Met Gly Ser Arg Lys Leu Lys Gln Thr Phe
            100                 105                 110

Leu Ser Val Leu Trp Gln Met Thr Cys
        115                 120
```

<210> SEQ ID NO 36
<211> LENGTH: 466
<212> TYPE: DNA
<213> ORGANISM: Homo sapiens

<400> SEQUENCE: 36

```
ctgtaactac tctagcaaac ctcataccct ttactctgag cctaatatgt tttctgctgt     60

taatctgttc tctttgtaaa catctcaaga agatgcggct ccatagcaaa ggatctcaag    120

atcccagcac caaggtccat ataaaagctt tgcaaactgt gacctccttc ctcatgttat    180

ttgccattta ctttctgtgt ataatcacat caacttggaa tcttaggaca cagcagagca    240

aacttgtact cctgctttgc caaactgttg caatcatgta tccttcattc cactcattca    300

tcctgattat gggaagtagg aagctaaaac agacctttct ttcagttttg tggcagatga    360

catgctgagt gaaagaagag aaaccctcaa ctccatagat tcacaagggg agcatcgtgg    420

gtcttctagc agaaaacaaa ctgatggtgt ctggaacatt ttatat                   466
```

<210> SEQ ID NO 37
<211> LENGTH: 129
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Variable amino acid

<400> SEQUENCE: 37

```
His Leu Xaa Arg Lys Ala Lys Ser Val Val Leu Val Ile Val Leu Gly
1               5                   10                  15

Ser Leu Phe Phe Leu Val Cys Gln Leu Val Met Lys Asn Thr Tyr Ile
            20                  25                  30

Asn Val Trp Thr Glu Glu Cys Glu Gly Asn Val Thr Trp Lys Ile Lys
        35                  40                  45

Leu Arg Asn Ala Met His Leu Ser Asn Leu Thr Val Ala Met Leu Ala
    50                  55                  60

Asn Leu Ile Pro Phe Thr Leu Thr Val Ile Ser Phe Leu Leu Leu Ile
65                  70                  75                  80

Tyr Ser Leu Cys Lys His Leu Lys Lys Met Gln Leu His Gly Lys Gly
                85                  90                  95

Ser Gln Asp Pro Ser Thr Lys Ile His Ile Lys Ala Leu Gln Thr Val
            100                 105                 110

Thr Ser Phe Leu Val Leu Leu Ala Ile Tyr Phe Leu Cys Leu Ile Ile
```

-continued

```
        115                 120                 125

Ser


<210> SEQ ID NO 38
<211> LENGTH: 397
<212> TYPE: DNA
<213> ORGANISM: Homo sapiens
<220> FEATURE:
<221> NAME/KEY: modified_base
<222> LOCATION: (12)..(12)
<223> OTHER INFORMATION: n is a, c, g, or t

<400> SEQUENCE: 38

ttcatcactt anaaaggaag gctaagagtg tagttctggt gatagtgttg gggtctttgt      60

tctttttggt ttgtcaactt gtgatgaaaa acacgtatat aaatgtgtgg acagaagaat     120

gtgaaggaaa cgtaacttgg aagatcaaac tgaggaatgc aatgcacctt tccaacttga     180

ctgtagccat gctagcaaac ttgataccat tcactctgac cgtgatatct tttctgctgt     240

taatctactc tctgtgtaaa catctgaaga agatgcagct ccatggcaaa ggatctcaag     300

atcccagcac caagatccac ataaaagctc tgcaaactgt gacctccttc ctcgtattac     360

ttgccattta ctttctgtgt ctaatcatat ccttttg                              397


<210> SEQ ID NO 39
<211> LENGTH: 299
<212> TYPE: PRT
<213> ORGANISM: Homo sapiens

<400> SEQUENCE: 39

Met Pro Pro Gly Ile Gly Asn Thr Phe Leu Ile Val Met Met Gly Glu
1               5                   10                  15

Phe Ile Ile Met Leu Gly Asn Gly Phe Ile Val Leu Val Asn Cys Ile
            20                  25                  30

Asp Trp Gly Val Lys Ser Tyr Thr Thr Ala Ser Ser Pro Ala Trp Leu
        35                  40                  45

Ser Pro Gln Ser Val Asn Phe Gly Tyr Tyr Leu Ile His Leu Gln His
    50                  55                  60

Tyr Gly His Ile Tyr Met Pro Ser Ile Asn Asn Leu Phe Ile Phe Phe
65                  70                  75                  80

Gly His Pro Ile Thr Leu Pro Gly Leu Leu Pro Cys Phe Leu Leu Leu
                85                  90                  95

Asn Thr Tyr Phe Ser His Pro Cys Phe Ile Trp Leu Arg Trp Arg Ile
            100                 105                 110

Ser Arg Thr Leu Leu Glu Leu Pro Leu Gly Ser Leu Leu Leu Leu Phe
        115                 120                 125

Phe Asn Leu Ala Leu Thr Gly Gly Leu Ser Asp Leu Trp Ile Asn Ile
    130                 135                 140

Tyr Thr Ile Tyr Glu Arg Asn Ser Thr Trp Ser Leu Asp Val Ser Lys
145                 150                 155                 160

Ile Leu Tyr Cys Ser Leu Trp Ile Leu Val Ser Leu Ile Tyr Leu Ile
                165                 170                 175

Ser Phe Leu Leu Ser Leu Ile Ser Leu Leu Leu Leu Ile Leu Ser Leu
            180                 185                 190

Met Arg His Ile Arg Asn Leu Gln Leu Asn Thr Met Gly Pro Arg Asp
        195                 200                 205

Leu Arg Met Lys Ala His Lys Arg Ala Met Lys Met Lys Met Lys Met
    210                 215                 220
```

-continued

```
Met Val Ser Phe Leu Leu Phe Phe Leu Val His Phe Ser Ser Leu Leu
225                 230                 235                 240

Pro Thr Gly Trp Ile Phe Leu Ile Gln Gln Lys Gln Ala Asn Phe Phe
                245                 250                 255

Val Leu Leu Thr Ser Ile Ile Phe Pro Ser Ser His Ser Phe Val Leu
            260                 265                 270

Ile Leu Glu Asn Cys Lys Leu Arg Gln Thr Ala Val Gly Pro Leu Trp
        275                 280                 285

His Leu Lys Cys His Leu Lys Arg Val Lys Leu
    290                 295


<210> SEQ ID NO 40
<211> LENGTH: 90
<212> TYPE: PRT
<213> ORGANISM: Homo sapiens
<220> FEATURE:
<221> NAME/KEY: MOD_RES
<222> LOCATION: (35)..(35)
<223> OTHER INFORMATION: Variable amino acid
<220> FEATURE:
<221> NAME/KEY: MOD_RES
<222> LOCATION: (39)..(39)
<223> OTHER INFORMATION: Variable amino acid
<220> FEATURE:
<221> NAME/KEY: MOD_RES
<222> LOCATION: (82)..(82)
<223> OTHER INFORMATION: Variable amino acid

<400> SEQUENCE: 40

Met Ala Thr Glu Ser Asp Thr Asn Leu Leu Ile Leu Ala Ile Ala Glu
1               5                   10                  15

Phe Ile Ile Ser Met Leu Gly Asn Val Phe Ile Gly Leu Val Asn Cys
            20                  25                  30

Ser Glu Xaa Ile Lys Asn Xaa Lys Val Phe Ser Ala Asp Phe Ile Leu
        35                  40                  45

Thr Cys Leu Ala Ile Ser His Asn Gly Gln Leu Leu Val Ile Leu Phe
    50                  55                  60

Asp Ser Phe Leu Val Gly Leu Ala Ser His Leu Tyr Thr Thr Tyr Arg
65                  70                  75                  80

Leu Xaa Lys Asn Cys Ile Met Leu Trp Thr
                85                  90


<210> SEQ ID NO 41
<211> LENGTH: 656
<212> TYPE: DNA
<213> ORGANISM: Homo sapiens
<220> FEATURE:
<221> NAME/KEY: modified_base
<222> LOCATION: (10)..(10)
<223> OTHER INFORMATION: n is a, c, g, or t
<220> FEATURE:
<221> NAME/KEY: modified_base
<222> LOCATION: (68)..(68)
<223> OTHER INFORMATION: n is a, c, g, or t
<220> FEATURE:
<221> NAME/KEY: modified_base
<222> LOCATION: (82)..(82)
<223> OTHER INFORMATION: n is a, c, g, or t
<220> FEATURE:
<221> NAME/KEY: modified_base
<222> LOCATION: (112)..(112)
<223> OTHER INFORMATION: n is a, c, g, or t
<220> FEATURE:
<221> NAME/KEY: modified_base
<222> LOCATION: (125)..(125)
<223> OTHER INFORMATION: n is a, c, g, or t
```

-continued

<220> FEATURE:
<221> NAME/KEY: modified_base
<222> LOCATION: (187)..(187)
<223> OTHER INFORMATION: n is a, c, g, or t
<220> FEATURE:
<221> NAME/KEY: modified_base
<222> LOCATION: (242)..(242)
<223> OTHER INFORMATION: n is a, c, g, or t
<220> FEATURE:
<221> NAME/KEY: modified_base
<222> LOCATION: (260)..(260)
<223> OTHER INFORMATION: n is a, c, g, or t
<220> FEATURE:
<221> NAME/KEY: modified_base
<222> LOCATION: (282)..(282)
<223> OTHER INFORMATION: n is a, c, g, or t
<220> FEATURE:
<221> NAME/KEY: modified_base
<222> LOCATION: (397)..(397)
<223> OTHER INFORMATION: n is a, c, g, or t
<220> FEATURE:
<221> NAME/KEY: modified_base
<222> LOCATION: (411)..(411)
<223> OTHER INFORMATION: n is a, c, g, or t
<220> FEATURE:
<221> NAME/KEY: modified_base
<222> LOCATION: (538)..(538)
<223> OTHER INFORMATION: n is a, c, g, or t
<220> FEATURE:
<221> NAME/KEY: modified_base
<222> LOCATION: (629)..(629)
<223> OTHER INFORMATION: n is a, c, g, or t

<400> SEQUENCE: 41
tatagggacn gtgatgcttc gtacactctc caagaagaaa cactccgtga ggtatgtgag 60
actgcatncc ttagtagatc tnttgggata tatattcata atatagaaaa anaggcaaag 120
acttncttaa gtatatgaga ctctatccaa cagcagaagg ttctgatcaa gactggaagt 180
gcaatanaag caatgaagat aagtatcaga tatgaatgct cttctgcaat ggtctgattg 240
tnacattatt aatgatacan agtattaaaa acttggattt tnttgtctct ggagatggcc 300
accgaatcgg acacaaatct tctgattctg gcaatagcag aattcatcat cagcatgctg 360
gggaatgtgt tcattggact ggtaaactgc tctgaangga tcaagaacca naaggtcttc 420
tcagctgact tcatcctcac ctgcttggct atctctcaca atggacaact gttggtgata 480
ctgtttgatt catttctagt gggacttgct tcacatctat ataccacata tagactanga 540
aaaaactgta ttatgctttg gacatgacta atcacttgac acactgcttc gcacgtgcta 600
gcatattcta ttcttagata gccacttcnc actccttgtc tctgctgaag tgggat 656

<210> SEQ ID NO 42
<211> LENGTH: 70
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: Variable amino acid
<220> FEATURE:
<221> NAME/KEY: MOD_RES
<222> LOCATION: (44)..(44)
<223> OTHER INFORMATION: Variable amino acid
<220> FEATURE:
<221> NAME/KEY: MOD_RES
<222> LOCATION: (47)..(47)
<223> OTHER INFORMATION: Variable amino acid
<220> FEATURE:
<221> NAME/KEY: MOD_RES
<222> LOCATION: (62)..(62)
<223> OTHER INFORMATION: Variable amino acid -continued

<400> SEQUENCE: 42

```
Val Ala Phe Val Leu Gly Asn Val Ala Asn Gly Phe Ile Ala Leu Val
1               5                   10                  15

Asn Val Ile Asp Xaa Val Asn Thr Arg Lys Ile Ser Ser Ala Glu Gln
            20                  25                  30

Ile Leu Thr Ala Leu Val Val Ser Arg Ile Gly Xaa Thr Leu Xaa His
        35                  40                  45

Ser Ile Pro Asp Ala Thr Arg Cys Ser Ala Leu Tyr Arg Xaa Glu Val
    50                  55                  60

Arg Ile Val Ala Ser Asn
65                  70
```

<210> SEQ ID NO 43
<211> LENGTH: 589
<212> TYPE: DNA
<213> ORGANISM: Homo sapiens
<220> FEATURE:
<221> NAME/KEY: modified_base
<222> LOCATION: (39)..(39)
<223> OTHER INFORMATION: n is a, c, g, or t
<220> FEATURE:
<221> NAME/KEY: modified_base
<222> LOCATION: (42)..(42)
<223> OTHER INFORMATION: n is a, c, g, or t
<220> FEATURE:
<221> NAME/KEY: modified_base
<222> LOCATION: (321)..(321)
<223> OTHER INFORMATION: n is a, c, g, or t
<220> FEATURE:
<221> NAME/KEY: modified_base
<222> LOCATION: (375)..(375)
<223> OTHER INFORMATION: n is a, c, g, or t
<220> FEATURE:
<221> NAME/KEY: modified_base
<222> LOCATION: (414)..(414)
<223> OTHER INFORMATION: n is a, c, g, or t
<220> FEATURE:
<221> NAME/KEY: modified_base
<222> LOCATION: (481)..(482)
<223> OTHER INFORMATION: n is a, c, g, or t
<220> FEATURE:
<221> NAME/KEY: modified_base
<222> LOCATION: (490)..(490)
<223> OTHER INFORMATION: n is a, c, g, or t
<220> FEATURE:
<221> NAME/KEY: modified_base
<222> LOCATION: (541)..(541)
<223> OTHER INFORMATION: n is a, c, g, or t

<400> SEQUENCE: 43

```
agggttgagt cgtgcttatc ttcacttaac ctagtatana antacagcat atagcaagga     60

gagaatgtat atgaagagga gtgaatttga gtctgtttga gaataatgac cttttctatt    120

tctataaaga cagttttgaa ttcatctatt agcatatgct ggtgcttgcc tgttgacact    180

agtcactgaa tttaaaggca gaaaatgtta ttgcacattt agtaatcaag tgttcatcga    240

agttaacatc tggatgttaa aggactcaga acaagtgtta ctaagcctgc atttttttat    300

ctgttcaaac atgatgtgtt ntctgctcat catttcatca attctggtag agttgcattt    360

gttcttggaa atgtngccaa tggcttcata gctctagtaa atgtcattga ctgngttaac    420

acacgaaaga tctcctcagc tgagcaaatt ctcactgctc tggtggtctc cagaattggt    480

nntactctgn gtcatagtat tccttgagat gcaactagat gttaatctgc tctatatagg    540

ntagaagtaa gaattgttgc ttctaatgcc tgagctcgta cgaaccatt                589
```

<210> SEQ ID NO 44

-continued

<211> LENGTH: 314
<212> TYPE: PRT
<213> ORGANISM: Homo sapiens

<400> SEQUENCE: 44

```
Met Ala Thr Glu Leu Asp Lys Ile Phe Leu Ile Leu Ala Ile Ala Glu
1               5                   10                  15

Phe Ile Ile Ser Met Leu Gly Asn Val Phe Ile Gly Leu Val Asn Cys
            20                  25                  30

Ser Glu Gly Ile Lys Asn Gln Lys Val Phe Ser Ala Asp Phe Ile Leu
        35                  40                  45

Thr Cys Leu Ala Ile Ser Thr Ile Gly Gln Leu Leu Val Ile Leu Phe
    50                  55                  60

Asp Ser Phe Leu Val Gly Leu Ala Ser His Leu Tyr Thr Thr Tyr Arg
65                  70                  75                  80

Leu Gly Lys Thr Val Ile Met Leu Trp His Met Thr Asn His Leu Thr
                85                  90                  95

Thr Trp Leu Ala Thr Cys Leu Ser Ile Phe Tyr Phe Phe Lys Ile Ala
            100                 105                 110

His Phe Pro His Ser Leu Phe Leu Trp Leu Arg Trp Arg Met Asn Gly
        115                 120                 125

Met Ile Val Met Leu Leu Ile Leu Ser Leu Phe Leu Leu Ile Phe Asp
    130                 135                 140

Ser Leu Val Leu Glu Ile Phe Ile Asp Ile Ser Leu Asn Ile Ile Asp
145                 150                 155                 160

Lys Ser Asn Leu Thr Leu Tyr Leu Asp Glu Ser Lys Thr Leu Tyr Asp
                165                 170                 175

Lys Leu Ser Ile Leu Lys Thr Leu Leu Ser Leu Thr Ser Phe Ile Pro
            180                 185                 190

Phe Ser Leu Phe Leu Thr Ser Leu Leu Phe Leu Phe Leu Ser Leu Val
        195                 200                 205

Arg His Thr Arg Asn Leu Lys Leu Ser Ser Leu Gly Ser Arg Asp Ser
    210                 215                 220

Ser Thr Glu Ala His Arg Arg Ala Met Lys Met Val Met Ser Phe Leu
225                 230                 235                 240

Phe Leu Phe Ile Val His Phe Phe Ser Leu Gln Val Ala Asn Gly Ile
                245                 250                 255

Phe Phe Met Leu Trp Asn Asn Lys Tyr Ile Lys Phe Val Met Leu Ala
            260                 265                 270

Leu Asn Ala Phe Pro Ser Cys His Ser Phe Ile Leu Ile Leu Gly Asn
        275                 280                 285

Ser Lys Leu Arg Gln Thr Ala Val Arg Leu Leu Trp His Leu Arg Asn
    290                 295                 300

Tyr Thr Lys Thr Pro Asn Ala Leu Pro Leu
305                 310
```

<210> SEQ ID NO 45
<211> LENGTH: 945
<212> TYPE: DNA
<213> ORGANISM: Homo sapiens

<400> SEQUENCE: 45

```
atggccaccg aattggacaa aatctttctg attctggcaa tagcagaatt catcatcagc     60

atgctgggga atgtgttcat tggactggta aactgctctg aagggatcaa gaaccaaaag    120

gtcttctcag ctgacttcat cctcacctgc ttggctatct ccacaattgg acaactgttg    180
```

-continued

```
gtgatactgt ttgattcatt tctagtggga cttgcttcac atttatatac cacatataga    240

ctaggaaaaa ctgttattat gctttggcac atgactaatc acttgacaac ctggcttgcc    300

acctgcctaa gcattttcta tttctttaag atagcccact tcccccactc ccttttcctc    360

tggctgaggt ggaggatgaa cggaatgatt gttatgcttc ttatattgtc tttgttctta    420

ctgatttttg acagtttagt gctagaaata tttattgata tctcactcaa tataatagat    480

aaaagtaatc tgactttata tttagatgaa agtaaaactc tctatgataa actctctatt    540

ttaaaaactc ttctcagctt aaccagtttt atcccctttt ctctgttcct gacctccttg    600

cttttttat ttctgtcctt ggtgagacat actagaaatt tgaagctcag ttccttgggc    660

tctagagact ccagcacaga ggcccatagg agggccatga aaatggtgat gtctttcctt    720

ttcctcttca tagttcattt tttttcctta caagtggcca atgggatatt ttttatgttg    780

tggaacaaca agtacataaa gtttgtcatg ttagccttaa atgcctttcc ctcgtgccac    840

tcatttattc tcattctggg aaacagcaag ctgcgacaga cagctgtgag gctactgtgg    900

catcttagga actatacaaa aacaccaaat gctttacctt tgtag                   945
```

<210> SEQ ID NO 46
<211> LENGTH: 72
<212> TYPE: PRT
<213> ORGANISM: Homo sapiens

<400> SEQUENCE: 46

```
Leu Ser Pro Phe Arg Met Leu Phe Ala Ile Tyr Phe Leu Cys Ile Ile
1               5                   10                  15

Thr Ser Thr Trp Asn Pro Arg Thr Gln Gln Ser Asn Leu Val Phe Leu
            20                  25                  30

Leu Tyr Gln Thr Leu Ala Ile Met Tyr Pro Ser Phe His Ser Phe Ile
        35                  40                  45

Leu Ile Met Arg Ser Arg Lys Leu Lys Gln Thr Ser Leu Ser Val Leu
    50                  55                  60

Cys Gln Val Thr Cys Trp Val Lys
65                  70
```

<210> SEQ ID NO 47
<211> LENGTH: 263
<212> TYPE: PRT
<213> ORGANISM: Homo sapiens

<400> SEQUENCE: 47

```
Met Pro Pro Gly Ile Gly Asn Thr Phe Leu Ile Val Met Met Gly Glu
1               5                   10                  15

Phe Ile Ile Met Leu Gly Asn Gly Phe Ile Val Leu Val Asn Cys Ile
            20                  25                  30

Asp Val Arg Ser Gln Met Ile Leu Leu Asp Asn Cys Ile Leu Thr Ser
        35                  40                  45

Leu Ala Ile Ser Thr Ile Ser Gln Leu Trp Ile Ile Leu Leu Asp Ser
    50                  55                  60

Phe Val Thr Ala Leu Trp Pro His Leu Tyr Ala Phe Asn Lys Leu Ile
65                  70                  75                  80

Lys Phe Ile His Ile Phe Trp Ala Leu Thr Asn His Leu Val Thr Trp
                85                  90                  95

Leu Ala Cys Cys Leu Ser Val Phe Tyr Phe Phe Lys Ile Ala Tyr Phe
            100                 105                 110
```

-continued

```
Ser His Pro Cys Phe Ile Trp Leu Arg Trp Arg Ile Ser Arg Thr Leu
        115                 120                 125

Leu Glu Leu Pro Leu Gly Ser Leu Leu Leu Leu Phe Phe Asn Leu Ala
    130                 135                 140

Leu Thr Gly Gly Leu Ser Asp Leu Trp Ile Asn Ile Tyr Thr Met Tyr
145                 150                 155                 160

Glu Arg Asn Ser Thr Trp Ser Leu Asp Val Ser Lys Ile Leu Tyr Cys
                165                 170                 175

Ser Leu Trp Ile Leu Val Ser Leu Ile Tyr Leu Ile Ser Phe Leu Leu
            180                 185                 190

Ser Leu Ile Ser Leu Leu Leu Leu Ile Leu Ser Leu Met Arg His Ile
        195                 200                 205

Arg Asn Leu Gln Leu Asn Thr Met Gly Pro Arg Asp Leu Arg Met Lys
    210                 215                 220

Ala His Lys Arg Ala Met Lys Met Lys Met Lys Met Met Val Ser Phe
225                 230                 235                 240

Leu Leu Phe Phe Leu Val His Phe Ser Ser Leu Leu Pro Thr Gly Trp
                245                 250                 255

Ile Phe Leu Ile Gln Gln Lys
            260


<210> SEQ ID NO 48
<211> LENGTH: 258
<212> TYPE: PRT
<213> ORGANISM: Homo sapiens

<400> SEQUENCE: 48

Leu Ala Asn Leu Ile Asp Trp Ala Glu Asn Gln Ile Cys Leu Met Asp
1               5                   10                  15

Phe Ile Leu Ser Ser Leu Ala Ile Cys Arg Thr Leu Leu Leu Gly Cys
            20                  25                  30

Cys Val Ala Ile Arg Cys Thr Tyr Asn Asp Tyr Pro Asn Ile Asp Ala
        35                  40                  45

Val Asn His Asn Leu Ile Lys Ile Ile Thr Ile Phe Asp Ile Leu Arg
    50                  55                  60

Leu Val Ser Lys Leu Gly Ile Trp Phe Ala Ser Tyr Leu Ser Ile Phe
65                  70                  75                  80

Tyr Leu Leu Lys Val Ala Leu Phe His His Ala Ile Phe Leu Trp Leu
                85                  90                  95

Lys Trp Arg Ile Ser Arg Ala Val Phe Thr Phe Leu Met Ile Phe Leu
            100                 105                 110

Phe Phe Tyr Ile Ser Ile Ile Ser Met Ile Lys Ile Lys Leu Phe Leu
        115                 120                 125

Asp Gln Cys Tyr Lys Ile Glu Lys Leu Leu Leu Glu Gly Arg Cys Glu
    130                 135                 140

Ser Pro Pro Ser Cys Pro Asp Ala His Pro Gly Val Val Tyr Ser Leu
145                 150                 155                 160

Tyr His Phe Ser Tyr Leu Met Phe Leu Val Cys Tyr Leu Pro Lys Gly
                165                 170                 175

Lys His Cys Thr Ala Val Val Ile Gly Asp Trp Leu Gln Arg Pro Arg
            180                 185                 190

Thr Glu Ala Tyr Val Arg Ala Met Asn Ile Met Ile Ala Phe Phe Phe
        195                 200                 205

His Leu Leu Tyr Ser Leu Gly Thr Ser Leu Ser Ser Val Ser Tyr Phe
    210                 215                 220
```

-continued

```
Leu Cys Lys Arg Lys Ile Val Ala Leu Gly Ala Tyr Leu Ser Tyr Pro
225                 230                 235                 240

Leu Ser His Ser Phe Ile Leu Ile Met Glu Asn Asn Lys Val Arg Lys
                245                 250                 255

Ala Leu


<210> SEQ ID NO 49
<211> LENGTH: 35
<212> TYPE: PRT
<213> ORGANISM: Homo sapiens

<400> SEQUENCE: 49

Asn Ile Cys Val Leu Leu Ile Ile Leu Ser Ile Leu Val Val Ser Ala
1               5                   10                  15

Phe Val Leu Gly Asn Val Ala Asn Gly Phe Ile Ala Leu Ile Asn Val
            20                  25                  30

Asn Asp Trp
        35


<210> SEQ ID NO 50
<211> LENGTH: 36
<212> TYPE: PRT
<213> ORGANISM: Homo sapiens

<400> SEQUENCE: 50

Met Gln Ala Ala Leu Thr Ala Phe Phe Val Leu Leu Phe Ser Leu Leu
1               5                   10                  15

Ser Leu Leu Gly Ile Ala Ala Asn Gly Phe Ile Val Leu Val Leu Gly
            20                  25                  30

Lys Glu Trp Leu
        35


<210> SEQ ID NO 51
<211> LENGTH: 319
<212> TYPE: PRT
<213> ORGANISM: Homo sapiens

<400> SEQUENCE: 51

Met Ile Thr Phe Leu Pro Ile Ile Phe Ser Ile Leu Val Val Val Thr
1               5                   10                  15

Phe Val Leu Gly Asn Phe Ser Asn Gly Phe Ile Ala Leu Val Asn Ser
            20                  25                  30

Ile Glu Trp Val Lys Thr Arg Lys Ile Ser Ser Ala Asp Gln Ile Leu
        35                  40                  45

Thr Ala Leu Val Val Ser Arg Val Gly Leu Leu Trp Val Ile Leu Leu
    50                  55                  60

His Trp Tyr Ala Asn Val Phe Asn Ser Ala Leu Tyr Ser Ser Glu Val
65                  70                  75                  80

Gly Ala Val Ala Ser Asn Ile Ser Ala Ile Ile Asn His Phe Ser Ile
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Lys Arg Ile Arg Ser Val
        115                 120                 125

Val Leu Val Ile Leu Leu Gly Pro Leu Val Phe Leu Ile Cys Asn Leu
    130                 135                 140

Ala Val Ile Thr Met Asp Asp Ser Val Trp Thr Lys Glu Tyr Glu Gly
```

-continued

```
145                 150                 155                 160

Asn Val Thr Trp Lys Ile Lys Leu Arg Asn Ala Ile His Leu Ser Asn
                165                 170                 175

Met Thr Val Ser Thr Leu Ala Asn Leu Ile Pro Phe Ile Leu Thr Leu
            180                 185                 190

Ile Cys Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Thr Ser Phe Leu Leu Leu Cys Ala Ile
225                 230                 235                 240

Tyr Phe Leu Ser Met Ile Ile Ser Val Cys Asn Phe Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Leu Arg His Val Arg Tyr Trp Val Lys Asp Arg
    290                 295                 300

Ser Leu Arg Leu His Arg Phe Thr Arg Gly Ala Leu Cys Val Phe
305                 310                 315
```

<210> SEQ ID NO 52
<211> LENGTH: 960
<212> TYPE: DNA
<213> ORGANISM: Homo sapiens

<400> SEQUENCE: 52

```
atgataactt ttctacccat catttttcc attctggtag tggttacatt tgttcttgga      60

aatttttcca atggcttcat agctctagta aattccattg agtgggtcaa gacacgaaag    120

atctcctcag ctgaccaaat cctcactgct ctggtggtct ccagagttgg tttactctgg    180

gtcatattat tacattggta tgcaaatgtg tttaattcag ctttatatag ttcagaagta    240

ggagctgttg cttctaatat ctcagcaata atcaaccatt tcagcatctg gcttgctact    300

agcctcagca tattttattt gctcaagatt gccaatttct ccaaccttat ttttctccac    360

ttaaagaaga gaattaggag tgttgttctg gtgatactgt tgggtccctt ggtatttttg    420

atttgtaatc ttgctgtgat aaccatggat gacagtgtgt ggacaaaaga atatgaagga    480

aatgtgactt ggaagatcaa attgaggaat gcaatacacc tttcaaatat gactgtaagc    540

acactagcaa acctcatacc cttcattctg accctaatat gttttctgct gttaatctgt    600

tctctgtgta aacatctcaa gaagatgcag ctccatggca aaggatctca agatcccagc    660

accaaggtcc acataaaagc tttgcaaact gtgacctcct ttcttctgtt atgtgccatt    720

tactttctgt ccatgatcat atcagtttgt aattttggga ggctggaaaa gcaacctgtc    780

ttcatgttct gccaagctat tatattcagc tatccttcaa cccacccatt catcctgatt    840

ttgggaaaca agaagctaaa gcagattttt ctttcagttt tgcggcatgt gaggtactgg    900

gtgaaagaca gaagccttcg tctccataga ttcacaagag gggcattgtg tgtcttctag    960
```

<210> SEQ ID NO 53
<211> LENGTH: 299
<212> TYPE: PRT
<213> ORGANISM: Homo sapiens
<220> FEATURE:

-continued

<221> NAME/KEY: MOD_RES
<222> LOCATION: (176)..(176)
<223> OTHER INFORMATION: Variable amino acid
<220> FEATURE:
<221> NAME/KEY: MOD_RES
<222> LOCATION: (184)..(184)
<223> OTHER INFORMATION: Variable amino acid

<400> SEQUENCE: 53

```
Met Thr Thr Phe Ile Pro Ile Ile Phe Ser Ser Val Val Val Val Leu
1               5                   10                  15
Phe Val Ile Gly Asn Phe Ala Asn Gly Phe Ile Ala Leu Val Asn Ser
            20                  25                  30
Ile Glu Arg Val Lys Arg Gln Lys Ile Ser Phe Ala Asp Gln Ile Leu
        35                  40                  45
Thr Ala Leu Ala Val Ser Arg Val Gly Leu Leu Trp Val Leu Leu Leu
    50                  55                  60
Asn Trp Tyr Ser Thr Val Phe Asn Pro Ala Phe Tyr Ser Val Glu Val
65                  70                  75                  80
Arg Thr Thr Ala Tyr Asn Val Trp Ala Val Thr Gly His Phe Ser Asn
                85                  90                  95
Trp Leu Ala Thr Ser Leu Ser Ile Phe Tyr Leu Leu Lys Ile Ala Asn
            100                 105                 110
Phe Ser Asn Leu Ile Phe Leu His Leu Lys Arg Arg Val Lys Ser Val
        115                 120                 125
Ile Leu Val Met Leu Leu Gly Pro Leu Leu Phe Leu Ala Cys Gln Leu
    130                 135                 140
Phe Val Ile Asn Met Lys Glu Ile Val Arg Thr Lys Glu Phe Glu Gly
145                 150                 155                 160
Asn Met Thr Trp Lys Ile Lys Leu Lys Ser Ala Met Tyr Phe Ser Xaa
                165                 170                 175
Met Thr Val Thr Ile Gly Ala Xaa Leu Val Pro Phe Thr Leu Ser Leu
            180                 185                 190
Ile Ser Phe Leu Met Leu Ile Cys Ser Leu Cys Lys His Leu Lys Lys
        195                 200                 205
Met Gln Leu His Gly Glu Gly Ser Gln Asp Leu Ser Thr Lys Val His
    210                 215                 220
Ile Lys Ala Leu Gln Thr Leu Ile Ser Phe Leu Leu Leu Cys Ala Ile
225                 230                 235                 240
Phe Phe Leu Phe Leu Ile Val Ser Val Trp Ser Pro Arg Arg Leu Arg
                245                 250                 255
Asn Asp Pro Val Val Met Val Ser Lys Ala Val Gly Asn Ile Tyr Leu
            260                 265                 270
Ala Phe Asp Ser Phe Ile Leu Ile Trp Arg Thr Lys Lys Leu Lys His
        275                 280                 285
Thr Phe Leu Leu Ile Leu Cys Gln Ile Arg Cys
    290                 295
```

<210> SEQ ID NO 54
<211> LENGTH: 900
<212> TYPE: DNA
<213> ORGANISM: Homo sapiens
<220> FEATURE:
<221> NAME/KEY: modified_base
<222> LOCATION: (526)..(526)
<223> OTHER INFORMATION: n is a, c, g, or t
<220> FEATURE:
<221> NAME/KEY: modified_base
<222> LOCATION: (550)..(550)
<223> OTHER INFORMATION: n is a, c, g, or t

<400> SEQUENCE: 54

```
atgacaactt ttatacccat catttttcc agtgtggtag tggttctatt tgttattgga     60

aattttgcta atggcttcat agcattggta aattccattg agcgggtcaa gagacaaaag    120

atctcttttg ctgaccagat tctcactgct ctggcggtct ccagagttgg tttgctctgg    180

gtattattat taaattggta ttcaactgtg tttaatccag ctttttatag tgtagaagta    240

agaactactg cttataatgt ctgggcagta accggccatt tcagcaactg gcttgctact    300

agcctcagca tattttattt gctcaagatt gccaatttct ccaaccttat ttttcttcac    360

ttaaagagga gagttaagag tgtcattctg gtgatgctgt tggggccttt actatttttg    420
```

-continued

```
gcttgtcaac tttttgtgat aaacatgaaa gagattgtac ggacaaaaga atttgaagga    480

aacatgactt ggaagatcaa attgaagagt gcaatgtact tttcanatat gactgtaacc    540

attggagcan acttagtacc ctttactctg tccctgatat cttttctgat gctaatctgt    600

tctctgtgta aacatctcaa gaagatgcag ctccatggag aaggatcgca agatctcagc    660

accaaggtcc acataaaagc tttgcaaact ctgatctcct tcctcttgtt atgtgccatt    720

ttctttctat tcctaatcgt ttcggtttgg agtcctagga ggctgcggaa tgacccggtt    780

gtcatggtta gcaaggctgt tggaaacata tatcttgcat tcgactcatt catcctaatt    840

tggagaacca agaagctaaa acacaccttt cttttgattt tgtgtcagat taggtgctga    900
```

```
<210> SEQ ID NO 55
<211> LENGTH: 20
<212> TYPE: PRT
<213> ORGANISM: Homo sapiens

<400> SEQUENCE: 55

His Ser Phe Met Leu Thr Met Gly Ser Arg Lys Pro Lys Gln Thr Phe
1               5                   10                  15

Leu Ser Ala Leu
            20


<210> SEQ ID NO 56
<211> LENGTH: 309
<212> TYPE: PRT
<213> ORGANISM: Homo sapiens

<400> SEQUENCE: 56

Met Val Tyr Phe Leu Pro Ile Ile Phe Ser Ile Leu Val Val Phe Ala
1               5                   10                  15

Phe Val Leu Gly Asn Phe Ser Asn Gly Phe Ile Ala Leu Val Asn Val
            20                  25                  30

Ile Asp Trp Val Lys Arg Gln Lys Ile Ser Ser Ala Asp Gln Ile Leu
        35                  40                  45

Thr Ala Leu Val Val Ser Arg Val Gly Leu Leu Trp Val Ile Leu Leu
    50                  55                  60

His Trp Tyr Ala Asn Val Phe Asn Ser Ala Leu Tyr Ser Leu Glu Val
65                  70                  75                  80

Arg Ile Val Ala Ser Asn Ile Ser Ala Val Ile Asn His Phe Ser Ile
                85                  90                  95

Trp Leu Ala Ala Ser Leu Ser Ile Phe Tyr Leu Leu Lys Ile Ala Asn
            100                 105                 110

Phe Ser Asn Leu Ile Phe Leu His Leu Lys Lys Arg Ile Lys Ser Val
        115                 120                 125

Val Leu Val Ile Leu Leu Gly Pro Leu Val Phe Leu Ile Cys Asn Leu
    130                 135                 140

Ala Val Ile Thr Met Asp Glu Arg Val Trp Thr Lys Glu Tyr Glu Gly
145                 150                 155                 160

Asn Val Thr Trp Lys Ile Lys Leu Arg Asn Ala Ile His Leu Ser Ser
                165                 170                 175

Leu Thr Val Thr Thr Leu Ala Asn Leu Ile Pro Phe Thr Leu Ser Leu
            180                 185                 190

Ile Cys Phe Leu Leu Leu Ile Cys Ser Leu Cys Lys His Leu Lys Lys
        195                 200                 205

Met Gln Leu His Ser Lys Gly Ser Gln Asp Pro Ser Thr Lys Val His
    210                 215                 220
```

-continued

```
Ile Lys Ala Leu Gln Thr Val Ile Ser Phe Leu Met Leu Cys Ala Ile
225                 230                 235                 240

Tyr Phe Leu Ser Ile Met Ile Ser Val Met Asn Leu Arg Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Phe Trp Gln Val Arg Tyr Trp Val Lys Gly Glu
    290                 295                 300

Lys Pro Ser Ser Pro
305
```

<210> SEQ ID NO 57
<211> LENGTH: 930
<212> TYPE: DNA
<213> ORGANISM: Homo sapiens

<400> SEQUENCE: 57

```
atggtatatt ttctgcccat catttttttcc attctggtag tgtttgcatt tgttcttgga     60

aatttttcca atggcttcat agctctagta aatgtcattg actgggttaa gagacaaaag    120

atctcctcag ctgaccaaat tctcactgct ctggtggtct ccagagttgg tttactctgg    180

gtcatattat tacattggta tgcaaatgtg tttaattcag ctttatatag tttagaagta    240

agaattgttg cttctaatat ctcagcagta atcaaccatt tcagcatctg gcttgctgct    300

agcctcagca tattttattt gctcaagatt gccaatttct ccaaccttat ttttctccac    360

ctaaagaaga gaattaagag tgttgttctg gtgatactgt tggggccctt ggtatttctg    420

atttgtaatc ttgctgtgat aaccatggat gagagagtgt ggacaaaaga atatgaagga    480

aatgtgactt ggaagatcaa attgaggaat gcaatacacc tttcaagctt gactgtaact    540

actctagcaa acctcatacc ctttactctg agcctaatat gttttctgct gttaatctgt    600

tctctttgta aacatctcaa gaagatgcag ctccatagca aaggatctca agatcccagc    660

accaaggtcc acataaaagc tttgcaaact gtgatctcct tcctcatgtt atgtgccatt    720

tactttctgt ccataatgat atcagtttgg aatcttagga gtctggaaaa caaacctgtc    780

ttcatgttct gcaaagctat tagattcagc tatccttcaa tccacccatt catcctgatt    840

tggggaaaca agaagctaaa gcagactttt ctttcagttt tttggcaagt gaggtactgg    900

gtgaaaggag agaagccttc atctccatag                                     930
```

<210> SEQ ID NO 58
<211> LENGTH: 100
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (34)..(34)
<223> OTHER INFORMATION: Variable amino acid
<220> FEATURE:
<221> NAME/KEY: MOD_RES
<222> LOCATION: (71)..(71)
<223> OTHER INFORMATION: Variable amino acid
<220> FEATURE:
<221> NAME/KEY: MOD_RES
<222> LOCATION: (85)..(85)

-continued

<223> OTHER INFORMATION: Variable amino acid

<400> SEQUENCE: 58

Gly Ser Ser Arg Xaa Lys Pro Pro Arg Ile Pro His Lys Lys Leu Cys
1               5                   10                  15

Lys Leu Gly Pro Ser Phe Pro His Asn Asn Leu Pro Ile Tyr Phe Leu
            20                  25                  30

Cys Xaa Asn His Ile Val Leu Glu Phe Leu Lys Met Arg Pro Lys Lys
        35                  40                  45

Lys Cys Ser Leu Met Leu Cys Gln Ala Phe Gly Ile Ile Tyr Pro Ser
    50                  55                  60

Phe His Ser Phe Ile Leu Xaa Trp Gly Asn Lys Thr Leu Lys Gln Thr
65                  70                  75                  80

Phe Leu Ser Val Xaa Trp Gln Val Thr Cys Trp Ala Lys Gly Gln Asn
                85                  90                  95

Gln Ser Thr Pro
            100

<210> SEQ ID NO 59
<211> LENGTH: 128
<212> TYPE: PRT
<213> ORGANISM: Homo sapiens
<220> FEATURE:
<221> NAME/KEY: MOD_RES
<222> LOCATION: (62)..(62)
<223> OTHER INFORMATION: Variable amino acid
<220> FEATURE:
<221> NAME/KEY: MOD_RES
<222> LOCATION: (72)..(72)
<223> OTHER INFORMATION: Variable amino acid

<400> SEQUENCE: 59

Asn Ala Ile Arg Pro Ser Lys Leu Trp Thr Val Thr Glu Ala Asp Lys
1               5                   10                  15

Thr Ser Gln Pro Gly Thr Ser Ala Asn Lys Ile Phe Ser Ala Gly Asn
            20                  25                  30

Leu Ile Ser His Val Asn Met Ser Arg Arg Met Gln Leu His Gly Lys
        35                  40                  45

Gly Ser Gln His Leu Ser Thr Arg Val His Ile Lys Ala Xaa Gln Thr
    50                  55                  60

Val Ile Ser Phe Leu Met Leu Xaa Ala Ile Tyr Phe Leu Cys Leu Ile
65                  70                  75                  80

Thr Ser Thr Trp Asn Pro Arg Thr Gln Gln Ser Lys Leu Val Phe Leu
                85                  90                  95

Leu Tyr Gln Thr Leu Gly Phe Met Tyr Leu Leu Phe His Ser Phe Ile
            100                 105                 110

Leu Thr Met Gly Ser Arg Lys Pro Lys Gln Thr Phe Leu Ser Ala Leu
        115                 120                 125

<210> SEQ ID NO 60
<211> LENGTH: 309
<212> TYPE: PRT
<213> ORGANISM: Homo sapiens

<400> SEQUENCE: 60

Met Ile Cys Phe Leu Leu Ile Ile Leu Ser Ile Leu Val Val Phe Ala
1               5                   10                  15

Phe Val Leu Gly Asn Phe Ser Asn Gly Phe Ile Ala Leu Val Asn Val
            20                  25                  30

-continued

```
Ile Asp Trp Val Lys Arg Gln Lys Ile Ser Ser Ala Asp Gln Ile Leu
        35                  40                  45

Thr Ala Leu Val Val Ser Arg Val Gly Leu Leu Trp Val Ile Leu Leu
    50                  55                  60

His Trp Tyr Ser Asn Val Leu Asn Ser Ala Leu Tyr Ser Ser Glu Val
65                  70                  75                  80

Ile Ile Phe Ile Ser Asn Ala Trp Ala Ile Ile Asn His Phe Ser Ile
                85                  90                  95

Trp Leu Ala Thr Ser Leu Ser Ile Phe Tyr Leu Leu Lys Ile Val Asn
            100                 105                 110

Phe Ser Arg Leu Ile Phe His His Leu Lys Arg Lys Ala Lys Ser Val
        115                 120                 125

Val Leu Val Ile Val Leu Gly Pro Leu Val Phe Leu Val Cys His Leu
    130                 135                 140

Val Met Lys His Thr Tyr Ile Asn Val Trp Thr Lys Glu Tyr Glu Gly
145                 150                 155                 160

Asn Val Thr Trp Lys Ile Lys Leu Arg Asn Ala Ile His Leu Ser Asn
                165                 170                 175

Leu Thr Val Ser Thr Leu Ala Asn Leu Ile Pro Phe Thr Leu Thr Leu
            180                 185                 190

Ile Ser Phe Leu Leu Leu Ile Tyr Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Thr Ser Phe Leu Leu Leu Cys Ala Ile
225                 230                 235                 240

Tyr Phe Leu Ser Met Ile Ile Ser Val Cys Asn Phe Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Phe Trp Gln Met Arg Tyr Trp Val Lys Gly Glu
    290                 295                 300

Lys Pro Ser Ser Pro
305
```

<210> SEQ ID NO 61
<211> LENGTH: 930
<212> TYPE: DNA
<213> ORGANISM: Homo sapiens

<400> SEQUENCE: 61

```
atgatatgtt ttctgctcat cattttatca attctggtag tgtttgcatt tgttcttgga      60

aatttttcca atggcttcat agctctagta aatgtcattg actgggtcaa gagacaaaag     120

atctcctcag ctgaccaaat cctcactgct ctggtggtct ccagagttgg tttactctgg     180

gtaatattat tacattggta ttcaaatgtg ttgaattcag ctttatatag ttcagaagta     240

ataattttta tttctaatgc ctgggcaata atcaaccatt tcagcatctg gcttgctact     300

agcctcagca tattttattt gctcaagatc gtcaatttct ccagacttat ttttcatcac     360

ttaaaaagga aggctaagag tgtagttctg gtgatagtgt tgggtccctt ggtatttttg     420

gtttgtcacc ttgtgatgaa acacacgtat ataaatgtgt ggacaaaaga atatgaagga     480

aatgtgactt ggaagatcaa actgaggaat gcaatacacc tttcaaactt gactgtaagc     540
```

-continued

```
acactagcaa acttgatacc cttcactctg accctgatat cttttctgct gttaatctac    600

tctctgtgta aacatctcaa gaagatgcag ctccatggca aaggatctca agatcccagc    660

accaaggtcc acataaaagc tttgcaaact gtgacctcct ttcttctgtt atgtgccatt    720

tactttctgt ccatgatcat atcagtttgt aattttggga ggctggaaaa gcaacctgtc    780

ttcatgttct gccaagctat tatattcagc tatccttcaa cccacccatt catcctgatt    840

ttgggaaaca agaagctaaa gcagattttt ctttcagttt tttggcaaat gaggtactgg    900

gtgaaaggag agaagccttc atctccatag                                     930
```

```
<210> SEQ ID NO 62
<211> LENGTH: 306
<212> TYPE: PRT
<213> ORGANISM: Homo sapiens

<400> SEQUENCE: 62

Met Ile Thr Phe Leu Pro Ile Ile Phe Ser Ile Leu Ile Val Val Thr
1               5                   10                  15
Phe Val Ile Gly Asn Phe Ala Asn Gly Phe Ile Ala Leu Val Asn Ser
            20                  25                  30
Ile Glu Trp Val Lys Arg Gln Lys Ile Ser Ser Ala Asp Gln Ile Ser
        35                  40                  45
His Cys Ser Gly Gly Val Gln Asn Trp Phe Thr Leu Gly His Ile Ile
    50                  55                  60
Thr Leu Val Cys Asn Cys Val Phe Gly Phe Ile Ile Arg Ser Lys Asn
65                  70                  75                  80
Phe Trp Phe Cys Leu Ser Asn Asn Gln Ala Phe Gln His Val Gly Val
                85                  90                  95
Thr Ser Leu Ser Ile Phe His Leu Leu Lys Thr Ala Asn Phe Ser Asn
            100                 105                 110
Leu Ile Phe Leu His Leu Lys Lys Arg Ile Lys Ser Val Gly Leu Val
        115                 120                 125
Ile Leu Leu Gly Pro Leu Leu Phe Phe Ile Cys Asn Leu Phe Val Ile
    130                 135                 140
Asn Met Asp Glu Ser Val Trp Thr Lys Glu Tyr Glu Gly Asn Val Thr
145                 150                 155                 160
Trp Lys Ile Lys Leu Arg Ser Ala Met Tyr His Ser Asn Met Thr Leu
                165                 170                 175
Thr Met Leu Ala Asn Phe Val Pro Phe Thr Leu Thr Leu Ile Ser Phe
            180                 185                 190
Leu Leu Leu Ile Cys Ser Leu Cys Lys His Leu Lys Lys Met Gln Leu
        195                 200                 205
His Gly Lys Gly Ser Gln Asp Pro Ser Thr Lys Val His Ile Lys Ala
    210                 215                 220
Leu Gln Thr Val Thr Ser Phe Leu Leu Leu Cys Ala Ile Tyr Phe Leu
225                 230                 235                 240
Ser Met Ile Ile Ser Val Cys Asn Leu Gly Arg Leu Glu Lys Gln Pro
                245                 250                 255
Val Phe Met Phe Cys Glu Ala Ile Ile Phe Ser Tyr Pro Ser Thr His
            260                 265                 270
Pro Phe Ile Leu Ile Leu Gly Asn Lys Lys Leu Lys Gln Ile Phe Leu
        275                 280                 285
Ser Val Leu Arg His Val Arg Tyr Trp Val Lys Gly Glu Lys Pro Ser
    290                 295                 300
Ser Ser
305
```

```
<210> SEQ ID NO 63
<211> LENGTH: 930
<212> TYPE: DNA
<213> ORGANISM: Homo sapiens

<400> SEQUENCE: 63

atgataactt ttctgcccat catttttcc attctaatag tggttacatt tgtgattgga      60

aattttgcta atggcttcat agctctagta aattccattg agtgggttaa gagacaaaag    120

atctcatcag ctgaccaaat ttctcactgc tctggtggtg tccagaattg gtttactctg    180

ggtcatatta ttacattggt atgcaactgt gtttaatttg gcttcatata gattagaagt    240
```

-continued

```
aagaatttttt ggttctaatg tctcagcaat aaccaagcat ttcagcatgt gggtgttact    300

agcctcagca tatttcattt gctcaagact gccaatttct ccaaccttat ttttctccac    360

ctaaagaaga ggattaagag tgttggtttg gtgatactat tggggccttt gctatttttc    420

atttgtaatc tttttgtgat aaacatggat gagagtgtat ggacaaaaga atatgaagga    480

aacgtgactt ggaagatcaa attgaggagt gcaatgtacc attcaaatat gactctaacc    540

atgctagcaa actttgtacc cttcactctg accctgatat cttttctgct gttaatctgt    600

tctctgtgta aacatctcaa gaagatgcag ctccatggca aaggatctca agatcccagc    660

accaaggtcc acataaaagc tttgcaaact gtgacctcct ttcttctgtt atgtgccatt    720

tactttctgt ccatgatcat atcagtttgt aatttgggga ggctggaaaa gcaacctgtc    780

ttcatgttct gcgaagctat tatattcagc tatccttcaa cccacccatt catcctgatt    840

ttgggaaaca agaagctaaa gcagattttt ctttcagttt tgcggcatgt gaggtactgg    900

gtgaaaggag agaagccttc atcttcatag                                      930
```

```
<210> SEQ ID NO 64
<211> LENGTH: 144
<212> TYPE: PRT
<213> ORGANISM: Homo sapiens

<400> SEQUENCE: 64

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Pro Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Ser Pro Gly Arg Ser Pro Val Pro Ser
    130                 135                 140


<210> SEQ ID NO 65
<211> LENGTH: 140
<212> TYPE: PRT
<213> ORGANISM: Homo sapiens

<400> SEQUENCE: 65

Leu Arg Asn Ala Gly Leu Asn Asp Ser Asn Ala Lys Leu Val Arg Asn
1               5                   10                  15

Asn Asp Leu Leu Leu Ile Asn Leu Ile Leu Leu Leu Pro Leu Ser Val
            20                  25                  30

Phe Val Met Cys Thr Ser Met Leu Phe Val Ser Leu Tyr Lys His Met
        35                  40                  45

His Trp Met Gln Ser Glu Ser His Lys Leu Ser Ser Ala Arg Thr Glu
    50                  55                  60
```

-continued

```
Ala His Ile Asn Ala Leu Lys Thr Val Thr Thr Phe Phe Cys Phe Phe
65                  70                  75                  80

Val Ser Tyr Phe Ala Ala Phe Met Ala Asn Met Thr Phe Arg Ile Pro
                85                  90                  95

Tyr Arg Ser His Gln Phe Phe Val Val Lys Glu Ile Met Ala Ala Tyr
            100                 105                 110

Pro Ala Gly His Ser Val Ile Ile Val Leu Ser Asn Ser Lys Phe Lys
        115                 120                 125

Asp Leu Phe Arg Arg Met Ile Cys Leu Gln Lys Glu
    130                 135                 140


<210> SEQ ID NO 66
<211> LENGTH: 71
<212> TYPE: PRT
<213> ORGANISM: Homo sapiens

<400> SEQUENCE: 66

Ser Gln Tyr Ser Leu Gly His Ser Tyr Val Val Ile Phe Gly Tyr Gly
1               5                   10                  15

Gln Met Lys Lys Thr Phe Leu Gly Ile Leu Trp His Leu Lys Cys Gly
            20                  25                  30

Leu Lys Gly Arg Ala Leu Leu Ala Thr Gln Val Gly Leu Arg Glu Lys
        35                  40                  45

Ser Thr Arg Ser Leu Gly Val Ile Phe Leu Ala Ser Ser Tyr Ser Phe
    50                  55                  60

Phe Val Tyr Val Leu Cys His
65                  70


<210> SEQ ID NO 67
<211> LENGTH: 308
<212> TYPE: PRT
<213> ORGANISM: Homo sapiens

<400> SEQUENCE: 67

Met Ile Thr Phe Leu Leu Ile Ile Leu Ser Ile Leu Val Val Phe Ala
1               5                   10                  15

Phe Val Leu Gly Asn Phe Ser Asn Gly Phe Ile Ala Leu Val Asn Val
            20                  25                  30

Ile Asp Trp Val Asn Thr Arg Lys Ile Ser Ser Ala Asp Gln Ile Leu
        35                  40                  45

Thr Ala Leu Ala Val Ser Arg Val Gly Leu Leu Trp Val Ile Leu Leu
    50                  55                  60

His Trp Tyr Ala Asn Val Leu Asn Pro Ala Leu Tyr Ser Ser Glu Val
65                  70                  75                  80

Ile Ile Phe Ile Ser Asn Ile Ser Ala Ile Ile Asn His Phe Ser Ile
                85                  90                  95

Trp Leu Ala Thr Ser Leu Ser Ile Phe Tyr Leu Leu Lys Ile Val Asn
            100                 105                 110

Phe Ser Arg Leu Ile Phe His His Leu Lys Arg Lys Ala Lys Ser Val
        115                 120                 125

Val Leu Val Ile Val Leu Gly Pro Leu Val Phe Leu Val Cys His Leu
    130                 135                 140

Val Met Lys His Thr Tyr Ile Asn Val Trp Thr Lys Glu Tyr Glu Gly
145                 150                 155                 160

Asn Val Thr Trp Lys Ile Lys Leu Arg Asn Ala Ile His Leu Ser Asn
                165                 170                 175
```

-continued

```
Leu Thr Val Ser Thr Leu Ala Asn Leu Ile Pro Phe Thr Leu Thr Leu
            180                 185                 190

Ile Ser Phe Leu Leu Leu Ile Cys Ser Leu Cys Lys His Leu Lys Lys
        195                 200                 205

Met Gln Leu His Ser Lys Gly Ser Gln Asp Pro Ser Thr Lys Val His
    210                 215                 220

Ile Lys Ala Leu Gln Thr Val Thr Ser Phe Leu Met Leu Phe Ala Ile
225                 230                 235                 240

Tyr Phe Leu Tyr Leu Ile Thr Ser Thr Trp Asn Leu Thr Gln Gln Ser
                245                 250                 255

Lys Leu Val Phe Met Phe Cys Gln Thr Leu Gly Ile Met Tyr Pro Ser
            260                 265                 270

Phe His Ser Phe Ile Leu Ile Met Gly Ser Arg Lys Leu Lys Gln Thr
        275                 280                 285

Phe Leu Ser Val Leu Cys Gln Val Thr Cys Leu Val Lys Gly Gln Gln
    290                 295                 300

Pro Ser Thr Pro
305


<210> SEQ ID NO 68
<211> LENGTH: 34
<212> TYPE: PRT
<213> ORGANISM: Homo sapiens

<400> SEQUENCE: 68

Phe Ile Gly Leu Thr Asp Cys Ile Ala Trp Met Arg Asn Gln Lys Leu
1               5                   10                  15

Cys Met Val Gly Phe Ile Leu Thr Arg Met Ala Leu Ala Arg Ile Asn
            20                  25                  30

Ile Leu


<210> SEQ ID NO 69
<211> LENGTH: 293
<212> TYPE: PRT
<213> ORGANISM: Homo sapiens
<220> FEATURE:
<221> NAME/KEY: MOD_RES
<222> LOCATION: (75)..(97)
<223> OTHER INFORMATION: Variable amino acid

<400> SEQUENCE: 69

Leu Glu Leu Ile Phe Ser Lys Val Val Ala Thr Arg Gly Leu Val Leu
1               5                   10                  15

Gly Met Leu Gly Asn Gly Leu Ile Gly Leu Val Asn Cys Ile Glu Trp
            20                  25                  30

Ala Lys Ser Trp Lys Val Ser Ser Ala Asp Phe Ile Leu Thr Ser Leu
        35                  40                  45

Ala Ile Val Arg Ile Ile Arg Leu Tyr Leu Ile Leu Phe Asp Ser Phe
    50                  55                  60

Ile Met Val Leu Ser Pro His Leu Tyr Thr Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Ser Leu Ser Ile Phe His Trp Phe Lys Thr Ala Asn Phe Ser Asn
            100                 105                 110

Leu Ile Phe Leu Pro Leu Lys Glu Glu Asp Asn Val Trp Leu Gly Asp
        115                 120                 125
```

-continued

```
Ala Val Gly Ala Leu Gly Ile Phe His Leu Ser Cys Ser Glu Asn His
    130                 135                 140

Gly Glu Val Cys Gly Gln Lys Asn Met Lys Glu Phe Cys Ser Gly Met
145                 150                 155                 160

Ile Lys Leu Arg Asn Ala Ile Gln Leu Ser Asn Leu Thr Val Thr Met
                165                 170                 175

Pro Ala Asn Val Thr Pro Cys Thr Leu Thr Leu Ile Ser Phe Leu Leu
            180                 185                 190

Leu Ile Tyr Ser Pro Cys Lys His Val Lys Lys Met Gln Leu His Gly
        195                 200                 205

Lys Gly Ser Gln His Leu Ser Thr Lys Val His Ile Lys Val Leu Gln
    210                 215                 220

Thr Val Ile Ser Phe Phe Leu Leu Cys Ala Ile Tyr Phe Val Ser Val
225                 230                 235                 240

Ile Ile Ser Val Trp Ser Phe Lys Asn Leu Glu Asn Lys Pro Val Phe
                245                 250                 255

Met Phe Cys Gln Ala Ile Gly Phe Ser Cys Ser Ser Ala His Pro Phe
            260                 265                 270

Ile Leu Thr Met Gly Asn Lys Lys Leu Lys Gln Thr Tyr Leu Ser Val
        275                 280                 285

Leu Trp Gln Met Arg
    290


<210> SEQ ID NO 70
<211> LENGTH: 319
<212> TYPE: PRT
<213> ORGANISM: Homo sapiens

<400> SEQUENCE: 70

Met Ile Thr Phe Leu Pro Ile Ile Phe Ser Ile Leu Ile Val Val Ile
1               5                   10                  15

Phe Val Ile Gly Asn Phe Ala Asn Gly Phe Ile Ala Leu Val Asn Ser
            20                  25                  30

Ile Glu Trp Val Lys Arg Gln Lys Ile Ser Phe Val Asp Gln Ile Leu
        35                  40                  45

Thr Ala Leu Ala Val Ser Arg Val Gly Leu Leu Trp Val Leu Leu Leu
    50                  55                  60

His Trp Tyr Ala Thr Gln Leu Asn Pro Ala Phe Tyr Ser Val Glu Val
65                  70                  75                  80

Arg Ile Thr Ala Tyr Asn Val Trp Ala Val Thr Asn His Phe Ser Ser
                85                  90                  95

Trp Leu Ala Thr Ser Leu Ser Met Phe Tyr Leu Leu Arg Ile Ala Asn
            100                 105                 110

Phe Ser Asn Leu Ile Phe Leu Arg Ile Lys Arg Arg Val Lys Ser Val
        115                 120                 125

Val Leu Val Ile Leu Leu Gly Pro Leu Leu Phe Leu Val Cys His Leu
    130                 135                 140

Phe Val Ile Asn Met Asp Glu Thr Val Trp Thr Lys Glu Tyr Glu Gly
145                 150                 155                 160

Asn Val Thr Trp Lys Ile Lys Leu Arg Ser Ala Met Tyr His Ser Asn
                165                 170                 175

Met Thr Leu Thr Met Leu Ala Asn Phe Val Pro Leu Thr Leu Thr Leu
            180                 185                 190

Ile Ser Phe Leu Leu Leu Ile Cys Ser Leu Cys Lys His Leu Lys Lys
```

-continued

```
        195                 200                 205

Met Gln Leu His Gly Lys Gly Ser Gln Asp Pro Ser Thr Lys Val His
    210                 215                 220

Ile Lys Ala Leu Gln Thr Val Thr Ser Phe Leu Leu Leu Cys Ala Ile
225                 230                 235                 240

Tyr Phe Leu Ser Met Ile Ile Ser Val Cys Asn Leu Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Leu Arg His Val Arg Tyr Trp Val Lys Asp Arg
    290                 295                 300

Ser Leu Arg Leu His Arg Phe Thr Arg Gly Ala Leu Cys Val Phe
305                 310                 315


<210> SEQ ID NO 71
<211> LENGTH: 314
<212> TYPE: PRT
<213> ORGANISM: Homo sapiens

<400> SEQUENCE: 71

Met Ala Thr Glu Leu Asp Lys Ile Phe Leu Ile Leu Ala Ile Ala Glu
1               5                   10                  15

Phe Ile Ile Ser Met Leu Gly Asn Val Phe Ile Gly Leu Val Asn Cys
            20                  25                  30

Ser Glu Gly Ile Lys Asn Gln Lys Val Phe Ser Ala Asp Phe Ile Leu
        35                  40                  45

Thr Cys Leu Ala Ile Ser Thr Ile Gly Gln Leu Leu Val Ile Leu Phe
    50                  55                  60

Asp Ser Phe Leu Val Gly Leu Ala Ser His Leu Tyr Thr Thr Tyr Arg
65                  70                  75                  80

Leu Gly Lys Thr Val Ile Met Leu Trp His Met Thr Asn His Leu Thr
                85                  90                  95

Thr Trp Leu Ala Thr Cys Leu Ser Ile Phe Tyr Phe Phe Lys Ile Ala
            100                 105                 110

His Phe Pro His Ser Leu Phe Leu Trp Leu Arg Trp Arg Met Asn Gly
        115                 120                 125

Met Ile Val Met Leu Leu Ile Leu Ser Leu Phe Leu Leu Ile Phe Asp
    130                 135                 140

Ser Leu Val Leu Glu Ile Phe Ile Asp Ile Ser Leu Asn Ile Ile Asp
145                 150                 155                 160

Lys Ser Asn Leu Thr Leu Tyr Leu Asp Glu Ser Lys Thr Leu Tyr Asp
                165                 170                 175

Lys Leu Ser Ile Leu Lys Thr Leu Leu Ser Leu Thr Ser Phe Ile Pro
            180                 185                 190

Phe Ser Leu Phe Leu Thr Ser Leu Leu Phe Leu Phe Leu Ser Leu Val
        195                 200                 205

Arg His Thr Arg Asn Leu Lys Leu Ser Ser Leu Gly Ser Arg Asp Ser
    210                 215                 220

Ser Thr Glu Ala His Arg Arg Ala Met Lys Met Val Met Ser Phe Leu
225                 230                 235                 240

Phe Leu Phe Ile Val His Phe Phe Ser Leu Gln Val Ala Asn Trp Ile
                245                 250                 255
```

-continued

```
Phe Phe Met Leu Trp Asn Asn Lys Cys Ile Lys Phe Val Met Leu Ala
            260                 265                 270

Leu Asn Ala Phe Pro Ser Cys His Ser Phe Ile Leu Ile Leu Gly Asn
        275                 280                 285

Ser Lys Leu Gln Gln Thr Ala Val Arg Leu Leu Trp His Leu Arg Asn
    290                 295                 300

Tyr Thr Lys Thr Pro Asn Pro Leu Pro Leu
305                 310


<210> SEQ ID NO 72
<211> LENGTH: 59
<212> TYPE: PRT
<213> ORGANISM: Homo sapiens

<400> SEQUENCE: 72

Met Ser Phe Leu His Ile Val Phe Ser Ile Leu Val Val Val Ala Phe
1               5                   10                  15

Ile Leu Gly Asn Phe Ala Asn Gly Phe Ile Ala Leu Ile Asn Phe Ile
            20                  25                  30

Ala Trp Val Lys Lys Gln Lys Ile Ser Ser Ala Asp Gln Ile Ile Ala
        35                  40                  45

Asp Lys Gln Ser Pro Glu Leu Val Cys Ser Gly
    50                  55


<210> SEQ ID NO 73
<211> LENGTH: 63
<212> TYPE: PRT
<213> ORGANISM: Homo sapiens

<400> SEQUENCE: 73

Met Leu Asn Ala Leu Tyr Ser Ile Leu Ile Ile Ile Ile Asn Ile Phe
1               5                   10                  15

Leu Ile Gly Ile Leu Gly Asn Gly Phe Ile Thr Leu Val Asn Gly Ile
            20                  25                  30

Asp Trp Val Lys Met Lys Arg Ser Ser Ile Leu Thr Ala Leu Thr Ile
        35                  40                  45

Ser Arg Ile Cys Leu Ile Ser Val Ile Met Val Arg Trp Phe Ile
    50                  55                  60


<210> SEQ ID NO 74
<211> LENGTH: 60
<212> TYPE: PRT
<213> ORGANISM: Homo sapiens

<400> SEQUENCE: 74

Val Ser Arg Val Gly Leu Leu Trp Val Ile Leu Leu His Trp Tyr Ser
1               5                   10                  15

Thr Val Leu Asn Pro Thr Ser Ser Asn Leu Lys Val Ile Ile Phe Ile
            20                  25                  30

Ser Asn Ala Trp Ala Val Thr Asn His Phe Ser Ile Trp Leu Ala Thr
        35                  40                  45

Ser Leu Ser Ile Phe Tyr Leu Leu Lys Ile Val Asn
    50                  55                  60


<210> SEQ ID NO 75
<211> LENGTH: 72
<212> TYPE: PRT
<213> ORGANISM: Homo sapiens

<400> SEQUENCE: 75
```

-continued

```
Thr Val Thr Met Leu Ala Asn Leu Val Pro Phe Thr Val Thr Leu Ile
1               5                   10                  15

Ser Phe Leu Leu Leu Val Cys Ser Leu Cys Lys His Leu Lys Lys Met
            20                  25                  30

His Leu His Gly Lys Gly Ser Gln Asp Pro Ser Thr Lys Val His Ile
        35                  40                  45

Lys Val Leu Gln Thr Val Ile Ser Phe Leu Leu Leu Cys Ala Ile Tyr
    50                  55                  60

Phe Val Ser Val Ile Ile Ser Ser
65                  70


<210> SEQ ID NO 76
<211> LENGTH: 299
<212> TYPE: PRT
<213> ORGANISM: Homo sapiens

<400> SEQUENCE: 76

Met Ile Thr Phe Leu Pro Ile Ile Phe Ser Ile Leu Val Val Val Thr
1               5                   10                  15

Phe Val Ile Gly Asn Phe Ala Asn Gly Phe Ile Ala Leu Val Asn Ser
            20                  25                  30

Thr Glu Trp Val Lys Arg Gln Lys Ile Ser Phe Ala Asp Gln Ile Val
        35                  40                  45

Thr Ala Leu Ala Val Ser Arg Val Gly Leu Leu Trp Val Leu Leu Leu
    50                  55                  60

Asn Trp Tyr Ser Thr Val Leu Asn Pro Ala Phe Tyr Ser Val Glu Leu
65                  70                  75                  80

Arg Thr Thr Ala Tyr Asn Ile Trp Ala Val Thr Gly His Phe Ser Asn
                85                  90                  95

Trp Pro Ala Thr Ser Leu Ser Ile Phe Tyr Leu Leu Lys Ile Ala Asn
            100                 105                 110

Phe Ser Asn Leu Ile Phe Leu Arg Leu Lys Arg Arg Val Lys Ser Val
        115                 120                 125

Ile Leu Val Val Leu Leu Gly Pro Leu Leu Phe Leu Ala Cys His Leu
    130                 135                 140

Phe Val Val Asn Met Asn Gln Ile Val Trp Thr Lys Glu Tyr Glu Gly
145                 150                 155                 160

Asn Met Thr Trp Lys Ile Lys Leu Arg Arg Ala Met Tyr Leu Ser Asp
                165                 170                 175

Thr Thr Val Thr Met Leu Ala Asn Leu Val Pro Phe Thr Val Thr Leu
            180                 185                 190

Ile Ser Phe Leu Leu Leu Val Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Val Leu Gln Thr Val Ile Ser Phe Phe Leu Leu Cys Ala Ile
225                 230                 235                 240

Tyr Phe Val Ser Val Ile Ile Ser Val Trp Ser Phe Lys Asn Leu Glu
                245                 250                 255

Asn Lys Pro Val Phe Met Phe Cys Gln Ala Ile Gly Phe Ser Cys Ser
            260                 265                 270

Ser Ala His Pro Phe Ile Leu Ile Trp Gly Asn Lys Lys Leu Lys Gln
        275                 280                 285

Thr Tyr Leu Ser Val Leu Trp Gln Met Arg Tyr
```

-continued

```
    290                 295


<210> SEQ ID NO 77
<211> LENGTH: 335
<212> TYPE: PRT
<213> ORGANISM: Rattus sp.

<400> SEQUENCE: 77

Met Met Glu Gly His Ile Leu Phe Phe Phe Leu Val Val Met Val Gln
1               5                   10                  15

Phe Val Thr Gly Val Leu Ala Asn Gly Leu Ile Val Val Val His Ala
            20                  25                  30

Ile Asp Leu Ile Met Trp Lys Lys Met Ala Pro Leu Asp Leu Leu Leu
        35                  40                  45

Phe Cys Leu Ala Thr Ser Arg Ile Ile Leu Gln Leu Cys Ile Leu Phe
    50                  55                  60

Ala Gln Leu Cys Leu Phe Ser Leu Val Arg His Thr Leu Phe Glu Asp
65                  70                  75                  80

Asn Ile Thr Phe Val Phe Ile Ile Asn Glu Leu Ser Leu Trp Phe Ala
                85                  90                  95

Thr Trp Leu Gly Val Phe Tyr Cys Ala Lys Ile Ala Thr Ile Pro His
            100                 105                 110

Pro Leu Phe Leu Trp Leu Lys Met Arg Ile Ser Arg Leu Val Pro Trp
        115                 120                 125

Leu Ile Leu Gly Ser Val Leu Tyr Val Ile Ile Thr Thr Phe Ile His
    130                 135                 140

Ser Arg Glu Thr Ser Ala Ile Leu Lys Pro Ile Phe Ile Ser Leu Phe
145                 150                 155                 160

Pro Lys Asn Ala Thr Gln Val Gly Thr Gly His Ala Thr Leu Leu Ser
                165                 170                 175

Val Leu Val Leu Gly Leu Thr Leu Pro Leu Phe Ile Phe Thr Val Ala
            180                 185                 190

Val Leu Leu Leu Ile Tyr Ser Leu Trp Asn Tyr Ser Arg Gln Met Arg
        195                 200                 205

Thr Met Val Gly Thr Arg Glu Tyr Ser Gly His Ala His Ile Ser Ala
    210                 215                 220

Met Leu Ser Ile Leu Ser Phe Leu Ile Leu Tyr Leu Ser His Tyr Met
225                 230                 235                 240

Val Ala Val Leu Ile Ser Thr Gln Val Leu Tyr Leu Gly Ser Arg Thr
                245                 250                 255

Phe Val Phe Cys Leu Leu Val Ile Gly Met Tyr Pro Ser Ile His Ser
            260                 265                 270

Ile Val Leu Ile Leu Gly Asn Pro Lys Leu Lys Arg Asn Ala Lys Met
        275                 280                 285

Phe Ile Val His Cys Lys Cys Cys His Cys Thr Arg Ala Trp Val Thr
    290                 295                 300

Ser Arg Ser Pro Arg Leu Ser Asp Leu Pro Val Pro Pro Thr His Pro
305                 310                 315                 320

Ser Ala Asn Lys Thr Ser Cys Ser Glu Ala Cys Ile Met Pro Ser
                325                 330                 335


<210> SEQ ID NO 78
<211> LENGTH: 1331
<212> TYPE: DNA
<213> ORGANISM: Rattus sp.
```

-continued

<400> SEQUENCE: 78

```
caggaatcat aaatggctga aactgggcag aactctatgc attatttaaa gaagtcattg      60
gtttgtcatt cttaaaatga tggaagggca tatactcttc ttctttttgg ttgtgatggt     120
gcagtttgtc actggggtct tggcaaatgg cctcattgtg gttgtccatg ctattgactt     180
gatcatgtgg aagaaaatgg ccccgttgga tctgcttcta ttttgcctgg cgacttctcg     240
gatcattctg cagttatgta tattgtttgc acaattgtgt ctattctctt tggtgagaca     300
cactttattt gaggacaata ttacctttgt cttcatcata aatgaactga gtctttggtt     360
tgctacatgg ctcggtgttt tctactgtgc caagattgct accattcctc acccactctt     420
tctgtggctg aagatgagga tatccaggtt ggtaccatgg ctgatcctgg gatctgtgct     480
ctatgtaatt attactactt tcatccatag cagagagact tcagcaatcc ttaaaccaat     540
ttttataagc ctttttccta aaaatgcaac tcaagtcgga acagggcatg ccacactact     600
ctcagtcctg gtccttgggc tcacactgcc gttgttcatc tttactgttg ctgttctgct     660
cttgatatac tccctgtgga attatagcag gcagatgagg actatggtag gcaccaggga     720
gtatagcgga catgctcaca tcagtgcaat gctgtccatt ctatcattcc tcatcctcta     780
tctctcccac tacatggtgg ctgttctgat ctctactcaa gtcctctacc ttggaagcag     840
aacctttgta ttctgcttac tggttattgg tatgtacccc tcaatacact cgattgtctt     900
aattttagga aatcctaagc tgaaacgaaa tgcaaaaatg ttcattgtcc attgtaagtg     960
ttgtcattgt acaagagctt gggtcacctc aaggagccca agactcagtg acttgccagt    1020
gcctcctact catccctcag ccaacaagac atcctgctca gaagcctgta taatgccatc    1080
ctaattgtcc agcctgaggt ttaatcctag gtttggtact atttcaaaga gtaaagttga    1140
tcattaaagc acaacatatg ttggtggatg acatcaaggt ccatatccca gttgtcaatt    1200
gtaaacctca ccttgcaaga tgatgtcact gagaaagcag gacaaatgga gtctaggtcc    1260
ttctgtatga cttgctgcag tatatgtgaa tctataattt tctccaaaaa aacaaaaaaa    1320
aaaaaaaaaa a                                                          1331
```

<210> SEQ ID NO 79
<211> LENGTH: 333
<212> TYPE: PRT
<213> ORGANISM: Rattus sp.

<400> SEQUENCE: 79

```
Met Phe Ser Gln Lys Thr Asn Tyr Ser His Leu Phe Thr Phe Ser Ile
1               5                   10                  15

Ile Phe Tyr Val Glu Ile Val Thr Gly Ile Leu Gly Asn Gly Phe Ile
            20                  25                  30

Ala Leu Val Asn Ile Met Asp Trp Leu Lys Arg Arg Arg Ile Ser Thr
        35                  40                  45

Ala Asp Gln Ile Leu Thr Ala Leu Ala Leu Thr Arg Leu Ile Tyr Val
    50                  55                  60

Trp Ser Val Leu Ile Cys Ile Leu Leu Leu Phe Leu Cys Pro His Leu
65                  70                  75                  80

Ser Met Arg Pro Glu Met Phe Thr Ala Ile Gly Val Ile Trp Val Val
                85                  90                  95

Asp Asn His Phe Ser Ile Trp Leu Ala Thr Cys Leu Gly Val Phe Tyr
            100                 105                 110

Phe Leu Lys Ile Ala Ser Phe Ser Asn Ser Leu Phe Leu Tyr Leu Lys
        115                 120                 125
```

-continued

```
Trp Arg Val Lys Lys Val Val Leu Met Ile Ile Leu Ile Ser Leu Ile
    130                 135                 140

Phe Leu Met Leu Asn Ile Ser Ser Leu Gly Met Tyr Asp His Phe Ser
145                 150                 155                 160

Ile Asp Val Tyr Glu Gly Asn Met Ser Tyr Asn Leu Val Asp Ser Thr
                165                 170                 175

His Phe Pro Arg Ile Phe Leu Phe Thr Asn Ser Ser Lys Val Phe Leu
            180                 185                 190

Ile Ala Asn Ser Ser His Val Phe Leu Pro Ile Asn Ser Leu Phe Met
        195                 200                 205

Leu Ile Pro Phe Thr Val Ser Leu Val Ala Phe Phe Val Leu Phe Leu
    210                 215                 220

Ser Leu Trp Lys His His Lys Lys Met Gln Val Asn Ala Lys Gly Pro
225                 230                 235                 240

Arg Asp Ala Ser Thr Met Ala His Thr Lys Ala Leu Gln Ile Gly Phe
                245                 250                 255

Ser Phe Leu Leu Leu Tyr Ala Ile Tyr Leu Leu Phe Ile Ile Thr Gly
            260                 265                 270

Ile Leu Asn Leu Asp Leu Met Arg Cys Ile Val Ile Leu Leu Phe Asp
        275                 280                 285

His Ile Ser Gly Ala Val Phe Ser Ile Ser His Ser Phe Val Leu Ile
    290                 295                 300

Leu Gly Asn Ser Lys Leu Arg Gln Ala Thr Leu Ser Val Leu Pro Cys
305                 310                 315                 320

Leu Arg Cys Arg Ser Lys Asp Met Asp Thr Val Val Phe
                325                 330
```

<210> SEQ ID NO 80
<211> LENGTH: 2438
<212> TYPE: DNA
<213> ORGANISM: Rattus sp.

<400> SEQUENCE: 80

```
attttgctcc actattttgc tcttctgcag taacacagac cacaaaacaa tggagccaat     60

gggtcaagag ctgaaacttc aggaagtggg agccaaattt tctttgtgat aggttggcat    120

atgagaattc attatttgat gcagcttctg aaaactggat gtgaaatact ggatgaagca    180

gaggtgatga cccctttgaa attaaaaagc caagatgttc atggagaaat tataaaacaa    240

tatctgggaa atttgatgct tcctaatcgg gtgtaaatgg gattttaaat gatgaacatt    300

ttgaatttcc aatgaccatt atgtaaagtt tttaaacaca gtagagacat cataaattga    360

agcatgttct cacagaaaac aaactacagc catttgttta ctttttcaat tattttttat    420

gtggaaatag taacaggaat cttaggaaat ggattcatag cactagtgaa tatcatggac    480

tggctcaaga ggaggaggat ctctactgca gatcagattc tcactgcttt ggcccttacc    540

agactcattt atgtgtggtc tgtactcatt tgtatattgt tactatttct gtgcccacat    600

ttgtctatga gaccagaaat gtttacagcg ataggtgtta tctgggtagt ggataaccac    660

ttcagcatct ggcttgctac atgtcttggt gtcttttatt tcctcaaaat agccagtttt    720

tctaactctt tgtttcttta cctaaagtgg agagttaaaa aagtggtttt aatgataata    780

ctgatatcac tgattttctt gatgttaaac atttcatcat tagggatgta tgatcatttc    840

tcaattgatg tttatgaagg taatatgtct tataatttgg tggattcaac acattttccc    900

agaattttct tattcacaaa ctcatctaag gtcttcttaa tcgccaattc atcccatgtt    960
```

-continued ttcttaccca tcaactcact cttcatgctc ataccettca cagtttccct ggtagctttt 1020
ttcgtgctct ttctctcact gtggaagcat cacaagaaga tgcaggtcaa tgccaaagga 1080
cccagagatg ccagcaccat ggcccacaca aaagccttgc aaattgggtt ctccttcctc 1140
ctgctgtatg caatatactt acttttcatt atcacaggaa ttttgaacct tgacttgatg 1200
agatgtatag taatactttt atttgaccac atatctggag cagttttttc tataagccac 1260
tcatttgtgc tgattctggg aaacagtaag ctgagacaag ccactctttc tgtgctgcct 1320
tgtcttaggt gccggtccaa agatatggac actgtcgttt tctaataaat tccagagtac 1380
attatgcaaa atcttgaggg tgatcagttc atagaaaaag taatcttaga ggggaaaata 1440
aaatattggg gcttcaaatg ttggatgggt aatacatagg aaggcaggac aaggatgaag 1500
gagactagca ttatataagt gatttcacag gggaaatggg aaagagggct tttatataat 1560
gaagaagaag ataaatgatg aaggatgagg aagagttaaa tatgtaaaat gacaatagag 1620
atggcatcat gccgttttaa gaaatttgga atgcatatgt atgtttatat attttttaat 1680
ttttattgaa tatatttatt tacattttaa atgttatcct gtttccccca cccaacctcc 1740
cacctcttcc cacctccttg ccctgacatt cccctgcact ggggaatcca gccttgacag 1800
gaccaagggc ttctcctccc tttgttgcca acaaggccat tctttgctac atgtgcagca 1860
ggagccatgg atctgtctat gtgtactctt tggatggtgg tttagtccct gggagctctt 1920
gttggttggt attgttgttc ttatggtgtt gcaactccct tcagctcctt caatccttcc 1980
tgtaactcct ccaatgtgga ccctgttctc agtccaatgg ttgactatga gcattcacct 2040
ctgtgattgt catgctctgg cacagcttct cagaagacag ctacatcagt ctcctataag 2100
agtgcacttc atggcatcag caatgttgtc ttgatttggt gtctgtatgt atatgggctg 2160
gatcccaggt ggggcaggcg ctgaatggtc attccttcag tctttgctcc aaactttgtc 2220
tttatatctc ctatgaatat ttttgttccc ccttataaga atgactgaag tatccacact 2280
ttggccatcc ttcttcatga gcttcatgtg gtctgtgaat tgtacattgt gtaatccaag 2340
cttttgggct aatatccaat tatagtgagt gcataccaaa aaaaaaaaaa aaaaaaaaaa 2400
aaaaaaaaaa aaaaaaaaaa aaaaaaaaaa aaaaaaaa 2438

<210> SEQ ID NO 81
<211> LENGTH: 299
<212> TYPE: PRT
<213> ORGANISM: Rattus sp.

<400> SEQUENCE: 81

Met Val Pro Thr Gln Val Thr Ile Phe Ser Ile Ile Met Tyr Val Leu
1 5 10 15

Glu Ser Leu Val Ile Ile Val Gln Ser Cys Thr Thr Val Ala Val Leu
20 25 30

Phe Arg Glu Trp Met His Phe Gln Arg Leu Ser Pro Val Glu Ile Ile
35 40 45

Leu Ile Ser Leu Gly Ile Ser His Phe Cys Leu Gln Trp Thr Ser Met
50 55 60

Leu Tyr Asn Phe Gly Thr Tyr Ser Arg Pro Val Leu Leu Phe Trp Lys
65 70 75 80

Val Ser Val Val Trp Glu Phe Met Asn Val Leu Thr Phe Trp Leu Thr
85 90 95

Ser Leu Leu Ala Val Leu Tyr Cys Val Lys Val Ser Ser Phe Ser His
100 105 110

-continued

```
Pro Val Phe Leu Trp Leu Arg Leu Lys Ile Leu Lys Leu Val Leu Trp
        115                 120                 125

Leu Leu Leu Gly Ala Leu Ile Ala Ser Cys Leu Ser Ile Ile Pro Ser
    130                 135                 140

Val Val Lys Tyr His Ile Gln Met Glu Leu Leu Thr Leu Asp His Leu
145                 150                 155                 160

Pro Lys Asn Ser Ser Leu Ile Leu Arg Leu Gln Met Phe Glu Trp Tyr
                165                 170                 175

Phe Ser Asn Pro Phe Lys Met Ile Gly Phe Gly Val Pro Phe Leu Val
            180                 185                 190

Phe Leu Ile Ser Ile Ile Leu Leu Thr Val Ser Leu Val Gln His Trp
        195                 200                 205

Gly Gln Met Lys His Tyr Ser Ser Ser Ser Ser Ser Leu Arg Ala Gln
    210                 215                 220

Cys Thr Val Leu Lys Ser Leu Ala Thr Phe Phe Ile Phe Phe Thr Ser
225                 230                 235                 240

Tyr Phe Leu Thr Ile Val Val Ser Phe Ile Gly Thr Val Phe Asp Lys
                245                 250                 255

Lys Ser Trp Phe Trp Val Cys Glu Ala Val Ile Tyr Gly Leu Val Cys
            260                 265                 270

Ile His Phe Thr Ser Leu Met Met Ser Asn Pro Thr Leu Lys Lys Ala
        275                 280                 285

Leu Arg Leu Gln Phe Trp Ser Pro Glu Ser Ser
    290                 295
```

<210> SEQ ID NO 82
<211> LENGTH: 6552
<212> TYPE: DNA
<213> ORGANISM: Rattus sp.
<220> FEATURE:
<221> NAME/KEY: modified_base
<222> LOCATION: (4085)..(4085)
<223> OTHER INFORMATION: n is a, c, g, or t
<220> FEATURE:
<221> NAME/KEY: modified_base
<222> LOCATION: (4087)..(4087)
<223> OTHER INFORMATION: n is a, c, g, or t
<220> FEATURE:
<221> NAME/KEY: modified_base
<222> LOCATION: (4101)..(4101)
<223> OTHER INFORMATION: n is a, c, g, or t
<220> FEATURE:
<221> NAME/KEY: modified_base
<222> LOCATION: (4144)..(4144)
<223> OTHER INFORMATION: n is a, c, g, or t
<220> FEATURE:
<221> NAME/KEY: modified_base
<222> LOCATION: (4153)..(4153)
<223> OTHER INFORMATION: n is a, c, g, or t
<220> FEATURE:
<221> NAME/KEY: modified_base
<222> LOCATION: (4203)..(4203)
<223> OTHER INFORMATION: n is a, c, g, or t

<400> SEQUENCE: 82

```
gcatggtgcc aacccaagtc accatcttct ctatcatcat gtatgtgctt gagtccttag      60

tcataattgt gcaaagttgc acaacggttg cagtgctgtt cagagagtgg atgcactttc     120

aaagactgtc gccggtggaa ataattctca tcagcctggg catttcacat ttctgtctac     180

agtggacatc gatgctgtac aactttggta cctactctag gcctgtcctt ttattttgga     240

aggtatcggt cgtctgggag ttcatgaacg ttttgacatt ctggctaacc agtttgcttg     300
```

-continued

```
ctgtcctcta ctgtgtcaag gtctcttcct tctctcaccc cgtcttcctc tggctgaggt    360
tgaaaatttt gaaactggtt ctctggttgc tattgggcgc tctgatagct tcttgtttgt    420
caatcatccc ttctgttgtt aaatatcata tccagatgga attactcacc ctagatcatt    480
tacccaaaaa cagttctttg attctaagac tgcaaatgtt cgagtggtat ttttctaatc    540
ctttcaaaat gattgggttt ggcgttcctt tcctcgtgtt cctgatttct atcatcttac    600
tcacagtctc gctggtccag cattgggggc agatgaaaca ctacagcagc agcagctcca    660
gcctgagagc tcagtgcact gttctgaagt ctcttgccac cttcttcatc ttcttcacat    720
cctattttct gactatagtc gtctccttta ttggcaccgt gtttgataag aagtcatggt    780
tctgggtctg cgaagctgtc atctatggtt tagtctgtat tcacttcact tccctgatga    840
tgagcaaccc tacactgaaa aaagcactca ggttgcagtt ctggagccca gagtcttcct    900
aaggcaggga attcagtgaa gcctctgggg taaggaggct ttgcattggc acagttctta    960
gagtgaaatg caaacgtgga cacgaacttc attctctttc atgtccacag atggatggat   1020
ctataaatca tcaccaatct tccctgtatt ctgacccatc cttttcctgt cctatccata   1080
gtccccaggt tggttttgat ttttctcatg atcacacctt agctttagcc accgttgcaa   1140
tatcaaacat gatctatatg ttacagccaa aatcattctc acaattgtca attgcttcac   1200
aaattcagat aaatccccct tcctgtcagg aatgtattgt ctgtgcattc aatgctcacc   1260
atgctaagcc attcattccc ttcctaactt gagtttaaga agaaaatgtc ttactgttgc   1320
ccatgtccta ttgtgctgct tctggatgtt ttatgcagtg atttagacac acgcccttgc   1380
ctgtctccaa atactggccc tttattcctt tataagtcta gtagaaaatg aactcgtctt   1440
tacttcattg acgaagacat tgtattcttc cccaaaatag tgtttaacta ctctagtctc   1500
atccataata tccctaaata tcagtgattt cagtgagtaa aacctgacaa cagttattgc   1560
tttgactctt aattcaattg tgctgtaaca tagaggaaac attctagaac atttccatat   1620
taatttgtgc ttgtagcaaa ccaaaattct ccccagttgg gtaaaaatat caaaagcaca   1680
gagtaatcaa ttttgaaatc actcagaaga catcattgtt ctatatatgt ttttttttaaa  1740
cttccctcta acaagtatca gatctttgcc tttacagggt ctggtcttac catgactata   1800
ttttatcacc atgacctatt ttctcttcat ctctttgttt tcactaactc agtagcaacc   1860
aaatatcaca ttaatagcta actctgggca cttatttctc agcctttatc tattccagac   1920
actttcaatg tatttctgct aaacacaatg acatctcttt ttgtgttcta acgacaagga   1980
atcataactt tccaactttt atacatggta gacatatttg gtgaacttaa cttctgactc   2040
tttctttaga agactgaaac tactccggaa agcaagcctt ctgatggaga aatagatacg   2100
ggtatcgtga ttcattgtga aagtgaattc cggtgcctgg aaagaaatgg atattttttt   2160
ttctcttgag tgtgtcactc tgacatatgt tccatgttga atccatattt gatactgata   2220
gcatgaatgt aagtaaagca tgtatgtaag taaagactgc taccaaaact tcgattcaac   2280
tttcctcagc agtatccctg atattgcata agaaagaaaa aacacgctgt cctacttgaa   2340
gaaggacgtg ttccatgcaa tgtggatgtg tcccaggcta cattggctca actgcagctg   2400
aaggtgggat gggaaatggt atagttagta atgtctgctg agctgtctca ctggaaagga   2460
ttctgagcag agtaaatgta agcaatgtgg ccaaggtctc ctaggaatgg gttgtaagct   2520
tgtaaggagt tgggttgtaa gagtttggga tcctttcaga atggattgag caagagccac   2580
tgaaacttgg actatacctt tgttatttgt atctaaatcc agaagggtct ttgcatgttc   2640
caaaatctca gatagctgga aggaagaagg actgttctct ttacaagtat ataaatagag   2700
```

-continued

```
aatgagctaa aaaggacccc ctcacccccg ccgtcacaca caggaatact attccagaaa   2760
ctagggagta tttttagtgt tctcactatt tccctttgaa aaaagtgcaa tggaaaactt   2820
atccatgaca tacatgaggt tggagtgata aaaacagctg aaggaagagg aagtctgaaa   2880
aaagatggaa acagcaatga tgcttgtcct atatatgtgt gacacccact agttcccaag   2940
gaaaccttac atccattatc tcatttcaag ctggaaggac aagtcaagat cactcaaccg   3000
acccagctgg aaaacagacc taagaatgtt aaactcatac tgatggttat ttctcactct   3060
aaagtcaatg caaatggata gcaaacaaag ggctatttt tttaagggac cagagggttt   3120
caatctagaa tcagagaaaa gataaaaagg gagatgctat agaaaaacaa tagagaagat   3180
gtggccaaga acaaggaaaa tctccagtta gcttggcact taggggccaa catgtttctg   3240
ttgttcggtc ttcaatactg tattgcatgt tgggctcact atgttttagt tgtgagtggg   3300
ttgtgcttcc tggaattaag aaaggtctgt ttctagattt caggtacaaa tgtttagaag   3360
cccattggta gcatcagtga aattaggaaa aaactgtgag cactgctggc tggacttggc   3420
aaagtcattc actatttaca catcaaatta ttagcaactt gaaagtaaat ctttgctcat   3480
catccagtgg cccccatgat cctggtgaat gacttgtaat actgtggaga ctggcaacga   3540
cggtgaattc ctagtaacac ttaccataga atctgttcat aattagactc gcccagattt   3600
tagttgctag agaacaatct ttctccttta cccacattcc tactgagtag gatgcatagg   3660
ttcggaaacc cccatggcat cgtttgactc ctcctggtag tcaagagagt ccagtcacca   3720
gtctccgaaa cacctgccaa gtcctaactc ccaacagtct acagtgtaaa cctcagtgtt   3780
tgcatgaggt ttatgtatct ccttaccatt tcctaaatgt caatacccgt gcacaggata   3840
tttgcatagg ctgcctccaa gcctgggaaa cactctcctc ctcgcatttg ctgggtttca   3900
cctttccaat tcagtgtgcc ctttaaaagg cactgctttt ctaggcccac cactattgct   3960
gctcacgcat gaacatcaaa tctaccacag gcttttgcct ctcagaatta ttcttctttc   4020
tactatgcaa tgtggtatcc atgagaactt tgtcacattg tcaaattcta cctttgtttt   4080
aatgngngcc tttgtaatag ngactatgcc cagaaattaa attatagtaa gatgggtaac   4140
aacncttcaa ttntggaatt tataattaaa taaatattat gtaatattat gacttattat   4200
aangtcaatc tactgtaccc tactcctact aggaatgcaa agacaaatag caatgtgatc   4260
agcatgtgct ctttcacaag atcatattgt gcatgttgct gatgatgccc acagtgcatc   4320
tatcagaata tctctgatca tttttttttt tttgcttttg agaagccccg gttggtgctg   4380
ggatgcttca tagcaggtcc accatagaca catgcttaga ggaaagctgc ctctctctct   4440
tcattcccaa ggaacagtaa aagcagaaaa ggctcttatg ttctaaagaa cagaaaatag   4500
cctgcatttc aactacctcc tgttcagaag gcaccgaaac acaccaccaa gcaagacacc   4560
cctttacttt ctcctgcttc cctcaatttg atgatcattt ggaaataaga agaaagaaaa   4620
agatgtggaa gccaattaaa aacagtcttg tctatctccc tggtgagctc tcaacttctt   4680
agtcagacca aagtaggtga aaaaataata atttttaatt tggtatgaga gtcatgttta   4740
ggctgaaaat cttaaaaaat cttagcataa aaacattttc ccctagaccc atgaaattta   4800
taatattatc tgtggttgag aaaggctagt tatagaaaaa tgtttagaat cagaatattt   4860
tgagggctct ttttttgttt tgcctaatca ttacatttgt tataagaagt ctaaaagttg   4920
gtatgctaca ggtcttgtca tattttctct gaggttgagt gccaagtagt ctgcattgtg   4980
tttaaatcct gcttaaaatt atcccaagac aatataactt ctcaggagct aagccaaggg   5040
```

-continued

```
ccccttttcag actaccttag tcctctctca ccgttgtcac cgtggctcat acatcagaat   5100

cctgagggag catcatgaaa tctaaggctt tacaacagaa tctttctatc cctggtagaa   5160

atcttttaac cttgggtttt attctcatgc cattctgatg ctcgtattta aattttatgt   5220

gttttttcat atgttcttgc atttctatcg ttaaattatg gtgacatact ttcaaatgct   5280

ttgttatttt aaaaagggac aaagagagat agaaagacag ggaaagatag acagaggctt   5340

gcctaataca gtcaagaaag aagctatcaa aagtatttag caatacaaca tttatgatat   5400

attcataact gttaaccatt tttaatattc taaaatttca cttttgtttc agaaatgtat   5460

attaagagaa tctgagaaac attttttttct catagatgta gaaaaacaca caaaataagg   5520

tataacacat ttaagtgatt gaaaataaaa acaaaagctt gcaaacagga ggaaaagtac   5580

attgtaggct ttcgacatgg agctgctact aggacccagg acttgtttat catttatttg   5640

ccaagtccca caaactcagg gcaatacatc tctgagacag tttcctatat tttaataaaa   5700

cttccaaaat tgatactcag tgtgaattgg ctagctttaa tggcagtcat tggataaaca   5760

attccaatgc caaatttccc taagttgata tatttgatta atatgtatat taaaacatca   5820

ggctatccat cggttggatc aaatacattc tttagggatc cattcttttc cttaaatttg   5880

acttatatgt ggattctttt cacaataaat aagtaaatga gcatttattt taaaactatt   5940

ttagacggaa ctgaattaca gccaaggtag tcaaaatgac tgagaataat cacttacata   6000

tttacaaggg aaagtgactc ttcagattta agtttaaaat tagaagagag ataaatttca   6060

caagctttca ctcctaaggc taaagatagg ctgtgtaggt agttatttct gagcacattg   6120

gcacatcacc attgtcagta cttgagggtt tgaatgaagc tcactcaaag aacttggaaa   6180

gaaggtggtc ttctgacatc aatcaagaaa caagctttcc tccctacttc ttccctaaat   6240

gcaacaacct aagaattatc cacaagatgg atggcgcaag ggttcctcaa tcaatttcag   6300

gatgtacatc aatgcgcagc ctatactaca ccgaaaagga agcgcatggg tcttaaaaag   6360

taaaggggat atcaaaaaat tcgcaaccaa acaaaaagtg gcacacattt aagctaggtc   6420

tatgtttggt cagttacacc tggagaaggg ggacatttgg tcagctcatt cgaacactgt   6480

caagtcctac caacaattcc tctatgctat tacccattaa acctcaggtc tcatcgaaaa   6540

aaaaaaaaaa aa                                                        6552
```

<210> SEQ ID NO 83
<211> LENGTH: 308
<212> TYPE: PRT
<213> ORGANISM: Rattus sp.

<400> SEQUENCE: 83

```
Met Leu Ser Ala Ala Glu Gly Ile Leu Leu Cys Val Val Thr Ser Glu
1               5                   10                  15

Ala Val Leu Gly Val Leu Gly Asp Thr Phe Ile Ala Leu Ala Asn Cys
            20                  25                  30

Met Glu Tyr Ala Lys Asn Lys Lys Leu Ser Lys Ile Gly Phe Ile Leu
        35                  40                  45

Ile Gly Leu Ala Ile Ser Arg Ile Gly Val Val Trp Ile Ile Ile Leu
    50                  55                  60

Gln Gly Tyr Met Gln Val Phe Phe Pro His Ile Leu Thr Phe Gly Asn
65                  70                  75                  80

Ile Thr Glu Tyr Ile Thr Tyr Ile Trp Val Phe Leu Asn His Leu Ser
                85                  90                  95

Val Trp Phe Ala Thr Asn Leu Asn Ile Leu Tyr Phe Leu Lys Ile Ala
```

-continued

```
            100                 105                 110

Asn Phe Ser Asn Ser Val Phe Leu Trp Leu Lys Ser Arg Val Arg Val
        115                 120                 125

Val Phe Ile Phe Leu Ser Gly Cys Leu Leu Thr Ser Trp Leu Leu Cys
    130                 135                 140

Phe Pro Gln Phe Ser Lys Met Leu Asn Asn Ser Lys Met Tyr Trp Gly
145                 150                 155                 160

Asn Thr Ser Trp Leu Gln Gln Gln Lys Asn Val Phe Leu Ile Asn Gln
                165                 170                 175

Ser Leu Thr Asn Leu Gly Ile Phe Phe Phe Ile Ile Val Ser Leu Ile
            180                 185                 190

Thr Cys Phe Leu Leu Ile Val Phe Leu Trp Arg His Ile Arg Gln Met
        195                 200                 205

His Ser Asp Gly Ser Gly Leu Arg Asp Leu Asn Thr Glu Ala His Val
    210                 215                 220

Lys Ala Met Arg Val Leu Ile Ser Phe Ala Val Leu Phe Ile Leu His
225                 230                 235                 240

Phe Val Gly Leu Ser Ile Gln Val Leu Cys Phe Phe Leu Pro Gln Asn
                245                 250                 255

Asn Leu Leu Phe Ile Thr Gly Leu Ile Ala Thr Cys Leu Tyr Pro Cys
            260                 265                 270

Gly His Ser Ile Ile Leu Ile Leu Gly Asn Lys Gln Leu Lys Gln Ala
        275                 280                 285

Ser Leu Lys Ala Leu Gln His Leu Thr Cys Cys Glu Thr Lys Arg Asn
    290                 295                 300

Leu Ser Val Thr
305


<210> SEQ ID NO 84
<211> LENGTH: 3449
<212> TYPE: DNA
<213> ORGANISM: Rattus sp.

<400> SEQUENCE: 84

tggttccatc acatgacaat aggcttgaaa aacttgcaga tagagaagac ataacccctc     60

caacaagaag ccaacatatg ggacattctc cagcagataa tttataacag atgcaacggg    120

agcaacttcg agatctgcaa agatgctgag tgcagcagaa ggcatcctcc tttgtgttgt    180

cactagtgag gcagtgctgg gggttttagg agacacattc attgcacttg caaactgcat    240

ggagtatgcc aagaacaaga agctctctaa gattggtttc attctcattg gcttggcgat    300

ttccagaatt ggtgtcgtat ggataataat tttacagggg tatatgcaag tatttttttcc    360

acacatactt acctttggaa acataactga atatattact tacatatggg tgtttctcaa    420

tcacttaagt gtctggtttg ctaccaacct caatatcctc tactttctaa agatagcaaa    480

tttttccaac tctgtatttc tctggctgaa aagtagagtc cgtgtggttt ttatctttct    540

gtcaggatgc ttacttacct cgtggttact atgttttcca caattttcaa agatgcttaa    600

caacagtaaa atgtactggg gaaacacgtc ttggctccag cagcagaaaa atgtcttcct    660

tattaaccaa agtttaacca atctgggaat cttctttttc attattgtat ccctgattac    720

ctgcttcctg ttgattgttt tcctctggag acacatcagg caaatgcact cagatggttc    780

aggactcaga gacctcaaca cagaagctca tgtgaaagcc atgagagttc taatatcttt    840

tgcggtactc tttatcctgc atttcgtagg tctttccata caagtgctat gctttttttct    900
```

-continued

```
gccacaaaac aacctactct ttataactgg tttgatagcc acatgcctct atccctgtgg    960
tcactcaatc atcttaattc taggaaacaa gcagctgaag caagcctcct tgaaggcact   1020
gcagcactta acgtgctgtg agacaaaaag aaatctctca gtcacataaa tgggtttgcc   1080
aattaatatc tgccatgtta ttccactgat ttttacctgt tagtttctct gtgtctctgt   1140
ttagtttctg tttccatgat ctgtccattg atgagcgtgg ggtgttgaaa tctccgacta   1200
ttgttgtgtg agatgaaatg tgtgctttga gctttagtaa gatttctttt gtgaatgtag   1260
gtgcttttgc atttggtgca tagatattta agattgagag ttcagcttgg tggatttttc   1320
ctttgatgaa tatgaagtgt ccttgcttat ctttttgat gacttttgat tgaacgtcaa   1380
ttttattgga tattagattg gcaactcaag attgcttctt gaggtcattt gcttggaaag   1440
ttgtttttca gccatttact ctgaggtagt gtctgtcttt gtctctgagg tgtgtttcct   1500
gcattcagca aaatgctggg tcctctttac atatccagtt tgttagtcta tgtcttttta   1560
ttggggaatt gagtccattg atgttgagag atattaatga atagtgatca ttgcttcctg   1620
ttattttcgt tgttagatgt ggaattatgt ttgtttgtct ctcttttggt tttattgcaa   1680
ggaaattata tacttgcttt ctgtatggtg tagtttctct ccttgtgttg cagttttcct   1740
tctattatcc tttgtagggc tagatttgaa gaaagatatt gcataagctt ggttttgtca   1800
tgggatatct tggtttctcc atctatgtta attgagagtt ttgcaggata tagtagcctg   1860
ggatgacatt tgtgttctct tagggtctgt atgacatctg tccaaaatct tctggctttc   1920
atagtctctg gtgagaaatc ggatgtaatt ctcataagtc tgccattata tgtcacttga   1980
ccttttttccc ttattgcttt ttatgttctt tctttgtttt gtgcatttgg tgttctgatt   2040
attatgtgat gtgaggtatt tctcttctgg tcaaatctat ttggagttct gtaggcttct   2100
tgtatgttta tgggcatctc tttctttagg ttatggatgt tttcttctat aattttgttg   2160
aatatatcta ctgtcccttt aagttaggag ccttcacttt cttctatacc tgttatcctt   2220
aggtttaatc ttctcactgg atttcctcga tgttttggac taggaacttt ttgcatttta   2280
cattatcttt gacaggtatt tcaatgtttt ctatggtatc ttctgccact gagattctct   2340
cttctagctc ttgtataatg ttggtgatgc ttgtacctgt gactccttgt ttcttcctta   2400
ggttttctat ctccagggtt gtctcccttt gtgctttttt tattgcttct atttccattc   2460
taaatcctgg atggttttgt tcaattcctt cacctctttg gttgtatttt cctgtaattc   2520
tttcagggat ttttgtgttt cctctttaag ggcttctact tgtttacttg tgttgtcctg   2580
tatttcttta aggtagttat ttatgtcctt cttgaagtcc tccatcatta tcaaaaaatg   2640
tgatttttaa atataaacct tgcttttctg gtgtgtttgg atgtcaagta ttttctttgc   2700
tgggagaact gggctctgat aatgccaagt tgtttgattt ctgttgctta gtttcctgtt   2760
cttgcctctc gccattgggt tttctctggt gtttgcttat cttgctgttt ctgagagtgg   2820
cttgacactc ttgtaggcat ctgtgtcagg cctcctgtag aactgtttcc ctgttttctt   2880
tcagcctttt ctgagaacag gtgctctgat ctcaggtgtg taggcattcc tggtgactat   2940
ctttcagctt taggagcagg caggaatcag aagggtcctg tccctgactg ctcctagatc   3000
cttgcaccca gggggcacag ttagcactag gcaattccct cttgtgtagg gaatgtgggt   3060
agaggatagt cgcctctgat ttctcaggaa tgtctgcact tctgaaagtc cagccctctc   3120
ccccacagga tttaggtgca gggagctgtt tgaccacttc aattcagtcc tgggtgtaga   3180
ccagaaccac aggtaaaaaa gaatgacttc attaaattag cagacaaatg ggtggaacta   3240
gaaaatgtca tcctgggctg gagagatggc tcagtggttc agaccactgg ctgctcttcc   3300
```

-continued

```
agaggtcctg agttcaattc ccaacaacta tatggtggct accaaccatt acaatgagat   3360

cagatgccct cctcttgtgt atctgaagag agtgacagtg tacttacata cataaaataa   3420

ataaataaat ctaaaaaaat gttaaaaaa                                     3449


<210> SEQ ID NO 85
<211> LENGTH: 309
<212> TYPE: PRT
<213> ORGANISM: Rattus sp.

<400> SEQUENCE: 85

Met Leu Gly Ala Met Glu Gly Val Leu Leu Ser Val Ala Thr Ser Glu
1               5                   10                  15

Ala Leu Leu Gly Ile Val Gly Asn Thr Phe Ile Ala Leu Val Asn Cys
            20                  25                  30

Met Asp Cys Thr Arg Asn Lys Asn Leu Tyr Asn Ile Gly Phe Ile Leu
        35                  40                  45

Thr Gly Leu Ala Ile Ser Arg Ile Cys Leu Val Trp Ile Leu Ile Thr
    50                  55                  60

Glu Ala Tyr Ile Lys Ile Phe Ser Pro Gln Leu Leu Ser Pro Ile Asn
65                  70                  75                  80

Ile Ile Glu Leu Ile Ser Tyr Leu Trp Ile Ile Thr Ser Gln Leu Asn
                85                  90                  95

Val Trp Phe Ala Thr Ser Leu Ser Ile Phe Tyr Phe Leu Lys Ile Ala
            100                 105                 110

Asn Phe Ser His His Ile Phe Leu Trp Leu Lys Arg Arg Ile Asn Ile
        115                 120                 125

Val Phe Ala Phe Leu Ile Gly Cys Leu Leu Met Ser Trp Leu Phe Ser
    130                 135                 140

Phe Pro Val Val Val Lys Met Val Lys Asp Lys Lys Met Leu Tyr Ile
145                 150                 155                 160

Asn Ser Ser Trp Gln Ile His Met Lys Lys Ser Glu Leu Ile Ile Asn
                165                 170                 175

Tyr Val Phe Thr Asn Gly Gly Val Phe Leu Leu Phe Ile Ile Met Leu
            180                 185                 190

Ile Val Cys Phe Leu Leu Ile Ile Ser Leu Trp Arg His Ser Lys Trp
        195                 200                 205

Met Gln Ser Asn Glu Ser Gly Phe Arg Asp Leu Asn Thr Glu Val His
    210                 215                 220

Val Lys Thr Ile Lys Val Leu Leu Ser Phe Ile Ile Leu Phe Ile Leu
225                 230                 235                 240

His Leu Ile Gly Ile Thr Ile Asn Val Ile Cys Leu Leu Val Pro Glu
                245                 250                 255

Asn Asn Leu Leu Phe Val Phe Gly Leu Thr Ile Ala Phe Leu Tyr Pro
            260                 265                 270

Cys Cys His Ser Leu Ile Leu Ile Leu Ala Asn Ser Arg Leu Lys Arg
        275                 280                 285

Cys Phe Val Arg Ile Leu Gln Gln Leu Met Cys Ser Glu Glu Gly Lys
    290                 295                 300

Glu Phe Arg Asn Thr
305


<210> SEQ ID NO 86
<211> LENGTH: 1127
<212> TYPE: DNA
```

-continued

<213> ORGANISM: Rattus sp.

<400> SEQUENCE: 86

```
aagagatttc agatactacc acaaacattt tttaaatata tgtaagtctt taaagaaaga     60
agggaaagcc actcctttat tgagcagcca atagattgcc atcttaaaat tctgtggcag    120
aagctatttt aaagatctgc gaagatgctg ggtgcaatgg aaggtgtcct cctttcagtt    180
gcaactagtg aggctttgct tggcattgta gggaacacat tcattgcact tgtgaactgc    240
atggactgta ccaggaacaa gaatctctat aatattggct tcattctcac tggcttggca    300
atttccagaa tctgcctcgt gtggatctta atcacagagg catacataaa aatattctct    360
ccacagttgc tgtctcctat caacataatt gaactcatca gttatctatg gataattacc    420
agtcaattga atgtttggtt tgctaccagc ctcagtatct tttatttcct caagatagca    480
aatttttccc accacatatt tctctggtta aaaagaagaa ttaatatagt ttttgccttc    540
ctgatagggt gcttacttat gtcatggcta ttttctttcc cagtagttgt gaagatggtt    600
aaagataaaa aaatgctgta tataaactca tcttggcaaa tccacatgaa gaaaagtgag    660
ttaatcatta actatgtttt caccaatggg ggagtatttt tactttttat aataatgtta    720
attgtatgtt ttctcttaat tatttccctt tggagacaca gcaagtggat gcaatcaaat    780
gaatcaggat tcagagatct caacacagaa gttcatgtga aaacaataaa agttttatta    840
tcttttatta tcctttttat attgcattta attggtatta ccatcaatgt catttgtctg    900
ttagtcccag aaaataactt gttattcgtg tttggtttga cgattgcatt cctctatccc    960
tgctgccact cacttatcct aattctagca aacagccggc tgaaacgatg ctttgtaagg   1020
atactgcaac aattaatgtg ctctgaggaa ggaaaagaat tcagaaacac atgacagtct   1080
ggaagacaaa caatcagaaa tagtaagtga aaaaaaaaaa aaaaaaa                 1127
```

<210> SEQ ID NO 87
<211> LENGTH: 297
<212> TYPE: PRT
<213> ORGANISM: Rattus sp.

<400> SEQUENCE: 87

```
Glu Ala Leu Val Gly Ile Leu Gly Asn Ala Phe Ile Ala Leu Val Asn
1               5                   10                  15

Phe Met Gly Trp Met Lys Asn Arg Lys Ile Thr Ala Ile Asp Leu Ile
            20                  25                  30

Leu Ser Ser Leu Ala Met Ser Arg Ile Cys Leu Gln Cys Ile Ile Leu
        35                  40                  45

Leu Asp Cys Ile Ile Leu Val Gln Tyr Pro Asp Thr Tyr Asn Arg Gly
    50                  55                  60

Lys Glu Met Arg Ile Ile Asp Phe Phe Trp Thr Leu Thr Asn His Leu
65                  70                  75                  80

Ser Val Trp Phe Ala Thr Cys Leu Ser Ile Phe Tyr Phe Phe Lys Ile
                85                  90                  95

Ala Asn Phe Phe His Pro Leu Phe Leu Trp Ile Lys Trp Arg Ile Asp
            100                 105                 110

Lys Leu Ile Leu Arg Thr Leu Leu Ala Cys Leu Ile Leu Ser Leu Cys
        115                 120                 125

Phe Ser Leu Pro Val Thr Glu Asn Leu Ala Asp Asp Phe Arg Arg Cys
    130                 135                 140

Val Lys Thr Lys Glu Arg Ile Asn Ser Thr Leu Arg Cys Lys Leu Asn
145                 150                 155                 160
```

-continued

```
Lys Ala Gly Tyr Ala Ser Val Lys Val Asn Leu Asn Leu Val Met Leu
                165                 170                 175

Phe Pro Phe Ser Val Ser Leu Val Ser Phe Leu Leu Leu Ile Leu Ser
            180                 185                 190

Leu Trp Arg His Thr Arg Gln Met Gln Leu Asn Val Thr Gly Tyr Asn
        195                 200                 205

Asp Pro Ser Thr Thr Ala His Val Lys Ala Thr Lys Ala Val Ile Ser
    210                 215                 220

Phe Leu Val Leu Phe Ile Val Tyr Cys Leu Ala Phe Leu Ile Ala Thr
225                 230                 235                 240

Ser Ser Tyr Phe Met Pro Glu Ser Glu Leu Ala Val Ile Trp Gly Glu
                245                 250                 255

Leu Ile Ala Leu Ile Tyr Pro Ser Ser His Ser Phe Ile Leu Ile Leu
            260                 265                 270

Gly Asn Ser Lys Leu Lys Gln Ala Ser Val Arg Val Leu Cys Arg Val
        275                 280                 285

Lys Thr Met Leu Lys Gly Arg Lys Tyr
    290                 295


<210> SEQ ID NO 88
<211> LENGTH: 1304
<212> TYPE: DNA
<213> ORGANISM: Rattus sp.

<400> SEQUENCE: 88

gtgaggcctt agtaggaatc ttaggaaatg cattcattgc attggtaaac ttcatgggct      60

ggatgaagaa taggaagatc actgctattg atttaatcct ctcaagtctg gctatgtcca     120

ggatttgtct acagtgtata attctattag attgtattat attggtgcag tatccagaca     180

cttacaacag ggtaaagaa atgaggatca ttgatttctt ctggacgctt accaaccatt      240

taagtgtctg gtttgccacc tgcctcagca ttttctattt cttcaagata gcaaacttct     300

tccatcctct tttcctctgg ataaagtgga gaattgacaa gctaattctg aggactctac     360

tggcatgctt gattctctcc ctatgcttta gcctcccagt cactgagaat ttggctgatg     420

atttcagacg ctgtgtcaag acaaaagaaa gaataaactc tactctgagg tgcaaattaa     480

ataaagctgg atatgcttct gtcaaggtaa atctcaactt ggtcatgctg ttcccctttt     540

ctgtgtccct tgtctcattc cttctcttga ttctctccct atggagacac accaggcaga     600

tgcaactcaa tgtaacaggg tacaatgatc ccagcacaac agctcatgtg aaagccacaa     660

aagcagtaat ttccttccta gttctgttta ttgtctactg cctggccttt cttatagcca     720

cttccagcta ctttatgcca gagagtgaat tagctgtaat ttggggtgag ctgatagctc     780

taatatatcc ctcaagccat tcatttatcc tgatccttgg gaacagtaaa ctaaaacagg     840

catctgtaag ggtgctttgt agagtaaaga ctatgttaaa gggaagaaaa tattagcatc     900

atggatatat ttgaagaaaa actatcactg tctaaagaaa aaggatgaca aatcattatc     960

tttcattctt atatgaatat tgctttcatg cggtaacatc ttttaacaaa cttaaatcaa    1020

atgttgggaa atctcatata cagcaacttt gcatgtctct ctgtctattt ccctctccct    1080

ttgtacatag ttgacataaa aaaagaattt tcatgacaaa attgtaataa atagctacag    1140

aggcagcaca ttttcatagt aagttctgaa tcactcttcc aaatgcaaag ctgcctgaca    1200

aattcaaaac aactgtaaca gtatttcact gctgtttgca ttctttggaa aagcaggtgg    1260

tttgttccta tgacctgact tggagttttc ttcttacatc actg                     1304
```

<210> SEQ ID NO 89
<211> LENGTH: 305
<212> TYPE: PRT
<213> ORGANISM: Rattus sp.

<400> SEQUENCE: 89

```
Met Gly Ser Ser Leu Tyr Asp Ile Leu Thr Ile Val Met Ile Ala Glu
1               5                   10                  15

Phe Ile Phe Gly Asn Val Thr Asn Gly Phe Ile Val Leu Thr Asn Cys
            20                  25                  30

Ile Ala Trp Leu Ser Lys Arg Thr Leu Ser Phe Ile Gly Trp Ile Gln
        35                  40                  45

Leu Phe Leu Ala Ile Ser Arg Val Val Leu Ile Trp Glu Met Leu Leu
    50                  55                  60

Ala Trp Leu Lys Tyr Met Lys Tyr Ser Phe Ser Tyr Leu Ala Gly Thr
65                  70                  75                  80

Glu Leu Arg Val Met Met Leu Thr Trp Val Val Ser Asn His Phe Ser
                85                  90                  95

Leu Trp Leu Ala Thr Ile Leu Ser Ile Phe Tyr Leu Leu Lys Ile Ala
            100                 105                 110

Ser Phe Ser Arg Pro Val Phe Leu Tyr Leu Lys Trp Arg Val Lys Lys
        115                 120                 125

Val Leu Leu Leu Ile Leu Leu Gly Asn Leu Ile Phe Leu Met Phe Asn
    130                 135                 140

Ile Leu Gln Ile Asn Thr His Ile Glu Asp Trp Met Asp Gln Tyr Lys
145                 150                 155                 160

Arg Asn Ile Thr Trp Asp Ser Arg Val Asn Glu Phe Val Gly Phe Ser
                165                 170                 175

Asn Leu Val Leu Leu Glu Met Ile Met Phe Ser Val Thr Pro Phe Thr
            180                 185                 190

Val Ala Leu Val Ser Phe Ile Leu Leu Ile Phe Ser Leu Trp Lys His
        195                 200                 205

Leu Gln Lys Met His Leu Ser Ser Arg Gly Glu Arg Asp Pro Ser Thr
    210                 215                 220

Lys Ala His Val Asn Ala Leu Arg Ile Met Val Ser Phe Leu Leu Leu
225                 230                 235                 240

Tyr Ala Thr Tyr Phe Ile Ser Phe Phe Ile Ser Leu Ile Pro Met Ala
                245                 250                 255

His Lys Lys Gly Leu Asp Leu Met Phe Ser Leu Thr Val Gly Leu Phe
            260                 265                 270

Tyr Pro Ser Ser His Ser Phe Ile Leu Ile Leu Gly His Ser Asn Leu
        275                 280                 285

Arg His Ser Ser Cys Leu Val Ile Thr Tyr Leu Arg Cys Lys Glu Lys
    290                 295                 300

Asp
305
```

<210> SEQ ID NO 90
<211> LENGTH: 3994
<212> TYPE: DNA
<213> ORGANISM: Rattus sp.
<220> FEATURE:
<221> NAME/KEY: modified_base
<222> LOCATION: (40)..(40)
<223> OTHER INFORMATION: n is a, c, g, or t
<220> FEATURE:

<221> NAME/KEY: modified_base
<222> LOCATION: (42)..(42)
<223> OTHER INFORMATION: n is a, c, g, or t

<400> SEQUENCE: 90

```
cagtagcaaa attttactat gttcattgat attatgtcan gncactacgt aagaaggaag     60
acttgaaaga aagcttatct gagtttttaa gaatacatgg acatttcagc ttggcaaatg    120
acgagctgtg aatttttgtc atctggacat gggaagcagc ctgtatgata tcttaactat    180
tgtcatgatt gcagagttta tattcggaaa tgtgaccaat ggattcatag tgctgacaaa    240
ctgtattgct tggctcagta aaagaactct ttctttcatt ggttggatcc agcttttctt    300
ggccatttcc agagtggttt tgatatggga aatgttacta gcatggctga aatatatgaa    360
gtattcattt tcatatttgg ctggcacaga attaagggtt atgatgttga cctgggtagt    420
ttccaatcac tttagtctct ggcttgccac cattctaagc atcttttatt tgctcaaaat    480
agctagtttc tccagacctg ttttcctgta tctgaagtgg agagtaaaaa aagtgctcct    540
gctgattctt ctcggaaatt taatcttcct gatgttcaat atattacaaa tcaacactca    600
catagaagac tggatggatc aatataagag aaatataacg tgggattcca gagtgaatga    660
atttgtgggg ttttcaaatc tggttttatt ggagatgatt atgttctctg taacaccatt    720
caccgtggct ctggtctcct tcatcctgtt aatcttctct ttatggaaac atctccagaa    780
gatgcatctc agttccagag gggaacgaga ccctagcaca aaagcccatg tgaatgccct    840
gagaattatg gtctccttcc tcttactcta tgccacttac ttcatatcct tttttatatc    900
attaattcct atggcacata aaaaaggact agatcttatg tttagcctaa ctgttggact    960
tttctaccct tcaagccact catttatctt gattttggga cattctaatc taaggcattc   1020
cagttgtctg gtgataacct atctgagatg taaggaaaag gattagaaat tcactattcc   1080
ataaggcagt taaaccacat gctattaggt atactcagtg ctagatccct aggcaagcat   1140
taacattaaa aatatataat ttctagattc ttctatttgt gataaaccac tcacttagaa   1200
taatgctaaa gtagcgtgat gttgtatata agtgtaagaa taaaatgtaa ttaatttagt   1260
ttaggcacaa taacatatgt ctactaagta aaaactaggc aggctgctac acgcatatta   1320
gaatccaggc tgaggtatat agactcaaga aatactgtgg aataaagatt ttaattttca   1380
ttctattgtg agttatgtga aatcaatgcc attaaaggca tacacaagat tttcacacac   1440
tgaaacaact tcttgcattt tgtcatattg tattggaagt aaattggaga taaacttaat   1500
atcaataaat tacaaaatgt aaacataaac agggtgatta aaaattagcc tctaggtcct   1560
ggggaaatga ttcaagtaaa gtgctttctt ttcaaatagg agaatctgat tgtaaatcat   1620
ctaaaagtct ggcataaaat gtcaatgaaa attgtatgta aaatatagct atggcmaaga   1680
gcaccmaaga aaagaaaatt tttgcctttg aaacccagta attgatatcc tttaaaaaag   1740
cagttacata tttttctgtt taagattttg tcaaagggta gctttgacaa ctaatataag   1800
ctgaggaagg tagcaagtgt gaagtcagct aatggggtca gtcaagtgct gttagcagca   1860
gatggaggcc actgctgaat ttagcaggca atttacaggg tgagcactgc tagtgctgac   1920
agaagaaaaa ctctgaaatt ttaactcttt agggtctggt gagaaagaaa aagagagaaa   1980
atcgcatata tatatatata tatatatata tatatatata tatatatata tatatatata   2040
tcatggaagc tctaacaagt tgactcaaac aactttatga tgtttttagg ccctttttatt  2100
ttaatgtcag tgaattaggt gtggtacagc aatattgcta cttttaaatt caaagcagtt   2160
gttttatata ttattcatta tataagctaa ttataagttt aaatcaaaag gtttatttgt   2220
```

-continued

```
ccatgatttt actttatcat tgggcacacc tgtgctctca tccttgggct tgacctagaa   2280
tgaaagttta tccttgatca tatgtctgtc acaagactac ttctcttcct atagtagttt   2340
atgtacttac aatatacaaa agtttattga attcctttta tcacttatgc agccttttct   2400
tactattcta ttctattcta ttctattcta ttctattcta ttctattcta ttctattcta   2460
ttctattcta ttctattcta gaatctaacc tatacattca tttctggcaa aacaacttat   2520
atcatctcct taattatttt atcaattaat ctaacatcct gaagttattt aaatctaata   2580
taaggactct gtaaagtcac aaatttattt atacttcaca aaattcatta ttttatggaa   2640
ctgcagcatt gcctgggcca ggagtcacaa gagttccaga gttgacttta ttggcatctg   2700
cctggctaac tgaaggatca gttttctgtg tacaataatt ttgtgtatct cttttgatgc   2760
aagatatgaa aaataatttc agtctaaaag tgtccttaaa tttgaaactc tctggccaga   2820
atctaactat tgatgaccag tttgcaccat ggactcagtg tcttctattg ctttaaaata   2880
agcaacatct tgaatgcttt tcttgtgtat taggcaaata attaacaaca tgtttctatg   2940
attgtctcaa taacaatact atatttctca cagtttttaa tttttatggc aaagttggct   3000
aataagaatt tttttcaaat tatcaaacgt gaagaaaact tgacatttta tttcatggag   3060
attctaaatg ttttcttagc atattgcctt tttactaact tgatttttat catgttttgg   3120
tagtatttct aattttcctt tttttctaag tatgttatgt agtaacacca ggagaatgaa   3180
acaaatgaca tttatactaa ggatgtgaca aataaggccc aaagaaagtt ttgaaaatca   3240
tgatctcatt tctattcttc tttattaagt atagcataag caaaattctg atggtggtct   3300
tggcccatat ctttgaacac agtgtagtgg tgaagacttt ttcaaatatt atgtcatatt   3360
tgtacccatc tctgtaccta tttcttctga tttcatgagg aaaaaatgag gaagggtttg   3420
tttgtgtgct ggagcagctg aagtggacca aggggcagga attctctctg ttcggtccta   3480
gtgtgactga tgatgctctc attgaaaaac aggaagaaga agaaagactt tatatgcacc   3540
attcactcct tccccctcct acattccacc tccctcttga aagagtgtct atctatatag   3600
atatagctat cctgaaatcc attaagtaga cctgactggc ttaaatctca cagaaattca   3660
cctacctttt ccatgattgc tgaaattaaa gacatgtgcc gacatattgg gcacattcag   3720
accttttgcc aactgtcttt caactcattt ggacctactg agaagtattc aaaatatttg   3780
gttgttttaa ataaaaggaa agtgggtcta tattacttga attggataga gaaattttca   3840
cttacaagtg atattgaaaa tgggggagaa tgtattttag cataagcacc agaacacaaa   3900
gcaattcttg ttaaaacttt atcgataaat tggataaatg ttaaaaaaga aaaaataaaa   3960
tatacgaact attatgaaaa aaaaaaaaaa aaaa                               3994
```

<210> SEQ ID NO 91
<211> LENGTH: 314
<212> TYPE: PRT
<213> ORGANISM: Rattus sp.

<400> SEQUENCE: 91

```
Met Glu Pro Val Ile His Val Phe Ala Thr Leu Leu Ile His Val Glu
1               5                   10                  15

Phe Ile Phe Gly Asn Leu Ser Asn Gly Leu Ile Val Leu Ser Asn Phe
            20                  25                  30

Trp Asp Trp Val Val Lys Arg Lys Leu Ser Thr Ile Asp Lys Ile Leu
        35                  40                  45

Leu Thr Leu Ala Ile Ser Arg Ile Thr Leu Ile Trp Glu Met Tyr Ala
```

-continued

```
    50                  55                  60

Cys Phe Lys Ile Val Tyr Gly Ser Ser Ser Phe Ile Phe Gly Met Lys
65                  70                  75                  80

Leu Gln Ile Leu Tyr Phe Ala Trp Ile Leu Ser Ser His Phe Ser Leu
                85                  90                  95

Trp Phe Ala Thr Ala Leu Ser Ile Phe Tyr Leu Leu Arg Ile Ala Asn
            100                 105                 110

Cys Ser Trp Lys Ile Phe Leu Tyr Leu Lys Trp Arg Leu Lys Gln Val
        115                 120                 125

Ile Val Gly Met Leu Leu Ala Ser Leu Val Phe Leu Pro Gly Ile Leu
    130                 135                 140

Met Gln Arg Thr Leu Glu Glu Arg Pro Tyr Gln Tyr Gly Gly Asn Thr
145                 150                 155                 160

Ser Glu Asp Ser Met Glu Thr Asp Phe Ala Lys Phe Thr Glu Leu Ile
                165                 170                 175

Leu Phe Asn Met Thr Ile Phe Ser Val Ile Pro Phe Ser Leu Ala Leu
            180                 185                 190

Ile Ser Phe Leu Leu Leu Ile Phe Ser Leu Trp Lys His Leu Gln Lys
        195                 200                 205

Met Gln Leu Ser Ser Arg Gly His Gly Asp Pro Ser Thr Lys Ala His
    210                 215                 220

Arg Asn Ala Leu Arg Ile Met Val Ser Phe Leu Leu Leu Tyr Thr Ser
225                 230                 235                 240

Tyr Phe Leu Ser Leu Leu Ile Ser Trp Ile Ala Gln Lys His His Ser
                245                 250                 255

Lys Leu Val Asp Ile Ile Gly Ile Ile Thr Glu Leu Met Tyr Pro Ser
            260                 265                 270

Val His Ser Phe Ile Leu Ile Leu Gly Asn Ser Lys Leu Lys Gln Thr
        275                 280                 285

Ser Leu Trp Ile Leu Ser His Leu Lys Cys Arg Leu Lys Gly Glu Asn
    290                 295                 300

Ile Leu Thr Pro Ser Gly Lys Pro Ile Asn
305                 310
```

<210> SEQ ID NO 92
<211> LENGTH: 1886
<212> TYPE: DNA
<213> ORGANISM: Rattus sp.
<220> FEATURE:
<221> NAME/KEY: modified_base
<222> LOCATION: (1351)..(1351)
<223> OTHER INFORMATION: n is a, c, g, or t

<400> SEQUENCE: 92

```
ctgcaggttg gtgatccagt aatgagcagc actgttatat ctcaggcttt ctaagatcat     60

ggaacctgtc attcacgtct ttgccactct actaatacat gtggagttca tttttgggaa    120

tctgagcaat ggattaatag tgttgtcaaa cttctgggac tgggtcgtta aacgaaaact    180

ttccacaatt gataaaattc ttcttacatt ggcaatttca agaatcactc tcatctggga    240

aatgtatgct tgttttaaaa ttgtatatgg ttcatcttca tttatatttg ggatgaagtt    300

acaaattctt tattttgcct ggatcctttc tagtcacttc agcctctggt ttgccacagc    360

tctcagcatc ttttacttac tcagaatagc taactgctcc tggaagatct tcctgtatct    420

gaaatggaga cttaaacaag tgattgtggg gatgttgctg gcaagcttgg tgttcttgcc    480

tggaatcctg atgcaaagga ctcttgaaga gaggccctat caatatggag gaaacacaag    540
```

-continued

```
tgaggattcc atggaaactg actttgcaaa gtttacagag ctgattcttt tcaacatgac    600

tatattctct gtaataccat tttcattggc cttgatttct tttctcctgc taatcttctc    660

tttgtggaaa catctccaga agatgcagct cagttccaga ggacatggag accctagcac    720

caaggcccac agaaatgctt tgagaattat ggtctccttc ctcttgctct acacttcata    780

tttcctgtct cttcttatat catggattgc tcagaagcat cacagtaaac tggttgacat    840

tattggtatt attactgaac tcatgtatcc ttcagtccac tcatttatcc tgattctagg    900

aaattctaaa ttaaagcaga cttctctttg gatactgagt catttgaaat gtagactgaa    960

aggagagaat attttaactc catctggcaa accaattaac tagctgttat atattctgta   1020

ttgcaaacaa atcagtgagt tagtggttca aggattccat ccttgactta ttgtatcatg   1080

gaagtcatat agggagaggc tgaacaagct atcttctgta aattggcaag ggttgcatat   1140

agtactggta ctgggacacc atccaaccat aaaaccttct aaccataacc tacctgactg   1200

caagatatgc tgggacaatg gtggctcaga gattttggga ctggccaacc aatgtctatt   1260

ctttcttgag gctcactcaa taaggaggcc atgcccaact cgtcctggat ggccaggaac   1320

cagaatctct gatggsccaa tgatctatgg nagaacccag cattactggg aaaaaagaat   1380

aatcactttg atgaatggtc aaatatttcc taaatatatt ctgatacact tgtacatcat   1440

ttctctttcc caatcatcat cacagggact tctccccagc acctgatggg aacagatacc   1500

aaaatctaca gccaaatact aaatgcaggt tggggaactc cacaaaagac tggaaggaag   1560

tactgtgaga gccagagtgg tccagaacac taggagaaca cagaacatcg aattaactaa   1620

gcagcactca tagggttaat gtaaaataaa gcagcagtca catagactgc acaggtgtac   1680

tctagatcct ctgcatatat gttgtggttg tcaaacttgg gagttttgtt ggactaataa   1740

caatgtgaat aagtaagtct ctgacactta ttcccgctct tggaaccctt ttccacattt   1800

tgtattgtct taccaccttg atatgaaggt ttctgaatag tccaaaaaaa aaaaaaaaaa   1860

aaaaaaaaaa aaaaaaaaaa aaaaaa                                        1886
```

```
<210> SEQ ID NO 93
<211> LENGTH: 309
<212> TYPE: PRT
<213> ORGANISM: Rattus sp.

<400> SEQUENCE: 93

Met Leu Ser Ala Ala Glu Gly Ile Leu Leu Ser Ile Ala Thr Val Glu
1               5                   10                  15

Ala Gly Leu Gly Val Leu Gly Asn Thr Phe Ile Ala Leu Val Asn Cys
            20                  25                  30

Met Asp Trp Ala Lys Asn Lys Lys Leu Ser Lys Ile Gly Phe Leu Leu
        35                  40                  45
Phe Gly Leu Ala Thr Ser Arg Ile Phe Ile Val Trp Ile Leu Ile Leu
    50                  55                  60

Asp Ala Tyr Ala Lys Leu Phe Phe Pro Gly Lys Tyr Leu Ser Lys Ser
65                  70                  75                  80

Leu Thr Glu Ile Ile Ser Cys Ile Trp Met Thr Val Asn His Met Thr
                85                  90                  95

Val Trp Phe Ala Thr Ser Leu Ser Ile Phe Tyr Phe Leu Lys Ile Ala
            100                 105                 110

Asn Phe Ser His Tyr Ile Phe Leu Trp Leu Lys Arg Arg Thr Asp Lys
        115                 120                 125

Val Phe Ala Phe Leu Leu Trp Cys Leu Leu Ile Ser Trp Ala Ile Ser
```

-continued

```
    130                 135                 140

Phe Ser Phe Thr Val Lys Val Met Lys Ser Asn Pro Lys Asn His Gly
145                 150                 155                 160

Asn Arg Thr Ser Gly Thr His Trp Glu Lys Arg Glu Phe Thr Ser Asn
                165                 170                 175

Tyr Val Leu Ile Asn Ile Gly Val Ile Ser Leu Leu Ile Met Thr Leu
            180                 185                 190

Thr Ala Cys Phe Leu Leu Ile Ile Ser Leu Trp Lys His Ser Arg Gln
        195                 200                 205

Met Gln Ser Asn Val Ser Gly Phe Arg Asp Leu Asn Thr Glu Ala His
    210                 215                 220

Val Lys Ala Ile Lys Phe Leu Ile Ser Phe Ile Ile Leu Phe Ile Leu
225                 230                 235                 240

Tyr Phe Ile Gly Val Ala Val Glu Ile Ile Cys Met Phe Ile Pro Glu
                245                 250                 255

Asn Lys Leu Leu Phe Ile Phe Gly Leu Thr Thr Ala Ser Val Tyr Pro
            260                 265                 270

Cys Cys His Ser Val Ile Leu Ile Leu Thr Asn Ser Gln Leu Lys Gln
        275                 280                 285

Ala Phe Val Lys Val Leu Glu Gly Leu Lys Phe Ser Glu Asn Gly Lys
    290                 295                 300

Asp Leu Arg Ala Thr
305


<210> SEQ ID NO 94
<211> LENGTH: 2596
<212> TYPE: DNA
<213> ORGANISM: Rattus sp.

<400> SEQUENCE: 94

ggacactgca gcagatctgc tatagaataa cagatacaaa catagcaacc tgcagagatg     60

ctcagtgcag cagaaggcat ccttctttcc attgcaactg ttgaagctgg gctgggagtt    120

ttagggaaca catttatcgc cctggttaac tgcatggatt gggccaagaa caagaagctc    180

tctaagattg gtttccttct ctttggctta gcaacttcca gaatttttat tgtatggata    240

ttaattttag acgcatatgc aaagctattc tttccgggga agtatttgtc taagagtctg    300

actgaaatca tctcttgtat atggatgact gtgaatcaca tgactgtctg gtttgccacc    360

agcctcagca tcttctattt cctaaaaata gcaaattttt cccactatat atttctctgg    420

ttaaagagga gaactgataa agtatttgcc tttctcttgt ggtgtttatt aatttcatgg    480

gcaatctcct tctcattcac tgtgaaagtg atgaagagca atccaaagaa tcatggaaac    540

aggaccagtg ggacacattg ggagaagaga gaattcacaa gtaactatgt tttaatcaat    600

attggagtca tttctctctt gatcatgacc ttaactgcat gtttcttgtt aattatttca    660

ctttggaaac acagcaggca gatgcagtct aatgtttcag gattcagaga tctcaacact    720

gaagctcatg tgaaagccat aaaattttta atttcattta tcatcctttt catcttgtac    780

tttataggtg ttgcagtaga aatcatctgc atgtttatcc cagaaaacaa actgctattt    840

atttttggtt tgacaactgc atccgtctat ccctgctgtc actcagtcat tctaattcta    900

acaaacagcc agctgaagca agcctttgta aaggtactgg agggattaaa gttctctgag    960

aacggaaaag atctcagggc cacatgagtc tggaacagaa atgggtagtc tggaataatt   1020

gtaaggaagt cgtagaaggt ctttttcatt tgtacagtgc tcttaccttg tttttgagga   1080
```

-continued

```
gatgtaaact tttttatttt tattttttat cctatgtgaa taagtgtgtg tgtgtgtgtg   1140

tgtgtttatg tgtgtgtgta tatatgtcta tgtgtgtttt aggaggttta agagggaaga   1200

gggaatagag gtatgttggt gtttttaaca tggatattca caggccaagg aacttgttct   1260

ctccttttac cttagggtag tgtcctttgt ggctgtcact ctgacagtct acactagttg   1320

aactaagagc ttttagccag ttcacttgtc taaacctccc ttctcatggt agcagtgttc   1380

tgattacaga atcatgctgt cacatacagc tttttaacaa ggttcccata gacagaattc   1440

atgtcaaacg gaatgcacag ctgtcactct tacccaccga tctctcttgc cagcccattc   1500

ctattgactt taaactgtag tattaaactt tactgaaatc ttctgcaacc agtctgacta   1560

tgtctcttga aatcacatga tatggtggaa ttttaatgcc atgtgaaaat ttgtttgttc   1620

agttagtttc ctactctgcc aaatcattct cttacacttg gcagaaaaaa accatcaact   1680

gtagactatt ttgtgtaaag actaatacag atagaataag tatcttaatc aagatgtcat   1740

tgtgattatc ctaatttccc cagagcactg gttccctttc cccagaaaga ctcacaaagg   1800

aactgaggca aacagttgtg gtcactcttg atatttacca gttgaaactg aagaacagtg   1860

tttcctttct gttcagtttt actacttaca gttactttat ttcatccatt aaatcccaaa   1920

gtgcttatta atagtagata tttgatgaag caacaatggt tataagagtg gatgtggatc   1980

tatgacaaag atctagagaa acagactatt tgtgaaagat ggatgaaagc cctgatgaaa   2040

ggattcttca tggtctttga ccccagggag ttttgaaatc aagcagccac agatcaaaga   2100

gagctgagaa gaggttctcc tgaagaaaat atccaaacac atggtgccag ccaaagcaga   2160

aaatagtgga caattcagtc caggacctga atgaggtaga caatgtcctg ttaagggttg   2220

gaacaaatat atagatatgg tcattcatat acagaaacct acaggcgtgt ttgaactctt   2280

ggtttctcag taatcaattc ttaaatcttt tttagaatgg attttttatc atcattcatg   2340

atctctcagc agagtctgca ggggctaaga gacacactaa gagtatctgg aggggggagt   2400

gtcttcctgc tctatcaacc cctaaagtca tatataacaa tacaaaattc cacattagtt   2460

aagttctttt ttttacatct ttattaaatt gggtatttct tatttacatt tcaaatgtga   2520

ttccctttcc tggtttccag gccaatatcc ccctaacctc tccccttcta tgtgggtatt   2580

ccctcgtgcc gaattc                                                   2596
```

<210> SEQ ID NO 95
<211> LENGTH: 137
<212> TYPE: PRT
<213> ORGANISM: Rattus sp.

<400> SEQUENCE: 95

```
Met Phe Leu His Thr Ile Lys Gln Arg Asp Ile Phe Thr Leu Ile Ile
1               5                   10                  15
Ile Phe Phe Val Glu Ile Thr Met Gly Ile Leu Gly Asn Gly Phe Ile
            20                  25                  30
Ala Leu Val Asn Ile Val Asp Trp Ile Lys Arg Arg Arg Ile Ser Ser
        35                  40                  45
Val Asp Lys Ile Leu Thr Thr Leu Ala Leu Thr Arg Leu Ile Tyr Ala
    50                  55                  60
Trp Ser Met Leu Ile Phe Ile Leu Leu Phe Ile Leu Gly Pro His Leu
65                  70                  75                  80
Ile Met Arg Ser Glu Ile Leu Thr Ser Met Gly Val Ile Trp Val Val
                85                  90                  95
Asn Asn His Phe Ser Ile Trp Leu Ala Thr Cys Leu Gly Val Phe Tyr
            100                 105                 110
Phe Leu Lys Ile Ala Asn Phe Ser Asn Ser Leu Phe Leu Tyr Leu Lys
        115                 120                 125
Trp Arg Val Lys Lys Val Val Leu Met
    130                 135
```

-continued

<210> SEQ ID NO 96
<211> LENGTH: 818
<212> TYPE: DNA
<213> ORGANISM: Rattus sp.

<400> SEQUENCE: 96
cccgggctgc aggattcggc acgagaatga aaacttttgc tctactattt tgctgttctg 60
tgataccaca gaccataaaa caatcgagcc aagggatcaa gagctgaaac ttcagaaagt 120
gggaatcaaa tttccttcct gataggttag cttatgagaa ttcagcatct tattcaactt 180
cagaaaattg gatataagat acagtgtctg gatgaagccg aattgatcta tttggggaga 240
aaaaacgcca acatttataa taaggtttta tgagacagtt cctgggaaat ttggatattt 300
cctagttagt aatgtgtaaa tgggatttta aaacatgatt attttgtatt tttaacaacc 360
aacatgagga gctttttaaa tgccacttag acattataaa ctgaagcatg ttcttacaca 420
caataaagca acgtgatatt tttactttga taatcatatt ttttgtggaa ataacaatgg 480
gaatcttagg aaatggattc atagcactag tgaacattgt ggactggatc aagagaagaa 540
ggatttcttc agtggataag attctcacta ccttggccct taccagactc atttatgcgt 600
ggtctatgct catttttata ttgttattca tactgggccc gcatttgatt atgagatcag 660
aaatacttac atcaatgggt gttatctggg tggtgaacaa tcacttcagc atctggcttg 720
ctacatgcct cggtgtcttt tattttctca agatagccaa tttttctaac tctttgtttc 780
tttacctaaa gtggagagtt aaaaaagtgg ttttaatg 818

<210> SEQ ID NO 97
<211> LENGTH: 104
<212> TYPE: PRT
<213> ORGANISM: Rattus sp.

<400> SEQUENCE: 97

Gly Ser Gly Asn Gly Phe Ile Val Ser Val Asn Gly Ser His Trp Phe
1               5                   10                  15

Lys Ser Lys Lys Ile Ser Leu Ser Asp Phe Ile Ile Thr Ser Leu Ala
            20                  25                  30

Leu Phe Arg Ile Phe Leu Leu Trp Ile Ile Phe Thr Asp Ser Leu Ile
        35                  40                  45

Ile Val Phe Ser Tyr His Ala His Asp Ser Gly Ile Arg Met Gln Leu
    50                  55                  60

Ile Asp Val Phe Trp Thr Phe Thr Thr His Phe Ser Ile Trp Leu Ile
65                  70                  75                  80

Ser Cys Leu Ser Val Phe Tyr Cys Leu Lys Ile Ala Thr Phe Ser His
                85                  90                  95

Pro Ser Phe Leu Leu Lys Ser Arg
            100

<210> SEQ ID NO 98
<211> LENGTH: 315
<212> TYPE: DNA
<213> ORGANISM: Rattus sp.

<400> SEQUENCE: 98
ggatccggaa acggttttat cgtgtcagtc aatggcagcc attggttcaa gagcaagaag 60
atttctttgt ctgacttcat cattaccagc ttggccctct tcaggatctt tctgctgtgg 120
atcatcttta ctgatagcct cataatagtg ttctcttacc acgcccacga ctcagggata 180

-continued

```
aggatgcaac ttattgatgt tttctggaca tttacaaccc acttcagtat ttggcttatc    240

tcctgtctca gtgttttcta ctgcctgaaa atagccactt tctcccaccc ctcattcctg    300

tagctcaaat ctaga                                                     315
```

<210> SEQ ID NO 99
<211> LENGTH: 308
<212> TYPE: PRT
<213> ORGANISM: Rattus sp.

<400> SEQUENCE: 99

```
Met Leu Ser Thr Val Ser Val Phe Phe Met Ser Ile Phe Val Leu Leu
1               5                   10                  15

Cys Phe Leu Gly Ile Leu Ala Asn Gly Phe Ile Val Leu Met Leu Ser
            20                  25                  30

Arg Glu Trp Leu Trp Arg Gly Arg Leu Leu Pro Ser Asp Met Ile Leu
        35                  40                  45

Leu Ser Leu Gly Thr Ser Arg Phe Cys Gln Gln Cys Val Gly Leu Val
    50                  55                  60

Asn Ser Phe Tyr Tyr Ser Leu His Leu Val Glu Tyr Ser Arg Ser Leu
65                  70                  75                  80

Ala Arg Gln Leu Ile Ser Leu His Met Asp Phe Leu Asn Ser Ala Thr
                85                  90                  95

Phe Trp Phe Gly Thr Trp Leu Ser Val Leu Phe Cys Ile Lys Ile Ala
            100                 105                 110

Asn Phe Ser His Pro Ala Phe Leu Trp Leu Lys Trp Arg Phe Pro Ala
        115                 120                 125

Leu Val Pro Trp Leu Leu Leu Gly Ser Ile Leu Val Ser Phe Ile Val
    130                 135                 140

Thr Leu Met Phe Phe Trp Gly Asn His Thr Val Tyr Gln Ala Phe Leu
145                 150                 155                 160

Arg Arg Lys Phe Ser Gly Asn Thr Thr Phe Lys Glu Trp Asn Arg Arg
                165                 170                 175

Leu Glu Ile Asp Tyr Phe Met Pro Leu Lys Leu Val Thr Thr Ser Ile
            180                 185                 190

Pro Cys Ser Leu Phe Leu Val Ser Ile Leu Leu Leu Ile Asn Ser Leu
        195                 200                 205

Arg Arg His Ser Gln Arg Met Gln His Asn Ala His Ser Leu Gln Asp
    210                 215                 220

Pro Asn Thr Gln Ala His Ser Arg Ala Leu Lys Ser Leu Ile Ser Phe
225                 230                 235                 240

Leu Val Leu Tyr Ala Leu Ser Tyr Val Ser Met Val Ile Asp Ala Thr
                245                 250                 255

Val Val Ile Ser Ser Asp Asn Val Trp Tyr Trp Pro Trp Gln Ile Ile
            260                 265                 270

Leu Tyr Leu Cys Met Ser Val His Pro Phe Ile Leu Ile Thr Asn Asn
        275                 280                 285

Leu Lys Phe Arg Gly Thr Phe Arg Gln Leu Leu Leu Leu Ala Arg Gly
    290                 295                 300

Phe Trp Val Thr
305
```

<210> SEQ ID NO 100
<211> LENGTH: 1295
<212> TYPE: DNA
<213> ORGANISM: Rattus sp.

-continued

<400> SEQUENCE: 100

```
gtgtgaggga ctgtgggtag gggctgggag gaggccagga accaaggcaa ccagtggtga     60
caggaggggc tgaaatgcta tcaactgtat cagttttctt catgtcgatc tttgttctgc    120
tctgtttcct gggaatcctg gcaaacggct tcattgtgct gatgctgagc agggaatggc    180
tatggcgcgg taggctgctc ccctcagaca tgatcctcct cagtttgggc acctcccgat    240
tctgccagca gtgcgttggg ctggtgaaca gtttctacta ttccctccac cttgttgagt    300
actccaggag ccttgcccgt caactcatta gtcttcacat ggacttcttg aactcagcca    360
ctttctggtt tggcacctgg ctcagcgtcc tgttctgtat caagattgct aacttctccc    420
atcctgcctt cctgtggttg aagtggagat tcccagcatt ggtgccttgg ctcctactgg    480
gctctatctt ggtgtccttc atcgtaactc tgatgttctt ttggggaaac cacactgtct    540
atcaggcatt cttaaggaga aagttttctg ggaacacaac ctttaaggag tggaacagaa    600
ggctggaaat agactatttc atgcctctga aacttgtcac cacgtcaatt ccttgctctc    660
tttttctagt ctcaattttg ctgttgatca attctctcag aaggcattca caaagaatgc    720
agcacaatgc tcacagcttg caagacccca acacccaggc tcacagcaga gccctgaagt    780
cactcatctc atttctggtt ctttacgcgc tgtcctatgt gtccatggtc attgacgcta    840
cagttgtcat ctcctcagat aacgtgtggt attggccctg gcaaattata ctttacttgt    900
gcatgtccgt acatccattt atccttatca ctaataatct caagttccga ggcaccttca    960
ggcagctact cctgttggcc aggggattct gggtgaccta gaaggtttgg tctctttatc   1020
tgtacccttt gaagagactt aggtgagggt gacttccctt ggaagtgatc tcatctacat   1080
ggaaatgtct ttgtaggctg acatggggtc atactatgtg gttcctcctt gggaaagagg   1140
agaagaaaat acagggattc tgagcgttct tccttatctt gggatattat gaaaatggac   1200
attctgaatc ctgaaccagt attgatctga agtgcaaagt acaatatgcc tgttcccttc   1260
atgtctgcta tcctcttggt acttattaat tccct                              1295
```

<210> SEQ ID NO 101
<211> LENGTH: 332
<212> TYPE: PRT
<213> ORGANISM: Rattus sp.

<400> SEQUENCE: 101

```
Met Cys Gly Phe Pro Leu Ser Ile Gln Leu Leu Thr Gly Leu Val Gln
1               5                   10                  15

Met Tyr Val Ile Leu Ile Ile Ala Val Phe Thr Pro Gly Met Leu Gly
            20                  25                  30

Asn Val Phe Ile Gly Leu Val Asn Tyr Ser Asp Trp Val Lys Asn Lys
        35                  40                  45

Lys Ile Thr Phe Ile Asn Phe Ile Leu Ile Cys Leu Ala Ala Ser Arg
    50                  55                  60

Ile Ser Ser Val Leu Val Val Phe Ile Asp Ala Ile Ile Leu Glu Leu
65                  70                  75                  80

Thr Pro His Val Tyr His Ser Tyr Ser Arg Val Lys Cys Ser Asp Ile
                85                  90                  95

Phe Trp Val Ile Thr Asp Gln Leu Ser Thr Trp Leu Ala Thr Cys Leu
            100                 105                 110

Ser Ile Phe Tyr Leu Leu Lys Ile Ala His Phe Ser His Pro Leu Phe
        115                 120                 125
```

-continued

```
Leu Trp Leu Lys Trp Arg Leu Arg Gly Val Leu Val Gly Phe Leu Leu
    130                 135                 140

Phe Ser Leu Phe Ser Leu Ile Val Tyr Phe Leu Leu Leu Glu Leu Leu
145                 150                 155                 160

Ser Ile Trp Gly Asp Ile Tyr Val Ile Pro Lys Ser Asn Leu Thr Leu
                165                 170                 175

Tyr Ser Glu Thr Ile Lys Thr Leu Ala Phe Gln Lys Ile Ile Val Phe
            180                 185                 190

Asp Met Leu Tyr Leu Val Pro Phe Leu Val Ser Leu Ala Ser Leu Leu
        195                 200                 205

Leu Leu Phe Leu Ser Leu Val Lys His Ser Gln Asn Leu Asp Arg Ile
    210                 215                 220

Ser Thr Thr Ser Glu Asp Ser Arg Ala Lys Ile His Lys Lys Ala Met
225                 230                 235                 240

Lys Met Leu Leu Ser Phe Leu Val Leu Phe Ile Ile His Ile Phe Cys
                245                 250                 255

Met Gln Leu Ser Arg Trp Leu Phe Phe Leu Phe Pro Asn Asn Arg Ser
            260                 265                 270

Thr Asn Phe Leu Leu Leu Thr Leu Asn Ile Phe Pro Leu Ser His Thr
        275                 280                 285

Phe Ile Ile Ile Leu Gly Asn Ser Lys Leu Arg Gln Arg Ala Met Arg
    290                 295                 300

Val Leu Gln His Leu Lys Ser Gln Leu Gln Glu Leu Ile Leu Ser Leu
305                 310                 315                 320

His Arg Leu Ser Arg Val Phe Thr Met Glu Ile Ala
                325                 330
```

<210> SEQ ID NO 102
<211> LENGTH: 1287
<212> TYPE: DNA
<213> ORGANISM: Rattus sp.

<400> SEQUENCE: 102

```
gggattcagt tggataagag aaaagtcaaa accctaagac taagaatttc cttaagtaga     60

tatcaatttc tatccattgg aaggagtttc caatcacact gaaattacaa taaaaaagga    120

gcaagataac tatgggaaag gatgattttc ggtggatgtt tgagaactga gcagcaaggc    180

aaattgatag atgtgtggat tccctctttc tattcaactg cttactggat tggttcaaat    240

gtacgtgata ttgataatag cagtgtttac acctggaatg ctggggaatg tgttcattgg    300

actggtaaac tactctgact gggtaaaaaa caagaaaatc accttcatca acttcatcct    360

gatctgtttg gcagcgtcca gaatcagctc tgtgttggtg gtatttattg atgcaatcat    420

cctagaacta actcctcatg tctatcattc ttacagtcga gtgaaatgct ctgatatatt    480

ctgggttata actgaccagc tgtcaacgtg gcttgccacc tgcctcagca ttttctactt    540

actcaaaata gcccacttct cccatcccct tttcctttgg ttgaagtgga gattgagagg    600

agtgcttgtt ggttttcttc tattttcttt gttctcattg attgtttatt ttctactcct    660

ggaattactg tctatttggg gagatattta tgtgatccct aaaagcaatc tgactttata    720

ttcagaaaca attaagaccc ttgcttttca aaagataatt gtttttgata tgctatattt    780

agtcccattt cttgtgtccc tagcctcatt gctcctttta tttttatcct tggtgaagca    840

ctcccaaaac cttgacagga tttctaccac ctctgaagat tccagagcca agatccacaa    900

gaaggccatg aaaatgctat tatctttcct cgttctcttt ataattcaca ttttttgcat    960
```

-continued

```
gcagttgtca cggtggttat tctttttgtt tccaaacaac aggtcaacta attttctttt   1020

gttaacatta aacatcttcc cattatctca tacattcatt atcatcctgg gaaacagcaa   1080

gcttcgacaa agagcaatga gggtcctgca acatcttaaa agccaacttc aagagttgat   1140

cctctccctt catagattgt ccagagtctt cactatggaa atagcttaaa ggggagactt   1200

ggaaggtcac tggtaacttg ttcttccgct gagttctgtt aagtaatgct ggacatatat   1260

gaactatccc tagtgcatac tgatatt                                       1287
```

<210> SEQ ID NO 103
<211> LENGTH: 68
<212> TYPE: PRT
<213> ORGANISM: Rattus sp.

<400> SEQUENCE: 103

```
Val Ala Asn Ile Met Asp Trp Val Lys Arg Arg Lys Leu Ser Ala Val
1               5                   10                  15

Asp Gln Leu Leu Thr Val Leu Ala Ile Ser Arg Ile Thr Leu Leu Trp
            20                  25                  30

Ser Leu Tyr Ile Leu Lys Ser Thr Phe Ser Met Val Pro Asn Phe Glu
        35                  40                  45

Val Ala Ile Pro Ser Thr Arg Leu Thr Asn Leu Val Trp Ile Ile Ser
    50                  55                  60

Asn His Phe Asn
65
```

<210> SEQ ID NO 104
<211> LENGTH: 206
<212> TYPE: DNA
<213> ORGANISM: Rattus sp.

<400> SEQUENCE: 104

```
ctgtggcaaa cataatggat tgggtcaaga gaaggaagct ctctgcagtg gatcagctcc     60

tcactgtgct ggccatctcc agaatcactc tgttgtggtc attgtacata ctgaaatcaa    120

cattttcaat ggtgccaaac tttgaggtag ctataccgtc aacaagacta actaatcttg    180

tctggataat ttctaaccat tttaat                                         206
```

<210> SEQ ID NO 105
<211> LENGTH: 327
<212> TYPE: PRT
<213> ORGANISM: Mus musculus

<400> SEQUENCE: 105

```
Met Gln His Leu Leu Lys Thr Ile Phe Val Ile Cys His Ser Thr Leu
1               5                   10                  15

Ala Ile Ile Leu Ile Phe Glu Leu Ile Ile Gly Ile Leu Gly Asn Gly
            20                  25                  30

Phe Met Ala Leu Val His Cys Met Asp Trp Val Lys Arg Lys Lys Met
        35                  40                  45

Ser Leu Val Asn Lys Ile Leu Thr Ala Leu Ala Ile Ser Arg Ile Phe
    50                  55                  60

His Leu Ser Leu Leu Leu Ile Ser Leu Val Ile Phe Phe Ser Tyr Ser
65                  70                  75                  80

Asp Ile Pro Met Thr Ser Arg Met Thr Gln Val Ser Asn Asn Val Trp
                85                  90                  95

Ile Ile Val Asn His Phe Ser Ile Trp Leu Ser Thr Cys Leu Ser Val
            100                 105                 110
```

-continued

```
Leu Tyr Phe Leu Lys Ile Ser Asn Phe Ser Asn Ser Phe Phe Leu Tyr
        115                 120                 125

Leu Lys Trp Arg Val Glu Lys Val Val Ser Val Thr Leu Leu Val Ser
    130                 135                 140

Leu Leu Leu Leu Ile Leu Asn Ile Leu Leu Ile Asn Leu Glu Ile Ser
145                 150                 155                 160

Ile Cys Ile Lys Glu Cys Gln Arg Asn Ile Ser Cys Ser Phe Ser Ser
                165                 170                 175

His Tyr Tyr Ala Lys Cys His Arg Gln Val Ile Arg Leu His Ile Ile
            180                 185                 190

Phe Leu Ser Val Pro Val Val Leu Ser Leu Ser Thr Phe Leu Leu Leu
        195                 200                 205

Ile Phe Ser Leu Trp Thr Leu His Gln Arg Met Gln Gln His Val Gln
    210                 215                 220

Gly Gly Arg Asp Ala Arg Thr Thr Ala His Phe Lys Ala Leu Gln Thr
225                 230                 235                 240

Val Ile Ala Phe Phe Leu Leu Tyr Ser Ile Phe Ile Leu Ser Val Leu
                245                 250                 255

Ile Gln Asn Glu Leu Leu Lys Lys Asn Leu Phe Val Val Phe Cys Glu
            260                 265                 270

Val Val Tyr Ile Ala Phe Pro Thr Phe His Ser Tyr Ile Leu Ile Val
        275                 280                 285

Gly Asp Met Lys Leu Arg Gln Ala Cys Leu Pro Leu Cys Ile Ile Ala
    290                 295                 300

Ala Glu Ile Gln Thr Thr Leu Cys Arg Asn Phe Arg Ser Leu Lys Tyr
305                 310                 315                 320

Phe Arg Leu Cys Cys Ile Phe
                325
```

```
<210> SEQ ID NO 106
<211> LENGTH: 1374
<212> TYPE: DNA
<213> ORGANISM: Mus musculus

<400> SEQUENCE: 106

agctgtgcgt gagcaaagca tttcttgtct gccacttctg agctgtgtga ggagacacat     60

tatcacggaa agagattcag actctgtcgc tgtcaaacct gtatgtttgc tcctctttta    120

ctgtgaaggc agagttacga aaaaaaatgt tatgagaacc aactcagaaa ttgacaaaaa    180

ttttctaaat gtcattttta aaaattatat ttcaaatgga aatgtgagca aatctttata    240

actaatatat aaaatgcagc atcttttaaa gacaatattt gttatctgcc atagcacact    300

tgcaatcatt ttaatctttg aattaataat tggaatttta ggaaatgggt tcatggccct    360

ggtgcactgt atggactggg ttaagagaaa gaaaatgtcc ttagttaata aaatcctcac    420

tgctttggca atctccagaa tttttcatct cagtttattg cttataagtt tagtcatatt    480

cttttcatat tctgatattc ctatgacttc aaggatgaca caagtcagta ataatgtttg    540

gattatagtc aatcatttca gtatctggct ttctacatgc ctcagtgtcc tttattttct    600

caagatatcc aatttttcta actctttttt tctttatcta aagtggagag ttgaaaaagt    660

agtttcagtt acactgttgg tgtcattgct cctcctgatt ttaaatattt tattaattaa    720

cttggaaatt agcatatgca taaaggaatg tcaaagaaac atatcatgca gcttcagttc    780

tcattactat gcaaagtgtc acaggcaggt gataaggctt cacattattt tcctgtctgt    840
```

-continued

```
ccccgttgtt ttgtccctgt caacttttct cctgctcatc ttctccctgt ggacacttca    900

ccagaggatg cagcagcatg ttcagggagg cagagatgcc agaaccacgg cccacttcaa    960

agccctacaa actgtgattg catttttcct actatattcc atttttattc tgtctgtctt   1020

aatacaaata tgaattactg aagaaaaatc ttttcgttgt attttgtgag gttgtatata   1080

tagcttttcc gacattccat tcatatattc tgattgtagg agacatgaag ctgagacagg   1140

cctgcctgcc tctctgtatt atcgcagctg aaattcagac tacactatgt agaaatttta   1200

gatcactaaa gtactttaga ttatgttgta tattctagac aaaaattaac tgatacaaat   1260

gtcttttgta tttttcattt taaatatcct ttaattttga ctgcatgaaa ttgatttctg   1320

cttgcaatta tcactgatta aaactattaa taatttaact agttgtatac aagg         1374
```

<210> SEQ ID NO 107
<211> LENGTH: 327
<212> TYPE: PRT
<213> ORGANISM: Mus musculus

<400> SEQUENCE: 107

```
Met Glu Ser Val Leu His Asn Phe Ala Thr Val Leu Ile Tyr Val Glu
1               5                   10                  15

Phe Ile Phe Gly Asn Leu Ser Asn Gly Phe Ile Val Leu Ser Asn Phe
            20                  25                  30

Leu Asp Trp Val Ile Lys Gln Lys Leu Ser Leu Ile Asp Lys Ile Leu
        35                  40                  45

Leu Thr Leu Ala Ile Ser Arg Ile Thr Leu Ile Trp Glu Ile Tyr Ala
    50                  55                  60

Trp Phe Lys Ser Leu Tyr Asp Pro Ser Ser Phe Leu Ile Gly Ile Glu
65                  70                  75                  80

Phe Gln Ile Ile Tyr Phe Ser Trp Val Leu Ser Ser His Phe Ser Leu
                85                  90                  95

Trp Leu Ala Thr Thr Leu Ser Val Phe Tyr Leu Leu Arg Ile Ala Asn
            100                 105                 110

Cys Ser Trp Gln Ile Phe Leu Tyr Leu Lys Trp Arg Leu Lys Gln Leu
        115                 120                 125

Ile Val Gly Met Leu Leu Gly Ser Leu Val Phe Leu Leu Gly Asn Leu
    130                 135                 140

Met Gln Ser Met Leu Glu Glu Arg Phe Tyr Gln Tyr Gly Arg Asn Thr
145                 150                 155                 160

Ser Val Asn Thr Met Ser Asn Asp Leu Ala Met Trp Thr Glu Leu Ile
                165                 170                 175

Phe Phe Asn Met Ala Met Phe Ser Val Ile Pro Phe Thr Leu Ala Leu
            180                 185                 190

Ile Ser Phe Leu Leu Leu Ile Phe Ser Leu Trp Lys His Leu Gln Lys
        195                 200                 205

Met Gln Leu Ile Ser Arg Arg His Arg Asp Pro Ser Thr Lys Ala His
    210                 215                 220

Met Asn Ala Leu Arg Ile Met Val Ser Phe Leu Leu Leu Tyr Thr Met
225                 230                 235                 240

His Phe Leu Ser Leu Leu Ile Ser Trp Ile Ala Gln Lys His Gln Ser
                245                 250                 255

Glu Leu Ala Asp Ile Ile Gly Met Ile Thr Glu Leu Met Tyr Pro Ser
            260                 265                 270

Val His Ser Cys Ile Leu Ile Leu Gly Asn Ser Lys Leu Lys Gln Thr
        275                 280                 285
```

```
Ser Leu Cys Met Leu Arg His Leu Arg Cys Arg Leu Lys Gly Glu Asn
    290                 295                 300

Ile Thr Ile Ala Tyr Ser Asn Gln Ile Thr Ser Phe Cys Val Phe Cys
305                 310                 315                 320

Val Ala Asn Lys Ser Met Arg
                325

<210> SEQ ID NO 108
<211> LENGTH: 1759
<212> TYPE: DNA
<213> ORGANISM: Mus musculus

<400> SEQUENCE: 108
```

| | | | | | |
|---|---|---|---|---|---|
| cagcacagtg | aaaaactcat | gggccacttg | gtcacccagg | gacaggcgac | gctgttatat | 60 |
| gccaagcttt | ctatgaacat | ggaatctgtc | cttcacaact | ttgccactgt | actaatatac | 120 |
| gtggagttta | tttttgggaa | tttgagcaat | ggattcatag | tgttgtcaaa | cttcttggac | 180 |
| tgggtcatta | aacaaaagct | ttccttaata | gataaaattc | ttcttacatt | ggcaatttca | 240 |
| agaatcactc | tcatctggga | aatatatgct | tggtttaaaa | gtttatatga | tccatcttcc | 300 |
| tttttaattg | gaatagaatt | tcaaattatt | tattttagct | gggtcctttc | tagtcacttc | 360 |
| agcctctggc | ttgccacaac | tctcagcgtc | ttttatttac | tcagaatagc | taactgctcc | 420 |
| tggcagatct | ttctctattt | gaaatggaga | cttaaacaac | tgattgtggg | gatgttgctg | 480 |
| ggaagcttgg | tgttcttgct | tggaaatctg | atgcaaagca | tgcttgaaga | gaggttctat | 540 |
| caatatggaa | ggaacacaag | tgtgaatacc | atgagcaatg | accttgcaat | gtggaccgag | 600 |
| ctgatctttt | tcaacatggc | tatgttctct | gtaataccat | ttacattggc | cttgatttct | 660 |
| tttctcctgc | taatcttctc | tttgtggaaa | catctccaga | agatgcagct | catttccaga | 720 |
| agacacagag | accctagcac | caaggcccac | atgaatgcct | tgagaattat | ggtgtccttc | 780 |
| ctcttgctct | ataccatgca | tttcctgtct | cttcttatat | catggattgc | tcaaaagcat | 840 |
| cagagtgaac | tggctgatat | tattggtatg | ataactgaac | tcatgtatcc | ttcagtccat | 900 |
| tcatgtatcc | tgattctagg | aaattctaaa | ttaaagcaga | cttctctttg | tatgctgagg | 960 |
| catttgagat | gtaggctgaa | aggagagaat | atcacaattg | catatagcaa | ccaaataact | 1020 |
| agcttttgtg | tattctgtgt | tgcaaacaaa | tctatgaggt | agttgttcaa | ggaatccttc | 1080 |
| cttgacttat | tgtatcatgg | aagtcatatg | ggggagtctg | aaagagctgt | cttctgtaag | 1140 |
| caaggtttgt | atacactagt | ggggctggga | caccaaccca | agcacaaaac | ctagctataa | 1200 |
| cctatcctgg | ctgcaggata | tgctggaaca | atggtggctt | ggaaattgtg | ggactggcaa | 1260 |
| agcaatagct | agtctaactt | gaggcccatt | ccacagcagg | aagctcatgc | ccacctctgc | 1320 |
| ctggatggcc | aggaagcaaa | atcttgatgg | ccccaagacc | tatggtaaac | tgaacactac | 1380 |
| tggaaaaaga | aagactcgtg | ttaatgatct | atcaaatatt | tcctaatgat | attctgataa | 1440 |
| actcatatat | tagtccctgt | cctaatcatc | atcactggga | ctccttccca | gcacctgatg | 1500 |
| ggagcagata | gagatctaca | tccaaatagt | aagtgtatct | tggggaactc | cacttaagaa | 1560 |
| tagaaggaac | aattatgaga | gccagagtga | tccagaacac | taggatcaca | gaatcaacta | 1620 |
| agcagcatgc | atagggatta | atggagactg | aagtggcaat | cacagagcct | gcataggtct | 1680 |
| acactaagtc | ctctgtgtat | atactgtggc | tgtttagctt | aggaattttg | ttggactcct | 1740 |
| aacaatggat | aaggaattc | | | | | 1759 |

-continued

```
<210> SEQ ID NO 109
<211> LENGTH: 312
<212> TYPE: PRT
<213> ORGANISM: Mus musculus

<400> SEQUENCE: 109

Met Val Leu Thr Ile Arg Ala Ile Leu Trp Val Thr Leu Ile Thr Ile
1               5                   10                  15

Ile Ser Leu Glu Phe Ile Ile Gly Ile Leu Gly Asn Val Phe Ile Ala
            20                  25                  30

Leu Val Asn Ile Ile Asp Trp Val Lys Arg Gly Lys Ile Ser Ala Val
        35                  40                  45

Asp Lys Thr Tyr Met Ala Leu Ala Ile Ser Arg Thr Ala Phe Leu Leu
    50                  55                  60

Ser Leu Ile Thr Gly Phe Leu Val Ser Leu Leu Asp Pro Ala Leu Leu
65                  70                  75                  80

Gly Met Arg Thr Met Val Arg Leu Leu Thr Ile Ser Trp Met Val Thr
                85                  90                  95

Asn His Phe Ser Val Trp Phe Ala Thr Cys Leu Ser Ile Phe Tyr Phe
            100                 105                 110

Leu Lys Ile Ala Asn Phe Ser Asn Ser Ile Phe Leu Val Leu Lys Trp
        115                 120                 125

Glu Ala Lys Lys Val Val Ser Val Thr Leu Val Val Ser Val Ile Ile
    130                 135                 140

Leu Ile Met Asn Ile Ile Val Ile Asn Lys Phe Thr Asp Arg Leu Gln
145                 150                 155                 160

Val Asn Thr Leu Gln Asn Cys Ser Thr Ser Asn Thr Leu Lys Asp Tyr
                165                 170                 175

Gly Leu Phe Leu Phe Ile Ser Thr Gly Phe Thr Leu Thr Pro Phe Ala
            180                 185                 190

Val Ser Leu Thr Met Phe Leu Leu Leu Ile Phe Ser Leu Trp Arg His
        195                 200                 205

Leu Lys Asn Met Cys His Ser Ala Thr Gly Ser Arg Asp Val Ser Thr
    210                 215                 220

Val Ala His Ile Lys Gly Leu Gln Thr Val Val Thr Phe Leu Leu Leu
225                 230                 235                 240

Tyr Thr Ala Phe Val Met Ser Leu Leu Ser Glu Ser Leu Asn Ile Asn
                245                 250                 255

Ile Gln His Thr Asn Leu Leu Ser His Phe Leu Arg Ser Ile Gly Val
            260                 265                 270

Ala Phe Pro Thr Gly His Ser Cys Val Leu Ile Leu Gly Asn Ser Lys
        275                 280                 285

Leu Arg Gln Ala Ser Leu Ser Val Ile Leu Trp Leu Arg Tyr Lys Tyr
    290                 295                 300

Lys His Ile Glu Asn Trp Gly Pro
305                 310


<210> SEQ ID NO 110
<211> LENGTH: 1484
<212> TYPE: DNA
<213> ORGANISM: Mus musculus

<400> SEQUENCE: 110

ctttaatagc agggtgtgaa tatttaaatt ttctttctgc agcaactact gagggcttca      60

gactgctgta tacagggcat gaagcatctg gatgaagttc agctgtgctg cctttgacaa     120
```

-continued

```
caattttttg tgtatgtgtg gagaacataa accatttcat tagtgaaatt tggcttttgg    180

gtgacattgt ctatgatagt tctgaaagtg attatgttaa gaatcagaca cagccgtcta    240

gaagattgta ttaacacatc tttggtagtt cagaagaaat tagatcatca tggtgttgac    300

aataagggct attttatggg taacattgat aactattata agtctggagt ttatcatagg    360

aattttagga aatgtattca tagctctcgt gaacatcata gactgggtta aaagaggaaa    420

gatctctgca gtggataaga cctatatggc cctggccatc tccaggactg ctttttttatt    480

gtcactaatc acagggttct tggtatcatt attggaccca gctttattgg gaatgagaac    540

gatggtaagg ctccttacta tttcctggat ggtgaccaat catttcagtg tctggtttgc    600

aacatgcctc agtatctttt attttctcaa gatagctaat ttctcaaatt ctattttcct    660

tgttctcaaa tgggaagcta aaaaagtggt atcagtgaca ttggtggtat ctgtgataat    720

cttgatcatg aacattatag tcataaacaa attcactgac agacttcaag taaacacact    780

ccagaactgt agtacaagta acactttaaa agattatggg ctctttttat tcattagcac    840

tgggtttaca ctcaccccat tcgctgtgtc tttgacaatg tttcttctgc tcatcttctc    900

cctgtggaga catctgaaga atatgtgtca cagtgcccaca ggctccagag atgtcagcac    960

agtggcccac ataaaaggct tgcaaactgt ggtaaccttc ctgttactat atactgcttt   1020

tgttatgtca cttctttcag agtctttgaa tattaacatt caacatacaa atcttctttc   1080

tcatttttta cggagtatag gagtagcttt tcccacaggc cactcctgtg tactgattct   1140

tggaaacagt aagctgaggc aagcctctct ttctgtgata ttgtggctga ggtataagta   1200

caaacatata gagaattggg gccccctaaat catatcaggg atccttttcc acattctaga   1260

aaaaaatcag ttaataagaa caggaattta ggaaggaatc tgaaattatg aatctcatag   1320

gccatgaacc ttcagacaaa ggattcatta gagagataga gagagaacat tgttatctgt   1380

aactggacag gcaacactgt agattatgaa aataaatgtc agtctgtaat ggaaagcaaa   1440

acatgctata ttttattaat tggttttggt ttaaggtcgg gata                    1484
```

```
<210> SEQ ID NO 111
<211> LENGTH: 302
<212> TYPE: PRT
<213> ORGANISM: Mus musculus

<400> SEQUENCE: 111

Met Leu Ser Ala Leu Glu Ser Ile Leu Leu Ser Val Ala Thr Ser Glu
1               5                   10                  15

Ala Met Leu Gly Val Leu Gly Asn Thr Phe Ile Val Leu Val Asn Tyr
            20                  25                  30

Thr Asp Trp Val Arg Asn Lys Lys Leu Ser Lys Ile Asn Phe Ile Leu
        35                  40                  45

Thr Gly Leu Ala Ile Ser Arg Ile Phe Thr Ile Trp Ile Ile Thr Leu
    50                  55                  60

Asp Ala Tyr Thr Lys Val Phe Leu Leu Thr Met Leu Met Pro Ser Ser
65                  70                  75                  80

Leu His Glu Cys Met Ser Tyr Ile Trp Val Ile Ile Asn His Leu Ser
                85                  90                  95

Val Trp Phe Ser Thr Ser Leu Gly Ile Phe Tyr Phe Leu Lys Ile Ala
            100                 105                 110

Asn Phe Ser His Tyr Ile Phe Leu Trp Met Lys Arg Arg Ala Asp Lys
        115                 120                 125

Val Phe Val Phe Leu Ile Val Phe Leu Ile Ile Thr Trp Leu Ala Ser
```

-continued

```
    130                 135                 140

Phe Pro Leu Ala Val Lys Val Ile Lys Asp Val Lys Ile Tyr Gln Ser
145                 150                 155                 160

Asn Thr Ser Trp Leu Ile His Leu Glu Lys Ser Glu Leu Leu Ile Asn
                165                 170                 175

Tyr Val Phe Ala Asn Met Gly Pro Ile Ser Leu Phe Ile Val Ala Ile
            180                 185                 190

Ile Ala Cys Phe Leu Leu Thr Ile Ser Leu Trp Arg His Ser Arg Gln
        195                 200                 205

Met Gln Ser Ile Gly Ser Gly Phe Arg Asp Leu Asn Thr Glu Ala His
    210                 215                 220

Met Lys Ala Met Lys Val Leu Ile Ala Phe Ile Ile Leu Phe Ile Leu
225                 230                 235                 240

Tyr Phe Leu Gly Ile Leu Ile Glu Thr Leu Cys Leu Phe Leu Thr Asn
                245                 250                 255

Asn Lys Leu Leu Phe Ile Phe Gly Phe Thr Leu Ser Ala Met Tyr Pro
            260                 265                 270

Cys Cys His Ser Phe Ile Leu Ile Leu Thr Ser Arg Glu Leu Lys Gln
        275                 280                 285

Asp Thr Met Arg Ala Leu Gln Arg Leu Lys Cys Cys Glu Thr
    290                 295                 300


<210> SEQ ID NO 112
<211> LENGTH: 1529
<212> TYPE: DNA
<213> ORGANISM: Mus musculus

<400> SEQUENCE: 112

ctgcagcagg taaatcacac cagatccagc agaagccttc ttggaaattg gcagagatgc     60

tgagtgcact ggaaagcatc ctcctttctg ttgccactag tgaagccatg ctgggagttt    120

tagggaacac atttattgta cttgtaaact acacagactg ggtcaggaat aagaaactct    180

ctaagattaa ctttattctc actggcttag caatttccag gatttttacc atatggataa    240

taactttaga tgcatataca aaggttttcc ttctgactat gcttatgccg agcagtctac    300

atgaatgcat gagttacata tgggtaatta ttaaccatct gagcgtttgg tttagcacca    360

gcctcggcat cttttatttt ctgaagatag caaatttttc ccactacata tttctctgga    420

tgaagagaag agctgataaa gtttttgtct ttctaattgt attcttaatt ataacgtggc    480

tagcttcctt tccgctagct gtgaaggtca ttaaagatgt taaaatatat cagagcaaca    540

catcctggct gatccacctg gagaagagtg agttacttat aaactatgtt tttgccaata    600

tggggcccat ttccctcttt attgtagcca taattgcttg tttcttgtta accatttccc    660

tttggagaca cagcaggcag atgcaatcca ttggatcagg attcagagat ctcaacacag    720

aagctcacat gaaagccatg aaagttttaa ttgcatttat catcctcttt atcttatatt    780

ttttgggtat tctcatagaa acattatgct tgtttcttac aaacaataaa cttctcttta    840

tttttggctt cactttgtca gccatgtatc cctgttgcca ttcctttatc ctaattctaa    900

caagcaggga gctgaagcaa gccactatga gggcactgca gagattaaaa tgctgtgaga    960

cttgacagag aaatgaatgt tctggcacag ttcagcaggg aatccctgga gccctttcca   1020

ttcccactat gttctcacac tgtctttagt tgaattgtta aaagtttttg aaacctttgg   1080

caactgattg actgcagcta cgccagtgta agattttcat agtaagagca aacattgaaa   1140

ataagacttc tcagtcttat ttcattgagt ttctaaagca ttgacaccca ttcaccagaa   1200
```

-continued

```
aaaccaaagg ggaagagagg agttttcaga catgtgtgat gaatcttgat atttaggaca   1260

tggaattgag gagccagagg gatgctaccg tgtgtctaca gctttgtttg ttaaatagct   1320

acttttcctt tcccagttag ttaaagtaga tgcttggagt agtggtgaaa atcatggcag   1380

tagatgggat ctgtgggaag tggttgagga agcaggctgt ttctgaacga agagaccaga   1440

ggactgattg aactggtcat tgtgtatatc aaaaatagtg atttcagatg aagccaagtt   1500

gtagagcaaa gatatctgag gaagaattc                                    1529
```

<210> SEQ ID NO 113
<211> LENGTH: 300
<212> TYPE: PRT
<213> ORGANISM: Mus musculus

<400> SEQUENCE: 113

```
Met Leu Ser Ala Ala Glu Gly Ile Leu Leu Ser Ile Ala Thr Val Glu
1               5                   10                  15

Ala Gly Leu Gly Val Leu Gly Asn Thr Phe Ile Ala Leu Val Asn Cys
            20                  25                  30

Met Asp Trp Ala Lys Asn Asn Lys Leu Ser Met Thr Gly Phe Leu Leu
        35                  40                  45

Ile Gly Leu Ala Thr Ser Arg Ile Phe Ile Val Trp Leu Leu Thr Leu
    50                  55                  60

Asp Ala Tyr Ala Lys Leu Phe Tyr Pro Ser Lys Tyr Phe Ser Ser Ser
65                  70                  75                  80

Leu Ile Glu Ile Ile Ser Tyr Ile Trp Met Thr Val Asn His Leu Thr
                85                  90                  95

Val Trp Phe Ala Thr Ser Leu Ser Ile Phe Tyr Phe Leu Lys Ile Ala
            100                 105                 110

Asn Phe Ser Asp Cys Val Phe Leu Trp Leu Lys Arg Arg Thr Asp Lys
        115                 120                 125

Ala Phe Val Phe Leu Leu Gly Cys Leu Leu Thr Ser Trp Val Ile Ser
    130                 135                 140

Phe Ser Phe Val Val Lys Val Met Lys Asp Gly Lys Val Asn His Arg
145                 150                 155                 160

Asn Arg Thr Ser Glu Met Tyr Trp Glu Lys Arg Gln Phe Thr Ile Asn
                165                 170                 175

Tyr Val Phe Leu Asn Ile Gly Val Ile Ser Leu Phe Met Met Thr Leu
            180                 185                 190

Thr Ala Cys Phe Leu Leu Ile Met Ser Leu Trp Arg His Ser Arg Gln
        195                 200                 205

Met Gln Ser Gly Val Ser Gly Phe Arg Asp Leu Asn Thr Glu Ala His
    210                 215                 220

Val Lys Ala Ile Lys Phe Leu Ile Ser Phe Ile Ile Leu Phe Val Leu
225                 230                 235                 240

Tyr Phe Ile Gly Val Ser Ile Glu Ile Ile Cys Ile Phe Ile Pro Glu
                245                 250                 255

Asn Lys Leu Leu Phe Ile Phe Gly Phe Thr Thr Ala Ser Ile Tyr Pro
            260                 265                 270

Cys Cys His Ser Phe Ile Leu Ile Leu Ser Asn Ser Gln Leu Lys Gln
        275                 280                 285

Ala Phe Val Lys Val Leu Gln Gly Leu Lys Phe Phe
    290                 295                 300
```

-continued

<210> SEQ ID NO 114
<211> LENGTH: 903
<212> TYPE: DNA
<213> ORGANISM: Mus musculus

<400> SEQUENCE: 114
atgctgagtg cggcagaagg catcctcctt tccattgcaa ctgttgaagc tgggctggga 60
gttttaggga acacatttat tgcactggta aactgcatgg actgggccaa gaacaataag 120
ctttctatga ctggcttcct tctcatcggc ttagcaactt ccaggatttt tattgtgtgg 180
ctattaactt tagatgcata tgcaaagcta ttctatccaa gtaagtattt ttctagtagt 240
ctgattgaaa tcatctctta tatatggatg actgtgaatc acctgactgt ctggtttgcc 300
accagcctaa gcatcttcta tttcctgaag atagccaatt tttccgactg tgtatttctc 360
tggttgaaga ggagaactga taaagctttt gtttttctct tggggtgttt gctaacttca 420
tgggtaatct ccttctcatt tgttgtgaag gtgatgaagg acggtaaagt gaatcataga 480
aacaggacct cggagatgta ctgggagaaa aggcaattca ctattaacta cgttttcctc 540
aatattggag tcatttctct ctttatgatg accttaactg catgtttctt gttaattatg 600
tcactttgga gacacagcag gcagatgcag tctggtgttt caggattcag agacctcaac 660
acagaagctc atgtgaaagc cataaaattt ttaatttcat ttatcatcct tttcgtcttg 720
tattttatag gtgtttcaat agaaattatc tgcatattta taccagaaaa caaactgcta 780
tttatttttg gtttcacaac tgcatccata tatccttgct gtcactcatt tattctaatt 840
ctatctaaca gccagctaaa gcaagccttt gtaaaggtac tgcaaggatt aaagttcttt 900
tag 903

<210> SEQ ID NO 115
<211> LENGTH: 308
<212> TYPE: PRT
<213> ORGANISM: Mus musculus

<400> SEQUENCE: 115

Met Leu Thr Val Ala Glu Gly Ile Leu Leu Cys Phe Val Thr Ser Gly
1 5 10 15

Ser Val Leu Gly Val Leu Gly Asn Gly Phe Ile Leu His Ala Asn Tyr
20 25 30

Ile Asn Cys Val Arg Lys Lys Phe Ser Thr Ala Gly Phe Ile Leu Thr
35 40 45

Gly Leu Ala Ile Cys Arg Ile Phe Val Ile Cys Ile Ile Ile Ser Asp
50 55 60

Gly Tyr Leu Lys Leu Phe Ser Pro His Met Val Ala Ser Asp Ala His
65 70 75 80

Ile Ile Val Ile Ser Tyr Ile Trp Val Ile Ile Asn His Thr Ser Ile
85 90 95

Trp Phe Ala Thr Ser Leu Asn Leu Phe Tyr Leu Leu Lys Ile Ala Asn
100 105 110

Phe Ser His Tyr Ile Phe Phe Cys Leu Lys Arg Arg Ile Asn Thr Val
115 120 125

Phe Ile Phe Leu Leu Gly Cys Leu Phe Ile Ser Trp Ser Ile Ala Phe
130 135 140

Pro Gln Thr Val Lys Ile Phe Asn Val Lys Lys Gln His Arg Asn Val
145 150 155 160

Ser Trp Gln Val Tyr Leu Tyr Lys Asn Glu Phe Ile Val Ser His Ile
165 170 175

-continued

```
Leu Leu Asn Leu Gly Val Ile Phe Phe Phe Met Val Ala Ile Ile Thr
            180                 185                 190

Cys Phe Leu Leu Ile Ile Ser Leu Trp Lys His Asn Arg Lys Met Gln
        195                 200                 205

Leu Tyr Ala Ser Arg Phe Lys Ser Leu Asn Thr Glu Val His Val Lys
    210                 215                 220

Val Met Lys Val Leu Ile Ser Phe Ile Ile Leu Leu Ile Leu His Phe
225                 230                 235                 240

Ile Gly Ile Leu Ile Glu Thr Leu Ser Phe Leu Lys Tyr Glu Asn Lys
                245                 250                 255

Leu Leu Leu Ile Leu Gly Leu Ile Ile Ser Cys Met Tyr Pro Cys Cys
            260                 265                 270

His Ser Phe Ile Leu Ile Leu Ala Asn Ser Gln Leu Lys Gln Ala Ser
        275                 280                 285

Leu Lys Ala Leu Lys Gln Leu Lys Cys His Lys Lys Asp Lys Asp Val
    290                 295                 300

Arg Val Thr Trp
305


<210> SEQ ID NO 116
<211> LENGTH: 1242
<212> TYPE: DNA
<213> ORGANISM: Mus musculus

<400> SEQUENCE: 116

tatagttgca gcagaagcaa cgttagggat ctgtagagat gctgactgta gcagaaggaa     60

tcctcctttg ttttgtaact agtggttcag tcctgggagt tctaggaaat ggatttatcc    120

tgcatgcaaa ctacattaac tgtgtcagaa agaagttctc cacagctggc tttattctca    180

caggcttggc tatttgcaga atctttgtca tatgtataat aatctctgat ggatatttaa    240

aattgttttc tccacatatg gttgcctctg atgcccacat tatagtgatt tcttacatat    300

gggtaattat caatcataca agtatatggt ttgccaccag cctcaacctc ttctatctcc    360

tgaagatagc aaatttttct cactacatct tcttctgctt gaagagaaga atcaatacag    420

tatttatctt tctcctggga tgcttattta tatcatggtc aattgctttc ccacaaacag    480

tgaagatatt taatgttaaa aagcagcaca gaaatgtttc ctggcaggtt tacctctata    540

agaatgagtt cattgtaagc cacattcttc tcaacctggg agttatattc ttctttatgg    600

tggctatcat tacatgcttc ctattaatta tttcactttg gaaacataac agaaagatgc    660

agttgtatgc ctcaagattc aaaagcctta acacagaagt acatgtgaaa gtcatgaaag    720

ttttaatttc ttttattatc ctgttaatct tgcatttcat agggattttg atagaaacat    780

tgagcttttt aaaatatgaa aataaactgc tacttatttt gggtttgata atttcatgca    840

tgtatccttg ctgtcattca tttatcctaa ttctagcaaa cagtcagctg aagcaggctt    900

ctttgaaggc actgaagcaa ttaaaatgcc ataagaaaga caaggacgtc agagtgacat    960

ggtagactta tggagaaatg aatggtcaca agaaatagcc tggtgtggag atgttgatat   1020

ctctaaagac cgtttcactt ccaaattctt gcaattattt aaaaaaaaaa gtcttgctga   1080

tatcatggaa tcatgggaaa tgttgcaatt gtgttttggg gacagggtga ccagtgaagg   1140

tatggttaag cagcgaaaca ctcatacagc tcgttcgttc tttttgtatt ttattttgtg   1200

ttggtggcct tccaagacat gatttctcta tgtaagtttt gg                      1242
```

-continued

<210> SEQ ID NO 117
<211> LENGTH: 308
<212> TYPE: PRT
<213> ORGANISM: Mus musculus

<400> SEQUENCE: 117

```
Met Leu Asn Ser Ala Glu Gly Ile Leu Leu Cys Val Val Thr Ser Glu
1               5                   10                  15

Ala Val Leu Gly Val Leu Gly Asp Thr Tyr Ile Ala Leu Phe Asn Cys
            20                  25                  30

Met Asp Tyr Ala Lys Asn Lys Lys Leu Ser Lys Ile Gly Phe Ile Leu
        35                  40                  45

Ile Gly Leu Ala Ile Ser Arg Ile Gly Val Val Trp Ile Ile Ile Leu
    50                  55                  60

Gln Gly Tyr Ile Gln Val Phe Phe Pro His Met Leu Thr Ser Gly Asn
65                  70                  75                  80

Ile Thr Glu Tyr Ile Thr Tyr Ile Trp Val Phe Leu Asn His Leu Ser
                85                  90                  95

Val Trp Phe Val Thr Asn Leu Asn Ile Leu Tyr Phe Leu Lys Ile Ala
            100                 105                 110

Asn Phe Ser Asn Ser Val Phe Leu Trp Leu Lys Arg Arg Val Asn Ala
        115                 120                 125

Val Phe Ile Phe Leu Ser Gly Cys Leu Leu Thr Ser Trp Leu Leu Cys
    130                 135                 140

Phe Pro Gln Met Thr Lys Ile Leu Gln Asn Ser Lys Met His Gln Arg
145                 150                 155                 160

Asn Thr Ser Trp Val His Gln Arg Lys Asn Tyr Phe Leu Ile Asn Gln
                165                 170                 175

Ser Val Thr Asn Leu Gly Ile Phe Phe Phe Ile Ile Val Ser Leu Ile
            180                 185                 190

Thr Cys Phe Leu Leu Ile Val Phe Leu Trp Arg His Val Arg Gln Met
        195                 200                 205

His Ser Asp Val Ser Gly Phe Arg Asp His Ser Thr Lys Val His Val
    210                 215                 220

Lys Ala Met Lys Phe Leu Ile Ser Phe Met Val Phe Phe Ile Leu His
225                 230                 235                 240

Phe Val Gly Leu Ser Ile Glu Val Leu Cys Phe Ile Leu Pro Gln Asn
                245                 250                 255

Lys Leu Leu Phe Ile Thr Gly Leu Thr Ala Thr Cys Leu Tyr Pro Cys
            260                 265                 270

Gly His Ser Ile Ile Val Ile Leu Gly Asn Lys Gln Leu Lys Gln Ala
        275                 280                 285

Ser Leu Lys Ala Leu Gln Gln Leu Lys Cys Cys Glu Thr Lys Gly Asn
    290                 295                 300

Phe Arg Val Lys
305
```

<210> SEQ ID NO 118
<211> LENGTH: 1754
<212> TYPE: DNA
<213> ORGANISM: Mus musculus

<400> SEQUENCE: 118

```
ttcataatga agaggaggca gggcaatgtt ggtttctgtt gtctgaccag tgtatttgac     60

agtgatacta cacatttgat tgctaaatgc aaatagttcc aaaggaacaa gtaaatttta    120
```

-continued

```
tgaaatagaa gcttctattt gcttattaac aaactgcaag caaacattag tctgcacaca    180
ttttatagac aagctaaatc ttcaaaagca ataaaaaaga gcacccataa agttctgact    240
ctatcacatg acaataggct tgaaaagatt gtctatgtag ataaagaaga tggcataact    300
tctccatcaa gaagccagta tatgggacat tctccagcag ataatttaca atagatgcag    360
cagaagtaac cttagagatc tgtaaagatg ctgaattcag cagaaggcat cctcctttgt    420
gttgtcacta gtgaggctgt gctcggagtt ttaggggaca catatattgc actttttaac    480
tgcatggact atgctaagaa caagaagctc tctaagatcg gtttcattct cattggcttg    540
gcgatttcca gaattggtgt tgtatggata ataattttac aagggtatat acaagtattt    600
tttccacaca tgcttacctc tggaaacata actgaatata ttacttacat atgggtattt    660
ctcaatcact taagtgtctg gtttgtcacc aacctcaaca tcctctactt tctaaagata    720
gctaattttt ccaactctgt atttctctgg ctgaaaagga gagtcaatgc agtttttatc    780
tttctgtcag gatgcttact tacctcatgg ttactatgtt ttccacaaat gacaaagata    840
cttcaaaata gtaaaatgca ccagagaaac acatcttggg tccaccagcg gaaaaattac    900
tttcttatta accaaagtgt gaccaatctg ggaatctttt tcttcattat tgtatccctg    960
attacctgct ttctgttgat tgttttcctc tggagacatg tcagacaaat gcactcagat   1020
gtttcaggat tcagagacca cagcacaaaa gtacatgtga aagctatgaa atttctaata   1080
tcttttatgg tcttctttat tctgcatttt gtaggccttt ccatagaagt gctatgcttt   1140
attctgccac aaaataaact gctctttata actggtttga cagccacatg cctctatccc   1200
tgcggtcact caatcatcgt aattttagga aataagcagt taaagcaagc ctctttgaag   1260
gcactgcagc aactaaaatg ctgtgagaca aaaggaaatt tcagagtcaa ataaatgggt   1320
ttgcaaataa atagctgcct tgttcttcca ctggttttta ccctgttagt tgatgttatg   1380
aaaagttcct gctatggttg atgacatctc aaggaatcta tttttctggt ggcatgttaa   1440
gtccacgtga agcctcactt catactgtga cttgactatg caaattcttt ccacaaaata   1500
accagataac attcagcctg gagataaatt catttaaagg cttttatggt gaggataaac   1560
aaaaaaaaaa aatcattttt ctgtgattca ctgtaactcc caggatgagt aaaagaaaac   1620
aagacaaatg gttgtgatca gcctttgtgt gtctagacag agctagggac cagatgttga   1680
tgcttgtgtg tggttttgag ttctttaaga agttattgcc tctctgccat tcggtattcc   1740
tcaggtgaga attc                                                     1754
```

<210> SEQ ID NO 119
<211> LENGTH: 297
<212> TYPE: PRT
<213> ORGANISM: Mus musculus

<400> SEQUENCE: 119

```
Met Leu Trp Glu Leu Tyr Val Phe Val Phe Ala Ala Ser Val Phe Leu
1               5                   10                  15

Asn Phe Val Gly Ile Ile Ala Asn Leu Phe Ile Ile Val Ile Ile Ile
            20                  25                  30

Lys Thr Trp Val Asn Ser Arg Arg Ile Ala Ser Pro Asp Arg Ile Leu
        35                  40                  45

Phe Ser Leu Ala Ile Thr Arg Phe Leu Thr Leu Gly Leu Phe Leu Leu
    50                  55                  60

Asn Ser Val Tyr Ile Ala Thr Asn Thr Gly Arg Ser Val Tyr Phe Ser
65                  70                  75                  80
```

-continued

```
Thr Phe Phe Leu Leu Cys Trp Lys Phe Leu Asp Ala Asn Ser Leu Trp
                85                  90                  95

Leu Val Thr Ile Leu Asn Ser Leu Tyr Cys Val Lys Ile Thr Asn Phe
            100                 105                 110

Gln His Pro Val Phe Leu Leu Leu Lys Arg Thr Ile Ser Met Lys Thr
        115                 120                 125

Thr Ser Leu Leu Leu Ala Cys Leu Leu Ile Ser Ala Leu Thr Thr Leu
    130                 135                 140

Leu Tyr Tyr Met Leu Ser Gln Ile Ser Arg Phe Pro Glu His Ile Ile
145                 150                 155                 160

Gly Arg Asn Asp Thr Ser Phe Asp Leu Ser Asp Gly Ile Leu Thr Leu
                165                 170                 175

Val Ala Ser Leu Val Leu Asn Ser Leu Leu Gln Phe Met Leu Asn Val
            180                 185                 190

Thr Phe Ala Ser Leu Leu Ile His Ser Leu Arg Arg His Ile Gln Lys
        195                 200                 205

Met Gln Arg Asn Arg Thr Ser Phe Trp Asn Pro Gln Thr Glu Ala His
    210                 215                 220

Met Gly Ala Met Arg Leu Met Ile Cys Phe Leu Val Leu Tyr Ile Pro
225                 230                 235                 240

Tyr Ser Ile Ala Thr Leu Leu Tyr Leu Pro Ser Tyr Met Arg Lys Asn
                245                 250                 255

Leu Arg Ala Gln Ala Ile Cys Met Ile Ile Thr Ala Ala Tyr Pro Pro
            260                 265                 270

Gly His Ser Val Leu Leu Ile Ile Thr His His Lys Leu Lys Ala Lys
        275                 280                 285

Ala Lys Lys Ile Phe Cys Phe Tyr Lys
    290                 295
```

<210> SEQ ID NO 120
<211> LENGTH: 1475
<212> TYPE: DNA
<213> ORGANISM: Mus musculus

<400> SEQUENCE: 120

```
aagcttgttt gtaattaggc attcctaaga aaataagaac aggagtgaag aaatagtaat      60

ttaatccttg aaagatttgc atctcagtaa aagcagctgc ctcttagacc agaaatggtg     120

tttgccatgc tggaaaataa aaaggagacc tctttccagg ctgcatcctg tgtctgctta     180

cttatttcag tttgttttca tcggcaccaa acgaggaaag atgctctggg aactgtatgt     240

atttgtgttt gctgcctcgg tttttttaaa ttttgtagga atcattgcaa atctatttat     300

tatagtgata attattaaga cttgggtcaa cagtcgcaga attgcctctc cggataggat     360

cctgttcagc ttggccatca ctagattcct gactttgggg ttgtttctac tgaacagtgt     420

ctacattgct acaaatactg gaaggtcagt ctacttttcc acattttttc tattgtgttg     480

gaagtttctg gatgcaaaca gtctctggtt agtgaccatt ctgaacagct tgtattgtgt     540

gaagattact aattttcaac acccagtgtt tctcctgttg aaacggacta tctctatgaa     600

gaccaccagc ctgctgttgg cctgtcttct gatttcagcc ctcaccactc tcctatatta     660

tatgctctca cagatatcac gttttcctga acacataatt gggagaaatg acacgtcatt     720

tgacctcagt gatggtatct tgacgttagt agcctctttg gtcctgaact cacttctaca     780

gtttatgctc aatgtgactt ttgcttcctt gttaatacat tccttgagaa gacatataca     840

gaagatgcag agaaacagga ccagcttttg gaatccccag acggaggctc acatgggtgc     900
```

-continued

```
tatgaggctg atgatctgtt tcctcgtgct ctacattcca tattcaattg ctaccctgct    960

ctatcttcct tcctatatga ggaagaatct gagagcccag gccatttgca tgattattac   1020

tgctgcttac cctccaggac attctgtcct cctcattatc acacatcata aactgaaagc   1080

taaagcaaag aagattttct gtttctacaa gtagcagaat ttcattagta gttaacagca   1140

tcaattcatg gtttggttgc attagaaatg tctcagtgat ctaaggactt aattttgtga   1200

tcttgtatct ggcatcctga ccctgagact aagtgcttat attttggtca atacagcatc   1260

ttttggctaa tattttaaag taaatcacat tccataagaa attgtttaag ggatttacgt   1320

atttttcatg gctatcacat tcctagacaa tggaaatcac catactgttt cgctagctac   1380

tgaagtacca ggggaaagtc catgaatgaa ggccacattg tgatgttctt ggttagcaca   1440

gattagagaa tttggcctca actgagcaag atatc                              1475
```

<210> SEQ ID NO 121
<211> LENGTH: 316
<212> TYPE: PRT
<213> ORGANISM: Mus musculus

<400> SEQUENCE: 121

```
Met Glu His Leu Leu Lys Arg Thr Phe Asp Ile Thr Glu Asn Ile Leu
1               5                   10                  15

Leu Ile Ile Leu Phe Ile Glu Leu Ile Ile Gly Leu Ile Gly Asn Gly
            20                  25                  30

Phe Thr Ala Leu Val His Cys Met Asp Trp Val Lys Arg Lys Lys Met
        35                  40                  45

Ser Leu Val Asn Lys Ile Leu Thr Ala Leu Ala Thr Ser Arg Ile Phe
    50                  55                  60

Leu Leu Trp Phe Met Leu Val Gly Phe Pro Ile Ser Ser Leu Tyr Pro
65                  70                  75                  80

Tyr Leu Val Thr Thr Arg Leu Met Ile Gln Phe Thr Ser Thr Leu Trp
                85                  90                  95

Thr Ile Ala Asn His Ile Ser Val Trp Phe Ala Thr Cys Leu Ser Val
            100                 105                 110

Phe Tyr Phe Leu Lys Ile Ala Asn Phe Ser Asn Ser Pro Phe Leu Tyr
        115                 120                 125

Leu Lys Arg Arg Val Glu Lys Val Val Ser Val Thr Leu Leu Val Ser
    130                 135                 140

Leu Val Leu Leu Phe Leu Asn Ile Leu Leu Leu Asn Leu Glu Ile Asn
145                 150                 155                 160

Met Cys Ile Asn Glu Tyr His Gln Ile Asn Ile Ser Tyr Ile Phe Ile
                165                 170                 175

Ser Tyr Tyr His Leu Ser Cys Gln Ile Gln Val Leu Gly Ser His Ile
            180                 185                 190

Ile Phe Leu Ser Val Pro Val Val Leu Ser Leu Ser Thr Phe Leu Leu
        195                 200                 205

Leu Ile Phe Ser Leu Trp Thr Leu His Lys Arg Met Gln Gln His Val
    210                 215                 220

Gln Gly Gly Arg Asp Ala Arg Thr Thr Ala His Phe Lys Ala Leu Gln
225                 230                 235                 240

Ala Val Ile Ala Phe Leu Leu Leu Tyr Ser Ile Phe Ile Leu Ser Leu
                245                 250                 255

Leu Leu Gln Phe Trp Ile His Gly Leu Arg Lys Lys Pro Pro Phe Ile
            260                 265                 270
```

-continued

```
Ala Phe Cys Gln Val Val Asp Thr Ala Phe Pro Ser Phe His Ser Tyr
        275                 280                 285

Val Leu Ile Leu Arg Asp Arg Lys Leu Arg His Ala Ser Leu Ser Val
    290                 295                 300

Leu Ser Trp Leu Lys Cys Arg Pro Asn Tyr Val Lys
305                 310                 315
```

<210> SEQ ID NO 122
<211> LENGTH: 1339
<212> TYPE: DNA
<213> ORGANISM: Mus musculus

<400> SEQUENCE: 122

```
gaattcagaa atcatcaaaa aatcttcaaa actacatgtt taaaatagca cttcaaatga     60

atacatttgc aaatctttac aactaataca taaaatggag catcttttga agagaacatt    120

tgatatcacc gagaacatac ttctaattat tttattcatt gaattaataa ttggacttat    180

aggaaacgga ttcacagcct tggtgcactg catggactgg gttaagagaa aaaaaatgtc    240

attagttaat aaaatcctca ccgctttggc aacttctaga attttcctgc tctggttcat    300

gctagtaggt tttccaatta gctcactgta cccatattta gttactacta gactgatgat    360

acagttcact agtactctat ggactatagc taaccatatt agtgtctggt ttgctacatg    420

cctcagtgtc ttttattttc tcaagatagc caatttttct aattctcctt ttctctatct    480

aaagaggaga gttgaaaaag tagtttcagt tacattactg gtgtctctgg tcctcttgtt    540

tttaaatatt ttactactta atttggaaat taacatgtgt ataaatgaat atcatcaaat    600

aaacatatca tacatcttca tttcttatta ccatttaagt tgtcaaattc aggtgttagg    660

aagtcacatt attttcctgt ctgtccccgt tgttttgtcc ctgtcaactt ttctcctgct    720

catcttctcc ctgtggacac ttcacaagag gatgcagcag catgttcagg gaggcagaga    780

tgccagaacc acggcccact tcaaagcctt gcaagcagtg attgcctttc tcctactata    840

ctccattttt atcctgtcac tgttactaca attttggatc catggattaa ggaagaaacc    900

tcctttcatt gcattttgtc aggttgtaga tacagctttt ccttcattcc attcatatgt    960

cttgattctg agagacagga agctgagaca cgcctctctc tctgtgttgt cgtggctgaa   1020

atgcaggcca aattatgtga aataatattt ctttgtattt tcattttcaa ttttaaaata   1080

ttcttagaat ttgactgcat gtatttcatc ttttatttga aacaaccact aattaaagct   1140

attactaatt tagcaagtcg tatacaaggt tattttttaa tacacatatc aaaaactgac   1200

atgtttatgt tctacaaaaa cctgaatata tcaaaattat ataaattttg tatcaacgat   1260

taacaatgga gttttttttat ttatgacctg tcacgggact ccggtggagt cagcttgtca  1320

gatgaaagtc tgaaagctt                                                1339
```

<210> SEQ ID NO 123
<211> LENGTH: 333
<212> TYPE: PRT
<213> ORGANISM: Mus musculus

<400> SEQUENCE: 123

```
Met Phe Ser Gln Ile Ile Ser Thr Ser Asp Ile Phe Thr Phe Thr Ile
1               5                   10                  15

Ile Leu Phe Val Glu Leu Val Ile Gly Ile Leu Gly Asn Gly Phe Ile
            20                  25                  30

Ala Leu Val Asn Ile Met Asp Trp Thr Lys Arg Arg Ser Ile Ser Ser
```

-continued

```
        35                  40                  45

Ala Asp Gln Ile Leu Thr Ala Leu Ala Ile Thr Arg Phe Leu Tyr Val
    50                  55                  60

Trp Phe Met Ile Ile Cys Ile Leu Leu Phe Met Leu Cys Pro His Leu
65                  70                  75                  80

Leu Thr Arg Ser Glu Ile Val Thr Ser Ile Gly Ile Ile Trp Ile Val
                85                  90                  95

Asn Asn His Phe Ser Val Trp Leu Ala Thr Cys Leu Gly Val Phe Tyr
            100                 105                 110

Phe Leu Lys Ile Ala Asn Phe Ser Asn Ser Leu Phe Leu Tyr Leu Lys
        115                 120                 125

Trp Arg Val Lys Lys Val Val Leu Met Ile Ile Gln Val Ser Met Ile
    130                 135                 140

Phe Leu Ile Leu Asn Leu Leu Ser Leu Ser Met Tyr Asp Gln Phe Ser
145                 150                 155                 160

Ile Asp Val Tyr Glu Gly Asn Thr Ser Tyr Asn Leu Gly Asp Ser Thr
                165                 170                 175

Pro Phe Pro Thr Ile Ser Leu Phe Ile Asn Ser Ser Lys Val Phe Val
            180                 185                 190

Ile Thr Asn Ser Ser His Ile Phe Leu Pro Ile Asn Ser Leu Phe Met
        195                 200                 205

Leu Ile Pro Phe Thr Val Ser Leu Val Ala Phe Leu Met Leu Ile Phe
    210                 215                 220

Ser Leu Trp Lys His His Lys Lys Met Gln Val Asn Ala Lys Pro Pro
225                 230                 235                 240

Arg Asp Ala Ser Thr Met Ala His Ile Lys Ala Leu Gln Thr Gly Phe
                245                 250                 255

Ser Phe Leu Leu Leu Tyr Ala Val Tyr Leu Leu Phe Ile Val Ile Gly
            260                 265                 270

Met Leu Ser Leu Arg Leu Ile Gly Gly Lys Leu Ile Leu Leu Phe Asp
        275                 280                 285

His Ile Ser Gly Ile Gly Phe Pro Ile Ser His Ser Phe Val Leu Ile
    290                 295                 300

Leu Gly Asn Asn Lys Leu Arg Gln Ala Ser Leu Ser Val Leu His Cys
305                 310                 315                 320

Leu Arg Cys Arg Ser Lys Asp Met Asp Thr Met Gly Pro
                325                 330
```

<210> SEQ ID NO 124
<211> LENGTH: 1371
<212> TYPE: DNA
<213> ORGANISM: Mus musculus

<400> SEQUENCE: 124

```
gaattcaaca tcttattcaa cttcagaaaa ctggatatta gacacagtgt ctggatgaag      60

cagaggtgat ctctttggga aaaaaagcca agtagtcata aagaatttat gaaacaattc     120

ctgggattgt ttatatttgt tacaaacaaa tttatatgtt tgttagtcag taatgtataa     180

gtgggatttt aaagcatgat tatcttgaat ttttaacaaa aaacatgtag tgctttttaa     240

atgtagcaga aacattaaaa attgaagcat gttctcacag ataataagca ccagtgatat     300

ttttactttt acaataatat tatttgtgga attagtaata ggaattttag gaaatggatt     360

catagcacta gtgaatatca tggactggac caagagaaga agcatttcat cagcggatca     420

gattctcact gctttggcca ttaccagatt tctctatgtg tggtttatga tcatttgtat     480
```

-continued

```
attgttattc atgctgtgcc cacatttgct tacaagatca gaaatagtaa catcaattgg    540

tattatttgg atagtgaata accatttcag cgtttggctt gccacatgcc tcggtgtctt    600

ttattttctg aagatagcca atttttctaa ctctttgttt ctttacctaa agtggagagt    660

taaaaaagta gttttaatga taatacaggt atcaatgatt ttcttgattt taaacctgtt    720

atctctaagc atgtatgatc agttctcaat tgatgtttat gaaggaaata catcttataa    780

tttaggggat tcaaccccat ttcccacaat ttccttattc atcaattcat caaaagtttt    840

cgtaatcacc aactcatccc atattttctt acccatcaac tccctgttca tgctcatacc    900

cttcacagtg tccctggtag cctttctcat gctcatcttc tcactgtgga agcatcacaa    960

aaagatgcag gtcaatgcca aaccacctag agatgccagc accatggccc acattaaagc   1020

cttgcaaaca gggttctcct tcctgctgct gtatgcagta tacttacttt ttattgtcat   1080

aggaatgttg agccttaggt tgataggagg aaaattaata cttttatttg accacatttc   1140

tggaataggt tttcctataa gccactcatt tgtgctgatt ctgggaaata acaagctgag   1200

acaagccagt ctttcagtgt tgcattgtct gaggtgccga tccaaagata tggacaccat   1260

gggtccataa aaaatttcag aggtcattgg gaaacatttt gagatcttat aggggaaaaa   1320

gaaaatgtgg ggcttcaaag ctggtaggag taatatagag aaggatagga g             1371


<210> SEQ ID NO 125
<211> LENGTH: 303
<212> TYPE: PRT
<213> ORGANISM: Mus musculus
<220> FEATURE:
<221> NAME/KEY: MOD_RES
<222> LOCATION: (169)..(169)
<223> OTHER INFORMATION: Variable amino acid

<400> SEQUENCE: 125

Met Glu His Pro Leu Arg Arg Thr Phe Asp Phe Ser Gln Ser Ile Leu
1               5                   10                  15

Leu Thr Ile Leu Phe Ile Glu Leu Ile Ile Gly Leu Ile Arg Asn Gly
            20                  25                  30

Leu Met Val Leu Val His Cys Ile Asp Trp Val Lys Arg Lys Lys Phe
        35                  40                  45

His Leu Leu Ile Lys Ser Ser Pro Leu Trp Gln Thr Ser Arg Ile Cys
    50                  55                  60

Leu Leu Trp Phe Met Leu Ile His Leu Leu Ile Thr Leu Leu Tyr Ala
65                  70                  75                  80

Asp Leu Ala Ser Thr Arg Thr Met Met Gln Phe Ala Ser Asn Pro Trp
                85                  90                  95

Thr Ile Ser Asn His Ile Ser Ile Trp Leu Ala Thr Cys Leu Gly Val
            100                 105                 110

Phe Tyr Phe Leu Lys Ile Ala Asn Phe Ser Asn Ser Thr Phe Leu Tyr
        115                 120                 125

Leu Lys Trp Arg Val Gln Phe Leu Leu Leu Asn Ile Leu Leu Val Lys
    130                 135                 140

Phe Glu Ile Asn Met Trp Ile Asn Glu Tyr His Gln Ile Asn Ile Pro
145                 150                 155                 160

Tyr Ser Phe Ile Ser Tyr Tyr Gln Xaa Cys Gln Ile Gln Val Leu Ser
                165                 170                 175

Leu His Ile Ile Phe Leu Ser Val Pro Phe Ile Leu Ser Leu Ser Thr
            180                 185                 190
```

-continued

```
Phe Leu Leu Leu Ile Phe Ser Leu Trp Thr Leu His Gln Arg Met Gln
        195                 200                 205

Gln His Val Gln Gly Tyr Arg Asp Ala Ser Thr Met Ala His Phe Lys
    210                 215                 220

Ala Leu Gln Ala Val Ile Ala Phe Leu Leu Ile His Ser Ile Phe Ile
225                 230                 235                 240

Leu Ser Leu Leu Leu Gln Leu Trp Lys His Glu Leu Arg Lys Lys Pro
                245                 250                 255

Pro Phe Val Val Phe Cys Gln Val Ala Tyr Ile Ala Phe Pro Ser Ser
            260                 265                 270

His Ser Tyr Val Phe Ile Leu Gly Asp Arg Lys Leu Arg Gln Ala Cys
        275                 280                 285

Leu Ser Val Leu Trp Arg Leu Lys Cys Arg Pro Asn Tyr Val Gly
    290                 295                 300


<210> SEQ ID NO 126
<211> LENGTH: 1108
<212> TYPE: DNA
<213> ORGANISM: Mus musculus

<400> SEQUENCE: 126

aataatgtat gtggaagagt taagtataaa tgttgtatga gaatgaactc agaaatcatc      60

aaaaatcttt aaaactgcat gttaaaaatc acacttcaaa tgaatatatt tgtaattctt     120

tagaactaat aaataaaatg gagcatcctt tgaggagaac atttgatttc tcccagagca     180

tacttctaac cattttattc attgaattaa taattggact tataagaaat ggattaatgg     240

tattggtgca ctgcatagat tgggttaaga gaaaaaaatt tcatttgtta atcaaatcct     300

caccactttg gcaaacttcc agaatttgtc tgctctggtt catgctaata catctcctga     360

ttactttatt gtatgcagat ttagctagta ctagaacgat gatgcaattc gctagcaatc     420

catggactat atctaaccat atcagcatct ggcttgctac atgccttggt gtcttttatt     480

ttctcaagat agccaatttt tctaactcta cttttctcta tctaaaatgg cgagttcagt     540

tcctcttgtt aaatatttta ctggttaaat ttgagattaa catgtggata aatgaatatc     600

atcaaataaa cataccatac agcttcattt cttattacca aattgtcaaa tacaggtgtt     660

aagtcttcac attattttcc tgtctgtccc ctttattttg tccctgtcaa cttttctcct     720

gctcatcttc tccctgtgga cacttcacca gaggatgcag cagcatgttc aaggatacag     780

agatgccagc acaatggccc acttcaaagc cttgcaagca gtgattgcct ttctcttaat     840

acactccatt tttatcctgt cactgttact acaactttgg aaacatgaat taaggaagaa     900

acctcctttt gttgtatttt gtcaggttgc atatatagct tttccttcat cccattcata     960

tgtcttcatt ctgggagaca gaaagctgag acaggcttgt ctctctgtgt tgtggaggct    1020

gaaatgcagg ccaaattatg tgggataaaa tctctttgtg ctttcatttc caattcttaa    1080

atattctttg attttgactg cataaatt                                        1108


<210> SEQ ID NO 127
<211> LENGTH: 150
<212> TYPE: PRT
<213> ORGANISM: Mus musculus

<400> SEQUENCE: 127

Gly Ala Ile Val Asn Val Asp Phe Leu Ile Gly Asn Val Gly Asn Gly
1               5                   10                  15

Phe Ile Val Val Ala Asn Ile Met Asp Leu Val Lys Arg Arg Lys Leu
```

-continued

```
            20                  25                  30

Ser Ser Val Asp Gln Leu Leu Thr Ala Leu Ala Val Ser Arg Ile Thr
        35                  40                  45

Leu Leu Trp Tyr Leu Tyr Ile Met Lys Arg Thr Phe Leu Val Asp Pro
    50                  55                  60

Asn Ile Gly Ala Ile Met Gln Ser Thr Arg Leu Thr Asn Val Ile Trp
65                  70                  75                  80

Ile Ile Ser Asn His Phe Ser Ile Trp Leu Ala Thr Thr Leu Ser Ile
                85                  90                  95

Phe Tyr Phe Leu Lys Ile Ala Asn Phe Ser Asn Ser Ile Phe Cys Tyr
            100                 105                 110

Leu Arg Trp Arg Phe Glu Lys Val Ile Leu Met Ala Leu Leu Val Ser
        115                 120                 125

Leu Val Leu Leu Phe Ile Asp Ile Leu Val Thr Asn Met Tyr Ile Asn
    130                 135                 140

Ile Trp Thr Asp Glu Phe
145                 150


<210> SEQ ID NO 128
<211> LENGTH: 520
<212> TYPE: DNA
<213> ORGANISM: Mus musculus

<400> SEQUENCE: 128

ttttcagcag tgactttggg aagcagaacg tcctcttaga gacagtgggt gctgctatcc     60

tagttaatgt ggagcaatag ttaatgtgga tttcctaatt ggaaatgttg ggaatggatt    120

cattgttgtg gcaaacataa tggacttggt caagagaaga aagctttctt cagtggatca    180

gctgctcact gcactggccg tctccagaat cactttgctg tggtacctgt acataatgaa    240

acgaacattt ttagtggatc caaacattgg tgcaattatg caatcaacaa gactgactaa    300

tgttatctgg ataatttcta accattttag tatatggctg gccaccaccc tcagcatctt    360

ttattttctc aagatagcaa atttttctaa ctctattttc tgttacctga ggtggagatt    420

tgaaaaggtg attttgatgg cattgctggt gtccctggtc ctcttgttta tagatatttt    480

agtaacaaac atgtacatta atatttggac tgatgaattc                          520


<210> SEQ ID NO 129
<211> LENGTH: 309
<212> TYPE: PRT
<213> ORGANISM: Mus musculus

<400> SEQUENCE: 129

Met Val Ala Val Leu Gln Ser Thr Leu Pro Ile Ile Phe Ser Met Glu
1               5                   10                  15

Phe Ile Met Gly Thr Leu Gly Asn Gly Phe Ile Phe Leu Ile Val Cys
            20                  25                  30

Ile Asp Trp Val Gln Arg Arg Lys Ile Ser Leu Val Asp Gln Ile Arg
        35                  40                  45

Thr Ala Leu Ala Ile Ser Arg Ile Ala Leu Ile Trp Leu Ile Phe Leu
    50                  55                  60

Asp Trp Trp Val Ser Val His Tyr Pro Ala Leu His Glu Thr Gly Lys
65                  70                  75                  80

Met Leu Ser Thr Tyr Leu Ile Ser Trp Thr Val Ile Asn His Cys Asn
                85                  90                  95

Phe Trp Leu Thr Ala Asn Leu Ser Ile Leu Tyr Phe Leu Lys Ile Ala
```

-continued

```
            100                 105                 110

Asn Phe Ser Asn Ile Ile Phe Leu Tyr Leu Lys Phe Arg Ser Lys Asn
        115                 120                 125

Val Val Leu Val Thr Leu Leu Val Ser Leu Phe Phe Leu Phe Leu Asn
    130                 135                 140

Thr Val Ile Ile Lys Ile Phe Ser Asp Val Cys Phe Asp Ser Val Gln
145                 150                 155                 160

Arg Asn Val Ser Gln Ile Phe Ile Met Tyr Asn His Glu Gln Ile Cys
                165                 170                 175

Lys Phe Leu Ser Phe Thr Asn Pro Met Phe Thr Phe Ile Pro Phe Val
            180                 185                 190

Met Ser Thr Val Met Phe Ser Leu Leu Ile Phe Ser Leu Trp Arg His
        195                 200                 205

Leu Lys Asn Met Gln His Thr Ala Lys Gly Cys Arg Asp Ile Ser Thr
    210                 215                 220

Thr Val His Ile Arg Ala Leu Gln Thr Ile Ile Val Ser Val Val Leu
225                 230                 235                 240

Tyr Thr Ile Phe Phe Leu Ser Phe Phe Val Lys Val Trp Ser Phe Val
                245                 250                 255

Ser Pro Glu Arg Tyr Leu Ile Phe Leu Phe Val Trp Ala Leu Gly Asn
            260                 265                 270

Ala Val Phe Ser Ala His Pro Phe Val Met Ile Leu Val Asn Arg Arg
        275                 280                 285

Leu Arg Leu Ala Ser Leu Ser Leu Ile Phe Trp Leu Trp Tyr Arg Phe
    290                 295                 300

Lys Asn Ile Glu Val
305
```

<210> SEQ ID NO 130
<211> LENGTH: 1199
<212> TYPE: DNA
<213> ORGANISM: Mus musculus

<400> SEQUENCE: 130

```
aagcttgttt gtgtttggat gaattctatt tatgtctatc aatttaagat tttcatatga      60
atcattaaga aatcttgata gttgtttgtg agatatcact tctgcaattt ttaaatgaaa     120
ttacactcat attttgaagg aacaatatgt tttaaaggaa tatattaaca aatcttcagc     180
agttacctca gaagtttggg tattgtttta cagaaaatgg tggcagttct acagagcaca     240
cttccaataa ttttcagtat ggaattcata atgggaacct taggaaatgg attcattttt     300
ctgatagtct gcatagactg ggtccaaaga agaaaaatct ctttagtgga tcaaatccgc     360
actgctctgg caattagcag aatcgctcta atttggttga tattcctaga ttggtgggtg     420
tctgttcatt acccagcatt acatgaaact ggtaagatgt tatcaacata tttgatttcc     480
tggacggtga tcaatcattg taacttttgg cttactgcaa acttgagcat cctttatttt     540
ctcaagatag ccaacttttc taacattatt tttctttatc taaagtttag atctaaaaat     600
gtggtattag tgaccctgtt agtgtctcta tttttcttgt tcttaaatac tgtaattata     660
aaaatatttt ctgatgtgtg ttttgatagt gttcaaagaa atgtgtctca aattttcata     720
atgtataacc atgaacaaat ttgtaaattt ctttccttta ctaaccctat gttcacattc     780
atacctttttg ttatgtccac ggtaatgttt tctttgctca tcttctccct gtggagacat     840
ctgaagaata tgcagcacac cgccaaagga tgcagagaca tcagcaccac agtgcacatc     900
```

-continued

```
agagccctgc aaaccatcat tgtgtctgta gtgctataca ctattttttt tctatcattt    960

tttgttaaag tttggagttt tgtgtcacca gagagatacc tgatcttttt gtttgtctgg   1020

gctctgggaa atgctgtttt ttctgctcac ccatttgtca tgattttggt aaacagaaga   1080

ttgagattgg cttctctctc tctgattttt tggctctggt acaggtttaa aaatatagaa   1140

gtatagggtc caaagaccac caaggaatca ttttccttat cctaaagaaa aatcaggag    1199
```

<210> SEQ ID NO 131
<211> LENGTH: 309
<212> TYPE: PRT
<213> ORGANISM: Mus musculus

<400> SEQUENCE: 131

```
Met Leu Ser Thr Met Glu Gly Val Leu Leu Ser Val Ser Thr Ser Glu
1               5                   10                  15

Ala Val Leu Gly Ile Val Gly Asn Thr Phe Ile Ala Leu Val Asn Cys
            20                  25                  30

Met Asp Tyr Asn Arg Asn Lys Lys Leu Ser Asn Ile Gly Phe Ile Leu
        35                  40                  45

Thr Gly Leu Ala Ile Ser Arg Ile Cys Leu Val Leu Ile Leu Ile Thr
    50                  55                  60

Glu Ala Tyr Ile Lys Ile Phe Tyr Pro Gln Leu Leu Ser Pro Val Asn
65                  70                  75                  80

Ile Ile Glu Leu Ile Ser Tyr Leu Trp Ile Ile Ile Cys Gln Leu Asn
                85                  90                  95

Val Trp Phe Ala Thr Ser Leu Ser Ile Phe Tyr Phe Leu Lys Ile Ala
            100                 105                 110

Asn Phe Ser His Tyr Ile Phe Val Trp Leu Lys Arg Arg Ile Asp Leu
        115                 120                 125

Val Phe Phe Phe Leu Ile Gly Cys Leu Leu Ile Ser Trp Leu Phe Ser
    130                 135                 140

Phe Pro Val Val Ala Lys Met Val Lys Asp Asn Lys Met Leu Tyr Ile
145                 150                 155                 160

Asn Thr Ser Trp Gln Ile His Met Lys Lys Ser Glu Leu Ile Ile Asn
                165                 170                 175

Tyr Val Phe Thr Asn Gly Gly Val Phe Leu Phe Phe Met Ile Met Leu
            180                 185                 190

Ile Val Cys Phe Leu Leu Ile Ile Ser Leu Trp Arg His Arg Arg Gln
        195                 200                 205

Met Glu Ser Asn Lys Leu Gly Phe Arg Asp Leu Asn Thr Glu Val His
    210                 215                 220

Val Arg Thr Ile Lys Val Leu Leu Ser Phe Ile Ile Leu Phe Ile Leu
225                 230                 235                 240

His Phe Met Gly Ile Thr Ile Asn Val Ile Cys Leu Leu Ile Pro Glu
                245                 250                 255

Ser Asn Leu Leu Phe Met Phe Gly Leu Thr Thr Ala Phe Ile Tyr Pro
            260                 265                 270

Gly Cys His Ser Leu Ile Leu Ile Leu Ala Asn Ser Arg Leu Lys Gln
        275                 280                 285

Cys Ser Val Met Ile Leu Gln Leu Leu Lys Cys Cys Glu Asn Gly Lys
    290                 295                 300

Glu Leu Arg Asp Thr
305
```

-continued

<210> SEQ ID NO 132
<211> LENGTH: 1535
<212> TYPE: DNA
<213> ORGANISM: Mus musculus

<400> SEQUENCE: 132
ctgcaggtat atacctaccc tgaaggcttc atctagagta aacaaagtag tctgtatagt 60
ctgccattcc tcagattctc ctcaacttcc caccctccag tgacctttct ccttttctac 120
agtcaaacta tggacctcac aacctgacac ttcttcagat gcaaaatatt ctcacagaga 180
caagtaaaac atacaaaaca aatactttaa tttgcctatt aacaaatggc aagaaaagat 240
tcaggcttga acatcctgta gacaagctaa ggacaggagc aactgaaggg atctccatga 300
agacctttca gatttctacc aaaagtaatt tttaactata tttaagtctt taaagaaaga 360
aagtaaagcc actcttttat tgaacagcaa tagattggaa tcttaaacaa ctgcaacaga 420
agccatttta aagatcaaca aagatgctga gcacaatgga aggtgtcctc ctttcagttt 480
caactagtga ggctgtgctg ggcattgtag ggaacacatt cattgcactt gtaaactgta 540
tggactataa caggaacaag aagctctcta atattggctt tattctcact ggcttggcaa 600
tttccagaat ttgccttgtg ttgatcttaa tcacagaggc atacataaaa atattctatc 660
cacagttgct gtctcctgtc aacataattg agctcatcag ttatctatgg ataattatct 720
gtcaattgaa tgtctggttt gccactagtc tcagtatttt ttatttcctg aagatagcaa 780
atttttccca ctacatattt gtctggttaa aaagaagaat tgatttagtt tttttcttcc 840
tgatagggtg cttgcttatc tcatggctat tttctttccc agttgttgcg aagatggtta 900
aagataataa aatgctgtat ataaacacat cttggcagat ccacatgaag aaaagtgagt 960
taatcattaa ctatgttttc accaatgggg gagtattttt attttttatg ataatgttaa 1020
ttgtatgttt cctgttaatc atttcacttt ggagacatcg caggcagatg gaatcaaata 1080
aattaggatt cagagatctc aacacagaag ttcatgtgag aacaataaaa gttttattgt 1140
cttttattat ccttttttata ttgcatttca tgggtattac cataaatgta atttgtctgt 1200
taatcccaga aagcaacttg ttattcatgt ttggtttgac aactgcattc atctatcccg 1260
gctgccactc acttatccta attctagcaa acagtcggct gaagcagtgc tctgtaatga 1320
tactgcaact attaaagtgc tgtgagaatg gtaaagaact cagagacaca tgacagtctg 1380
gaacacatgc aatctggaat tgtcagtgga aaaagttact gaagatcttt tcacttgcac 1440
tatgctcttt tattgatttg gcatcattat caaacactgt tggagccttg tgaactcttg 1500
ttcagagtct tctgcctctc aaggaatcac actcc 1535

<210> SEQ ID NO 133
<211> LENGTH: 310
<212> TYPE: PRT
<213> ORGANISM: Mus musculus

<400> SEQUENCE: 133

Met Cys Ala Val Leu Arg Ser Ile Leu Thr Ile Ile Phe Ile Leu Glu
1               5                   10                  15

Phe Phe Ile Gly Asn Leu Gly Asn Gly Phe Ile Ala Leu Val Gln Cys
            20                  25                  30

Met Asp Leu Arg Lys Arg Arg Thr Phe Pro Ser Ala Asp His Phe Leu
        35                  40                  45

Thr Ala Leu Ala Ile Ser Arg Leu Ala Leu Ile Trp Val Leu Phe Leu
    50                  55                  60

-continued

```
Asp Ser Phe Leu Phe Ile Gln Ser Pro Leu Leu Met Thr Arg Asn Thr
65                  70                  75                  80

Leu Arg Leu Ile Gln Thr Ala Trp Asn Ile Ser Asn His Phe Ser Ile
                85                  90                  95

Trp Phe Ala Thr Ser Leu Ser Ile Phe Tyr Leu Phe Lys Ile Ala Ile
            100                 105                 110

Phe Ser Asn Tyr Leu Phe Phe Tyr Leu Lys Arg Arg Val Lys Arg Val
        115                 120                 125

Val Leu Val Ile Leu Leu Leu Ser Met Ile Leu Leu Phe Phe Asn Ile
    130                 135                 140

Phe Leu Glu Ile Lys His Ile Asp Val Trp Ile Tyr Gly Thr Lys Arg
145                 150                 155                 160

Asn Ile Thr Asn Gly Leu Ser Ser Asn Ser Phe Ser Glu Phe Ser Arg
                165                 170                 175

Leu Ile Leu Ile Pro Ser Leu Met Phe Thr Leu Val Pro Phe Gly Val
            180                 185                 190

Ser Leu Ile Ala Phe Leu Leu Leu Ile Phe Ser Leu Met Lys His Val
        195                 200                 205

Arg Lys Met Gln Tyr Tyr Thr Lys Gly Cys Lys Asp Val Arg Thr Met
    210                 215                 220

Ala His Thr Thr Ala Leu Gln Thr Val Val Ala Phe Leu Leu Leu Tyr
225                 230                 235                 240

Thr Thr Phe Phe Leu Ser Leu Val Val Glu Val Ser Thr Leu Glu Met
                245                 250                 255

Asp Glu Ser Leu Met Leu Leu Phe Ala Lys Val Thr Ile Met Ile Phe
            260                 265                 270

Pro Ser Ile His Ser Cys Ile Phe Ile Leu Lys His Asn Lys Leu Arg
        275                 280                 285

Gln Asp Leu Leu Ser Val Leu Lys Trp Leu Gln Tyr Trp Cys Lys Arg
    290                 295                 300

Glu Lys Thr Leu Asp Ser
305                 310
```

<210> SEQ ID NO 134
<211> LENGTH: 1482
<212> TYPE: DNA
<213> ORGANISM: Mus musculus

<400> SEQUENCE: 134

```
aataatagat tttttaatat tcagaatttt taagtaatgt agtattgtta gcagcatagc     60

ttataggaaa agttccaagt aattttgatt ttgtaattct gattccccca aatcaagtat    120

caagtttacc tgcacagaca agggaagaag tggcaaaatg tgcaaatgag agcaacttta    180

tttgactgtc agtacgttga aattcagtgt ttccttaatc agttatggat tgacatttat    240

gtgcacagaa cctggaagaa tttcagccaa gctggaggta aaaatccaaa attctgatga    300

taaaaccaaa agtaaatcac aggtaaatct tctttatttt tcttttttaa tactgtatat    360

ggacattttt taatacagca tatttttttt ttgaaattta gaaaaaaacc actaagaaat    420

attcaccaat ggaatagact ttaaagtcac ttagagaatg tgtgctgttc tacgtagcat    480

actgacaatc attttcattt tggagttctt cattggaaat ctggggaatg gattcatagc    540

tctggtacaa tgcatggact tacgaaagag aagaacgttc ccttcagcag atcatttcct    600

cactgctctg gccatctcca ggcttgctct gatatgggtt ttatttctag attcatttct    660

gtttatacaa tccccattac tgatgactag aaatacatta agactgattc agactgcctg    720
```

-continued

```
gaatataagc aatcatttca gtatatggtt tgctaccagc ctcagcatct tttatctctt    780

caagatagcc attttttcta actatctttt cttctacctg aagcggagag ttaaaagggt    840

ggttttggtg atactgctgc tatccatgat ccttttgttt tttaatatat ttttagaaat    900

caaacatatt gatgtctgga tctatggaac caaaagaaac ataactaatg gtttgagttc    960

aaacagtttt tcagagtttt ccaggcttat tttaattcca agtttaatgt tcacattagt   1020

accctttggt gtatccttga tagctttcct cctcctaatc ttttccctta tgaaacatgt   1080

aaggaagatg cagtactaca ccaaaggatg caaagatgtc agaaccatgg cccacaccac   1140

agccctgcag actgtggttg ccttcctcct attatatact actttctttc tgtctctagt   1200

tgtggaagtt tcaacacttg aaatggatga aagtctgatg cttctgtttg caaaagttac   1260

tataatgatt tttccttcca tccactcctg tattttcatt ttgaaacata ataagttgag   1320

acaggacttg ctttcagtac tgaagtggct acagtattgg tgcaagcgtg agaaaacctt   1380

ggattcatag accattgtat gcatcacctt gaatattcta gaggggtgta ggttcatatg   1440

aaagtattga atttttaaat ttgagccttt tgtatatttt ct                      1482
```

<210> SEQ ID NO 135
<211> LENGTH: 305
<212> TYPE: PRT
<213> ORGANISM: Mus musculus

<400> SEQUENCE: 135

```
Met Asn Gly Val Leu Gln Val Thr Phe Ile Val Ile Leu Ser Val Glu
1               5                   10                  15

Phe Ile Ile Gly Ile Phe Gly Asn Gly Phe Ile Ala Val Val Asn Ile
            20                  25                  30

Lys Asp Leu Val Lys Gly Arg Lys Ile Ser Ser Val Asp Gln Ile Leu
        35                  40                  45

Thr Ala Leu Ala Ile Ser Arg Ile Ala Leu Leu Trp Leu Ile Leu Val
    50                  55                  60

Ser Trp Trp Ile Phe Val Leu Tyr Pro Gly Gln Trp Met Thr Asp Arg
65                  70                  75                  80

Arg Val Ser Ile Met His Ser Ile Trp Thr Thr Phe Asn Gln Ser Ser
                85                  90                  95

Leu Trp Phe Ala Thr Ser Leu Ser Ile Phe Tyr Phe Phe Lys Ile Ala
            100                 105                 110

Asn Phe Ser Asn Pro Ile Phe Leu Tyr Leu Lys Val Arg Leu Lys Lys
        115                 120                 125

Val Met Ile Gly Thr Leu Ile Met Ser Leu Ile Leu Phe Cys Leu Asn
    130                 135                 140

Ile Ile Ile Met Asn Ala Pro Glu Asn Ile Leu Ile Thr Glu Tyr Asn
145                 150                 155                 160

Val Ser Met Ser Tyr Ser Leu Ile Leu Asn Asn Thr Gln Leu Ser Met
                165                 170                 175

Leu Phe Pro Phe Ala Asn Thr Met Phe Gly Phe Ile Pro Phe Ala Val
            180                 185                 190

Ser Leu Val Thr Phe Val Leu Leu Val Phe Ser Leu Trp Lys His Gln
        195                 200                 205

Arg Lys Met Gln His Ser Ala His Gly Cys Arg Asp Ala Ser Thr Lys
    210                 215                 220

Ala His Ile Arg Ala Leu Gln Thr Leu Ile Ala Ser Leu Leu Leu Tyr
225                 230                 235                 240
```

-continued

```
Ser Ile Phe Phe Leu Ser His Val Met Lys Val Trp Ser Ala Leu Leu
                245                 250                 255

Leu Glu Arg Thr Leu Leu Leu Leu Ile Thr Gln Val Ala Arg Thr Ala
            260                 265                 270

Phe Pro Ser Val His Ser Trp Val Leu Ile Leu Gly Asn Ala Lys Met
        275                 280                 285

Arg Lys Ala Ser Leu Tyr Val Phe Leu Trp Leu Arg Cys Arg His Lys
    290                 295                 300

Glu
305


<210> SEQ ID NO 136
<211> LENGTH: 1316
<212> TYPE: DNA
<213> ORGANISM: Mus musculus

<400> SEQUENCE: 136

tttatgatgg aaagaataaa accattagca aggcttaatg gcttgtttgg tattagacct     60

gtacattgtt tatggaacat gatatggagc tttgtttatt gaatatgcac aatattttag    120

aagcatgttt caaagaatct taagtaatta caatagaaat tgaagcatcc aagtgaagat    180

gaatggtgtc ctacaggtta catttatagt cattttgagt gtggaattta taattggcat    240

ctttggcaat ggattcatag cggtggtgaa cataaaggac ttggtcaagg gaaggaagat    300

ctcttcagtg gatcagatcc tcactgctct ggccatctcc agaattgcac tgctgtggtt    360

aatattagta agttggtgga tatttgtgct ttacccagga caatggatga ctgatagaag    420

agttagcata atgcacagta tatggacaac attcaaccag agtagtctct ggtttgctac    480

aagtctcagc atcttttatt ttttcaagat agcaaatttt tccaacccta tttttcttta    540

tttaaaggtc agacttaaaa aagtcatgat agggacattg ataatgtctt tgattctctt    600

ttgtttaaat attatcatta tgaatgcacc tgagaacatt ttaatcactg aatataatgt    660

atctatgtct tacagcttga ttttgaataa cacacagctt tctatgctgt ttccatttgc    720

caacaccatg tttgggttca taccttttgc tgtgtcactg gtcacttttg tccttcttgt    780

tttctccctg tggaaacatc agagaaagat gcaacacagt gcccatggat gcagagatgc    840

cagcactaag gcccacatca gagccttgca gacattgatt gcctccctcc tcctgtattc    900

cattttcttc ctgtctcatg ttatgaaggt ttggagtgct ctgcttctgg agaggacact    960

cctgcttttg atcacacagg ttgcaagaac agcttttccg tcagtgcact cctgggtcct   1020

gattctgggc aatgctaaga tgagaaaggc ttctctctat gtattcctgt ggctgaggtg   1080

caggcacaaa gaatgaaacc ctacagtgta cagacctggg gtatatttat gtggatgatc   1140

ttacatatct tagaggaaaa tggattaaaa gaaattctca tatttataaa tttttaggtc   1200

tgaattacat aaaaatgtat ataatatttt caaagtacaa gatagtagtt tataacttac   1260

atgataaata ctgtctatgc atcttctagt ctttgtagaa tatgtaaaaa catgtt       1316


<210> SEQ ID NO 137
<211> LENGTH: 330
<212> TYPE: PRT
<213> ORGANISM: Mus musculus

<400> SEQUENCE: 137

Met Lys His Phe Trp Lys Ile Leu Ser Val Ile Ser Gln Ser Thr Leu
1               5                   10                  15
```

-continued

```
Ser Val Ile Leu Ile Val Glu Leu Val Ile Gly Ile Ile Gly Asn Gly
            20                  25                  30

Phe Met Val Leu Val His Cys Met Asp Trp Val Lys Lys Lys Lys Met
        35                  40                  45

Ser Leu Val Asn Gln Ile Leu Thr Ala Leu Ser Ile Ser Arg Ile Phe
    50                  55                  60

Gln Leu Cys Leu Leu Phe Ile Ser Leu Val Ile Asn Phe Ser Tyr Thr
65                  70                  75                  80

Asp Leu Thr Thr Ser Ser Arg Met Ile Gln Val Met Tyr Asn Ala Trp
                85                  90                  95

Ile Leu Ala Asn His Phe Ser Ile Trp Ile Ala Thr Cys Leu Thr Val
            100                 105                 110

Leu Tyr Phe Leu Lys Ile Ala Asn Phe Ser Asn Ser Phe Phe Leu Tyr
        115                 120                 125

Leu Lys Trp Arg Val Glu Lys Val Val Ser Val Thr Leu Leu Val Ser
    130                 135                 140

Leu Leu Leu Leu Ile Leu Asn Ile Leu Leu Thr Asn Leu Glu Thr Asp
145                 150                 155                 160

Met Trp Thr Asn Glu Tyr Gln Arg Asn Ile Ser Cys Ser Phe Ser Ser
                165                 170                 175

His Tyr Tyr Ala Lys Cys His Arg Gln Val Leu Arg Leu His Ile Ile
            180                 185                 190

Phe Leu Ser Val Pro Val Val Leu Ser Leu Ser Thr Phe Leu Leu Leu
        195                 200                 205

Ile Phe Ser Leu Trp Thr His His Lys Arg Met Gln Gln His Val Gln
    210                 215                 220

Gly Gly Arg Asp Ala Arg Thr Thr Ala His Phe Lys Ala Leu Gln Thr
225                 230                 235                 240

Val Ile Ala Phe Phe Leu Leu Tyr Ser Ile Phe Ile Leu Ser Val Leu
                245                 250                 255

Ile Gln Ile Trp Lys Tyr Glu Leu Leu Lys Lys Asn Leu Phe Val Val
            260                 265                 270

Phe Cys Glu Val Val Tyr Ile Ala Phe Pro Thr Phe His Ser Tyr Ile
        275                 280                 285

Leu Ile Val Gly Asp Met Lys Leu Arg Gln Ala Cys Leu Pro Leu Cys
    290                 295                 300

Ile Ile Ala Ala Glu Ile Gln Thr Thr Leu Cys Arg Asn Phe Arg Ser
305                 310                 315                 320

Leu Lys Tyr Phe Arg Leu Cys Cys Ile Phe
                325                 330
```

<210> SEQ ID NO 138
<211> LENGTH: 1354
<212> TYPE: DNA
<213> ORGANISM: Mus musculus

<400> SEQUENCE: 138

```
gaattctggt ctggcacccc tgagctgtgt gagtagacac attatcatgg aaagagattc      60

agaatctgtc actgtcaaaa ctgcatgttt gctcctctgt tagtgtgttg ggaaagttta     120

agaaaaatac attttatgag aatcaactca gaggttgtca gaaattgtcg aaacagcatt     180

ttaaaaattt acatctcaac tggatatatg agcaagtctt tataactgat atataaaatg     240

aagcactttt ggaagatatt atctgttatc tcccagagca cactttcagt cattttaatc     300

gtggaattag taattggaat tataggaaat gggttcatgg tcctggtcca ctgtatggac     360
```

-continued

```
tgggttaaga aaaagaaaat gtccctagtt aatcaaattc ttactgcttt gtcaatctcc    420

agaatttttc agctctgttt attgtttata agtttagtaa tcaacttttc atatacagat    480

ttaactacaa gttcaaggat gatacaagtc atgtacaatg cttggatttt agccaaccat    540

ttcagcatct ggattgctac atgcctcact gtcctttatt ttctaaagat agccaatttt    600

tctaactctt tttttcttta tctaaagtgg agagttgaaa aagtagtttc agttacactg    660

ttggtgtcat tgctcctcct gattttaaat attttactaa ctaacttgga aaccgacatg    720

tggacaaatg aatatcaaag aaacatatca tgcagcttca gttctcatta ctatgcaaag    780

tgtcacaggc aggtgttaag gcttcacatt attttcctgt ctgtccccgt tgttttgtcc    840

ctgtcaactt ttctcctgct catcttctcc ctgtggacac atcacaagag gatgcagcag    900

catgttcagg gaggcagaga tgccagaacc acggcccact tcaaagccct acaaactgtg    960

attgcatttt tcctactata ttccattttt attctgtctg tcttaataca aatttggaaa   1020

tatgaattac tgaagaaaaa tcttttcgtt gtattttgtg aggttgtata tatagctttt   1080

ccgacattcc attcatatat tctgattgta ggagacatga agctgagaca ggcctgcctg   1140

cctctctgta ttatcgcagc tgaaattcag actacactat gtagaaattt tagatcacta   1200

aagtacttta gattatgttg tatattctag acaaaaatta actgatacaa atgtcttttg   1260

tatttttcat tttaaatatc ctttaatttt gactgcatga aattgatttc tgcttgcaat   1320

tatcactgat taaaactatt aataatttaa ctag                                1354
```

```
<210> SEQ ID NO 139
<211> LENGTH: 299
<212> TYPE: PRT
<213> ORGANISM: Mus musculus

<400> SEQUENCE: 139

Met Val Pro Thr Gln Val Thr Ile Phe Ser Ile Ile Met Tyr Val Leu
1               5                   10                  15
Glu Ser Leu Val Ile Ile Val Gln Ser Cys Thr Thr Val Ala Val Leu
            20                  25                  30
Phe Arg Glu Trp Met His Phe Gln Arg Leu Ser Pro Val Glu Thr Ile
        35                  40                  45
Leu Ile Ser Leu Gly Ile Ser His Phe Cys Leu Gln Trp Thr Ser Met
    50                  55                  60
Leu Tyr Asn Phe Gly Thr Tyr Ser Arg Pro Val Leu Leu Phe Trp Lys
65                  70                  75                  80
Val Ser Val Val Trp Glu Phe Met Asn Ile Leu Thr Phe Trp Leu Thr
                85                  90                  95
Ser Trp Leu Ala Val Leu Tyr Cys Val Lys Val Ser Ser Phe Thr His
            100                 105                 110
Pro Ile Phe Leu Trp Leu Arg Met Lys Ile Leu Lys Leu Val Leu Trp
        115                 120                 125
Leu Ile Leu Gly Ala Leu Ile Ala Ser Cys Leu Ser Ile Ile Pro Ser
    130                 135                 140
Val Val Lys Tyr His Ile Gln Met Glu Leu Val Thr Leu Asp Asn Leu
145                 150                 155                 160
Pro Lys Asn Asn Ser Leu Ile Leu Arg Leu Gln Gln Phe Glu Trp Tyr
                165                 170                 175
Phe Ser Asn Pro Leu Lys Met Ile Gly Phe Gly Ile Pro Phe Phe Val
            180                 185                 190
Phe Leu Ala Ser Ile Ile Leu Leu Thr Val Ser Leu Val Gln His Trp
        195                 200                 205
Val Gln Met Lys His Tyr Ser Ser Ser Asn Ser Ser Leu Lys Ala Gln
    210                 215                 220
Phe Thr Val Leu Lys Ser Leu Ala Thr Phe Phe Thr Phe Phe Thr Ser
225                 230                 235                 240
Tyr Phe Leu Thr Ile Val Ile Ser Phe Ile Gly Thr Val Phe Asp Lys
                245                 250                 255
Lys Ser Trp Phe Trp Val Cys Glu Ala Val Ile Tyr Gly Leu Val Cys
            260                 265                 270
Ile His Phe Thr Ser Leu Met Met Ser Asn Pro Ala Leu Lys Lys Ala
        275                 280                 285
```

-continued

```
Leu Lys Leu Gln Phe Trp Ser Pro Glu Pro Ser
    290                 295
```

<210> SEQ ID NO 140
<211> LENGTH: 2887
<212> TYPE: DNA
<213> ORGANISM: Mus musculus
<220> FEATURE:
<221> NAME/KEY: modified_base
<222> LOCATION: (1083)..(1083)
<223> OTHER INFORMATION: n is a, c, g, or t

<400> SEQUENCE: 140

```
gcgtgcttca cagagcagta tactacaaag caaatgtcat tgctgccatt gtatatttct     60

ctaaagacat ttcacatttt atctccctgt cccattgtgt gcagagccca cacttcaatc    120

aatcaattcc ttaattataa gctattgttt cattatttca tttcctacgt ttttttgcat    180

ttttactaaa actccaaagc agacattttc taattataat cctacatgta gttagaattt    240

taaaaattat atactatttt ctttgcacca ctgagttcag taggttttga aggtttatgc    300

ttaacaattg aacatttcat gttagattat tcctgccttc ctaatcttga ataattaaat    360

gtccatccag gcttagaatt cacagagtca acagctttca ccttgattct ctcactatct    420

atcaatgact agaatctgtc tgtcactttt gaaaccgcta attaaatagt tggtgcttat    480

ttaaagggtg ccccatgcca agagaaaatg tatttcttct ctagatgcct tcgtccttta    540

caagttacat gctttactga tggtgaattg gttttcttcc agttcatctg ggttaagtga    600

cctaagaacc tagccatgga aggagaaaca gaagcaaata ttaacgatac aagaacaagt    660

tccagaacat tggaaagtac ttagtaaagg cattggaatt agcaaaagaa tagtagcgaa    720

gcaaaaaata cttcatctcc attgggaggt caagaaagac tatgcagtgt ttttgatgca    780

acttgtcatc tctgagttag acgattcagc acacactttt gagattgaac ttcaacaggt    840

ggagccagca gacctgagct ttaggaatga tggtggaatt tccaagcaaa gacttccgtt    900

acctttttga tgtcccctaa caattcggtt gcaatgctca caccgcccaa ctgttgaaat    960

gcttgggaaa agggattctg agactggcat tagtatgtca tttgacagaa tggaaacatt   1020

gcccagggca ttaatgcaca gtaaaggatt caccttttct aagtgctcaa attttaaatt   1080

tgnatatttt tagaagacat tatttaaaag aaaggtggag aggatatcca aacagcacct   1140

tgagcagata aagaggtgaa gaagaaaaaa caacatgcgt acatgatgga tttctcttta   1200

tgaaaatgat caaatgatct taggatcaag aatccacacc tgaatgagat ttgcttgtat   1260

ccctgtgtga atttgaccta acaagcaaag cacagacaaa tgctgtagat agggaaatgt   1320

ctatgtcaaa tgtgtgtaag gaggatttgc atccacaaag aagtgccctc ttatactgag   1380

agtgctaaga acacatgtcc gtttcatatt cggaaagtgg tatagagctg ttgagtcttt   1440

ggctaggaag agacttcaga gtggaagcat ggtgccaacg caagtcacca tcttctccat   1500

catcatgtat gtgcttgagt ccttagtaat aattgtgcaa agttgcacaa cggttgcagt   1560

gctattcaga gagtggatgc actttcaaag actgtcaccg gtggagacga ttctcatcag   1620

cctgggcatc tcacatttct gtctacagtg gacatcaatg ctatacaact ttggtactta   1680

ttctaggcct gtccttttat tttggaaggt atcagtcgtc tgggagttca tgaacatttt   1740

gacattctgg ttaaccagtt ggcttgctgt cctctactgt gtcaaggtct cttccttcac   1800

tcaccccatc ttcctctggc tgaggatgaa aatcttgaaa ctggttctct ggttgatact   1860

gggtgctctg atagcttctt gtttgtcaat catcccttct gttgttaaat atcacatcca   1920
```

-continued

```
gatggaatta gtcaccctag ataatttacc caagaacaat tctttgattc taagactaca   1980

acagtttgaa tggtattttt ctaatccttt aaaaatgatt ggctttggta ttcctttctt   2040

cgtgttcctg gcttctatca tcttactcac agtctcattg gtccaacact gggtgcagat   2100

gaaacactac agcagcagca actccagcct gaaagctcag ttcactgttc tgaagtctct   2160

tgctaccttc ttcaccttct tcacatccta ttttctgact atagtcatct cctttattgg   2220

cactgtgttt gataagaaat cttggttctg ggtctgcgaa gctgtcatct atggtttagt   2280

ctgtattcac ttcacttcac tgatgatgag caaccctgca ttgaaaaagg cactgaagct   2340

gcagttctgg agcccagagc cttcctgagg caggaaacac agttaagcct ctagggtaag   2400

gagactttgc attggcacag tccctatagt gtaatgcaaa cttgaacaca aacttcatcc   2460

cttttcacat ccacaaatgg ctgcatctat acatcatcac cagtcttccc tgtattctga   2520

cccattctct tcctgtccta tccatagtcc ccaggttggt tttgattttt ctcatgatca   2580

caccaactct gcttagcttt tgccaccact gtaatagtaa acatggggtg ttctatatat   2640

tacagtcaaa atcattctca cattgttgat tgcctcacaa attcatataa atccccccttc  2700

gtgtcaggaa tttattgtct gctcacttaa tgctcaccat atattaaagc cattaattcc   2760

cccttcctac cttgagttta agaaggaaaa tgtcttacca ttgcccacaa cctattctgc   2820

tgcttctaga cttttatgca agtgatttat acacacacac acacacacac acacacatac   2880

aaacaac                                                             2887
```

<210> SEQ ID NO 141
<211> LENGTH: 335
<212> TYPE: PRT
<213> ORGANISM: Mus musculus

<400> SEQUENCE: 141

```
Met Met Glu Gly His Met Leu Phe Phe Leu Leu Val Val Val Val Gln
1               5                   10                  15

Phe Leu Thr Gly Val Leu Ala Asn Gly Leu Ile Val Val Val Asn Ala
            20                  25                  30

Ile Asp Leu Ile Met Trp Lys Lys Met Ala Pro Leu Asp Leu Leu Leu
        35                  40                  45

Phe Cys Leu Ala Thr Ser Arg Ile Ile Leu Gln Leu Cys Ile Leu Phe
    50                  55                  60

Ala Gln Leu Gly Leu Ser Cys Leu Val Arg His Thr Leu Phe Ala Asp
65                  70                  75                  80

Asn Val Thr Phe Val Tyr Ile Ile Asn Glu Leu Ser Leu Trp Phe Ala
                85                  90                  95

Thr Trp Leu Gly Val Phe Tyr Cys Ala Lys Ile Ala Thr Ile Pro His
            100                 105                 110

Pro Leu Phe Leu Trp Leu Lys Met Arg Ile Ser Arg Leu Val Pro Trp
        115                 120                 125

Leu Ile Leu Ala Ser Val Val Tyr Val Thr Val Thr Thr Phe Ile His
    130                 135                 140

Ser Arg Glu Thr Ser Glu Leu Pro Lys Gln Ile Phe Ile Ser Phe Phe
145                 150                 155                 160

Ser Lys Asn Thr Thr Arg Val Arg Pro Ala His Ala Thr Leu Leu Ser
                165                 170                 175

Val Phe Val Phe Gly Leu Thr Leu Pro Phe Leu Ile Phe Thr Val Ala
            180                 185                 190

Val Leu Leu Leu Leu Ser Ser Leu Trp Asn His Ser Arg Gln Met Arg
```

-continued

```
        195                 200                 205

Thr Met Val Gly Thr Arg Glu Pro Ser Arg His Ala Leu Val Ser Ala
    210                 215                 220

Met Leu Ser Ile Leu Ser Phe Leu Ile Leu Tyr Leu Ser His Asp Met
225                 230                 235                 240

Val Ala Val Leu Ile Cys Thr Gln Gly Leu His Phe Gly Ser Arg Thr
                245                 250                 255

Phe Ala Phe Cys Leu Leu Val Ile Gly Met Tyr Pro Ser Leu His Ser
            260                 265                 270

Ile Val Leu Ile Leu Gly Asn Pro Lys Leu Lys Arg Asn Ala Lys Thr
        275                 280                 285

Phe Ile Val His Cys Lys Cys Cys His Cys Ala Arg Ala Trp Val Thr
    290                 295                 300

Ser Arg Asn Pro Arg Leu Ser Asp Leu Pro Val Pro Ala Thr His His
305                 310                 315                 320

Ser Ala Asn Lys Thr Ser Cys Ser Glu Ala Cys Ile Met Pro Ser
                325                 330                 335


<210> SEQ ID NO 142
<211> LENGTH: 1698
<212> TYPE: DNA
<213> ORGANISM: Mus musculus

<400> SEQUENCE: 142

ctgcagccta gagaactaat gcataggaaa cttatattcc cacctccgtg acgtcactct      60

gacagaagtg aacttatatt cccacctccg tgacgtcact ctgacagaag tgacttgttt     120

ttgtatgatg ctccaggatg cctcattagc attgaggaca atcataatta agtaaggcaa     180

ggcatgaagg tggtcctcac taggtacctg gaggcttctg gttgcatgat ttacttgtga     240

tgactctgac acttaagaag acctgaaaaa tgcaaaagct gtcataaggc acagttcgtt     300

tctatggtat ctcttcctta tttgactgac attgagttga gaaggcagca ctataaacaa     360

atgggcccca ccttcctctt ccattgtctt tgggttggca tcatctccaa aggaaccttg     420

gtctagttga aagaagccag aaatcataca tggctgagac tgtgcataac tctatgtatc     480

atttaaagaa gtcattggtt cttcttattt taaaatgatg gaaggtcata tgctcttctt     540

ccttctggtc gtggtagtgc agtttttaac tggggtcttg gcaaatggcc tcattgtggt     600

tgtcaatgcc atcgacttga tcatgtggaa gaaaatggcc ccactggatc tgcttctttt     660

ttgcctggcg acttctcgga tcattcttca attgtgtata ttgtttgcac agctgggtct     720

atcctgtttg gtgagacaca cgttatttgc tgacaatgtt acctttgtct acattataaa     780

cgaactgagt ctctggtttg ccacatggct tggtgttttc tactgtgcca agattgctac     840

catccctcac ccactctttc tgtggctgaa gatgaggata tccaggttgg tgccatggct     900

gatcctggca tctgtggtct atgtaactgt tactactttc atccatagca gagagacttc     960

agaacttcct aagcaaatct ttataagctt tttttctaaa aatacaactc gggtcagacc    1020

agcgcatgcc acactactct cagtctttgt ctttgggctc acactaccat ttctcatctt    1080

cactgttgct gttctgctct tgttgtcctc cctgtggaac cacagccggc agatgaggac    1140

tatggtggga actagggaac ctagcagaca tgccctcgtc agtgcgatgc tctccattct    1200

gtcattcctc atcctctatc tctcccatga catggtagct gttctgatct gtacccaagg    1260

cctccacttt ggaagcagaa cctttgcatt ctgcttattg gttattggta tgtacccctc    1320

cttacactcg attgtcttaa ttttaggaaa ccctaagctg aaacgaaatg caaaaacgtt    1380
```

-continued

```
cattgtccat tgtaagtgtt gtcattgtgc aagagcttgg gtcacctcaa ggaacccaag   1440

actcagcgac ttgccagtgc ctgctactca tcactcagcc aacaagacat cctgctcaga   1500

agcctgtata atgccatctt aattgtccaa cctgaggctt aatcatttca aagggtaaat   1560

tgatgatcaa agcccaacac atgatatgac atcaaggtcc atatcccagt agtcatgtgg   1620

aaataccacc ttgcaaaatg atgtcattga gaaaccaggg caaatggagt ctaggtcttt   1680

cagtatgatt tgctgcag                                                 1698
```

<210> SEQ ID NO 143
<211> LENGTH: 295
<212> TYPE: PRT
<213> ORGANISM: Mus musculus

<400> SEQUENCE: 143

```
Met Asn Leu Val Glu Trp Ile Val Thr Ile Ile Met Met Thr Glu Phe
1               5                   10                  15

Leu Leu Gly Asn Cys Ala Asn Val Phe Ile Thr Ile Val Asn Phe Ile
            20                  25                  30

Asp Cys Val Lys Arg Arg Lys Ile Ser Ser Ala Asp Arg Ile Ile Thr
        35                  40                  45

Ala Ile Ala Ile Phe Arg Ile Gly Leu Leu Trp Ala Met Leu Thr Asn
    50                  55                  60

Trp His Ser His Val Phe Thr Pro Asp Thr Asp Asn Leu Gln Met Arg
65                  70                  75                  80

Val Phe Gly Gly Ile Thr Trp Ala Ile Thr Asn His Phe Thr Thr Trp
                85                  90                  95

Leu Gly Thr Ile Leu Ser Met Phe Tyr Leu Phe Lys Ile Ala Asn Phe
            100                 105                 110

Ser Asn Ser Leu Phe Leu His Leu Lys Arg Lys Leu Asp Asn Val Leu
        115                 120                 125

Leu Val Ile Phe Leu Gly Ser Ser Leu Phe Leu Val Ala Tyr Leu Gly
    130                 135                 140

Met Val Asn Ile Lys Lys Ile Ala Trp Met Ser Ile His Glu Gly Asn
145                 150                 155                 160

Val Thr Thr Lys Ser Lys Leu Lys His Val Thr Ser Ile Thr Asn Met
                165                 170                 175

Leu Leu Phe Ser Leu Ile Asn Ile Val Pro Phe Gly Ile Ser Leu Asn
            180                 185                 190

Cys Val Leu Leu Leu Ile Tyr Ser Leu Ser Lys His Leu Lys Asn Met
        195                 200                 205

Lys Phe Tyr Gly Lys Gly Cys Gln Asp Gln Ser Thr Met Val His Ile
    210                 215                 220

Lys Ala Leu Gln Thr Val Val Ser Phe Leu Leu Leu Tyr Ala Thr Tyr
225                 230                 235                 240

Ser Ser Cys Val Ile Ile Ser Gly Trp Ser Leu Gln Asn Ala Pro Val
                245                 250                 255

Phe Leu Phe Cys Val Thr Ile Gly Ser Phe Tyr Pro Ala Gly His Ser
            260                 265                 270

Cys Ile Leu Ile Trp Gly Asn Gln Lys Leu Lys Gln Val Phe Leu Leu
        275                 280                 285

Leu Leu Arg Gln Met Arg Cys
    290                 295
```

-continued

<210> SEQ ID NO 144
<211> LENGTH: 1394
<212> TYPE: DNA
<213> ORGANISM: Mus musculus

<400> SEQUENCE: 144
ctagatgggc tgtttcatat aatgactgga actccctaca tgctccacgt cttgagttct 60
aaaatttcac taacaaattt ttgactgcca taaataatga aggtttaaag aaagaacaac 120
atttgaagca atggaccaga attcctcttt atttgactct tagcaaattg gaatgcagca 180
tcctttcaag agcagcactg aaatatacca gtcaatggca gagagtaaaa aagtatgcaa 240
ttggagacat tatggtaata taaatttcca ttaaaaatga gactgcattc acctattaca 300
acacattgct attctgctca acacagagtt aaaaagaaac aagaactctt gtatacattc 360
agttagtcac aagtataatt atgttcacat attttaaaaa aatgaatcat gatctgtgaa 420
ttgagcctgg cttttttgt ctctctcttt ttattctttt cctttagaca gacacaatga 480
atttggtaga atggattgtt accatcataa tgatgacaga atttctctta ggaaactgtg 540
ccaatgtctt cataaccata gtgaacttca tcgactgtgt gaagagaaga aagatctcct 600
cagctgatcg aattataact gctattgcca tcttcagaat tggtttgttg tgggcaatgt 660
taacgaactg gcattcacat gtgtttactc cagacacaga caatttacaa atgagagttt 720
tcggtggaat tacctgggct ataaccaacc attttaccac ttggctgggg accatactga 780
gcatgtttta tttattcaag atagccaatt tttccaacag tctatttctt catctaaaaa 840
gaaaacttga caatgttcta cttgtgattt tcctgggatc gtctctgttt ttggttgcat 900
atcttgggat ggtgaacatc aagaagattg cttggatgag tattcatgaa ggaaatgtga 960
ccacaaagag caaactgaag catgtaacaa gcatcacaaa tatgcttctc ttcagcctga 1020
taaacattgt accatttggt atatcactga actgtgttct gctcttaatc tattccctga 1080
gtaaacatct caagaatatg aaattctatg gcaaaggatg tcaagatcag agcaccatgg 1140
tccacataaa ggccttgcaa actgtggtct cttttctctt gttatatgcc acatactctt 1200
cctgtgtcat tatatcaggt tggagtttgc aaaatgcacc agtcttcctg ttttgtgtga 1260
caattggatc cttctaccca gcaggtcatt cttgtatctt gatttgggga aaccagaaac 1320
ttaaacaggt ctttctgttg ttgctgaggc agatgagatg ctgactgaaa aaatgaaagt 1380
ccccctgtct ctag 1394

<210> SEQ ID NO 145
<211> LENGTH: 305
<212> TYPE: PRT
<213> ORGANISM: Mus musculus

<400> SEQUENCE: 145

Met Gly Ser Asn Val Tyr Gly Ile Leu Thr Met Val Met Ile Ala Glu
1 5 10 15

Phe Val Phe Gly Asn Met Ser Asn Gly Phe Ile Val Leu Ile Asn Cys
20 25 30

Ile Asp Trp Val Arg Lys Gly Thr Leu Ser Ser Ile Gly Trp Ile Leu
35 40 45

Leu Phe Leu Ala Ile Ser Arg Met Val Leu Ile Trp Glu Met Leu Ile
50 55 60

Thr Trp Ile Lys Tyr Met Lys Tyr Ser Phe Ser Phe Val Thr Gly Thr
65 70 75 80

Glu Leu Arg Gly Ile Met Phe Thr Trp Val Ile Ser Asn His Phe Ser

-continued

```
                85                  90                  95

Leu Trp Leu Ala Thr Ile Leu Ser Ile Phe Tyr Leu Leu Lys Ile Ala
            100                 105                 110

Ser Phe Ser Lys Pro Val Phe Leu Tyr Leu Lys Trp Arg Glu Lys Lys
        115                 120                 125

Val Leu Leu Ile Val Leu Leu Gly Asn Leu Ile Phe Leu Met Leu Asn
    130                 135                 140

Ile Leu Gln Ile Asn Lys His Ile Glu His Trp Met Tyr Gln Tyr Glu
145                 150                 155                 160

Arg Asn Ile Thr Trp Ser Ser Arg Val Ser Asp Phe Ala Gly Phe Ser
                165                 170                 175

Asn Leu Val Leu Leu Glu Met Ile Val Phe Ser Val Thr Pro Phe Thr
            180                 185                 190

Val Ala Leu Val Ser Phe Ile Leu Leu Ile Phe Ser Leu Trp Lys His
        195                 200                 205

Leu Gln Lys Met His Leu Asn Ser Arg Gly Glu Arg Asp Pro Ser Thr
    210                 215                 220

Lys Ala His Val Asn Ala Leu Arg Ile Met Val Ser Phe Leu Leu Leu
225                 230                 235                 240

Tyr Ala Thr Tyr Phe Ile Ser Phe Phe Leu Ser Leu Ile Pro Met Ala
                245                 250                 255

His Lys Thr Arg Leu Gly Leu Met Phe Ser Ile Thr Val Gly Leu Phe
            260                 265                 270

Tyr Pro Ser Ser His Ser Phe Ile Leu Ile Leu Gly His Ser Asn Leu
        275                 280                 285

Arg Gln Ala Ser Leu Trp Val Met Thr Tyr Leu Lys Cys Gly Gln Lys
    290                 295                 300

His
305
```

<210> SEQ ID NO 146
<211> LENGTH: 2567
<212> TYPE: DNA
<213> ORGANISM: Mus musculus

<400> SEQUENCE: 146

```
ctcttttgaa gacaatagtt gttctactag ctattgatag catgtttaca tttgtcattt     60

tcaagtatgt tcagaaacaa agctacatat tgtggggagt atataaaata tgaaagcatg    120

ccattcccag gcatccaagg atccctgtgt attaaaaggc aacaaagcag aaccaaatgt    180

tctgttttgg acatgagctt cttccaattc aactgctgaa aaatttggat aactacatat    240

aaaactaaga acacagagtg tcacagagca gtctctgctc tccaattcac caggattaat    300

attgacagac ccaaaagatg tcatttaggt aaattttgga tgaatcatat tgttgtcacc    360

tttgtgctct agaacataag ctgatagaat caaattttct ttagcagaga caatgcaaat    420

tgatataaca gtgaaagaga atatatcttt atttgcatgt tagcaaatga cagctggatg    480

cacttcatga ttttctgcaa tctagttcag tctttagaag gatatatata tatatatata    540

tatatatata tatatatata tatatatata tataaacctt agtcttgaaa gatatcagaa    600

agaaggattt cacaagaatg tacagagcca ttagcaaaat tttaatatac tcatcgacat    660

taggtcagtc actacataag aaggacttga atgaaagctt atcttagttt ttgagactac    720

agggacattt caccttgcca aatgagaagc agtgagtctt ctttgtctgg acatgggaag    780

caatgtgtat ggtatcttaa ctatggttat gattgcagag tttgtatttg gaaatatgag    840
```

-continued

```
caatggattc atagtgctga taaactgcat tgattgggtc aggaaaggaa ctctttcttc    900
cattggttgg atcctgcttt tcttggccat ttcaagaatg gtgttgatat gggaaatgtt    960
aataacatgg ataaaatata tgaagtattc attttcattt gtgactggaa cagaattacg   1020
gggtatcatg tttacctggg taatttccaa tcacttcagt ctctggcttg ccactattct   1080
cagcatcttt tatttgctca aaatagccag tttctccaaa ccggtttttc tctatttgaa   1140
gtggagagag aagaaagtgc ttctgattgt ccttctggga aatttgatct tcttgatgct   1200
caacatatta caaataaaca aacatataga acactggatg tatcaatatg agagaaatat   1260
aacttggagt tctagagtga gtgactttgc agggttttca aatctggtct tattggagat   1320
gattgtgttc tctgtaacac cattcacagt ggccctggtc tccttcatcc tgttaatctt   1380
ctccttgtgg aaacatctac agaaaatgca tctcaattct agaggggaac gagaccccag   1440
cactaaagcc catgtgaatg ccttgagaat tatggtctcc ttcctcttac tctatgccac   1500
ttacttcata tctttttttc tatcattgat tcccatggca cataaaacac gactgggtct   1560
tatgtttagc ataactgttg ggcttttcta cccttcaagc cactcattta tcttaatttt   1620
gggacattct aatttaaggc aagccagtct ttgggtgatg acatatctta aatgtgggca   1680
aaagcattag aatttcacta ttccataagg cagccaaacc acgtgctact aggtatatga   1740
tactactcag tggtaaagcc ctaggcaaac attaacctta gaaaatatat aattttgtga   1800
ctcttctgta tttgataaat cactcacata tttagaagaa tgctacagta gtgtgatctt   1860
gtacatgatt gtaacaattc aattttatta atatagttca ggcatgataa catacccctg   1920
ataactgaaa agtaagtagg atgctacata tatatttaga tctagactta ggggcaaaga   1980
gagacccagc tgatagctgt gcaataaaga ttttaatttt catcctgttg tgagttatct   2040
gaaatctatg tcactgaagg cataagcaag attttcacac actgaaacaa tctcttatgc   2100
tttcttatat tgttttaaaa gtaaattaga aaatttaaat aaacttaatg gcaattgaaa   2160
ttacaaaagc taaacacatg tggttattag aaattagact gtatgtaggt cctaggggat   2220
ggcttagtaa agtgctttgt tgcaagcttc aggatatgat tctaaatccc tagattcaat   2280
taaaaacctg gcataaatag ccaatgtaaa atttgtctgt aaaatgtaac cagtgctaag   2340
agtaccaaga caacaaaatg tttactttta aaaccattta ttgatattct tttaaaaata   2400
ggtatgtatt ttactattta aataagattt tgtcaaaagc tagtcttgac accttaggta   2460
aacataggaa ggcaacaagt ttgaagtcag ctactgggga cagtgctgct agcagctgac   2520
agaggccact gctgactaca gcagatcatt tacaggttca gcactag                 2567
```

<210> SEQ ID NO 147
<211> LENGTH: 309
<212> TYPE: PRT
<213> ORGANISM: Mus musculus

<400> SEQUENCE: 147

```
Met Ser Ser Leu Leu Glu Ile Phe Phe Val Ile Ile Ser Val Val Glu
1               5                   10                  15

Phe Ile Ile Gly Thr Leu Gly Asn Gly Phe Ile Val Leu Ile Asn Ser
            20                  25                  30

Thr Ser Trp Phe Lys Asn Gln Lys Ile Ser Val Ile Asp Phe Ile Leu
        35                  40                  45

Thr Trp Leu Ala Ile Ser Arg Met Cys Val Leu Trp Thr Thr Ile Ala
    50                  55                  60
```

-continued

```
Gly Ala Ser Leu Arg Lys Phe Tyr Lys Thr Leu Ser Tyr Ser Lys Asn
65                  70                  75                  80

Phe Lys Phe Cys Phe Asp Ile Ile Trp Thr Gly Ser Asn Tyr Leu Cys
                85                  90                  95

Ile Ala Cys Thr Thr Cys Ile Ser Val Phe Tyr Leu Phe Lys Ile Ala
            100                 105                 110

Asn Phe Ser Asn Ser Ile Phe Phe Trp Ile Lys Gln Arg Ile His Ala
        115                 120                 125

Val Leu Leu Ala Ile Val Leu Gly Thr Leu Met Tyr Phe Ile Leu Phe
    130                 135                 140

Leu Ile Phe Met Lys Met Ile Ala Asn Asn Phe Ile Tyr Lys Trp Thr
145                 150                 155                 160

Lys Leu Glu Gln Asn Thr Thr Phe Pro Val Leu Asp Thr Leu Ser Gly
                165                 170                 175

Phe Leu Val Tyr His Ser Leu Tyr Asn Gly Ile Leu Ile Phe Phe Phe
            180                 185                 190

Ile Val Ser Leu Thr Ser Phe Leu Leu Leu Ile Phe Ser Leu Trp Ser
        195                 200                 205

His Leu Arg Arg Met Lys Leu Gln Gly Ile His Thr Lys Asp Ile Ser
    210                 215                 220

Thr Glu Ala His Ile Lys Ala Met Lys Thr Met Met Ser Phe Leu Leu
225                 230                 235                 240

Phe Phe Ile Ile Tyr Tyr Ile Ser Asn Ile Met Leu Ile Val Ala Ser
                245                 250                 255

Ser Ile Leu Asp Asn Val Val Ala Gln Ile Phe Ser Tyr Asn Leu Ile
            260                 265                 270

Phe Leu Tyr Leu Ser Val His Pro Phe Leu Leu Val Leu Trp Asn Ser
        275                 280                 285

Lys Leu Lys Trp Thr Phe Gln His Val Leu Arg Lys Leu Val Cys His
    290                 295                 300

Cys Gly Gly Tyr Ser
305
```

<210> SEQ ID NO 148
<211> LENGTH: 1488
<212> TYPE: DNA
<213> ORGANISM: Mus musculus

<400> SEQUENCE: 148

```
aaatgaataa tttcatgcaa aggataccat tagaatatga tcactattta aattttagca     60

aatacatatt caaataccag cacaatgttt caaatttaaa atataaacat tataaaaccc    120

agcagagaac aaaatgatag ccttgataat tgttggtttg ctcaagaaaa atgggtgtat    180

actttaacat ttaattggga actcagttga gagcatacat ttagggtttt acagaggtat    240

tcattgccca tttaagattt ggattcacac atctacatca atgtggctgt aatccatttt    300

cccatgatga aataaggtag agactgccta ttaaacgaca tgtcgagcct actggagatt    360

ttctttgtga tcatttcggt tgtagaattc ataataggaa ctttgggaaa tggatttatt    420

gtcctgataa acagtacttc ttggttcaag aatcagaaaa tctctgtaat tgatttcatt    480

cttacttggt tggccatctc cagaatgtgt gttctatgga caacaattgc tggtgcctct    540

ctcaggaaat tctacaagac gttaagttac tctaagaatt tcaaattttg ttttgacatt    600

atctggacag gatccaacta tttatgcata gcctgtacaa cgtgcatcag tgtcttctac    660

ttgttcaaga ttgccaactt ttctaattcc attttcttct ggattaaaca gagaattcat    720
```

-continued

```
gcagtacttc tggctattgt cctaggcaca ctcatgtatt tcattttatt tctcattttt    780

atgaaaatga tagctaataa ttttatctac aaatggacaa aattggaaca aaacacaaca    840

ttccctgttt tagatactct aagtggtttc ttagtctacc atagcctcta caatgggatt    900

ctcattttct tttttatagt gtctctgacc tcatttcttc ttttaatctt ctctttatgg    960

agccacctta ggaggatgaa actacagggc atacatacca aagacataag cacagaagca   1020

cacataaaag ctatgaaaac tatgatgtca ttccttttgt tcttcatcat atattatatt   1080

agcaacatta tgcttattgt ggcaagctcc attcttgaca atgtggttgc acaaattttc   1140

tcttataacc taatatttct gtatttatct gttcatcctt ttcttctggt tttatggaac   1200

agcaaattga aatggacatt ccagcatgta ttgagaaagc tggtgtgtca ttgtggaggt   1260

tattcttgat ttcagtaaat acactcaata taactgatgg atttctaagg taagaaaaat   1320

ggaacaagga ataaagagga gaaatatatt ccttttcaga tcatctgctc tgtcattctg   1380

tccttagcat gctattaaga attgttgact aaatccagtc atttttaaca tgaggaaagg   1440

atgtttcaat ccaacttaga gagggtacaa aatagtccta ggaggcag               1488
```

```
<210> SEQ ID NO 149
<211> LENGTH: 333
<212> TYPE: PRT
<213> ORGANISM: Mus musculus

<400> SEQUENCE: 149

Met Phe Ser Gln Lys Ile Asn Tyr Ser His Leu Phe Thr Phe Ser Ile
1               5                   10                  15

Thr Leu Tyr Val Glu Ile Val Thr Gly Ile Leu Gly His Gly Phe Ile
            20                  25                  30

Ala Leu Val Asn Ile Met Asp Trp Val Lys Arg Arg Arg Ile Ser Ser
        35                  40                  45

Val Asp Gln Ile Leu Thr Ala Leu Ala Leu Thr Arg Phe Ile Tyr Val
    50                  55                  60

Leu Ser Met Leu Ile Cys Ile Leu Leu Phe Met Leu Cys Pro His Leu
65                  70                  75                  80

Pro Arg Arg Ser Glu Met Leu Ser Ala Met Gly Ile Phe Trp Val Val
                85                  90                  95

Asn Ser His Phe Ser Ile Trp Leu Thr Thr Cys Leu Gly Val Phe Tyr
            100                 105                 110

Phe Leu Lys Ile Ala Asn Phe Ser Asn Ser Phe Phe Leu Tyr Leu Lys
        115                 120                 125

Trp Arg Val Lys Lys Val Ile Leu Ile Ile Ile Leu Ala Ser Leu Ile
    130                 135                 140

Phe Leu Thr Leu His Ile Leu Ser Leu Gly Ile Tyr Asp Gln Phe Ser
145                 150                 155                 160

Ile Ala Ala Tyr Val Gly Asn Met Ser Tyr Ser Leu Thr Asp Leu Thr
                165                 170                 175

Gln Phe Ser Ser Thr Phe Leu Phe Ser Asn Ser Ser Asn Val Phe Leu
            180                 185                 190

Ile Thr Asn Ser Ser His Val Phe Leu Pro Ile Asn Ser Leu Phe Met
        195                 200                 205

Leu Ile Pro Phe Thr Val Ser Leu Val Ala Phe Leu Met Leu Ile Phe
    210                 215                 220

Ser Leu Trp Lys His His Lys Lys Met Gln Val Asn Ala Lys Gln Pro
225                 230                 235                 240
```

-continued

```
Arg Asp Val Ser Thr Met Ala His Ile Lys Ala Leu Gln Thr Val Phe
                245                 250                 255

Ser Phe Leu Leu Leu Tyr Ala Ile Tyr Leu Leu Phe Leu Ile Ile Gly
            260                 265                 270

Ile Leu Asn Leu Gly Leu Met Glu Lys Ile Val Ile Leu Ile Phe Asp
        275                 280                 285

His Ile Ser Gly Ala Val Phe Pro Ile Ser His Ser Phe Val Leu Ile
    290                 295                 300

Leu Gly Asn Ser Lys Leu Arg Gln Ala Ser Leu Ser Val Leu Pro Cys
305                 310                 315                 320

Leu Arg Cys Gln Ser Lys Asp Met Asp Thr Met Gly Leu
                325                 330
```

<210> SEQ ID NO 150
<211> LENGTH: 1442
<212> TYPE: DNA
<213> ORGANISM: Mus musculus

<400> SEQUENCE: 150

```
aattttcagc aaccaatatg tagactgctt aaatgcatca gaaacattat aaattgaagc     60

atgttttcac agaaaataaa ctacagccat ttgtttactt tttcaatcac cttgtatgtg    120

gaaatagtaa cgggaatctt aggacatgga ttcatagcat tagtgaacat catggactgg    180

gtcaaaagaa gaaggatctc ttcagtggat cagattctca ctgctttggc ccttaccaga    240

ttcatttatg tcttgtctat gctgatttgc atattgttat tcatgctgtg cccacatttg    300

cctaggagat cagaaatgct ttcagcaatg ggtattttct gggtagtcaa cagccatttt    360

agcatctggc ttactacatg cctcggtgtc ttttattttc tcaagatagc caatttttct    420

aactcttttt ttctttatct aaagtggaga gttaaaaaag tgattttaat aataatcctg    480

gcatcactga ttttcttgac tttacacatt ttatctttag ggatatatga tcagttctca    540

attgctgctt atgtaggaaa tatgtcttat agtttgacag atttaacaca attttccagt    600

actttcttat tctccaactc atccaatgtt ttcttaatca ccaactcatc ccatgttttc    660

ttacccatca actccctgtt catgctcata cccttcacag tgtccctggt agcctttctc    720

atgctcatct tctcactgtg gaagcatcac aaaaagatgc aggtcaatgc caaacaacct    780

agagatgtca gtactatggc ccacattaaa gccttgcaaa ctgtgttctc cttcctgctg    840

ctgtatgcca tatacttact tttccttatc ataggaattt tgaaccttgg attgatggag    900

aaaatagtga tactgatatt tgaccacatt tctggagcag tttttcctat aagccactca    960

tttgtactga ttctgggaaa cagtaagctg agacaagcca gtctttctgt gttgccttgt   1020

ctaaggtgcc agtccaaaga tatggacacc atgggtctct agtaaattcc agagtacatt   1080

ttgtaaaaat cttgaggatg atcagttcat agaaaaaagt taccttatgg gggaaaataa   1140

aaagtggggc ttcaatcctg ggagtaataa tacacaggag ggtaggacag catgaaggag   1200

actagcacta tataagtggt ctcatacagg atatgggaaa ggaaagattt atgcaataaa   1260

gagggagatc atattggagg atgaggaggc attacatatg taaaatgact ataagaatgg   1320

aatcatgcta atctaaaaaa atctgtaatg catttcattc agactatata catatatgcc   1380

tatatatgga tatatgggga tatatattct atacatattt taaaagaacc tttcttatat   1440

ag                                                                  1442
```

<210> SEQ ID NO 151

-continued

<211> LENGTH: 309
<212> TYPE: PRT
<213> ORGANISM: Mus musculus

<400> SEQUENCE: 151

```
Met Val Pro Val Leu His Ser Leu Ser Thr Ile Ile Leu Ile Ala Glu
1               5                   10                  15

Phe Val Trp Gly Asn Leu Ser Asn Gly Leu Ile Val Leu Lys Asn Cys
            20                  25                  30

Ile Asp Trp Ile Asn Lys Lys Glu Leu Ser Thr Val Asp Gln Ile Leu
        35                  40                  45

Ile Val Leu Ala Ile Ser Arg Ile Ser Leu Ile Trp Glu Thr Leu Ile
    50                  55                  60

Ile Trp Val Lys Asp Gln Leu Ile Ser Ser Ile Thr Ile Glu Glu Leu
65                  70                  75                  80

Lys Ile Ile Val Phe Ser Phe Ile Leu Ser Ser His Phe Ser Leu Trp
                85                  90                  95

Leu Ala Thr Ala Leu Ser Ile Phe Tyr Leu Phe Arg Ile Pro Asn Cys
            100                 105                 110

Tyr Trp Gln Ile Phe Leu Tyr Leu Lys Trp Arg Ile Lys Gln Leu Ile
        115                 120                 125

Val His Met Leu Leu Gly Ser Leu Val Phe Leu Val Ala Asn Met Ile
    130                 135                 140

Gln Ile Thr Ile Thr Leu Glu Glu Arg Phe Tyr Gln Tyr Gly Gly Asn
145                 150                 155                 160

Thr Ser Val Asn Ser Met Glu Thr Glu Phe Ser Ile Leu Ile Glu Leu
                165                 170                 175

Met Leu Phe Asn Met Thr Met Phe Ser Ile Ile Pro Phe Ser Leu Ala
            180                 185                 190

Leu Ile Ser Phe Leu Leu Leu Ile Phe Ser Leu Trp Lys His Leu Gln
        195                 200                 205

Lys Met Pro Leu Asn Ser Arg Gly Asp Arg Asp Pro Ser Ala Thr Ala
    210                 215                 220

His Arg Asn Ala Leu Arg Ile Leu Val Ser Phe Leu Leu Leu Tyr Thr
225                 230                 235                 240

Ile Tyr Phe Leu Ser Leu Leu Ile Ser Trp Val Ala Gln Lys Asn Gln
                245                 250                 255

Ser Glu Leu Val His Ile Ile Cys Met Ile Thr Ser Leu Val Tyr Pro
            260                 265                 270

Ser Phe His Ser Tyr Ile Leu Ile Leu Gly Asn Tyr Lys Leu Lys Gln
        275                 280                 285

Thr Ser Leu Trp Val Met Arg Gln Leu Gly Cys Arg Met Lys Arg Gln
    290                 295                 300

Asn Thr Pro Thr Thr
305
```

<210> SEQ ID NO 152
<211> LENGTH: 1465
<212> TYPE: DNA
<213> ORGANISM: Mus musculus

<400> SEQUENCE: 152

```
caaagaggag aaatatttag ctacacagtg taccacatac aagccgttca atcagtataa     60

ggggagcagt catatagaat ttgggctttc tttcttttaa tatggtacct gttctgcaca    120

gtctctccac catcatacta attgcagagt ttgtttgggg aaatttgagc aatggtttga    180
```

-continued

```
tagtgttgaa gaactgcatt gactggatca ataaaaaaga gctctccaca gttgatcaaa    240

tactcattgt cttggcaatt tcaagaatta gtctcatctg ggaaacacta attatatggg    300

ttaaagatca actaatttca tctattacta ttgaagaatt aaaaataatt gtgttcagct    360

ttatactatc tagccacttc agtctctggc ttgctacagc tctcagcatc ttctatttat    420

tcagaatacc taattgctac tggcagatct ttctctactt gaaatggaga ataaagcaac    480

tgattgtcca catgcttctg ggaagcttgg tgttcttggt tgcaaatatg atacagataa    540

ccatcactct tgaagagagg ttctatcaat atggaggaaa tacaagtgta aattccatgg    600

agactgagtt ctcaattttg atagagctga tgttatttaa catgactatg ttctccatta    660

taccattttc attggcctta atttcttttc ttctgctaat cttctcttta tggaaacatc    720

tccagaagat gccactcaat tctagaggag atagagaccc tagtgctacg gcccacagaa    780

atgccttgag aattttggtc tccttcctct tgctctatac tatatatttc ctgtctcttc    840

ttatatcatg ggttgctcag aagaatcaaa gtgaactggt tcacattatt tgtatgataa    900

cttcactcgt gtatccttca ttccactcat atatcctgat tctgggaaat tataaattaa    960

agcagacctc tctttgggta atgaggcagc tgggatgtag gatgaaaaga cagaatacac   1020

caactacata aggcagccaa acagtctatt gggttttaga taacaaatct aaatctatga   1080

ggaagtagtt caataacatt tttccccttg acatggagta gcagggtttt tttttattag   1140

atattttctt tacttacatt tcaaatgcta tcccgaaaat tccctgtacc ctctccctgt   1200

cctgttcccc tacccaccca ctcccacttc ttggccctgg cattcccctg gagtatcagt   1260

tttttattag tcaaactatc tcactgacta agggtcataa aacaagttat tttaacacta   1320

atttcaatta aatcaaaggt aaagtgtcag cacatgcctt taatcacaca attccatcaa   1380

attcagcact caggagaggg tgatctctgt gaattccagc acactggcgg ccgttactag   1440

tggatccgag ctcggtacca agctt                                         1465
```

<210> SEQ ID NO 153
<211> LENGTH: 311
<212> TYPE: PRT
<213> ORGANISM: Mus musculus

<400> SEQUENCE: 153

```
Met Met Gly Ile Ala Ile Asp Ile Leu Trp Ala Ala Ile Ile Ile Val
1               5                   10                  15

Gln Phe Ile Ile Gly Asn Ile Ala Asn Gly Phe Ile Ala Leu Val Asn
            20                  25                  30

Ile Ile Asp Trp Val Lys Arg Arg Lys Ile Ser Leu Met Asp Lys Ile
        35                  40                  45

Ile Thr Ala Leu Ala Ile Ser Arg Ile Tyr Leu Leu Trp Ser Thr Phe
    50                  55                  60

Leu Ile Thr Leu Thr Ser Ser Leu Asp Pro Asp Ile Lys Met Ala Val
65                  70                  75                  80

Lys Ile Ile Arg Ile Ser Asn Asn Thr Trp Ile Ile Ala Asn His Phe
                85                  90                  95

Ser Ile Trp Phe Ala Thr Cys Leu Ser Ile Phe Tyr Phe Leu Lys Ile
            100                 105                 110

Ala Asn Phe Ser Asn Tyr Ile Phe Leu Tyr Leu Arg Trp Arg Phe Lys
        115                 120                 125

Lys Val Val Ser Val Thr Leu Leu Ile Ser Leu Ile Phe Leu Leu Leu
    130                 135                 140
```

-continued

```
Asn Ile Leu Leu Met Asn Met His Ile Asp Ile Trp Ser Asp Lys Ser
145                 150                 155                 160

Lys Arg Asn Leu Ser Phe Ser Val Arg Ser Asn Asn Cys Thr Gln Phe
                165                 170                 175

Pro Arg Leu Val Leu Leu Ile Asn Thr Met Phe Thr Ser Ile Pro Phe
            180                 185                 190

Thr Val Ser Leu Leu Ala Phe Leu Leu Leu Ile Phe Ser Leu Trp Arg
        195                 200                 205

His Leu Lys Thr Met Gln Tyr Tyr Ala Lys Gly Ser Glu Asp Thr Thr
    210                 215                 220

Thr Ala Ala His Ile Lys Ala Leu His Met Val Val Ala Phe Leu Leu
225                 230                 235                 240

Phe Tyr Thr Val Phe Phe Leu Ser Leu Ala Ile Gln Tyr Trp Thr Ser
                245                 250                 255

Gly Ser Gln Glu Asn Asn Asn Leu Phe Tyr Ala Thr Ile Val Ile Thr
            260                 265                 270

Phe Pro Ser Val His Ser Cys Ile Leu Ile Leu Arg Asn Ser Gln Leu
        275                 280                 285

Arg Gln Ala Ser Leu Leu Val Leu Trp Trp Leu Leu Cys Lys Ser Lys
    290                 295                 300

Asp Val Arg Met Leu Val Pro
305                 310
```

<210> SEQ ID NO 154
<211> LENGTH: 1103
<212> TYPE: DNA
<213> ORGANISM: Mus musculus

<400> SEQUENCE: 154

```
aaaactattc gaattgaaca cagtaaccaa ttcttcagcg gacttacaca aatcaagcta     60

ttatcttatg gatgatgggt attgccatag atatcttatg ggcagctatt atcattgtgc    120

aattcataat tgggaatatt gcaaatggat tcatagcatt ggtgaacatc atagactggg    180

tgaagagaag aaaaatctct ttaatggata agatcattac tgctttggca atctctagga    240

tttatctgct gtggtctaca ttcttaatta cactaacatc ttcactggat ccagatatta    300

aaatggctgt gaaaatcatt agaataagca ataacacctg gattattgca aatcatttca    360

gcatttggtt tgctacatgt ctcagcatct tttattttct caagatagcc aatttttcta    420

actatatttt tctctactta aggtggagat ttaagaaggt ggtttcagtg acattgctaa    480

tctctcttat cttcctgctt ttaaatattt tactgatgaa catgcatatt gatatctgga    540

gtgataagtc caaaagaaac ctttctttta gtgtcagatc aaataattgc actcagtttc    600

ccagacttgt ccttttaatc aacacaatgt tcacatcaat ccccttcact gtgtccctgt    660

tggcttttct gcttctcatc ttctccctgt ggagacacct gaaaaccatg caatactatg    720

ctaaaggctc cgaagacacc accacagctg cacatataaa ggccttgcac atggtagtgg    780

cctttctcct gttctacaca gtttctttt tgtctcttgc catacaatat tggacctctg     840

ggtctcaaga gaataacaac ctgttttatg ccacaattgt aattactttc ccttcagtcc    900

attcatgtat cctgattctg agaaacagcc agctgaggca ggcatctctg ttggtgctgt    960

ggtggctgct gtgcaagtcc aaagatgtac ggatgttggt tccctgaaat actctgtcaa   1020

tgctctttag tagtgaagaa gaaaatagct tagttaagga aattcttgtt cattaccgaa   1080

gtatactttc aagtttatgt atc                                           1103
```

-continued

<210> SEQ ID NO 155
<211> LENGTH: 308
<212> TYPE: PRT
<213> ORGANISM: Mus musculus

<400> SEQUENCE: 155

```
Met Leu Pro Thr Leu Ser Val Phe Phe Met Leu Thr Phe Val Leu Leu
1               5                   10                  15

Cys Phe Leu Gly Ile Leu Ala Asn Gly Phe Ile Val Leu Met Leu Ser
            20                  25                  30

Arg Glu Trp Leu Leu Arg Gly Arg Leu Leu Pro Ser Asp Met Ile Leu
        35                  40                  45

Phe Ser Leu Gly Thr Ser Arg Phe Phe Gln Gln Cys Val Gly Leu Val
    50                  55                  60

Asn Ser Phe Tyr Tyr Phe Leu His Leu Val Glu Tyr Ser Gly Ser Leu
65                  70                  75                  80

Ala Arg Gln Leu Ile Ser Leu His Trp Asp Phe Leu Asn Ser Ala Thr
                85                  90                  95

Phe Trp Phe Cys Thr Trp Leu Ser Val Leu Phe Cys Ile Lys Ile Ala
            100                 105                 110

Asn Phe Ser His Pro Ala Phe Leu Trp Leu Lys Trp Arg Phe Pro Ala
        115                 120                 125

Leu Val Pro Trp Phe Leu Leu Gly Ser Ile Leu Val Ser Val Ile Val
    130                 135                 140

Thr Leu Leu Phe Phe Trp Gly Asn His Thr Ile Tyr Gln Ala Phe Leu
145                 150                 155                 160

Arg Arg Lys Phe Thr Gly Asn Thr Thr Phe Lys Glu Trp Asn Arg Arg
                165                 170                 175

Leu Glu Ile Asp Tyr Phe Met Pro Leu Lys Val Val Thr Met Ser Ile
            180                 185                 190

Pro Cys Ser Leu Phe Leu Val Ser Ile Leu Leu Leu Ile Ser Ser Leu
        195                 200                 205

Arg Arg His Ser Leu Arg Met Gln His Asn Thr His Ser Leu Gln Asp
    210                 215                 220

Pro Asn Val Gln Ala His Ser Arg Ala Leu Lys Ser Leu Ile Ser Phe
225                 230                 235                 240

Leu Val Leu Tyr Ala Val Ser Phe Val Ser Met Ile Ile Asp Ala Thr
                245                 250                 255

Val Phe Ile Ser Ser Asp Asn Val Trp Tyr Trp Pro Trp Gln Ile Ile
            260                 265                 270

Leu Tyr Phe Cys Met Ser Val His Pro Phe Ile Leu Ile Thr Asn Asn
        275                 280                 285

Leu Arg Phe Arg Gly Thr Phe Arg Gln Leu Leu Leu Leu Ala Arg Gly
    290                 295                 300

Phe Trp Val Ala
305
```

<210> SEQ ID NO 156
<211> LENGTH: 3437
<212> TYPE: DNA
<213> ORGANISM: Mus musculus

<400> SEQUENCE: 156

```
gaattctaga caaggaaaga cacacactaa atgactttac ttgtgggacc taaaataacc     60
```

-continued

```
aaaataagtc aaaatcacag tgatgttact agggatctag gataagggaa tgaagagaaa    120
gatgttggtc atagagtaca aaaattcagc taagaactca gtcctggagg ctgaatgtat    180
agctgtgtga cagacagcag ctagccatac cagagtatac acttgcctct tgctgaaaga    240
gtagatctta tgtgtccttg tcacacataa aagtaattga aaaagtaact ctctgagatg    300
acagatacgt taaaatggtt ttacttttca acctgctcca gtaggggtcc ctttaatgtt    360
tgtgctagta gatgggggac tctcaagtat ctttgtggta gacaaatcta aggtggcctt    420
catgaatacc aacccagact tttgtgactt tgtgatcccc cacttttgaa gtggataaga    480
gctgtgactt gagtctaatc aaaggagtcc aacgtgttgt ttattctgta acagtgcttt    540
gtgtttctag ttaataacac aggcaaagaa ggctagggtg acattcctag gattgtgtta    600
tttctatctt gctcatgcct ccctctgctg gtctaatgaa ataagtcagt ggccatattt    660
aaatatgact acgtggcaaa tactgatgat agcctgtgtg ttccaacaaa tatccagtag    720
gagacctagg cattcagtcc tgcagccaca aggaaatagg ttctttcact ggaaaaagag    780
cagtttagat ggttataaat tacttaatcc atagaagcca taggggcttt atgtagagat    840
ttgggtagag aggtagacct agatattgac ttaggagtgg ctattcctga gtgggggtag    900
atatatggca gggaaactca gataagaaag acttctttag tgtcacgatt tttcctaggt    960
atctccttgt gccagatatc tatgcgtcta tgtacctacc tacctaccta cctacctacc   1020
tacctaccta cctactgaca cctaatagga agaggcaagt ggtcacaacc tgcaatgatg   1080
ggataagaat gatggaactc agttaccaag attaaaatac cttccccact gatgttattg   1140
caagcatggc agcatgtagg caaaatcaga gaaggcaaat catgagcagc tgctgcccca   1200
tggtacccga gcccgggaaa tatttgcatc atatctgagc caaaagcaca ccttttatct   1260
actgcctgag catttttcac attgaagttc tggctcacat gcagaatcca accatttatc   1320
tcctgtctcc agaagggagt gtcagggact gtgggtaggg gcagggagga ggccaggaac   1380
caaggcaatc agtggtgaca ggaggaggga ctgaaatgct accaacatta tcagttttct   1440
tcatgttgac ctttgttctg ctctgtttcc tggggatcct ggccaacggc ttcattgtgc   1500
tgatgctgag cagggaatgg ctactgcgtg gtaggctgct cccctcggac atgatcctct   1560
tcagtttggg cacctcccga ttcttccagc agtgtgtggg attggtcaac agtttctatt   1620
acttcctcca tctggttgag tactccggga gccttgcccg gcagctcatt agtcttcact   1680
gggacttctt gaactcagcc actttctggt tttgtacctg gctcagcgtc ctgttctgta   1740
tcaagattgc taacttctcc catcctgcct tcctgtggtt gaagtggaga ttcccagcgt   1800
tggtgccctg gttcttgttg ggctctatct tggtgtccgt cattgtaact ctgctgttct   1860
tttggggaaa ccacactata tatcaggcat tcttaaggag aaagtttact gggaacacaa   1920
cctttaagga gtggaacaga aggctggaaa tagactattt catgcctctg aaagttgtca   1980
ccatgtcaat tccttgttct ctttttctgg tctcaatttt gctgttgatc agttctctca   2040
gaaggcattc gctaagaatg cagcacaata ccccacagct gcaagacccc aacgtccagg   2100
ctcacagcag agccctgaag tcactcatct cattcctggt tctttatgcg gtgtcctttg   2160
tgtccatgat cattgatgct acagtcttca tctcctcaga taatgtgtgg tattggccct   2220
ggcaaattat actttacttt tgcatgtctg tacatccatt tatcctcatc accaataatc   2280
tcaggttccg cggcaccttc aggcagctac tcctgttggc caggggattc tgggtggcct   2340
agaaggcttg gtctctttat ctagagcctt tgaagagact caggtgaggg taacttcact   2400
tggaagtgag ctcatctacg tggaaatgtc tttgtaggca ggcatggggt catactgtga   2460
```

-continued

```
ggttcctcat tgggaaagag gagaagaaaa tacagagtgt ccttccttac cttaggatat   2520

tatgaaagtg gaaattccga atcctggacc agtattgatc taagtgcaaa gtacaatatg   2580

tcctgttcct ttcatgtctg ttttcctttt gttactgatt cattctctag ggaatagtct   2640

tgatcaactg aatcatctca tctggctggc cactggggag gtaaaagaac tttgtgtcac   2700

tgctgcattg ggatatacat gggtgggaag caagtgtccc tgaggcagag tagcactcag   2760

tatgagaacc tcaaagagca ggtggctgtg catgcagggg ctggggcaag gagtcctgat   2820

cactcttcac tgtatgggga ttatttgtct cttgccaaaa tttggagact ttggctttag   2880

ttttgtgaag atgactggaa aaattcttaa tgctaccctg tatcatttct caataatatt   2940

ttccttttcc tgcctttaat tttctcctat ctgcagcgcc ccttgcttgt tatccgtaaa   3000

taaataaata aataaataaa taagcccaat cctcattttc ctgtctttgg gaacccttttt  3060

acttccccag gtatacgcta caaagccact tctgcattga ataaacatta tctttcattc   3120

agaaaaagac ttaagaatct cacctttaca aaaaaaaaaa aaaaagaatc tcacttattt   3180

tatattcaaa ttccattttt aaaaagaaaa gcacagcatt aatttttcta aatactgttt   3240

ataaaaataa cttgctctaa gaattataca aatgttttga aaggtaactt tggaaaaaaa   3300

gtgtgattag acatggatgt ttgtaagaca gaacaaagag ctcttggaag tccatggcag   3360

ctcattggtc ttgccttcag tagagcctgt ctgaatcctg taacctctta tgccctttttg  3420

tagcttttct gcagatc                                                 3437
```

<210> SEQ ID NO 157
<211> LENGTH: 340
<212> TYPE: DNA
<213> ORGANISM: Mus musculus

<400> SEQUENCE: 157

```
gaattcgccc ttgcgggatc cgggaacgga ttcatagcac tggtaaactt catgggctgg     60

atgaagaata ggaagattgc ctccattgat ttaatcctca caagtctggc catatccaga    120

atttgtctat tgtgcgtaat actattagat tgttttatat tggtgctata tccagatgtc    180

tatgccactg gtaaagaaat gagaatcatt gacttcttct ggacactaac caatcactta    240

agtatctggt ttgcaacctg cctcagcatt tactatttct tcaagatagg taatttcttt    300

cacccacttt tcctatgcct caagtctaga cgccaagggc                          340
```

<210> SEQ ID NO 158
<211> LENGTH: 82
<212> TYPE: PRT
<213> ORGANISM: Mus musculus

<400> SEQUENCE: 158

```
Gly Arg Glu Trp Leu Arg Tyr Gly Arg Leu Leu Pro Leu Asp Met Ile
1               5                   10                  15

Leu Ile Ser Leu Gly Ala Ser Arg Phe Cys Leu Gln Leu Val Gly Thr
            20                  25                  30

Val His Asn Phe Tyr Tyr Ser Ala Gln Lys Val Glu Tyr Ser Gly Gly
        35                  40                  45

Leu Gly Arg Gln Phe Phe His Leu His Trp His Phe Leu Asn Ser Ala
    50                  55                  60

Thr Phe Trp Phe Cys Ser Trp Leu Ser Val Leu Phe Cys Val Lys Ile
65                  70                  75                  80

Ala Asn
```

-continued

<210> SEQ ID NO 159
<211> LENGTH: 341
<212> TYPE: DNA
<213> ORGANISM: Mus musculus

<400> SEQUENCE: 159
gaattcgccc ttgcgggatc cgggaacggg tttattgtgc tggtgctggg cagggagtgg 60
ctgcgatatg gcaggttgct gcccttggat atgatcctca ttagcttggg tgcctcccgc 120
ttctgcctgc agttggttgg gacggtgcac aacttctact actctgccca gaaggtcgag 180
tactctgggg gtctcggccg acagttcttc catctacact ggcacttcct gaactcagcc 240
accttctggt tttgcagctg gctcagtgtc ctgttctgtg tgaagattgc taacatcaca 300
cactccacct tcctgtgtct caagtctaga cgccaagggc g 341

<210> SEQ ID NO 160
<211> LENGTH: 320
<212> TYPE: PRT
<213> ORGANISM: Mus musculus

<400> SEQUENCE: 160

Met Asp Gly Ile Val Gln Asn Met Phe Thr Phe Ile Val Ile Val Glu
1               5                   10                  15

Ile Ile Ile Gly Trp Ile Gly Asn Gly Phe Ile Ala Leu Val Asn Cys
            20                  25                  30

Ile His Trp Tyr Lys Arg Arg Lys Ile Ser Ala Leu Asn Gln Ile Leu
        35                  40                  45

Thr Ala Leu Ala Phe Ser Arg Ile Tyr Leu Leu Leu Thr Val Phe Thr
    50                  55                  60

Val Ile Ala Val Ser Thr Leu Tyr Thr His Val Leu Val Thr Arg Arg
65                  70                  75                  80

Val Val Lys Leu Ile Asn Phe His Leu Leu Phe Ser Asn His Phe Ser
                85                  90                  95

Met Trp Leu Ala Ala Cys Leu Gly Leu Tyr Tyr Phe Leu Lys Ile Ala
            100                 105                 110

His Phe Pro Asn Ser Ile Phe Val Tyr Leu Lys Met Arg Ile Asn Gln
        115                 120                 125

Val Val Ser Gly Thr Leu Leu Met Ser Leu Gly Leu Leu Phe Leu Asn
    130                 135                 140

Thr Leu Leu Ile Asn Ser Tyr Ile Asp Thr Lys Ile Asp Asp Tyr Arg
145                 150                 155                 160

Glu His Leu Leu Tyr Asp Phe Thr Ser Asn Asn Thr Ala Ser Phe Tyr
                165                 170                 175

Arg Val Ile Leu Val Ile Asn Asn Cys Ile Phe Thr Ser Ile Pro Phe
            180                 185                 190

Thr Leu Ser Gln Ser Thr Phe Leu Leu Leu Ile Phe Ser Leu Trp Arg
        195                 200                 205

His Tyr Lys Lys Met Gln Gln His Ala Gln Arg Cys Arg Asp Val Leu
    210                 215                 220

Ala Asp Ala His Ile Arg Val Leu Gln Thr Met Val Thr Tyr Val Leu
225                 230                 235                 240

Leu Cys Ala Ile Phe Phe Leu Ser Leu Ser Met Gln Ile Leu Arg Ser
                245                 250                 255

Glu Leu Leu Lys Asn Ile Leu Tyr Val Arg Phe Cys Glu Ile Val Ala
            260                 265                 270

-continued

```
Ala Val Phe Pro Ser Gly His Ser Cys Val Leu Ile Cys Arg Asp Thr
        275                 280                 285

Asn Leu Arg Gly Thr Phe Leu Ser Val Leu Ser Trp Leu Lys Gln Arg
    290                 295                 300

Phe Thr Ser Trp Ile Pro Asn Ile Asn Cys Arg Ser Ser Cys Ile Phe
305                 310                 315                 320


<210> SEQ ID NO 161
<211> LENGTH: 1108
<212> TYPE: DNA
<213> ORGANISM: Mus musculus

<400> SEQUENCE: 161

agcttgatat ttcctatttg ttactgcaca gagttttttt taaaaattga gtttgttatg      60

tggattcaat actcagatag agctctttaa tttttttaca gtgacctcat gaatcataac     120

ttgccttaca gacaatggat ggaatcgtac agaacatgtt tacattcatt gtaattgtgg     180

aaataataat aggatggatt ggaaatggat tcatagctct ggtgaactgc atacactggt     240

acaagagaag aaagatctct gcactgaatc aaatactcac agccttggct ttctccagaa     300

tctaccttct tttaacagta ttcactgtta tagcagtgtc tacgctatac acacacgtgt     360

tggtaactag aagagtggta aaactgatta atttccattt gcttttcagc aatcatttta     420

gcatgtggct tgctgcatgc cttggccttt attattttct taaaatagct cattttccta     480

actctatttt tgtttactta aagatgagaa ttaaccaggt ggtttcaggg actttgctca     540

tgtctttggg cctcttgttt ctaaacactc tgctgataaa ctcatacatt gataccaaga     600

tagatgacta cagagaacat ctactgtatg atttcacttc gaataatact gcttcatttt     660

acagggttat tttagtcatt aacaactgta ttttcacatc tatacccttt acactttccc     720

agtccacttt tctcctgctc atcttctccc tgtggagaca ttacaagaag atgcaacagc     780

atgcacaaag atgcagagat gtccttgcag atgcccacat cagagtcttg caaaccatgg     840

tcacctatgt cctactctgt gccattttct ttctgtctct ttccatgcaa attttgagga     900

gtgagttgtt gaagaacatt ctttacgtta ggttctgcga gattgttgca gcagtttttc     960

cttcaggaca ctcctgtgtc ttaatctgta gagacacaaa cctgagaggg acctttcttt    1020

ctgtgctatc gtggctgaag cagaggttta catcatggat tcctaacata aattgcagat    1080

catcttgcat attctaaaag aaactgag                                       1108


<210> SEQ ID NO 162
<211> LENGTH: 312
<212> TYPE: PRT
<213> ORGANISM: Mus musculus

<400> SEQUENCE: 162

Met Thr Tyr Glu Thr Asp Thr Thr Leu Met Leu Val Ala Val Gly Glu
1               5                   10                  15

Ala Leu Val Gly Ile Leu Gly Asn Ala Phe Ile Ala Leu Val Asn Phe
            20                  25                  30

Met Gly Trp Met Lys Asn Arg Lys Ile Ala Ser Ile Asp Leu Ile Leu
        35                  40                  45

Ser Ser Val Ala Met Ser Arg Ile Cys Leu Gln Cys Ile Ile Leu Leu
    50                  55                  60

Asp Cys Ile Ile Leu Val Gln Tyr Pro Asp Thr Tyr Asn Arg Gly Lys
65                  70                  75                  80
```

-continued

```
Glu Met Arg Thr Val Asp Phe Phe Trp Thr Leu Thr Asn His Leu Ser
                85                  90                  95

Val Trp Phe Ala Thr Cys Leu Ser Ile Phe Tyr Leu Phe Lys Ile Ala
            100                 105                 110

Asn Phe Phe His Pro Leu Phe Leu Trp Ile Lys Trp Arg Ile Asp Lys
        115                 120                 125

Leu Ile Leu Arg Thr Leu Leu Ala Cys Val Ile Ile Ser Leu Cys Phe
    130                 135                 140

Ser Leu Pro Val Thr Glu Asn Leu Ser Asp Asp Phe Arg Arg Cys Val
145                 150                 155                 160

Lys Thr Lys Glu Arg Ile Asn Ser Thr Leu Arg Cys Lys Val Asn Lys
                165                 170                 175

Ala Gly His Ala Ser Val Lys Val Asn Leu Asn Leu Val Met Leu Phe
            180                 185                 190

Pro Phe Ser Val Ser Leu Val Ser Phe Leu Leu Leu Ile Leu Ser Leu
        195                 200                 205

Trp Arg His Thr Arg Gln Ile Gln Leu Ser Val Thr Gly Tyr Lys Asp
    210                 215                 220

Pro Ser Thr Thr Ala His Val Lys Ala Met Lys Ala Val Ile Ser Phe
225                 230                 235                 240

Leu Ala Leu Phe Val Val Tyr Cys Leu Ala Phe Leu Ile Ala Thr Ser
                245                 250                 255

Ser Tyr Phe Met Pro Glu Ser Glu Leu Ala Val Ile Trp Gly Glu Leu
            260                 265                 270

Ile Ala Leu Ile Tyr Pro Ser Ser His Ser Phe Ile Leu Ile Leu Gly
        275                 280                 285

Ser Ser Lys Leu Lys Gln Ala Ser Val Arg Val Leu Cys Arg Val Lys
    290                 295                 300

Thr Met Leu Lys Gly Lys Lys Tyr
305                 310


<210> SEQ ID NO 163
<211> LENGTH: 3775
<212> TYPE: DNA
<213> ORGANISM: Mus musculus

<400> SEQUENCE: 163

aaaaatgttc attgtttatc taaaattcaa atttaactga gtgccctaca tttttattta      60

ttcaatctag tagctgtact gaggttatta gtgtgatttc tgaagcccaa atttgtaaaa     120

cttagcctca gataaacagc ttgagaccat ggaaagtaat ttggtaaatt tgcatcttag     180

caaatagtag ctcagcctaa attaactgtg tgtagaaaag aatgacctgc ggagaagata     240

aatggacata caatatccag gctaaggatt gccaaacaca ctgtttttaa gactaattga     300

gatttagata aactatctac agtcttcatg tataattctc atcttcatca caagacagac     360

ttcaacttaa ggaggtaaag acaaggacag cgaaccctaa acagccaagt gtagaaacca     420

aactgcatca aatcagccag aaactaattg gatacttctc tactttaaaa tgacatacga     480

aacagatact accttaatgc ttgtagctgt tggtgaggcc ttagtaggga ttttaggaaa     540

tgcattcatt gcactggtaa acttcatggg ctggatgaag aataggaaga ttgcctctat     600

tgatttaatc ctctcaagtg tggccatgtc cagaatttgt ctacagtgta taatcctatt     660

agattgtatt atattggtgc agtatccaga cacctacaac agaggtaaag aaatgaggac     720

cgttgacttc ttctggacac ttaccaacca tttaagtgtc tggtttgcca cctgcctcag     780
```

-continued

```
cattttctat ttattcaaga tagcaaactt cttccaccct cttttcctct ggataaagtg    840
gagaattgac aagctaattc tcagaactct actggcatgt gtgattatct ccctgtgttt    900
tagcctccca gtcactgaaa atctgagtga tgatttcaga cgttgtgtta agacaaagga    960
gagaataaac tctactttga gatgcaaagt aaataaagct ggacatgcct ctgtcaaggt   1020
aaatctcaac ttggtcatgc tgttcccctt ttctgtgtct ctggtctcct ttctcctctt   1080
gatcctctcc ctgtggagac acaccaggca gatacaactc agtgtaacag ggtacaaaga   1140
tcccagcaca acagctcatg tgaaagccat gaaagcagta atttccttcc tggccctgtt   1200
tgttgtctac tgcctagcct ttctcatagc cacctccagc tactttatgc cagagagtga   1260
attagctgta atatggggtg agctgatagc tctaatctat ccttcaagcc attcatttat   1320
cctcatcctg ggagtagta aactaaaaca agcatctgtg agggtgcttt gtagagtaaa    1380
gaccatgtta aagggaaaaa aatattagca tcatgagcat atctgaagaa aaactatcac   1440
tttctaagag aaaggaagac acgatcatta tccgtccttt tcacatgaat attgatttca   1500
tgcagtgaca tcctcttaac aaacttaaat tgaaccttga gaaatctcat atacagcaac   1560
tttgcatgtc tctatctctg ctttttctct cctttttcaat atgagttgac ataaaaaata  1620
attttcagaa caaattataa cagaagaaag ggcattttca taatcagttc tgaatcactc   1680
ctccaaatgc aaagctgcct gacaaattca aaacaattgt aacagcatct cactgtcgtt   1740
tgcattcttt ggaaaagcag gtggtttgtt cttggagcct ggcttagagt tttcttctta   1800
gaccattgaa ttatgttcat gattggagaa gagtcaagta ccaagtaaca atttttattg   1860
tgaagatggg tgttcatcat gtgattttgg ctggcctgga acttgttatg tagactagtc   1920
tgtcatcaaa cacacaaaga tctgcctgcc tcacctgcca gttctaggat tcaaggaatg   1980
caccaccaca gcttgttcaa gtgacaattc ttacaaatgt tttagaaata aataatatac   2040
tagaaattaa cactgaatgt aagtgctgtt taggtataaa ttatgattaa atgttatagt   2100
tagaaaatta tttaagatta tagatcagtg atgaaaatat tctagaataa gttttatgaa   2160
gaaactttta taaagaaact ggaaaaaaat ctcttgattg catattgaaa caaatttctc   2220
caaaaagaac acctacaaat ttgctctaga catctagact gtatcaaaca gtgaatatga   2280
aaatatcata acaggatata gcctttagta ttgaagacag gttcatctat attaaacctg   2340
catacatacc taaaagacta agtcaatatc ccacaaacat atttgcacta tcatgtctat   2400
tgaaacacta ttcatagtag ctaaaatatg gcacaaaact agacattcat caatagatga   2460
atcaataaag caaatgtaca tacacaagat gaaattgtat tcaggcataa agaagaatgc   2520
agtcatgtca ttagcaaaaa cataaacaga attggaggtc attgtgataa ttgaaataaa   2580
ccagacctgg aaaaaacaaa acctgtgtaa tttttctgaa gtagagaata tactcttgga   2640
tggatagatg ggtactgtta tagtataaaa tgtgtgtgtg tgtgtgtgtg tgtgtgtgtg   2700
tatttcatga aagcaagaat gggactgctt agagaaagaa aaggacaaac aggtgaaggg   2760
gtgaaagaaa aaggcaatga caaggagtaa tgatatgagc aaagtaccat tattaaacat   2820
gtgacaatat tatatagaaa cacatgattt tgtgtgccta ccaaaactgg ataataattt   2880
ttaaaatgta tctattaaaa ggaaagaaaa gaaagtgcaa gcccaggaaa gggagaaaag   2940
gaaacaatga gagagaaatg gaaaatggtg agaagtgaag agaacaaaaa gaaatggagt   3000
aagtgtggcc aggaatgaag gatctcagct atagttatcc cagtacggta atacaaatct   3060
gtgactccag cacttgacaa ggctgagaga tgtgagagag ggccagttaa caaccagtct   3120
gggcttattc caagagataa gaagattggg ggaaagtatg tagaagggtt tggagggaag   3180
```

agagagaaga gggaaatgat gtaatgatag tacaaatcaa aagttatttt ttctaaaaaa 3240
gcaatgggac aggaaaccaa cctaacaagt aaaggtgctt ggttcacaag accagcaacc 3300
tgagtgcatc cttgctagaa tgaaattggc cttactctgg aaagcttact tcctcagtgt 3360
attcattgtt aaaattcatg tggagatttt aaagaaaaaa ggaaaaaaaa agttaaatgg 3420
tagatttgtg taggggaata ttcccctaat taattgatta gataataaag atgacaagca 3480
aattgctgtg caaaaaggaa gacaaggtct aagaggggaa gaggggacac gggaggaaaa 3540
aaaacggccc tttttaaagc aaggtgggga gtgagggaag cgagatgtag acagggaact 3600
gttagacctg gtggcagctt ctgccacctg aagattttca acatagtata gttcatgagt 3660
ttaggaagat atgttccctg cccagcggtt gtatcatctg ttgattttaa actaagattg 3720
tctggtgttt tccatttgcg gagactcaag tagaccaaag ggaaagaatg aattc 3775

<210> SEQ ID NO 164
<211> LENGTH: 310
<212> TYPE: PRT
<213> ORGANISM: Mus musculus

<400> SEQUENCE: 164

Met Tyr Met Ile Leu Val Arg Ala Val Phe Ile Thr Gly Met Leu Gly
1               5                   10                  15

Asn Met Phe Ile Gly Leu Ala Asn Cys Ser Asp Trp Val Lys Asn Gln
            20                  25                  30

Lys Ile Thr Phe Ile Asn Phe Ile Met Val Cys Leu Ala Ala Ser Arg
        35                  40                  45

Ile Ser Ser Val Leu Met Leu Phe Ile Asp Ala Thr Ile Gln Glu Leu
    50                  55                  60

Ala Pro His Phe Tyr Tyr Ser Tyr Arg Leu Val Lys Cys Ser Asp Ile
65                  70                  75                  80

Phe Trp Val Ile Thr Asp Gln Leu Ser Thr Trp Leu Ala Thr Cys Leu
                85                  90                  95

Ser Ile Phe Tyr Leu Phe Lys Val Ala His Ile Ser His Pro Leu Phe
            100                 105                 110

Leu Trp Leu Lys Trp Arg Leu Arg Gly Val Leu Val Val Phe Leu Val
        115                 120                 125

Phe Ser Leu Phe Leu Leu Ile Ser Tyr Phe Leu Leu Leu Glu Thr Leu
    130                 135                 140

Pro Ile Trp Gly Asp Ile Tyr Val Thr Leu Lys Asn Asn Leu Thr Leu
145                 150                 155                 160

Phe Ser Gly Thr Ile Lys Thr Thr Ala Phe Gln Lys Ile Ile Val Phe
                165                 170                 175

Asp Ile Ile Tyr Leu Val Pro Phe Leu Val Ser Leu Ala Ser Leu Leu
            180                 185                 190

Leu Leu Phe Leu Ser Leu Val Lys His Ser Arg Ser Leu Asp Leu Ile
        195                 200                 205

Ser Thr Thr Ser Glu Asp Ser Arg Thr Lys Ile His Lys Lys Ala Met
    210                 215                 220

Lys Met Leu Val Ser Phe Leu Ile Leu Phe Ile Ile His Ile Phe Phe
225                 230                 235                 240

Met Gln Leu Ala Arg Trp Leu Leu Phe Leu Phe Pro Met Ser Arg Pro
                245                 250                 255

Ile Asn Phe Ile Leu Thr Leu Asn Ile Phe Ala Leu Thr His Ser Phe
            260                 265                 270

-continued

```
Ile Leu Ile Leu Gly Asn Ser Asn Leu Arg Gln Arg Ala Met Arg Ile
        275                 280                 285

Leu Gln His Leu Lys Ser Gln Leu Gln Glu Leu Ile Leu Ser Leu His
    290                 295                 300

Arg Phe Ser Ser Leu Tyr
305                 310


<210> SEQ ID NO 165
<211> LENGTH: 4675
<212> TYPE: DNA
<213> ORGANISM: Mus musculus
<220> FEATURE:
<221> NAME/KEY: modified_base
<222> LOCATION: (612)..(612)
<223> OTHER INFORMATION: n is a, c, g, or t
<220> FEATURE:
<221> NAME/KEY: modified_base
<222> LOCATION: (624)..(624)
<223> OTHER INFORMATION: n is a, c, g, or t
<220> FEATURE:
<221> NAME/KEY: modified_base
<222> LOCATION: (3277)..(3277)
<223> OTHER INFORMATION: n is a, c, g, or t

<400> SEQUENCE: 165

ctgcagcttt ctagaaatct caccagaatg tctttgtgca gctttaatag ttcctggtta     60

taccttgtca cattataagc taagacatct ttggtgccac aatatactct cactaatcag    120

agagattaga cagaaaaata agtttcttaa caactgtttt agatagggtc atgaaatgac    180

ataaaacacc aatgctaagg caatccatta tgtttctca tgaggagccc atatgtacac    240

ttgagtgtgt cttattattt ccctgagtga ttttgtaatt ttattaaaca cttaactgtg    300

attcatacta gttagttctg aaattctttt cttcatcaaa gccattaatc ctggggtttt    360

ttaaatggag aaccccaaaa caaagtgaaa tgttgtgtgt ggagcaggct gtcttcccac    420

acactaccat gagatgctca ttctgtaatt gttccccgga ataggaaatg ccctgaattc    480

aggcacacaa gagctagtct gtgcaccatg tctggttctt gcattaatac ccacttttgt    540

cacgaagctt cattgattcg catcttcaga agctggtatc attattagtt tctttcctca    600

ggtgactctg gnccaaaata ttanggcgcc ctttaaaaaa gtaaaactac aaaatttctt    660

tataattttc tttaagtttg ttataatata gcatgaccta cacacacaca cacacacaca    720

cacacacaca cacacacaca agtatgcctc tcctttcctt ctaaaaatct cacttaaagc    780

aattgtttag ctgtcttcga agtctagact gccactgtcg tgcttctagc caaaacaaat    840

gcaacacata aaatgataga gctcaaaact taggaatcta tttaactgtg aagatcacgc    900

aagcaaacct gagaaacctc tagaaggaaa ccacagcaaa tcactggaga gaaggtgtta    960

atctagtaag aatagttttt attttgggta tccttttgta gattggttag ttcatccaaa   1020

atccaacttg ttagttcttc ataaattgta agtgtctcca acatcaaagc accacttctc   1080

tcttttcccc tgtatgaaga tgctttaagt acagagttac tctttttctg tactgacagt   1140

aatttaaaaa aattgttcac tcattctttt ttggtgttgt tattctgtgt tcctcaatgt   1200

tatctttttt ttttcaaaac tttcttttat aaaaagtcat acacatagca aatgcagtgc   1260

atgtttatgg aatccataac taacttattg agacttctcc tagtactttc tttgaacagt   1320

aacaaagata tctgcttcta cagagtgcag tgtttcaggt gaggaggaac atattataca   1380

aatcagtgaa aaaaaaatct gattcaaatt tgtattttaa tatatttgac tttatcactt   1440

cagatattac atcaatggga attttgaagg cacacaagtg atgatgtggg catagagact   1500
```

-continued

```
gtctgtacta gaatttaata tttcttttaa atatctttaa ataaaaatat gatgctgtat   1560
tcataaacag atctttatag attaagtatg agattaaagt tggaaaaaca aaagacaaaa   1620
acctaggact aagaatttcc ttaagtatgt gtgaatatca acctaatgga ggaagtttcc   1680
aatcaaagct gaaattacag taaaaaggag gaagataaat atggaaaagg atgattttct   1740
gtggaagttt gtttgagaac tgatccacga gacaaattgc tagaagtgtg gattcccttt   1800
tactattcaa ctgcttatag gactggatca aatgtatatg atactggtaa gagcagtatt   1860
tataactgga atgctgggaa atatgttcat tggactggca aactgctctg actgggtcaa   1920
gaaccagaaa atcaccttca tcaacttcat catggtctgt ttggcagctt ccagaatcag   1980
ctctgtgctg atgttattta ttgatgcaac catacaagaa ctagcgcctc atttctatta   2040
ttcttaccgt ctagtaaaat gctctgatat attctgggtt ataactgatc aactatcaac   2100
atggcttgcc acctgcctga gcatattcta cttattcaaa gtagcccaca tttcccatcc   2160
ccttttcctc tggttgaagt ggagattgag aggtgtgctt gttgtttttc ttgtattttc   2220
tttgttctta ttgatttctt attttctact gcttgaaaca cttcctattt ggggagatat   2280
ttatgtaacc cttaaaaaca atctgacctt attttcaggt acaattaaga ccactgcttt   2340
tcaaaagata attgtttttg atataatata tttagtccca tttcttgtgt ccctagcatc   2400
attgctcctt ttatttttgt ccttggtgaa acactcccga agccttgacc tgatttctac   2460
cacttctgaa gattccagaa ccaagattca taagaaggcc atgaaaatgc tggtgtcttt   2520
cctcattctc tttataattc acattttttt catgcagtta gcacggtggt tattattttt   2580
gtttccaatg agcaggccaa ttaatttcat cttaacatta aatatctttg ccttaactca   2640
ctcatttatt ctcatcctgg gaaatagcaa tcttcgacag agagcaatga ggatcctgca   2700
acatcttaaa agccagcttc aagagctgat cctctccctt catagattct ccagtcttta   2760
ctagaggaac agcttaacag ggagacttgg aaggtcactg gcaaattatt cttctttgat   2820
ttcttttaag tactgctgaa catatatgaa ctgtccccag agcatagtgc tatcttatga   2880
gaaggatatc atctcacagt ctggttataa aacacaaacc aatcttttta taatttcttt   2940
acagcattgc taataaaaga cttgtagtct caaatatttt aaagagaata attaatttta   3000
taggcaaaag gtatgaaatt acaattcaca gggaaggttc atgactcctt agatattaaa   3060
gttaattgta agccacaata ggcagaagat gagcaaaatg ttgataggag ataaataaaa   3120
tctaaagtta cggagaaaaa aaacatcaac ttgcctttta gattacttta aagctctctc   3180
tctcgctctc tctctctgta tctacttact ttatatatac aaatgttttg tctgcatgta   3240
tttctttgca ccatataaat gtctaagtat ccagaangtc agcagagggc atcaaattct   3300
ctggaaagag agttacaaat tgctgtgggt aacactgggt gctgggaact aacctgagtc   3360
ctctgccaca gcaactgctc ttccctgctg agtcatgttt taagtctcca caacttaaac   3420
tcattgttga tgtggtcatt gcataatgat gaatttacat tctaaggttt gtatcatagg   3480
taggagggct ggttttaatc atattctaat gttcttatac aaacccaggt tttgtaagag   3540
actgtattct atcatgagac tctttcccca caccgccaat gtaacatttt tattaatttt   3600
gaggggaatt ttatacagtg taccctgatc acccttgctt cccactcctt gcaggtctac   3660
cctcccacca ttgctcaatc ccccctaaaa gagagagaaa caaaccatgt ccaatttgtg   3720
ttggacacat actcagtgga acatggccaa acccctagtg agcagttcct taaagaaaac   3780
taagctgcct ccccaccact accaccatag ggcattaact gtgaagagct acactttagc   3840
```

-continued

```
tattttatca ccaatttaaa agactgtctt caatagcttc ctctatggac tgtttctggt   3900

tttagtggga cagggagaag gggtcaagag gttgtcacag aaacttttga tgtctcttat   3960

tctcagttaa agtccactgc aaaagaagtc tgctggctct aataaagctt gcaacagcat   4020

gggccagtga catcatcatg atttctggca acaatatgga ccacaaatat catggctcag   4080

gtggcattac ggaccacaga catcaacatg gtctctggca gcaagaacca gaatcttttg   4140

aggaggcttc attcagaaaa tgaatttttc ttcatcccag atatactgat gttgctcaat   4200

cagagtatta gtatggttgg gcaccatatt tggggacagg accttcaata tttccaggct   4260

gctgtgtaac acattatctt tagtgtcagg tgcccttagt gtcaggacat gaccatcatg   4320

tatgcgcctg tgggcagaaa tacatctttg tactttctta cacctagcag ggtgagtagc   4380

aggagcagcg gcattaatac ttccatacct ctgggcagcc tatcaggtat catctaggca   4440

aggtaagccc agtagtggcc caaggctcct ggtgtctact tggcaacaac atgctccttt   4500

gtctgcactg ccatatctat ggctggttct ccatccctag ttctgcttct ctcaggtttt   4560

atacgactct attccacatt ctatttttcc agttccatga aaccagtgtt taaaagtatc   4620

atcccataag accggccttt taaaggttat tctggagata ttgcagagtc tgcag        4675


<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence: Synthetic
      T2R Family Consensus Sequence 1
<220> FEATURE:
<221> NAME/KEY: MOD_RES
<222> LOCATION: (2)
<223> OTHER INFORMATION: Phe or Ala
<220> FEATURE:
<221> NAME/KEY: MOD_RES
<222> LOCATION: (3)
<223> OTHER INFORMATION: Ile, Val or Leu
<220> FEATURE:
<221> NAME/KEY: MOD_RES
<222> LOCATION: (4)
<223> OTHER INFORMATION: Val or Leu
<220> FEATURE:
<221> NAME/KEY: MOD_RES
<222> LOCATION: (6)
<223> OTHER INFORMATION: Ile or Val
<220> FEATURE:
<221> NAME/KEY: MOD_RES
<222> LOCATION: (7)
<223> OTHER INFORMATION: Leu or Val
<220> FEATURE:
<221> NAME/KEY: MOD_RES
<222> LOCATION: (10)
<223> OTHER INFORMATION: Gly or Thr
<220> FEATURE:
<221> NAME/KEY: MOD_RES
<222> LOCATION: (13)
<223> OTHER INFORMATION: Val or Ala
<220> FEATURE:
<221> NAME/KEY: MOD_RES
<222> LOCATION: (18)
<223> OTHER INFORMATION: Ile or Met

<400> SEQUENCE: 166

Glu Xaa Xaa Xaa Gly Xaa Xaa Gly Asn Xaa Phe Ile Xaa Leu Val Asn
1               5                   10                  15

Cys Xaa Asp Trp
            20


<210> SEQ ID NO 167
```

-continued

<211> LENGTH: 14
<212> TYPE: PRT
<213> ORGANISM: Artificial Sequence
<220> FEATURE:
<223> OTHER INFORMATION: Description of Artificial Sequence: Synthetic
T2R Family Consensus Sequence 2
<220> FEATURE:
<221> NAME/KEY: MOD_RES
<222> LOCATION: (1)
<223> OTHER INFORMATION: Asp or Gly
<220> FEATURE:
<221> NAME/KEY: MOD_RES
<222> LOCATION: (2)
<223> OTHER INFORMATION: Phe or Leu
<220> FEATURE:
<221> NAME/KEY: MOD_RES
<222> LOCATION: (3)
<223> OTHER INFORMATION: Ile or Leu
<220> FEATURE:
<221> NAME/KEY: MOD_RES
<222> LOCATION: (5)
<223> OTHER INFORMATION: Thr or Ile
<220> FEATURE:
<221> NAME/KEY: MOD_RES
<222> LOCATION: (6)
<223> OTHER INFORMATION: Gly, Ala or Ser
<220> FEATURE:
<221> NAME/KEY: MOD_RES
<222> LOCATION: (13)
<223> OTHER INFORMATION: Cys, Gly or Phe

<400> SEQUENCE: 167

Xaa Xaa Xaa Leu Xaa Xaa Leu Ala Ile Ser Arg Ile Xaa Leu
1               5                   10

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence: Synthetic
T2R Family Consensus Sequence 3
<220> FEATURE:
<221> NAME/KEY: MOD_RES
<222> LOCATION: (3)
<223> OTHER INFORMATION: Leu or Phe
<220> FEATURE:
<221> NAME/KEY: MOD_RES
<222> LOCATION: (4)
<223> OTHER INFORMATION: Ser, Thr or Asn
<220> FEATURE:
<221> NAME/KEY: MOD_RES
<222> LOCATION: (5)
<223> OTHER INFORMATION: Leu, Ile or Val
<220> FEATURE:
<221> NAME/KEY: MOD_RES
<222> LOCATION: (7)
<223> OTHER INFORMATION: Phe or Leu
<220> FEATURE:
<221> NAME/KEY: MOD_RES
<222> LOCATION: (8)
<223> OTHER INFORMATION: Ala or Thr
<220> FEATURE:
<221> NAME/KEY: MOD_RES
<222> LOCATION: (10)
<223> OTHER INFORMATION: Cys, Ser or Asn
<220> FEATURE:
<221> NAME/KEY: MOD_RES
<222> LOCATION: (12)
<223> OTHER INFORMATION: Ser, Asn or Gly
<220> FEATURE:
<221> NAME/KEY: MOD_RES
<222> LOCATION: (13)
<223> OTHER INFORMATION: Ile or Val

<400> SEQUENCE: 168

-continued

```
Asn His Xaa Xaa Xaa Trp Xaa Xaa Thr Xaa Leu Xaa Xaa
1               5                   10


<210> SEQ ID NO 169
<211> LENGTH: 18
<212> TYPE: PRT
<213> ORGANISM: Artificial Sequence
<220> FEATURE:

<223> OTHER INFORMATION: Description of Artificial Sequence: Synthetic
      T2R Family Consensus Sequence 4
<220> FEATURE:
<221> NAME/KEY: MOD_RES
<222> LOCATION: (2)
<223> OTHER INFORMATION: Phe or Cys
<220> FEATURE:
<221> NAME/KEY: MOD_RES
<222> LOCATION: (7)
<223> OTHER INFORMATION: Asn or Ser
<220> FEATURE:
<221> NAME/KEY: MOD_RES
<222> LOCATION: (10)
<223> OTHER INFORMATION: His or Asn
<220> FEATURE:
<221> NAME/KEY: MOD_RES
<222> LOCATION: (11)
<223> OTHER INFORMATION: Pro or Ser
<220> FEATURE:
<221> NAME/KEY: MOD_RES
<222> LOCATION: (12)
<223> OTHER INFORMATION: Leu, Ile or Val
<220> FEATURE:
<221> NAME/KEY: MOD_RES
<222> LOCATION: (15)
<223> OTHER INFORMATION: Trp or Tyr

<400> SEQUENCE: 169

Phe Tyr Xaa Leu Lys Ile Ala Xaa Phe Ser Xaa Xaa Xaa Phe Leu Xaa
1               5                   10                  15

Leu Lys


<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      T2R Family Consensus Sequence 5
<220> FEATURE:
<221> NAME/KEY: MOD_RES
<222> LOCATION: (4)
<223> OTHER INFORMATION: Ile, Phe or Val
<220> FEATURE:
<221> NAME/KEY: MOD_RES
<222> LOCATION: (8)
<223> OTHER INFORMATION: Lys or Arg
<220> FEATURE:
<221> NAME/KEY: MOD_RES
<222> LOCATION: (10)
<223> OTHER INFORMATION: Ser or Thr
<220> FEATURE:
<221> NAME/KEY: MOD_RES
<222> LOCATION: (11)
<223> OTHER INFORMATION: Lys or Arg
<220> FEATURE:
<221> NAME/KEY: MOD_RES
<222> LOCATION: (12)
<223> OTHER INFORMATION: Gln or Lys
<220> FEATURE:
<221> NAME/KEY: MOD_RES
<222> LOCATION: (13)
<223> OTHER INFORMATION: Met or Ile
<220> FEATURE:
<221> NAME/KEY: MOD_RES
<222> LOCATION: (14)
```

-continued

<223> OTHER INFORMATION: Gln or Lys

<400> SEQUENCE: 170

Leu Leu Ile Xaa Ser Leu Trp Xaa His Xaa Xaa Xaa Xaa Xaa
1 5 10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
T2R Family Consensus Sequence 6
<220> FEATURE:
<221> NAME/KEY: MOD_RES
<222> LOCATION: (3)
<223> OTHER INFORMATION: Phe or Leu
<220> FEATURE:
<221> NAME/KEY: MOD_RES
<222> LOCATION: (4)
<223> OTHER INFORMATION: Ile or Val
<220> FEATURE:
<221> NAME/KEY: MOD_RES
<222> LOCATION: (7)
<223> OTHER INFORMATION: Leu or Met
<220> FEATURE:
<221> NAME/KEY: MOD_RES
<222> LOCATION: (8)
<223> OTHER INFORMATION: Gly, Ser or Thr
<220> FEATURE:
<221> NAME/KEY: MOD_RES
<222> LOCATION: (10)
<223> OTHER INFORMATION: Pro, Ser or Asn
<220> FEATURE:
<221> NAME/KEY: MOD_RES
<222> LOCATION: (13)
<223> OTHER INFORMATION: Lys or Arg
<220> FEATURE:
<221> NAME/KEY: MOD_RES
<222> LOCATION: (14)
<223> OTHER INFORMATION: Gln or Arg

<400> SEQUENCE: 171

His Ser Xaa Xaa Leu Ile Xaa Xaa Asn Xaa Lys Leu Xaa Xaa
1 5 10

<210> SEQ ID NO 172
<211> LENGTH: 1002
<212> TYPE: DNA
<213> ORGANISM: Homo sapiens

<400> SEQUENCE: 172
atgttgactc taactcgcat ccgcactgtg tcctatgaag tcaggagtac atttctgttc 60
atttcagtcc tggagtttgc agtggggttt ctgaccaatg ccttcgtttt cttggtgaat 120
ttttgggatg tagtgaagag gcaggcactg agcaacagtg attgtgtgct gctgtgtctc 180
agcatcagcc ggcttttcct gcatggactg ctgttcctga gtgctatcca gcttacccac 240
ttccagaagt tgagtgaacc actgaaccac agctaccaag ccatcatcat gctatggatg 300
attgcaaacc aagccaacct ctggcttgct gcctgcctca gcctgcttta ctgctccaag 360
ctcatccgtt tctctcacac cttcctgatc tgcttggcaa gctgggtctc caggaagatc 420
tcccagatgc tcctgggtat tattctttgc tcctgcatct gcactgtcct ctgtgtttgg 480
tgctttttta gcagacctca cttcacagtc acaactgtgc tattcatgaa taacaataca 540
aggctcaact ggcagattaa agatctcaat ttattttatt cctttctctt ctgctatctg 600
tggtctgtgc ctcctttcct attgtttctg gtttcttctg ggatgctgac tgtctccctg 660

-continued

```
ggaaggcaca tgaggacaat gaaggtctat accagaaact ctcgtgaccc cagcctggag    720

gcccacatta aagccctcaa gtctcttgtc tcctttttct gcttctttgt gatatcatcc    780

tgtgttgcct tcatctctgt gcccctactg attctgtggc gcgacaaaat aggggtgatg    840

gtttgtgttg ggataatggc agcttgtccc tctgggcatg cagccatcct gatctcaggc    900

aatgccaagt tgaggagagc tgtgatgacc attctgctct gggctcagag cagcctgaag    960

gtaagagccg accacaaggc agattcccgg acactgtgct ga                      1002
```

```
<210> SEQ ID NO 173
<211> LENGTH: 333
<212> TYPE: PRT
<213> ORGANISM: Homo sapiens

<400> SEQUENCE: 173

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Ala Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
    130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Thr Val Leu Phe Met
                165                 170                 175

Asn Asn Asn Thr Arg Leu Asn Trp Gln Ile Lys Asp Leu Asn Leu Phe
            180                 185                 190

Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
    210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Val Ala Phe Ile Ser Val Pro Leu Leu Ile Leu
            260                 265                 270

Trp Arg Asp Lys Ile Gly Val Met Val Cys Val Gly Ile Met Ala Ala
        275                 280                 285

Cys Pro Ser Gly His Ala Ala Ile Leu Ile Ser Gly Asn Ala Lys Leu
    290                 295                 300

Arg Arg Ala Val Met Thr Ile Leu Leu Trp Ala Gln Ser Ser Leu Lys
305                 310                 315                 320
```

-continued

```
Val Arg Ala Asp His Lys Ala Asp Ser Arg Thr Leu Cys
                325                 330


<210> SEQ ID NO 174
<211> LENGTH: 966
<212> TYPE: DNA
<213> ORGANISM: Homo sapiens

<400> SEQUENCE: 174

atgactaaac tctgcgatcc tgcagaaagt gaattgtcgc catttctcat caccttaatt     60

ttagcagttt tacttgctga atacctcatt ggtatcattg caaatggttt catcatggct    120

atacatgcag ctgaatgggt tcaaaataag gcagtttcca caagtggcag gatcctggtt    180

ttcctgagtg tatccagaat agctctccaa agcctcatga tgttagaaat taccatcagc    240

tcaacctccc taagttttta ttctgaagac gctgtatatt atgcattcaa aataagtttt    300

atattcttaa atttttgtag cctgtggttt gctgcctggc tcagtttctt ctactttgtg    360

aagattgcca atttctccta ccccctttc ctcaaactga ggtggagaat tactggattg    420

ataccctggc ttctgtggct gtccgtgttt atttccttca gtcacagcat gttctgcatc    480

aacatctgca ctgtgtattg taacaattct ttccctatcc actcctccaa ctccactaag    540

aaaacatact tgtctgagat caatgtggtc ggtctggctt ttttctttaa cctggggatt    600

gtgactcctc tgatcatgtt catcctgaca gccaccctgc tgatcctctc tctcaagaga    660

cacaccctac acatgggaag caatgccaca gggtccaacg accccagcat ggaggctcac    720

atgggggcca tcaaagctat cagctacttt ctcattctct acattttcaa tgcagttgct    780

ctgtttatct acctgtccaa catgtttgac atcaacagtc tgtggaataa tttgtgccag    840

atcatcatgg ctgcctaccc tgccagccac tcaattctac tgattcaaga taaccctggg    900

ctgagaagag cctggaagcg gcttcagctt cgacttcatc tttacccaaa agagtggact    960

ctgtga                                                               966


<210> SEQ ID NO 175
<211> LENGTH: 321
<212> TYPE: PRT
<213> ORGANISM: Homo sapiens

<400> SEQUENCE: 175

Met Thr Lys Leu Cys Asp Pro Ala Glu Ser Glu Leu Ser Pro Phe Leu
1               5                   10                  15

Ile Thr Leu Ile Leu Ala Val Leu Leu Ala Glu Tyr Leu Ile Gly Ile
            20                  25                  30

Ile Ala Asn Gly Phe Ile Met Ala Ile His Ala Ala Glu Trp Val Gln
        35                  40                  45

Asn Lys Ala Val Ser Thr Ser Gly Arg Ile Leu Val Phe Leu Ser Val
    50                  55                  60

Ser Arg Ile Ala Leu Gln Ser Leu Met Met Leu Glu Ile Thr Ile Ser
65                  70                  75                  80

Ser Thr Ser Leu Ser Phe Tyr Ser Glu Asp Ala Val Tyr Tyr Ala Phe
                85                  90                  95

Lys Ile Ser Phe Ile Phe Leu Asn Phe Cys Ser Leu Trp Phe Ala Ala
            100                 105                 110

Trp Leu Ser Phe Phe Tyr Phe Val Lys Ile Ala Asn Phe Ser Tyr Pro
        115                 120                 125

Leu Phe Leu Lys Leu Arg Trp Arg Ile Thr Gly Leu Ile Pro Trp Leu
```

-continued

```
    130                 135                 140

Leu Trp Leu Ser Val Phe Ile Ser Phe Ser His Ser Met Phe Cys Ile
145                 150                 155                 160

Asn Ile Cys Thr Val Tyr Cys Asn Asn Ser Phe Pro Ile His Ser Ser
                165                 170                 175

Asn Ser Thr Lys Lys Thr Tyr Leu Ser Glu Ile Asn Val Val Gly Leu
            180                 185                 190

Ala Phe Phe Phe Asn Leu Gly Ile Val Thr Pro Leu Ile Met Phe Ile
        195                 200                 205

Leu Thr Ala Thr Leu Leu Ile Leu Ser Leu Lys Arg His Thr Leu His
    210                 215                 220

Met Gly Ser Asn Ala Thr Gly Ser Asn Asp Pro Ser Met Glu Ala His
225                 230                 235                 240

Met Gly Ala Ile Lys Ala Ile Ser Tyr Phe Leu Ile Leu Tyr Ile Phe
                245                 250                 255

Asn Ala Val Ala Leu Phe Ile Tyr Leu Ser Asn Met Phe Asp Ile Asn
            260                 265                 270

Ser Leu Trp Asn Asn Leu Cys Gln Ile Ile Met Ala Ala Tyr Pro Ala
        275                 280                 285

Ser His Ser Ile Leu Leu Ile Gln Asp Asn Pro Gly Leu Arg Arg Ala
    290                 295                 300

Trp Lys Arg Leu Gln Leu Arg Leu His Leu Tyr Pro Lys Glu Trp Thr
305                 310                 315                 320

Leu


<210> SEQ ID NO 176
<211> LENGTH: 972
<212> TYPE: DNA
<213> ORGANISM: Homo sapiens

<400> SEQUENCE: 176

atggcaacgg tgaacacaga tgccacagat aaagacatat ccaagttcaa ggtcaccttc      60

actttggtgg tctccggaat agagtgcatc actggcatcc ttgggagtgg cttcatcacg     120

gccatctatg gggctgagtg ggccaggggc aaaacactcc ccactggtga ccgcattatg     180

ttgatgctga gcttttccag gctcttgcta cagatttgga tgatgctgga gaacattttc     240

agtctgctat tccgaattgt ttataaccaa aactcagtgt atatcctctt caaagtcatc     300

actgtctttc tgaaccattc caatctctgg tttgctgcct ggctcaaagt cttctattgt     360

cttagaattg caaacttcaa tcatcctttg ttcttcctga tgaagaggaa aatcatagtg     420

ctgatgcctt ggcttctcag gctgtcagtg ttggtttcct taagcttcag ctttcctctc     480

tcgagagatg tcttcaatgt gtatgtgaat agctccattc ctatcccctc ctccaactcc     540

acggagaaga agtacttctc tgagaccaat atggtcaacc tggtattttt ctataacatg     600

gggatcttcg ttcctctgat catgttcatc ctggcagcca ccctgctgat cctctctctc     660

aagagacaca ccctacacat gggaagcaat gccacagggt ccagggaccc cagcatgaag     720

gctcacatag ggccatcaa agccaccagc tactttctca tcctctacat tttcaatgca     780

attgctctat ttcttttccac gtccaacatc tttgacactt acagttcctg gaatattttg     840

tgcaagatca tcatggctgc ctaccctgcc ggccactcag tacaactgat cttgggcaac     900

cctgggctga gaagagcctg gaagcggttt cagcaccaag ttcctcttta cctaaaaggg     960

cagactctgt ga                                                         972
```

-continued

<210> SEQ ID NO 177
<211> LENGTH: 323
<212> TYPE: PRT
<213> ORGANISM: Homo sapiens

<400> SEQUENCE: 177

```
Met Ala Thr Val Asn Thr Asp Ala Thr Asp Lys Asp Ile Ser Lys Phe
1               5                   10                  15

Lys Val Thr Phe Thr Leu Val Val Ser Gly Ile Glu Cys Ile Thr Gly
            20                  25                  30

Ile Leu Gly Ser Gly Phe Ile Thr Ala Ile Tyr Gly Ala Glu Trp Ala
        35                  40                  45

Arg Gly Lys Thr Leu Pro Thr Gly Asp Arg Ile Met Leu Met Leu Ser
    50                  55                  60

Phe Ser Arg Leu Leu Leu Gln Ile Trp Met Met Leu Glu Asn Ile Phe
65                  70                  75                  80

Ser Leu Leu Phe Arg Ile Val Tyr Asn Gln Asn Ser Val Tyr Ile Leu
                85                  90                  95

Phe Lys Val Ile Thr Val Phe Leu Asn His Ser Asn Leu Trp Phe Ala
            100                 105                 110

Ala Trp Leu Lys Val Phe Tyr Cys Leu Arg Ile Ala Asn Phe Asn His
        115                 120                 125

Pro Leu Phe Phe Leu Met Lys Arg Lys Ile Ile Val Leu Met Pro Trp
    130                 135                 140

Leu Leu Arg Leu Ser Val Leu Val Ser Leu Ser Phe Ser Phe Pro Leu
145                 150                 155                 160

Ser Arg Asp Val Phe Asn Val Tyr Val Asn Ser Ser Ile Pro Ile Pro
                165                 170                 175

Ser Ser Asn Ser Thr Glu Lys Lys Tyr Phe Ser Glu Thr Asn Met Val
            180                 185                 190

Asn Leu Val Phe Phe Tyr Asn Met Gly Ile Phe Val Pro Leu Ile Met
        195                 200                 205

Phe Ile Leu Ala Ala Thr Leu Leu Ile Leu Ser Leu Lys Arg His Thr
    210                 215                 220

Leu His Met Gly Ser Asn Ala Thr Gly Ser Arg Asp Pro Ser Met Lys
225                 230                 235                 240

Ala His Ile Gly Ala Ile Lys Ala Thr Ser Tyr Phe Leu Ile Leu Tyr
                245                 250                 255

Ile Phe Asn Ala Ile Ala Leu Phe Leu Ser Thr Ser Asn Ile Phe Asp
            260                 265                 270

Thr Tyr Ser Ser Trp Asn Ile Leu Cys Lys Ile Ile Met Ala Ala Tyr
        275                 280                 285

Pro Ala Gly His Ser Val Gln Leu Ile Leu Gly Asn Pro Gly Leu Arg
    290                 295                 300

Arg Ala Trp Lys Arg Phe Gln His Gln Val Pro Leu Tyr Leu Lys Gly
305                 310                 315                 320

Gln Thr Leu
```

<210> SEQ ID NO 178
<211> LENGTH: 930
<212> TYPE: DNA
<213> ORGANISM: Homo sapiens

<400> SEQUENCE: 178

```
atgataactt ttctacccat cattttttcc agtctggtag tggttacatt tgttattgga     60
```

-continued

```
aattttgcta atggcttcat agcactggta aattccattg agtggttcaa gagacaaaag    120

atctcctttg ctgaccaaat tctcactgct ctggcggtct ccagagttgg tttgctctgg    180

gtattattat taaactggta ttcaactgtg ttgaatccag cttttaatag tgtagaagta    240

agaactactg cttataatat ctgggcagtg atcaaccatt tcagcaactg gcttgctact    300

accctcagca tattttattt gctcaagatt gccaatttct ccaactttat ttttcttcac    360

ttaaagagga gagttaagag tgtcattctg gtgatgttgt tggggccttt gctatttttg    420

gcttgtcatc tttttgtgat aaacatgaat gagattgtgc ggacaaaaga atttgaagga    480

aacatgactt ggaagatcaa attgaagagt gcaatgtact tttcaaatat gactgtaacc    540

atggtagcaa acttagtacc cttcactctg accctactat cttttatgct gttaatctgt    600

tctttgtgta aacatctcaa gaagatgcag ctccatggta aaggatctca agatcccagc    660

accaaggtcc acataaaagc tttgcaaact gtgatctcct tcctcttgtt atgtgccatt    720

tactttctgt ccataatgat atcagtttgg agttttggaa gtctggaaaa caaacctgtc    780

ttcatgttct gcaaagctat tagattcagc tatccttcaa tccacccatt catcctgatt    840

tggggaaaca agaagctaaa gcagactttt ctttcagttt tttggcaaat gaggtactgg    900

gtgaaaggag agaagacttc atctccatag                                     930
```

<210> SEQ ID NO 179
<211> LENGTH: 309
<212> TYPE: PRT
<213> ORGANISM: Homo sapiens

<400> SEQUENCE: 179

```
Met Ile Thr Phe Leu Pro Ile Ile Phe Ser Ser Leu Val Val Val Thr
1               5                   10                  15

Phe Val Ile Gly Asn Phe Ala Asn Gly Phe Ile Ala Leu Val Asn Ser
            20                  25                  30

Ile Glu Trp Phe Lys Arg Gln Lys Ile Ser Phe Ala Asp Gln Ile Leu
        35                  40                  45

Thr Ala Leu Ala Val Ser Arg Val Gly Leu Leu Trp Val Leu Leu Leu
    50                  55                  60

Asn Trp Tyr Ser Thr Val Leu Asn Pro Ala Phe Asn Ser Val Glu Val
65                  70                  75                  80

Arg Thr Thr Ala Tyr Asn Ile Trp Ala Val Ile Asn His Phe Ser Asn
                85                  90                  95

Trp Leu Ala Thr Thr Leu Ser Ile Phe Tyr Leu Leu Lys Ile Ala Asn
            100                 105                 110

Phe Ser Asn Phe Ile Phe Leu His Leu Lys Arg Arg Val Lys Ser Val
        115                 120                 125

Ile Leu Val Met Leu Leu Gly Pro Leu Leu Phe Leu Ala Cys His Leu
    130                 135                 140

Phe Val Ile Asn Met Asn Glu Ile Val Arg Thr Lys Glu Phe Glu Gly
145                 150                 155                 160

Asn Met Thr Trp Lys Ile Lys Leu Lys Ser Ala Met Tyr Phe Ser Asn
                165                 170                 175

Met Thr Val Thr Met Val Ala Asn Leu Val Pro Phe Thr Leu Thr Leu
            180                 185                 190

Leu Ser Phe Met Leu Leu Ile Cys Ser Leu Cys Lys His Leu Lys Lys
        195                 200                 205

Met Gln Leu His Gly Lys Gly Ser Gln Asp Pro Ser Thr Lys Val His
```

-continued

```
    210                 215                 220

Ile Lys Ala Leu Gln Thr Val Ile Ser Phe Leu Leu Leu Cys Ala Ile
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Phe Trp Gln Met Arg Tyr Trp Val Lys Gly Glu
    290                 295                 300

Lys Thr Ser Ser Pro
305


<210> SEQ ID NO 180
<211> LENGTH: 930
<212> TYPE: DNA
<213> ORGANISM: Homo sapiens

<400> SEQUENCE: 180

atgatgagtt ttctacacat tgtttttttcc attctagtag tggttgcatt tattcttgga      60

aattttgcca atggctttat agcactgata aatttcattg cctgggtcaa gagacaaaag     120

atctcctcag ctgatcaaat tattgctgct ctggcagtct ccagagttgg tttgctctgg     180

gtaatattat tacattggta ttcaactgtg ttgaatccaa cttcatctaa tttaaaagta     240

ataattttta tttctaatgc ctgggcagta accaatcatt tcagcatctg gcttgctact     300

agcctcagca tattttattt gctcaagatc gtcaatttct ccagacttat ttttcatcac     360

ttaaaaagga aggctaagag tgtagttctg gtgatagtgt tggggtcttt gttctttttg     420

gtttgtcacc ttgtgatgaa acacacgtat ataaatgtgt ggacagaaga atgtgaagga     480

aacgtaactt ggaagatcaa actgaggaat gcaatgcacc tttccaactt gactgtagcc     540

atgctagcaa acttgatacc attcactctg accctgatat cttttctgct gttaatctac     600

tctctgtgta aacatctgaa gaagatgcag ctccatggca aaggatctca agatcccagc     660

accaagatcc acataaaagc tctgcaaact gtgacctcct tcctcatatt acttgccatt     720

tactttctgt gtctaatcat atcgttttgg aattttaaga tgcgaccaaa agaaattgtc     780

ttaatgcttt gccaagcttt tggaatcata tatccatcat tccactcatt cattctgatt     840

tgggggaaca agacgctaaa gcagaccttt ctttcagttt tgtggcaggt gacttgctgg     900

gcaaaaggac agaaccagtc aactccatag                                       930


<210> SEQ ID NO 181
<211> LENGTH: 309
<212> TYPE: PRT
<213> ORGANISM: Homo sapiens

<400> SEQUENCE: 181

Met Met Ser Phe Leu His Ile Val Phe Ser Ile Leu Val Val Val Ala
1               5                   10                  15

Phe Ile Leu Gly Asn Phe Ala Asn Gly Phe Ile Ala Leu Ile Asn Phe
            20                  25                  30

Ile Ala Trp Val Lys Arg Gln Lys Ile Ser Ser Ala Asp Gln Ile Ile
        35                  40                  45

Ala Ala Leu Ala Val Ser Arg Val Gly Leu Leu Trp Val Ile Leu Leu
    50                  55                  60
```

-continued

His Trp Tyr Ser Thr Val Leu Asn Pro Thr Ser Ser Asn Leu Lys Val
65 70 75 80

Ile Ile Phe Ile Ser Asn Ala Trp Ala Val Thr Asn His Phe Ser Ile
85 90 95

Trp Leu Ala Thr Ser Leu Ser Ile Phe Tyr Leu Leu Lys Ile Val Asn
100 105 110

Phe Ser Arg Leu Ile Phe His His Leu Lys Arg Lys Ala Lys Ser Val
115 120 125

Val Leu Val Ile Val Leu Gly Ser Leu Phe Phe Leu Val Cys His Leu
130 135 140

Val Met Lys His Thr Tyr Ile Asn Val Trp Thr Glu Glu Cys Glu Gly
145 150 155 160

Asn Val Thr Trp Lys Ile Lys Leu Arg Asn Ala Met His Leu Ser Asn
165 170 175

Leu Thr Val Ala Met Leu Ala Asn Leu Ile Pro Phe Thr Leu Thr Leu
180 185 190

Ile Ser Phe Leu Leu Leu Ile Tyr Ser Leu Cys Lys His Leu Lys Lys
195 200 205

Met Gln Leu His Gly Lys Gly Ser Gln Asp Pro Ser Thr Lys Ile His
210 215 220

Ile Lys Ala Leu Gln Thr Val Thr Ser Phe Leu Ile Leu Leu Ala Ile
225 230 235 240

Tyr Phe Leu Cys Leu Ile Ile Ser Phe Trp Asn Phe Lys Met Arg Pro
245 250 255

Lys Glu Ile Val Leu Met Leu Cys Gln Ala Phe Gly Ile Ile Tyr Pro
260 265 270

Ser Phe His Ser Phe Ile Leu Ile Trp Gly Asn Lys Thr Leu Lys Gln
275 280 285

Thr Phe Leu Ser Val Leu Trp Gln Val Thr Cys Trp Ala Lys Gly Gln
290 295 300

Asn Gln Ser Thr Pro
305

<210> SEQ ID NO 182
<211> LENGTH: 930
<212> TYPE: DNA
<213> ORGANISM: Homo sapiens

<400> SEQUENCE: 182
atgacaactt ttatacccat catttttttcc agtgtggtag tggttctatt tgttattgga 60
aattttgcta atggcttcat agcattggta aattccattg agcgggtcaa gagacaaaag 120
atctcttttg ctgaccagat tctcactgct ctggcggtct ccagagttgg tttgctctgg 180
gtattattat taaattggta ttcaactgtg tttaatccag ctttttatag tgtagaagta 240
agaactactg cttataatgt ctgggcagta accggccatt tcagcaactg gcttgctact 300
agcctcagca tattttattt gctcaagatt gccaatttct ccaaccttat ttttcttcac 360
ttaaagagga gagttaagag tgtcattctg gtgatgctgt tggggccttt actatttttg 420
gcttgtcaac tttttgtgat aaacatgaaa gagattgtac ggacaaaaga atatgaagga 480
aacttgactt ggaagatcaa attgaggagt gcagtgtacc tttcagatgc gactgtaacc 540
acgctaggaa acttagtgcc cttcactctg accctgctat gttttttgct gttaatctgt 600
tctctgtgta aacatctcaa gaagatgcag ctccatggta aaggatctca agatcccagc 660

-continued

```
accaaggtcc acataaaagc tttgcaaact gtgatctttt tcctcttgtt atgtgccgtt    720

tactttctgt ccataatgat atcagtttgg agttttggga gtctggaaaa caaacctgtc    780

ttcatgttct gcaaagctat tagattcagc tatccttcaa tccacccatt catcctgatt    840

tggggaaaca agaagctaaa gcagactttt ctttcagttt tgcggcaagt gaggtactgg    900

gtgaaaggag agaagccttc atctccatag                                     930


<210> SEQ ID NO 183
<211> LENGTH: 309
<212> TYPE: PRT
<213> ORGANISM: Homo sapiens

<400> SEQUENCE: 183

Met Thr Thr Phe Ile Pro Ile Ile Phe Ser Ser Val Val Val Val Leu
1               5                   10                  15

Phe Val Ile Gly Asn Phe Ala Asn Gly Phe Ile Ala Leu Val Asn Ser
            20                  25                  30

Ile Glu Arg Val Lys Arg Gln Lys Ile Ser Phe Ala Asp Gln Ile Leu
        35                  40                  45

Thr Ala Leu Ala Val Ser Arg Val Gly Leu Leu Trp Val Leu Leu Leu
    50                  55                  60

Asn Trp Tyr Ser Thr Val Phe Asn Pro Ala Phe Tyr Ser Val Glu Val
65                  70                  75                  80

Arg Thr Thr Ala Tyr Asn Val Trp Ala Val Thr Gly His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Ile Leu Val Met Leu Leu Gly Pro Leu Leu Phe Leu Ala Cys Gln Leu
    130                 135                 140

Phe Val Ile Asn Met Lys Glu Ile Val Arg Thr Lys Glu Tyr Glu Gly
145                 150                 155                 160

Asn Leu Thr Trp Lys Ile Lys Leu Arg Ser Ala Val Tyr Leu Ser Asp
                165                 170                 175

Ala Thr Val Thr Thr Leu Gly Asn Leu Val Pro Phe Thr Leu Thr Leu
            180                 185                 190

Leu Cys Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Ile Phe Phe Leu Leu Leu Cys Ala Val
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Leu Arg Gln Val Arg Tyr Trp Val Lys Gly Glu
    290                 295                 300

Lys Pro Ser Ser Pro
305
```

<210> SEQ ID NO 184
<211> LENGTH: 900
<212> TYPE: DNA
<213> ORGANISM: Homo sapiens

<400> SEQUENCE: 184

```
atgatgtgtt ttctgctcat catttcatca attctggtag tgtttgcatt tgttcttgga      60
aatgttgcca atggcttcat agccctagta aatgtcattg actgggttaa cacacgaaag     120
atctcctcag ctgagcaaat tctcactgct ctggtggtct ccagaattgg tttactctgg     180
gtcatgttat tcctttggta tgcaactgtg tttaattctg ctttatatgg tttagaagta     240
agaattgttg cttctaatgc ctgggctgta acgaaccatt tcagcatgtg gcttgctgct     300
agcctcagca tattttgttt gctcaagatt gccaatttct ccaaccttat ttctctccac     360
ctaaagaaga gaattaagag tgttgttctg gtgatactgt tggggccctt ggtatttctg     420
atttgtaatc ttgctgtgat aaccatggat gagagagtgt ggacaaaaga atatgaagga     480
aatgtgactt ggaagatcaa attgaggaat gcaatacacc tttcaagctt gactgtaact     540
actctagcaa acctcatacc ctttactctg agcctaatat gttttctgct gttaatctgt     600
tctctttgta aacatctcaa gaagatgcgg ctccatagca aaggatctca agatcccagc     660
accaaggtcc atataaaagc tttgcaaact gtgacctcct tcctcatgtt atttgccatt     720
tactttctgt gtataatcac atcaacttgg aatcttagga cacagcagag caaacttgta     780
ctcctgcttt gccaaactgt tgcaatcatg tatccttcat tccactcatt catcctgatt     840
atgggaagta ggaagctaaa acagaccttt ctttcagttt tgtggcagat gacacgctga     900
```

<210> SEQ ID NO 185
<211> LENGTH: 299
<212> TYPE: PRT
<213> ORGANISM: Homo sapiens

<400> SEQUENCE: 185

```
Met Met Cys Phe Leu Leu Ile Ile Ser Ser Ile Leu Val Val Phe Ala
1               5                   10                  15

Phe Val Leu Gly Asn Val Ala Asn Gly Phe Ile Ala Leu Val Asn Val
            20                  25                  30

Ile Asp Trp Val Asn Thr Arg Lys Ile Ser Ser Ala Glu Gln Ile Leu
        35                  40                  45

Thr Ala Leu Val Val Ser Arg Ile Gly Leu Leu Trp Val Met Leu Phe
    50                  55                  60

Leu Trp Tyr Ala Thr Val Phe Asn Ser Ala Leu Tyr Gly Leu Glu Val
65                  70                  75                  80

Arg Ile Val Ala Ser Asn Ala Trp Ala Val Thr Asn His Phe Ser Met
                85                  90                  95

Trp Leu Ala Ala Ser Leu Ser Ile Phe Cys Leu Leu Lys Ile Ala Asn
            100                 105                 110

Phe Ser Asn Leu Ile Ser Leu His Leu Lys Lys Arg Ile Lys Ser Val
        115                 120                 125

Val Leu Val Ile Leu Leu Gly Pro Leu Val Phe Leu Ile Cys Asn Leu
    130                 135                 140

Ala Val Ile Thr Met Asp Glu Arg Val Trp Thr Lys Glu Tyr Glu Gly
145                 150                 155                 160

Asn Val Thr Trp Lys Ile Lys Leu Arg Asn Ala Ile His Leu Ser Ser
                165                 170                 175

Leu Thr Val Thr Thr Leu Ala Asn Leu Ile Pro Phe Thr Leu Ser Leu
```

-continued

```
            180                 185                 190

Ile Cys Phe Leu Leu Leu Ile Cys Ser Leu Cys Lys His Leu Lys Lys
        195                 200                 205

Met Arg Leu His Ser Lys Gly Ser Gln Asp Pro Ser Thr Lys Val His
    210                 215                 220

Ile Lys Ala Leu Gln Thr Val Thr Ser Phe Leu Met Leu Phe Ala Ile
225                 230                 235                 240

Tyr Phe Leu Cys Ile Ile Thr Ser Thr Trp Asn Leu Arg Thr Gln Gln
                245                 250                 255

Ser Lys Leu Val Leu Leu Leu Cys Gln Thr Val Ala Ile Met Tyr Pro
            260                 265                 270

Ser Phe His Ser Phe Ile Leu Ile Met Gly Ser Arg Lys Leu Lys Gln
        275                 280                 285

Thr Phe Leu Ser Val Leu Trp Gln Met Thr Arg
    290                 295


<210> SEQ ID NO 186
<211> LENGTH: 900
<212> TYPE: DNA
<213> ORGANISM: Homo sapiens

<400> SEQUENCE: 186

atgataactt ttctatacat ttttttttca attctaataa tggttttatt tgttctcgga     60

aactttgcca atggcttcat agcactggta aatttcattg actgggtgaa gagaaaaaag    120

atctcctcag ctgaccaaat tctcactgct ctggcggtct ccagaattgg tttgctctgg    180

gcattattat taaattggta tttaactgtg ttgaatccag ctttttatag tgtagaatta    240

agaattactt cttataatgc ctgggttgta accaaccatt tcagcatgtg gcttgctgct    300

aacctcagca tattttattt gctcaagatt gccaatttct ccaaccttct tttcttcat     360

ttaaagagga gagttaggag tgtcattctg gtgatactgt tggggacttt gatatttttg    420

gtttgtcatc ttcttgtggc aaacatggat gagagtatgt gggcagaaga atatgaagga    480

aacatgactg ggaagatgaa attgaggaat acagtacatc tttcatattt gactgtaact    540

accctatgga gcttcatacc ctttactctg tccctgatat cttttctgat gctaatctgt    600

tctctgtgta aacatctcaa gaagatgcag ctccatggag aaggatcgca agatctcagc    660

accaaggtcc acataaaagc tttgcaaact ctgatctcct tcctcttgtt atgtgccatt    720

ttctttctat tcctaatcgt ttcggtttgg agtcctagga ggctgcggaa tgacccggtt    780

gtcatggtta gcaaggctgt tggaaacata tatcttgcat tcgactcatt catcctaatt    840

tggagaacca agaagctaaa acacaccttt cttttgattt tgtgtcagat taggtgctga    900


<210> SEQ ID NO 187
<211> LENGTH: 299
<212> TYPE: PRT
<213> ORGANISM: Homo sapiens

<400> SEQUENCE: 187

Met Ile Thr Phe Leu Tyr Ile Phe Phe Ser Ile Leu Ile Met Val Leu
1               5                   10                  15

Phe Val Leu Gly Asn Phe Ala Asn Gly Phe Ile Ala Leu Val Asn Phe
            20                  25                  30

Ile Asp Trp Val Lys Arg Lys Lys Ile Ser Ser Ala Asp Gln Ile Leu
        35                  40                  45

Thr Ala Leu Ala Val Ser Arg Ile Gly Leu Leu Trp Ala Leu Leu Leu
```

-continued

```
    50                  55                  60

Asn Trp Tyr Leu Thr Val Leu Asn Pro Ala Phe Tyr Ser Val Glu Leu
65                  70                  75                  80

Arg Ile Thr Ser Tyr Asn Ala Trp Val Val Thr Asn His Phe Ser Met
                85                  90                  95

Trp Leu Ala Ala Asn Leu Ser Ile Phe Tyr Leu Leu Lys Ile Ala Asn
            100                 105                 110

Phe Ser Asn Leu Leu Phe Leu His Leu Lys Arg Arg Val Arg Ser Val
        115                 120                 125

Ile Leu Val Ile Leu Leu Gly Thr Leu Ile Phe Leu Val Cys His Leu
    130                 135                 140

Leu Val Ala Asn Met Asp Glu Ser Met Trp Ala Glu Glu Tyr Glu Gly
145                 150                 155                 160

Asn Met Thr Gly Lys Met Lys Leu Arg Asn Thr Val His Leu Ser Tyr
                165                 170                 175

Leu Thr Val Thr Thr Leu Trp Ser Phe Ile Pro Phe Thr Leu Ser Leu
            180                 185                 190

Ile Ser Phe Leu Met Leu Ile Cys Ser Leu Cys Lys His Leu Lys Lys
        195                 200                 205

Met Gln Leu His Gly Glu Gly Ser Gln Asp Leu Ser Thr Lys Val His
    210                 215                 220

Ile Lys Ala Leu Gln Thr Leu Ile Ser Phe Leu Leu Leu Cys Ala Ile
225                 230                 235                 240

Phe Phe Leu Phe Leu Ile Val Ser Val Trp Ser Pro Arg Arg Leu Arg
                245                 250                 255

Asn Asp Pro Val Val Met Val Ser Lys Ala Val Gly Asn Ile Tyr Leu
            260                 265                 270

Ala Phe Asp Ser Phe Ile Leu Ile Trp Arg Thr Lys Lys Leu Lys His
        275                 280                 285

Thr Phe Leu Leu Ile Leu Cys Gln Ile Arg Cys
    290                 295
```

<210> SEQ ID NO 188
<211> LENGTH: 924
<212> TYPE: DNA
<213> ORGANISM: Homo sapiens

<400> SEQUENCE: 188

```
atgcaagcag cactgacggc cttcttcgtg ttgctcttta gcctgctgag tcttctgggg     60

attgcagcga atggcttcat tgtgctggtg ctgggcaggg agtggctgcg atatggcagg    120

ttgctgccct tggatatgat cctcattagc ttgggtgcct cccgcttctg cctgcagttg    180

gttgggacgg tgcacaactt ctactactct gcccagaagg tcgagtactc tgggggtctc    240

ggccgacagt tcttccatct acactggcac ttcctgaact cagccacctt ctggttttgc    300

agctggctca gtgtcctgtt ctgtgtgaag attgctaaca tcacacactc caccttcctg    360

tggctgaagt ggaggttccc agggtgggtg ccctggctcc tgttgggctc tgtcctgatc    420

tccttcatca taaccctgct gttttttggg gtgaactacc ctgtatatca agaattttta    480

attagaaaat tttctgggaa catgacctac aagtggaata caaggataga aacatactat    540

ttcccatccc tgaaactggt catctggtca attccttttt ctgtttttct ggtctcaatt    600

atgctgttaa ttaattctct gaggaggcat actcagagaa tgcagcacaa cgggcacagc    660

ctgcaggacc ccagcaccca ggctcacacc agagctctga agtccctcat ctccttcctc    720
```

-continued

```
attctttatg ctctgtcctt tctgtccctg atcattgatg ccgcaaaatt tatctccatg    780

cagaacgact tttactggcc atggcaaatt gcagtctacc tgtgcatatc tgtccatccc    840

ttcatcctca tcttcagcaa cctcaagctt cgaagcgtgt tctcgcagct cctgttgttg    900

gcaaggggct tctgggtggc ctag                                            924
```

<210> SEQ ID NO 189
<211> LENGTH: 307
<212> TYPE: PRT
<213> ORGANISM: Homo sapiens

<400> SEQUENCE: 189

```
Met Gln Ala Ala Leu Thr Ala Phe Phe Val Leu Leu Phe Ser Leu Leu
1               5                   10                  15

Ser Leu Leu Gly Ile Ala Ala Asn Gly Phe Ile Val Leu Val Leu Gly
            20                  25                  30

Arg Glu Trp Leu Arg Tyr Gly Arg Leu Leu Pro Leu Asp Met Ile Leu
        35                  40                  45

Ile Ser Leu Gly Ala Ser Arg Phe Cys Leu Gln Leu Val Gly Thr Val
    50                  55                  60

His Asn Phe Tyr Tyr Ser Ala Gln Lys Val Glu Tyr Ser Gly Gly Leu
65                  70                  75                  80

Gly Arg Gln Phe Phe His Leu His Trp His Phe Leu Asn Ser Ala Thr
                85                  90                  95

Phe Trp Phe Cys Ser Trp Leu Ser Val Leu Phe Cys Val Lys Ile Ala
            100                 105                 110

Asn Ile Thr His Ser Thr Phe Leu Trp Leu Lys Trp Arg Phe Pro Gly
        115                 120                 125

Trp Val Pro Trp Leu Leu Leu Gly Ser Val Leu Ile Ser Phe Ile Ile
    130                 135                 140

Thr Leu Leu Phe Phe Trp Val Asn Tyr Pro Val Tyr Gln Glu Phe Leu
145                 150                 155                 160

Ile Arg Lys Phe Ser Gly Asn Met Thr Tyr Lys Trp Asn Thr Arg Ile
                165                 170                 175

Glu Thr Tyr Tyr Phe Pro Ser Leu Lys Leu Val Ile Trp Ser Ile Pro
            180                 185                 190

Phe Ser Val Phe Leu Val Ser Ile Met Leu Leu Ile Asn Ser Leu Arg
        195                 200                 205

Arg His Thr Gln Arg Met Gln His Asn Gly His Ser Leu Gln Asp Pro
    210                 215                 220

Ser Thr Gln Ala His Thr Arg Ala Leu Lys Ser Leu Ile Ser Phe Leu
225                 230                 235                 240

Ile Leu Tyr Ala Leu Ser Phe Leu Ser Leu Ile Ile Asp Ala Ala Lys
                245                 250                 255

Phe Ile Ser Met Gln Asn Asp Phe Tyr Trp Pro Trp Gln Ile Ala Val
            260                 265                 270

Tyr Leu Cys Ile Ser Val His Pro Phe Ile Leu Ile Phe Ser Asn Leu
        275                 280                 285

Lys Leu Arg Ser Val Phe Ser Gln Leu Leu Leu Leu Ala Arg Gly Phe
    290                 295                 300

Trp Val Ala
305
```

<210> SEQ ID NO 190
<211> LENGTH: 930

-continued

```
<212> TYPE: DNA
<213> ORGANISM: Homo sapiens

<400> SEQUENCE: 190

atgataactt ttctgcccat catttttcc attctaatag tggttacatt tgtgattgga      60

aattttgcta atggcttcat agcattggta aattccattg agtggttcaa gagacaaaag     120

atctcttttg ctgaccaaat tctcactgct ctggcagtct ccagagttgg tttactctgg     180

gtattagtat taaattggta tgcaactgag ttgaatccag cttttaacag tatagaagta     240

agaattactg cttacaatgt ctgggcagta atcaaccatt tcagcaactg gcttgctact     300

agcctcagca tattttattt gctcaagatt gccaatttct ccaaccttat ttttcttcac     360

ttaaagagga gagttaagag tgttgttctg gtgatactat tggggccttt gctatttttg     420

gtttgtcatc tttttgtgat aaacatgaat cagattatat ggacaaaaga atatgaagga     480

aacatgactt ggaagatcaa actgaggagt gcaatgtacc tttcaaatac aacggtaacc     540

atcctagcaa acttagttcc cttcactctg accctgatat cttttctgct gttaatctgt     600

tctctgtgta aacatctcaa aaagatgcag ctccatggca aaggatctca agatcccagc     660

atgaaggtcc acataaaagc tttgcaaact gtgacctcct tcctcttgtt atgtgccatt     720

tactttctgt ccataatcat gtcagtttgg agttttgaga gtctggaaaa caaacctgtc     780

ttcatgttct gccaagctat tgcattcagc tatccttcaa cccacccatt catcctgatt     840

tggggaaaca agaagctaaa gcagactttt ctttcagttt tgtggcatgt gaggtactgg     900

gtgaaaggag agaagccttc atcttcatag                                      930


<210> SEQ ID NO 191
<211> LENGTH: 309
<212> TYPE: PRT
<213> ORGANISM: Homo sapiens

<400> SEQUENCE: 191

Met Ile Thr Phe Leu Pro Ile Ile Phe Ser Ile Leu Ile Val Val Thr
1               5                   10                  15

Phe Val Ile Gly Asn Phe Ala Asn Gly Phe Ile Ala Leu Val Asn Ser
            20                  25                  30

Ile Glu Trp Phe Lys Arg Gln Lys Ile Ser Phe Ala Asp Gln Ile Leu
        35                  40                  45

Thr Ala Leu Ala Val Ser Arg Val Gly Leu Leu Trp Val Leu Val Leu
    50                  55                  60

Asn Trp Tyr Ala Thr Glu Leu Asn Pro Ala Phe Asn Ser Ile Glu Val
65                  70                  75                  80

Arg Ile Thr Ala Tyr Asn Val Trp Ala Val Ile Asn His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Val Leu Val Ile Leu Leu Gly Pro Leu Leu Phe Leu Val Cys His Leu
    130                 135                 140

Phe Val Ile Asn Met Asn Gln Ile Ile Trp Thr Lys Glu Tyr Glu Gly
145                 150                 155                 160

Asn Met Thr Trp Lys Ile Lys Leu Arg Ser Ala Met Tyr Leu Ser Asn
                165                 170                 175

Thr Thr Val Thr Ile Leu Ala Asn Leu Val Pro Phe Thr Leu Thr Leu
```

-continued

```
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Met Lys Val His
    210                 215                 220

Ile Lys Ala Leu Gln Thr Val Thr Ser Phe Leu Leu Ile Cys Ala Ile
225                 230                 235                 240

Tyr Phe Leu Ser Ile Ile Met Ser Val Trp Ser Phe Glu Ser Leu Glu
                245                 250                 255

Asn Lys Pro Val Phe Met Phe Cys Glu Ala Ile Ala Phe Ser Tyr Pro
            260                 265                 270

Ser Thr His Pro Phe Ile Leu Ile Trp Gly Asn Lys Lys Leu Lys Gln
        275                 280                 285

Thr Phe Leu Ser Val Leu Trp His Val Arg Tyr Trp Val Lys Gly Glu
    290                 295                 300

Lys Pro Ser Ser Ser
305
```

<210> SEQ ID NO 192
<211> LENGTH: 930
<212> TYPE: DNA
<213> ORGANISM: Homo sapiens

<400> SEQUENCE: 192

```
atggtatatt ttctgctcat cattttatca attctggtag tgtttgcatt tgttcttgga     60

aatttttcca atggcttcat agctctagta aatgtcattg actgggttaa gacacgaaag    120

atctcctcag ctgaccaaat cctcactgct ctggtggtct ccagaattgg tttactctgg    180

gtcatattat tacattggta tgcaaatgtg tttaattcag ctttatatag ttcagaagta    240

ggagctgttg cttctaatat ctcagcaata atcaaccatt tcagcatctg gcttgctgct    300

agcctcagca tattttattt gctcaagatt gccaatttct ccaaccttat ttttctccac    360

ctaaagaaga gaattaggag tgttgttctg gtgatactgt tgggtccctt ggtatttttg    420

atttgtaatc ttgctgtgat aaccatggat gacagtgtgt ggacaaaaga atatgaagga    480

aatgtgactt ggaagatcaa attgaggaat gcaatacacc tttcaaactt gactgtaagc    540

acactagcaa acctcatacc cttcattctg accctaatat gttttctgct gttaatctgt    600

tctctgcata aacatctcaa gaagatgcag ctccatggca aaggatctca agatctcagc    660

accaaggtcc acataaaagc tttgcaaact gtgatctcct tcctcatgtt atatgccatt    720

tactttctgt atctaatcac attaacctgg aatctttgaa cacagcagaa caaacttgta    780

ttcctgcttt gccaaactct tggaatcatg tatccttcat tccactcatt cttcctgatt    840

atgggaagca ggaaactaaa acagacgttt ctttcagttt tatgtcaggt cacatgctta    900

gtgaaaggac agcaaccctc aactccatag                                     930
```

<210> SEQ ID NO 193
<211> LENGTH: 885
<212> TYPE: DNA
<213> ORGANISM: Homo sapiens

<400> SEQUENCE: 193

```
atgatatgtt ttctgctcat cattttatca attctggtag tgtttgcatt tgttcttgga     60

aatgttgcca atggcttcat agctctagta ggtgtccttg agtgggttaa gacacaaaag    120

atctcatcag ctgaccaaat ttctcactgc tctggtggtg tccagagttg gtttactctg    180
```

-continued

```
ggtcatatta ttacattggt atgcaactgt gtttaatttg gcttcacata gattagaagt    240

aagaattttt ggttctaatg tctcagcaat aaccaagcat ttcagcatct gggtgttact    300

agcctcagca tatttcattt gctcaagact gccaatttct ccaaccttat ttttctccac    360

ctaaagaaaa ggattaagaa tgttggtttg gtgatgctgt tggggccctt ggtatttttc    420

atttgtaatc ttgctctgat aaccacgggt gagagtgtgt ggacaaaaga atatgaagga    480

aatttgtctt ggatgatcaa attgaggaat gcaatacagc tttcaaactt gactgtaacc    540

atgccagcaa acgtcacacc ctgcactctg acactaatat cttttctgct gttaatctat    600

tctccatgta aacatgtcaa gaagatgcag ctccatggca aaggatctca acatctcagc    660

accaaggtgc acataaaagc tttgcaaact gtgatctcct tccttatgtt atttgccatt    720

tactttctgt gtctaatcac atcaacttgg aatcctagga ctcagcagag caaacttgta    780

ttcctgcttt accaaactct tggattcatg tatcttttgt tccactcatt catcctgact    840

atgggaagta ggaagccaaa acagaccttt ctttcagctt tgtga                    885
```

<210> SEQ ID NO 194
<211> LENGTH: 912
<212> TYPE: DNA
<213> ORGANISM: Mus musculus

<400> SEQUENCE: 194

```
atgacctccc ctttcccagc tatttatcac atggtcatca tgacagcaga gtttctcatc     60

gggactacag tgaatggatt ccttatcatt gtgaactgct atgacttgtt caagagccga    120

acgttcctga tcctgcagac cctcttgatg tgcacagggc tgtccagact cggtctgcag    180

ataatgctca tgacccaaag cttcttctct gtgttctttc catactctta tgaggaaaat    240

atttatagtt cagatataat gttcgtctgg atgttcttca gctcgattgg cctctggttt    300

gccacatgtc tctctgtctt ttactgcctc aagatttcag gcttcactcc accctggttt    360

ctttggctga aattcagaat ttcaaagctc atattttggc tgcttctggg cagcttgctg    420

gcctctctgg gcactgcaac tgtgtgcatc gaggtaggtt tccctttaat tgaggatggc    480

tatgtcctga gaaacgcagg actaaatgat agtaatgcca agctagtgag aaataatgac    540

ttgctcctca tcaacctgat cctcctgctt cccctgtctg tgtttgtgat gtgcacctct    600

atgttatttg tttctcttta caagcacatg cactggatgc aaagcgaatc tcacaagctg    660

tcaagtgcca gaaccgaagc tcatataaat gcattaaaga cagtgacaac attcttttgt    720

ttctttgttt cttactttgc tgccttcatg gcaaatatga catttagaat tccatacaga    780

agtcatcagt tcttcgtggt gaaggaaatc atggcagcat atcccgccgg ccactctgtc    840

ataatcgtct tgagtaactc taagttcaaa gacttattca ggagaatgat ctgtctacag    900

aaggaagagt ga                                                         912
```

<210> SEQ ID NO 195
<211> LENGTH: 303
<212> TYPE: PRT
<213> ORGANISM: Mus musculus

<400> SEQUENCE: 195

```
Met Thr Ser Pro Phe Pro Ala Ile Tyr His Met Val Ile Met Thr Ala
1               5                   10                  15

Glu Phe Leu Ile Gly Thr Thr Val Asn Gly Phe Leu Ile Ile Val Asn
            20                  25                  30
```

-continued

```
Cys Tyr Asp Leu Phe Lys Ser Arg Thr Phe Leu Ile Leu Gln Thr Leu
        35                  40                  45

Leu Met Cys Thr Gly Leu Ser Arg Leu Gly Leu Gln Ile Met Leu Met
    50                  55                  60

Thr Gln Ser Phe Phe Ser Val Phe Phe Pro Tyr Ser Tyr Glu Glu Asn
65                  70                  75                  80

Ile Tyr Ser Ser Asp Ile Met Phe Val Trp Met Phe Phe Ser Ser Ile
                85                  90                  95

Gly Leu Trp Phe Ala Thr Cys Leu Ser Val Phe Tyr Cys Leu Lys Ile
            100                 105                 110

Ser Gly Phe Thr Pro Pro Trp Phe Leu Trp Leu Lys Phe Arg Ile Ser
        115                 120                 125

Lys Leu Ile Phe Trp Leu Leu Leu Gly Ser Leu Leu Ala Ser Leu Gly
    130                 135                 140

Thr Ala Thr Val Cys Ile Glu Val Gly Phe Pro Leu Ile Glu Asp Gly
145                 150                 155                 160

Tyr Val Leu Arg Asn Ala Gly Leu Asn Asp Ser Asn Ala Lys Leu Val
                165                 170                 175

Arg Asn Asn Asp Leu Leu Leu Ile Asn Leu Ile Leu Leu Leu Pro Leu
            180                 185                 190

Ser Val Phe Val Met Cys Thr Ser Met Leu Phe Val Ser Leu Tyr Lys
        195                 200                 205

His Met His Trp Met Gln Ser Glu Ser His Leu Lys Ser Ser Ala Arg
    210                 215                 220

Thr Glu Ala His Ile Asn Ala Leu Lys Thr Val Thr Thr Phe Phe Cys
225                 230                 235                 240

Phe Phe Val Ser Tyr Phe Ala Ala Phe Met Ala Asn Met Thr Phe Arg
                245                 250                 255

Ile Pro Tyr Arg Ser His Gln Phe Phe Val Val Lys Glu Ile Met Ala
            260                 265                 270

Ala Tyr Pro Ala Gly His Ser Val Ile Ile Val Leu Ser Asn Ser Lys
        275                 280                 285

Phe Lys Asp Leu Phe Arg Arg Met Ile Cys Leu Gln Lys Glu Glu
    290                 295                 300
```

<210> SEQ ID NO 196
<211> LENGTH: 858
<212> TYPE: PRT
<213> ORGANISM: Mus musculus

<400> SEQUENCE: 196

```
Met Pro Gly Leu Ala Ile Leu Gly Leu Ser Leu Ala Ala Phe Leu Glu
1               5                   10                  15

Leu Gly Met Gly Ser Ser Leu Cys Leu Ser Gln Gln Phe Lys Ala Gln
            20                  25                  30

Gly Asp Tyr Ile Leu Gly Gly Leu Phe Pro Leu Gly Thr Thr Glu Glu
        35                  40                  45

Ala Thr Leu Asn Gln Arg Thr Gln Pro Asn Gly Ile Leu Cys Thr Arg
    50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Pro
            100                 105                 110
```

-continued

```
Ser Leu Met Phe Met Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Asp Tyr Gly Arg Glu Gly Leu Ser
    210                 215                 220

Ile Phe Ser Gly Leu Ala Asn Ser Arg Gly Ile Cys Ile Ala His Glu
225                 230                 235                 240

Gly Leu Val Pro Gln His Asp Thr Ser Gly Gln Gln Leu Gly Lys Val
                245                 250                 255

Val Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
        275                 280                 285

Leu His Asp Leu Ser Pro Lys Val Trp Val Ala Ser Glu Ser Trp Leu
    290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr Arg Leu Ala Leu Ala Ala Asp Pro Thr Phe Cys Ala
            340                 345                 350

Ser Leu Lys Ala Glu Leu Asp Leu Glu Glu Arg Val Met Gly Pro Arg
        355                 360                 365

Cys Ser Gln Cys Asp Tyr Ile Met Leu Gln Asn Leu Ser Ser Gly Leu
    370                 375                 380

Met Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Thr Ser Glu Pro Val Gln Pro Trp Gln
            420                 425                 430

Leu Leu Glu Asn Met Tyr Asn Met Ser Phe Arg Ala Arg Asp Leu Thr
        435                 440                 445

Leu Gln Phe Asp Ala Lys Gly Ser Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln His Ser Lys Met Tyr Trp Pro Gly
                485                 490                 495

Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
        515                 520                 525
```

-continued

```
Cys Lys Ala Gly Ser Tyr Arg Lys His Pro Asp Asp Phe Thr Cys Thr
    530                 535                 540

Pro Cys Gly Lys Asp Gln Trp Ser Pro Glu Lys Ser Thr Thr Cys Leu
545                 550                 555                 560

Pro Arg Arg Pro Lys Phe Leu Ala Trp Gly Glu Pro Ala Val Leu Ser
                565                 570                 575

Leu Leu Leu Leu Leu Cys Leu Val Leu Gly Leu Thr Leu Ala Ala Leu
            580                 585                 590

Gly Leu Phe Val His Tyr Trp Asp Ser Pro Leu Val Gln Ala Ser Gly
        595                 600                 605

Gly Ser Leu Phe Cys Phe Gly Leu Ile Cys Leu Gly Leu Phe Cys Leu
    610                 615                 620

Ser Val Leu Leu Phe Pro Gly Arg Pro Arg Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Ile Phe Val Glu Ser Glu Leu Pro Leu Ser
            660                 665                 670

Trp Ala Asn Trp Leu Cys Ser Tyr Leu Arg Gly Pro Trp Ala Trp Leu
        675                 680                 685

Val Val Leu Leu Ala Thr Leu Val Glu Ala Ala Leu Cys Ala Trp Tyr
    690                 695                 700

Leu Met Ala Phe Pro Pro Glu Val Val Thr Asp Trp Gln Val Leu Pro
705                 710                 715                 720

Thr Glu Val Leu Glu His Cys Arg Met Arg Ser Trp Val Ser Leu Gly
                725                 730                 735

Leu Val His Ile Thr Asn Ala Val Leu Ala Phe Leu Cys Phe Leu Gly
            740                 745                 750

Thr Phe Leu Val Gln Ser Gln Pro Gly Arg Tyr Asn Arg Ala Arg Gly
        755                 760                 765

Leu Thr Phe Ala Met Leu Ala Tyr Phe Ile Ile Trp Val Ser Phe Val
    770                 775                 780

Pro Leu Leu Ala Asn Val Gln Val Ala Tyr Gln Pro Ala Val Gln Met
785                 790                 795                 800

Gly Ala Ile Leu Phe Cys Ala Leu Gly Ile Leu Ala Thr Phe His Leu
                805                 810                 815

Pro Lys Cys Tyr Val Leu Leu Trp Leu Pro Glu Leu Asn Thr Gln Glu
            820                 825                 830

Phe Phe Leu Gly Arg Ser Pro Lys Glu Ala Ser Asp Gly Asn Ser Gly
        835                 840                 845

Ser Ser Glu Ala Thr Arg Gly His Ser Glu
    850                 855
```

<210> SEQ ID NO 197
<211> LENGTH: 841
<212> TYPE: PRT
<213> ORGANISM: Homo sapiens

<400> SEQUENCE: 197

```
Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45
```

-continued

```
Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Leu Gln Lys Phe Gly Trp
        195                 200                 205

Thr Trp Ile Ser Leu Val Gly Ser Ser Asp Asp Tyr Gly Gln Leu Gly
    210                 215                 220

Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
            260                 265                 270

Val Phe Ser Ser Arg Gln Leu Ala Arg Val Phe Phe Glu Ser Val Val
        275                 280                 285

Leu Thr Asn Leu Thr Gly Lys Val Trp Val Ala Ser Glu Ala Trp Ala
    290                 295                 300

Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
            340                 345                 350

His Lys Gly Ser Trp Cys Ser Ser Asn Gln Leu Cys Arg Glu Cys Gln
        355                 360                 365

Ala Phe Met Ala His Thr Met Pro Lys Leu Lys Ala Phe Ser Met Ser
    370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Gly Arg Val
                405                 410                 415

Tyr Pro Trp Gln Leu Leu Glu Gln Ile His Lys Val His Phe Leu Leu
            420                 425                 430

His Lys Asp Thr Val Ala Phe Asn Asp Asn Arg Asp Pro Leu Ser Ser
        435                 440                 445

Tyr Asn Ile Ile Ala Trp Asp Trp Asn Gly Pro Lys Trp Thr Phe Thr
    450                 455                 460
```

-continued

```
Val Leu Gly Ser Ser Thr Trp Ser Pro Val Gln Leu Asn Ile Asn Glu
465                 470                 475                 480

Thr Lys Ile Gln Trp His Gly Lys Asp Asn Gln Val Pro Lys Ser Val
                485                 490                 495

Cys Ser Ser Asp Cys Leu Glu Gly His Gln Arg Val Val Thr Gly Phe
            500                 505                 510

His His Cys Cys Phe Glu Cys Val Pro Cys Gly Ala Gly Thr Phe Leu
        515                 520                 525

Asn Lys Ser Asp Leu Tyr Arg Cys Gln Pro Cys Gly Lys Glu Glu Trp
    530                 535                 540

Ala Pro Glu Gly Ser Gln Thr Cys Phe Pro Arg Thr Val Val Phe Leu
545                 550                 555                 560

Ala Leu Arg Glu His Thr Ser Trp Val Leu Leu Ala Ala Asn Thr Leu
                565                 570                 575

Leu Leu Leu Leu Leu Leu Gly Thr Ala Gly Leu Phe Ala Trp His Leu
            580                 585                 590

Asp Thr Pro Val Val Arg Ser Ala Gly Gly Arg Leu Cys Phe Leu Met
        595                 600                 605

Leu Gly Ser Leu Ala Ala Gly Ser Gly Ser Leu Tyr Gly Phe Phe Gly
    610                 615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
                645                 650                 655

Ile Ile Ile Phe Lys Phe Ser Thr Lys Val Pro Thr Phe Tyr His Ala
            660                 665                 670

Trp Val Gln Asn His Gly Ala Gly Leu Phe Val Met Ile Ser Ser Ala
        675                 680                 685

Ala Gln Leu Leu Ile Cys Leu Thr Trp Leu Val Val Trp Thr Pro Leu
    690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
                725                 730                 735

Leu Leu Ser Ile Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Phe
        755                 760                 765

Asn Phe Val Ser Trp Ile Ala Phe Phe Thr Thr Ala Ser Val Tyr Asp
    770                 775                 780

Gly Lys Tyr Leu Pro Ala Ala Asn Met Met Ala Gly Leu Ser Ser Leu
785                 790                 795                 800

Ser Ser Gly Phe Gly Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
        835                 840
```

<210> SEQ ID NO 198
<211> LENGTH: 839
<212> TYPE: PRT
<213> ORGANISM: Homo sapiens

<400> SEQUENCE: 198

-continued

```
Met Gly Pro Arg Ala Lys Thr Ile Cys Ser Leu Phe Phe Leu Leu Trp
1               5                   10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
    50                  55                  60

Lys Val Ile Gly Tyr Asn Leu Met Gln Ala Met Arg Phe Ala Val Glu
65                  70                  75                  80

Glu Ile Asn Asn Asp Ser Ser Leu Leu Pro Gly Val Leu Leu Gly Tyr
                85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175

Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Pro Leu Ser Arg
            340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415
```

-continued

```
Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Lys Pro Val Gly Ile His Val
            500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
    530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590

Thr Pro Ile Val Arg Ser Ala Gly Gly Pro Met Cys Phe Leu Met Leu
        595                 600                 605

Thr Leu Leu Leu Val Ala Tyr Met Val Val Pro Val Tyr Val Gly Pro
    610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
            660                 665                 670

Val Arg Tyr Gln Gly Pro Tyr Val Ser Met Ala Phe Ile Thr Val Leu
        675                 680                 685

Lys Met Val Ile Val Val Ile Gly Met Leu Ala Thr Gly Leu Ser Pro
    690                 695                 700

Thr Thr Arg Thr Asp Pro Asp Asp Pro Lys Ile Thr Ile Val Ser Cys
705                 710                 715                 720

Asn Pro Asn Tyr Arg Asn Ser Leu Leu Phe Asn Thr Ser Leu Asp Leu
                725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
        755                 760                 765

Tyr Phe Thr Ser Ser Val Ser Leu Cys Thr Phe Met Ser Ala Tyr Ser
    770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
```

-continued

```
        835


<210> SEQ ID NO 199
<211> LENGTH: 852
<212> TYPE: PRT
<213> ORGANISM: Homo sapiens

<400> SEQUENCE: 199

Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
    290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365
```

-continued

```
Arg Cys Pro Gln Cys Asp Cys Ile Thr Leu Gln Asn Val Ser Ala Gly
    370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
        435                 440                 445

Asn Val Asp Met Glu Tyr Asp Leu Lys Leu Trp Val Trp Gln Gly Ser
    450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
        515                 520                 525

Tyr Arg Gln Asn Pro Asp Asp Ile Ala Cys Thr Phe Cys Gly Gln Asp
    530                 535                 540

Glu Trp Ser Pro Glu Arg Ser Thr Arg Cys Phe Arg Arg Arg Ser Arg
545                 550                 555                 560

Phe Leu Ala Trp Gly Glu Pro Ala Val Leu Leu Leu Leu Leu Leu Leu
                565                 570                 575

Ser Leu Ala Leu Gly Leu Val Leu Ala Ala Leu Gly Leu Phe Val His
            580                 585                 590

His Arg Asp Ser Pro Leu Val Gln Ala Ser Gly Gly Pro Leu Ala Cys
        595                 600                 605

Phe Gly Leu Val Cys Leu Gly Leu Val Cys Leu Ser Val Leu Leu Phe
    610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
                645                 650                 655

Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
        675                 680                 685

Met Leu Val Glu Val Ala Leu Cys Thr Trp Tyr Leu Val Ala Phe Pro
    690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
                725                 730                 735

Asn Ala Thr Leu Ala Phe Leu Cys Phe Leu Gly Thr Phe Leu Val Arg
            740                 745                 750

Ser Gln Pro Gly Arg Tyr Asn Arg Ala Arg Gly Leu Thr Phe Ala Met
        755                 760                 765

Leu Ala Tyr Phe Ile Thr Trp Val Ser Phe Val Pro Leu Leu Ala Asn
    770                 775                 780

Val Gln Val Val Leu Arg Pro Ala Val Gln Met Gly Ala Leu Leu Leu
```

-continued

```
785                 790                 795                 800

Cys Val Leu Gly Ile Leu Ala Ala Phe His Leu Pro Arg Cys Tyr Leu
                805                 810                 815

Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
        835                 840                 845

Gly Lys His Glu
    850


<210> SEQ ID NO 200
<211> LENGTH: 2526
<212> TYPE: DNA
<213> ORGANISM: Homo sapiens

<400> SEQUENCE: 200

atgctgctct gcacggctcg cctggtcggc ctgcagcttc tcatttcctg ctgctgggcc      60

tttgcctgcc atagcacgga gtcttctcct gacttcaccc tccccggaga ttacctcctg     120

gcaggcctgt tccctctcca ttctggctgt ctgcaggtga ggcacagacc cgaggtgacc     180

ctgtgtgaca ggtcttgtag cttcaatgag catggctacc acctcttcca ggctatgcgg     240

cttggggttg aggagataaa caactccacg gccctgctgc ccaacatcac cctggggtac     300

cagctgtatg atgtgtgttc tgactctgcc aatgtgtatg ccacgctgag agtgctctcc     360

ctgccagggc aacaccacat agagctccaa ggagaccttc tccactattc ccctacggtg     420

ctggcagtga ttgggcctga cagcaccaac cgtgctgcca ccacagccgc cctgctgagc     480

cctttcctgg tgcccatgat tagctatgcg gccagcagcg agacgctcag cgtgaagcgg     540

cagtatccct ctttcctgcg caccatcccc aatgacaagt accaggtgga gaccatggtg     600

ctgctgctgc agaagttcgg gtggacctgg atctctctgg ttggcagcag tgacgactat     660

gggcagctag ggtgcaggc actggagaac caggccactg gtcaggggat ctgcattgct      720

ttcaaggaca tcatgccctt ctctgcccag gtgggcgatg agaggatgca gtgcctcatg     780

cgccacctgg cccaggccgg ggccaccgtc gtggttgttt tttccagccg gcagttggcc     840

agggtgtttt tcgagtccgt ggtgctgacc aacctgactg gcaaggtgtg ggtcgcctca     900

gaagcctggg ccctctccag gcacatcact ggggtgcccg ggatccagcg cattgggatg     960

gtgctgggcg tggccatcca gaagagggct gtccctggcc tgaaggcgtt tgaagaagcc    1020

tatgcccggg cagacaagaa ggcccctagg ccttgccaca agggctcctg gtgcagcagc    1080

aatcagctct gcagagaatg ccaagctttc atggcacaca cgatgcccaa gctcaaagcc    1140

ttctccatga gttctgccta caacgcatac cgggctgtgt atgcggtggc ccatggcctc    1200

caccagctcc tgggctgtgc ctctggagct tgttccaggg gccgagtcta cccctggcag    1260

cttttggagc agatccacaa ggtgcatttc cttctacaca aggacactgt ggcgtttaat    1320

gacaacagag atcccctcag tagctataac ataattgcct gggactggaa tggacccaag    1380

tggaccttca cggtcctcgg ttcctccaca tggtctccag ttcagctaaa cataaatgag    1440

accaaaatcc agtggcacgg aaaggacaac caggtgccta agtctgtgtg ttccagcgac    1500

tgtcttgaag ggcaccagcg agtggttacg ggtttccatc actgctgctt tgagtgtgtg    1560

ccctgtgggg ctgggacctt cctcaacaag agtgacctct acagatgcca gccttgtggg    1620

aaagaagagt gggcacctga gggaagccag acctgcttcc cgcgcactgt ggtgtttttg    1680

gctttgcgtg agcacacctc ttgggtgctg ctggcagcta acacgctgct gctgctgctg    1740
```

-continued

```
ctgcttggga ctgctggcct gtttgcctgg cacctagaca cccctgtggt gaggtcagca   1800
gggggccgcc tgtgctttct tatgctgggc tccctggcag caggtagtgg cagcctctat   1860
ggcttctttg ggaacccac aaggcctgcg tgcttgctac gccaggccct ctttgccctt   1920
ggtttcacca tcttcctgtc ctgcctgaca gttcgctcat tccaactaat catcatcttc   1980
aagttttcca ccaaggtacc tacattctac cacgcctggg tccaaaacca cggtgctggc   2040
ctgtttgtga tgatcagctc agcggcccag ctgcttatct gtctaacttg gctggtggtg   2100
tggaccccac tgcctgctag ggaataccag cgcttccccc atctggtgat gcttgagtgc   2160
acagagacca actccctggg cttcatactg gccttcctct acaatggcct cctctccatc   2220
agtgcctttg cctgcagcta cctgggtaag gacttgccag agaactacaa cgaggccaaa   2280
tgtgtcacct tcagcctgct cttcaacttc gtgtcctgga tcgccttctt caccacggcc   2340
agcgtctacg acggcaagta cctgcctgcg gccaacatga tggctgggct gagcagcctg   2400
agcagcggct tcggtgggta ttttctgcct aagtgctacg tgatcctctg ccgcccagac   2460
ctcaacagca cagagcactt ccaggcctcc attcaggact acacgaggcg ctgcggctcc   2520
acctga                                                               2526
```

```
<210> SEQ ID NO 201
<211> LENGTH: 2559
<212> TYPE: DNA
<213> ORGANISM: Homo sapiens

<400> SEQUENCE: 201
```

```
atgctgggcc ctgctgtcct gggcctcagc ctctgggctc tcctgcaccc tgggacgggg     60
gccccattgt gcctgtcaca gcaacttagg atgaaggggg actacgtgct ggggggctg    120
ttcccccctgg gcgaggccga ggaggctggc ctccgcagcc ggacacggcc cagcagccct    180
gtgtgcacca ggttctcctc aaacggcctg ctctgggcac tggccatgaa aatggccgtg    240
gaggagatca acaacaagtc ggatctgctg cccgggctgc gcctgggcta cgacctcttt    300
gatacgtgct cggagcctgt ggtggccatg aagcccagcc tcatgttcct ggccaaggca    360
ggcagccgcg acatcgccgc ctactgcaac tacacgcagt accagccccg tgtgctggct    420
gtcatcgggc cccactcgtc agagctcgcc atggtcaccg gcaagttctt cagcttcttc    480
ctcatgcccc aggtcagcta cggtgctagc atggagctgc tgagcgcccg ggagaccttc    540
ccctccttct tccgcaccgt gcccagcgac cgtgtgcagc tgacggccgc cgcggagctg    600
ctgcaggagt tcggctggaa ctgggtggcc gccctgggca gcgacgacga gtacggccgg    660
cagggcctga gcatcttctc ggccctggcc gcggcacgcg gcatctgcat cgcgcacgag    720
ggcctggtgc cgctgccccg tgccgatgac tcgcggctgg ggaaggtgca ggacgtcctg    780
caccaggtga accagagcag cgtgcaggtg gtgctgctgt tcgcctccgt gcacgccgcc    840
cacgccctct tcaactacag catcagcagc aggctctcgc ccaaggtgtg ggtggccagc    900
gaggcctggc tgacctctga cctggtcatg gggctgcccg gcatggccca gatgggcacg    960
gtgcttggct tcctccagag gggtgcccag ctgcacgagt tcccccagta cgtgaagacg   1020
cacctggccc tggccaccga cccggccttc tgctctgccc tgggcgagag ggagcagggt   1080
ctggaggagg acgtggtggg ccagcgctgc ccgcagtgtg actgcatcac gctgcagaac   1140
gtgagcgcag ggctaaatca ccaccagacg ttctctgtct acgcagctgt gtatagcgtg   1200
gcccaggccc tgcacaacac tcttcagtgc aacgcctcag gctgccccgc gcaggacccc   1260
```

-continued

```
gtgaagccct ggcagctcct ggagaacatg tacaacctga ccttccacgt gggcgggctg   1320

ccgctgcggt tcgacagcag cggaaacgtg gacatggagt acgacctgaa gctgtgggtg   1380

tggcagggct cagtgcccag gctccacgac gtgggcaggt tcaacggcag cctcaggaca   1440

gagcgcctga agatccgctg gcacacgtct gacaaccaga agcccgtgtc ccggtgctcg   1500

cggcagtgcc aggagggcca ggtgcgccgg gtcaaggggt tccactcctg ctgctacgac   1560

tgtgtggact gcgaggcggg cagctaccgg caaaacccag acgacatcgc ctgcaccttt   1620

tgtggccagg atgagtggtc cccggagcga agcacacgct gcttccgccg caggtctcgg   1680

ttcctggcat ggggcgagcc ggctgtgctg ctgctgctcc tgctgctgag cctggcgctg   1740

ggccttgtgc tggctgcttt ggggctgttc gttcaccatc gggacagccc actggttcag   1800

gcctcggggg ggcccctggc ctgctttggc ctggtgtgcc tgggcctggt ctgcctcagc   1860

gtcctcctgt tccctggcca gcccagccct gcccgatgcc tggcccagca gcccttgtcc   1920

cacctcccgc tcacgggctg cctgagcaca ctcttcctgc aggcggccga gatcttcgtg   1980

gagtcagaac tgcctctgag ctgggcagac cggctgagtg gctgcctgcg ggggccctgg   2040

gcctggctgg tggtgctgct ggccatgctg gtggaggtcg cactgtgcac ctggtacctg   2100

gtggccttcc cgccggaggt ggtgacggac tggcacatgc tgcccacgga ggcgctggtg   2160

cactgccgca cacgctcctg ggtcagcttc ggcctagcgc acgccaccaa tgccacgctg   2220

gcctttctct gcttcctggg cactttcctg gtgcggagcc agccgggccg ctacaaccgt   2280

gcccgtggcc tcacctttgc catgctggcc tacttcatca cctgggtctc ctttgtgccc   2340

ctcctggcca atgtgcaggt ggtcctcagg cccgccgtgc agatgggcgc cctcctgctc   2400

tgtgtcctgg gcatcctggc tgccttccac ctgcccaggt gttacctgct catgcggcag   2460

ccagggctca acaccccga gttcttcctg ggaggggcc ctggggatgc ccaaggccag   2520

aatgacggga acacaggaaa tcaggggaaa catgagtga                        2559
```

<210> SEQ ID NO 202
<211> LENGTH: 2519
<212> TYPE: DNA
<213> ORGANISM: Homo sapiens

<400> SEQUENCE: 202

```
atggggccca gggcaaagac catctgctcc ctgttcttcc tcctatgggt cctggctgag     60

ccggctgaga actcggactt ctacctgcct ggggattacc tcctgggtgg cctcttctcc    120

ctccatgcca acatgaaggg cattgttcac cttaacttcc tgcaggtgcc catgtgcaag    180

gagtatgaag tgaaggtgat aggctacaac ctcatgcagg ccatgcgctt cgcggtggag    240

gagatcaaca atgacagcag cctgctgcct ggtgtgctgc tgggctatga gatcgtggat    300

gtgtgctaca tctccaacaa tgtccagccg gtgctctact tcctggcaca cgaggacaac    360

ctccttccca tccaagagga ctacagtaac tacatttccc gtgtggtggc tgtcattggc    420

cctgacaact ccgagtctgt catgactgtg gccaacttcc tctccctatt tctccttcca    480

cagatcacct acagcgccat cagcgatgag ctgcgagaca aggtgcgctt cccggctttg    540

ctgcgtacca cacccagcgc cgaccaccac gtcgaggcca tggtgcagct gatgctgcac    600

ttccgctgga actggatcat tgtgctggtg agcagcgaca cctatggccg cgacaatggc    660

agctgcttgg cgagcgcgtg gcccggcgcg acatctgcat cgccttccag gagacgctgc    720

ccacactgca gcccaaccag aacatgacgt cagaggagcg ccagcgcctg gtgaccattg    780

tggacaagct gcagcagagc acagcgcgcg tcgtggtcgt gttctcgccc gacctgaccc    840
```

-continued

```
tgtaccactt cttcaatgag gtgctgcgcc agaacttcac gggcgccgtg tggatcgcct     900
ccgagtcctg ggccatcgac ccggtcctgc acaacctcac ggagctgggc cacttgggca     960
ccttcctggg catcaccatc cagagcgtgc ccatcccggg cttcagtgag ttccgcgagt    1020
ggggcccaca ggctgggccg ccacccctca gcaggaccag ccagagctat acctgcaacc    1080
aggagtgcga caactgcctg aacgccacct tgtccttcaa caccattctc aggctctctg    1140
gggagcgtgt cgtctacagc gtgtactctg cggtctatgc tgtggcccat gccctgcaca    1200
gcctcctcgg ctgtgacaaa agcacctgca ccaagagggt ggtctacccc tggcagctgc    1260
ttgaggagat ctggaaggtc aacttcactc tcctggacca ccaaatcttc ttcgacccgc    1320
aaggggacgt ggctctgcac ttggagattg tccagtggca atgggaccgg agccagaatc    1380
ccttccagag cgtcgcctcc tactaccccc tgcagcgaca gctgaagaac atccaagaca    1440
tctcctggca caccgtcaac aacacgatcc ctatgtccat gtgttccaag aggtgccagt    1500
cagggcaaaa gaagaagcct gtgggcatcc acgtctgctg cttcgagtgc atcgactgcc    1560
ttcccggcac cttcctcaac cacactgaag atgaatatga atgccaggcc tgcccgaata    1620
acgagtggtc ctaccagagt gagacctcct gcttcaagcg gcagctggtc ttcctggaat    1680
ggcatgaggc acccaccatc gctgtggccc tgctggccgc cctgggcttc ctcagcaccc    1740
tggccatcct ggtgatattc tggaggcact tccagacacc catagttcgc tcggctgggg    1800
gccccatgtg cttcctgatg ctgacactgc tgctggtggc atacatggtg gtcccggtgt    1860
acgtggggcc gcccaaggtc tccacctgcc tctgccgcca ggccctcttt cccctctgct    1920
tcacaatttg catctcctgt atcgccgtgc gttctttcca gatcgtctgc gccttcaaga    1980
tggccagccg cttcccacgc gcctacagct actgggtccg ctaccagggg ccctacgtct    2040
ctatggcatt tatcacggta ctcaaaatgg tcattgtggt aattggcatg ctggccacgg    2100
gcctcagtcc caccacccgt actgaccccg atgaccccaa gatcacaatt gtctcctgta    2160
accccaacta ccgcaacagc ctgctgttca acaccagcct ggacctgctg ctctcagtgg    2220
tgggtttcag cttcgcctac atgggcaaag agctgcccac caactacaac gaggccaagt    2280
tcatcaccct cagcatgacc ttctatttca cctcatccgt ctccctctgc accttcatgt    2340
ctgcctacag cggggtgctg gtcaccatcg tggacctctt ggtcactgtg ctcaacctcc    2400
tggccatcag cctgggctac ttcggcccca agtgctacat gatcctcttc tacccggagc    2460
gcaacacgcc cgcctacttc aacagcatga tccagggcta caccatgagg agggactag     2519
```

<210> SEQ ID NO 203
<211> LENGTH: 2577
<212> TYPE: DNA
<213> ORGANISM: Rattus sp.

<400> SEQUENCE: 203

```
atgccgggtt tggctatctt gggcctcagt ctggctgctt tcctggagct tgggatgggg      60
tcctctttgt gtctgtcaca gcaattcaag gcacaagggg actatatatt gggtggacta     120
tttcccctgg gcacaactga ggaggccact ctcaaccaga gaacacagcc caacggcatc     180
ctatgtacca ggttctcgcc ccttggtttg ttcctggcca tggctatgaa gatggctgta     240
gaggagatca acaatggatc tgccttgctc cctgggctgc gactgggcta tgacctgttt     300
gacacatgct cagagccagt ggtcaccatg aagcccagcc tcatgttcat ggccaaggtg     360
ggaagtcaaa gcattgctgc ctactgcaac tacacacagt accaaccccg tgtgctggct     420
```

-continued

```
gtcattggtc cccactcatc agagcttgcc ctcattacag gcaagttctt cagcttcttc    480
ctcatgccac aggtcagcta tagtgccagc atggatcggc taagtgaccg ggaaacattt    540
ccatccttct tccgcacagt gcccagtgac cgggtgcagc tgcaggccgt tgtgacactg    600
ttgcagaatt tcagctggaa ctgggtggct gccttaggta gtgatgatga ctatggccgg    660
gaaggtctga gcatcttttc tggtctggcc aactcacgag gtatctgcat tgcacacgag    720
ggcctggtgc cacaacatga cactagtggc caacaattgg gcaaggtggt ggatgtgcta    780
cgccaagtga accaaagcaa agtacaggtg gtggtgctgt ttgcatctgc ccgtgctgtc    840
tactcccttt ttagctacag catccttcat gacctctcac ccaaggtatg ggtggccagt    900
gagtcctggc tgacctctga cctggtcatg acacttccca atattgcccg tgtgggcact    960
gttcttgggt ttctgcagcg cggtgcccta ctgcctgaat ttcccattta tgtggagact   1020
cgccttgccc tagctgctga cccaacattc tgtgcctccc tgaaagctga gttggatctg   1080
gaggagcgcg tgatggggcc acgctgttca caatgtgact acatcatgct acagaacctg   1140
tcatctgggc tgatgcagaa cctatcagct gggcagttgc accaccaaat atttgcaacc   1200
tatgcagctg tgtacagtgt ggctcaggcc cttcacaaca ccctgcagtg caatgtctca   1260
cattgccaca catcagagcc tgttcaaccc tggcagctcc tggagaacat gtacaatatg   1320
agtttccgtg ctcgagactt gacactgcag tttgatgcca aagggagtgt agacatggaa   1380
tatgacctga agatgtgggt gtggcagagc cctacacctg tactacatac tgtaggcacc   1440
ttcaacggca cccttcagct gcagcactcg aaaatgtatt ggccaggcaa ccaggtgcca   1500
gtctcccagt gctcccggca gtgcaaagat ggccaggtgc gcagagtaaa gggctttcat   1560
tcctgctgct atgactgtgt ggactgcaag gcagggagct accggaagca tccagatgac   1620
ttcacctgta ctccatgtgg caaggatcag tggtccccag aaaaaagcac aacctgctta   1680
cctcgcaggc ccaagtttct ggcttggggg gagccagctg tgctgtcact tctcctgctg   1740
ctttgcctgg tgctgggcct gacactggct gccctggggc tctttgtcca ctactgggac   1800
agccctcttg ttcaggcctc aggtgggtca ctgttctgct ttggcctgat ctgcctaggc   1860
ctcttctgcc tcagtgtcct tctgttccca ggacgaccac gctctgccag ctgccttgcc   1920
caacaaccaa tggctcacct ccctctcaca ggctgcctga gcacactctt cctgcaagca   1980
gccgagatct ttgtggagtc tgagctgcca ctgagttggg caaactggct ctgcagctac   2040
cttcggggcc cctgggcttg gctggtggta ctgctggcca ctcttgtgga ggctgcacta   2100
tgtgcctggt acttgatggc tttccctcca gaggtggtga cagattggca ggtgctgccc   2160
acggaggtac tggaacactg ccgcatgcgt tcctgggtca gcctgggctt ggtgcacatc   2220
accaatgcag tgttagcttt cctctgcttt ctgggcactt tcctggtaca gagccagcct   2280
ggtcgctata accgtgcccg tggcctcacc ttcgccatgc tagcttattt catcatctgg   2340
gtctcttttg tgcccctcct ggctaatgtg caggtggcct accagccagc tgtgcagatg   2400
ggtgctatct tattctgtgc cctgggcatc ctggccacct tccacctgcc caaatgctat   2460
gtacttctgt ggctgccaga gctcaacacc caggagttct tcctgggaag gagccccaag   2520
gaagcatcag atgggaatag tggtagtagt gaggcaactc ggggacacag tgaatga      2577
```

<210> SEQ ID NO 204
<211> LENGTH: 137
<212> TYPE: PRT
<213> ORGANISM: Fugu rubripes

<400> SEQUENCE: 204

-continued

```
Pro Ser Pro Phe Arg Asp Ile Val Ser Tyr Pro Asp Lys Ile Ile Leu
1               5                   10                  15

Gly Cys Phe Met Asn Leu Lys Thr Ser Ser Val Ser Phe Val Leu Leu
            20                  25                  30

Leu Leu Leu Cys Leu Leu Cys Phe Ile Phe Ser Tyr Met Gly Lys Asp
        35                  40                  45

Leu Pro Lys Asn Tyr Asn Glu Ala Lys Ala Ile Thr Phe Cys Leu Leu
    50                  55                  60

Leu Leu Ile Leu Thr Trp Ile Ile Phe Thr Thr Ala Ser Leu Leu Tyr
65                  70                  75                  80

Gln Gly Lys Tyr Ile His Ser Leu Asn Ala Leu Ala Val Leu Ser Ser
                85                  90                  95

Ile Tyr Ser Phe Leu Leu Trp Tyr Phe Leu Pro Lys Cys Tyr Ile Ile
            100                 105                 110

Ile Phe Gln Pro Gln Lys Asn Thr Gln Lys Tyr Phe Gln Gly Leu Ile
        115                 120                 125

Gln Asp Tyr Thr Lys Thr Ile Ser Gln
    130                 135


<210> SEQ ID NO 205
<211> LENGTH: 242
<212> TYPE: PRT
<213> ORGANISM: Tetraodon nigroviridis
<220> FEATURE:
<221> NAME/KEY: MOD_RES
<222> LOCATION: (120)..(121)
<223> OTHER INFORMATION: Variable amino acid

<400> SEQUENCE: 205

Phe Ala Val Asn Tyr Asn Thr Pro Val Val Arg Ser Ala Gly Gly Pro
1               5                   10                  15

Met Cys Phe Leu Ile Leu Gly Cys Leu Ser Leu Cys Ser Ile Ser Val
            20                  25                  30

Phe Phe Tyr Phe Glu Arg Pro Thr Glu Ala Phe Cys Ile Leu Arg Phe
        35                  40                  45

Met Pro Phe Leu Leu Phe Tyr Ala Val Cys Leu Ala Cys Phe Ala Val
    50                  55                  60
Arg Ser Phe Gln Ile Val Ile Ile Phe Lys Ile Ala Ala Lys Phe Pro
65                  70                  75                  80

Arg Val His Ser Trp Trp Met Lys Tyr His Gly Gln Trp Leu Val Ile
                85                  90                  95

Ser Met Thr Phe Val Leu Gln Ala Val Val Ile Val Ile Gly Phe Ser
            100                 105                 110

Ser Asn Pro Pro Leu Pro Tyr Xaa Xaa Phe Val Ser Tyr Pro Asp Lys
        115                 120                 125

Ile Ile Leu Gly Cys Asp Val Asn Leu Asn Met Ala Ser Thr Ser Phe
    130                 135                 140

Phe Leu Leu Leu Leu Leu Cys Ile Leu Cys Phe Thr Phe Ser Tyr Met
145                 150                 155                 160

Gly Lys Asp Leu Pro Lys Asn Tyr Asn Glu Ala Lys Ala Ile Thr Phe
                165                 170                 175

Cys Leu Leu Leu Leu Ile Leu Thr Trp Ile Ile Phe Ala Thr Ala Phe
            180                 185                 190

Met Leu Tyr His Gly Lys Tyr Ile His Thr Leu Asn Ala Leu Ala Val
        195                 200                 205

Leu Ser Ser Ala Tyr Cys Phe Leu Leu Trp Tyr Phe Leu Pro Lys Cys
```

-continued

```
    210                 215                 220

Tyr Ile Ile Ile Phe Gln Pro His Lys Asn Thr Gln Lys Tyr Phe Gln
225                 230                 235                 240

Leu Ser


<210> SEQ ID NO 206
<211> LENGTH: 165
<212> TYPE: PRT
<213> ORGANISM: Fugu rubripes

<400> SEQUENCE: 206

Lys Lys Gln Gly Pro Glu Val Asp Ile Phe Ile Val Ser Val Thr Ile
1               5                   10                  15

Leu Cys Ile Ser Val Leu Gly Val Ala Val Gly Pro Pro Glu Pro Ser
            20                  25                  30

Gln Asp Leu Asp Phe Tyr Met Asp Ser Ile Val Leu Glu Cys Ser Asn
        35                  40                  45

Thr Leu Ser Pro Gly Ser Phe Ile Glu Leu Cys Tyr Val Cys Val Leu
    50                  55                  60

Ser Val Leu Cys Phe Phe Phe Ser Tyr Met Gly Lys Asp Leu Pro Ala
65                  70                  75                  80

Asn Tyr Asn Glu Ala Lys Cys Val Thr Phe Ser Leu Met Val Tyr Met
                85                  90                  95

Ile Ser Trp Ile Ser Phe Phe Thr Val Tyr Leu Ile Ser Arg Gly Pro
            100                 105                 110

Phe Thr Val Ala Ala Tyr Val Cys Ala Thr Leu Val Ser Val Leu Ala
        115                 120                 125

Phe Phe Gly Gly Tyr Phe Leu Pro Lys Ile Tyr Ile Ile Val Leu Lys
    130                 135                 140

Pro Gln Met Asn Thr Thr Ala His Phe Gln Asn Cys Ile Gln Met Tyr
145                 150                 155                 160

Thr Met Ser Lys Gln
                165


<210> SEQ ID NO 207
<211> LENGTH: 236
<212> TYPE: PRT
<213> ORGANISM: Tetraodon nigroviridis
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (15)..(15)
<223> OTHER INFORMATION: Variable amino acid
<220> FEATURE:
<221> NAME/KEY: MOD_RES
<222> LOCATION: (59)..(59)
<223> OTHER INFORMATION: Variable amino acid
<220> FEATURE:
<221> NAME/KEY: MOD_RES
<222> LOCATION: (62)..(62)
<223> OTHER INFORMATION: Variable amino acid
<220> FEATURE:
<221> NAME/KEY: MOD_RES
<222> LOCATION: (76)..(76)
<223> OTHER INFORMATION: Variable amino acid
<220> FEATURE:
<221> NAME/KEY: MOD_RES
<222> LOCATION: (117)..(117)
<223> OTHER INFORMATION: Variable amino acid
<220> FEATURE:
<221> NAME/KEY: MOD_RES
```

-continued

<222> LOCATION: (128)..(128)
<223> OTHER INFORMATION: Variable amino acid
<220> FEATURE:
<221> NAME/KEY: MOD_RES
<222> LOCATION: (136)..(136)
<223> OTHER INFORMATION: Variable amino acid
<220> FEATURE:
<221> NAME/KEY: MOD_RES
<222> LOCATION: (168)..(168)
<223> OTHER INFORMATION: Variable amino acid
<220> FEATURE:
<221> NAME/KEY: MOD_RES
<222> LOCATION: (173)..(173)
<223> OTHER INFORMATION: Variable amino acid
<220> FEATURE:
<221> NAME/KEY: MOD_RES
<222> LOCATION: (175)..(176)
<223> OTHER INFORMATION: Variable amino acid
<220> FEATURE:
<221> NAME/KEY: MOD_RES
<222> LOCATION: (203)..(203)
<223> OTHER INFORMATION: Variable amino acid
<220> FEATURE:
<221> NAME/KEY: MOD_RES
<222> LOCATION: (226)..(226)
<223> OTHER INFORMATION: Variable amino acid

<400> SEQUENCE: 207

```
Ala Pro Lys Ser Ser Gln Arg Xaa Leu Arg Arg Thr Arg Leu Xaa Leu
1               5                   10                  15

Glu Trp Asp His Pro Met Ser Val Ala Leu Leu Phe Phe Leu Val Cys
            20                  25                  30

Cys Leu Leu Met Thr Ser Ser Ser Ala Val Ile Leu Leu Leu Asn Ile
        35                  40                  45

Asn Thr Pro Val Ala Lys Ser Ala Gly Gly Xaa Thr Cys Xaa Leu Lys
    50                  55                  60

Leu Ala Ala Leu Thr Ala Ala Ala Met Ser Ser Xaa Cys His Phe Gly
65                  70                  75                  80

Gln Pro Ser Pro Leu Ala Ser Lys Leu Lys Gln Pro Gln Phe Thr Phe
                85                  90                  95

Ser Phe Thr Val Cys Leu Ala Cys Asn Arg Cys Ala Leu Ala Thr Gly
            100                 105                 110

His Leu His Phe Xaa Ile Arg Val Ala Leu Pro Pro Ala Tyr Asn Xaa
        115                 120                 125

Trp Ala Lys Asn His Gly Pro Xaa Ala Thr Ile Phe Ile Ala Ser Ala
    130                 135                 140

Ala Ile Leu Cys Val Leu Cys Leu Arg Val Ala Val Gly Pro Pro Gln
145                 150                 155                 160

Pro Ser Gln Asx Leu Asx Phe Xaa Thr Asn Ser Ile Xaa Leu Xaa Xaa
                165                 170                 175

Ser Asn Thr Leu Ser Pro Gly Ser Phe Val Glu Leu Cys Asn Val Ser
            180                 185                 190

Leu Leu Ser Ala Val Cys Phe Val Phe Ser Xaa Met Gly Lys Asx Leu
        195                 200                 205

Pro Ala Asn Tyr Asn Glu Ala Lys Cys Val Thr Phe Ser Leu Met Val
    210                 215                 220

Asn Xaa Ile Ser Trp Ile Ser Phe Phe Thr Val Tyr
225                 230                 235
```

<210> SEQ ID NO 208
<211> LENGTH: 7
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 208

Phe Lys Lys Ser Phe Lys Leu
1               5


<210> SEQ ID NO 209
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Arg Arg Leu Ile Glu Asp Ala Glu Tyr Ala Ala Arg Gly
1               5                   10


<210> SEQ ID NO 210
<211> LENGTH: 11
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 210

ggggactttc c                                                            11
```

FUNCTIONAL COUPLING OF T1RS AND T2RS BY GI PROTEINS, AND CELLS-BASED ASSAYS FOR THE IDENTIFICATION OF T1R AND T2R MODULATORS

PRIORITY INFORMATION

This application claims benefit or priority to U.S. Provisional Ser. No. 60/457,318 filed Mar. 26, 2003 and U.S. Ser. No. 60/444,172 filed on Feb. 3, 2003. Both of these applications are incorporated by reference in their entireties herein.

FIELD OF THE INVENTION

The present invention relates to novel methods and materials for the identification of modulators, e.g., enhancers, agonists and antagonists of G protein-coupled receptor (GPCRs) involved in taste, i.e., T1Rs and T2Rs. These modulators may be used as flavor-affecting additives, e.g., in foods, beverages and medicines for human or animal consumption. More specifically, the present invention provides MAP Kinase, cAMP and adenylyl cyclase cell-based assays for the identification of modulators of GPCRs involved in taste modulation, i.e., T2Rs and T1Rs, preferably human T1Rs and T2Rs.

Further, the invention provides cell based assays, e.g., MAP Kinase, cAMP accumulation and adenylyl cyclase cell-based assays that rely on the discovery that G proteins other than gustducin and promiscuous and pernicious, G proteins such as $G\alpha_{15}$, i.e., $G_i$ proteins functionally couple to T1Rs and T2Rs and use $G\alpha i$ to transmit signals to downstream effectors.

BACKGROUND OF THE INVENTION

The family of receptors that transmit signals through the activation of heterotrimeric GTP binding proteins (G proteins) constitutes the largest group of cell surface proteins involved in signal transduction. These receptors participate in a broad range of important biological functions and are implicated in a number of disease states. More than half of all drugs currently available influence GPCRs. These receptors affect the generation of small molecules that act as intracellular mediators or second messengers, and can regulate a highly interconnected network of biochemical routes controlling the activity of several members of the mitogen-activated protein kinase (MAPK) superfamily.

In fact, the activation of members of the mitogen-activated protein kinase (MAPK) family represents one of one of the major mechanisms used by eukaryotic cells to transduce extracellular signals into cellular responses (J. Blenis, *Proc. Natl. Acad. Sci.,* USA 90:5889 (1993) (1); Blumer et al., *TIBS* 19:236 (1994) (2); Cano et al., *TIBS* 20:117 (1995) (3); Seger et al., *FASEB J.* 9:726 (1995) (4); R. J. Davis, *TIBS* 19:470 (1994) (5)). The MAPK superfamily consists of the p42 (ERK2)/p44 (ERK1) MAPKs and the stress-activated protein kinases, c-Jun N-terminal kinase (JNK) and p38 MAPK. (Robinson and Dickenson, Eur. *J. Pharmacol.* 413(2–3):151–61 (2001)(6)).

Mitogen-activated protein kinase (MAPKs) (also called extracellular signal-regulated kinases or ERKs) are rapidly activated in response to ligand binding by both growth factor receptors that function as tyrosine kinases (such as the epidermal growth factor (EGF) receptor) and receptors that are complexed with heterodimeric guanine nucleotide binding proteins (G proteins) such as the thrombin receptor. In addition, receptors like the T cell receptor (TCR) and B cell receptor (BCR) are non-covalently associated with src family tyrosine kinases which activate MAPK pathways. Specific cytokines like tumor necrosis factor (TNFalpha) can also regulate MAPK pathways. The MAPKs appear to integrate multiple intracellular signals transmitted by various second messengers. MAPKs phosphorylate and regulate the activity of enzymes and transcription factors including the EGF receptor, Rsk 90, phospholipase $A_2$, c-Myc, c-Jun and E1K-1/TCF. Although the rapid activation of MAPKs by tyrosine kinase receptors is dependent on Ras, G protein-mediated activation of MAPK also occurs through pathways dependent and independent of Ras.

Particularly, it is known that the activation of MAP/ERK kinase which is induced by GPCRs involves both the G alpha and G beta gamma subunits and further involves a common signaling pathway with receptor-tyrosine-kinases. (Lopez-Ilasaca, *Biochem. Pharmacol.* 56(3): 269–77 (1998) (7)). For example, the G protein beta gamma subunit has been shown to activate Ras, Raf and MAP kinase in HEK293 cells. (Ito et al., *FEBS Lett.* 368(1): 183–7 (1995) (8)).

Additionally of relevance to the present invention, within the last several years, a number of groups including the present assignee Senomyx Inc., have reported the identification and cloning of genes from two GPCR families that are involved in taste modulation and have obtained experimental results that provide a greater understanding of taste biology. These results indicate that bitter, sweet and amino acid taste, also referred as umami taste, is triggered by activation of two types of specific receptors located at the surface of taste receptor cells (TRCs) on the tongue i.e., T2Rs and T1Rs (9–11) (Gilbertson et al., *Corr. Opin. Neurobiol.,* 10(4):519–27 (2000); Margolskee, R F, *J. Biol. Chem.* 277(1):1–4 (2002); Montmayeur et al., *Curr. Opin. Neurobiol.,* 12(4):366–71 (2002)). It is currently believed that at least 26 and 33 genes encode functional receptors (T2Rs) for bitter tasting substances in human and rodent respectively (11–13) (Montmayour et al., *Curr. Opin. Neurobiol.,* 12(4):366–71 (2002); Adler et al., *Cell* 100(6) :693–702 (2000); Matsunami et al., *Nature* 404(6678) :601–4 (2000)). By contrast there are only 3 T1Rs, T1R1, T1R2 and T1R3, which are involved in umami and sweet taste (14–16) (Li et al., *Proc. Natl Acad Sci., USA* 99(7) :4692–6 (2002); Nelson et al., *Nature* (6877):199–202 (2002); Nelson et al., *Cell* 106(3):381–96 (2001)). Structurally, the T1R and T2R receptors possess the hallmark of G protein-coupled receptors (GPCRs), i.e., 7 transmembrane domains flanked by small extracellular and intracellular amino- and carboxyl-termini respectively.

T2Rs which have been cloned from different mammals including rats, mice and humans (12) (Adler et al., *Cell* 100(6): 611–8 (2000)). T2Rs comprise a novel family of human and rodent G protein-coupled receptors that are expressed in subsets of taste receptor cells of the tongue and palate epithelia. These taste receptors are organized in clusters in taste cells and are genetically linked to loci that influence bitter taste. The fact that T2Rs modulate bitter taste has been demonstrated in cell-based assays. For example, mT2R-5, hT2R-4 and mT2R-8 have been shown to be activated by bitter molecules in in vitro gustducin assays, providing experimental proof that T2Rs function as bitter taste receptors. (80) (Chandrasheker et al., *Cell* 100(6): 703 (2000)).

The present assignee has filed a number of patent applications relating to various T2R genes and the corresponding polypeptides and their use in assays, preferably high throughput cell-based assays for identifying compounds that modulate the activity of T2Rs. These Senomyx applications i.e., U.S. Ser. No. 09/825,882, filed on Apr. 5, 2001, U.S. Ser. No. 191,058 filed Jul. 10, 2002 and U.S. Provisional Application Ser. No. 60/398,727, filed on Jul. 29, 2002 all incorporated by reference in their entireties herein. Additionally, the present assignee has exclusively licensed patent applications relating to T2R genes which were filed by the University of California i.e., U.S. Ser. No. 09/393,634, filed on Sep. 10, 1999 (recently allowed) and U.S. Ser. No. 09/510,332, filed Feb. 22, 2000, that describe various mouse, rat and human T2R sequences and the use thereof in assays for identifying molecules that modulate specific T2Rs and which modulate (enhance or block) bitter taste. These applications and the sequences contained therein are also incorporated by reference in their entireties herein.

Further, the present assignee and its exclusive licensor, the University of California, have filed a number of patent applications relating to human and rodent T1R taste receptors. Specifically, Senomyx has filed patent applications Ser. No. 09/897,427, filed on Jul. 3, 2001, U.S. Ser. No. 10/179,373, filed on Jun. 26, 2002, and U.S. Ser. No. 09/799,629, filed on Mar. 7, 2001, all of which and the sequences contained therein are incorporated by reference in their entirety herein. Additionally, the University of California has filed a number of applications exclusively licensed by Senomyx including U.S. Ser. No. 09/361,631, filed Jul. 27, 1999, now U.S. Pat. No. 6,383,778, issued on May 7, 2002 and U.S. Ser. No. 09/361,652, filed on Jul. 27, 1999, which relates to cloned rat, mouse and human T1R1 and T1R2 genes and the use of the genes and corresponding polypeptides to identify T1R modulators. These University of California applications and the sequences contained therein are also incorporated by reference in their entirety herein.

The three T1R gene members T1R1, T1R2 and T1R3 form functional heterodimers that specifically recognize sweeteners and amino acids (14–16) (Li et al., *Proc. Natl Acad Sci., USA* 99(7):4692–6 (2002); Nelson et al., *Nature* (6877):199–202 (2002); Nelson et al., *Cell* 106(3):381–96 (2001)). Functional studies performed in HEK293 cells expressing the promiscuous G protein $G\alpha_{15/16}$, also disclosed therein have shown that the rodent and human T1R2/T1R3 combination recognizes natural and artificial sweeteners (14–16) (Li et al., *Proc. Natl Acad Sci., USA* 99(7):4692–6 (2002); Nelson et al., *Nature* (6877):199–202 (2002); Nelson et al., *Cell* 106(3):381–96 (2001)) while the rodent and human T1R1/T1R3 combination recognizes several L-amino acids and monosodium glutamate (MSG), respectively (14, 15) (Li et al., *Proc. Natl Acad Sci., USA* 99(7):4692–6 (2002); Nelson et al., *Nature* (6877):199–202 (2002)). These results, demonstrate that T1Rs are involved in sweet and umami taste.

Particularly, the co-expression of T1R1 and T1R3 in recombinant host cells results in a hetero-oligomeric taste receptor that responds to umami taste stimuli. Umami taste stimuli include by way of example monosodium glutamate and other molecules that elicit a "savory" taste sensation. By contrast, the co-expression of T1R2 and T1R3 in recombinant host cells results in a hetero-oligomeric sweet taste receptor that responds to both naturally occurring and artificial sweeteners. As with T2Rs, T1R DNAs and the corresponding polypeptides have significant application in cell and other assays, preferably high throughput assays, for identifying molecules that modulate T1R taste receptors; particularly the T1R2/T1R3 receptor (sweet receptor) and the T1R1/T1R3 receptor (umami receptor). T1R modulators can be used as flavor-affecting additives in foods, beverages and medicines.

The patents and patent application referenced above, which are incorporated by reference in their entirety herein, disclose a number of assay methods, including cell-based high throughput screening assays for identifying T1R and T2R agonists and antagonists. However, notwithstanding what is disclosed therein, novel and improved assays for identifying T1R and T2R agonists and antagonists are still needed. In particular other high throughput assays that provide for the rapid and accurate identification of T1R or T2R agonists and antagonists would be beneficial. Also, a greater understanding of what conditions and materials yield functional T1Rs and T2Rs and assays based on this greater understanding would further be beneficial.

OBJECTS OF THE INVENTION

Toward that end, it is an object of the invention to provide a greater understanding of the means by which T1Rs and T2Rs functionally couple to G proteins and their signaling pathways.

More particularly, it is an object of the invention to identify G proteins other than $G\alpha_{15}$ and gustducin ($G_i$ proteins) which functionally couple to GPCRs involved in taste, i.e., T1Rs and T2Rs.

It is specifically an object of the invention to provide assays, preferably cell-based assays which exploit the discovery that T1Rs and T2Rs functionally couple to $G_i$ proteins, e.g., $G\alpha_i$.

Thus, it is an object of the invention to provide cell-based assays for identifying T1R and T2R modulators that use techniques which assay the effect of putative modulator on $G\alpha_i$ signaling pathways.

It is a more specific object of the present invention to provide cell-based assays for identifying T1R and T2R modulators that use techniques which assay the effect of a putative T1R or T2R modulator on at least one of MAPK activity, cAMP accumulation and adenylyl cyclase activity.

More specifically, it is an object of the invention to provide novel cell-based assays for identifying T1R and T2R agonists or antagonists or enhancers that modulate MAPK activation independent of PLC activation.

It is another specific object of the invention to provide cell-based assays for identifying T1R and T2 R modulators that use techniques which assay the effect of said putative modulators on $G\alpha_i$ signaling pathways that affect downstream effectors including but not exclusive to cAMP and MAPK.

It is another specific object of the invention to provide cell-based assays for identifying T1R or T2R modulators comprising:

(i) contacting a eukaryotic cell that stably or transiently expresses at least one T1R or T2R and a G protein that functionally couples therewith, e.g., Gαi with a putative T1R or T2R modulator compound;

(ii) assaying the effect of said putative modulator compound on at least one of MAPK activation, cAMP or adenylyl cyclase activity; and (iii) identifying whether said compound is a T1R or T2R agonist, antagonist or allosteric modulator compound based on whether it modulates the amount of activated MAPK, intracellular levels of cAMP or adenylyl cyclase activity that is expressed by said eukaryotic cell.

It is another specific object of the invention to provide novel cell-based assays for identifying compounds that modulate the effect of a known T1R or T2R activating compound, e.g., a known sweetener, umami or bitter compound comprising:

(i) contacting a eukaryotic cell that stably or transiently expresses at least one T1R or T2R and a G protein that functionally couples preferably thereto, e.g., $G_{\alpha i}$, with a putative T1R or T2R modulator and with a compound that is known to activate at least one T1R or T2R, wherein said compound and said putative agonist or antagonist compound are contacted with the eukaryotic cell separately or in combination;

(ii) assaying whether said putative modulator compounds affect at least one of MAPK activation, intracellular levels of cAMP or adenylyl cyclase activity expressed by said eukaryotic cell;

(iii) identifying whether said compound is a T1R or T2R modulator compound based on whether it results in a detectable change in activated MAPK, cAMP or adenylyl cyclase activity expressed by said eukaryotic cell.

In preferred embodiments of the invention, MAPK activation will be measured using polyclonal or monoclonal antibodies that specifically recognize activated forms of MAPK, e.g., antibodies that specifically bind p42/p44 MAPK or p38 MAPK or will be measured using proximity assays (e.g., AlphaScreen™ from Packard or High Content Screening Systems (e.g., ERK, MAPK Activation HitKit™ from Cellomics).

Also, in preferred embodiments, cAMP levels are measured by immunoassay methods, optionally after cAMP accumulation is induced by the use of a compound such as forskolin.

It is a preferred object of the invention to use the subject cell-based assays, e.g., MAPK, cAMP or adenylyl cyclase assays to identify compounds that themselves elicit sweet taste by activating the T1R2/T1R3 sweet receptor or which modulate (enhance or inhibit (block)) sweet taste elicited by another compound that activates the T1R2/T1R3 sweet receptor such as saccharin, cyclamate, saccharin, D-tryptophan, monellin, xorbitol, xylitol, L-tryptophan, and other known sweeteners.

It is another preferred object of the invention to use the subject cell-based assays, preferably MAPK, cAMP or adenylyl cyclase assays to identify compounds that themselves elicit a bitter taste or which modulate (enhance or inhibit (block)) the bitter taste elicited by another compound that activates the particular T2R, e.g., cycloheximide, denotonium, quinine, lidocaine, etc.

It is another preferred object of the invention to use the subject cell-based preferably MAPK, cAMP or adenylyl cyclase assays to identify compounds that themselves elicit umami taste by activating the T1R1/T1R3 receptor or which modulate (enhance or block) umami taste elicited by another compound that activates the T1R1/T1R3 umami receptor such as a glutamate or another savory amino acid containing compound, optionally in conjunction with inosine monophosphate.

It is another object of the invention to provide T2R or T1R agonists or antagonists identified using the subject cell-based assays that monitor the effects of a compound on $G_{\alpha i}$ mediated signaling pathways, e.g., cAMP, MAPK and adenylyl cyclase assays.

It is still another object of the invention to use said T2R or T1R modulatory compounds as flavor-affecting additives, e.g., in foods, beverages and medicaments for human or animal consumption.

It is yet another object of the invention to produce compositions containing T2R or T1R modulatory compounds identified using the subject cell-based MAPK and cAMP assays.

It is a specific object of the invention to provide assays for identifying modulators of T1R or T2R taste receptors wherein at least one T1R to T2R is stably or transiently expressed in a cell preferably a mammalian cell line such as HEK-293, together with a $G_i$ protein that functionally couples therewith, e.g., $G\alpha_i$, and the modulator is identified based on its effect on $G\alpha_i$ mediated signaling pathways that affect the expression of downstream effectors such as cAMP, MAPK and adenylyl cyclase.

DETAILED DESCRIPTION OF FIGURES

FIG. 1 contains the results of an experiment showing that mT2R5 couples to activation of ERK1/2 MAPK. Panel A contains results of an experiment wherein mT2R5-expressing HEK293 cells were incubated with buffer alone (HBSS), 100 ng/mL EGF, 40 μM cycloheximide, 250 μM quinine, 2 mM denatonium, 2 mM saccharin, 100 mM sucrose, or 5 mM MSG/1 mM IMP in HBSS for 5 minutes at 37° C. Cell lysate proteins were resolved by SDS-PAGE, transferred to nitrocellulose membranes and then blotted using antibodies directed against phosphorylated ERK1/2 MAPK. PTX-treated cells were incubated with 100 ng/mL PTX overnight prior to experiment. Panel B contains an experiment that measured the course of cycloheximide-induced ERK1/2 phosphorylation in mT2R5-expressing cells. Panel C contains an experiment wherein HEK293 cells transiently expressing rT2R9 were treated as described in Panel A. Panel D contains an experiment showing the effect of increasing concentrations of cycloheximide on ERK1/2 activation mT2R5-expressing HEK293 cells were incubated with cycloheximide diluted in HBSS (0.1 to 100 NM) for 5 minutes at 37° C. Cell lysate proteins were analyzed as described in Panel A. Bands (inset) were quantified and data were normalized to maximal stimulation of phospho-ERK1/2 MAPK (at 100 μM cycloheximide). Panel E contains an experiment wherein naive HEK293 cells were treated as described in Panel A. The results in Panels A, D and E are representative of at least 3 independent experiments. The results in Panels B and C are representative of two independent experiments.

Figure 2:
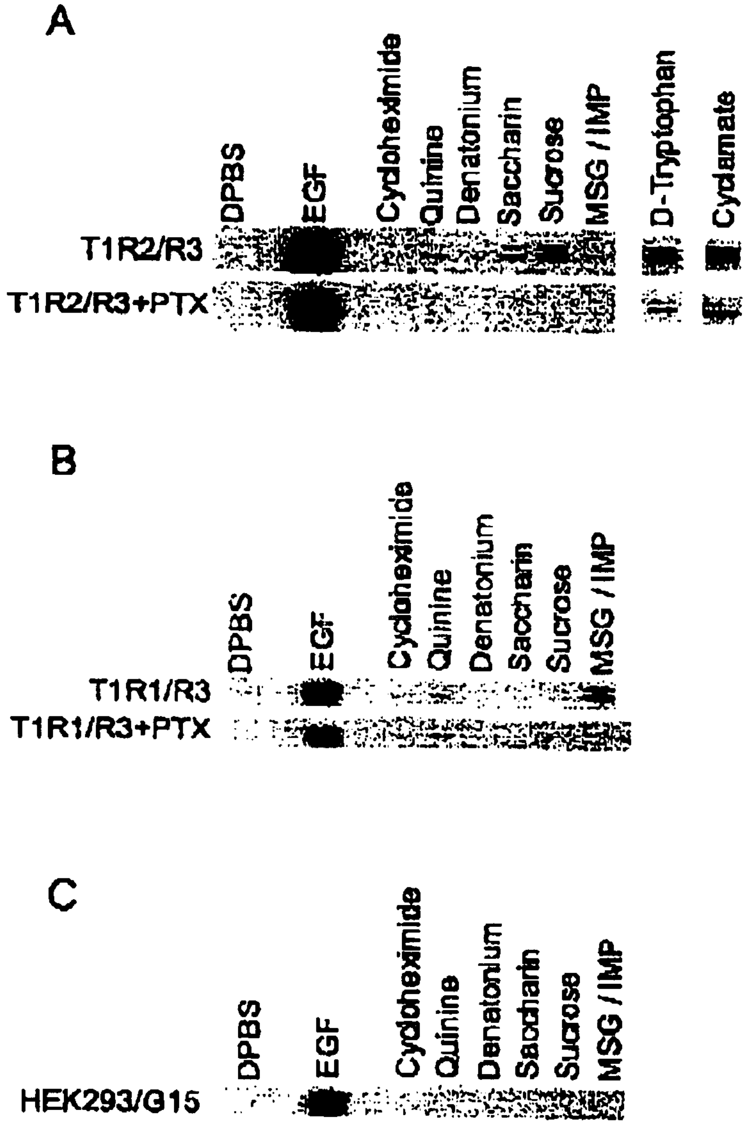

FIG. 2 contains experiments which demonstrate that hT1R2/R3 and hT1R1/R3 couple to activation of ERK1/2 MAPK. Panel A contains an experiment wherein hT1R2/R3-expressing HEK293/G15 cells incubated with buffer alone (D-PBS), 100 ng/mL EGF, 40 μM cycloheximide, 250 μM quinine, 2 mM denatonium, 2 mM saccharin, 100 mM sucrose, 5 mM MSG/7 mM IMP, 4 mM D-tryptophane and 10 mM cyclamate in D-PBS for 5 minutes at 37° C. Cell lysate proteins were resolved by SDS-PAGE, transferred to nitrocellulose membranes and then blotted using antibodies directed against phosphorylated ERK1/2 MAPK. PTX-treated cells were incubated with 100 ng/mL PTX overnight prior to the experiment. Panel B contains an experiment wherein hT1R1/hT1R3-expressing HEK293/G15 cells were treated with mifepristone to induce receptor expression (described infra) 48 hours later, cells were incubated with buffer alone (D-PBS), 100 ng/mL EGF, 40 μM cycloheximide, 250 μM quinine, 2 mM denatonium, 2 mM saccharin, 100 mM sucrose and 5 mM MSG/1 mM IMP in D-PBS for 5 minutes at 37° C. Cell lysate proteins were analyzed as described in Panel A. Panel C contains an experiment wherein naive HEK293/G15 cells were treated as described in Panel B. (Results therein are representative of at least 3 independent experiments).

Figure 3:
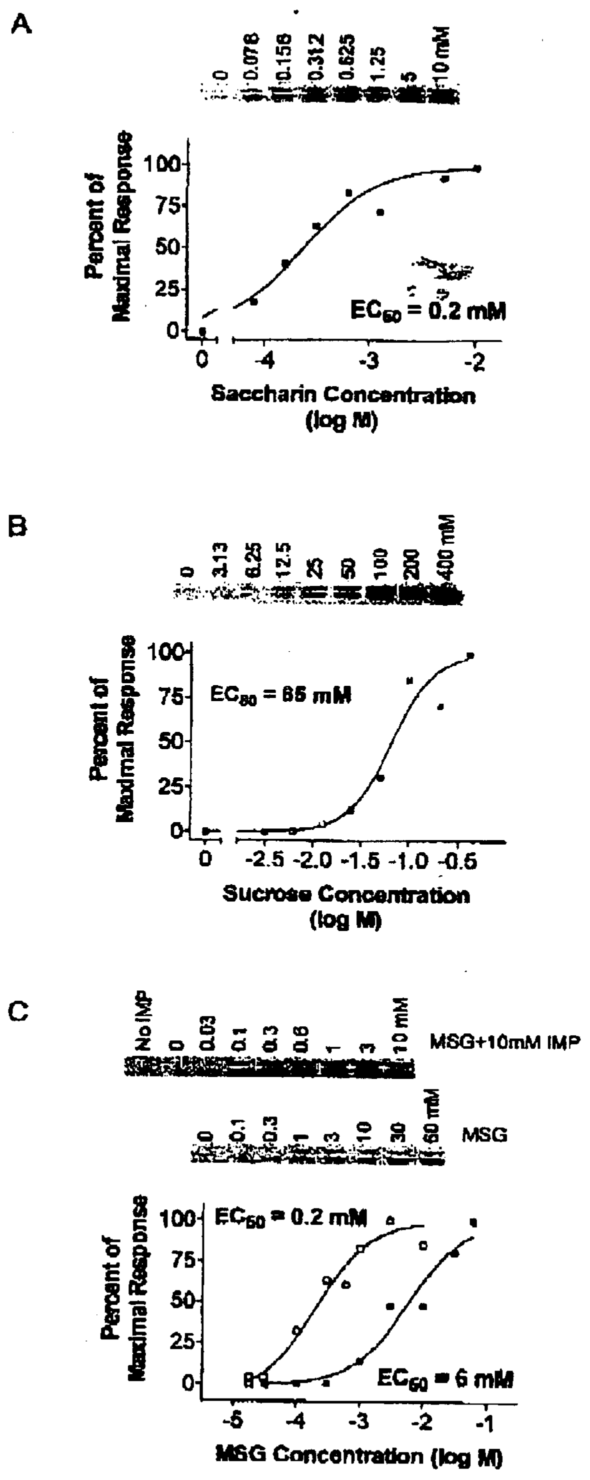

FIG. 3 contains experiments showing the effects of increasing concentrations of sweeteners and MSG on ERK1/2 activation. Panels A and B contain experiments wherein hT1R2/hT1R3-expressing HEK293/$G_{15}$ cells were incubated with increasing concentrations of either saccharin (Panel A) (0.078 to 10 mM) or sucrose (Panel B) (3.13 to 400 mM) for 5 minutes at 37° C. Cell lysate proteins were resolved by SDS-PAGE, transferred to nitrocellulose membranes and then blotted using antibodies directed against phosphorylated ERK1/2 MAPK. Bands (insets) were quantified and data were normalized to maximal stimulation of phospho-ERK1/2 MAPK (at 10 mM and 400 mM saccharin and sucrose respectively). Panel C contains an experiment wherein hT1R1/hT1R3-expressing HEK293/G15 cells were induced for receptor expression as described in the methods section (infra). Cells were then incubated with increasing concentrations of MSG (0.03 to 60 mM) in the absence or presence of 10 mM IMP for 5 minutes at 37° C. Cell lysate proteins were then analyzed as described in A. Bands (inset) were quantified and data were normalized to maximal stimulation of phospho-ERK1/2 MAPK (at 10 mM and 60 mM MSG). These results are representative of at least three independent experiments.

Figure 4:
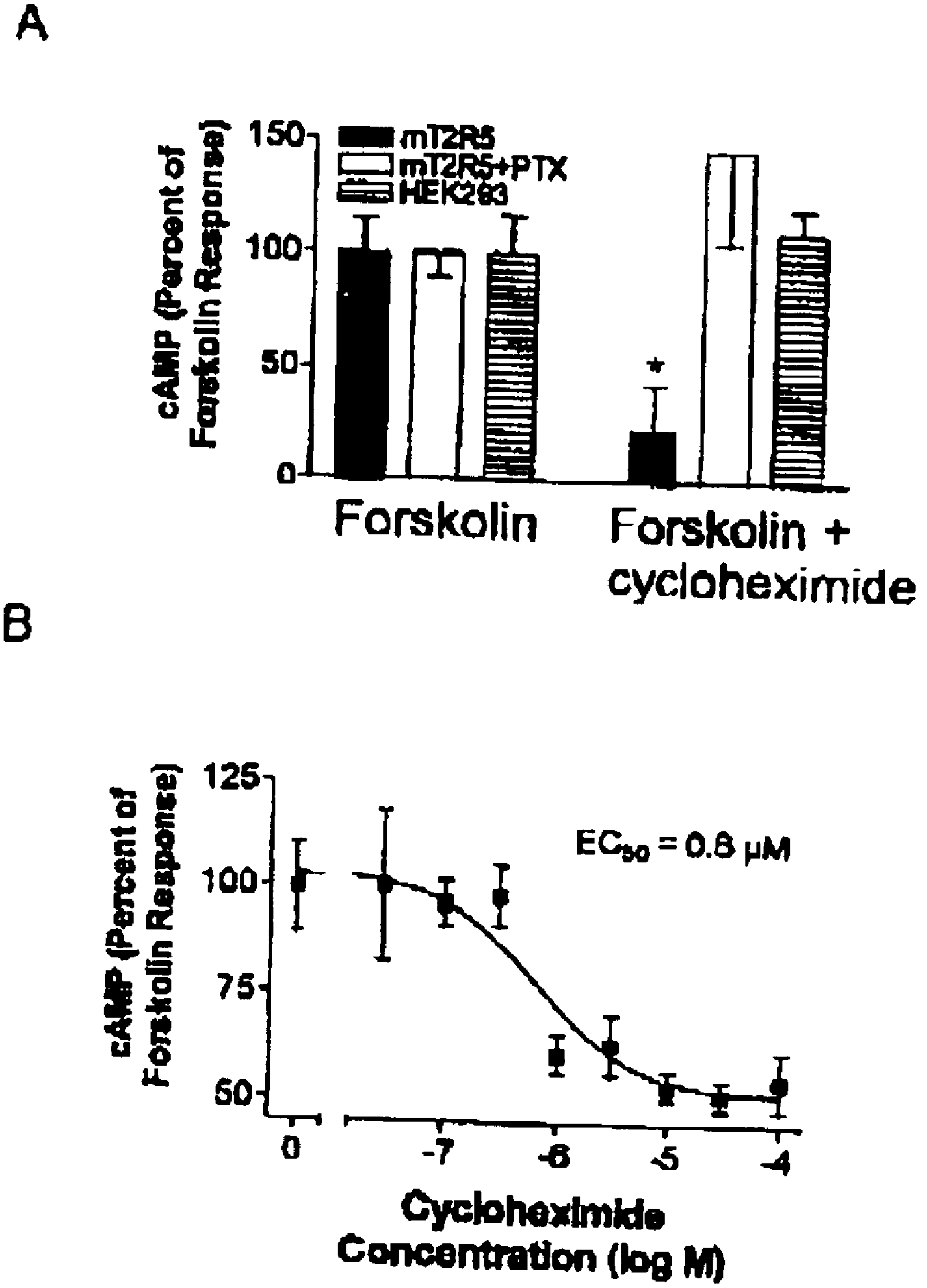

FIG. 4 contains experiments which show that cycloheximide inhibits cAMP accumulation in mT2R5-expressing cells. Panel A contains an experiment wherein mT2R5-expressing HEK293 and naive HEK293 cells were incubated with 0.7 μM forskolin and 50 μM rolipram in the absence and presence of 40 μM cycloheximide in HBSS for 15 minutes at 37° C. cAMP levels were determined as described in the methods section infra. cAMP content of mT2R5-expressing cells stimulated with buffer (0.525% DMSO in HBSS) was 5 pmol/well. cAMP content of mT2R5-expressing cells stimulated with forskolin was 73 pmol/well. Cells were also treated with 100 ng/ml PTX for 4 hours at 37° C. and then stimulated as described above. Under these conditions the cAMP content of mT2R5-expressing cells stimulated with buffer (0.525% DMSO in HBSS) was 4 pmol/well and cAMP content of mT2R5-expressing cells stimulated with forskolin was 80 pmol/well. Panel B contains an experiment comparing the effect of increasing concentrations of cycloheximide on forskolin-induced cAMP accumulation. mT2R5-expressing HEK293 cells were incubated with 0.7 μM forskolin and 50 μM rolipram in the presence of cycloheximide diluted in HBSS (0.03 to 100 μM) for 15 minutes at 37° C. and cAMP levels were determined as described in the methods section infra. Results in Panel A correspond to the mean±SD of three independent experiments performed in quadruplicates. Results in Panel B are representative of three similar experiments. In the figure, * means that the result is significantly different than forskolin response, $p<0.05$.

Figure 5:
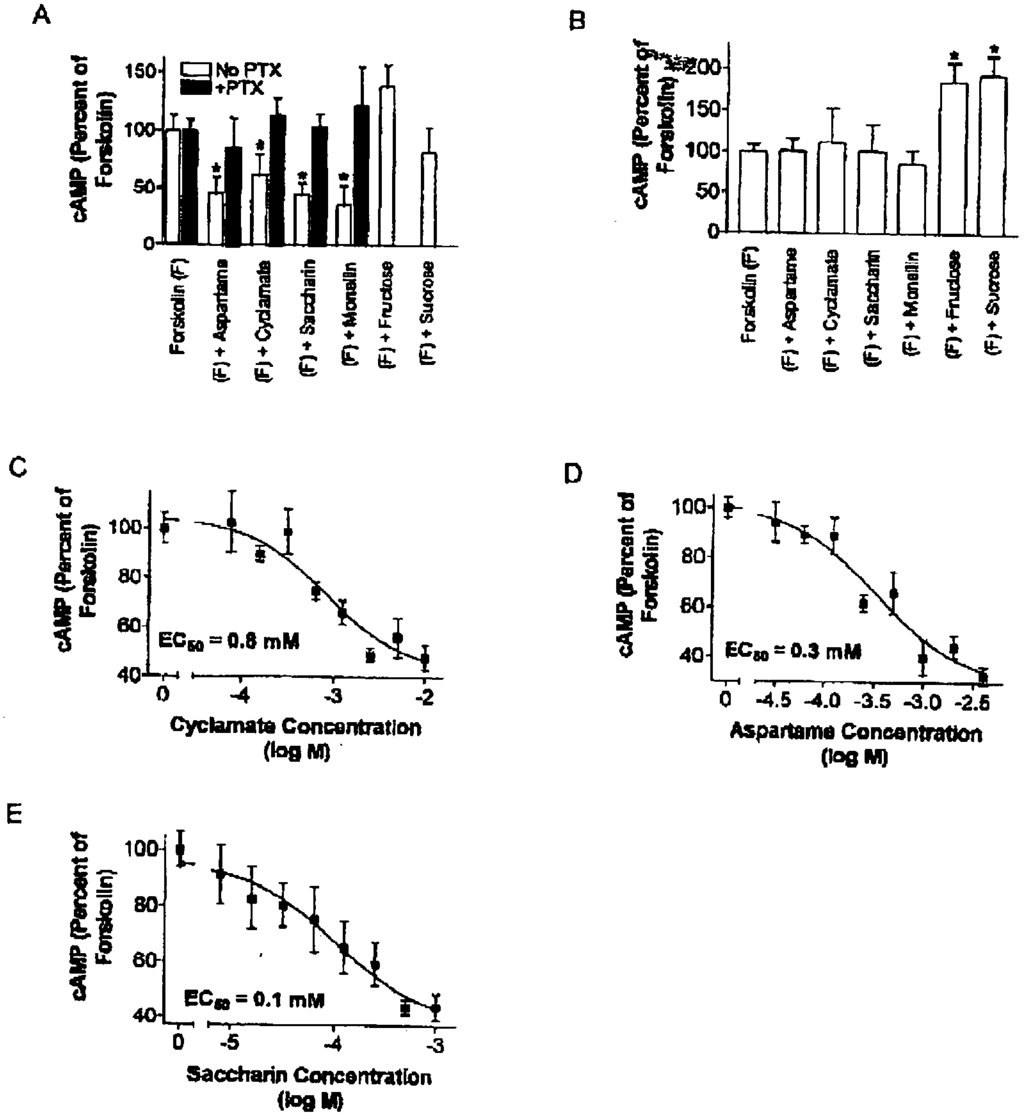

FIG. 5 contains experiments indicating that sweeteners inhibit cAMP accumulation in hT1R2/hT1R3 expressing cells. Panel A contains an experiment wherein hT1R2/hT1R3-expressing HEK293/G15 cells were incubated with 5 μM forskolin and 50 μM rolipram in the absence and presence of either 200 mM fructose, 200 mM sucrose, 1 mM aspartame, 3 mM cyclamate, 2 mM saccharin or 50 μM monellin in D-PBS for 15 minutes at 37° C. and cAMP levels were determined as described in the methods section. cAMP content of cells stimulated with buffer (0.525% DMSO in D-PBS) was 3 pmol/well. cAMP content of mT2R5-expressing cells stimulated with forskolin was 23 pmol/well. Cells were also treated with 100 ng/ml PTX for 4 hours at 37° C. and then stimulated as described above. Under these conditions, the cAMP content of cells stimulated with buffer (0.525% DMSO in D-PBS) was 4 pmol/well and cAMP content of cells stimulated with forskolin was 149 pmol/well. Panel B shows naive HEK293/G15 cells that were treated as in Panel A. Cells stimulated with buffer (0.525% DMSO in D-PBS) was 4 pmol/well and cAMP content of cells stimulated with forskolin was 90 pmol/well. Panel C contains an experiment comparing the effects of increasing concentrations of cyclamate on forskolin-induced cAMP accumulation. Cells were incubated with of 5 μM forskolin and 50 μM rolipram in the absence or presence of increasing concentrations of cyclamate (0.08 to 10 mM). cAMP content of cells stimulated with forskolin alone was 11 pmol/well. Panel D contains an experiment comparing the effects of increasing concentration of aspartame on forskolin-induced cAMP accumulation. Cells were incubated with of 5 μM forskolin and 50 μM rolipram in the absence or presence of increasing concentrations of aspartame (0.03 to 4 mM). cAMP content of cells stimulated with forskolin alone was 14 pmol/well. Panel E contains an experiment comparing the effects of increasing concentration of saccharin on forskolin-induced cAMP accumulation. Cells were incubated with of 5 μM forskolin and 50 μM rolipram in the absence or presence of increasing concentrations of saccharin (0.008 to 1 mM). cAMP content of cells stimulated with forskolin alone was 24 pmol/well. Results in Panels A and B correspond to the mean±SD of three to six independent experiments performed in quadruplicates. Results in Panel C–E are representative of three similar experiments. In the figure, * means that the result was significantly different than the forskolin response, $p<0.05$.

Figure 6:
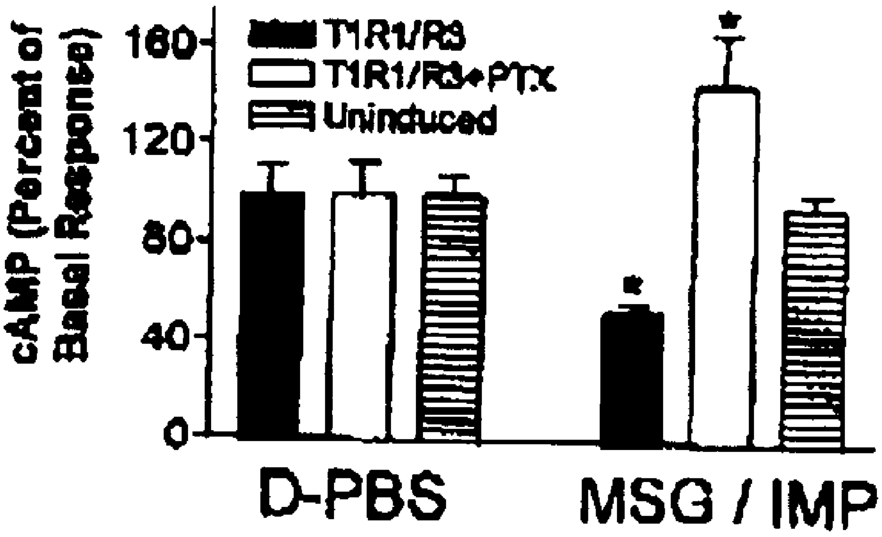

FIG. 6 contains experiments which demonstrate that MSG inhibits cAMP accumulation in hT1R1/hT1R3-expressing cells. hT1R1/hT1R3-expressing HEK293/G15 cells were induced for receptor expression as described in the methods section. (infra) Cells were incubated with 50 μM rolipram in the absence and presence of 3 mM MSG/10 mM IMP in D-PBS for 15 minutes at 37° C. and cAMP levels were determined as described in the methods section. cAMP content of cells in the presence of rolipram was 120 pmol/well. Cells were also treated with 100 ng/ml PTX for 4 hours at 37° C. and then stimulated as described above. Under these conditions cAMP content of hT1R1/hT1R3-expressing cells was 95 pmol/well. Results correspond to the mean±SD of three independent experiments performed in quadruplicates. In the figure, * means that the result was significantly different than the forskolin response, $p<0.05$.

Figure 7:
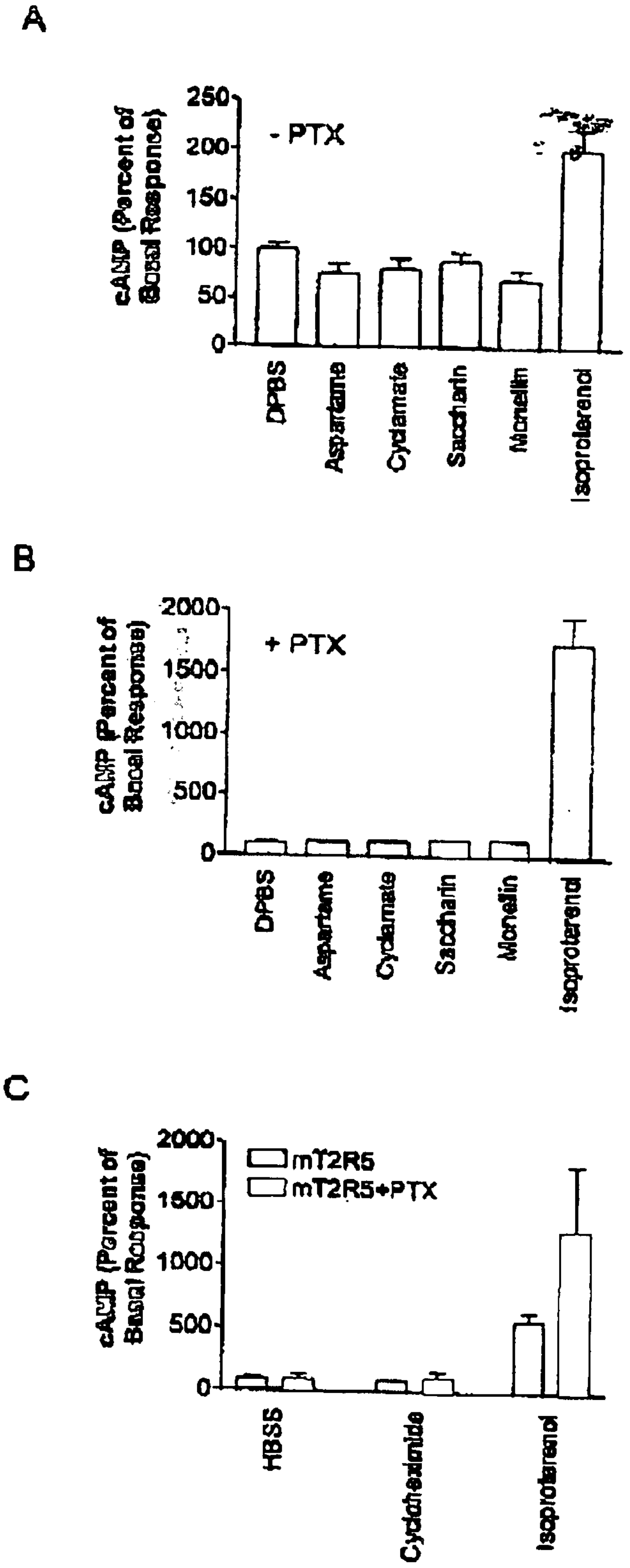

FIG. 7 contains experiments showing the mT2R5 and hT1R2/hT1R3 do not functionally couple to $G_s$. Panel A contains an experiment wherein hT1R2/hT1R3-expressing HEK293/G15 cells were incubated with 50 μM rolipram in the absence and presence of either 1 mM aspartame, 3 mM cyclamate, 2 mM saccharin, 50 μM monellin and 10 μM isoproterenol in D-PBS for 15 minutes at 37° C. and cAMP levels were determined as described in the methods section infra. Under these conditions basal level of cAMP was 2 pmol/well. Panel B contains an experiment wherein hT1R2/hT1R3-expressing cells were treated with 100 ng/ml PTX for 4 hours at 37° C. and then stimulated as described above. Under these conditions the basal level of cAMP was 1.3 pmol/well. Panel C contains an experiment wherein mT2R5-expressing HEK293 cells were incubated with 50 μM rolipram in the absence and presence of 40 μM cycoheximide or 10 μM isoproterenol in HBSS for 15 minutes at 37° C. Under these conditions basal level of cAMP was 5 pmol/well. Cells were also treated with 100 ng/ml PTX for 4 hours at 37° C. and then stimulated as described above. Under these conditions basal level of cAMP was 4 pmol/well. Results correspond to the mean±SD of three independent experiments performed in quadruplicates.

Figure 8:
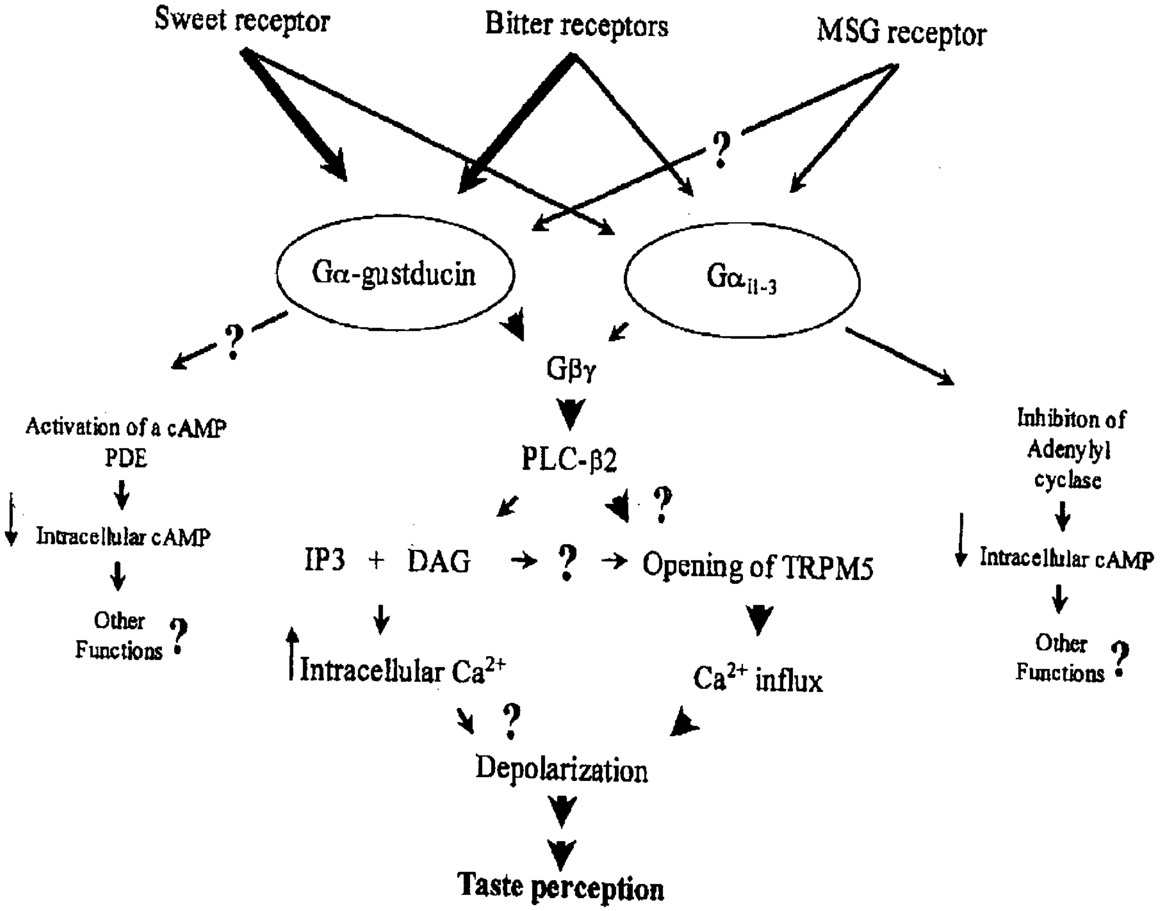

FIG. 8 contains a schematic showing how $G\alpha_i$ is believed to complement α-gustducin signaling pathways in TRCs.

Sweet and bitter receptors functionally couple to α-gustducin (thick arrows) (10, 17) Margolskee, R F, *J. Biol. Chem.* 277(1):1–4 (2002); Wong et al., *Nature* 381(6585): 796–800 (1996)). It is not known yet if the MSG (umami) receptor couples to α-gustducin but our results point to $G\alpha_i$ as a strong candidate for its cognate G protein in TRCs. Alpha-gustducin is thought to directly couple to calcium mobilization via Gβγ and activation of PLCβ2 (9, 10) (Gilbertson et al., *Curr. Opin. Neurobiol.,* 10(4):519–27 (2000); Margolskee, R F, *J. Biol. Chem.* 277(1):1–4 (2002)). Action of PLC-β2 produces two second messengers, inositol triphosphate (IP3) and diacylglycerol (DAG). IP3 triggers the release of calcium from intracellular stores. This event is not sufficient to fully depolarize TRCs (18) (Zhang et al., *Cell* 112(3):293–301 (2003)). DAG (19) or PLCβ2 activity itself (18) (Zhang et al., *Cell* 112(3):293–301 (2003)) may somehow activate a cell surface trp channel, TRPM5, leading to extracellular calcium influx in TRCs, followed by depolarization and ultimately taste perception. As disclosed in detail infra, the results of the present invention suggest that $G\alpha_i$ is capable of complementing α-gustducin function in TRCs. Indeed, PLCβ2 is known to be activated by the Gβγ subunit of G proteins belonging to the $G_i$ family (20–24) (Li et al., *Science* 287(54–55):1046–9 (2000); Wu et al., *Proc. Natl Acad Sci., USA* 90(11):5297–5301 (1993); Katan, *Biochem. Biophys. Acta* 1436(1–2):5–17 (1998); Smrcka et al., *J. Biol. Chem.* 272(24):15045–48 (1993); Rhee et al., *J. Biol. Chem.* 272(24):15045–8 (1997)), and $G\alpha_{i1\text{-}2}$ are expressed in TRCs (25, 26) (Kusakabe et al., *Chem. Senses* 25(5):525–31 (2000); Asano-Miyoshi *Neurosci. Lett.* 283(1):64 (2000)). This alternative pathway could explain the residual responsiveness of α-gustducin-deficient mouse to bitter substances and sweeteners (17, 27, 28) (Wong et al., *Nature* 381(6585): 796–800 (1996); He et al., *Chem. Senses* 27(8):719–27 (2002); Ruiz-Avila et al., *Proc. Natl Acad Sci., USA* 98(15):2868–73 (2001)). Current models (9, 10) (Gilbertson et al., *Curr. Opin. Neurobiol.,* 10(4) :519–27 (2000); Margolskee, R F, *J. Biol. Chem.* 277(1):1–4 (2002)) also suggest that α-gustducin couples to the activation of a PDE leading to a decrease of cAMP in TRCs. It is not yet known how a-gustducin may activate PDE(s). The decrease of cAMP mediated by $G\alpha_i$ could also complement this signaling cascade. Modulation of cAMP levels in TRCs could have roles that are not yet fully defined such as defining the tone of paracrine transmission between TRCs (29) (Harness et al., *J. Physiol.* 543(Pt. 2):601–614 (2002)) and modulating gene expression through a balance between CREB and phosphorylated-CREB (30) (Cao et al., *Neuroreport* 13(10):1321–25 (2002)).

DETAILED DESCRIPTION OF THE INVENTION

The present invention provides cell-based assays for identifying compounds that modulate, e.g., enhance agonize or antagonize the activity of specific T1R or T2R taste receptors or that modulate the effect of another T1R or T2R activator compound preferably by assaying their effect on the expression of an activated form of MAPK, cAMP levels or adenylyl cyclase activity by a eukaryotic cell that stably or transiently expresses at least one functional T1R or T2R. In its broadest embodiment, the cell-based assays encompass the identification of T1R or T2R modulator by detecting its effect on any $G_{\alpha i}$ associated signaling pathway.

The invention specifically provides cell-based assays that relate to the discovery that T1Rs and T2Rs both functionally couple to G proteins other than α-gustducin or $G\alpha_{15}$, particularly $G_i$ proteins such as $G\alpha_i$. As discussed in detail infra, it has been shown that bitter compounds such as cycloheximide specifically activate ERK1/2 mitogen activated kinases in cells expressing a T2R and $G\alpha_i$ and also that cycloheximide inhibits forskolin-induced cAMP accumulation. Further, it has been shown that natural and artificial sweetener compounds activate ERK1/2 in cells expressing hT1R2/hT2R13 and $G\alpha_i$, and that monosodium glutamate specifically activates ERK1/2 in cells expressing hT1R1/ht1R3 and $G\alpha_i$ protein and further completely inhibits forskolin-induced cAMP accumulation in such cells; and that activation of ERK1/2 by these compounds is totally abolished by treatment with pertussin toxin. These results provide compelling evidence that the T1R and T2R receptors indeed couple and activate ERK1/2 and inhibit adenylyl cyclase through $G\alpha_i$.

Thus, the invention provides cell-based assays for the identification of taste modulatory compounds that rely on these discoveries. These taste modulatory compounds have potential utility as flavor enhancers or flavor additives for incorporation in foods and beverages for human or animal consumption.

DEFINITIONS AND ABBREVIATIONS

Prior to providing a detailed description of the invention, and its preferred embodiments, the following definitions and abbreviations are provided. Otherwise all terms have their ordinary meaning as they would be construed by one skilled in the relevant art.

ABBREVIATIONS USED

Some abbreviations used in this application are set forth below.

cAMP: 3' 5'-cyclic adenosine monophsphate, TRCs: Taste receptor cells, GPCRs: G protein-coupled receptors, MSG: Monosodium glutamate, PDE: phosphodiesterase; MAPK: Mitogen activated protein kinase, IMP: inosine monophosphate, PTX: pertussis toxin, EGF: Epidermal growth factor, PKC: Protein kinase C, RTKs: Receptor tyrosine kinases, PKA: Protein kinase A, ACs: Adenylyl cyclases, cNMP: cyclic nucleotide monophosphate, CREB: cAMP response element-binding protein, PLCβ2: Phospholipase Cβ2, Trp: Transient receptor potential.

"Taste cells" include neuroepithelial cells that are organized into groups to form taste buds of the tongue, e.g., foliate, fungiform, and circumvallate cells (see, e.g., Roper et al., Ann. Rev. Neurosci. 12:329–353 (1989)) (31). Taste cells are also found in the palate and other tissues, such as the esophagus and the stomach.

"T1R" refers to one or more members of a family of G protein-coupled receptors that are expressed in taste cells such as foliate, fungiform, and circumvallate cells, as well as cells of the palate, and esophagus (see, e.g., Hoon et al., *Cell,* 96:541–551 (1999), (32) herein incorporated by reference in its entirety). The definition of "T1R" should further be construed based on DNA and amino acid sequences disclosed in the Senomyx and University of California patent applications and publications incorporated by reference herein. (See e.g., 10–12) Members of this family are also referred to as GPCR-B3 and TR1 in WO 00/06592 as well as GPCR-B4 and TR2 in WO 00/06593. GPCR-B3 is also herein referred to as rT1R1, and GPCR-B4 is referred to as rT1T2. Taste receptor cells can also be identified on the basis of morphology (see, e.g., 31), or by the expression of proteins specifically expressed in taste cells. T1R family members may have the ability to act as receptors for sweet or umami taste transduction, or to distinguish between various other taste modalities. T1R sequences, including hT1R1, hT1R2 and hT1R3 are identified in the Senomyx and University of California patent applications incorporated by reference in their entirety herein and are provided infra, in an Appendix after the claims.

"T1R" nucleic acids encode a family of GPCRs with seven transmembrane regions that have "G protein-coupled receptor activity," e.g., they may bind to G proteins in response to extracellular stimuli and promote production of second messengers such as IP3, cAMP, cGMP, and $Ca^{2+}$ via stimulation of enzymes such as phospholipase C and adenylate cyclase (for a description of the structure and function of GPCRs, see, e.g., Fong, *TM Cells Signal.* 8(3):217–224 (1996) (33) and Baldwin, et al., *J. Mol. Biol.* 272(1):144–164 (1997) (34). A single taste cell may contain many distinct T1R polypeptides.

The term "T1R" family therefore refers to polymorphic variants, alleles, mutants, and interspecies homologus that: (1) have at least about 35 to 50% amino acid sequence identity, optionally about 60, 75, 80, 85, 90, 95, 96, 97, 98, or 99% amino acid sequence identity to a T1R polypeptide, preferably those identified in the patent applications incorporated by reference herein, over a window of about 25 amino acids, optionally 50–100 amino acids; (2) specifically bind to antibodies raised against an immunogen comprising an amino acid sequence preferably selected from the group consisting of the T1R polypeptide sequence disclosed in the patent applications incorporated by reference herein and conservatively modified variants thereof; (3) are encoded by a nucleic acid molecule which specifically hybridize (with a size of at least about 100, optionally at least about 500–1000 nucleotides) under stringent hybridization conditions to a sequence selected from the group consisting of the T1R nucleic acid sequences contained in the applications incorporated by reference in their entirety herein, and conservatively modified variants thereof; or (4) comprise a sequence at least about 35 to 50% identical to an amino acid sequence selected from the group consisting of the T1R amino acid sequence identified in the patent applications incorporated by reference in their entirety herein.

The term "T2R" refers to one or more members of a family of G protein coupled receptors that are expressed in taste cells, specifically, the tongue and palate epithelia. In particular, T2R includes the particular genes identified in the Senomyx and University of California applications relating to T2Rs incorporated by reference in their entirety herein. T2Rs are genetically linked to loci associated with bitter taste perception in mice and humans. More specifically, the term "T2R" and terms including T2R, e.g., T2R04 or T2R05 refers generally to isolated T2R nucleic acids, isolated polypeptides encoded by T2R nucleic acids, and activities thereof. T2R nucleic acids and polypeptides can be derived from any organism. The terms "T2R" and terms including "T2R" also refer to polypeptides comprising receptors that are activated by bitter compounds, and to nucleic acids encoding the same. Thus both T1Rs and T2Rs comprise different families of chemosensory GPCRs. Sequences of various T2Rs are also contained in the Appendix that precedes the claims.

G proteins are heterotrimeric proteins composed of a single α subunit complexed with the βγ dimer. Molecular cloning has resulted in the identification of 18 distinct .α. subunits, 5β subunits, and 12γ subunits. G proteins are usually divided into four subfamilies $G_i$, $G_s$, $G_q$, and $G_{12}$ based on the sequence similarity of the Gα subunit. Several lines of evidence suggest that the interaction between a given GPCR and its cognate G protein involves multiple sites of contact on both proteins. All three intracellular loops as well as the carboxyl terminal tail of the receptor have been implicated. The GPCR is though to interact with all three subunits of the G protein. As the receptor-G protein interaction can be disrupted by a number of treatments that block the carboxyl terminus, including pertussis toxin-catalyzed ADP-ribosylation of $G_\alpha$ and binding of monoclonal antibodies, the carboxy terminal region of the Gα subunit has been the most intensely investigated contact site. These studies have shown that the $G_\alpha$, carboxy-terminal region is important not only to the interaction, but also plays a critical role in defining receptor specificity (Hamm et al., Science 241: 832–5 (1988); Osawa et al., J. Biol. Chem. 270: 31052–8 (1995); Garcia et al., EMBO 14: 4460–9 (1995); Sullivan et al., Nature 330: 758–760 (1987); Rasenick et al., J. Biol. Chem. 269: 21519–21525 (1994); West et al., J. Biol. Chem. 260: 14428–30 (1985); Conklin et al., 1993, Nature 363: 274–276; Conklin et al., Mol. Pharmacol. 50: 885–890 (1996)) (35–42). Furthermore, it has been shown that peptides corresponding to the carboxy terminal region of a $G_{\alpha i}$ subunit can block GPCR signaling events (Hamm et al., Science 241: 832–5 (1988); Gilchrist et al., J. Biol. Chem 273: 14912–19 (1998)) (35, 43). However, prior to the present invention, it was unknown that $G_i$ proteins were capable of functionally coupling to T1Rs and T2Rs.

Topologically, certain chemosensory GPCRs have an "N-terminal domain;" "extracellular domains;" "transmembrane domains" comprising seven transmembrane regions, and corresponding cytoplasmic, and extracellular loops; "cytoplasmic domains," and a "C-terminal domain" (see, e.g., Hoon et al., *Cell,* 96:541–551 (1999) (115); Buck & Axel, *Cell,* 65:175–187 (1991)) (44). These domains can be structurally identified using methods known to those of skill in the art, such as sequence analysis programs that identify hydrophobic and hydrophilic domains (see, e.g., Stryer, *Biochemistry,* (3rd ed. 1988) (45); see also any of a number of Internet based sequence analysis programs. Such domains are useful for making chimeric proteins and for in vitro assays of the invention, e.g., ligand binding assays.

"Extracellular domains" therefore refers to the domains of T1R and T2R polypeptides that protrude from the cellular membrane and are exposed to the extracellular face of the cell. Such domains generally include the "N terminal domain" that is exposed to the extracellular face of the cell, and optionally can include portions of the extracellular loops of the transmembrane domain that are exposed to the extracellular face of the cell, i.e., the loops between transmembrane regions 2 and 3, between transmembrane regions 4 and 5, and between transmembrane regions 6 and 7.

The "N-terminal domain" region starts at the N-terminus and extends to a region close to the start of the first transmembrane domain. More particularly, in one embodiment of the invention, this domain starts at the N-terminus and ends approximately at the conserved glutamic acid at amino acid position 563 plus or minus approximately 20 amino acids. These extracellular domains are useful for in vitro ligand-binding assays, both soluble and solid phase. In addition, transmembrane regions, described below, can also bind ligand either in combination with the extracellular domain, and are therefore also useful for in vitro ligand-binding assays.

"Transmembrane domain," which comprises the seven "transmembrane regions," refers to the domain of T1R or T2R polypeptides that lies within the plasma membrane, and may also include the corresponding cytoplasmic (intracellular) and extracellular loops. In one embodiment, this region corresponds to the domain of T1R or T2R family members. In the case of T1R family member this starts approximately at the conserved glutamic acid residue at amino acid position 563 plus or minus 20 amino acids and ends approximately at the conserved tyrosine amino acid residue at position 812 plus or minus approximately 10 amino acids. The seven transmembrane regions and extracellular and cytoplasmic loops can be identified using standard methods, as described in Kyte & Doolittle, *J. Mol. Biol.,* 157:105–32 (1982)) (46), or in Stryer, supra (45).

"Cytoplasmic domains" refers to the domains of T1R or T2R polypeptides that face the inside of the cell, e.g., the "C-terminal domain" and the intracellular loops of the transmembrane domain, e.g., the intracellular loop between transmembrane regions 1 and 2, the intracellular loop between transmembrane regions 3 and 4, and the intracellular loop between transmembrane regions 5 and 6. "C-terminal domain" refers to the region that spans the end of the last transmembrane domain and the 0-terminus of the protein, and which is normally located within the cytoplasm. In one embodiment, this region starts at the conserved tyrosine amino acid residue at position 812 plus or minus approximately 10 amino acids and continues to the C-terminus of the polypeptide.

The term "ligand-binding region" or "ligand-binding domain" refers to sequences derived from a taste receptor, particularly a taste receptor that substantially incorporates at least the extracellular domain of the receptor. In one embodiment, the extracellular domain of the ligand-binding region may include the N-terminal domain and, optionally, portions of the transmembrane domain, such as the extracellular loops of the transmembrane domain. The ligand-binding region may be capable of binding a ligand, and more particularly, a compound that enhances, mimics, blocks, and/or modulates taste, e.g., sweet, bitter, or umami taste. In the case of T2Rs, the compound bound by the ligand binding region will modulate bitter taste. In the case of T1Rs, the compound bound by the ligand-binding region will modulate sweet or umami taste.

The phrase "heteromultimer" or "heteromultimeric complex" in the context of the T1R receptors or polypeptides used in the assays of the present invention refers to a functional association of at least one T1R receptor and another receptor, typically another T1R receptor polypeptide (or, alternatively another non-T1R receptor polypeptide). For clarity, the functional co-dependence of the T1Rs is described in this application as reflecting their possible function as heterodimeric taste receptor complexes. However, as discussed in Senomyx patent applications and publications which are incorporated by reference herein, (10–12) functional co-dependence may alternatively reflect an indirect interaction. For example, T1R3 may function solely to facilitate surface expression of T1R1 and T1R2, which may act independently as taste receptors. Alternatively, a functional taste receptor may be comprised solely of T1R3, which is differentially processed under the control of T1R1 or T1R2, analogous to RAMP-dependent processing of the calcium-related receptor. By contrast, in the case of T2Rs the eukaryotic cells used in the subject MAPK assays will preferably express a single T2R.

The phrase "modulator" or "modulatory compound" means any compound that itself affects the activity of a T1R or T2R or modulates (affects) the effect of another compound on T1R or T2R activity. Typically, modulation is determined by cell-based assays that detect the effect of a putative modulator or Gi signaling pathways, e.g., assays that detect the effect of a compound on MAPK activity, cAMP levels or adenylyl cyclase activity.

The phrase "functional effects" in the context of assays for testing compounds that modulate at least one T1R or T2R family member mediated taste transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, conformation change-based assays, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release. In the present invention, the assays will generally measure the effect of a compound on MAPK activation, cAMP accumulation or adenylyl cyclase activity in cell-based expression systems whereby the T1R or T2R is functionally coupled to a $G_i$ protein such as $G_{\alpha i}$ and the assays are used to screen for putative sweeteners or sweet taste modulators or enhancers, umami taste modulators or enhancers, or bitter compounds or bitter taste modulators or enhancers, e.g., bitter taste blockers. Such modulators have application for incorporation in foods, beverages, pharmaceuticals, and the like for human or animal consumption.

By "determining the functional effect" in the context of assays is meant assays for a compound that increases or decreases a parameter that is indirectly or directly under the influence of at least one T1R or T2R family member, e.g., functional, physical and chemical effects. Such functional effects can be measured by any means known to those skilled in the art, e.g., changes in spectroscopic characteristics (e.g., fluorescence, absorbency, refractive index), hydrodynamic (e.g., shape), chromatographic, or solubility properties, patch clamping, voltage-sensitive dyes, whole cell currents, radioisotope efflux, inducible markers, oocyte T1R or T2R gene expression; tissue culture cell T1R or T2R expression; transcriptional activation of T1R or T2R genes; ligand-binding assays; voltages, membrane potential and conductance changes; ion flux assays; changes in intracellular second messengers such as cAMP, cGMP, and inositol triphosphate (IP3); changes in intracellular calcium levels; neurotransmitter release, conformational assays and the like. In the present invention, the effect of a putative modulator compound will be preferably assayed based on its effect on MAPK activation, cAMP accumulation, or adenylyl cyclase activity.

"Inhibitors," "activators," "enhancer," and "modulators" of T1R or T2R genes or proteins are used to refer to inhibitory, activating, or modulating molecules identified using in vitro and in vivo assays for taste transduction, e.g., ligands, agonists, antagonists, inversed agonists, and their homologues and mimetics. These compounds themselves modulate T1R or T2R activity or modulate the effect of another compound on T1R or T2R activity. In the present invention these molecules will preferably be identified using the subject cell-based MAPK or cAMP assays. In preferred embodiments, the "inhibitors" will block taste of a known bitter compound or enhance the taste of a known sweet or umami compound or compounds.

Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate taste transduction, e.g., agonists. Modulators include compounds that, e.g., alter the interaction of a receptor with: extracellular proteins that bind activators or inhibitor (e.g., ebnerin and other members of the hydrophobic carrier family); G proteins; kinases (e.g., homologues of rhodopsin kinase and beta adrenergic receptor kinases that are involved in deactivation and desensitization of a receptor); and arrestins, which also deactivate and desensitize receptors. Modulators can include genetically modified versions of T1R or T2R family members, e.g., with altered activity, as well as naturally occurring and synthetic ligands, antagonists, agonists, small chemical molecules and the like. Such assays for inhibitors and activators include, e.g., expressing T1R or T2R family members in cells or cell membranes, applying putative modulator compounds, in the presence or absence of tastants, e.g., sweet, umami or bitter tastants, and then determining the functional effects on taste transduction, as described above. Samples or assays comprising T1R or T2R family members that are treated with a potential activator, inhibitor, or modulator are compared to control samples without the inhibitor, activator, or modulator to examine the extent of modulation. Positive control samples (e.g. a sweet, umami, or bitter tastant without added modulators) are assigned a relative T1R or T2R activity value of 100%.

Negative control samples (e.g., buffer without an added taste stimulus) are assigned a relative T1R or T2R activity value of 0%. Inhibition of a T1R or T2R is achieved when a mixture of the positive control sample and a modulator result in the T1R or T2R activity value relative to the positive control is about 80%, optionally 50% or 25–0%. Activation of a T1R or T2R by a modulator alone is achieved when the T1R activity value relative to the positive control sample is 10%, 25%, 50%, 75%, optionally 100%, optionally 150%, optionally 200–500%, or 1000–3000% higher.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated," when referring to a nucleic acid or protein, also refers to a state of purification or concentration different than that which occurs naturally in the mammalian, especially human body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

The term "nucleic acid" or "nucleic acid sequence" refers to a deoxyribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones (see e.g., *Oligonucleotides and Analogues, a Practical Approach,* ed. F. Eckstein, Oxford Univ. Press (1991); *Antisense Strategies, Annals of the N.Y. Academy of Sciences,* Vol. 600, Eds. Baserga et al. (NYAS 1992); Milligan J. *Med. Chem.* 36:1923–1937 (1993); *Antisense Research and Applications* (1993, CRC Press), Mata, *Toxicol. Appl. Pharmacol.* 144:189–197 (1997); Strauss-Soukup, *Biochemistry* 36:8692–8698 (1997); Samstag, *Antisense Nucleic Acid Drug Dev,* 6:153–156 (1996)) (47–53).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al, *Nucleic Acid Res.,* 19:5081 (1991); Ohtsuka et al., J. Biol. Chem., 260:2605 . 2608 (1985); Rossolini et al., *Mol. Cell. Probes,* 8:91–98 (1994)) (54–56). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "plasma membrane translocation domain" or simply "translocation domain" means a polypeptide domain that, when incorporated into a polypeptide coding sequence, can with greater efficiency "chaperone" or "translocate" the hybrid ("fusion") protein to the cell plasma membrane than without the domain. For instance, a "translocation domain" may be derived from the amino terminus of the bovine rhodopsin receptor polypeptide, a 7-transmembrane receptor. However, rhodopsin from any mammal may be used, as can other translocation facilitating sequences. Thus, the translocation domain is particularly efficient in translocating 7-transmembrane fusion proteins to the plasma membrane, and a protein (e.g., a taste receptor polypeptide) comprising an amino terminal translocating domain will be transported to the plasma membrane more efficiently than without the domain. However, if the N-terminal domain of the polypeptide is active in binding, as with the T1R or T2R receptors of the present invention, the use of other translocation domains may be preferred. For instance, a PDZ domain-interacting peptide, as described herein, may be used.

The "translocation domain," "ligand-binding domain", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid, which encodes a polypeptide, is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gin; ile/leu or val; leu/ile or val; lys/arg or gln or glu; met/leu or tyr or lie; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (T), Leucine (L), Methionine (M), Valine (V); and 6) Phenylalanine (F), Tyrosine (Y), Tryptophan (W); (see also, e.g., Creighton, *Proteins,* W.H. Freeman and Company (1984); Schultz and Schimer, *Principles of Protein Structure,* Springer-Verlag (1979)) (57–58). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The term "mimetic" and "peptidomimetic" refer to a synthetic chemical compound that has substantially the same structural and/or functional characteristics of the polypeptides, e.g., translocation domains, ligand-binding domains, or chimeric receptors of the invention. The mimetic can be either entirely composed of synthetic, non-natural analogs of amino acids, or may be a chimeric molecules of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., $—C(═O)—CH_2—$ and $—C(═O)—NH—$), aminomethylene (CH2—NH), ethylene, olefin (CH═CH), ether ($CH_2—O$), thioether (CH2—S), tetrazole ($CN_4$), thiazole, retroamide, thioamide, or ester (see, e.g., Spatola, *Chemistry and Biochemistry of Amino Acids, Peptides and Proteins,* Vol. 7, pp 267–357, "Peptide Backbone Modifications," Marcell Dekker, NY (1983)) (157). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogene, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions.

An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

As used herein, a "stable cell line" refers to a cell line, which stably, i.e. over a prolonged period, expresses a heterologous nucleic sequence, i.e., a T1R, T2R or G protein. In preferred embodiments, such stable cell lines will be produced by transfecting appropriate cells, typically mammalian cells, e.g. HEK293 cells, with a linearized vector that contains a T1R or T2R expression construct that expresses at least one T1R or T2R, i.e., T1R1, T1R2 and/or T1R3 or a T2R. Most preferably, such stable cell lines that express a functional T1R or T2R receptor will be produced by co-transfecting two linearized plasmids that express hT1R1 and hT1R3 or hT1R2 and hT1R3 or a single line plasmid that expresses a specific T2R and an appropriate selection procedure to generate cell lines having these genes stably integrated therein. Most preferably, the cell line will also stably express a G protein preferably a $G_i$ such as $G_{\alpha i}$ or $G_{\alpha 15}$.

"Antibody" refers to a polypeptide comprising a framework region from an immunoglobulin gene or fragment thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms "variable light chain" (VL) and "variable heavy chain" (VH) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-T1R" antibody is an antibody or antibody fragment that specifically binds a polypeptide encoded by a T1R gene, cDNA, or a subsequence or variant thereof.

An "anti-T2R" antibody is an antibody or antibody fragment that specifically binds a polypeptide encoded by T2R gene, cDNA, or a subsequence or variant thereof.

An "anti-activated MAPK antibody" or an "anti-phospho MAPK antibody" refers to an antibody or antibody fragment that specifically binds to an activated (phosphorylated) form of MAPK.

A "ligand that detects cAMP" is any moiety that specifically detects cAMP levels.

The term "immunoassay" is an assay that uses an antibody to specifically bind an antigen. The immunoassay is characterized by the use of specific binding properties of a particular antibody to isolate, target, and/or quantify the antigen. In a preferred embodiment of the invention, MAPK activity or cAMP levels will be immunoassayed in eukaryotic cells using an antibody that specifically recognizes an activated form of MAPK or cAMP.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a T1R or T2R family member from specific species such as rat, mouse, or human can be selected to obtain only those polyclonal antibodies that are specifically immunoreactive with the T1R or T2R polypeptide or an immunogenic portion thereof and not with other proteins, except for orthologs or polymorphic variants and alleles of the T1R or T2R polypeptide. This selection may be achieved by subtracting out antibodies that cross-react with T1R or T2R molecules from other species or other T1R or T2R molecules. Antibodies can also be selected that recognize only T1R GPCR family members but not GPCRs from other families. In the case of antibodies to activated MAPKs, suitable polyclonal and monoclonal antibodies are commercially available.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual,* (1988) (59), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as *E. coli,* or eukaryotic cells such as yeast, insect, amphibian, worm or mammalian cells such as CHO, Hela, BHK, HEK-293, and the like, e.g., cultured cells, explants, and cells in vivo.

The terms "a," "an," and "the" are used in accordance with long-standing convention to refer to one or more.

The term "about", as used herein when referring to a measurable value such as a percentage of sequence identity (e.g., when comparing nucleotide and amino acid sequences as described herein below), a nucleotide or protein length, an amount of binding, etc. is meant to encompass variations of ±20% or ±10%, more preferably ±5%, even more preferably ±1, and still more preferably ±1% from the specified amount, as such variations are appropriate to perform a disclosed method or otherwise carry out the present invention.

The term "substantially identical", is used herein to describe a degree of similarity between nucleotide sequences, and refers to two or more sequences that have at least about least 60%, preferably at least about 70%, more preferably at least about 80%, more preferably about 90% to 99%, still more preferably about 95% to about 99%, and most preferably about 99% nucleotide identify, when compared and aligned for maximum correspondence, as measured using one of the following sequence comparison algorithms or by visual inspection. Preferably, the substantial identity exists in nucleotide sequences of at least about 100 residues, more preferably in nucleotide sequences of at least about 150 residues, and most preferably in nucleotide sequences comprising a full length coding sequence. The term "full length" is used herein to refer to a complete open reading frame encoding a functional T1R or T2R polypeptide, as described further herein below. Methods for determining percent identity between two polypeptides are defined herein below under the heading "Nucleotide and Amino Acid Sequence Comparisons".

In one aspect, substantially identical sequences can be polymorphic sequences. The term "polymorphic" refers to the occurrence of two or more genetically determined alternative sequences or alleles in a population. An allelic difference can be as small as one base pair.

In another aspect, substantially identical sequences can comprise mutagenized sequences, including sequences comprising silent mutations. A mutation can comprise one or more residue changes, a deletion of residues, or an insertion of additional residues.

Another indication that two nucleotide sequences are substantially identical is that the two molecules hybridize specifically to or hybridize substantially to each other under stringent conditions. In the context of nucleic acid hybridization, two nucleic acid sequences being compared can be designated a "probe" and a "target." A "probe" is a reference nucleic acid molecule, and a "target" is a test nucleic acid molecule, often found within a heterogeneous population of nucleic acid molecules. A "target sequence" is synonymous with a "test sequence."

A preferred nucleotide sequence employed for hybridization studies or assays includes probe sequences that are complementary to or mimic at least an about 14 to 40 nucleotide sequence of a nucleic acid molecule of the present invention. Preferably, probes comprise 14 to 20 nucleotides, or even longer where desired, such as 30, 40, 50, 60, 100, 200, 300, or 500 nucleotides or up to the full length of the particular T1R or T2R. Such fragments can be readily prepared by, for example, chemical synthesis of the fragment, by application of nucleic acid amplification technology, or by introducing selected sequences into recombinant vectors for recombinant production.

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" and "stringent hybridization wash conditions" refer to conditions under which a probe will hybridize to its target subsequence, typically in a complex mixture of nucleic acids but to no other sequences. Stringent conditions are sequence-dependent and will be different in different circumstances. Longer sequences hybridize specifically at higher temperatures. An extensive guide to the hybridization of nucleic acids is that in Tigssen, *Techniques in Biochemistry and Molecular Biology—Hybridization With Nucleic Probes,* "Overview of principles of hybridization and the strategy of nucleic acid assays." (1973) Generally, highly stringent hybridization and wash conditions are selected to be about 5–10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium).

Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the additional of destablizing agents such as formamide. For selective or specific hybridization, a positive signal is at least two times background, optionally 10 times background hybridization. Exemplary stringent hybridization conditions are:

50% formamide, 5×SSC, and 1% SDS, incubating at 42° C. or 5×SSC, 1% SDS, incubating at 65° C. The hybridization and wash steps effected in said exemplary stringent hybridization conditions are each effected for at least 1, 2, 5, 10, 15, 30, 60, or more minutes. Preferably, the wash and hybridization steps are each effected for at least 5 minutes, and more preferably, 10 minutes, 15 minutes, or more than 15 minutes.

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook et al., eds (1989) *Molecular Cloning: A Laboratory Manual,* Cold Spring Harbor Laboratory Press, Cold Spring Harbor, N.Y. (60) for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1 M $Na^+$ ion, typically about 0.01 to 1 M $Na^+$ ion concentration (or other salts) at pH 7.0–8.3, and the temperature is typically at least about 30° C. Stringent conditions can also be achieved with the addition of destablizing agents such as formamide. In general, a signal to noise ratio of 2-fold (or higher) than that observed for an unrelated probe in the particular hybridization assay indicates detection of a specific hybridization.

The following are additional examples of hybridization and wash conditions that can be used to identify nucleotide sequences that are substantially identical to reference nucleotide sequences of the present invention: a probe nucleotide sequence preferably hybridizes to a target nucleotide sequence in 7% sodium dodecyl sulphate (SDS), 0.5M $NaPO_4$, 1 mM EDTA at 50° C. followed by washing in 2×SSC, 0.1% SDS at 50° C.; more preferably, a probe and target sequence hybridize in 7% sodium dodecyl sulphate (SDS), 0.5M $NaPO_4$, 1 mM EDTA at 50° C. followed by washing in 1×SSC, 0.1% SDS at 50° C.; more preferably, a probe and target sequence hybridize in 7% sodium dodecyl sulphate (SDS), 0.5M NaPO4, 1 MM EDTA at 50° C. followed by washing in 0.5×SSC, 0.1% SDS at 50° C.; more preferably, a probe and target sequence hybridize in 7% sodium dodecyl sulphate (SIDS), 0.5M $NaPO_4$, 1 mM EDTA at 50° C. followed by washing in 0.1×SSC, 0.1 SDS at 50° C.; more preferably, a probe and target sequence hybridize in 7% sodium dodecyl sulphate (SDS), 0.5M $NaPO_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, or are biologically functional equivalents. Nucleic acid molecules that do not hybridize to each other under stringent conditions are still substantially identical if the corresponding proteins are substantially identical. This can occur, for example, when two nucleotide sequences comprise conservatively substituted variants as permitted by the genetic code.

Nucleic acids that do not hybridize to each other under stringent conditions are still substantially related if the polypeptides that they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. Preferably, the wash and hybridization steps are each effected for at least 5 minutes. A positive hybridization is at least twice background. Those of ordinary skill will readily recognize that alternative hybridization and wash conditions can be utilized to provide conditions of similar stringency.

The term "conservatively substituted variants" refers to nucleic acid sequences having degenerate codon substitutions wherein the third position of one or more selected (or all) codons is substituted with mixed-base and/or deoxyinosine residues. See Batzer et al. (1991) *Nucleic Acids Res* 19:5081; Ohtsuka et al. (1985) *J Biol Chem* 260:2605–2608; and Rossolini et al. (1994) *Mol Cell Probes* 8:91–98 (54–56).

The term T1R or T2R also encompasses nucleic acids comprising subsequences and elongated sequences of a T1R or T2R nucleic acid, including nucleic acids complementary to a T1R or T2R nucleic acid, T1R or T2R RNA molecules, and nucleic acids complementary to T1R or T2R RNAs (cRNAs).

The term "subsequence" refers to a sequence of nucleic acids that comprises a part of a longer nucleic acid sequence. An exemplary subsequence is a probe, described herein above, or a primer. The term "primer" as used herein refers to a contiguous sequence comprising about 8 or more deoxyribonucleotides or ribonucleotides, preferably 10–20 nucleotides, and more preferably 20–30 nucleotides of a selected nucleic acid molecule. The primers of the invention encompass oligonucleotides of sufficient length and appropriate sequence so as to provide initiation of polymerization on a nucleic acid molecule of the present invention.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The term "complementary sequences," as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison methods set forth below, or is defined as being capable of hybridizing to the nucleic acid segment in question under relatively stringent conditions such as those described herein. A particular example of a complementary nucleic acid segment is an antisense oligonucleotide.

The term "gene" refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "chimeric gene," as used herein, refers to a promoter region operatively linked to a T1R or T2R sequence, including a T1R or T2R cDNA, a T1R or T2R nucleic acid encoding an antisense RNA molecule, a T1R or T2R nucleic acid encoding an RNA molecule having tertiary structure (e.g., a hairpin structure) or a T1R or T2R nucleic acid encoding a double-stranded RNA molecule. The term "chimeric gene" also refers to a T1R or T2R promoter region operatively linked to a heterologous sequence.

The term "operatively linked", as used herein, refers to a functional combination between a promoter region and a nucleotide sequence such that the transcription of the nucleotide sequence is controlled and regulated by the promoter region. Techniques for operatively linking a promoter region to a nucleotide sequence are known in the art.

The term "vector" is used herein to refer to a nucleic acid molecule having nucleotide sequences that enable its replication in a host cell. A vector can also include nucleotide sequences to permit ligation of nucleotide sequences within the vector, wherein such nucleotide sequences are also replicated in a host cell. Representative vectors include plasmids, cosmids, and viral vectors. A vector can also mediate recombinant production of a T1R or T2R polypeptide, as described further herein below.

The term "construct", as used herein to describe a type of construct comprising an expression construct, refers to a vector further comprising a nucleotide sequence operatively inserted with the vector, such that the nucleotide sequence is recombinantly expressed.

The terms "recombinantly expressed" or "recombinantly produced" are used interchangeably to refer generally to the process by which a polypeptide encoded by a recombinant nucleic acid is produced.

The term "heterologous nucleic acids" refers to a sequence that originates from a source foreign to an intended host cell or, if from the same source, is modified from its original form. Thus, preferably recombinant T1R or T2R nucleic acids comprise heterologous nucleic acids. A heterologous nucleic acid in a host cell can comprise a nucleic acid that is endogenous to the particular host cell but has been modified, for example by mutagenesis or by isolation from native cis-regulatory sequences. A heterologous nucleic acid also includes non-naturally occurring multiple copies of a native nucleotide sequence. A heterologous nucleic acid can also comprise a nucleic acid that is incorporated into a host cell's nucleic acids at a position wherein such nucleic acids are not ordinarily found.

Nucleic acids used in the cell-based assays of the present invention preferably MAPK and cAMP assays can be cloned, synthesized, altered, mutagenized, or combinations thereof. Standard recombinant DNA and molecular cloning techniques used to isolate nucleic acids are known in the art. Site-specific mutagenesis to create base pair changes, deletions, or small insertions are also known in the art. See e.g., Sambrook et al. (eds.) *Molecular Cloning: A Laboratory Manual.* Cold Spring Harbor Laboratory Press, Cold Spring Harbor, N.Y. (1989); Silhavy et al. *Experiments with Gene Fusions.* Cold Spring Harbor Laboratory Press, Cold Spring Harbor, N.Y. (1984); Glover & Hames *DNA Cloning: A Practical Approach,* 2nd ed. IRL Press and Oxford University Press, Oxford, N.Y. (1995); Ausubel (ed.) *Short Protocols in Molecular Biology,* 3rd ed. Wiley, N.Y. (1995) (60–63).

The term "substantially identical", as used herein to describe a level of similarity between a particular T1R or T2R protein and a protein substantially identical to the T1R or T2R protein, refers to a sequence that is at least about 35% identical to the particular T1R or T2R protein, when compared over the full length of the T1R or T2R protein. Preferably, a protein substantially identical to the T1R or T2R protein used in the present invention comprises an amino acid sequence that is at least about 35% to about 45% identical to a particular T1R or T2R, more preferably at least about 45% to about 55% identical thereto, even more preferably at least about 55% to about 65% identical thereto, still more preferably at least about 65% to about 75% identical thereto, still more preferably at least about 75% to about 85% identical thereto, still more preferably at least about 85% to about 95% identical thereto, and still more preferably at least about 95% to about 99% identical thereto when compared over the full length of the particular T1R or T2R. The term "full length" refers to a functional T1R or T2R polypeptide. Methods for determining percent identity between two polypeptides are also defined herein below under the heading "Nucleotide and Amino Acid Sequence Comparisons".

The term "substantially identical," when used to describe polypeptides, also encompasses two or more polypeptides sharing a conserved three-dimensional structure. Computational methods can be used to compare structural representations, and structural models can be generated and easily tuned to identify similarities around important active sites or ligand binding sites. See Saqi et al. *Bioinformatics* 15:521–522 (1999); Barton *Acta Crystallogr D Biol Crystallogr* 54:1139–1146 (1998); Henikoff et al. *Electrophoresis* 21:1700–1706 (2000); and Huang et al. *Pac Symp Biocomput:*230–241 (2000) (64–67).

Substantially identical proteins also include proteins comprising amino acids that are functionally equivalent to a T1R or T2R according to the invention. The term "functionally equivalent" in the context of amino acids is known in the art and is based on the relative similarity of the amino acid side-chain substituents. See Henikoff & Henikoff *Adv. Protein Chem* 54:73–97 (2000) (68). Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape.

By this analysis, described further herein below, arginine, lysine, and histidine; alanine, glycine, and serine; and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., *J. Mol. Biol.* 157(1):105–32 (1982)) (69). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101 describes that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

The term "substantially identical" also encompasses polypeptides that are biologically functional equivalents of a particular T1R or T2R polypeptide. The term "functional" includes an activity of an T1R or T2R polypeptide, for example activating intracellular signaling pathways (e.g., coupling with gustducin) and mediating taste perception. Preferably, such activation shows a magnitude and kinetics that are substantially similar to that of a cognate T1R or T2R polypeptide in vivo. Representative methods for assessing T1R or T2R activity are described in the patent applications incorporated by reference herein.

The assays of the present invention also can use functional fragments of a particular T1R or T2R polypeptide. Such functional portion need not comprise all or substantially all of the amino acid sequence of a native T1R or T2R gene product. The assays of the present invention also can use functional polypeptide sequences that are longer sequences than that of a native T1R or T2R polypeptide. For example, one or more amino acids can be added to the N-terminus or C-terminus of a T1R or T2R polypeptide. Such additional amino acids can be employed in a variety of applications, including but not limited to purification applications. Methods of preparing elongated proteins are known in the art.

"MAPK" or "MAP Kinase" refers to a mitogen activated protein kinase, the expression of which is activated by some functional GPCRs, i.e., T2Rs and T1Rs.

"MAPK" or "MAP Kinase" activation specific ligands" refers to a ligand, preferably a polyclonal or monoclonal antibody or fragment thereof that specifically binds an activated form of MAPK, e.g., p42/p44 MAPK or p38/MAPK. Antibodies that specifically bind the activated (phosphorylated) form of MAPK are commercially available and include the phosph-p44/p42 MAP Kinase antibody #9106 available from Cell Signaling Technologies, the polyclonal anti-phospho-p44/42 MAPK and anti-phospho-p38 MAPK antibodies available from UBI, (Lake Placid, N.Y., USA) and New England Biolabs (Beverly, Mass., USA), the anti-phospho-p44/42 MAPK antibodies reported by Discovery Research Laboratories III, Takeda Chemical Indust. Ltd., (Oskaka Japan) (Tan et al., J. Immunol. Meth. 232(1–2): 87–97 (1998)) (70).

"Ligand" or "compound" that "activates MAPK" refers to a compound which when contacted with a eukaryotic cell that expresses a functional GPCR, herein at least one functional T1R or T2R, results in a detectable increase in the activated form of MAPK. This increase will preferably will be detected by antibody-based detection methods that use an antibody that specifically binds to an activated form of MAPK.

"PLC" refers to phospholipase C. In the present invention, "a ligand or compound that activates MAPK" may activate MAPK in cells via a pathway that is independent of PLC activation.

Cell Based Assays of the Present Invention

This, in one aspect, present invention generally relates to cell-based assays for identifying compounds that modulate the activity of at least one T1R or T2R taste receptor, wherein the assays comprise contacting a eukaryotic cell that stably or transiently expresses at least one functional T1R or T2R and a G protein that functionally couples therewith, e.g. a $G_i$ protein such as $G\alpha_i$ with a putative modulator of said functional T1R or T2R, and assaying the effect of said putative agonist or antagonist compound on $G_i$ mediated signaling pathways, e.g., by assaying the effect of said putative modulation on MAPK activation, cAMP accumulation or adenylyl cyclase activity. For example, a modulator compound will result, e.g., in a detectable increase or decrease in the amount of an activated form of MAPK, i.e., phosphorylated MAPK, e.g., phosphorylated p44/42 MAP Kinase or phosphorylated p38 MAP Kinase, and will elicit this effect on MAPK activation by a pathway independent of PLC activation or will result in detectable increase or decrease in cAMP accumulation, or will result in a change (e.g., decrease) in adenylyl cyclase activity. However, the invention embraces any cell-based assays that identify compounds that modulate to a TRGPCR (T1R or T2R)/$G_{\alpha i}$ mediated signaling pathway.

The eukaryotic cells used in the subject assays, preferably MAPK, cAMP or adenylyl cyclase assays, will stably or transiently express at least one functional T1R or T2R. Preferably, the eukaryotic cell will either stably or transiently express a functional T1R1/T1R3 umami taste receptor or a functional T1R2/T1R3 sweet taste receptor or will stably or transiently express a desired functional T2R, preferably a functional human T1R or T2R taste receptor. In order to produce a functional taste receptor, the eukaryotic cell will further be transfected to stably or transiently express or will endogenously express a G protein that couples with said T1R(s) or T2R thereby resulting in a functional taste receptor. Examples of suitable G proteins are known in the art and are referred in the patent applications incorporated by reference herein. In a preferred embodiment, the G protein will comprise a Gi protein selected from $G\alpha_i$, i.e. $G\alpha_{i1\text{-}1}$, $G\alpha_{i1\text{-}2}$, $G\alpha_{i1\text{-}3}$, $G\alpha_{i0\text{-}1}$, and $G\alpha_{i0\text{-}2}$. Alternatively, the G protein will comprise $G\alpha_{15}$, α-transcucin, gustducin, $G_{\alpha z}$ or a functional chimera or variant thereof that couples with the T1R(s) or T2R expressed by the eukaryotic cell.

The present assays can be effected using any eukaryotic cell that functionally expresses the particular T1R(s) or T2R, and which cell, when contacted with an activator of said T1R or T1R results in an increase in an activated form of MAPK, or a decrease in cAMP accumulation or a reduction in adenylyl cyclase activity by a pathway that is independent of PLC activation. Examples of suitable eukaryotic cells include amphibian, yeast, insect, amphibian, worm and mammalian cells. Specific examples of suitable cells for use in the subject cell-based assays include HEK293 cells, BHK cells, CHO cells, Hela cells and Xenopus oocytes.

In a preferred embodiment the eukaryotic cells used in the subject cell-based assays, e.g., MAPK, cAMP and adenylyl cyclase assays will comprise HEK293 cells that stably or transiently express at least one or functional T1R or T2R taste receptor by the transfection of such cells with a cDNA or cDNAs encoding said at least one T1R or T2R. For example, HEK293 cells stably expressing the large T cell antigen and the promiscuous G protein $G\alpha_{15}$ (HEK293T-$G\alpha_{15}$) or $G_{\alpha i}$ can be transiently transfected with a particular taste receptor plasmid by known transfection methods, e.g., by use of $Ca^{2+}$ phosphate or lipid-based systems, or other transformation methods referenced supra. As noted previously, the T1R or T2R expressing cell will further express endogenously or be engineered to express a G protein that functionally couples therewith, e.g., a G protein selected from the $G_{\alpha i}$ proteins identified previously.

Cells that stably or transiently express the particular taste receptor are used in assays that measure the effect of at least one putative T1R or T2R modulatory compound on $G_{\alpha i}$-mediated signaling pathways, e.g., by measuring its effect on MAPK activation, cAMP accumulation or adenylyl cyclase activity. The MAPK or cAMP assays of the present invention can use immobilized cells or cells in suspension. In a preferred embodiment the taste receptor expressing cells will be seeded into multi-well culture plates, e.g., 6-well culture plates. However, other in vitro cell culture devices can be substituted therefore, and is not critical to the invention.

In a typical MAPK or cAMP assay according to the invention, functional expression of the T1R or T2R expressing eukaryotic cell is allowed to proceed for a certain time, e.g., on the order of about 48 hours, and then taste receptor expressing cells are stimulated with a putative modulatory compound for a fixed time, e.g., about 5 minutes, and then the reaction is then stopped, e.g., by the addition of ice-cold buffer, and the cells are then assayed for changes in activated MAPK, cAMP or adenylyl cyclase activity. However, these reaction times may be shortened or lengthened within wide limits.

The level of activated MAPK produced by such cells is detected in whole cells or cell lysates. In a preferred embodiment, cell lysates are prepared by known methods, and detected by activated cAMP, MAPK or adenylyl cyclase activity is detected by known methods. For example, activated MAPK can be the use of a polyclonal or monoclonal antibody or fragment thereof that specifically recognizes an activated (phosphorylated) form of MAPK. In a preferred embodiment, activation of MAPK is detected by Western analysis of cell lysates using a specific monoclonal antibody that recognizes phosphorylated (active) MAPK (Phospho-p44/42 MAP Kinase antibody #9106 available from Cell Signaling Technologies) or another commercially available antibody that specifically recognizes activated MAPK.

Exemplification of Cell-Based Assays According to the Invention

The following are exemplary of cell-based assays that may be used according to the invention for detecting the effect of a putative modulator on T1R or T2R activity.

1. GTP Assay

For GPCRs T1R or T2R, a measure of receptor activity is the binding of GTP by cell membranes containing receptors. In the method described by Traynor and Nahorski, 1995, Mol. Pharmacol. 47: 848–854, (1995) (130) one essentially measures G-protein coupling to membranes by detecting the binding of labelled GTP. For GTP binding assays, membranes isolated from cells expressing the receptor are incubated in a buffer containing 20 mM HEPES, pH 7.4, 100 mM NaCl, and 10 mM $MgCl_2$, 80 pM . . . $^{35}S$-GTPγS and 3 μM GDP.

The assay mixture is incubated for 60 minutes at 30° C., after which unbound labelled GTP is removed by filtration onto GF/B filters. Bound, labelled GTP is measured by liquid scintillation counting. The presence and absence of a candidate modulator of T1R or T2R activity. A decrease of 10% of more in labelled GTP binding as measured by scintillation counting in an assay of this kind containing a candidate modulator, relative to an assay without the modulator, indicates that the candidate modulator inhibits T1R or T2R activity. A compound is considered an agonist if it induces at least 50% of the level of GTP binding when the compound is present at 1 μM or less.

GTPase activity is measured by incubating the membranes containing a T1R or T2R polypeptide with .$\gamma^{32}P$-GTP. Active GTPase will release the label as inorganic phosphate, which is detected by separation of free inorganic phosphate in a 5% suspension of activated charcoal in 20 mM $H_3PO_4$, followed by scintillation counting. Controls include assays using membranes isolated from cells not expressing T1R or T2R (mock-transfected), in order to exclude possible non-specific effects of the candidate compound.

In order to assay for the effect of a candidate modulator on T1R or T2R-regulated GTPase activity, membrane samples are incubated with and without the modulator, followed by the GTPase assay. A change (increase or decrease) of 10% of more in the level of GTP binding or GTPase activity relative to samples without modulator is indicative of T1R or T2R modulation by a candidate modulator.

2. Downstream Pathway Activation Assays:

i) Calcium Flux—The Aequorin-based Assay:

The aequorin assay takes advantage of the responsiveness of mitochondrial apoaequorin to intracellular calcium release induced by the activation of GPCRs (Stables et al., Anal. Biochem. 252:115–126 (1997); Detheux et al., 2000, J. Exp. Med., 192 1501–1508 (2000) (131–132); both of which are incorporated herein by reference). Briefly, T1R or T2R-expressing clones are transfected to coexpress mitochondrial apoaequorin and $G_{\alpha 16}$. Cells are incubated with 5 μM Coelenterazine H (Molecular Probes) for 4 hours at room temperature, washed in DMEM-F12 culture medium and resuspended at a concentration of 0.5.times.10.sup.6 cells/ml. Cells are then mixed with test agonist molecules and light emission by the aequorin is recorded with a luminometer for 30 seconds. Results are expressed as Relative Light Units (RLU). Controls include assays using membranes isolated from cells not expressing T1R or T2R (mock transfected), in order to exclude possible non-specific effects of the candidate compound.

Aequorin activity or intracellular calcium levels are "changed" if light intensity increases or decreases by 10% or more in a sample of cells, expressing a T1R or T2R polypeptide and treated with a candidate modulator, relative to a sample of cells expressing the T1R or T2R polypeptide but not treated with the candidate modulator or relative to a sample of cells not expressing the T1R or T2R polypeptide (mock-transfected cells) but treated with the candidate modulator.

ii) Adenylate Cyclase Assay:

Assays for adenylate cyclase activity are described by Kenimer & Nirenberg, Mol. Pharmacol. 20: 585–591 (1981) (133). That assay is a modification of the assay taught by Solomon et al., 1974, Anal. Biochem. 58: 541–548 (1974) (134), also incorporated herein by reference. Briefly, 100 μl reactions contain 50 mM Tris-Hcl (pH 7.5), 5 mM $MgCl_2$, 20 mM creatine phosphate (disodium salt), 10 units (71 .μg of protein) of creatine phosphokinase, 1 mM $\alpha$-$_{32P}$ (tetrasodium salt, 2 $\mu C_i$), 0.5 mM cyclic AMP, $G^{\cdot 3H}$-labeled cyclic AMP (approximately 10,000 cpm), 0.5 mM Ro20-1724, 0.25% ethanol, and 50–200 μg of protein homogenate to be tested (i.e., homogenate from cells expressing or not expressing a T1R or T2R polypeptide, treated or not treated with a candidate modulator). Reaction mixtures are generally incubated at 37° C. for 6 minutes. Following incubation, reaction mixtures are deproteinized by the addition of 0.9 ml of cold 6% trichloroacetic acid. Tubes are centrifuged at 1800×g for 20 minutes and each supernatant solution is added to a Dowex AG50W-X4 column. The cAMP fraction from the column is eluted with 4 ml of 0.1 mM imidazole-HCl (pH 7.5) into a counting vial. Assays should be performed in triplicate. Control reactions should also be performed using protein homogenate from cells that do not express a T1R or T2R polypeptide.

According to the invention, adenylate cyclase activity is "changed" if it increases or decreases by 10% or more in a sample taken from cells treated with a candidate modulator of T1R or T2R activity, relative to a similar sample of cells not treated with the candidate modulator or relative to a sample of cells not expressing the T1R or T2R polypeptide (mock-transfected cells) but treated with the candidate modulator.

iii) cAMP Assay:

Intracellular or extracellular cAMP is measured using a cAMP radioimmunoassay (RIA) or cAMP binding protein according to methods widely known in the art. For example, Horton & Baxendale, *Methods Mol. Biol.* 41: 91–105 (1995) (135), which is incorporated herein by reference, describes an RIA for cAMP.

A number of kits for the measurement of cAMP are commercially available, such as the High Efficiency Fluorescence Polarization-based homogeneous assay marketed by LJL Biosystems and NEN Life Science Products. Control reactions should be performed using extracts of mock-transfected cells to exclude possible non-specific effects of some candidate modulators.

The level of cAMP is "changed" if the level of cAMP detected in cells, expressing a T1R or T2R polypeptide and treated with a candidate modulator of T1R or T2R activity (or in extracts of such cells), using the RIA-based assay of Horton & Baxendale, 1995 (135), increases or decreases by at least 10% relative to the cAMP level in similar cells not treated with the candidate modulator.

iv) Phospholipid Breakdown, DAG Production and Inositol Triphosphate Levels:

Receptors that activate the breakdown of phospholipids can be monitored for changes due to the activity of known or suspected modulators of T1R or T2R by monitoring phospholipid breakdown, and the resulting production of second messengers DAG and/or inositol triphosphate ($IP_3$). Methods of detecting each of these are described in Phospholipid Signalling Protocols, edited by Ian M. Bird, Totowa, N.J., Humana Press, (1998) (136), which is incorporated herein by reference. See also Rudolph et al., *J. Biol. Chem.* 274: 11824–11831 (1999) (137), which also describes an assay for phosphatidylinositol breakdown. Assays should be performed using cells or extracts of cells expressing T1R or T2R, treated or not treated or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol triphosphate levels are "changed" if they increase or decrease by at least 10% in a sample from cells expressing a T1R or T2R polypeptide and treated with a candidate modulator, relative to the level observed in a sample from cells expressing a T1R or T2R polypeptide that is not treated with the candidate modulator.

v) PKC Activation Assays:

Growth factor receptor tyrosine kinases can signal via a pathway involving activation of Protein Kinase C (PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, the activity of receptors that signal via PKC can be monitored through the use of reporter gene constructs driven by the control sequences of genes activated by PKC activation. This type of reporter gene-based assay is discussed in more detail below.

For a more direct measure of PKC activity, the method of Kikkawa et al., 1982, J. Biol. Chem. 257: 13341 (1982) (138), can be used. This assay measures phosphorylation of a PKC substrate peptide, which is subsequently separated by binding to phosphocellulose paper. This PKC assay system can be used to measure activity of purified kinase, or the activity in crude cellular extracts. Protein kinase C sample can be diluted in 20 mM HEPES/2 mM DTT immediately prior to assay.

The substrate for the assay is the peptide Ac-FKKSFKL-$NH_2$ (SEQ ID NO: 208), derived from the myristoylated alanine-rich protein kinase C substrate protein (MARCKS). The $K_m$ of the enzyme for this peptide is approximately 50 μM. Other basic, protein kinase C-selective peptides known in the art can also be used, at a concentration of at least 2–3 times their $K_m$. Cofactors required for the assay include calcium, magnesium, ATP, phosphatidylserine and diacylglycerol. Depending upon the intent of the user, the assay can be performed to determine the amount of PKC present (activating conditions) or the amount of active PKC present (non-activating conditions). For most purposes according to the invention, non-activating conditions will be used, such that the PKC, that is active in the sample when it is isolated, is measured, rather than measuring the PKC that can be activated. For non-activating conditions, calcium is omitted from the assay in favor of EGTA.

The assay is performed in a mixture containing 20 mM HEPES, pH 7.4, 1–2 mM DTT, 5 mM $MgCl_2$, 100 μM ATP, .about. 1 $\mu C_i \cdot \gamma^{32}$P-ATP, 100 μg/ml peptide substrate (~100 μM), 140 μM/3.8 μM phosphatidylserine/diacylglycerol membranes, and 100 μM calcium (or 500 μM EGTA). 48 μL of sample, diluted in 20 mM HEPES, pH 7.4, 2 mM DTT is used in a final reaction volume of 80 μl. Reactions are performed at 30° C. for 5–10 minutes, followed by addition of 25 μl of 100 mM ATP, 100 mM EDTA, pH 8.0, which stops the reactions.

After the reaction is stopped, a portion (85 μl) of each reaction is spotted onto a Whatman P81 cellulose phosphate filter, followed by washes: four times 500 ml in 0.4% phosphoric acid, (5–10 min per wash); and a final wash in 500 ml 95% EtOH, for 2–5 min. Bound radioactivity is measured by scintillation counting. Specific activity (cpm/nmol) of the labelled ATP is determined by spotting a sample of the reaction onto PS1 paper and counting without washing. Units of PKC activity, defined as nmol phosphate transferred per min, are then calculated by known methods.

An alternative assay can be performed using a Protein Kinase C Assay Kit sold by Pan Vera (Cat. #P2747).

Assays are performed on extracts from cells expressing a T1R or T2R polypeptide, treated or not treated with a candidate modulator. Control reactions should be performed using mock-transfected cells, or extracts from them in order to exclude possible non-specific effects of some candidate modulators.

According to the invention, PKC activity is “changed” by a candidate modulator when the units of PKC measured by either assay described above increase or decrease by at least 10%, in extracts from cells expressing T1R or T2R and treated with a candidate modulator, relative to a reaction performed on a similar sample from cells not treated with a candidate modulator.

iv) Kinase Assays:

MAP Kinase assays have already been described supra. MAP kinase activity can be assayed using any of several kits available commercially, for example, the p38 MAP Kinase assay kit sold by New England Biolabs (Cat #9820) or the FlashPlate™ MAP Kinase assays sold by Perkin-Elmer Life Sciences.

MAP Kinase activity is “changed” if the level of activity is increased or decreased by 10% or more in a sample from cells, expressing a T1R or T2R polypeptide, treated with a candidate modulator relative to MAP kinase activity in a sample from similar cells not treated with the candidate modulator.

Direct assays for tyrosine kinase activity using known synthetic or natural tyrosine kinase substrates and labeled phosphate are well known, as are similar assays for other types of kinases (e.g., Ser/Thr Kinases). Kinase assays can be performed with both purified kinases and crude extracts prepared from cells expressing a T1R or T2R polypeptide, treated with or without a candidate modulator. Control reactions should be performed using mock-transfected cells, or extracts from them in order to exclude possible non-specific effects of some candidate modulators. Substrates can be either full-length protein or synthetic peptides representing the substrate. Pinna & Ruzzene (Biochem. Biophys. Acta 1314: 191–225 (1996) (139)) list a number of phosphorylation substrate sites useful for detecting kinase activities. A number of kinase substrate peptides are commercially available. One that is particularly useful is the “Src-related peptide,” RRLIEDAEYAARG (SEQ ID NO: 209) (available from Sigma #A7433), which is a substrate for many receptor and nonreceptor tyrosine kinases. Because the assay described below required binding of peptide substrates to filters, the peptide substrates should have a net positive charge to facilitate binding. Generally, peptide substrates should have at least 2 basic residues and a free amino terminus. Reactions generally use a peptide concentration of 0.7–1.5 mM.

Assays are generally carried out in a 25 μl volume comprising 5 .mu.l of 5× kinase buffer (5 mg/mL BSA, 150 mM Tris-Cl (pH 7.5), 100 mM $MgCl_2$; depending upon the exact kinase assayed for, $MnCl_2$ can be used in place of or in addition to the $MgCl_2$), 5 .mu.l of 1.0 mM ATP (0.2 mM final concentration), $\gamma^{32}$P-ATP (100–500 cpm/pmol), 3 μl of 10 mM peptide substrate (1.2 mM final concentration), cell extract containing kinase to be tested (cell extracts used for kinase assays should contain a phosphatase inhibitor (e.g. 0.1–1 mM sodium orthovanadate)), and $H_2O$ to 25 μl. Reactions are performed at 30° C., and are initiated by the addition of the cell extract.

Kinase reactions are performed for 30 seconds to about 30 minutes, followed by the addition of 45 μl of ice-cold 10% trichloroacetic acid (TCA). Samples are spun for 2 minutes in a microcentrifuge, and 35 μl of the supernatant is spotted onto Whatman P81 cellulose phosphate filter circles. The filters are washed three times with 500 ml cold 0.5% phosphoric acid, followed by one wash with 200 ml of acetone at room temperature for 5 minutes. Filters are dried and incorporated $^{32}$P is measured by scintillation counting. The specific activity of ATP in the kinase reaction (e.g. in cpm/pmol) is determined by spotting a small sample (2–5 μl) of the reaction onto a P81 filter circle and counting directly, without washing. Counts per minute obtained in the kinase reaction (minus blank) are then divided by the specific activity to determine the moles of phosphate transferred in the reaction.

Tyrosine kinase activity is “changed” if the level of kinase activity is increased or decreased by 10% or more in a sample from cells, expressing a T1R or T2R polypeptide, treated with a candidate modulator relative to kinase activity in a sample from similar cells not treated with the candidate modulator.

vii) Transcriptional Reporters for Downstream Pathway Activation:

The intracellular signal initiated by binding of an agonist to a receptor, e.g., T1R or T2R, sets in motion a cascade of intracellular events, the ultimate consequence of which is a rapid and detectable change in the transcription or translation of one or more genes. The activity of the receptor can therefore be monitored by detecting the expression of a reporter gene driven by control sequences responsive to T1R or T2R activation.

As used herein "promoter" refers to the transcriptional control elements necessary for receptor-mediated regulation of gene expression, including not only the basal promoter, but also any enhancers or transcription-factor binding sites necessary for receptor-regulated expression. By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, CAT, GFP, β-lactamase or β-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful for making reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

An example of a gene that is responsive to a number of different stimuli is the c-fos proto-oncogene. The c-fos gene is activated in a protein-synthesis-independent manner by growth factors, hormones, differentiation-specific agents, stress, and other known inducers of cell surface proteins. The induction of c-fos expression is extremely rapid, often occurring within minutes of receptor stimulation. This characteristic makes the c-fos regulatory regions particularly attractive for use as a reporter of receptor activation.

The c-fos regulatory elements include (see, Verma et al., Cell 51: 513–514) (1987) (140): a TATA box that is required for transcription initiation; two upstream elements for basal transcription, and an enhancer, which includes an element with dyad symmetry and which is required for induction by TPA, serum, EGF, and PMA.

The 20 bp c-fos transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is, as the name implies, responsive to levels of intracellular cAMP. Therefore, the activation of a receptor that signals via modulation of cAMP levels can be monitored by detecting either the binding of the transcription factor, or the expression of a reporter gene linked to a CREB-binding element (termed the CRE, or cAMP response element). The DNA sequence of the CRE is TGACGTCA. (Reporter constructs responsive to CREB binding activity are described in U.S. Pat. No. 5,919,649) (141).

Other promoters and transcriptional control elements, in addition to the c-fos elements and CREB-responsive constructs, include the vasoactive intestinal peptide (VIP) gene promoter (cAMP responsive; Fink et al., 1985, *Proc. Natl. Acad. Sci.* 85:6662–6666) (1988) (142); the somatostatin gene promoter (cAMP responsive; Montminy et al., *Proc. Natl. Acad. Sci.* 83:6682–6686 (1986) (143); the proenkephalin promoter (responsive to cAMP, nicotinic agonists, and phorbol esters; Comb et al., *Nature* 323:353–356 (1986) (144); the phosphoenolpyruvate carboxy-kinase (PEPCK) gene promoter (cAMP responsive; Short et al., *J. Biol. Chem.* 261:9721–9726 (1986) (145)).

Additional examples of transcriptional control elements that are responsive to changes in GPCR activity include, but are not limited to those responsive to the AP-1 transcription factor and those responsive to NF-KB activity. The consensus AP-1 binding site is the palindrome TGA(C/G)TCA (Lee et al., *Nature* 325: 368–372 (1987) (146); Lee et al., *Cell* 49: 741–752 (1987) (147)). The AP-1 site is also responsible for mediating induction by tumor promoters such as the phorbol ester 12-O-tetradecanoylphorbol-.beta.-acetate (TPA), and are therefore sometimes also referred to as a TRE, for TPA-response element. AP-1 activates numerous genes that are involved in the early response of cells to growth stimuli. Examples of AP-1 responsive genes include, but are not limited to the genes for Fos and Jun (which proteins themselves make up AP-1 activity), Fos-related antigens (Fra) 1 and 2, I Kβα, ornithine decarboxylase, and annexins I and II.

The NF-KB binding element has the consensus sequence GGGGACTTTCC (SEQ ID NO: 210). A large number of genes have been identified as NF-KB responsive, and their control elements can be linked to a reporter gene to monitor GPCR activity. A small sample of the genes responsive to NF-KB includes those encoding IL-1β. (Hiscott et al., *Mol. Cell. Biol.* 13:6231–6240 (1993)(148)), TNF-α (Shakhov et al., *J. Exp. Med.* 171: 35–47 (1990)(149)), CCR5 (Liu et al., AIDS Res. Hum. Retroviruses 14: 1509–1519 (1998) (150)), P-selectin (Pan & McEver, *J. Biol. Chem.* 270: 23077–23083 (1995) (151)), Fas ligand (Matsui et al., *J. Immunol.* 161: 3469–3473 (1998) (152)), GM-CSF (Schreck & Baeuerle, *Mol. Cell. Biol.* 10: 1281–1286 (1990) (153)) and IKβα (Haskill et al., *Cell* 65: 1281–1289 (1991) (154)). Vectors encoding NF-KB-responsive reporters are also known in the art or can be readily made by one of skill in the art using, for example, synthetic NF-KB elements and a minimal promoter, or using the NF-KB-responsive sequences of a gene known to be subject to NF-KB regulation. Further, NF-KB responsive reporter constructs are commercially available e.g. from CLONTECH.

To screen for agonists, the cells are left untreated, exposed to candidate modulators, and expression of the reporter is measured. An increase of at least 50% in reporter expression in the presence of a candidate modulator indicates that the candidate is a modulator of T1R or T2R activity. An agonist will induce at least as many, and preferably the same amount or more of reporter expression than buffer alone. This approach can also be used to screen for inverse agonists where cells express a T1R or T2R polypeptide at levels such that there is an elevated basal activity of the reporter. A decrease in reporter activity of 10% or more in the presence of a candidate modulator, relative to its absence, indicates that the compound is an inverse agonist.

To screen for antagonists, the cells expressing T1R or T2R and carrying the reporter construct are contacted in the presence and absence of a candidate modulator. A decrease of 10% or more in reporter expression in the presence of candidate modulator, relative to the absence of the candidate modulator, indicates that the candidate is a modulator of T1R or T2R activity.

Controls for transcription assays include cells not expressing T1R or T2R but carrying the reporter construct, as well as cells with a promoterless reporter construct. Compounds that are identified as modulators of T1R or T2R-regulated transcription should also be analyzed to determine whether they affect transcription driven by other regulatory sequences and by other receptors, in order to determine the specificity and spectrum of their activity.

The transcriptional reporter assay, and most cell-based assays, are well suited for screening expression libraries for proteins for those that modulate T1R or T2R activity. The libraries can be, for example, cDNA libraries from natural sources, e.g., plants, animals, bacteria, etc., or they can be libraries expressing randomly or systematically mutated variants of one or more polypeptides. Genomic libraries in viral vectors can also be used to express the mRNA content of one cell or tissue, in the different libraries used for screening of T1R or T2R.

viii) Inositol Phosphate (IP) Measurement:

Cells of the invention are labelled for 24 hours with 10 μCi/ml$^3$H] inositol in inositol free DMEM containing 5% FCS, antibiotics, amphotericin, sodium pyruvate and 400 μg/ml G418. Cells are incubated for 2 h in Krebs-Ringer Hepes (KRH) buffer of the following composition (124 mM NaCl, 5 mM KCl, 1.25 mM $MgSO_4$, 1.45 mM $CaCl_2$, 1.25 mM $KH_2PO_4$, 25 mM Hepes (pH: 7.4) and 8 mM glucose). The cells are then challenged with various nucleotides for 30 s. The incubation is stopped by the addition of an ice cold 3% perchloric acid solution. IP are extracted and separated on Dowex columns as previously described. 2 MeSATP and ATP solutions (1 mM) are treated at room temperature with 20 units/ml CPK and 10 Mm cp for 90 min to circumvent problems arising from the contamination and degradation of triphosphate nucleotide solutions.

T1R or T2R Assay

The invention provides for an assay for detecting the assay of a receptor of the invention in a sample. For example, T1R or T2R activity can be measured in a sample comprising a cell or a cell membrane that expresses T1R or T2R. The assay is performed by incubating the sample in the presence or absence of a modulator and carrying out a second messenger assay, as described above. The results of the second messenger assay performed in the presence or absence of the activator are compared to determine if the T1R or T2R receptor is active.

Any of the assays of receptor activity, including but not limited to the GTP-binding, GTPase, adenylate cyclase, cAMP, phospholipid-breakdown, diacylglycerol, inositol triphosphate, arachidonic acid release (see below), PKC, kinase and transcriptional reporter assays, can be used to determine the presence of an agent in a sample, e.g., a tissue sample, that affects the activity of the T1R or T2R receptor molecule. To do so, T1R or T2R polypeptide is assayed for activity in the presence and absence of the sample or an extract of the sample. An increase in T1R or T2R activity in the presence of the sample or extract relative to the absence of the sample indicates that the sample contains an agonist of the receptor activity. A decrease in receptor activity in the presence of an agonist and the sample, relative to receptor activity in the absence thereof, indicates that the sample contains an antagonist of T1R or T2R activity.

The amount of increase or decrease in measured activity necessary for a sample to be said to contain a modulator depends upon the type of assay used. Generally, a 10% or greater change (increase or decrease) relative to an assay performed in the absence of a sample indicates the presence of a modulator in the sample. One exception is the transcriptional reporter assay, in which at least a two-fold increase or 10% decrease in signal is necessary for a sample to be said to contain a modulator. It is preferred that an agonist stimulates at least 50%, and preferably 75% or 100% or more, e.g., 2-fold, 5-fold, 10-fold or greater receptor activation.

Other functional assays include, for example, microphysiometer or biosensor assays (see Hafner, 2000, Biosens. Bioelectron. 15: 149–158) (2000) (155)).

As described in detail infra, it has been found that cell-based assays according to the invention, e.g., MAPK and cAMP assay methods exemplified, enable the detection of robust activation of bitter taste receptors (mT2R05) and hT2R04 as well as the sweet receptor (T1R2/T1R3) and umami receptor (T1R1/T1R3). (These results are discussed in detail in the examples and the figures referred to therein.) It is anticipated further, based on these results, that cell-based assays that detect the effect of putative modulator on $G_i$/T1R or $G_i$/TR mediated signaling pathways, e.g., MAPK and cAMP assays, will be identify compounds that modulate the activity of any functional taste receptor comprising a T1R or T2R polypeptide or functional fragment.

Additionally, the results obtained indicate that the responses obtained are receptor-dependent and receptor-specific. For example, the parental cell lines HEK293 or HEK293T-$G_{15}$ do not exhibit comparable activation of MAPK or a reduction in cAMP (See FIGS. 1–7) when stimulated with the same agonists.

Further, it has been found that treatment of taste-receptor expressing cells with pertussis toxin (PTX), which blocks functional coupling between GPCRs and Gi proteins, prevents MAPK activation and prevents a decrease in cAMP accumulation. These results indicate that the subject MAPK and cAMP assay systems provide an efficient means for identifying compounds that modulate, e.g., enhance, agonize or antagonize the activity of specific taste receptors i.e., T1R2/T1R3 (sweet receptor) or T1R1/T1R3 (umami receptors) or specific T2Rs (bitter receptors).

The subject MAPK assays are exemplified by the above-described antibody-based methods for detecting MAPK activation. As noted supra, however, the invention encompasses any suitable assay system for detecting activated MAPK. (71) Vaster et al., *Biochem. J.* 350:717–22 (2000), incorporated by reference in its entirety herein, describes a phosphospecific cell-based ELISA for detecting p42/p44 MAPK, p38MAPK, protein kinase B and cAMP response-element binding protein. This assay, referred to as "PACE", (phosphospecific antibody cell-based ELISA) detects activated MAPK without the use of radioactive labels, and can use adherent cells or cells in suspension.

Alternatively, the detection of MAPK activation can be effected by the use of proximity assays (AlphaScreenTM) from Packard or by use of High Content Screen System (ERK MAPK Activation HitKit™) from Cellomics. These assays or other available MAPK assays, can be used as part of a high throughput screening platform for identifying bitter, sweet and umami receptor agonists and antagonists.

In the preferred embodiment, cAMP accumulation is measured by an immunofluorescence assay as described in the examples. However, as noted supra, the subject invention embraces the use of any suitable means for detecting cAMP levels. Such methods include the detection of cAMP using anti-cAMP antibodies in an ELISA-based format, or by second messenger reporter system assays. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. As discussed supra, reporter systems can be constructed which have a promoter containing multiple cAMP response elements before a reporter gene, e.g., beta-galactosidase or luciferase. In this assay, a constitutively activated $G_i$ linked receptor causes a reduction in cAMP that results in inhibition of the gene expression and reduced expression of the reporter gene. The reporter protein can be detected using standard biochemical assays.

Functional Coupling of $G_i$ Proteins to T1Rs and T2Rs

In another aspect, the present invention relates to the discovery that T1Rs and T2Rs functionally couple to G proteins other than promiscuous G proteins such as $G\alpha_{15}$ or gustducin. Particularly, the invention involves the discovery that T1Rs and T2Rs functionally couple to $G_i$ proteins and use $G_{\alpha i}$ to transmit signals to downstream effectors, e.g., adenylyl cyclase and MAP Kinase.

$G_s$ stimulates the enzyme adenylyl cyclase. By contrast, $G_i$ (and $G_z$ and $G_0$) inhibit this enzyme. Adenylyl cyclase catalyzes the conversion of ATP to cAMP. Thus, constitutively activated GPCRs that couple $G_i$ (or $G_z$ and $G_0$) protein associated with a decrease in cellular levels of cAMP. See, generally, "Indirect Mechanisms of Synoptic Transmission," Chapter 8, From *Neuron to Brain* (*3rd Edition*), Nichols, J. G. et al etds., Sinaver Associates, Inc. (1992). Thus, assays that detect cAMP can be utilized to determine if a compound is e.g., an inverse agonist to the receptor (i.e., such a compound would decrease the levels of cAMP). As noted previously, a variety of approaches can be used to measure cAMP, e.g., anti-cAMP antibodies in an ELISA method, or the second messenger reporter system assays described supra.

As noted, a $G_i$ protein coupled receptor is known to inhibit adenylyl cyclase, resulting in a decrease in cAMP production. Another effective technique for measuring the decrease in production of cAMP as an indication of constitutive activation of a receptor that predominantly couples $G_i$ upon activation can be accomplished by co-transfecting a signal enhancer, e.g., a non-endogenous, constitutively activated receptor that predominantly couples with $G_s$ upon activation with the $G_i$ linked GPCR, i.e., a T1R or T2R. In contrast to $G_i$ coupled GPCRs, constitutive activation of a $G_s$ coupled receptor can be determined based upon an increase in production of cAMP. Thus, this construction approach is intended to advantageously exploit these "opposite" effects. For example, co-transfection of a non-endogenous, constitutively activated $G_s$ coupled receptor ("signal enhancer") with the $G_i$ coupled receptor (T1R or T2R) provides a baseline cAMP signal (i.e., although the $G_i$ coupled receptor will decrease cAMP levels, this "decrease" will be relative to the substantial increase in cAMP levels established by constitutively activated $G_s$ coupled signal enhancer). By then co-transfecting the signal enhancer with a constitutively activated version of the target receptor, cAMP will decrease further (relative to the baseline) due to the increased functional activity of the $G_i$ target, i.e., T1R or T2R, which decreases cAMP.

Screening for potential T1R or T2R modulators using such a cAMP assay can then be accomplished with two provisos: first, relative to the $G_i$ coupled target receptor (T1R or T2R), "opposite" effects will result, i.e., an inverse agonist of the $G_i$ coupled target receptor will decrease this signal; second candidate modulators that are identified using this approach should be assessed independently to ensure that these compounds do not target the signal enhancing receptor (this can be accomplished prior to or after screening against co-transfected receptor).

Additionally, as described above, other assays can be designed which assess the effects of cAMP on other cellular events. Alteration of the intracellular concentration of cAMP is known to affect many cellular reactions. For example, an increase in cAMP intracellular concentrations stimulates the activity of protein Kinases. For a general review of cAMP and secondary messenger systems associated therewith, reference is made to "Molecular Cell Biology", Darnell et al, Chapter 16 (1986) (156).

Particular signal substances that use cAMP as a second messenger include by way of example calcitonin, chorionic gonadotropin, corticotrophin, epinephrine, follicle-stimulating homone, glucagon, leutenizing hormone, lipotropin, melanocyte-stimulating hormone, norepinephrine, parathyroid hormone (PTH), thyroid-stimulating hormone and vasopressin.

The subject assays which measure the effect of a putative modulator or TR/$G_i$ associated signaling pathways were not suggested by the state of the art. In vivo, receptors for bitter and sweet taste functionally couple to the taste-specific G-protein α-gustducin to initiate the transduction cascade leading to taste perception. In heterologous cells, however, previously there was no direct evidence of functional coupling to G-proteins other than $G\alpha_{16}$, a promiscuous G-protein widely used for receptor deorphaning. Unexpectedly, the present inventors have demonstrated that receptors for bitter, sweet and also umami taste couple effectively to $G_i$-signaling pathways when expressed in human embryonic kidney cells. For example, cycloheximide, a bitter compound, specifically activates ERK1/2 mitogen-activated kinases in cells expressing the mouse bitter receptor mT2R5 and the rat bitter receptors rT2R9. Consistent with the foregoing, activation of ERK1/2 is totally abolished upon treatment with pertussis toxin indicating that these receptors couple to ERK1/2 activation through $G\alpha_i$. Also in agreement with these observations, cycloheximide inhibits the forskolin-induced cAMP accumulation in mT2R5-expressing cells by 70%. Similarly, as shown infra in the examples, natural and artificial sweeteners such as sucrose, D-tryptophan, saccharin and cyclamate (known activates of T1R2/T1R3 sweet receptors) activate ERK1/2 in cells expressing the human sweet receptor hT1R2/hT1R3. Also, as shown in detail infra, monosodium glutamate exclusively activates ERK1/2 in cells expressing the human umami receptor hT1R1/hT1R3 and the effect is greatly enhanced by the presence of inosine monophosphate. Again, consistent with Gi coupling, these responses are prevented by treatment with pertussis toxin.

Further, as shown in detail infra, sweeteners including cyclamate, aspartame, saccharin, and monellin significantly inhibit the forskolin-induced cAMP accumulation in hT1R2/hT1R3-expressing cells by 50–70%. Monosodium glutamate also decreases basal levels of cAMP in hT1R1/hT1R3-expressing cells by 50%.

While the results obtained are unexpected, some earlier information relating to taste-specific GPCRs is consistent with these results. Particularly it was known that taste-specific GPCRs use heterotrimeric G proteins to relay intracellular signals leading to cell depolarization and, subsequently, taste perception. Also, it was known that deletion of the gene encoding a taste-specific G protein subunit, α-gustducin (73) (McLaughlin et al., *Nature* 357:563–569 (1992)), produces mice that are defective in detection of bitter and sweet substances (17). The visual G-protein α-transducin is also expressed in taste tissue (74, 75) (Ruiz-Avila et al., *Nature* 376:80–85 (1995); McLaughlin et al., *Phys. Behav.* 56(6):1157–64 (1994)) and its selective expression in α-gustducin deficient TRCs partially rescues the tasting phenotype to sweet and bitter substances (27) He et al, *Chem. Senses,* 27(8): 719–27 (2002). In biochemical assays, bitter tasting substances activate α-gustducin (127) Ming et al., *Proc. Natl Acad Sci, USA* 95(10): 8933–8 (1992) and α-transducin (128) Ruiz-Avila et al., *Chem Senses,* 20(4): 361–8 (2000). Similarly, cyclohexímide induces α-gustducin activation in cell membranes derived from mT2R5-expressing cells Chandrashekar et al. *Cell* 100(6): 703–711 (2000) (80).

It has also been suggested that taste GPCRs use G-proteins other than α-gustducin to relay intracellular signals and that TRCs express a vast repertoire of different G protein subunits. Expression of $G\alpha_s$, $G\alpha_{15}$, $G\alpha_{i1\text{-}1}$, $G\alpha_{i1\text{-}2}$, $G\alpha_{l\text{-}3}$ and $G\alpha_q$ has been detected in taste tissues using RT-PCR (15, 25). $G\alpha_{i1\text{-}2}$ can also be detected by in situ hybridization (25, 26) and immunostaining (25) in TRCs and a study by Hoon et al., (32) reported that $G_i$ proteins are expressed in almost all TRCs. As a result, $G\alpha_{i1\text{-}2}$ positive cells are thought to be larger in number than Gα-gustducin-positive cells in rat circumvallate papillae (Kusakabe et al., *Chem. Senses* 25(5):525–31 (2000) (25)). Also, α-gustducin deficient mice retain residual responsiveness to bitter and sweet stimuli (Wong et al., *Nature* 381:796–800 (1996); He et al, *Chem Senses* 27(8): 719–27 (2002); Ruiz-Avila et al, *PNC Natl Acad Sci, USA* 98(15): 541–551 (2001) (17, 27, 28)) suggesting that another G protein may complement α-gustducin functions in TRCs.

Further, some earlier biochemical studies have suggested the possible existence of signaling pathways parallel to α-gustducin in TRCs. For example, the application of bitter-tasting substances (Yan et al, *Am. J. Physiol Cell Physiol.* 280(2): C742–751 (2001) (76)) to taste tissue reduces the levels of 3', 5'-cyclic nucleotide monophosphate (cAMP) in taste tissue papillae. By contrast, the application of sweeteners to taste tissue membranes has been reported to increase levels of cAMP Naim et al, *Comp. Biochem Physiol B* 100(3): 455–8 (1991); Striem et al, *Biochem J.* 260(1): 121–6 (1989) (77, 78). However, prior to this invention there existed no direct evidence of functional coupling between taste GPCRs and G-proteins other than α-gustducin, α-transducin and $G\alpha_{15/16}$, a promiscuous G-protein widely used for receptor deorphaning (79) (Kostensis, *Trends Pharmacol Sci* 22(11) 560–564 (2001)) and none of these G-proteins were known to directly activate effectors capable of modulating the levels of cyclic nucleotides in TRCs.

Current models that do not take into account the experimental results herein suggested that the sweet taste receptor can also couple to $G\alpha_s$ and that α-gustducin activates, by unknown mechanisms, a taste specific cyclic nucleotide phosphodiesterase (PDE) (9, 10) (Gilbertson et al., *Curr. Opin. Neurobiol.* 10(4): 519–27 (2000); Margolskee, R. F., *J. Biol Chem* 277(1):1–4 (2002)). However, these hypothetical signaling pathways have not yet been definitely linked to taste receptor activation in TRCs or in fact any other cell types.

By contrast, the present inventors have studied coupling of receptors for bitter, sweet and umami taste to classical GPCR-linked signaling pathways in HEK293 cells, and the results obtained surprisingly demonstrate that these taste receptors can effectively couple to $G\alpha_i$-dependent activation of mitogen activated protein (MAP) kinases ERK1 and ERK2 (ERK1/2) and $G\alpha_i$-dependent inhibition of cAMP accumulation. Also, these results further surprisingly indicate that the sweet receptor does not couple to $G_s$ stimulation and accumulation of cAMP. Functional coupling to $G\alpha_i$ may explain, in part, the observations that bitter-tasting substances and MSG decrease the level of cyclic nucleotides in TRCs. Moreover, these results suggest that $G\alpha_i$ can functionally complement α-gustducin functions in TRCs.

Applications of the Subject Assays

The present invention provides cell-based assay methods that rely on the discovery that T1Rs or T2Rs functionally couple to $G_i$ proteins e.g., $G\alpha_i$ and transmit signals to downstream effectors, e.g., cAMP, MAP Kinase, and adenylyl cyclase that enable the identification of modulators, e.g., agonists, antagonists, inverse agonists enhancers of a T1R or T2R polypeptide. The T2R modulators of the invention are useful for altering taste perception, for example to induce, suppress or enhance bitter taste perception in a subject. The T1R2/T1R3 modulators are useful for modulating sweet taste, e.g., by enhancing the taste of another sweet tasting compound such as saccharin. The T1R1/T1R3 modulators identified according to the invention are useful for modulating umami taste, e.g., by enhancing the taste of a umami compound such as monosodium glutamate.

Compositions

In accordance with the methods of the present invention, a composition that is administered to alter taste perception in a subject will comprise an effective amount of a T1R or T2R modulator (agonist, antagonist, or enhancer). A T1R or T2R activator or modulator can comprise any substance, e.g., small molecule, peptide, protein, carbohydrate, oligosaccharide, glycoprotein, amino acid derivative, and the like. In general, compounds will be identified by screening libraries of potential taste modulatory compounds, which may be comprised of synthetic or naturally occurring compounds. The library may be random or may comprise compounds having related structures or are structures or substitutions. After lead candidates are identified, compound libraries having similar structure will be produced and screened for T1R or T2R modulatory activity according to the invention. T1R or T2R modulators identified as disclosed herein can be used to prepare compositions suitable for oral use, including but not limited to food, beverages, oral washes, dentifrices, cosmetics, and pharmaceuticals. T1R or T2R modulators can also be used as additives to alter the sweet, umami or bitter taste of a compound that is of palatable but undesirable for oral use, for example compounds comprised in household cleansers, poisons, etc. Such modulators will alter bitter, sweet or umami tasting compounds contained therein.

For example, representative foods having an undesirable or bitter taste include, but are not limited to, citrus fruits such as grapefruit, orange, and lemon; vegetables such as tomato, pimento, celery, melon, carrot, potato, and asparagus; seasoning or flavoring materials such as flavor, sauces, soy sauce, and red pepper; foods originating from soybean; emulsion foods such as cream, dressing, mayonnaise, and margarine; processed marine products such as fish meat, ground fish meat, and fish eggs; nuts such as peanuts; fermented foods such as fermented soybean; meats and processed meats; pickles; noodles; soups including powdery soups; dairy products such as cheese; breads and cakes; confectioneries such as candies, chewing gum, and chocolate; and specifically prepared foods for health.

Representative cosmetics eliciting bitter taste (e.g., skin lotions, creams, face packs, lip sticks, foundations, shaving preparations, after-shave lotions, cleansing foams, and cleansing gels) include but are not limited to those compositions that include surfactants such as sodium alkyl sulfate and sodium monoalkyl phosphate; fragrances such as menthol, linalool, phenylethyl alcohol, ethyl propionate, geraniol, linalyl acetate and benzyl acetate; antimicrobials such as methyl paraben, propyl paraben and butyl paraben; humectants such as lactic acid and sodium lactate; alcohol-denaturating agents such as sucrose octaacetate and brucine; and astringents such as aluminum lactate.

Representative pharmaceuticals having a bitter taste include acetaminophen, terfenadine, guaifenesin, trimethoprim, prednisolone, ibuprofen, prednisolone sodium phosphate, methacholine, pseudoephedrine hydrochloride, phenothiazine, chlorpromazine, diphenylhydantoin, caffeine, morphine, demerol, codeine, lomotil, lidocaine, salicyclic acid, sulfonamides, chloroquine, a vitamin preparation, minerals and penicillins, neostigmine, epinephrine, albuterol, dephenhydramine, chlorpheniramine maleate, chlordiazepoxide, amitriptyline, barbiturates, diphenylhydantoin, caffeine, morphine, demerol, codeine, lomotil, lidocaine, salicyclic acid, sulfonamides, chloroquine, a vitamin preparation, minerals and penicillins.

Representative sweeteners which may be modulated by compounds according to the invention include xylitol, sorbitol, saccharin, sucrose, glucose, fructose, cyclamate, aspartame, monellin, and the like, and derivatives thereof.

Representative umami compounds, the taste which may be modulated according to the invention include L-glutamate, L-asparate, monosodium glutamate, derivatives thereof, compounds containing and the like.

These taste modulators can also be administered as part of prepared food, beverage, oral wash, dentifrice, cosmetic, or drug. To prepare a composition suitable for administration to a subject, a T1R or T2R modulator can be admixed with a compound, the taste of which is to be modulated in amount comprising about 0.001% to about 10% by weight, preferably from about 0.01% to about 8% by weight, more preferably from about 0.1% to about 5% by weight, and most preferably from about 0.5% to about 2% by weight.

Suitable formulations include solutions, extracts, elixirs, spirits, syrups, suspensions, powders, granules, capsules, pellets, tablets, and aerosols. Optionally, a formulation can include a pharmaceutically acceptable carrier, a suspending agent, a solubilizer, a thickening agent, a stabilizer, a preservative, a flavor, a colorant, a sweetener, a perfume, or a combination thereof. T1R or T2R modulators and compositions can be presented in unit-dose or multi-dose sealed containers, such as ampules and vials.

Administration

T1R or T2R modulators can be administered directly to a subject for modulation of taste perception. Preferably, a modulator of the invention is administered orally or nasally.

In accordance with the methods of the present invention, an effective amount of a T1R or T2R modulator is administered to a subject. The term "effective amount" refers to an amount of a composition sufficient to modulate T1R or T2R activation and/or to modulate taste perception, e.g., bitter, sweet or umami taste perception.

An effective amount can be varied so as to administer an amount of an T1R or T2R modulator that is effective to achieve the desired taste perception. The selected dosage level will depend upon a variety of factors including the activity of the T1R or T2R modulator, formulation, combination with other compositions (e.g., food, drugs, etc.), the intended use (e.g., as a food additive, dentifrice, etc.), and the physical condition and prior medical history of the subject being treated.

An effective amount or dose can be readily determined using in vivo assays of taste perception as are known in the art. Representative methods for assaying taste perception are described infra.

EXAMPLES

The invention is further illustrated by the following non-limiting examples wherein the following materials and methods are used.

Materials and Methods

Sweeteners, agonists and toxins. Sucrose, aspartame, cyclamate, monellin, monosodium glutamate, inosine monophosphate, isoproterenol, epidermal growth factor, denatonium benzoate, quinine sulfate, cycloheximide, rolipram and forskolin were from Sigma (St-Louis, Mo.). Pertussis toxin (PTX) was from List Biological Laboratories (Campbell, Calif.).

Establishment of stable cell lines. An inducible expression system was used for the umami taste receptor line (hT1R1/hT1R3). Vectors were prepared using the GeneSwitch inducible system (Invitrogen, Carlsbad, Calif.). hT1R1 and hT1R3 vectors were prepared by cloning receptor cDNA into pGene/V5-His A at EcoRI/Not I sites. A modified pSwitch vector was also prepared by replacing the hygromycin β resistance gene with the puromycin resistance gene. The cDNAs for hT1R1, hT1R3, and puromycin resistance were co-transfected into HEK293 cells stably expressing $G\alpha_{15}$ (Aurora Biosciences, San Diego, (80) Chandraskekar et al, *Cell* 100(6): 703–11 (2000). hT1R1/hT1R3 stable cell lines were selected and maintained in high-glucose DMEM media containing 100 μg/mL zeocin, 0.5 μg/mL puromycin, 2 mM GlutaMAX 1, 10% dialyzed fetal bovine serum, 3 μg/mL blasticidin and penicillin/streptomyocin. To improve cell adhesion, cell flasks were pre-coated with Matrigel (Becton-Dickinson, Bedford, Mass.) at a dilution of 1:400. Expression of hT1R1 and hT1R3 was induced by treatment of cells with $6\times10^{-11}$M mifepristone for 48 hours prior to experiments. Clones were tested and selected for mifepristone-induced responsiveness to MSG/IMP using calcium-imaging experiments (data not shown). The clone used in this study did not show any functional expression of hT1R1/R3 without induction (data not shown).

Establishment of the sweet (hT1R2/R3) receptor line stable cell line has already been described Li et al., *Proc. Natl Acad. Sci, USA* 99(7): 4692–6 (2002) (14). Cells were maintained in low-glucose DMEM media containing 10% heat-inactivated dialyzed FIBS, penicillin/streptomyocin, 3 μg/mL blasticidin, 100 ug/ml zeocin, and 0.5 ug/ml puromycin in Matrigel-coated flasks.

HEK293 cells were transfected with 5 μg of linearized Rho-mT2R5 plasmid (80) Chandraskekar et al (2000) in pEAK10 (Edge biosystems) using the Transit transfection reagent (Panvera). Cells were selected in the presence of 0.5 μg/ml puromycin, clones were isolated, expanded and analyzed by fluorescence-activated cell sorting for the presence of Rho tag immunoreactivity at the cell surface using a monoclonal antibody; raised against the first 40 amino acids of rhodopsin (80, 81) (Chandrashekar et al (2000); Adamus et al., *Vision Res.* 31(1): 17–31 (1991)).

Example 1

MAP Kinase Assays

Transient transfection of HEK293 cells for ERK112 assay. Subclonfluent HEK293 cells in 10 cm dishes were transfected with 4 μg of Rho-rT2R9 plasmid (Chandrashekar et al (2000); Bufe et al., *J. Receptor Signal Transduct. Res.* 20(2–3): 153–166 (2000)) pEAK10 (Edge Biosystems, Gaithersburg, Md. (80, 82)) and 2 μg pUC-18 as a carrier DNA using the Transit transfection reagent (Panvera). 24 hours later, cells were harvested using Hank's balanced salt solution without calcium or magnesium and containing 1 mM EDTA (HBSS/EDTA), and plated into 6 well plates. ERK1/2 assay was performed 48 hours post-transfection.

Determination of ERK112 phosphorylation Cells were seeded into matrigel-coated 6-well plates at a density of 0.4–0.8 million cells per well 48 hours prior to experiment. When necessary, receptor induction was initiated on the same day with 6×10-1 IM mifepristone. 16 hours prior to experiment, cells were starved using serum-free growth media containing 1% fatty acid-free bovine serum albumin (Sigma, St-Louis, Mo.). Cells were then stimulated with 2× agonist solutions in HBSS or Dulbelcco's phosphate buffered saline (D-PBS) (Invitrogen, Carlsbad, Calif.) for 5 minutes at 37° C. Following stimulation, cells were placed on ice and washed once with ice-cold buffer. Lysis buffer containing 150 mM NaCl, 50 mM TrisHE1 pH 8., 0.25% sodium deoxycholate, 1% igepal (NP-40), 2 mM sodium orthovanadate, 1 mM sodium fluoride, and protease inhibitors were then added and cells were scraped off the plates. Lysates were frozen immediately in liquid nitrogen and kept at −80° C. until further analysis.

Lysate protein concentration was determined using the Bradford method (Amresco, Solon, Ohio). Cell lysate proteins (22 FLg/lane) were resolved by SDS-PAGE using 4–20% Tris-glycine gels (Invitrogen, Carlsbad, Calif.). Following electrophoresis, proteins were transferred to nitrocellulose membranes that were subsequently blocked with 5% fat-free milk in Tris-buffer saline containing 0.2% tween-20 (TBST). Membranes were immunoblotted with phospho-p44/42 MAPK monoclonal antibody (Cell Signaling Technology, Beverly, Mass.) diluted 1:1000 in 5% milk/TBST overnight at 4° C. Secondary antibody was HRP-linked anti-mouse IgG diluted 1:2000 in 5% milk/TBST. Immunoreactive proteins were revealed using SuperSignal ECL solution (Pierce Chemical, Rockford, Ill.). Results were quantified using Kodak Image Station 440CF. In all experiments, we also assessed total amount of p44/42 MAPK loaded in each lane.

Membranes were stripped of phospho-specific antibodies using 0.2 M glycine pH 2.5 and re-blotted with p44/42 polyclonal antibodies (Cell Signaling Technology, Beverly, Mass.) diluted 1:1000 in 5% milk/TBST overnight at 4° C. Secondary antibody was HRP-linked anti-rabbit IgG diluted 1:2000 in 5% milk/TBST.

Example 2 cAMP Experiments cAMP content of cells was determined by a commercially-available chemiluminescent immunoassay kit (Applied Biosystems, Foster City, Calif.). Assay plates (96-well) were precoated with matrigel at a dilution of 1:400, and cells were seeded at a density of 60,000 cells/well (mT2R5), 75,000 cells/well (hT1R2/hT1R3) and 50,000 cells/well (hT1R1/R3) 48 hours prior to experiment. Induction of hT1R1/R3 expression was also initiated 48 hours prior to experiment. Cell media was aspirated and 90 μl of pre-warmed HBSS or D-PBS was added to each well. Cells were incubated for 45 minutes at 37° C., buffer was aspirated and 90 μl of pre-warmed agonist solutions in HBSS or D-PBS containing 50 μM rolipram and 0.7 to 5 μM forskolin was added to each of the corresponding wells. Plates were incubated for 15 minutes at 37° C. Agonists were aspirated and stimulation was terminated with addition of 60 μl of lysis buffer into each well. cAMP levels were then determined as described by the kit instructions. An independent cAMP standard curve was performed on each 96-well plates used. Chemiluminescent signals were detected using a TopCount-NXT (PerkinElmer, Wellesley, Mass.) set at a read-time of 2 seconds/well.

Example 3

Taste Study

A flavor acceptance study is conducted using a test composition comprising a T1R or T2R modulator identified according to the foregoing examples. A control composition lacking the T1R or T2R modulator, but which is otherwise substantially similar or identical to the test composition, is also used. The study employs a two-way crossover design, with all subjects evaluating both compositions, which are administered in one or more same amounts or doses. The test and control compositions are evaluated on a single study day. The sequence for administering the test and control compositions is randomized among subjects. All enrolled subjects complete all aspects of the study protocol. Subjects respond to each of the test and control compositions using ordinal taste scores (e.g., in the case of a putative T2R modulator 1=very bitter, 2=bitter, 3=indifferent, 4'not that bitter, 5=not bitter at all). Adverse events are recorded. Effectiveness of a T1R or T2R modulator is determined by measuring a significant difference in palatability of the test composition when compared to the control composition.

Results

The results of the MAP Kinase assays described supra demonstrate that the sweet and umami receptors activate ERK1/2 in a pertussis toxin sensitive fashion. The inventors used mT2R5, a mouse bitter receptor that recognizes cycloheximide (80) Chandrashekar et al. (2000), and the hT1R2/hT1R3 (hT1R2/R3) and hT1R1/hT1R3 (hT1R1/R3) combinations, the recently identified human receptors for sweet (14, 15) and MSG (umami) taste (14, 15) (Li et al (2002); Nelson et al (2002)) respectively. A clone stably expressing mT2R5 shows robust induction of ERK1/2 phosphorylation upon exposure to cycloheximide (FIG. 1A). Activation of ERK1/2 by cycloheximide in mT2R5-expressing cells peaks at 3–5 minutes post-stimulation (FIG. 1B). Other bitter substances including quinine and denatonium benzoate, sweeteners such as saccharin or sucrose and MSG do not induce ERK1/2 activation in mT2R5-expressing cells (FIG. 1A). Similarly, stimulation of rT2R9, the rat receptor orthologue of mT2R5 (85) Bufe et al, *Nat. Genet.* 32(3): 397–401, with cycloheximide leads to ERK1/2 activation in transiently transfected HEK293 cells (FIG. 1C). Sweeteners such as sucrose, saccharin, cyclamate and the sweet tasting amino acid D-tryptophan activate ERK1/2 in hT1R2/R3-expressing cells (FIG. 2A). Here again, the effect is specific for sweeteners as bitter substances and MSG fail to activate ERK1/2 in hT1R2/R3-expressing cells (FIG. 2B). MSG induces ERK1/2 activation in hT1R1/R3 expressing cells (FIG. 2B). Sweeteners and bitter substances have no significant effect on the level of activated ERK1/2 in these cells (FIG. 2B). The effects of cycloheximide on mT2R5, of saccharin, cyclamate, D-tryptophan and sucrose on hT1R2/R3 and of MSG on hT1R1/R3 are receptor dependent since naive cells do not respond significantly to any of these modalities (FIG. 1E and FIG. 2C and results not shown).

Cycloheximide activates ERK1/2 in a dose-dependent fashion in mT2R5-expressing cells with an $EC_{50}$ of 1.1±0.4 μM (mean±SD of three independent determinations) (FIG. 1D). Saccharin and sucrose also induce ERK1/2 activation in a dose-dependent fashion in hT1R2/R3-expressing cells (FIG. 3A and 3B). As expected from taste thresholds (14) (Li et al (2002)), saccharin is much more potent with an $EC_{50}$ of 277±47 RM compare to an $EC_{50}$ of 73±37 mM for sucrose (mean±SD of three independent determinations) (FIGS. 3A and 3B). One of the hallmarks of umami taste is its spectacular enhancement by inosine monophosphate (IMP) (86) Yamaguchi et al, *Physiol. Behav.* 49(5): 833–841 (1991). Accordingly, in the ERK1/2 assay, we observe a leftward shift of MSG $EC_{50}$ of about 30 folds in presence of 10 mM IMP (FIG. 3C) ($EC_{50}$ MSG: 6.7±3.4 mM, $EC_{50}$ MSG in the presence of 10 MM IMP: 0.4±0.3 mM; mean±SD of three independent determinations). PTX has been widely used as a powerful tool to discriminate among the different pathways used by GPCRs to activate ERK1/2 (87) Liebmann et al., *Cell Signal* 13(11): 833–41 (2001). Treatment of HEK293 cells with PTX prevents stimulation of ERK1/2 by cycloheximide (FIG. 2A), by sucrose, saccharin, D-tryptophan and cyclamate (FIG. 2A) and by MSG (FIG. 2B) without affecting the response of epidermal growth factor (EGF), a known tyrosine kinase receptor agonist. Collectively, these results indicate that taste receptors functionally couple to G; proteins to induce ERK1/2 activation in HEK293 cells.

Activation of bitter, sweet and umami receptors inhibit cAMP accumulation in HEK293 cells. Results described in FIGS. 2 and 3 suggest that taste receptors should also functionally couple to an inhibition of adenylyl cyclase and a reduction of cAMP levels in HEK293 cells. FIG. 4A shows that cycloheximide leads to a 70% reduction of forskolin-induced cAMP accumulation in mT2R5-expressing cells. In agreement with the involvement of G; proteins, PTX treatment fully abolishes the inhibition (FIG. 5A). The effect of cycloheximide on cAMP accumulation is mT2R5-dependent since cAMP levels remain unchanged if the same experimental conditions are applied on naive HEK293 cells (FIG. 4A). Cycloheximide inhibits cAMP accumulation in a dose-dependent fashion in mT2R5-expressing cells with an $EC_{50}$ of 1.2±0.7 μM (FIG. 5A) (mean±SD of three independent determinations) a value similar to the $EC_{50}$ calculated for ERK1/2 activation (FIG. 5D). The sweet taste hT1R2/R3 receptor also functionally couples to a robust inhibition of cAMP accumulation in HEK293 cells. Sweeteners such as aspartame, cyclamate, saccharin and monellin decrease forskolin-induced cAMP accumulation levels by 55%, 40%, 55% and 64% respectively and in a PTX-sensitive fashion (FIG. 5A). Fructose and sucrose do not inhibit cAMP accumulation in hT1R2/R3-expressing cells, on the contrary; fructose apparently increase cAMP levels (FIG. 5A). The lack of apparent effect of fructose and sucrose in the inhibition assay can be explained by the fact that these two sweeteners consistently increase cAMP levels in HEK293 cells not expressing the sweet receptor (FIG. 5B). Cyclamate (FIG. 5C), aspartame (FIG. 5D) and saccharin (FIG. 5E) inhibit cAMP accumulation in a dose-dependent fashion with $EC_{50}$s of 1.2±0.7 mM, 350±60 μM and 61±33 μM respectively (FIG. 5C) (mean±SD of three independent determinations). Our hT1R1/hT1R3 umami taste receptor line exhibits a very high basal cAMP level relative to our mT2R5 and hT1R2/hT1R3 lines (mT2R5 line: 2.8±1.9 pmol/well, T2R2/R3 line: 4.5±1.9 pmol/well, hT1R1/hT1R3 line: 180±30 pmol/well). Under experimental conditions similar to the one used for the mT2R5 and hT1R2/hT1R3 lines (in the presence of forskolin), cAMP levels more than often reached non-linear range values with the hT1R1/hT1R3 line (results not shown). However, in the absence of forskolin, MSG decreases basal levels of cAMP by 50% in this cell line (FIG. 6). On the other hand, cAMP levels remain unchanged even in the presence of MSG when receptor expression is not induced (FIG. 6).

Sweet and bitter receptors do not couple to $G_s$-stimulation in HEK293 cells. Current models suggest that the sweet receptor may couple to GS to increase cAMP levels in TRCs (9, 10) (Gilbertson et al (2000); Margolskee (2002)). Clearly, our results with ERK1/2 activation and inhibition of cAMP accumulation point to a direct coupling to $G_i$ proteins (FIGS. 2, 3 and 5). However, it is still possible that this receptor could have dual properties, coupling to both $G_i$ and $G_s$. Therefore, we sought to determine if we could detect an agonist-induce increase in cAMP levels in the hT1R2/R3 sweet taste receptor line. Under these experimental conditions (i.e. in the absence of forskolin), cAMP levels remain unchanged after stimulation with aspartame, cyclamate, saccharin and monellin (FIG. 7A). On the other hand, a β-adrenergic receptor (β2AR) agonist, isoproterenol, induces a 100% increase of cAMP accumulation in hT1R2/hT1R3-expressing cells indicating that a functional receptor/$G_s$ interaction can be detected under these experimental conditions. The sweeteners do not induce an increase of CAMP levels even after inhibiting functional coupling to $G_i$ With PTX (FIG. 7B). On the other hand, the isoproterenol response increases significantly (by more than 17 fold) under these conditions, confirming that the β2AR couples to both $G_i$ and $G_s$ proteins in HEK293 cells (88) (Paaka et al, *Nature* 390:88–91 (1997). Our experiments with mT2R5 suggest that bitter receptors do not functionally couple to $G_s$ either. Cycloheximide does not increase levels of cAMP in HEK293 cells, even after inhibiting coupling to $G_i$ proteins with PTX (FIG. 7C). Interestingly, inhibiting functional coupling to $G_i$ with PTX in the umami taste hT1R1/hT1R3 line uncovers a modest increase of 25% in cAMP levels (FIG. 6). Further experiments are necessary to determine if hT1R1/hT1R3 can indeed couple to $G_s$-signaling pathways in a significant fashion.

Conclusions

In this application, the present inventors have investigated the functional coupling of taste receptors to ERK1/2 activation and to the modulation of intracellular cAMP levels, two classical signaling events activated by dozens of GPCRs (89, 90, 91) (Morris et al., *Physiol. Rev.* 79(4): 1373–1430 (1999); Chin et al., *Ann. NY Acad. Sci.* 968: 49–64 (2002); Liebmann et al., *J. Biol Chem.* 271(49); 31098–31105 (1996)). cAMP is a universal second messenger used by a plethora of cell surface receptors to relay signals from the extracellular milieu to the intracellular signaling machinery such as protein kinases, transcription factors and ion channels (89, 90, 92) (Morris and Malbon (1999); Chin et al (2002); Robinson-White and Stratakis, *Ann NY Acad. Sci.* 968: 256–270 (2002)). GPCRs activation of Gαs and $G\alpha_i$ respectively increase and decrease intracellular cAMP levels (Hanoune and Defer, *Annu Rev. Pharmacol. Toxical* 42: 145–174 (2001) (39)) (Hansom and Defr (2001)). The GTP-bound form of $G\alpha_s$ directly interacts and activates the 9 types of membrane-bound adenylyl cyclase (AC) known (93). Conversely, the GTP-bound form of $G\alpha_i$ can directly interact and inhibit up to 6 different types of AC (39). ERK1/2 is activated by $G_q$, $G_s$ and Gi-coupled GPCRs (Liebmann et al (1996); Pierce et al., *Oncogene* 20(13): 1532–1539 (2001); Gutkind, J. S., *J. Biol Chem* 273(4): 1839–42 (1998) (91, 94, 95)) and, depending on the cellular context, several signaling pathways can be triggered to activate ERK1/2. Specifically, it is thought that $G_i$-coupled GPCRs activate ERK1/2 mainly via the free (activated) Gβγ subunits (Crespo et al. *Nature* 369: 418–20 (1994); Faure et al., *J. Biol Chem.* 269(11): 7852–7854 (1999) (96, 97)) that recruit and activate soluble tyrosine kinases of the Src (Gutkind, 1998(95)) and Bruton families (Wan et al., *J. Biol Chem.* 272(27): 17209–15 (1997) (98)) or somehow transactivate receptor tyrosine kinases (RTKs) at the cell surface to initiate the cascade Liebmann et al. (2001); Wu et al. *Bioch. Biophys Acta.* 1582:100–106 (2002) (87, 99)).

We have shown that a rodent bitter receptor, mT2R5, the human sweet taste receptor, hT1R2/hT1R3, and the human umami taste receptor, hT1R1/R3, couples to the activation of ERK1/2 and the inhibition of cAMP accumulation in HEK293 cells. The bitter substance cycloheximide, the sweeteners saccharin, sucrose, cyclamate, D-tryptophan and the flavory amino acid MSG activate ERK1/2 exclusively in cells expressing their respective receptors. The effects of cycloheximide on mT2R5, saccharin and sucrose on hT1R2/R3 and MSG on hT1R1/R3 reach saturation at higher concentrations and their potency at activating ERK1/2 is similar to the ones reported for the $G_{15}$-induced calcium mobilization in HEK293 (80, 14) (Chandrashekar et al (2000); Li et al., (2002)). Similarly, cycloheximide, artificial sweeteners, a sweet protein as well as MSG decrease cAMP levels exclusively in cells expressing their respective taste receptors. Here again, the effects are receptor dependent and the potency of these compounds at inhibiting cAMP accumulation is in agreement with taste thresholds and $EC_{50}$'s reported for the $G_{\alpha 15}$-induced calcium mobilization in HEK293 (Chandrashekar (2000); Li et al. (2002); Temussi et al. *FEBS Lett.* 526(1–3): 1–4 (2002) (80, 14, 100)). Collectively, these results indicate that bitter compounds, sweeteners and MSG specifically activate their taste receptors to induce ERK1/2 activation and the reduction of cAMP accumulation in heterologous cells.

α-subunits of the $G_i$ family including $G\alpha_{i1\text{-}1}$, $G\alpha_{i1\text{-}2}$, $G\alpha_{i1\text{-}3}$, $G\alpha_{i0\text{-}1}$, $G\alpha_{i0\text{-}2}$, α-transducin and α-gustducin contain a conserved carboxyl-terminal cystein residue that is a site for modification by PTX, a 5'-diphosphate-ribosyltransferase isolated from *Bortadella* pertussis (101) (Fields et al. *Biochem J.* 321(P1–3): 561–71 (1997)). PTX specifically and irreversibly modifies these G-protein subunits in vivo with attachment of an ADP-ribose moiety and, as a result, this covalent modification physically uncouples the G-protein from activation by GPCRs (101) (Fields et al. (1997)). In our assays, incubation of cells with PTX abolishes the activation of ERK1/2 by the bitter, sweet and umami taste receptors indicating that one or more members of the $G_i$ family functionally link the taste receptors to this signaling pathway in HEK293 cells. It is very likely that a-subunits of $G\alpha_{i1\text{-}3}$ subfamily are involved since expression of $G\alpha_{i1\text{-}2}$ is restricted to the brain (Offermanns, S. Naunyn Schmiedz Berg, *Arch Pharmacol.* 360(1): 5–13 (1999) (102)) and that α-transducin and α-gustducin expression is mostly restricted to the eye and the tongue (McLaughlin et al. (1994); Offermanns (1999) (75, 102)). Similarly, PTX prevents activation of ERK1/2 by other $G_i$-coupled GPCRs expressed in HEK293 cells or different cell lines (Della Rocca et al (1997); Della Rocca et al (1999); Soeder et al., *J. Biol Chem.* 274(17): 12017–12026 (1999); Alderton et al., *J. Biol Chem.* 276(16): 13152–13460 (2001)—Alderton et al., *Br. J. Pharmacol.* 1341(1): 6-4 (2001) (83, 84, 103–105)). Every taste GPCR that we studied also couples to the inhibition of forskolin-induced cAMP accumulation in HEK293 cells and PTX-treatment totally abolishes the inhibition. This result clearly indicates that taste receptors directly couple to one or more member of the $G\alpha_{i1\text{-}3}$ subfamily in these cells. In this signaling pathway, activated $G\alpha_i$ proteins directly interact and inhibit the membrane bound adenylyl cyclase. There is indeed no evidence yet for direct regulation of cAMP-phosphodiesterases (PDEs) by the $G\alpha_{i1\text{-}3}$ subfamily or, in fact, by any member of the Gi family (Hanoune and Defer (2001) (93)).

It has been postulated that cyclic nucleotides such as cAMP and cGMP are involved in taste transduction (10, Margolskee (2002)). Denatonium benzoate and strychnine, two extremely bitter substances, were shown to decrease the level of cAMP and cGMP in mouse taste bud homogenates (Yan et al. (2001) (76)). In 1995, Margolskee and colleagues reported the purification of a transducin-activated PDE activity from TRCs (Ruiz-Avila et al (2001) (28)). These results have inspired a model in which bitter taste receptors couple to α-gustducin/α-transducin that in turn couples to the activation of a PDE in TRCs (10). $G\alpha_i$ subunits are highly expressed in TRCs (McLaughlin et al. (1994); Katsukobe et al. (2000); Asano-Miyoshi (2000) (75, 25, 26)). We propose, as depicted schematically in FIG. 8, that in addition to the hypothetical α-gustducin/α-transducin-PDE pathway, that bitter receptors may decrease intracellular levels of cAMP in TRCs through the direct inhibition of ACs by activated $G_{\alpha 15}$ (FIG. 8). It is not yet clear what could be the role of cAMP in TRCs functions. A decrease of cAMP in TRCs has been proposed to activate a cyclic nucleotide monophosphate (cNMP)-suppressible channel, leading to depolarization (Kolesnikov and Margolskee, *Nature* 376:80–88 (1995) (106)). (10) A recent study (Zhang et al., (2003) (18)) showing the essential requirement of the PLCβ2 pathway for the detection of sweeteners, bitter compounds and amino acids in rodents suggest that the cAMP pathway plays only a minor role in taste perception, if any. Still, modulation of cAMP levels in TRCs could have other effects than perception per se (FIG. 8). A recent report suggests that adrenergic transmission within the taste bud could play a paracrine role in taste physiology (29, Harness et al. (2002)). In this scenario, cAMP could have more of a modulator role, controlling intensity and/or the duration of taste sensation. In addition, the cAMP response element-binding protein (CREB) and phosphorylated-CREB have been recently localized in TRCs (55), suggesting that gene expression regulation can be potentially controlled, at least in part, by the level of cAMP in TRCs.

Over the past decade, three independent lines of observations had pointed to a potential role of cAMP in modulating sweet-taste signaling and sensation. First, early experiments showed that cAMP caused membrane depolarization of electrode-clamped mouse receptor cells (Tonosaki et al., *Nature* 331:304–6 (1988) (107)) and of patch-clamped frog receptor cells (Avanet et al, *Nature* 331:351–9 (1988)). Further investigation suggested that this depolarization could be mediated by a cAMP-dependent protein kinase inactivating an outward potassium current (Avanet et al (1988) (108)). Second, sweeteners and membrane permeant analogues of cAMP were shown to activate the same subset of hamster TRCs in vitro (Cummings and Kinnamon, *J. Neurophysiol.* 70(6): 2326–2336 (1993) (109)). In addition, just like cAMP (Avanet et al (1988) (108)), saccharin was shown to depolarize hamster and gerbil TRCs by reducing outward potassium currents (Cummings and Kinnamon, *J. Neurophysiol.* 75(3):1256–63 (1996); Uchida and Sato,

*Chem. Senses* 22(3): 163–164 (1997) (110, 111)). Lastly, sweeteners such as saccharin and sucrose were shown to increase cAMP levels in rat taste epithelium (Striem et al., 1989 (78)), in mouse fungiform taste buds (Nakashima and Ninomiya, *Cell Physiol. Biochem.* 9(2):90–98 (1999) (112)) and in pig circumvallate papillae (77, Naim et al., 1991). Together these observations have led to the suggestion that the sweet receptor couples to $G_s$ in TRCs (9, 10). In our hands, however, the sweet receptor clearly couples to a reduction of intracellular cAMP levels and activation of ERK1/2 through the direct functional coupling with $G_i$. Moreover, we have consistently failed in detecting a sweetener-induced accumulation of cAMP, even after inhibiting functional coupling of hT1R2/R3 to $G_i$ proteins. It is noteworthy that we can detect a fructose or sucrose-induced cAMP accumulation in naive HEK293 cells. As mentioned above, we strongly suspect that this is a direct result of the osmotic shock triggered by the high concentration of sucrose and fructose used in our experiments. Similarly, in an independent study, sucrose was shown to induce cAMP accumulation in tongue muscle membranes (Striem et al., (1989) (78)), a non-taste tissue. It is therefore possible that the sweeteners-induced increase in cAMP levels observed in rat taste epithelium (Striem et al (1989) (78)), in mouse fungiform taste buds (78) and in pig circumvallate papillae (Naim et al. (1991) (77)) occurs through a receptor-independent mechanism. In any case, our results do not support the hypothesis of a direct functional coupling of the sweet receptor to $G_s$ (Gilbertson et al, 2000; Marlgokskee (2002) (9, 10)). The effect of MSG on the level of cyclic nucleotides in TRCs is much less understood. One report suggests that MSG induces a decrease in cAMP levels in circumvallate and foliate taste buds (Chaudhuri and Roper, *Ann NY Acad. Sci.* 855:398–406 (1998) (113)) while another report claims an increase in cAMP levels in fungiform papillae (Ninomiya et al., *J. Nutr.* 130 (3S Suppl) :9500–9530 (2001) (114)). Our data clearly demonstrates that the umami receptor functionally couples to a reduction of intracellular cAMP levels and to the $G_i$-induced activation of ERK1/2 in HEK293 cells. It is not known yet if the MSG (umami) receptor couples to α-gustducin in vivo. Our results point to $G\alpha_i$ as a strong candidate for its cognate G protein in TRCs (FIG. 8).

These results suggest that gustducin is not the only Gα-subunit used for taste transduction. The level of co-expression in TRCs between T1R1 and T1R2 and α-gustducin is estimated at around −15% in rodents (Hoon et al., *Cell* 96(4): 541–551 (1999) (115)). Similarly, another study reported that only about 10% of T1R3 positive cells were also α-gustducin positive in mouse TRCs (Montmayeur et al., *Nat. Neurosci.* 4(5):492–498 (2001) (116)). Thus, in conclusion, most cells expressing the sweet and umami receptor subunits do not express α-gustducin. In consequence, one could expect that sweet and umami taste perception is mediated, in part, by a different G-protein. Perhaps the most compelling other evidence suggesting the involvement of other G-proteins is the residual responsiveness of α-gustducin deficient mice to bitter and sweet stimuli (Wang et al., (1996); He et al., (2002); Ruiz-Avila et al. (2001) (17, 27, 28)). A recent study shows that expression of a dominant negative form of α-gustducin, from the gustducin promoter in these deficient mice, further decreases the residual responsiveness to sweet bitter stimuli, substantiating the notion on the involvement of another G protein (28, Ruiz-Avila et al., 2001). Independent studies report that umami (117) (Caicedo and Roper, *J. Physiol.* 544(pt 2): 501–509 (2002), sweet (117, 118) (Caicedo and Roper (2002); Bernhardt et al., *J. Physiol.* 490(Pt. 2): 320–336 (1996)) and bitter (Caicedo and Roper, 2002; Caicedo and Roper, *Science* 291:1557–60 (2001); Akrabas et al., *Science,* 242:1047–1050 (1988) (117, 119, 120)) modalities trigger an increase of intracellular calcium concentration in TRCs. Moreover, bitter compounds lead to PTX-sensitive accumulation of inositol triphosphate in TRCs (121, 122). These cells are enriched in classical G protein-signaling effectors such as phospholipase C-β2 (PLCβ2) (18, 23, 26, 124), an enzyme known to be activated by the Gβγ subunit of G proteins belonging to the $G_i$ family (20–24), the type-III inositol triphosphate receptor (IP3R-III) (123, 124) and a transient receptor potential (trp) channel TRPM5 (53, 72, 78) (FIG. 8). PLCβ2 and TRPM5 are essential for taste perception of sweeteners, bitter substances and amino acids in rodents (18). Collectively, these observations suggest that the major taste transduction pathway in TRCs links α-gustducin to the activation of PLCβ2 and TRPM5, these events ultimately leading to membrane depolarization and taste perception (FIG. 8) (18). We propose that Gβγ subunits released from activated $G_{\alpha i}$ could also contribute to activation of PLCβ2 in TRCs (FIG. 8). Herein, it was shown the mRNAs for PLβ32 and $G\alpha_{i-2}$ co-exist in the same TRCs and that $G\alpha_{i-2}$-positive cells also express bitter taste receptors (26). This pathway would directly complement the lack of α-gustducin in mice and would account for the residual responsiveness to bitter compounds and even possibly sweeteners. Confirmation of this signaling pathway can be evaluated in genetically engineered mice lacking α-gustducin in addition to one or more $G\alpha_i$ subunits.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the claims which follow.

REFERENCES*

1. Blenis, *Proc. Natl Acad. Sci, USA* 90: 5889 (1993)
2. Blumer et al., *TIBS* 19:235 (1994)
3. Camp et al., *TIBS* 20:117 (1995)
4. Seger et al. *FASEB J.* 9:726 (1995)
5. David, R. J. *TIBS* 19:470 (1994)
6. Robinson and Dickinson *Eur. J. Pharmacol.* 413(2–3) :151–61 (2001)
7. Lopaz-Ilasaca, *Biochem Pharmacol.* 56637:269–77 (1998)
8. Ito et al., *FEBS Lett.* 368(1):183–7 (1995)
9. Gilbertson et al., *Corr. Opin. Neurobiol.* 10(4):519–27 (2000)
10. Margolskee, R F, *J. Bio., Chem.* 277(1):1–4 (2002)
11. Montmayeur et al., *Corr. Opin. Neurobiol.,* 12(4) :366–71 (2002)
12. Adler et al., *Cell* 100(6):693–702 (2000)
13. Matsunami et al., *Nature* 404(6678):601–4 (2000)
14. Li et al., *Proc. Natl Acad Sci., USA* 99(7):4692–6 (2002)
15. Nelson et al., *Nature* (6877):199–202 (2002)
16. Nelson et al., *Cell* 106(3):381–96 (2001)
17. Wong et al., *Nature* 381(6585): 796–800 (1996)
18. Zhang et al., *Cell* 112(3):293–301 (2003)
19. Hoffman et al., *Nature* 397(6716): 259–263 (1999)
20. Li et al., *Science* 287(54–55):1046–9 (2000)
21. Wu et al., *Proc. Natl Acad Sci., USA* 90(11):5297–5301 (1993)
22. Katan, *Biochem Biophys. Acta* 1436(1–2):5–17 (1998)

23. Smrcka et al., *J. Biol Chem.* 272(24):15045–48 (1993)
24. Rhee et al., *J. Biol. Chem.* 272(24):15045–8 (1997)
25. Kusakabe et al., *Chem. Senses* 25(5):525–31 (2000)
26. Asano-Miyoshi *Neurosci. Lett.* 283(1):64 (2000)
27. He et al, *Chem. Senses* 27(8):719–27 (2002)
28. Ruiz-Avila et al, *Proc. Natl Acad Sci., USA* 98(15):2868–73 (2001)
29. Harness et al., *J. Physiol.* 543(Pt. 2):601–614 (2002)
30. Cao et al., *Neuroreport* 13(10):1321–25 (2002)
31. Roper et al., *Ann. Rev. Neurosci.* 12:329–53 (1989)
32. Hoon et al., *Cell* 96:541–551 (1999)
33. Fong, T M *Cell Signal.* 8(3):217–24 (1996)
34. Baldwin et al., *J. Mol. Biol.* 272(1):144–64 (1997)
35. Hamm et al., *Science* 241:832–5 (1988)
36. Osawa et al., *J. Biol. Chem.* 270:31052–8 (1995)
37. Garcia et al., *EMBO* 13:4460–9 (1995)
38. Sullivan et al., *Nature* 330:758–60 (1987)
39. Resenick et al., *J. Biol Chem.* 269:21519–21525 (1994)
40. West et al., *J. Biol Chem.,* 260:14428–30 (1985)
41. Conklin et al., *Nature* 363:274–276 (1993)
42. Conklin et al., *Mol. Pharmacol.* 50:885–890 (1996)
43. Gilchrist et al., *J. Biol. Chem.* 273:14912–19 (1998)
44. Buck and Axel, *Cell* 65:175–187 (1991)
45. Stryer, *Biochemistry,* 3*d ed.* 1988.
46. Kyte & Doolittle, *J. Mol. Biol.* 157:103–32 (1982)
47. *Oligonocleotides and Analogues a Practical Approach,* et. F. Ecksten, Oxford, Univ. Press (1991)
48. *Antisense Strategies, Annals of the NY Acad. Sciences,* 600 eds. Baserga et al., (NYAS 1992)
49. Milligan, *J. Med. Chem.* 36:1923–37 (1995)
50. *Antisense Research and Applications,* (1993, CRC Press)
51. Matag, *Toxicol. Appl. Pharmacol.* 144:189–197 (1997)
52. Strauss-Soukup, *Biochem.* 36:8692–8 (1997)
53. Samstag, *Antisense Nucl. Acid Drug Dev.* 6:153–6 (1996)
54. Batzer et al., *Nucl. Acids Rev.* 19:5081 (1991)
55. Ohtsuka et al., *J. Biol Chem.* 260:2605–8 (1985)
56. Rossolini et al., *Mol. Cell. Probes* 8:91–98 (1994)
57. Creighton, *Proteins,* W. H. Freeman and Co. (1984)
58. Schultz and Schimer, *Principles of Protein Structure,* Springer-Verlog (1979)
59. Harlow & Lane, *Antibodies, A. Laboratory Manual* (1988)
60. Sambrook et al., (eds.), *Molecular Cloning: A Laboratory Manual,* Cold Spring Harbor Laboratory Press, Cold Spring Harbor, N.Y.
61. Silhavy, *Experiments With Gene Fusions,* Cold Spring Laboratory Press, Cold Spring Harbor, N.Y. (1984)
62. Glover & Hanes, *DNA Cloning: A Practical Approach,* $2^{nd}$ ed. IRL Press and Oxford University Press, Oxford, N.Y. (1995)
63. Ausubel (ed.), *Short Protocols in Mol. Biol.,* $3^{rd}$ ed., Wiley, N.Y. (1995)
64. Saqi et al., *Bioinformatics* 15:521–22 (1999)
65. Barton, *Acta Crystollagr. D. Biol. Crystallogr.* 54:1139–46 (1998)
66. Henikoff et al., *Electrophoresis* 21:1700–1706 (2000)
67. Huang et al., *Pac. Symp. Biocomp.:*230–241 (2000)
68. Henikoff et al., *Adv. Protein Chem.* 54:73–97 (2000)
69. Kyte et al., *J. Mol. Biol.* 157(1):105–32 (1982)
70. Tan et al., *J. Immunol. Meth.* 232(1–2):87–97 (1998)
71. Vaster et al., *Biochem. J.* 350:717–22 (2000)
72. "Indirect Mechanisms of Synaptic Transmission," Chapter 8, *From Neuron to Brain* ($3^{rd}$ edition) Nichols, J. G. et al., eds., Sinauer Associates, Inc. (1992)
73. McLaughlin et al., *Nature* 357:563–9 (1992)
74. Ruiz-Avila et al., *Nature* 376:80–85 (1995)
75. McLaughlin et al., *Phys. Behav.* 56(6):1157–64 (1994)
76. Yan et al, *Am. J. Physiol. Cell Physiol.* 280(4):C742–751 (2001)
77. Naim et al, *Comp. Biochem Physiol B.,* 100(3):455–8 (1991)
78. Striem et al., *Biochem J.* 260(1):121–126 (1989)
79. Kostensis, *Trends Pharmacol. Sci.,* 22(11):560–4 (2001)
80. Chandrashekar et al. *Cell* 100(6):703–11 (2000)
81. Adamus et al., *Vision Res.* 31(1):17–31 (1991)
82. Bufe et al., *J. Receptor Signal Transduct. Res.* 20(2–3):153–166
83. Della Rocca et al., *J. Biol. Chem.* 272(31):19125–19132 (1997)
84. Della Rocca et al., *J. Biol. Chem.* 274(2):13978–13984 (1999)
85. Bufe et al., *Nat. Genet.* 32(3):397–401
86. Yamaguchi et al., *Physiol Behav.* 49(5):833–841 (1991)
87. Liebmann et al., *Cell Signal* 13(11):777–785 (2001)
88. Daaka et al., *Nature* 390:88–91 (1997)
89. Morris and Milbon *Physiol Rev.* 79(4):1373–1430 (1999)
90. Chin et al., *Ann. NY Acad Sci.* 968:49–64 (2002)
91. Liebmann et al., *J. Biol. Chem* 271(49):31098–31105 (1996)
92. Robinson-White and Stratakis, *Ann. NY Acad. Sci.* 968:256–270 (2002)
93. Hanoune and Defer, *Ann. Rev. Pharmacol. Toxicol.* 41:145–174 (2001)
94. Pierce et al., *Oncogene* 20(13):1532–1539 (2001)
95. Gutkind, J. S., *J. Biol Chem.* 273(4):1839–42 (1998)
96. Crespo et al. *Nature* 369:418–20 (1994)
97. Faure et al., *J. Biol Chem.* 269(11):7851–9 (1994)
98. Wan et al., *J. Biol Chem.* 272(27):17209–17215 (1997)
99. Wu et al. *Biochem Biophys Acta* 1582(1–3):100–106 (2002)
100. Temussi P A, *FEBS Lett.* 526(1–3):1–4 (2002)
101. Fields T A and Casey, P J, *Biochem J.* 321(Pt. 3):561–71 (1997)
102. Offermanns S., Naunyn Schmeideberg, *Arch Pharmacol.* 360(1):5–13 (1999)
103. Soeder et al., *J. Biol. Chem.* 274(17):12017–12022 (1999)
104. Alderton et al., *J. Biol Chem.* 276(16):13452–13460 (2001)
105. Alderton et al., *Br. J. Pharmacol.* 134(1):6–9 (2001)
106. Kolesnikov and Margolskee, *Nature* 376:85–8 (1995)
107. Tonosaki et al., *Nature* 331:354–6 (1988)
108. Avanet et al, *Nature* 331:351–354 (1988)
109. Cummings and Kinnamon, *J. Neurophysiol* 70(6):2326–2336 (1993)
110. Cummings and Kinnamon, *J. Neurophysiol.* 75(3):1236–63 (1996)
111. Uchida and Sato, *Chem. Senses* 22(3):163–164 (1997)
112. Nakashima and Ninomiya, *Cell Physiol Biochem.* 9(2):90–98 (1999)
113. Chaudhuri and Roper, *Ann. NY Acad. Sci.* 855:398–406 (1998)
114. Ninomiya et al., *J. Nutr.* 130(445 Suppl.) 9505–9535 (2000)
115. Hoon et al., *Cell* 96(4):541–551 (1999)
116. Montmayeur et al., *Nat. Neurosci.* 4(5):492–498 (2001)
117. Caicedo and Roper, *J. Physiol.* 544(Pt. 2):501–504 (2002)
118. Bernhardt et al., *J. Physiol.* 490(Pt. 2):325–336 (1996)
119. Caicedo and Roper, *Science* 291:1557–1560 (2001)
120. Akabas et al., *Science,* 242:1047–1050 (1988)
121. Spielman et al., *Physiol Behav.* 56660:1149–1153 (1994)

122. Speilman et al., *Am J. Physiol.* 270(3 Pt. 1) C926–931 (1996)
123. Clapp et al., *BMC Neurosci.,* 21(1):6 (2001)
124. Perez et al., *Nat. Neurosci.* 5(11):1169–1176 (2002)
125. Lush, I. E., and Holland, G. (1988) *Genet Res* 52(3), 207–212.
126. Kim, U. K., Jorgenson, E., Coon, H., Leppert, M., Risch, N., and Drayna, D. (2003) *Science* 299(5610), 1221–1225.
127. Ming, D., Ruiz-Avila, L., and Margolskee, R. F. (1998) *Proc Natl Acad Sci USA* 96(15),8933–8938.
128. Ruiz-Avila, L., Ming, D., and Margolskee, R. F. (2000) *Chem Senses* 25(4), 361–368.
129. Ogura, T., Margolskee, R. F., and Kinnamon, S. C. (2002) *J Neurophysiol* 87(6), 3152–3155.
130. Traynor and Nohorski, *Mol. Pharmacol.* 47:848–854 (1995)
131. Stabbis, et al., *Annal. Biochem.* 252:115–126 (1997)
132. Dethux et al., *J. Exp. Med.* 192:15018 (2000)
133. Kenimer & Nirenberg, *Mol. Pharmacol.* 20:585–591
134. Solomon, et al., *Anal. Biochem.* 58:541–8 (1974)
135. Horton & Baxendale, *Methods Mol. Biol.* 41:91–105 (1993)
136. Phospholipid Signalling Protocols, edited by Ian M. Bird, Totowa, N.J., Humana Press, (1998)
137. Rudolph et al., *J. Biol. Chem.* 274: 11824–11831 (1999)
138. Kikkawa et al., *J. Biol. Chem* 257:13341 (1982)
139. Pinna & Ruzzenc, *Biochem. Biophys Acta* 1314:191–225 (1996)
140. Verma et al., *Cell* 51:513–514 (1987)
141. U.S. Pat. No. 5,519,649
142. Fink et al., 1988, *Proc. Natl. Acad. Sci.* 85:6662–6666) (1988)
143. Montminy et al., *Proc. Natl. Acad. Sci.* 83:6682–6686 (1986)
144. Comb et al., *Nature* 323:353–356 (1986)
145. Short et al., *J. Biol. Chem.* 261:9721–9726 (1986)
146. Lee et al., *Nature* 325: 368–372 (1987)
147. Lee et al., *Cell* 49: 741–752 (1987)
148. Hiscott et al., *Mol. Cell. Biol.* 13:6231–6240 (1993)
149. Shakhov et al., *J. Exp. Med.* 171: 35–47 (1990)
150. Liu et al., AIDS Res. Hum. Retroviruses 14: 1509–1519 (1998)
151. Liu et al., AIDS Res. Hum. Retroviruses 14: 1509–1519 (1998)
152. Matsui et al., *J. Immunol.* 161: 3469–3473 (1998)
153. Schreck & Baeuerle, *Mol. Cell. Biol.* 10: 1281–1286 (1990)
154. Haskill et al., *Cell* 65: 1281–1289 (1991)
155. Hafner, 2000, Biosens. Bioelectron. 15: 149–158 (2000)
156. *Molecular Cell Biology,* Darnell et al, Chapter 16 (1986)
157. Spatola, *Chemistry and Biochemistry of Amino Acids, Peptides and Proteins,* Vol. 7, pp 267–357, "Peptide Backbone Modifications," Marcell Dekker, NY (1983)

*All of the Patents and literature references cited in this application are incorporated by reference in their entireties herein.

SEQUENCE LISTING

SEQ ID NO:1

Human T2R01 Nucleotide Sequence

MLESHLIIYFLLAVIQFLLGIFTNGIIV-
VVNGIDLIKHRKMAPLDLLLSCLAVSRIFLQL
FIFYVNVIVIFFIEFIMCSANCAILL-
FINELELWLATWLGVFYCAKVASVRHPLFIWLKM

RISKLVPWMILGSLLYVSMICVFHSKY-
AGFMVPYFLRKFFSQNATIQKEDTLAIQIFSFV AEFS-
VPLLIFLFAVLLLIFSLGRHTRQMRN-
TVAGSRVPGRGAPISALLSILSFLILYFSH
CMIKVFLSSLKFHIRRFIFLFFILVIGI-
YPSGHSLILILGNPKLKQNAKKFLLHSKCCQ

SEQ ID NO:2

Human T2R01 Nucleotide Sequence

ATGCTAGAGTCTCACCTCATTATC-
TATTTTCTTCTTGCAGTGATACAATTTCTTCTTGGG
ATTTTCACAAATGGCATCATTGTGGTG-
GTGAATGGCATTGACTTGATCAAGCACAGAAAA
ATGGCTCCGCTGGATCTCCTTCTTTCT-
TGTCTGGCAGTTTCTAGAATTTTTCTGCAGTTG
TTCATCTTCTACGTTAATGTGATTGT-
TATCTTCTTCATAGAATTCATCATGTGTTCTGCG
AATTGTGCAATTCTCTTATTTATAAAT-
GAATTGGAACTTTGGCTTGCCACATGGCTCGGC
GTTTTCTATTGTGCCAAGGTTGC-
CAGCGTCCGTCACCCACTCTTCATCTG-
GTTGAAGATG AGGATATCCAAGCTGGTCCCATG-
GATGATCCTGGGGTCTCTGCTATATGTATCTATGATT
TGTGTTTTCCATAGCAAATATG-
CAGGGTTTATGGTCCCATACTTCCTAAG-
GAAATTTTTC TCCCAAAATGCCACAATTCAAAAA-
GAAGATACACTGGCTATACAGATTTTCTCTTTTGTT
GCTGAGTTCTCAGTGCCATTGCTTATCT-
TCCTTTTTGCTGTTTTGCTCTTGATTTTCTCT
CTGGGGAGGCACACCCGGCAAAT-
GAGAAACACAGTGGCCGGCAGCAGGGT-
TCCTGGCAGG GGTGCACCCATCAGCGCGTTGCT-
GTCTATCCTGTCCTTCCTGATCCTCTACTTCTCCCAC
TGCATGATAAAAGTTTTTCTCTCT-
TCTCTAAAGTTTCACATCAGAAGGTTCATCTTTCTG
TTCTTCATCCTTGTGATTGGTATATAC-
CCTTCTGGACACTCTCTCATCTTAATTTTAGGA
AATCCTAAATTGAAACAAAATG-
CAAAAAGTTCCTCCTCCACAGTAAGT-
GCTGTCAGTGA

SEQ ID NO:3

Human T2R02 Amino Acid Sequence

MALSFSAILHIIMMSAEFFTGITVNG-
FLIIVNCNELIKHRKLMPIQILLMCIGMSRFGLQ
MVLMVQSFFSVFFPLLYVKIIYGAAM-
MFLWMFFSSISLWFATCLSVFYCLKISGFTQSCF
LWLKFRIPKLIPWLFWEAFWPL*ALHLCVEVDYAKN
VEEDALRNTTLKKSKTKIKKISEV LLVNLALIF-
PLAIFVMCTSMLLISLYKHTHRMQHGSH-
GFRNANTEAHINALKTVITFFCF FISYFAAFMTNMTF-
SLPYRSHQFFMLKDIMAAYPSGHSVIIILSNSKFQQSF
RRILCLKK KL

SEQ ID NO:4

Human T2R02 Nucleotide Sequence

ATGGCCTTGTCTTTTTCAGCTATTCT-
TCATATTATCATGATGTCAGCAGAATTCTTCACA
GGGATCACAGTAAATGGATTTCTTAT-
CATTGTTAACTGTAATGAATTGATCAAACATAGA
AAGCTAATGCCAATTCAAATCCTCT-
TAATGTGCATAGGGATGTCTAGATTTGGTCTGCAG
ATGGTGTTAATGGTA-
CAAAGTTTTTTCTCTGTGTTCTTTC-

CACTCCTTTACGTCAAAATA ATTTATGGTGCAG-
CAATGATGTTCCTTTGGATGTTTTTTAGCTCTATCAG
CCTATGGTTT GCCACTTGCCTTTCTGTATTTTACT-
GCCTCAAGATTTCAGGCTTCACTCAGTCCTGTTTT
CTTTGGTTGAAATTCAGGATCCCAAAGT-
TAATACCTTGGCTGCTTCTGGGAAGCGTTCTG
GCCTCTGTGAGCATTGCATCTGTGTGTC-
GAGGTAGATTACGCTAAAAATGTGGAAGAGGA
TGCCCTCAGAAACACCACACTAAAAAA-
GAGTAAAACAAAGATAAAGAAAATTAGTGAAGT
GCTTCTTGTCAACTTGGCAT-
TAATATTTCCTCTAGCCATATTTGTGAT-
GTGCACTTCTAT GTTACTCATCTCTCTTTACAAGCA-
CACTCATCGGATGCAACATGGATCTCATGGCTTTAG
AAATGCCAACACAGAAGCCCATATAAAT-
GCATTAAAAACAGTGATAACATTCTTTTGCTT CTT-
TATTTCTTATTTTGCTGCCTTCATGA-
CAAATATGACATTTAGTTTACCTTACAGAAG
TCACCAGTTCTTTATGCTGAAGGACAT-
AATGGCAGCATATCCCTCTGGCCACTCGGTTAT
AATAATCTTGAGTAATTCTAAGTTCCAA-
CAATCATTTAGAAGAATTCTCTGCCTCAAAAA
GAAACTATGA

SEQ ID NO:5

Human T2R03 Amino Acid Sequence

MMGLTEGVFLILSGTQFTLGIL-
VNCFIELVNGSSWFKTKRMSLSDFIITTLALLRIILLC
IILTDSFLIEFSPNTHDSGIIMQIID-
VSWTFTNHLSIWLATCLGVLYCLKIASFSHPTFL
WLKWRVSRVMVWMLLGALLLSCG-
STASLINEFKLYSVFRGIEATRNVTEHFRKKKSEYYL
IHVLGTLWYLPPLIVSLASYSLLIFS-
LGRHTRQMLQNGTSSRDPTTEAHKRAIRIILSFF
FLFLLYFLAFLIASFGNFLPKTKMAKMI-
GEVMTMFYPAGHSFILILGNSKLKQTFVVMLR CES-
GHLKPGSKGPIFS

SEQ ID NO:6

Human T2R03 Nucleotide Sequence

ATGATGGGACTCACCGAGGGGGTGTTC-
CTGATTCTGTCTGGCACTCAGTTCACACTGGGA
ATTCTGGTCAATTGTTTCATTGAGTTG-
GTCAATGGTAGCAGCTGGTTCAAGACCAAGAGA
ATGTCTTTGTCTGACTTCATCATCAC-
CACCCTGGCACTCTTGAGGATCATTCTGCTGTGT
ATTATCTTGACTGATAGTTTTTTAATA-
GAATTCTCTCCCAACACACATGATTCAGGGATA
ATAATGCAAATTATTGATGTTTCCTGGA-
CATTTACAAACCATCTGAGCATTTGGCTTGCC
ACCTGTCTTGGTGTCCTCTACTGCCT-
GAAAATCGCCAGTTTCTCTCACCCCACATTCCTC
TGGCTCAAGTGGAGAGTTTCTAGGGT-
GATGGTATGGATGCTGTTGGGTGCACTGCTCTTA
TCCTGTGGTAGTACCGCATCTCTGAT-
CAATGAGTTTAAGCTCTATTCTGTCTTTAGGGGA
ATTGAGGCCACCAGGAATGTGACTGAA-
CACTTCAGAAAGAAGAGGAGTGAGTATTATCTG
ATCCATGTTCTTGGGACTCTGTGGTAC-
CTGCCTCCCTTAATTGTGTCCCTGGCCTCCTAC
TCTTTGCTCATCTTCTCCCTGGGGAG-
GCACACACGGCAGATGCTGCAAAATGGGACAAGC
TCCAGAGATCCAACCACTGAGGCCCA-
CAAGAGGGCCATCAGAATCATCCTTTCCTTCTTC
TTTCTCTTCTTACTTTACTTTCT-
TGCTTTCTTAATTGCATCATTTGGTAATTTCCTACCA
AAAACCAAGATGGCTAAGATGATTGGC-
GAAGTAATGACAATGTTTTATCCTGCTGGCCAC
TCATTTATTCTCATTCTGGGGAACAG-
TAAGCTGAAGCAGACATTTGTAGTGATGCTCCGG
TGTGAGTCTGGTCATCTGAAGCCTG-
GATCCAAGGGACCCATTTTCTCTTAG

SEQ ID NO:7

Human T2R04 Amino Acid Sequence

MLRLFYFSAIIASVILNFVGIIMN-
LFITVVNCKTWVKSHRISSSDRILFSLGITRFLMLG
LFLVNTIYFVSSNTERSVYLSAFFVL-
CFMFLDSSSVMFVTLLNILYCVKITNFQHSVFLL
LKRNISPKIPRLLLACVLISAFTTCLY-
ITLSQASPFPELVTTRNNTSFNISEGILSLVVS LVLSSS-
LQFIINVTSASLLTHSLRRHIQKM-
QKNATGFWNPQTEAHVGAMKLMVYFLILYI
PYSVATLVQYLPFYAGMDMGTKSICLI-
FATLYSPGHSVLIIITHPKLKTTAKKILCFKK

SEQ ID NO:8

Human T2R04 Nucleotide Sequence

ATGCTTCGGTTATTCTATTTCTCTGC-
TATTATTGCCTCAGTTATTTTAAATTTTGTAGGA
ATCATTATGAATCTGTTTATTACAGTG-
GTCAATTGCAAAACTTGGGTCAAAAGCCATAGA
ATCTCCTCTTCTGATAGGATTCTGT-
TCAGCCTGGGCATCACCAGGTTTCTTATGCTGGGA
CTATTTCTGGTGAACACCATCTACT-
TCGTCTCTTCAAATACGGAAAGGTCAGTCTACCTG
TCTGCTTTTTTTGTGTTGTGTTTCAT-
GTTTTTGGACTCGAGCAGTGTCTGGTTTGTGACC
TTGCTCAATATCTTGTACTGTGTGAA-
GATTACTAACTTCCAACACTCAGTGTTTCTCCTG
CTGAAGCGGAATATCTCCCCAAAGATC-
CCCAGGCTGCTGCTGGCCTGTGTGCTGATTTCT
GCTTTCACCACTTGCCTGTACAT-
CACGCTTAGCCAGGCATCACCTTTTCCT-
GAACTTGTG ACTACGAGAAATAACACATCATT-
TAATATCAGTGAGGGCATCTTGTCTTTAGTGGTTTCT
TTGGTCTTGAGCTCATCTCTCCAGT-
TCATCATTAATGTGACTTCTGCTTCCTTGCTAATA
CACTCCTTGAGGAGACATATACAGAA-
GATGCAGAAAAATGCCACTGGTTTCTGGAATCCC
CAGACGGAAGCTCATGTAGGTGCTAT-
GAAGCTGATGGTCTATTTCCTCATCCTCTACATT
CCATATTCAGTTGCTACCCTGGTCCAG-
TATCTCCCCTTTTATGCAGGGATGGATATGGGG
ACCAAATCCATTTGTCTGATTTTTGC-
CACCCTTTACTCTCCAGGACATTCTGTTCTCATT
ATTATCACACATCCTAAACTGAAAACAA-
CAGCAAAGAAGATTCTTTGTTTCAAAAAATAG

SEQ ID NO:9

Human T2R05 Amino Acid Sequence

MLSAGLGLLMLVAVVEFLIGLIGNGSLV-
VWSFREWIRKFNWSSYNLIILGLAGCRFLLQW
LIILDLSLFPLFQSSRWLRYLSIFWV-
LVSQASLWFATFLSVFYCKKITTFDRPAYLWLKQ
RAYNLSLWCLLGYFIINLLLTVQIGLT-
FYHPPQGNSSIRYPFESWQYLYAFQLNSGSYLP
LVVFLVSSGMLIVSLYTHHKKMKVH-

SAGRROVRAKAHITALKSLGCFLLLHLVYIMASPF
SITSKTYPPDLTSVFIWETLMAAYPSLH-
SLILIMGIPRVKQTCQKILWKTVCARRCWGP

SEQ ID NO:10

Human T2R05 Nucleotide Sequence

ATGCTGAGCGCTGGCCTAGGACTGCT-
GATGCTGGTGGCAGTGGTTGAATTTCTCATCGGT
TTAATTGGAAATGGAAGCCTGGTG-
GTCTGGAGTTTTAGAGAATGGATCA-
GAAAATTCAAC TGGTCCTCATATAACCTCATTATC-
CTGGGCCTGGCTGGCTGCCGATTTCTCCTGCAGTGG
CTGATCATTTTGGACTTAAGCTTGTTTC-
CACTTTTCCAGAGCAGCCGTTGGCTTCGCTAT
CTTAGTATCTTCTGGGTCCTGGTAAGC-
CAGGCCAGCTTATGGTTTGCCACCTTCCTCAGT
GTCTTCTATTGCAAGAAGATCACGACCT-
TCGATCGCCCGGCCTACTTGTGGCTGAAGCAG
AGGGCCTATAACCTGAGTCTCTGGTGC-
CTTCTGGGCTACTTTATAATCAATTTGTTACTT
ACAGTCCAAATTGGCTTAACATTCTAT-
CATCCTCCCCAAGGAAACAGCAGCATTCGGTAT
CCCTTTGAAAGCTGGCAGTACCTGTATG-
CATTTCAGCTCAATTCAGGAAGTTATTTGCCT
TTAGTGGTGTTTCTTGTTTCCTCTGG-
GATGCTGATTGTCTCTTTGTATACACACCACAAG
AAGATGAAGGTCCATTCAGCTGGTAG-
GAGGGATGTCCGGGCCAAGGCTCACATCACTGCG
CTGAAGTCCTTGGGCTGCTTCCTCT-
TACTTCACCTGGTTTATATCATGGCCAGCCCCTTC
TCCATCACCTCCAAGACTTATCCTCCT-
GATCTCACCAGTGTCTTCATCTGGGAGACACTC
ATGGCAGCCTATCCTTCTCTTCAT-
TCTCTCATATTGATCATGGGGATTCCTAGGGTGAAG
CAGACTTGTCAGAAGATCCTGTGGAAGA-
CAGTGTGTGCTCGGAGATGCTGGGGCCCATGA

SEQ ID NO:11

Human T2R06 Amino Acid Sequence

MLAAALGLLMPIAGAEFLIGLVGNGVPVVCSFRG
WVKKM*GVPINSHDSGK*PLSPTQAD
HVGHKSVSTFPEQWLALLS*CLRVLVSQANM*FATFF
SGFCCMEIMTFVXXXXXXXXXXX
XXXXXXXXXLLVSFKITFYFSALVGWTL*KPLTGNSN
ILHPILNLLFL*IAVQ*RRLIAI
CDVSVPLVFL*RHHRKMEDHTAVRRRLKPRXXXXXX
XXXXXXXXXLYMVSALARHFSMTF *SPSDLTILAIS-
ATLMAVYTSFPSIVMVMRNQTCQRIL*
EMICTWKS

SEQ ID NO:12

Human T2R06 Nucleotide Sequence

ATGTTGGCGGCTGCCCTAGGATTGCT-
GATGCCCATTGCAGGGGCTGAATTTCTCATTGGC
CTGGTTGGAAATGGAGTCCCTGTGGTCT-
GCAGTTTTAGAGGATGGGTCAAAAAAATGTAA
GGAGTCCCTATAAATTCTCATGATTCTG-
GTAAGTAGCCACTTTCTCCTACTCAGGCCGAT CAT-
GTTGGACATAAGTCTGTTTCCACTTTC-
CCAGAGCAGTGGTTGGCTTTACTATCTTAA
TGTCTTCGAGTCCTGGTAAGCCAGGC-
CAACATGTAGTTTGCCACTTTCTTCAGTGGCTTC
TGCTGCATGGAGATCATGACCTTTGTC-
CCGCTGACTTCTTGTAGCTGAAAAGACTGGGTT
TTTGTTTTTTGCTAGTGTCTTTCAAGAT-
CACTTTTTATTTCTCAGCTCTTGTTGGCTGGA
CCCTTTAAAAACCCTTAACAGGAAACAG-
CAACATCCTGCATCCCATTTTAAATCTGTTAT TTT-
TATAGATTGCTGTCCAGTGAAGGAGACT-
GATTGCTATTTGTGATGTTTCTGTTCCAC
TTGTCTTTTTGTAAAGACATCACAGGAA-
GATGGAGGACCACACAGCTGTCAGGAGGAGGC
TCAAACCAAGGTGCTCATCGCTCT-
GAACTTCCCCCTTTACATGGTTTCTGCCTTGGCCAG
ACACTTTTCCATGACCTTCTAATCTC-
CCTCTGATCTCACCATTCTTGCCATCTCTGCAAC
ACTCATGGCTGTTTATACTTCATTTC-
CGTCTATTGTAATGGTTATGAGGAATCAGACTTG
TCAGAGAATTCTGTAGGAGATGATATG-
TACATGGAAATCCTAG

SEQ ID NO:13

Human T2R07 Amino Acid Sequence

MADKVQTTLLFLAVGEFS-
VGILGNAFIGLVNCMDMVKKRKIASID-
LILTSLAISRICLLC VILLDCFILVLYPDVYATGKEMRI-
IDFFWTLTNHLSIWFATCLSIYYFFKIGNFFHPLFL
WMKWRIDRVISWILLGCVVLSVFISL-
PATENLNADFRFCVKAKRKTNLTWSCRVNKTQHA
STKLFLNLATLLPFCVCLMSFFLLILSL-
RRHIRRMQLSATGCRDPSTEAHVRALKAVISF LLLFI-
AYYLSFLIATSSYFMPETELAVIFGE-
SIALIYPSSHSFILILGNNKLRHASLKVI
WKVMSILKGRKFQQHKQI

SEQ ID NO:14

Human T2R07 Nucleotide Sequence

ATGGCAGATAAAGTGCAGACTACTTTAT-
TGTTCTTAGCAGTTGGAGAGTTTTCAGTGGGG
ATCTTAGGGAATGCATTCATTGGATTGG-
TAAACTGCATGGACTGGGTCAAGAAGAGGAAA
ATTGCCTCCATTGATTTAATCCTCA-
CAAGTCTGGCCATATCCAGAATTTGTCTATTGTGC
GTAATACTATTAGATTGTTTTATATTG-
GTGCTATATCCAGATGTCTATGCCACTGGTAAA
GAAATGAGAATCATTGACTTCTTCTGGA-
CACTAACCAATCATTTAAGTATCTGGTTTGCAACCT-
GCCTCAGCATTTACTATTTCTTCAAGAT-
AGGTAATTTCTTTCACCCACTTTTCCTC
TGGATGAAGTGGAGAATTGACAGGGT-
GATTTCCTGGATTCTACTGGGGTGCGTGGTTCTC
TCTGTGTTTATTAGCCTTCCAGCCACT-
GAGAATTTGAACGCTGATTTCAGGTTTTGTGTG
AAGGCAAAGAGGAAAACAAACTTAACT-
TGGAGTTGCAGAGTAAATAAAACTCAACATGCT
TCTACCAAGTTATTTCTCAACCTG-
GCAACGCTGCTCCCCTTTTGTGTGTGCCTAATGTCC
TTTTTCCTCTTGATCCTCTCCCTGCG-
GAGACATATCAGGCGAATGCAGCTCAGTGCCACA
GGGTGCAGAGACCCCAGCACAGAAGC-
CCATGTGAGAGCCCTGAAAGCTGTCATTTCCTTC
CTTCTCCTCTTTATTGCCTAC-
TATTTGTCCTTTCTCATTGCCACCTC-
CAGCTACTTTATG CCAGAGACGGAATTAGCTGT-
GATTTTTGGTGAGTCCATAGCTCTAATCTACCCCTCA
AGT CATTCATTTATCCTAATACTGGGGAA-
CAATAAATTAAGACATGCATCTCTAAAGGTGATT
TGGAAAGTAATGTCTATTCTAAAAGGAA-
GAAAATTCCAACAACATAAACAAATCTGA

SEQ ID NO:15

Human T2R08 Amino Acid Sequence

MFSPADNIFIILITGEFILGILGNGY-
IALVNWIDWIKKKKISTVDYILTNLVIARICLIS VMV-

VNGIVIVLNPDVYTKNKQQIVIFTFWT-FANYLNMWITTCLNVFYFLKIASSSHPLFLWLKWKIDMVVHWILLGCFAISLLVS-LIAAIVLSCDYRFHAIAKHKRNITEMFHVSKIPYFEPLTLFNLFAIVPFIVSLISFFLLVRSL-WRHTKQIKLYATGSRDPSTEVHVRAIKTMTSF IFFFF-LYYISSILMTFSYLMTKYKLAVEFGE-IAAILYPLGHSLILIVLNNKLRQTFVRML TCRKIACMI

SEQ ID NO:16

Human T2R08 Nucleotide Sequence

ATGTTCAGTCCTGCAGATAACATCTT-TATAATCCTAATAACTGGAGAATTCATACTAGGAATATTGGGGAATGGATACATTGCAC-TAGTCAACTGGATTGACTGGATTAAGAAGAAAAAGATTTCCACAGTTGACTACATCCTTAC-CAATTTAGTTATCGCCAGAATTTGTTTGATCAGTGTAATGGTTGTAAATGGCATTGTAATAG-TACTGAACCCAGATGTTTATACAAAAAATAAA CAA-CAGATAGTCATTTTTACCTTCTGGA-CATTTGCCAACTACTTAAATATGTGGATTACCACCTGCCTTAATGTCTTCTATTTTCT-GAAGATAGCCAGTTCCTCTCATCCACTTTTTCTCTGGCTGAAGTGGAAAATTGATATGGTG-GTGCACTGGATCCTGCTGGGATGCTTTGCCATTTCCTTGTTGGTCAGCCTTATAGCAG-CAATAGTACTGAGTTGTGATTATAGGTTTCATGCAATTGCCAAACATAAAAGAAACATTACT-GAAATGTTCCATGTGAGTAAAATACCATACTTTGAACCCTTGACTCTCTTTAACCTGTTTG-CAATTGTCCCATTTATTGTGTCACTGATATCATTTTTCCTTTTAGTAAGATCTTTATG-GAGACATACCAAGCAAATAAAACTCTATGCTACCGGCAGTAGAGACCCCAGCACAGAAGT-TCATGTGAGAGCCATTAAAACTATGACTTCATTTATCTTCTTTTTTTTCCTATAC-TATATTTCTTCTATTTTGATGACCTT-TAGCTATCTTATG ACAAAATACAAGTTAGCTGTG-GAGTTTGGAGAGATTGCAGCAATTCTCTACCCCTTGGGT CACTCACTTATTTTAATTGTTT-TAAATAATAAACTGAGGCAGACATTTGT-CAGAATGCTG ACATGTAGAAAAATTGCCTGCAT-GATATGA

SEQ ID NO:17

Human T2R09 Amino Acid Sequence

MPSAIEAIYIILIAGELTIGIWGNGFIV-LVNCIDWLKRRDISLIDIILISLAISRICLLC VISLDG-FFMLLFPGTYGNSVLVSIVNVVWT-FANNSSLWFTSCLSIFYLLKIANISHPFFFWLKLKINKVMLAILLGSFLISLIISVP-KNDDMWYHLFKVSHEENITWKFKVSKIPGTFKQLTLNLGVMVPFILCLISFFLLLFS-LVRHTKQIRLHATGFRDPSTEAHMRAIKAVIIFLLLLIVYYPVFLVMTSSALIPQGKLVL-MIGDIVTVIFPSSHSFILIMGNSKLREAFLKMLRFVKCFLRRRKPFVP

SEQ ID NO:18

Human T2R09 Nucleotide Sequence

ATGCCAAGTGCAATAGAG-GCAATATATATTATTTTAATTGCTGGT-GAATTGACCATAGGG ATTTGGGGAAATGGATTCAT-TGTACTAGTTAACTGCATTGACTGGCTCAAAAGAAGAGAT ATTTCCTTGATTGACATCATCCTGAT-CAGCTTGGCCATCTCCAGAATCTGTCTGCTGTGTGTAATATCATTAGATGGCTTCTTTAT-GCTGCTCTTTCCAGGTACATATGGCAATAGCGTGCTAGTAAGCATTGTGAATGTTGTCTGGA-CATTTGCCAATAATTCAAGTCTCTGGTTTACT TCT-TGCCTCAGTATCTTCTATTTACTCAA-GATAGCCAATATATCGCACCCATTTTTCTTCTGGCTGAAGCTAAAGATCAACAAGGT-CATGCTTGCGATTCTTCTGGGGTCCTTTCTTATCTCTTTAATTATTAGTGTTCCAAAGAAT-GATGATATGTGGTATCACCTTTTCAAAGTCAGT CAT-GAAGAAAACATTACTTGGAAAT-TCAAAGTGAGTAAAATTCCAGGTACTTTCAAACAGTTAACCCTGAACCTGGGGGTGATGGTTC-CCTTTATCCTTTGCCTGATCTCATTTTTCTTGTTACTTTTCTCCCTAGTTAGACACAC-CAAGCAGATTCGACTGCATGCTACAGGGTTCAGAGACCCCAGTACAGAGGCCCACAT-GAGGGCCATAAAGGCAGTGAT-CATCTTTCTGCTCCTC CTCATCGTGTACTAC-CCAGTCTTTCTTGTTATGACCTCTAGCGCTCTGATTCCTCAGGGA AAATTAGTGTTGATGATTGGTGACAT-AGTAACTGTCATTTTCCCATCAAGCCATTCATTCATTCTAATTATGGGAAATAGCAAGT-TGAGGGAAGCTTTTCTGAAGATGTTAAGATTTGTGAAGTGTTTCCTTAGAAGAAGAAAGC-CTTTTGTTCCATAG

SEQ ID NO:19

Human T2R10 Amino Acid Sequence

MLRVVEGIFIFVVVSESVFGVLGNG-FIGLVNCIDCAKNKLSTIGFILTGLAISRIFLIWI IITDG-FIQIFSPNIYASGNLIEYISYFWVIGN-QSSMWFATSLSIFYFLKIANFSNYIFLWLKSRTNMVLPFMIVFLLISSLLNFAY-IAKILNDYKTKNDTVWDLNMYKSEYFIKQILLNLGVIFFFTLSLITCIFLIISLWRHNRQM-QSNVTGLRDSNTEAHVKAMKVLISFIILFILYFIGMAIEISCFTVRENKLLLMFGMTT-TAIYPWGHSFILILGNSKLKQASLRVLQQLKCCEKRKNLRVT

SEQ ID NO:20

Human T2R10 Nucleotide Sequence

ATGCTACGTGTAGTGGAAGGCATCT-TCATTTTTGTTGTAGTTAGTGAGTCAGTGTTTGGGGTTTTGGGGAATGGATTTATTGGACTTG-TAAACTGCATTGACTGTGCCAAGAATAAGTTATCTACGATTGGCTTTATTCTCACCGGCT-TAGCTATTTCAAGAATTTTTCTGATATGGATA ATAAT-TACAGATGGATTTATACAGATAT-TCTCTCCAAATATATATGCCTCCGGTAACCTAATTGAATATATTAGTTACTTTTGGG-TAATTGGTAATCAATCAAGTATGTGGTTTGCCACCAGCCTCAGCATCTTCTATTTCCTGAA-GATAGCAAATTTTTCCAACTACATATTTCTCTGGTTGAAGAGCAGAACAAATATGGTTCTTC-CCTTCATGATAGTATTCTTACTTATTTCATCG TTACT-TAATTTTGCATACATTGCGAAGATTCT-TAATGATTATAAAACGAAGAATGACACAGTCTGGGATCTCAACATGTATAAAAGT-GAATACTTTATTAAACAGATTTTGCTAAATCTGGGAGTCATTTTCTTCTTTACACTATC-

CCTAATTACATGTATTTTTTTAATCATTTCCCTT
TGGAGACACAACAGGCAGATGCAATC-
GAATGTGACAGGATTGAGAGACTCCAACACAGAA
GCTCATGTGAAGGCAAT-
GAAAGTTTTGATATCTTTCATCATC-
CTCTTTATCTTGTATTTT ATAGGCATGGCCATA-
GAAATATCATGTTTTACTGTGCGAGAAAACAAACTG
CTGCTTATG TTTGGAATGACAACCACAGCCATC-
TATCCCTGGGGTCACTCATTTATCTTAATTCTAGGA
AACAGCAAGCTAAAGCAAGC-
CTCTTTGAGGGTACTGCAGCAAT-
TGAAGTGCTGTGAGAAA AGGAAAAATCTCAGAGT-
CACATAG

SEQ ID NO:21

Human T2R11 Amino Acid Sequence

MANMLKNMLTMISAIDFIMGIQRSRVMV-
LVHCIDWIRRWKLSLIDFILTCWAISRIFXXX
XXXXXXXXXXXXXXXXXXXXXXXXXXXXXNHCL
T*FATCLAVFYFLKIVNFSYLFYFWLK
WRINKVAFILPLVSAFSVYQLSFDVHF*CLLVSCPKKY
ERHMTGLLNVSNNKNVNNIIIF
FIGSLSSFSISSIFFLLLLLLSS*RHMKHIRFNFRDCRTPV
YGPISEPRKRFSFFVLLLYK NLPFS

SEQ ID NO:22

Human T2R12 Amino Acid Sequence

MSSIWETLFIRILVV*FIMGTVGN*FIVLVNIID*IRN*
KVSLIDFILNCLAISRICFL* ITILATSFNIGYEKMPD-
SKNLAVSFDILWTGSSYFCLSCTTCLSV-
FYFLKVANFSNPIEL
WMKWKIHKVLLFIVLEATISFCTTSILKEIIINSLI*ERV
TIKGNLTFNYMDTMHDFTSL FLLQMMFILPFVET-
LASILLLILSLWSHTRQMKLHGIYSRDP-
STEAHVKPIKAIISFLLL FIVHYFISIILTLACPLLD-
FVAARTFSSVLVFFHPSGHSFLLILRDSKLKQASLCVL
KKM KYAKKDIISHFYKHA

SEQ ID NO:23

Human T2R12 Nucleotide Sequence

ATGTCAAGCATTTGGGAGACACTGTT-
TATAAGAATTCTTGTAGTGTAATTCATAATGGGG
ACTGTGGGAAATTGATTCATTGTATTG-
GTTAATATCATTGACTGAATCAGGAACTGAAAG
GTCTCCCTGATTGATTTTATTCTCAACT-
GCTTGGCCATCTCCAGGATATGTTTCCTGTAG
ATAACAATTTTAGCTAC-
CTCTTTCAATATAGGCTATGAGAAAAT-
GCCTGATTCTAAGAAT CTTGCAGTAAGTTTTGA-
CATTCTCTGGACAGGATCCAGCTATTTCTGCCTGTC
CTGTACC ACTTGCCTCAGTGTCTTCTATTTCCT-
CAAGGTAGCCAACTTCTCCAATCCCATTTTCCTC
TGGATGAAATGGAAAATTCACAAGGT-
GCTTCTCTTTATTGTACTAGAGGCAACGATCTCT
TTCTGCACAACTTCCATTCTGAAG-
GAAATAATAATTAATAGTTTAATCTAAGAACGGGTA
ACAATAAAAGGCAACTTGACATTTAAT-
TATATGGATACCATGCATGATTTCACTTCTCTG
TTTCTCCTTCAGATGATGTTCATCCTTC-
CTTTTGTGGAAACACTGGCTTCCATTCTTCTC
TTAATCCTCTCCTTATGGAGCCACAC-
CAGGCAGATGAAGCTACATGGTATTTATTCCAGG
GATCCCAGCACAGAAGCCCATGTAAAAC-
CTATAAAAGCTATAATTTCATTTCTACTCCTC TTTAT-
TGTGCATTATTTCATCAGTATCATAC-
TAACATTGGCCTGTCCTCTTCTAGACTTC
GTTGCGGCAAGGACTTTTAGTAGTGT-
GCTGGTATTTTTCCATCCATCTGGCCATTCATTT
CTTCTAATTTTACGGGACAGCAAACT-
GAAGCAAGCTTCTCTCTGTGTCCTGAAGAAGATG
AAGTATGCCAAAAGGACATAATCTC-
TATTTTTATAAACATGCCTGA

SEQ ID NO:24

Human T2R13 Amino Acid Sequence

MESALPSIFTLVIIAEFIIGNLSNGFIV-
LINCIDWVSKRELSSVDKLLIILAISRIGLIW EIL-
VSWFLALHYLAIFVSGTGLRIMIFSWIV-
SNHFNLWLATIFSIFYLLKIASFSSPAFL
YLKWRVNKVILMILLGTLVFLFLNLI-
QINMHIKDWLDRYERNTTWNFSMSDFETFSVSVK
FTMTMFSLTPFTVAFISFLLLIFS-
LQKHLQKMQLNYKGHRDPRTKVHTNALKIVISFLLF
YASFFLCVLISWISELYQNTVIYMLCE-
TIGVFSPSSHSFLLILGNAKLRQAFLLVAAKVW AKR

SEQ ID NO:25

Human T2R13 Nucloetide Sequence

ATGGAAAGTGCCCTGCCGAGTATCT-
TCACTCTTGTAATAATTGCAGAATTCATAATTGGG
AATTTGAGCAATGGATTTATAGTACT-
GATCAACTGCATTGACTGGGTCAGTAAAAGAGAG
CTGTCCTCAGTCGATAAACTCCTCAT-
TATCTTGGCAATCTCCAGAATTGGGCTGATCTGG
GAAATATTAGTAAGTTGGTTTT-
TAGCTCTGCATTATCTAGCCATATTTGT-
GTCTGGAACA GGATTAAGAATTATGATTTT-
TAGCTGGATAGTTTCTAATCACTTCAATCTCTGGCTT
GCT ACAATCTTCAGCATCTTTTATTTGCT-
CAAAATAGCGAGTTTCTCTAGCCCTGCTTTTCTC
TATTTGAAGTGGAGAGTAAACAAAGT-
GATTCTGATGATACTGCTAGGAACCTTGGTCTTC
TTATTTTTAAATCTGATACAAATAAA-
CATGCATATAAAAGACTGGCTGGACCGATATGAA
AGAAACACAACTTGGAATTTCAGTAT-
GAGTGACTTTGAAACATTTTCAGTGTCGGTCAAA
TTCACTATGACTATGTTCAGTCTAACAC-
CATTTACTGTGGCCTTCATCTCTTTTCTCCTG
TTAATTTTCTCCCTGCAGAAACATCTC-
CAGAAAATGCAACTCAATTACAAAGGACACAGA
GACCCCAGGACCAAGGTCCATACAAAT-
GCCTTGAAAATTGTGATCTCATTCCTTTTATTC TAT-
GCTAGTTTCTTTCTATGTGTTCTCATAT-
CATGGATTTCTGAGCTGTATCAGAACACA
GTGATCTACATGCTTTGTGAGACGATTG-
GAGTCTTCTCTCCTTCAAGCCACTCCTTTCTT
CTGATTCTAGGAAACGCTAAGTTAAGA-
CAGGCCTTTCTTTTGGTGGCAGCTAAGGTATGG
GCTAAACGATGA

SEQ ID NO:26

Human T2R14 Amino Acid Sequence

MGGVIKSIFTFVLIVEFIIGNLGNSFI-
ALVNCIDWVKGRKISSVDRILTALAISRISLVW LIFG-
SWCVSVFFPALFATEKMFRMLTNI-
WTVINHFSVWLATGLGTFYFLKIANFSNSIFL
YLKWRVKKVVLVLLLVTSV-
FLFLNIALINIHINASINGYRRNKTCSS-
DSSNFTRFSSLIV LTSTVFIFIPFTLSLAMFLLLIFSM-

WKHRKKMQHTVKISGDASTRAHRGVKSVITFFLLY
AIFSLSFFISVWTSERLEENLI-
ILSQVMGMAYPSCHSCVLILGNKKL-
RQASLSVLLWLRY MFKDGEPSGHKEFRESS

SEQ ID NO:27

Human T2R14 Nucleotide Sequence

ATGGGTGGTGTCATAAAGAGCATATTTA-
CATTCGTTTTAATTGTGGAATTTATAATTGGA AATT-
TAGGAAATAGTTTCATAGCACTGGT-
GAACTGTATTGACTGGGTCAAGGGAAGAAAG
ATCTCTTCGGTTGATCGGATCCTCACT-
GCTTTGGCAATCTCTCGAATTAGCCTGGTTTGG
TTAATATTCGGAAGCTGGTGTGTGTCT-
GTGTTTTTCCCAGCTTTATTTGCCACTGAAAAA
ATGTTCAGAATGCTTACTAATATCTGGA-
CAGTGATCAATCATTTTAGTGTCTGGTTAGCT
ACAGGCCTCGGTACTTTTTATTTTCT-
CAAGATAGCCAATTTTTCTAACTCTATTTTTCTC
TACCTAAAGTGGAGGGTTAAAAAGGTG-
GTTTTGGTGCTGCTTCTTGTGACTTCGGTCTTC
TTGTTTTTAAATATTGCACTGATAAA-
CATCCATATAAATGCCAGTATCAATGGATACAGA
AGAAACAAGACTTGCAGTTCTGAT-
TCAAGTAACTTTACACGATTTTCCAGTCTTATTGTA
TTAACCAGCACTGTGTTCATTTTCATAC-
CCTTTACTTTGTCCCTGGCAATGTTTCTTCTC
CTCATCTTCTCAATGTGGAAACATCG-
CAAGAAGATGCAGCACACTGTCAAAATATCCGGA
GACGCCAGCACCAAAGCCCACAGAG-
GAGTTAAAAGTGTGATCACTTTCTTCCTACTCTAT
GCCATTTTCTCTCTGTCTTTTTTCATAT-
CAGTTTGGACCTCTGAAAGGTTGGAGGAAAAT
CTAATTATTCTTTCCCAGGTGATGG-
GAATGGCTTATCCTTCATGTCACTCATGTGTTCTG
ATTCTTGGAAACAAGAAGCTGAGACAG-
GCCTCTCTGTCAGTGCTACTGTGGCTGAGGTAC
ATGTTCAAAGATGGGGAGCCCTCAGGT-
CACAAAGAAATTTAGAGAATCATCTTGA

SEQ ID NO:28

Human T2R15 Amino Acid Sequence

MITFLPIIFSILVVVTFVLGNFANGFIV-
LVNSIEWVKRQKISFADQILTALAVSRVGLLW VILLH-
WYATVLNPGSYSLGVRITTINAWAVT-
NHFSIWVATSLSIFYFLKIANFSNFIFLH
LKRRIKSVIPVILLGSLLFLVCHLVVVN-
MDESMWTKEYEGNVSWEIKLSDPTHLSDMTVT
TLANLIPFTLSLLSFLLLICSLCKHLKK-
MQFHGKGSPDSNTKVHIKALQTVTSFLLLFAV
YFLSLITSIWNFRRRL*NEPVLMLSQTTAIIYPSFHSFIL
IWGSKKLKQTFLLILCQIKC

SEQ ID NO:29

Human T2R15 Nucleotide Sequence

ATGATAACTTTTCTACCCAT-
CATTTTTTCCATTCTAGTAGTGGTTA-
CATTTGTTCTTGGG AATTTTGCTAATGGCTTCAT-
AGTGTTGGTAAATTCCATTGAGTGGGTCAAGAGAC
AAAAG ATCTCCTTTGCTGACCAAATTCTCACT-
GCTCTGGCAGTCTCCAGAGTTGGTTTGCTCTGG
GTAATATTATTACATTGGTATGCAACT-
GTTTTGAATCCAGGTTCATATAGTTTAGGAGTA
AGAATTACTACTATTAATGCCTGGGCTG-
TAACCAACCATTTCAGCATCTGGGTTGCTACT AGC-
CTCAGCATATTTTATTTCCTCAAGAT-
TGCCAATTTCTCCAACTTTATTTTTCTTCAC
TTAAAAAGGAGAATTAAGAGTGTCATTC-
CAGTGATACTATTGGGGTCTTTGTTATTTTTG
GTTTGTCATCTTGTTGTGGTAAACATG-
GATGAGAGTATGTGGACAAAAGAATATGAAGGA
AACGTGAGTTGGGAGATCAAATTGAGT-
GATCCGACGCACCTTTCAGATATGACTGTAACC
ACGCTTGCAAACTTAATACCCTT-
TACTCTGTCCCTGTTATCTTTTCTGCTCTTAATCTGT
TCTTTGTGTAAACATCTCAAGAAGATG-
CAGTTCCATGGCAAAGGATCTCCAGATTCCAAC
ACCAAGGTCCACATAAAAGCTTTG-
CAAACGGTGACCTCCTTCCTCTTGTTATTTGCTGTT
TACTTTCTGTCCCTAATCACATC-
GATTTGGAATTTTAGGAGGAGGCTGTA-
GAACGAACCT GTCCTCATGCTCAGCCAAACTACT-
GCAATTATATACCCTTCATTTCATTCATTCATCCTA
ATTTGGGGAAGCAAGAAGCTGAAACA-
GACCTTTCTTTTGATTTTGTGTCAGATTAAGTGC
TGA

SEQ ID NO:30

Human T2R16 Amino Acid Sequence

MIPIQLTVFFMIIYVLESLTIIVQSS-
LIVAVLGREWLQVRRLMPVDMILISLGISRFCLQ
WASMLNNFCSYFNLNYVLCNLTITWEFF-
NILTFWLNSLLTVFYCIKVSSFTHHIFLWLRW RILRLF-
PWILLGSLMITCVTIIPSAIGNYI-
QIQLLTMEHLPRNSTVTDKLENFHQYQFQA
HTVALVIPFILFLASTIFLMASLTK-
QIQHHSTGHCNPSMKARFTALRSLAVLFIVFTSYF
LTILITIIGTLFDKRCWLWVWEAFVYA-
FILMHSTSLMLSSPTLKRILKGKC

SEQ ID NO:31

Human T2R16 Nucleotide Sequence

ATGATACCCATCCAACTCACTGTCTTCT-
TCATGATCATCTATGTGCTTGAGTCCTTGACA
ATTATTGTGCAGAGCAGCCTAATTGTTG-
CAGTGCTGGGCAGAGAATGGCTGCAAGTCAGA
AGGCTGATGCCTGTGGACATGATTCT-
CATCAGCCTGGGCATCTCTCGCTTCTGTCTACAG
TGGGCATCAATGCTGAA-
CAATTTTTGCTCCTATTTTAATTTGAAT-
TATGTACTTTGCAAC TTAACAATCACCTGG-
GAATTTTTTAATATCCTTACATTCTGGTTAAACAGCT
TGCTTACC GTGTTCTACTGCATCAAGGTCTCT-
TCTTTCACCCATCACATCTTTCTCTGGCTGAGGTGG
AGAATTTTGAGGTTGTTTCCCTGGATAT-
TACTGGGTTCTCTGATGATTACTTGTGTAACA
ATCATCCCTTCAGCTATTGGGAATTA-
CATTCAAATTCAGTTACTCACCATGGAGCATCTA
CCAAGAAACAGCACTGTAACTGA-
CAAACTTGAAAATTTTCATCAGTAT-
CAGTTCCAGGCT CATACAGTTGCATTGGTTATTC-
CTTTCATCCTGTTCCTGGCCTCCACCATCTTTCTCAT
G GCATCACTGACCAAGCAGATACAACAT-
CATAGCACTGGTCACTGCAATCCAAGCATGAAA
GCGCGCTTCACTGCCCTGAGGTCCCT-
TGCCGTCTTATTTATTGTGTTTACCTCTTACTTT
CTAACCATACTCATCACCATTATAGG-
TACTCTATTTGATAAGAGATGTTGGTTATGGGTC
TGGGAAGCTTTTGTCTATGCTTTCATCT-

TAATGCATTCCACTTCACTGATGCTGAGCAGC CTACGTTGAAAAGGATTCTAAAGGGAAAGTGCTAG

SEQ ID NO:32

Human T2R17 Amino Acid Sequence

MCSAXLLIILSILVVFAFVLGNVANG-FIALINVNDWVKTQKISSTDQIVTALAFSRIGLL XTLI-ILLHWYATVFNSALYSLEVRIVPSNV-SAIINHFSIWLATSLSIFYLFKIANFSNFI FLHLKKRIKSVLLVILLGSLVFLICN-LAVVTMDDSVWTKEFEGNVTWKIELRNAIHLSNM TITNHASKLHTVHSDSNIFSAVSLFSXT-MLANFTLFILTLISFLLLVCSPCKHLKMMQLH GKG-SQDLSTKVHIKPLQTVISFRMLFAIY-FLCIITSTWNPRTQQSNLVFLLYQTLAIMYP SFHSFILIMRSRKLKQTSLSVLCQVTCWVK

SEQ ID NO:33

Human T2R18 Amino Acid Sequence

MFVGINIFFLVVATRGLVLGM-LGNGLIGLVNCIEWAKSWKVSSADFILTSLAIVRIIRLY LILFDSFIMVLSPHLYTIRKLVKLFTILWALINQLSI*FA TCLSIFYLLKIANFSHSLFL WLKWRMNGMIVML-LILSLFLLIFDSLVLEIFIDISLNIIDK-SNLTLYLDESKTLYDKLSI LKTLLSLTYVIP-FLLTLTSLLLLFISLVRHTKNLQLNSLGSRDSSTEAHK RAMKMVIAFL LLFIINFISTLIGDWIFLEVENYQVM-MFIMMILLAFPSGHSFIIILGNNKLRQSSLRLLW HLKFSLKKAKPLTS

SEQ ID NO:34

Human T2R18 Nucleotide Sequence

ATGTTCGTTGGAAT-TAATATTTTCTTTCTGGTGGTGGCAA-CAAGAGGACTTGTCTTAGGA ATGCTGG-GAAACGGGCTCATTGGACTGGTAAACTGCATTGAG TGGGCCAAGAGTTGGAAG GTCTCATCAGCT-GATTTCATCCTCACCAGCTTGGCTAT-AGTCAGAATCATTCGACTGTAT TTAATAC-TATTTGATTCATTTATAATGGTATTGTCCCCTCATCTA TATACCATCCGTAAA CTAGTAAAACTGTTTACTAT-TCTTTGGGCATTAATTAATCAGTTAAG-TATCTAGTTTGCC ACCTGCCTAAGCATTTTCTACT-TGCTTAAGATAGCCAATTTCTCCCACTCCCTTTTCC TC TGGCTGAAGTGGAGAATGAACGGAAT-GATTGTTATGCTTCTTATATTGTCTTTGTTCTTA CTGATTTTTGACAGTTTAGTGCTA-GAAATATTTATTGATATCTCACTCAATATAATAGAT AAAAGTAATCTGACTTTATATTTAGAT-GAAAGTAAAACTCTCTATGATAAACTCTCTATT TTAAAAACTCTTCTCAGCTTGACAT-ACGTTATTCCCTTTCTTCTGACTCTGACCTCTTTG CTCCTTTTATTTATATCCTTAGTGAGA-CACACCAAGAATTTGCAGCTCAACTCTCTGGGC TCAAGGGACTCCAGCACAGAGGCCCAT-AAAAGGGCCATGAAAATGGTGATAGCCTTCCTC CTCCTTTTTATTATTAACTTTATTTC-CACTTTAATAGGAGATTGGATCTTCCTTGAGGTA GAGAATTATCAGGTCATGATGTTTAT-TATGATGATTTTACTTGCCTTTCCCTCAGGCCAC TCATTTATTATAATTTTGGGAAACAA-CAAGCTAAGACAGAGCTCCTTGAGACTACTGTGG CATCTTAAATTCTCTCTGAAAAAAG-CAAAACCTTTAACTTCATAG

SEQ ID NO:35

Human T2R19 Amino Acid Sequence

VTTLANLIPFTLSLICFLLLICS-LCKHLKKMRLHSKGSQDPST-KVHIKALQTVTSFLMLF AIYFLCIITSTWNL-RTQQSKLVLLLCQTVAIMYPSFHSFILIMGSRKLKQT FLSVLWQMT C

SEQ ID NO:36

Human T2R19 Nucleotide Sequence

CTGTAACTACTCTAGCAAACCTCATAC-CCTTTACTCTGAGCCTAATATGTTTTCTGCTGT TAATCTGTTCTCTTTGTAAACATCTCAA-GAAGATGCGGCTCCATAGCAAAGGATCTCAAG ATCCCAGCACCAAGGTC-CATATAAAAGCTTTGCAAACTGTGAC-CTCCTTCCTCATGTTAT TTGCCATTTACTTTCTGTG-TATAATCACATCAACTTGGAATCTTAGGACACAGCA GAGCA AACTTGTACTCCTGCTTTGCCAAACTGT-TGCAATCATGTATCCTTCATTCCACTCATTCA TCCT-GATTATGGGAAGTAGGAAGCTAAAACA-GACCTTTCTTTCAGTTTTGTGGCAGATGA CATGCTGAGTGAAAGAAGAGAAACCCCT-CAACTCCATAGATTCACAAGGGGAGCATCGTGG GTCTTCTAGCAGAAAACAAACTGATGGT-GTCTGGAACATTTTATAT

SEQ ID NO:37

Human T2R20 Amino Acid Sequence

HLXRKAKSVVLVIVLGSLFFLVC-QLVMKNTYINVWTEECEGNVTWKIKLR-NAMHLSNLTV AMLANLIPFTLTVISFLLLTYS-LCKHLKKMQLHGKGSQDPSTKIHIKALQTVTSFLVLL A IYFLCLIIS

SEQ ID NO:38

Human T2R20 Nucleotide Sequence

TTCATCACTTANAAAGGAAGGCTAA-GAGTGTAGTTCTGGTGATAGTGTTGGGGTCTTTGT TCTTTTTGGTTTGTCAACTTGTGAT-GAAAAACACGTATATAAATGTGTGGACAGAAGAAT GTGAAGGAAACGTAACTTGGAAGAT-CAAACTGAGGAATGCAATGCACCTTTCCAACTTGA CTGTAGCCATGCTAGCAAACTTGATAC-CATTCACTCTGACCGTGATATCTTTTCTGCTGT TAATCTACTCTCTGTGTAAACATCTGAA-GAAGATGCAGCTCCATGGCAAAGGATCTCAAG ATCCCAGCACCAAGATCCACAT-AAAAGCTCTGCAAACTGTGACCTCCTTC-CTCGTATTAC TTGCCATTTACTTTCTGTGTCTAAT-CATATCCTTTTG

SEQ ID NO:39

Human T2R21 Amino Acid Sequence

MPPGIGNTFLIVMMGEFII*MLGNGFIVLVNCIDW* GVK*SY*TTASSPAWLSPQSVNFG *YYLIHL*QHYGHIYMPSIN**NLFIFFGH*PIT*LPGLL P*CFLLL*NTYFSHPCFIWL RWRISRTLLEL-PLGSLLLLFFNLALTGGLSDLWIN-IYTIYERNSTWSLDVSKILYCSLWI LVSLIYLIS-

FLLSLISLLLLILSLMRHIRNLQLNTMGPRDLRMKAH KRAMKMKMKMMVSF LLFFLVHFSSLLPTGWIFLIQQK*QANFFVLLTSIIFPSS HSFVLILENCKLRQTAVGPL WHLKCHLKRVKL

SEQ ID NO:40

Human T2R22 Amino Acid Sequence

MATESDTNLLILAIAEFIISMLGNVFIGLVNCSEXIK NXKVFSADFILTCLAISHNGQLL VILFDSFLVGLASHLYTTYRLXKNCIMLWT

SEQ ID NO:41

Human T2R22 Nucleotide Sequence

TATAGGGACNGTGATGCTTCGTA-CACTCTCCAAGAAGAAACACTCCGTGAG-GTATGTGAG ACTGCATNCCTTAGTAGATCTNTTGG-GATATATATTCATAATATAGAAAAANAGGCAAAG ACTTNCTTAAGTATATGAGACTCTATC-CAACAGCAGAAGGTTCTGATCAAGACTGGAAGT GCAATANAAGCAATGAAGATTAGTATCA-GATATGAATGCTCTTCTGCAATGGTCTGATTG TNA-CATTATTAATGATACANAGTAT-TAAAAACTTGGATTTTNTTGTCTCTGGAGATGGCC ACCGAATCGGACACAAATCTTCTGAT-TCTGGCAATAGCAGAATTCATCATCAGCATGCTG GGGAATGTGTTCATTGGACTGGTAAACT-GCTCTGAANGGATCAAGAACCANAAGGTCTTC TCAGCTGACTTCATCCTCACCTGCTTG-GCTATCTCTCACAATGGACAACTGTTGGTGATA CTGTTTGATTCATTTCTAGTGGGACT-TGCTTCACATCTATATACCACATATAGACTANGA AAAAACTGTATTATGCTTTGGACATGAC-TAATCACTTGACACACTGCTTCGCACGTGCTA GCATATTCTATTCTTAGATAGCCACTTC-NCACTCCTTGTCTCTGCTGAAGTGGGAT

SEQ ID NO:42

Human T2R23 Amino Acid Sequence

VAFVLGNVANGFIALVNVIDXVNTRKISSAEQILTA LVVSRIGXTLXHSIP*DATRC*SA LYRXEVRIVASN

SEQ ID NO:43

Human T2R23 Nucleotide Sequence

AGGGTTGAGTCGTGCTTATCTTCACT-TAACCTAGTATANAANTACAGCATATAGCAAGGA GAGAATGTATATGAAGAGGAGT-GAATTTGAGTCTGTTTGAGAATAATGAC-CTTTTCTATT TCTATAAAGACAGTTTTGAATTCATC-TATTAGCATATGCTGGTGCTTGCCTGTTGACACT AGTCACTGAATTTAAAGGCAGAAAATGT-TATTGCACATTTAGTAATCAAGTGTTCATCGA AGT-TAACATCTGGATGTTAAAGGACTCAGAA-CAAGTGTTACTAAGCCTGCATTTTTTTAT CTGTTCAAACATGATGTGTTNTCTGCT-CATCATTTCATCAATTCTGGTAGAGTTGCATTT GTTCTTGGAAATGTNGCCAATGGCT-TCATAGCTCTAGTAAATGTCATTGACTGNGTTAAC ACACGAAAGATCTCCTCAGCTGAG-CAAATTCTCACTGCTCTGGTGGTCTCCAGAATTGGT NNTACTCTGNGTCATAGTATTCCT-TGAGATGCAACTAGATGTTAATCTGCTCTATATAGG NTAGAAGTAAGAATTGTTGCTTCTAAT-GCCTGAGCTCGTACGAACCATT

SEQ ID NO:44

Human T2R24 Amino Acid Sequence

MATELDKIFLILAIAEFIISMLGNV-FIGLVNCSEGIKNQKVFSADFILTCLAISTIGQLL VIL-FDSFLVGLASHLYTTYRLGKTVIMLWH-MTNHLTTWLATCLSIFYFFKIAHFPHSLFL WLRWRMNGMIVMLLILSLFLLIFDSLV-LEIFIDISLNIIDKSNLTLYLDESKTLYDKLSI LKTLLSLTSFIPFSLFLTSLL-FLFLSLVRHTRNLKLSSLGSRDSSTEAH-HRAMKMVMSFL FLFIVHFFSLQVANGIFFMLWNN-KYIKFVMLALNAFPSCHSFILILGNSKLRQTAVRLLW HLRNYTKTPNALPL

SEQ ID NO:45

Human T2R24 Nucleotide Sequence

ATGGCCACCGAATTGGA-CAAAATCTTTCTGATTCTGGCAATAGCA-GAATTCATCATCAGC ATGCTGGGGAATGTGTTCAT-TGGACTGGTAAACTGCTCTGAAGGGATCAAGAACC AAAAG ATGCTGGGGAATGTGTTCATTGGACTGG-TAAACTGCTCTGAAGGGATCAAGAACCAAAAG GTCTTCTCAGCTGACTTCATCCTCACCT-GCTTGGCTATCTCCACAATTGGACAACTGTTG GTGATACTGTTTGATTCATTTCTAGTGG-GACTTGCTTCACATTTATATACCACATATAGA CTAG-GAAAAACTGTTATTATGCTTTGGCACAT-GACTAATCACTTGACAACCTGGCTTGCC ACCTGCCTAAGCATTTTCTATTTCTT-TAAGATAGCCCACTTCCCCCACTCCCTTTTCCTC TGGCTGAGGTGGAGGATGAACGGAAT-GATTGTTATGCTTCTTATATTGTCTTTGTTCTTA CTGATTTTTGACAGTTTAGTGCTA-GAAATATTTATTGATATCTCACTCAATATAATAGAT AAAAGTAATCTGACTTTATATTTAGAT-GAAAGTAAAACTCTCTATGATAAACTCTCTATT TTAAAAACTCTTCTCAGCTTAAC-CAGTTTTATCCCCTTTTGTCTGTTCCTGACCTCCTTG CTTTTTTTATTTCTGTCCTTGGTGAGA-CATACTAGAAATTTGAAGCTCAGTTCCTTGGGC TCTAGAGACTCCAGCACAGAGGCCCAT-AGGAGGGCCATGAAAATGGTGATGTCTTTCCTT TTCCTCTTCATAGTTCATTTTTTTTCCT-TACAAGTGGCCAATGGGATATTTTTTATGTTG TGGAACAACAAGTACATAAAGTTTGT-CATGTTAGCCTTAAATGCCTTTCCCTCGTGCCAC TCATTTATTCTCATTCTGGGAAACAG-CAAGCTGCGACAGACAGCTGTGAGGCTACTGTGG CATCTTAGGAACTATACAAAAACAC-CAAATGCTTTACCTTTGTAG

SEQ ID NO:46

Human T2R25 Amino Acid Sequence

LSPFRMLFAIYFLCIITSTWNPRTQQSN-LVFLLYQTLAIMYPSFHSFILIMRSRKLKQTS LSVL-CQVTCWVK

SEQ IN NO:47

Human T2R26 Amino Acid Sequence

MPPGIGNTFLIVMMGEFII*MLGNGFIVLVNCIDVRS QMILLDNCILTSLAISTISQLWI ILLDSFVTALWPH-LYAFNKLIKFIHIFWALTNHLVTWLAC-

CLSVFYFFKIAYFSHPCFIW LRWRISRTLLEL-
PLGSLLLLFFNLALTGGLSDLWINTYTMYERNSTWSL
DVSKILYCSLW ILVSLIYLISFLLSLISLLLLILSLM-
RHIRNLQLNTMGPRDLRMKAHKRAMKMK-
MKMMVS FLLFFLVHFSSLLPTGWIFLIQQK

SEQ ID NO:48

Human T2R27 Amino Acid Sequence

LANLIDWAENQICLMDFILSSLA-
ICRTLLLGCCVAIRCTYNDYPNIDAVNHNLIKIITIF
DILRLVSK*LGIWFASYLSIFYLLKVALFHHAIFLWLK
WRISRAVFTFLMIFLFFYISII
SMIKIKLFLDQC*YKI*EKLLLEGRCE*SPPSC*PDAH*
PGVVYSLYHFSYLMFLVCYLP KGKHCTAVVIGD-
WLQRPRTEAYVRAMNIMIAFFFHLLYS-
LGTSLSSVSYFLCKRKIVALG AYLSYPLSHSFILI-
MENNKVRKAL

SEQ ID NO:49

Human T2R28 Amino Acid Sequence

NICVLLIILSILVVSAFVLGNVANGFIALINVNDW

SEQ ID NO:50

Human T2R29 Amino Acid Sequence

MQAALTAFFVLLFSLLSLLGIAANGFIVLVLGKEWL

SEQ ID NO:51

Human T2R30 Amino Acid Sequence

MITFLPIIFSILVVVTFVLGNFSNGFI-
ALVNSIEWVKTRKISSADQILTALVVSRVGLLW
VILLHWYANVFNSALYSSEVGAVASNI-
SAIINHFSIWLATSLSIFYLLKIANFSNLIFLH LKKR-
IRSVVLVILLGPLVFLICNLAVITMDDS-
VWTKEYEGNVTWKIKLRNAIHLSNMTVS
TLANLIPFILTLICFLLLICSLCKHLKK-
MQLHGKGSQDPSTKVHIKALQTVTSFLLLCAI
YFLSMIISVCNFGRLEKQPVFMFCQAI-
IFSYPSTHPFILILGNKKLKQIFLSVLRHVRYW
VKDRSLRLHRFTRGALCVF

SEQ IN NO:52

Human T2R30 Nucleotide Sequence

ATGATAACTTTTCTACCCAT-
CATTTTTTCCATTCTGGTAGTGGTTA-
CATTTGTTCTTGGA AATTTTTCCAATGGCTTCAT-
AGCTCTAGTAAATTCCATTGAGTGGGTCAAGACAC
GAAAG ATCTCCTCAGCTGACCAAATCCTCACT-
GCTCTGGTGGTCTCCAGAGTTGGTTTACTCTGG
GTCATATTATTACATTGGTATGCAAAT-
GTGTTTAATTCAGCTTTATATAGTTCAGAAGTA
GGAGCTGTTGCTTCTAATATCTCAG-
CAATAATCAACCATTTCAGCATCTGGCTTGCTACT
AGCCTCAGCATATTTTATTTGCTCAA-
GATTGCCAATTTCTCCAACCTTATTTTTCTCCAC
TTAAAGAAGAGAATTAGGAGTGTTGT-
TCTGGTGATACTGTTGGGTCCCTTGGTATTTTTG
ATTTGTAATCTTGCTGTGATAACCATG-
GATGACAGTGTGTGGACAAAAGAATATGAAGGA
AATGTGACTTGGAAGATCAAATTGAG-
GAATGCAATACACCTTTCAAATATGACTGTAAGC
ACACTAGCAAACCTCATACCCTTCAT-
TCTGACCCTAATATGTTTTCTGCTGTTAATCTGT
TCTCTGTGTAAACATCTCAAGAAGATG-
CAGCTCCATGGCAAAGGATCTCAAGATCCCAGC
ACCAAGGTCCACATAAAAGCTTTG-
CAAACTGTGACCTCCTTTCTTCTGTTATGTGCCATT
TACTTTCTGTCCATGATCATAT-
CAGTTTGTAATTTTGGGAGGCTG-
GAAAAGCAACCTGTC TTCATGTTCTGCCAAGCTAT-
TATATTCAGCTATCCTTCAACCCACCCATTCATCCTG
ATT TTGGGAAACAAGAAGCTAAAGCA-
GATTTTTCTTTCAGTTTTGCGGCATGT-
GAGGTACTGG GTGAAAGACAGAAGCCTTCGTCTC-
CATAGATTCACAAGAGGGGCATTGTGTGTCTTCTAG

SEQ ID NO:53

Human T2R31 Amino Acid Sequence

MTTFIPIIFSSVVVVLFVIGNFANGFI-
ALVNSIERVKRQKISFADQILTALAVSRVGLLW
VLLLNWYSTVFNPAFYSVEVRTTAYNV-
WAVTGHFSNWLATSLSIFYLLKIANFSNLIFLH
LKRRVKSVILVMLLGPLLFLACQLFVIN-
MKEIVRTKEFEGNMTWKIKLKSAMYFSXMTVT
IGAXLVPFTLSLISFLMLICSLCKHLKK-
MQLHGEGSQDLSTKVHIKALQTLISFLLICAI
FFLFLIVSVWSPRRLRNDPVVM-
VSKAVGNIYLAFDSFILIWRTKKLKHTFLLILCQIRC

SEQ ID NO:54

Human T2R31 Nucleotide Sequence

ATGACAACTTTTATACCCAT-
CATTTTTTCCAGTGTGGTAGTGGTTC-
TATTTGTTATTGGA AATTTTGCTAATGGCTTCATAG-
CATTGGTAAATTCCATTGAGCGGGTCAAGAGACAA
AAG ATCTCTTTTGCTGACCAGATTCTCACT-
GCTCTGGCGGTCTCCAGAGTTGGTTTGCTCTGG
GTATTATTATTAAATTGGTATTCAACT-
GTGTTTAATCCAGCTTTTTATAGTGTAGAAGTA
AGAACTACTGCTTATAATGTCTGGGCAG-
TAACCGGCCATTTCAGCAACTGGCTTGCTACT AGC-
CTCAGCATATTTTATTTGCTCAAGAT-
TGCCAATTTCTCCAACCTTATTTTTCTTCAC
TTAAAGAGGAGAGTTAAGAGTGTCAT-
TCTGGTGATGCTGTTGGGGCCTTTACTATTTTTG
GCTTGTCAACTTTTTGTGATAAACAT-
GAAAGAGATTGTACGGACAAAAGAATTTGAAGGA
AACATGACTTGGAAGATCAAATTGAA-
GAGTGCAATGTACTTTTCANATATGACTGTAACC
ATTGGAGCANACTTAGTACCCTT-
TACTCTGTCCCTGATATCTTTTCTGATGCTAATCTGT
TCTCTGTGTAAACATCTCAAGAAGATG-
CAGCTCCATGGAGAAGGATCGCAAGATCTCAGC
ACCAAGGTCCACATAAAAGCTTTG-
CAAACTCTGATCTCCTTCCTCTTGTTATGTGCCATT
TTCTTTCTATTCCTAATCGTTTCG-
GTTTGGAGTCCTAGGAGGCTGCGGAAT-
GACCCGGTT GTCATGGTTAGCAAGGCTGTTG-
GAAACATATATCTTGCATTCGACTCATTCATCCTAAT
T TGGAGAACCAAGAAGCTAAAACACAC-
CTTTCTTTTGATTTGTGTCAGATTAGGTGCTGA

SEQ ID NO:55

Human T2R32 Amino Acid Sequence

HSFMLTMGSRKPKQTFLSAL

SEQ ID NO:56

Human T2R33 Amino Acid Sequence

MVYFLPIIFSILVVFAFVLGNFSNGFI-
ALVNVIDWVKRQKISSADQILTALVVSRVGLLW
VILLHWYANVFNSALYSLEVRIVAS-
NISAVINHFSIWLAASLSIFYLLKIANFSNLIFLH
LKKRIKSVVLVILLGPLVFLICNLAVIT-
MDERVWTKEYEGNVTWKIKLRNAIHLSSLTVT
TLANLIPFTLSLICFLLLICSLCKHLKK-
MQLHSKGSQDPSTKVHIKALQTVISFLMLCAI YFLSI-
MISVWNLRSLENKPVFMFCKAIRF-
SYPSIHPFILIWGNKKLKQTFLSVFWQVRYW
VKGEKPSSP

SEQ ID NO:57

Human T2R33 Nucleotide Sequence

ATGGTATATTTTCTGCCCAT-
CATTTTTTCCATTCTGGTAGTGTTTG-
CATTTGTTCTTGGA AATTTTTCCAATGGCTTCAT-
AGCTCTAGTAAATGTCATTGACTGGGTTAAGAGACA
AAAG ATCTCCTCAGCTGACCAAATTCTCACT-
GCTCTGGTGGTCTCCAGAGTTGGTTTACTCTGG
GTCATATTATTACATTGGTATGCAAAT-
GTGTTTAATTCAGCTTTATATAGTTTAGAAGTA
AGAATTGTTGCTTCTAATATCTCAGCAG-
TAATCAACCATTTCAGCATCTGGCTTGCTGCT AGC-
CTCAGCATATTTTATTTGCTCAA-
GAITGCCAATTTCTCCAACCTTATTTTTCTCCAC
CTAAAGAAGAGAATTAAGAGTGTTGT-
TCTGGTGATACTGTTGGGGCCCTTGGTATTTCTG
ATTTGTAATCTTGCTGTGATAACCATG-
GATGAGAGAGTGTGGACAAAAGAATATGAAGGA
AATGTGACTTGGAAGATCAAATTGAG-
GAATGCAATACACCTTTCAAGCTTGACTGTAACT
ACTCTAGCAAACCTCATACCCTT-
TACTCTGAGCCTAATATGTTTCTGCTGTTAATCTGT
TCTCTTTGTAAACATCTCAAGAAGATG-
CAGCTCCATAGCAAAGGATCTCAAGATCCCAGC
ACCAAGGTCCACATAAAAGCTTTG-
CAAACTGTGATCTCCTTCCTCATGTTATGTGCCATT
TACTTTCTGTCCATAATGATAT-
CAGTTTGGAATCTTAGGAGTCTGGAAAA-
CAAACCTGTC TTCATGTTCTGCAAAGCTATTAGAT-
TCAGCTATCCTTCAATCCACCCATTCATCCTGATT
TGGGGAAACAAGAAGCTAAAGCA-
GACTTTTCTTTCAGTTTTTTGGCAAGT-
GAGGTACTGG GTGAAAGGAGAGAAGCCT-
TCATCTCCATAG

SEQ ID NO:58

Human T2R34 Amino Acid Sequence

GSSRXKPPRIPHKKLCKLGPSF-
PHNNLPIYFLCXNHIVLEFLKMRPKKKC-
SLMLCQAFGI IYPSFHSFILXWGNKTLKQTFLSVX-
WQVTCWAKGQNQSTP

SEQ ID NO:59

Human T2R35 Amino Acid Sequence

NAIRPSKLWTVTEADKTSQPGTSANKIF-
SAGNLISHVNMSRRMQLHGKGSQHLSTRVHIK
AXQTVISFLMLXAIYFLCLITSTWN-
PRTQQSKLVFLLYQTLGFMYLLFHSFILTMGSRKP
KQTFLSAL

SEQ ID NO:60

Human T2R36 Amino Acid Sequence

MICFLLIILSILVVFAFVLGNFSNGFI-
ALVNVIDWVKRQKISSADQILTALVVSRVGLLW
VILLHWYSNVLNSALYSSEVIIFIS-
NAWAIINHFSIWLATSLSIFYLLKIVNFSRLIFHH
LKRKAKSVVLVIVLGPLV-
FLVCHLVMKHTYINVWTKEYEGNVTWK-
IKLRNAIHLSNLTVS TLANLIPFTLTLISFLLLIYS-
LCKHLKKMQLHGKGSQDPSTKVHIKALQTVTSFLLL
CAI YFLSMIISVCNFGRLEKQPVFMFCQAI-
IFSYPSTHPFILILGNKKLKQIFLSVFWQMRYW
VKGEKPSSP

SEQ ID NO:61

Human T2R36 Nucleotide Sequence

ATGATATGTTTTCTGCTCATCATTTTAT-
CAATTCTGGTAGTGTTTGCATTTGTTCTTGGA
AATTTTTCCAATGGCTTCATAGCTCTAG-
TAAATGTCATTGACTGGGTCAAGAGACAAAAG
ATCTCCTCAGCTGACCAAATCCTCACT-
GCTCTGGTGGTCTCCAGAGTTGGTTTACTCTGG
GTAATATTATTACATTGGTATTCAAAT-
GTGTTGAATTCAGCTTTATATAGTTCAGAAGTA
ATAATTTTTATTTCTAATGC-
CTGGGCAATAATCAACCATTTCAG-
CATCTGGCTTGCTACT AGCCTCAGCATATTT-
TATTTGCTCAAGATCGTCAATTTCTCCAGACTTATTT
TTCATCAC TTAAAAAGGAAGGCTAAGAGTGTAGT-
TCTGGTGATAGTGTTGGGTCCCTTGGTATTTTTG
GTTTGTCACCTTGTGATGAAACACACG-
TATATAAATGTGTGGACAAAAGAATATGAAGGA
AATGTGACTTGGAAGATCAAACTGAG-
GAATGCAATACACCTTTCAAACTTGACTGTAAGC
ACACTAGCAAACTTGATACCCT-
TCACTCTGACCCTGATATCTTTTCTGCT-
GTTAATCTAC TCTCTGTGTAAACATCTCAAGAA-
GATGCAGCTCCATGGCAAAGGATCTCAAGATCCCA
GC ACCAAGGTCCACATAAAAGCTTTG-
CAAACTGTGACCTCCTTTCTTCTGTTATGTGCCATT
TACTTTCTGTCCATGATCATAT-
CAGTTTGTAATTTTGGGAGGCTG-
GAAAAGCAACCTGTC TTCATGTTCTGCCAAGCTAT-
TATATTCAGCTATCCTTCAACCCACCCATTCATCCTG
ATT TTGGGAAACAAGAAGCTAAAGCA-
GATTTTTCTTTCAGTTTTTTGGCAAAT-
GAGGTACTGG GTGAAAGGAGAGAAGCTTCATCTC-
CATAG

SEQ ID NO:62

Human T2R37 Amino Acid Sequence

MITFLPIIFSILIVVTFVIGNFANGFI-
ALVNSIEWVKRQKISSADQISHCSGGVQNWFTL
GHIITLVCNCV*FGFI*IRSKNFWF*CLSNNQAFQHVG
VTSLSIFHLLKTANFSNLIFLH LKKRIKSVGLVILLG-
PLLFFICNLFVINMDESVWTKEYEGN-
VTWKIKLRSAMYHSNMTLT MLANFVPFTLTLISFLL-
LICSLCKHLKKMQLHGKGSQDPSTKVHIKALQTVTS
FLLLCAI YFLSMIISVCNLGRLEKQPVFMFCEAI-
IFSYPSTHPFILILGNKKLKQIFLSVLRHVRYW
VKGEKPSSS

SEQ ID NO:63

Human R2R37 Nucleotide Sequence

ATGATAACTTTTCTGCCCAT-
CATTTTTTCCATTCTAATAGTGGTTA-

CATTTGTGATTGGA AATTTTGCTAATGGCTTCAT-AGCTCTAGTAAATTCCATTGAGTGGGTTAAGAGACA AAAG ATCTCATCAGCTGACCAAATTTCTCACT-GCTCTGGTGGTGTCCAGAATTGGTTTACTCTG GGT-CATATTATTACATTGGTATGCAACTGT-GTTTAATTTGGCTTCATATAGATTAGAAGT AAGAATTTTTGGTTCTAATGTCTCAG-CAATAACCAAGCATTTCAGCATGTGGGTGTTACT AGCCTCAGCATATTTCATTTGCTCAA-GACTGCCAATTTCTCCAACCTTATTTTTCTCCAC CTAAAGAAGAGGATTAAGAGTGTTG-GTTTGGTGATACTATTGGGGCCTTTGCTATTTTTC ATTTGTAATCTTTTTGTGATAAACATG-GATGAGAGTGTATGGACAAAAGAATATGAAGGA AACGTGACTTGGAAGATCAAATTGAG-GAGTGCAATGTACCATTCAAATATGACTCTAACC ATGCTAGCAAACTTTGTACCCT-TCACTCTGACCCTGATATCTTTTCTGCT-GTTAATCTGT TCTCTGTGTAAACATCTCAAGAA-GATGCAGCTCCATGGCAAAGGATCTCAAGATCCCA GC ACCAAGGTCCACATAAAAGCTTTG-CAAACTGTGACCTCCTTTCTTCTGTTATGTGCCATT TACTTTCTGTCCATGATCATAT-CAGTTTGTAATTTGGGGAGGCTG-GAAAAGCAACCTGTC TTCATGTTCTGCGAAGCTAT-TATATTCAGCTATCCTTCAACCCACCCATTCATCCTG ATT TTGGGAAACAAGAAGCTAAAGCA-GATTTTTCTTTCAGTTTTGCGGCATGT-GAGGTACTGG GTGAAAGGAGAGAAGCCTTCATCT-TCATAG

SEQ ID NO:64

Human T2R38 Amino Acid Sequence

MLTLTRIRTVSYEVRSTFLFISVLE-FAVGFLTNAFVFLVNFWDVVKRQPLSNSDCVLLCL SISRLFLHGLLFLSAIQLTHFQKLSE-PLNHSYQAIIMLWMIANQANLWLAACLSLLYCSK LIRFSHTFLICLASWSPGRSPVPS

SEQ ID NO:65

Human T2R39 Amino Acid Sequence

LRNAGLNDSNAKLVRNNDLLLINLILLLPLSVFVM CTSMLFVSLYKHMHWMQSESHKLSS ARTEAHINALKTVTTFFCFFVSYFAAFMANMTERI PYRSHQFFVVKEIMAAYPAGHSVII VLSNSKFKDLFRRMICLQKE

SEQ ID NO:66

Human T2R40 Amino Acid Sequence

SQYSLGHSYVVIFGYGQMKKTFLGIL-WHLKCGLKGRALLATQVGLREKSTRSLGVIFLAS SYSFFVYVLCH

SEQ ID NO:67

Human T2R41 Amino Acid Sequence

MITFLLIILSILVVFAFVLGNFSNGFI-ALVNVIDWVNTRKISSADQILTALAVSRVGLLW VILLHWYANVLNPALYSSEVIIFISNI-SAIINHFSIWLATSLSIFYLLKIVNFSRLIFHH LKRKAKSVVLVIVLGPLV-FLVCHLVMKHTYINVWTKEYEGNVTWK-IKLRNAIHLSNLTVS TLANLIPFTLTLISFLLLICS-

LCKHLKKMQLHSKGSQDPSTKVHIKALQTVTSFLML FAI YFLYLITSTWNL*TQQSKLVFMFCQTLGIMYPSFHSFI LIMGSRKLKQTFLSVLCQVTCL VKGQQPSTP

SEQ ID NO:68

Human T2R42 Amino Acid Sequence

FIGLTDCIAWMRNQKLCMVGFILTRMALARINIL

SEQ ID NO:69

Human T2R43 Amino Acid Sequence

LELIFS*KVVATRGLVLGMLGNGLIGLVNCIEWAKS WKVSSADFILTSLAIVRIIRLYLI LFDSFIMVLSPH-LYTXXXXXXXXXXXXXXXXXXXXXXX-SLSIFHWFKTANFSNLIFLPLK EED*NVWLGDAVGALGIFHL*SCSENHG*EVCGQKN MKEFCSGMIKLRNAIQLSNLTVTM PANVTPCTLTLIS-FLLLIYSPCKHVKKMQLHGKGSQHLST-KVHIKVLQTVISFFLLCAIY FVSVIISVWSFKNLENK-PVFMFCQAIGFSCSSAHPFILTMGKKLKQTYLSVLWQ MR

SEQ ID NO:70

Human T2R44 Amino Acid Sequence

MITFLPIIFSILIVVIFVIGNFANGFI-ALVNSIEWVKRQKISFVDQILTALAVSRVGLLW VLLLHWYATQLNPAFYSVEVRITAYNV-WAVTNHFSSWLATSLSMFYLLRIANFSNLIFLR IKRRVKSVVLVILLGPLLFLVCHLFVIN-MDETVWTKEYEGNVTWKIKLRSAMYHSNMTLT MLANFVPLTLTLISFLLLICSLCKHLKK-MQLHGKGSQDPSTKVHIKALQTVTSFLLLCAI YFLSMIISVCNLGRLEKQPVFMFCQAI-IFSYPSTHPFILILGNKKLKQIFLSVLRHVRYW VKDRSLRLHRFTRGALCVF

SEQ ID NO:71

Human T2R45 Amino Acid Sequence

MATELDKIFLILAIAEFIISMLGNV-FIGLVNCSEGIKNQKVFSADFILTCLAISTIGQLL VIL-FDSFLVGLASHLYTTYRLGKTVIMLWH-MTNHLTTWLATCLSIFYFFKIAHFPHSLFL WLRWRMNGMIVMLLILSLFLLIFDSLV-LEIFIDISLNIIDKSNLTLYLDESKTLYDKLSI LKTLLSLTSFIPFSLFLTSLL-FLFLSLVRHTRNLKLSSLG-SRDSSTEAHRRAMKMVMSFL FLFIVHFFSLQVAN-WIFFMLWNNKCIKFVMLALNAFPSCHSFILILGNSKL QQTAVRLLW HLRNYTKTPNPLPL

SEQ ID NO:72

Human T2R46 Amino Acid Sequence

MSFLHIVFSILVVVAFILGNFANGFI-ALINFIAWVKKQKISSADQIIADKQSPELVCSG

SEQ ID NO:73

Human T2R47 Amino Acid Sequence

MLNALYSILIIIINI*FLIGILGNGFITLVNGIDWVKM* KRSSILTALTISRICLISVIM VRWFI

SEQ ID NO:74

Human T2R48 Amino Acid Sequence

VSRVGLLWVILLHWYSTVLNPTSSN-LKVIIFISNAWAVTNHFSIWLATSLSIFYLLKIVN

SEQ ID NO:75

Human T2R49 Amino Acid Sequence

TVTMLANLVPFTVTLISFLLLVCS-LCKHLKKMHLHGKGSQDPSTKVHIKVLQTVISFLLLCAIYFVSVIISS

SEQ ID NO:76

Human T2R50 Amino Acid Sequence

MITFLPIIFSILVVVTFVIGNFANGFI-ALVNSTEWVKRQKISFADQIVTALAVSRVGLLWVLLLNWYSTVLNPAFYSVELRTTAYNI-WAVTGHFSNWPATSLSIFYLLKIANFSNLIFLRLKRRVKSVILVVLLGPLLFLACHLFVVN-MNQIVWTKEYEGNMTWKIKLRRAMYLSDTTVTMLANLVPFTVTLISFLLLVCSLCKHLKK-MQLHGKGSQDPSTKVHIKVLQTVISFFLLCAI YFVS-VIISVWSFKNLENKPVFMFCQAIGFSCS-SAHPFILIWGNKKLKQTYLSVLWQMRY

SEQ ID NO:77

Rat T2R01 Amino Acid Sequence

MMEGHILFFFLVVMVQFVTGVLANGLIV-VVHAIDLIMWKKMAPLDLLLFCLATSRIILQL CIL-FAQLCLFSLVRHTLFEDNITFVFI-INELSLWFATWLGVFYCAKIATIPHPLFLWLKMRISRLVPWLILGSVLYVIITTFIHSRET-SAILKPIFISLFPKNATQVGTGHATLLSVLVL GLTL-PLFIFTVAVLLLIYSLWNYSRQMRTM-VGTREYSGHAHISAMLSILSFLILYLSHYMVAVLISTQVLYLGSRTFVFCLLVIG-MYPSIHSIVLILGNPKLKRNAKMFIVHCKCCHCTRAWVTSRSPRLSDLPVPPTHPSANKTSCSEACIMPS

SEQ ID NO:78

Rat T2R01 Nucleotide Sequence

CAGGAATCATAAATGGCT-GAAACTGGGCAGAACTCTATGCATTATT-TAAAGAAGTCATTG GTTTGTCATTCTTAAAAT-GATGGAAGGGCATATACTCTTCTTCTTTTTGGTTGTGATGGT GCAGTTTGTCACTGGGGTCTTG-GCAAATGGCCTCATTGTGGTTGTCCAT-GCTATTGACTT GATCATGTGGAAGAAAATGGC-CCCGTTGGATCTGCTTCTATTTTGCCTGGCGACTTCTCG GATCATTCTGCAGTTATGTATAT-TGTTTGCACAATTGTGTCTAT-TCTCTTTGGTGAGACA CACTTTATTTGAGGA-CAATATTACCTTTGTCTTCATCATAAATGAACTGAGTCTTTGGTT TGCTACATGGCTCGGTGTTTTCTACTGT-GCCAAGATTGCTACCATTCCTCACCCACTCTT TCT-GTGGCTGAAGATGAGGATATCCAGGTTG-GTACCATGGCTGATCCTGGGATCTGTGCTCTATGTAATTATTACTACTTTCATCCAT-AGCAGAGAGACTTCAGCAATCCTTAAACCAAT TTT-TATAAGCCTTTTTCCTAAAAATGCAACT-CAAGTCGGAACAGGGCATGCCACACTACTCTCAGTCCTGGTCCTTGGGCTCACACT-GCCGTTGTTCATCTTTACTGTTGCTGTTCTGCTCTTGATATACTCCCTGTGGAATTATAG-CAGGCAGATGAGGACTATGGTAGGCACCAGGGAGTATAGCGGACATGCTCACATCAGTG-CAATGCTGTCCATTCTATCATTCCTCATCCTCTATCTCTCCCACTACATGGTGGCTGTTCT-GATCTCTACTCAAGTCCTCTACCTTGGAAGCAGAACCTTTGTATTCTGCTTACTGGTTAT-TGGTATGTACCCCTCAATACACTCGATTGTCTTAATTTTAGGAAATCCTAAGCTGAAAC-GAAATGCAAAAATGTTCATTGTCCATTGTAAGTGTTGTCATTGTACAAGAGCTTGGGTCAC-CTCAAGGAGCCCAAGACTCAGTGACTTGCCAGTGCCTCCTACTCATCCCTCAGCCAACAA-GACATCCTGCTCAGAAGCCTGTATAATGCCATCCTAATTGTCCAGCCTGAGGTTTAATC-CTAGGTTTGGTACTATTTCAAAGAGTAAAGTTGATCATTAAAGCACAACATATGTTGGTG-GATGACATCAAGGTCCATATCCCAGTTGTCAATTGTAAACCTCACCTTGCAAGATGATGT-CACTGAGAAAGCAGGACAAATGGAGTCTAGGTCCTTCTGTATGACTTGCTGCAGTATATGT-GAATCTATAATTTTCTCCAAAAAAACAAAAAAAAAAAAAAAAAA

SEQ ID NO:79

Rat T2R02 Amino Acid Sequence

MFSQKTNYSHLFTFSIIFYVEIVT-GILGNGFIALVNIMDWLKRRRISTADQILTALALTRLIYVWSVLICILLLFLCPHLSMRPEM-FTAIGVIWVVDNHFSIWLATCLGVFYFLKIASFSNSLFLYLKWRVKKVVLMIILIS-LIFLMLNISSLGMYDHFSIDVYEGNM-SYNLVDSTHFPR IFLFTNSSKVFLIANSSHVFLPIN-SLFMLIPFTVSLVAFEVLFLSLWKHHKKMQVNAKGPRDASTMAHTKALQIGFSFLLLYAIYLL-FIITGILNLDLMRCIVILLFDHISGAVFSISHSFVLILGNSKLRQATLSVLPCLRCRSKDMDTVVF

SEQ ID NO:80

Rat T2R02 Nucleotide Sequence

ATTTGCTCCACTATTTTGCTCTTCTG-CAGTAACACAGACCACAAAACAATGGAGCCAATGGGTCAAGAGCTGAAACTTCAG-GAAGTGGGAGCCAAATTTTCTTTGTGAT-AGGTTGGCAT ATGAGAATTCATTATTTGATGCAGCT-TCTGAAAACTGGATGTGAAATACTGGATGAAGCAGAGGTGATGACCCCTTTGAAAT-TAAAAAGCCAAGATGTTCATGGAGAAAT-TATAAAACAA TATCTGGGAAATTTGATGCTTC-CTAATCGGGTGTAAATGGGATTTTAAATGATGAACATT TTGAATTTCCAATGACCATTATG-TAAAGTTTTTAAACACAGTAGAGACAT-CATAAATTGA AGCATGTTCTCACAGAAAACAAAC-TACAGCCATTTGTTTACTTTTTCAATTATTTTTTATGTGGAAATAGTAACAGGAATCTTAG-GAAATGGATTCATAGCACTAGTGAATATCATGGACTGGCTCAAGAGGAGGAGGATCTCTACTG-CAGATCAGATTCTCACTGCTTTGGCCCTTACCAGACTCATTTATGTGTGGTCTGTACT-CATTTGTATATTGTTACTATTTCTGTGCCCACATTTGTCTATGAGACCAGAAATGTTTA-CAGCGATAGGTGTTATCTGGGTAGTGGATAACCACTTCAGCATCTGGCTTGCTACATGTCTTG-

GTGTCTTTTATTTCCTCAAAATAGCCAGTTTT
TCTAACTCTTTGTTTCTTTAC-
CTAAAGTGGAGAGTTAAAAAAGTGGTTT-
TAATGATAATA CTGATATCACTGATTTTCTTGATGT-
TAAACATTTCATCATTAGGGATGTATGATCATTTC
TCAATTGATGTTTATGAAGGTAATAT-
GTCTTATAATTTGGTGGATTCAACACATTTTCCC
AGAATTTTCTTATTCACAAACT-
CATCTAAGGTCTTCTTAATCGCCAAT-
TCATCCCATGTT TTCTTACCCATCAACTCACTCT-
TCATGCTCATACCCTTCACAGTTTCCCTGGTAGCTT
TT TTCGTGCTCTTTCTCTCACTGTGGAAG-
CATCACAAGAAGATGCAGGTCAATGCCAAAGGA
CCCAGAGATGCCAGCACCATGGCCCACA-
CAAAAGCCTTGCAAATTGGGTTCTCCTTCCTC
CTGCTGTATGCAATATACT-
TACTTTTCATTATCACAG-
GAATTTTGAACCTTGACTTGATG AGATGTATAG-
TAATACTTTTATTTGACCACATATCTGGAGCAGTTTT
TTCTATAAGCCAC TCATTTGTGCTGATTCTGG-
GAAACAGTAAGCTGAGACAAGC-
CACTCTTTCTGTGCTGCCT TGTCTTAGGTGCCG-
GTCCAAAGATATGGACACTGTCGTTTTCTAATAAAT
TCCAGAGTAC ATTATGCAAAATCTTGAGGGTGAT-
CAGTTCATAGAAAAAGTAATCTTA-
GAGGGGAAAATA AAATATTGGGGCTTCAAATGT-
TGGATGGGTAATACATAGGAAGGCAGGACAAGGAT
GAAG GAGACTAGCATTATATAAGTGATTTCA-
CAGGGGAAATGGGAAAGAGGGCTTTTAT
ATAAT GAAGAAGAAGATAAATGATGAAGGAT-
GAGGAAGAGTTAAATATGTAAAATGACAATAGAG
ATGGCATCATGCCGTTTTAAGAAATTTG-
GAATGCATATGTATGTTTATATATTTTTTAAT TTTTAT-
TGAATATATTTATTTACATTTTAAATGT-
TATCCTGTTTCCCCCACCCAACCTCC
CACCTCTTCCCACCTCCTTGCCCTGA-
CATTCCCCTGCACTGGGGAATCCAGCCTTGACAG
GACCAAGGGCTTCTCCTCCCTTTGTTGC-
CAACAAGGCCATTCTTTGCTACATGTGCAGCA
GGAGCCATGGATCTGTCTATGTG-
TACTCTTTGGATGGTGGTTTAGTC-
CCTGGGAGCTCTT GTTGGTTGGTATTGTTGTTCT-
TATGGTGTTGCAACTCCCTTCAGCTCCTTCAATCCT
TCC TGTAACTCCTCCAATGTGGACCCTGT-
TCTCAGTCCAATGGTTGACTATGAGCATTCACCT
CTGTGATTGTCATGCTCTGGCACAGCT-
TCTCAGAAGACAGCTACATCAGTCTCCTATAAG
AGTGCACTTCATGGCATCAGCAATGT-
TGTCTTGATTTGGTGTCTGTATGTATATGGGCTG
GATCCCAGGTGGGGCAGGCGCTGAATG-
GTCATTCCTTCAGTCTTTGCTCCAAACTTTGTC
TTTATATCTCCTATGAATATTTTTGTTC-
CCCCTTATAAGAATGACTGAAGTATCCACACT TTG-
GCCATCCTTCTTCATGAGCTTCATGTG-
GTCTGTGAATTGTACATTGTGTAATCCAAG
CTTTTGGGCTAATATCCAATTATAGT-
GAGTGCATACCAAAAAAAAAAAAAAAAAAAAAAAA
AAAAAAAAAAAAAAAAAAAAAAAAAAAAAAAA
AAAAA

SEQ ID NO:81

Rat T2R03 Amino Acid Sequence

MVPTQVTIFSIIMYVLESLVIIVQSCT-
TVAVLFREWMHFQRLSPVEIILISLGISHFCLQ WTSM-
LYNFGTYSRPVLLFWKVSVVWEFMNVLT-
FWLTSLLAVLYCVKVSSFSHPVFLWLRL
KILKLVLWLLLGALIASCLSIIPSVVKY-
HIQMELLTLDHLPKNSSLILRLQMFEWYFSNP
FKMIGFGVPFLVFLISIILLTVSLVQH-
WGQMKHYSSSSSSLRAQCTVLKSLATFFIFETS
YFLTIVVSFIGTVFD-
KKSWEWVCEAVIYGLVCIH-
FTSLMMSNPTLKKALRLQFWSPESS

SEQ ID NO:82

Rat T2R03 Nucleotide Sequence

GCATGGTGCCAACCCAAGTCACCATCT-
TCTCTATCATCATGTATGTGCTTGAGTCCTTAG
TCATAATTGTGCAAAGTTGCACAACGGT-
TGCAGTGCTGTTCAGAGAGTGGATGCACTTTC
AAAGACTGTCGCCGGTGGAAATAATTCT-
CATCAGCCTGGGCATTTCACATTTCTGTCTAC
AGTGGACATCGATGCTGTACAACTTTGG-
TACCTACTCTAGGCCTGTCCTTTTATTTTGGA AGG-
TATCGGTCGTCTGGGAGTTCAT-
GAACGTTTTGACATTCTGGCTAACCAGTTTGCTTG
CTGTCCTCTACTGTGTCAAGGTCTCTTC-
CTTCTCTCACCCCGTCTTCCTCTGGCTGAGGT
TGAAAATTTTGAAACTGGTTCTCTGGT-
TGCTATTGGGCGCTCTGATAGCTTCTTGTTTGT
CAATCATCCCTTCTGTTGTTAAATAT-
CATATCCAGATGGAATTACTCACCCTAGATCATT
TACCCAAAAAACAGTTCTTTGATTCTAA-
GACTGCAAATGTTCGAGTGGTATTTTTCTAATC
CTTTCAAAATGATTGGGTTTGGCGTTC-
CTTTCCTCGTGTTCCTGATTTCTATCATCTTAC TCA-
CAGTCTCGCTGGTCCAGCATTGGGGGCA-
GATGAAACACTACAGCAGCAGCAGCTCCA
GCCTGAGAGCTCAGTGCACTGTTCT-
GAAGTCTCTTGCCACCTTCTTCATCTTCTTCACAT
CCTATTTTCTGACTATAGTCGTCTCCTT-
TATTGGCACCGTGTTTGATAAGAAGTCATGGT
TCTGGGTCTGCGAAGCTGTCATCTATG-
GTTTAGTCTGTATTCACTTCACTTCCCTGATGA
TGAGCAACCCTACACTGAAAAAAGCACT-
CAGGTTGCAGTTCTGGAGCCCAGAGTCTTCCT
AAGGCAGGGAATTCAGTGAAGC-
CTCTGGGGTAAGGAGGCTTTGCATTG-
GCACAGTTCTTA GAGTGAAATGCAAACGTGGA-
CACGAACTTCATTCTCTTTCATGTCCACAGATGGAT
GGAT CTATAAATCATCACCAATCTTCCCTG-
TATTCTGACCCATCCTTTTCCTGTCCTATCCATA
GTCCCCAGGTTGGTTTTGATTTTTCT-
CATGATCACACCTTAGCTTTAGCCACCGTTGCAA
TATCAAACATGATCTATATGTTACAGC-
CAAAATCATTCTCACAATTGTCAATTGCTTCAC
AAATTCAGATAAATCCCCCTTCCTGT-
CAGGAATGTATTGTCTGTGCATTCAATGCTCACC
ATGCTAAGCCATTCATTCCCTTC-
CTAACTTGAGTTTAAGAAGAAAATGTCT-
TACTGTTGC CCATGTCCTATTGTGCTGCTTCTGGAT-
GTTTTATGCAGTGATTTAGACACACGCCCTTGC
CTGTCTCCAAATACTGGCCCTTTATTC-
CTTTATAAGTCTAGTAGAAAATGAACTCGTCTT
TACTTCATTGACGAAGACATTGTATTCT-
TCCCCAAAATAGTGTTTAACTACTCTAGTCTC ATC-
CATAATATCCCTAAATATCAGT-
GATTTCAGTGAGTAAAACCTGACAACAGTTATTGC
TTTGACTCTTAATTCAATTGTGCTGTAA-
CATAGAGGAAACATTCTAGAACATTTCCATAT
TAATTTGTGCTTGTAGCAAACCAAAAT-
TCTCCCCAGTTGGGTAAAAATATCAAAGCACA

GAGTAATCAATTTTGAAATCACTGAGAA-
GACATCATTGTTCTATATATGTTTTTTTTAAA CTTC-
CCTCTAACAAGTATCAGATCTTTGCCTT-
TACAGGGTCTGGTCTTACCATGACTATA
TTTTATCACCATGACCTATTTTCTCT-
TCATCTCTTTGTTTTCACTAACTCAGTAGCAACC
AAATATCACATTAAT-
AGCTAACTCTGGGCACTTATTTCTCAGC-
CTTTATCTATTCCAGAC ACTTTCAATGTATTTCT-
GCTAAACACAATGACATCTCTTTTTGTGTTCTAACG
ACAAGGA ATCATAACTTTCCAACTTTTATACATGG-
TAGACATATTTGGTGAACTTAACTTCTGACTC
TTTCTTTAGAAGACTGAAACTACTCCG-
GAAAGCAAGCCTTCTGATGGAGAAATAGATACG
GGTATCGTGATTCATTGTGAAAGTGAAT-
TCCGGTGCCTGGAAAGAAATGGATATTTTTTT
TTCTCTTGAGTGTGTCACTCTGACATAT-
GTTCCATGTTGAATCCATATTTGATACTGATA GCAT-
GAATGTAAGTAAAGCATGTATGTAAG-
TAAAGACTGCTACCAAAACTTCGATTCAAC
TTTCCTCAGCAGTATCCCTGATATTG-
CATAAGAAAGAAAAAACACGCTGTCCTACTTGAA
GAAGGACGTGTTCCATGCAATGTGGAT-
GTGTCCCAGGCTACATTGGCTCAACTGCAGCTG
AAGGTGGGATGGGAAATGGTATAGTTAG-
TAATGTCTGCTGAGCTGTCTCACTGGAAAGGA
TTCTGAGCAGAGTAAATGTAAGCAAT-
GTGGCCAAGGTCTCCTAGGAATGGGTTGTAAGCT
TGTAAGGAGTTGGGTTGTAAGAGTTTGG-
GATCCTTTCAGAATGGATTGAGCAAGAGCCAC
TGAAACTTGGACTATACCTTTGT-
TATTTGTATCTAAATCCA-
GAAGGGTCTTTGCATGTTC CAAAATCTCAGAT-
AGCTGGAAGGAAGAAGGACTGTTCTCTTTACAAGT
ATATAAATAGAG AATGAGCTAAAAAGGACCCCCT-
CACCCCCGCCGTCACACACAGGAATAC-
TATTCCAGAAA CTAGGGAGTATTTTTAGTGTTCT-
CACTATTTCCCTTTGAAAAAAGTGCAATGGAAAAC
TT ATCCATGACATACATGAGGTTGGAGT-
GATAAAAACAGCTGAAGGAAGAGGAAGTCTGAAA
AAAGATGGAAACAGCAATGATGCTTGTC-
CTATATATGTGTGACACCAACTAGTTCCCAAG
GAAACCTTACATCCATTATCT-
CATTTCAAGCTGGAAGGACAAGTCAA-
GATCACTCAACCG ACCCAGCTGGAAAACAGAC-
CTAAGAATGTTAAACTCATACTGATGGTTATTTCTCA
CTCT AAAGTCAATGCAAATGGATAGCAAA-
CAAAGGGGCTATTTTTTTAAGGGACCAGAGGGTTT
CAATCTAGAATCAGAGAAAA-
GATAAAAAGGGAGATGCTATAGAAAAA-
CAATAGAGAAGAT GTGGCCAAGAACAAG-
GAAAATCTCCAGTTAGCTTGGCACTTAGGGGCCAA
CATGTTTCTG TTGTTCGGTCTTCAATACTGTATTG-
CATGTTGGGCTCACTATGTTTTAGTTGTGAGTGGG
TTGTGCTTCCTGGAATTAAGAAAGGTCT-
GTTTCTAGATTTCAGGTACAAATGTTTAGAAG
CCCATTGGTAGCATCAGTGAAATTAG-
GAAAAAACTGTGAGCACTGCTGGCTGGACTTGGC
AAAGTCATTCACTATTTACACATCAAAT-
TATTAGCAACTTGAAAGTAAATCTTTGCTCAT CATC-
CAGTGGCCCCCATGATCCTGGTGAAT-
GACTTGTAATACTGTGGAGACTGGCAACGA
CGGTGAATTCCTAGTAACACTTACCATA-
GAATCTGTTCATAATTAGACTCGCCCAGATTT TAGT-
TGCTAGAGAACAATCTTTCTCCTTTAC-
CCACATTCCTACTGAGTAGGATGCATAGG
TTCGGAAACCCCCATG-

GCATCGTTTGACTCCTCCTGGTAGTCAA-
GAGAGTCCAGTCACCA GTCTCCGAAACACCTGC-
CAAGTCCTAACTCCCAACAGTCTACAGTGTAAACC
TCAGTGTT TGCATGAGGTTTATGTATCTCCTTAC-
CATTTCCTAAATGTCAATACCCGTGCACAGGATA
TTTGCATAGGCTGCCTCCAAGCCTGG-
GAAACACTCTCCTCCTCGCATTTGCTGGGTTTCA
CCTTTCCAATTCAGTGTGCCCTT-
TAAAAGGCACTGCTTTTCTAGGCCCAC-
CACTATTGCT GCTCACGCATGAACATCAAATCTAC-
CACAGGCTTTTGCCTCTCAGAATTATTCTTCTTTC
TACTATGCAATGTGGTATCCAT-
GAGAACTTTGTCACATTGTCAAATTC-
TACCTTTGTTTT AATGnGnGCCTTTGTAATAGnGAC-
TATGCCCAGAAATTAAATTATAGTAAGATGGGTAAC
AACnCTTCAATTnTGGAATTTATAAT-
TAAATAAATATTATGTAATATTATGACTTATTAT
AAnGTCAATCTACTGTACCCTACTC-
CTACTAGGAATGCAAAGACAAATAGCAATGTGATC
AGCATGTGCTCTTTCACAAGATCATAT-
TGTGCATGTTGCTGATGATGCCCACAGTGCATC
TATCAGAATATCTCTGAT-
CATTTTTTTTTTTTTGCTTTTGAGAAGC-
CCCGGTTGGTGCTG GGATGCTTCATAGCAGGTC-
CACCATAGACACATGCTTAGAGGAAAGCTGCCTCT
CTCTCT TCATTCCCAAGGAACAGTAAAAGCA-
GAAAAGGCTCTTATGTTCTAAAGAACAGAAAATAG
CCTGCATTTCAACTACCTCCTGTTCA-
GAAGGCACCGAAACACACCACCAAGCAAGACACC
CCTTTACTTTCTCCTGCTTCCCT-
CAATTTGATGATCATTTGGAAATAAGAA-
GAAAGAAAA AGATGTGGAAGCCAATTAAAAA-
CAGTCTTGTCTATCTCCCTGGTGAGCTCTCAACTTC
TT AGTCAGACCAAAGTAGGT-
GAAAAAATAATAATTTTTAATTTGGTAT-
GAGAGTCATGTTTA GGCTGAAAATCT-
TAAAAAATCTTAGCATAAAAACATTTTCCCCTAGAC
CCATGAAATTTA TAATATTATCTGTGGTTGAGAAAG-
GCTAGTTATAGAAAAATGTTTAGAATCAGAATATTT
TGAGGGCTCTTTTTTTGTTTTGCCTAAT-
CATTACATTTGTTATAAGAAGTCTAAAAGTTG GTAT-
GCTAGAGGTCTTGTCATATTTTCTCT-
GAGGTTGAGTGCCAAGTAGTCTGCATTGTG
TTTAAATCCTGCTTAAAATTATCCCAA-
GACAATATAACTTCTCAGGAGCTAAGCCAAGGG
CCCCTTTCAGACTACCTTAGTCCTCTCT-
CACCGTTGTCACCGTGGCTCATACATCAGAAT CCT-
GAGGGAGCATCATGAAATCTAAGGCTT-
TACAACAGAATCTTTCTATCCCTGGTAGAA
ATCTTTTAACCTTGGGTTTTATTCTCAT-
GCCATTCTGATGCTCGTATTTAAATTTTATGT
GTTTTTTCATATGTTCTTGCATTTC-
TATCGTTAAATTATGGTGACATACTTTCAAATGCT
TTGTTATTTTAAAAAGGGACAAA-
GAGAGATAGAAAGACAGGGAAAGATAGA-
CAGAGGCTT GCCTAATACAGTCAAGAAAGAAGC-
TATCAAAAGTATTTAGCAATACAACATTTATGATAT
ATTCATAACTGTTAACCATTTTTAATAT-
TCTAAAATTTCACTTTTGTTTCAGAAATGTAT
ATTAAGAGAATCTGAGAAA-
CATTTTTTTCTCATAGATGTAGAAAAA-
CACACAAAATAAGG TATAACACATTTAAGTGAT-
TGAAAATAAAAACAAAAGCTTGCAAACAGGAGGA
AAAGTAC ATTGTAGGCTTTCGACATGGAGCTGC-
TACTAGGACCCAGGACTTGTTTATCATTTATTTG
CCAAGTCCCACAAACTCAGGGCAATA-
CATCTCTGAGACAGTTTCCTATATTTTAATAAAA

CTTCCAAAATTGATACTCAGTGTGAAT-
TGGCTAGCTTTAATGGCAGTCATTGGATAAACA
ATTCCAATGCCAAATTTCCCTAAGT-
TGATATATTTGATTAATATGTATATTAAAACATCA
GGCTATCCATCGGTTGGATCAAATACAT-
TCTTTAGGGATCCATTCTTTTCCTTAAATTTG ACT-
TATATGTGGATTCTTTTCA-
CAATAAATAAGTAAATGAGCATTTATTTTAAAACTAT
T TTAGACGGAACTGAATTACAGCCAAGG-
TAGTCAAAATGACTGAGAATAATCACTTACATA
TTTACAAGGGAAAGTGACTCTTCAGATT-
TAAGTTTAAAATTAGAAGAGAGATAAATTTCA
CAAGCTTTCACTCCTAAGGCTAAAGAT-
AGGCTGTGTAGGTAGTTATTTCTGAGCACATTG
GCACATCACCATTGTCAGTACT-
TGAGGGTTTGAATGAAGCTCACTCAAA-
GAACTTGGAAA GAAGGTGGTCTTCTGACATCAAT-
CAAGAAACAAGCTTTCCTCCCTACTTCTTCCCTAAA
T GCAACAACCTAAGAATTATCCACAA-
GATGGATGGCGCAAGGGTTCCTCAATCAATTTCAG
GATGTACATCAATGCGCAGCCTATACTA-
CACCGAAAAGGAAGCGCATGGGTCTTAAAAAG
TAAAGGGGATATCAAAAAATTCGCAAC-
CAAACAAAAAGTGGCACACATTTAAGCTAGGTC
TATGTTTGGTCAGTTACACCTG-
GAGAAGGGGGACATTTGGTCAGCTCAT-
TCGAACACTGT CAAGTCCTACCAACAATTCCTC-
TATGCTATTACCCATTAAACCTCAGGTCTCATCGAAA
A AAAAAAAAAAAA

SEQ ID NO:83

Rat T2R04 Amino Acid Sequence

MLSAAEGILLCVVTSEAVLGVLGDTFI-
ALANCMEYAKNKKLSKIGFILIGLAISRIGVVW
IIILQGYMQVFFPHILTFGNITEYITYI-
WVFLNHLSVWFATNLNILYFLKIANFSNSVFL WLK-
SRVRVVFIFLSGCLLTSWLLCFPQFSK-
MLNNSKMYWGNTSWLQQQKNVFLINQSLTN
LGIFFFIIVSLITCFLLIVFLWRHIRQM-
HSDGSGLRDLNTEAHVKAMRVLISFAVLFILH FVGL-
SIQVLCFELPQNNLLFITGLIAT-
CLYPCGHSIILILGNKQLKQASLKALQHLTCCE
TKRNLSVT

SEQ ID NO:84

Rat T2R04 Nucleotide Sequence

TGGTTCCATCACATGACAATAGGCT-
TGAAAAACTTGCAGATAGAGAAGACATAACCCCTC
CAACAAGAAGCCAACATATGGGACAT-
TCTCCAGCAGATAATTTATAACAGATGCAACGGG
AGCAACTTCGAGATCTGCAAAGATGCT-
GAGTGCAGCAGAAGGCATCCTCCTTTGTGTTGT
CACTAGTGAGGCAGTGCTGGGGGTTT-
TAGGAGACACATTCATTGCACTTGCAAACTGCAT
GGAGTATGCCAAGAACAA-
GAAGCTCTCTAAGATTGGTTTCATTCT-
CATTGGCTTGGCGAT TTCCAGAATTGGTGTCG-
TATGGATAATAATTTTACAGGGGTATATGCAAGTATT
TTTTCC ACACATACTTACCTTTGGAAACATAACT-
GAATATATTACTTACATATGGGTGTTTCTCAA
TCACTTAAGTGTCTGGTTTGCTACCAAC-
CTCAATATCCTCTACTTTCTAAAGATAGCAAA
TTTTTCCAACTCTGTATTTCTCTGGCT-
GAAAAGTAGAGTCCGTGTGGTTTTTATCTTTCT
GTCAGGATGCTTACTTACCTCGTGGT-
TACTATGTTTTCCACAATTTTCAAAGATGCTTAA
CAACAGTAAAATGTACTGGGGAAA-
CACGTCTTGGCTCCAGCAGCAGAAAAAT-
GTCTTCCT TATTAACCAAAGTTTAACCAATCTGG-
GAATCTTCTTTTTCATTATTGTATCCCTGATTAC
CTGCTTCCTGTTGATTGTTTTCCTCTG-
GAGACACATCAGGCAAATGCACTCAGATGGTTC
AGGACTCAGAGACCTCAACACAGAAGCT-
CATGTGAAAGCCATGAGAGTTCTAATATCTTT
TGCGGTACTCTTTATCCTGCATTTCG-
TAGGTCTTTCCATACAAGTGCTATGCTTTTTTCT
GCCACAAAACAACCTACTCTT-
TATAACTGGTTTGATAGCCACATGCCTC-
TATCCCTGTGG TCACTCAATCATCTTAATTCTAG-
GAAACAAGCAGCTGAAGCAAGCCTCCTTGAAGGC
ACT GCAGCACTTAACGTGCTGTGAGA-
CAAAAAGAAATCTCTCAGTCACAT-
AAATGGGTTTGCC AATTAATATCTGCCATGTTATTC-
CACTGATTTTTACCTGTTAGTTTCTCTGTGTCTCTGT
TTAGTTTCTGTTTCCATGATCTGTCCAT-
TGATGAGCGTGGGGTGTTGAAATCTCCGACTA
TTGTTGTGTGAGATGAAATGTGT-
GCTTTGAGCTTTAGTAA-
GATTTCTTTTGTGAATGTAG GTGCTTTTGCATTTG-
GTGCATAGATATTTAAGATTGAGAGTTCAGCTTGGT
GGATTTTTC CTTTGATGAATATGAAGTGTCCTTGCT-
TATCTTTTTTGATGACTTTTGATTGAACGTCAA TTT-
TATTGGATATTAGATTGGCAACTCAA-
GATTGCTTCTTGAGGTCATTTGCTTGGAAAG
TTGTTTTTCAGCCATTTACTCTGAGG-
TAGTGTCTGTCTTTGTCTCTGAGGTGTGTTTCCT
GCATTCAGCAAAATGCTGGGTCCTCTT-
TACATATCCAGTTTGTTAGTCTATGTCTTTTTA
TTGGGGAATTGAGTCCATTGATGT-
TGAGAGATATTAATGAATAGTGATCATTGCTTCCTG
TTATTTTCGTTGTTAGATGTGGAATTAT-
GTTTGTTTGTCTCTCTTTTGGTTTTATTGCAA
GGAAATTATATACTTGCTTTCTGTATG-
GTGTAGTTTCTCTCCTTGTGTTGCAGTTTTCCT
TCTATTATCCTTTGTAGGGCTA-
GATTTGAAGAAAGATATTGCATAAGCT-
TGGTTTTGTCA TGGGATATCTTGGTTTCTCCATC-
TATGTTAATTGAGAGTTTTGCAGGATATAGTAGCCTG
GGATGACATTTGTGTTCTCTTAGGGTCT-
GTATGACATCTGTCCAAAATCTTCTGGCTTTC
ATAGTCTCTGGTGAGAAATCGGATG-
TAATTCTCATAAGTCTGCCATTATATGTCACTTGA
CCTTTTTCCCTTATTGCTTTTTATGT-
TCTTTCTTTGTTTTGTGCATTTGGTGTTCTGATT
ATTATGTGATGTGAGGTATTTCTCT-
TCTGGTCAAATCTATTTGGAGTTCTGTAGGCTTCT
TGTATGTTTATGGGCATCTCTTTCTT-
TAGGTTATGGATGTTTTCTTCTATAATTTTGTTG
AATATATCTACTGTCCCTTTAAGTTAG-
GAGCCTTCACTTTCTTCTATACCTGTTATCCTT
AGGTTTAATCTTCTCACTGGATTTCCTC-
GATGTTTTGGACTAGGAACTTTTTGCATTTTA CAT-
TATCTTTGACAGGTATTTCAATGTTTTC-
TATGGTATCTTCTGCCACTGAGATTCTCT
CTTCTAGCTCTTGTATAATGTTGGTGAT-
GCTTGTACCTGTGACTCCTTGTTTCTTCCTTA
GGTTTTCTATCTCCAGGGTTGTCTC-
CCTTTGTGCTTTTTTTATTGCTTCTATTTCCATTC
TAAATCCTGGATGGTTTTGTTCAATTC-
CTTCACCTCTTTGGTTGTATTTTCCTGTAATTC
TTTCAGGGATTTTTGTGTTTCCTCTT-
TAAGGGCTTCTACTTGTTTACTTGTGTTGTCCTG

TATTTCTTTAAGGTAGTTATTTATGTC-
CTTCTTGAAGTCCTCCATCATTATCAAAAAATG
TGATTTTTAAATATAAACCT-
TGCTTTTCTGGTGTGTTTGGATGTCAAG-
TATTTTCTTTGC TGGGAGAACTGGGCTCTGATAAT-
GCCAAGTTGTTTGATTTCTGTTGCTTAGTTTCCTGTT
CTTGCCTCTCGGCATTGGGTTTTCTCTG-
GTGTTTGCTTATCTTGCTGTTTCTGAGAGTGG
CTTGACACTCTTGTAGGCATCTGTGT-
CAGGCCTCCTGTAGAACTGTTTCCCTGTTTTCTT
TCAGCCTTTTCTGAGAACAGGTGCTCT-
GATCTCAGGTGTGTAGGCATTCCTGGTGACTAT
CTTTCAGCTTTAGGAGCAGGCAGGAAT-
CAGAAGGGTCCTGTCCCTGACTGCTCCTAGATC
CTTGCACCCAGGGGGCACAGTTAGCAC-
TAGGCAATTCCCTCTTGTGTAGGGAATGTGGGT
AGAGGATAGTCGCCTCTGATTTCTCAG-
GAATGTCTGCACTTCTGAAAGTCCAGCCCTCTC
CCCCACAGGATTTAGGTGCAGGGAGCT-
GTTTGACCACTTCAATTCAGTCCTGGGTGTAGA
CCAGAACCACAGGTAAAAAAGAATGACT-
TCATTAAATTAGCAGACAAATGGGTGGAACTA
GAAAATGTCATCCTGGGCTGGAGAGATG-
GCTCAGTGGTTCAGACCACTGGCTGCTCTTCC
AGAGGTCCTGAGTTCAATTCCCAACAAC-
TATATGGTGGCTACCAACCATTACAATGAGAT
CAGATGCCCTCCTCTTGTGTATCTGAA-
GAGAGTGACAGTGTACTTACATACATAAAATAA
ATAAATAAATCTAAAAAAATGTTAAAAAA

SEQ ID NO:85

Rat T2R05 Amino Acid Sequence

MLGAMEGVLLSVATSEALLGIVGNTFI-
ALVNCMDCTRNKNLYNIGFILTGLAISRICLVW
ILITEAYIKIFSPQLLSPINIIELISYL-
WIITSQLNVWFATSLSIFYFLKIANFSHHIFL
WLKRRINIVFAFLIGCLLMSWLFSFPV-
VVKMVKDKKMLYINSSWQIHMKKSELIINYVFT
NGGVFLLFIIMLIVCFLLIISLWRHSKW-
MQSNESGFRDLNTEVHVKTIKVLLSFIILFIL HLIGIT-
INVICLLVPENNLLFVFGLTIAFLY-
PCCHSLILILANSRLKRCFVRILQQLMCS
EEGKEFRNT

SEQ ID NO:86

Rat T2R05 Nucleotide Sequence

AAGAGATTTCAGATACTACCACAAA-
CATTTTTTAAATATATGTAAGTCTTTAAAGAAAGA
AGGGAAAGCCACTCCTTTATTGAGCAGC-
CAATAGATTGCCATCTTAAAATTCTGTGGCAG
AAGCTATTTTAAAGATCTGCGAAGAT-
GCTGGGTGCAATGGAAGGTGTCCTCCTTTCAGTT
GCAACTAGTGAGGCTTTGCTTGGCATTG-
TAGGGAACACATTCATTGCACTTGTGAACTGC ATG-
GACTGTACCAGGAACAAGAATCTC-
TATAATATTGGCTTCATTCTCACTGGCTTGGCA
ATTTCCAGAATCTGCCTCGTGTGGATCT-
TAATCACAGAGGCATACATAAAAATATTCTCT CCA-
CAGTTGCTGTCTCCTATCAACATAAT-
TGAACTCATCAGTTATCTATGGATAATTACC
AGTCAATTGAATGTTTGGTTTGCTAC-
CAGCCTCAGTATCTTTTATTTCCTCAAGATAGCA
AATTTTTCCCACCACATATTTCTCTGGT-
TAAAAAGAAGAATTAATATAGTTTTTGCCTTC
CTGATAGGGTGCTTACTTATGTCATGGC-
TATTTTCTTTCCCAGTAGTTGTGAAGATGGTT AAA-
GATAAAAAAATGCTGTATATAAACT-
CATCTTGGCAAATCCACATGAAGAAAAGTGAG
TTAATCATTAACTATGTTTTCAC-
CAATGGGGGAGTATTTTTACTTTTTATAATAATGTTA
ATTGTATGTTTTCTCTTAATTATTTC-
CCTTTGGAGACACAGCAAGTGGATGCAATCAAAT
GAATCAGGATTCAGAGATCTCAACACA-
GAAGTTCATGTGAAAACAATAAAAGTTTTATTA
TCTTTTATTATCCTTTTTATATTGCATT-
TAATTGGTATTACCATCAATGTCATTTGTCTG
TTAGTCCCAGAAAATAACTTGTTAT-
TCGTGTTTGGTTTGACGATTGCATTCCTCTATCCC
TGCTGCCACTCACTTATCCTAATTCTAG-
CAAACAGCCGGCTGAAACGATGCTTTGTAAGG
ATACTGCAACAATTAATGTGCTCTGAG-
GAAGGAAAAGAATTCAGAAACACATGACAGTCT
GGAAGACAAACAATCAGAAATAGTAAGT-
GAAAAAAAAAAAAAAAAAA

SEQ ID NO:87

Rat T2R06 Amino Acid Sequence

EALVGILGNAFIALVNFMGWMKNRKI-
TAIDLILSSLAMSRICLQCIILLDCIILVQYPDT
YNRGKEMRIIDFFWTLTNHLSVWFAT-
CLSIFYFFKIANFFHPLFLWIKWRIDKLILRTLL
ACLILSLCFSLPVTENLADDFRRCVKTK-
ERINSTLRCKLNKAGYASVKVNLNLVMLFPFS
VSLVSFLLLLILSLWRHTRQMQLNVTG-
YNDPSTTAHVKATKAVISFLVLFIVYCLAFLIAT SSY-
FMPESELAVIWGELIALIYPSSHSFIL-
ILGNSKLKQASVRVLCRVKTMLKGRKY

SEQ ID NO:88

Rat T2R06 Nucleotide Sequence

GTGAGGCCTTAGTAGGAATCTTAG-
GAAATGCATTCATTGCATTGGTAAACTTCATGGGCT
GGATGAAGAATAGGAAGATCACTGCTAT-
TGATTTAATCCTCTCAAGTCTGGCTATGTCCA
GGATTTGTCTACAGTGTATAATTC-
TATTAGATTGTATTATATTGGTCGAGTATCCAGACA
CTTACAACAGGGGTAAAGAAATGAGGAT-
CATTGATTTCTTCTGGACGCTTACCAACCATT
TAAGTGTCTGGTTTGCCACCTGCCTCAG-
CATTTTCTATTTCTTCAAGATAGCAAACTTCT
TCCATCCTCTTTTCCTCTGGATAAAGTG-
GAGAATTGACAAGCTAATTCTGAGAACTCTAC
TGGCATGCTTGATTCTCTCCCTATGCTT-
TAGCCTCCCAGTCACTGAGAATTTGGCTGATG
ATTTCAGACGCTGTGTCAAGACAAAA-
GAAAGAATAAACTCTACTCTGAGGTGCAAATTAA
ATAAAGCTGGATATGCTTCTGTCAAGG-
TAAATCTCAACTTGGTCATCGTGTTCCCCTTTT
CTGTGTCCCTTGTCTCATTCCTTCTCT-
TGATTCTCTCCCTATGGAGACACACCAGGCAGA
TGCAACTCAATGTAACAGGGTACAAT-
GATCCCAGCACAACAGCTCATGTGAAAGCCACAA
AAGCAGTAATTTCCTTCCTAGTTCTGTT-
TATTGTCTACTGCCTGGCCTTTCTTATAGCCA CTTC-
CAGCTACTTTATGCCAGAGAGTGAATT-
AGCTGTAATTTGGGGTGAGCTGATAGCTC
TAATATATCCCTCAAGCCATTCATT-
TATCCTGATCCTTGGGAACAGTAAACTAAAACAGG
CATCTGTAAGGGTGCTTTGTAGAGTAAA-
GACTATGTTAAAGGGAAGAAAATATTAGCATC ATG-

GATATATTTGAAGAAAAACTATCACT-
GTCTAAAGAAAAAGGATGACAAATCATTATC
TTTCATTCTTATATGAATAT-
TGCTTTCATGCGGTAACATCTTTTAA-
CAAACTTAAATCAA ATGTTGGGAAATCTCATATA-
CAGCAACTTTGCATGTCTCTCTGTCTATTTCCCTCTC
CCT TTGTACATAGTTGACATAAAAAAA-
GAATTTTCATGACAAAATTGTAATAAATAGCTACAG
AGGCAGCACATTTTCATAGTAAGTTCT-
GAATCACTCTTCCAAATGCAAAGCTGCCTGACA
AATTCAAAACAACTGTAACAG-
TATTTCACTGCTGTTTGCATTCTTTG-
GAAAAGCAGGTGG TTTGTTCCTATGACCTGACT-
TGGAGTTTCTTCTTACATCACTG

SEQ ID NO:89

Rat T2R07 Amino Acid Sequence

MGSSLYDILTIVMIAEFIFGNVTNGFIV-
LTNCIAWLSKRTLSFIGWIQLFLAISRVVLIW EML-
LAWLKYMKYSFSYLAGTELRVMMLTWV-
VSNHFSLWLATILSIFYLLKIASFSRPVFL
YLKWRVKKVLLLILLGNLIFLMFNIL-
QINTHIEDWMDQYKRNITWDSRVNEFVGFSNLVL
LEMIMFSVTPFTVALVSFILLIFSL-
WKHLQKMHLSSRGERDPSTKAHVNALRIMVSFLLL
YATYFISFFISLIPMAHKKGLDLMFS-
LTVGLFYPSSHSFILILGHSNLRHSSCLVITYLR
CKEKD

SEQ ID NO:90

Rat T2R07 Nucleotide Sequence

CAGTAGCAAAATTTTACTATGTTCAT-
TGATATTATGTCAnGnCACTACGTAAGAAGGAAG
ACTTGAAAGAAAGCTTATCTGAGTTTT-
TAAGAATACATGGACATTTCAGCTTGGCAAATG
ACGAGCTGTGAATTTTTGTCATCTGGA-
CATGGGAAGCAGCCTGTATGATATCTTAACTAT TGT-
CATGATTGCAGAGTTTATATTCGGAAAT-
GTGACCAATGGATTCATAGTGCTGACAAA
CTGTATTGCTTGGCTCAGTAAAA-
GAACTCTTTCTTTCATTGGTTGGATC-
CAGCTTTTCTT GGCCATTTCCAGAGTG-
GTTTTGATATGGGAAATGTTACTAGCATGGCTGAAA
TATATGAA GTATTCATTTTCATATTTGGCTGGCACA-
GAATTAAGGGTTATGATGTTGACCTGGGTAGT TTC-
CAATCACTTTAGTCTCTGGCTTGCCAC-
CATTCTAAGCATCTTTTATTTGCTCAAAAT
AGCTAGTTTCTCCAGACCTGTTTTCCTG-
TATCTGAAGTGGAGAGTAAAAAAAGTGCTCCT
GCTGATTCTTCTCGGAAATTTAATCTTC-
CTGATGTTCAATATATTACAAATCAACACTCA CATA-
GAAGACTGGATGGATCAATATAA-
GAGAAATATAACGTGGGATTCCAGAGTGAATGA
ATTTGTGGGGTTTTCAAATCTGGTTT-
TATTGGAGATGATTATGTTCTCTGTAACACCATT
CACCGTGGCTCTGGTCTCCTTCATCCT-
GTTAATCTTCTCTTTATGGAAACATCTCCAGAA GAT-
GCATCTCAGTTCCAGAGGGGAACGAGAC-
CCTAGCACAAAAGCCCATGTGAATGCCCT
GAGAATTATGGTCTCCTTCCTCTTACTC-
TATGCCACTTACTTCATATCCTTTTTTATATC
ATTAATTCCTATGGCACATAAAAAAG-
GACTAGATCTTATGTTTAGCCTAACTGTTGGACT
TTTCTACCCTTCAAGCCACTCATT-
TATCTTGATTTTGGGACATTCTAATCTAAGGCATTC

CAGTTGTCTGGTGATAACCTATCT-
GAGATGTAAGGAAAAGGATTAGAAAT-
TCACTATTCC ATAAGGCAGTTAAACCACATGCTATT-
AGGTATACTCAGTGCTAGATCCCTAGGCAAGCAT
TAACATTAAAAATATATAATTTCTAGAT-
TCTTCTATTTGTGATAAACCACTCACTTAGAA TAAT-
GCTAAAGTAGCGTGATGTTG-
TATATAAGTGTAAGAATAAAATGTAATTAATTTAGT
TTAGGCACAATAACATATGTCTACTAAG-
TAAAAACTAGGCAGGCTGCTACACGCATATTA
GAATCCAGGCTGAGGTATATAGACTCAA-
GAAATACTGTGGAATAAAGATTTTAATTTTCA TTC-
TATTGTGAGTTATGTGAAATCAATGC-
CATTAAAGGCATACACAAGATTTTCACACAC
TGAAACAACTTCTTGCATTTTGTCATAT-
TGTATTGGAAGTAAATTGGAGATAAACTTAAT
ATCAATAAATTACAAAATGTAAACAT-
AAACAGGGTGATTAAAAATTAGCCTCTAGGTCCT
GGGGAAATGATTCaAGTAAAGT-
GCTTTCTTTTCAAATAGGAGAATCTGAT-
TGTAAATCAT CTAAAAGTCTGGCATAAAATGT-
CAATGAAAATTGTATGTAAAATATAGCTATgGCmAA
GA GCACCmAAGAAAAGAAAATTTTTGC-
CTTTGAAACCCAGTAATTGATATCCTTTAAAAAAG
CAGTTACATATTTTTCTGTTTAA-
GATTTTGTCAAAGGGTAGCTTTGACAAC-
TAATATAAG CTGAGGAAGGTAGCAAGTGTGAAGT-
CAGCTAATGGGGTCACTCAAGTGCTGTTAGCAGCA
GATGGAGGCCACTGCTGAATTTAGCAG-
GCAATTTACAGGGTGAGCACTGCTAGTGCTGAC
AGAAGAAAAACTCTGAAATTT-
TAACTCTTTAGGGTCTGGTGAGAAA-
GAAAAAGAGAGAAA ATCG-
CATATATATATATATATATATATATATATATATATATATAT
ATATATATATATATA TCATGGAAGCTCTAACAAGT-
TGACTCAAACAACTTTATGATGTTTT-
TAGGCCCTTTTATT TTAATGTCAGTGAATTAGGT-
GTGGTACAGCAATATTGCTACTTTTAAATTCAAAGC
AGTT GTTTTATATATTATTCAT-
TATATAAGCTAATTATAAGTTTAAAT-
CAAAAGGTTTATTTGT CCATGATTTTACTTTATCAT-
TGGGCACACCTGTGCTCTCATCCTTGGGCTTGACCT
AGAA TGAAAGTTTATCCTTGATCATATGTCT-
GTCACAAGACTACTTCTCTTCCTATAGTAGTTT ATG-
TACTTACAATATACAAAAGTTTAT-
TGAATTCCTTTTATCACTTATGCAGCCTTTTCT
TACTATTCTATTCTATTCTATTCTATTC-
TATTCTATTCTATTCTATTCTATTCTATTCTA TTCTAT-
TCTATTCTATTCTAGAATCTAACCTATA-
CATTCATTTCTGGCAAAACAACTTAT
ATCATCTCCTTAATTATTTTATCAAT-
TAATCTAACATCCTGAAGTTATTTAAATCTAATA
TAAGGACTCTGTAAAGTCACAAATT-
TATTTATACTTCACAAAATTCATTATTTTATGGAA
CTGCAGCATTGCCTGGGCCAGGAGTCA-
CAAGAGTTCCAGAGTTGACTTTATTGGCATCTG
CCTGGCTAACTGAAGGATCAGTTTTCT-
GTGTACAATAATTTTGTGTATCTCTTTTGATGC
AAGATAT-
GAAAAATAATTTCAGTCTAAAAGTGTC-
CTTAAATTTGAAACTCTCTGGCCAGA ATCTAAC-
TATTGATGACCAGTTTGCACCATGGACTCAGTGTC
TTCT
ATTGCTTTAAAATA AGCAACATCTTGAAT-
GCTTTTCTTGTGTATTAGGCAAATAAT-
TAACAACATGTTTCTATG ATTGTCTCAATAA-
CAATACTATATTTCTCACAGTTTTTAATTTTTATGGCA

AAGTTGGCT AATAAGAATTTTTTTCAAATTAT-
CAAACGTGAAGAAAACTTGACATTT-
TATTTCATGGAG ATTCTAAATGTTTTCTTAGCATAT-
TGCCTTTTTACTAACTTGATTTTTATCATGTTTTGG
TAGTATTTCTAATTTTC-
CTTTTTTTCTAAGTATGTTATGTAGTAA-
CACCAGGAGAATGAA ACAAATGACATTTATAC-
TAAGGATGTGACAAATAAGGCCCAAAGAAAGTTTT
GAAAATCA TGATCTCATTTCTATTCTTCTTTAT-
TAAGTATAGCATAAGCAAAATTCTGATGGTGGTCT
TGGCCCATATCTTTGAACACAGTG-
TAGTGGTGAAGACTTTTTCAAATATTATGTCATATT
TGTACCCATCTCTGTACCTATTTCTTCT-
GATTTCATGAGGAAAAAATGAGGAAGGGTTTG
TTTGTGTGCTGGAGCAGCTGAAGTGGAC-
CAAGGGGCAGGAATTCTCTCTGTTCGGTCCTA
GTGTGACTGATGATGCTCTCAT-
TGAAAAACAGGAAGAAGAAGAAAGACTT-
TATATGCACC ATTCACTCCTTCCCCCTCCTACATTC-
CACCTCCCTCTTGAAAGAGTGTCTATCTATATAG
ATATAGCTATCCTGAAATCCATTAAGTA-
GACCTGACTGGCTTAAATCTCACAGAAATTCA
CCTACCTTTTCCATGATTGCTGAAAT-
TAAAGACATGTGCCGACATATTGGGCACATTCAG
ACCTTTTGCCAACTGTCTTTCAACT-
CATTTGGACCTACTGAGAAGTATTCAAAATATTTG
GTTGTTTTAAATAAAAGGAAAGTGGGTC-
TATATTACTTGAATTGGATAGAGAAATTTTCA CTTA-
CAAGTGATATTGAAAATGGGGGAGAATG-
TATTTTAGCATAAGCACCAGAACACAAA
GCAATTCTTGTTAAAACTTTATC-
GATAAATTGGATAAATGTTAAAAAA-
GAAAAAATAAAA TATACGAACTATTAT-
GAAAAAAAAAAAAAAAAAA

SEQ ID NO:91

Rat T2R08 Amino Acid Sequence

MEPVIHVFATLLIHVEFIFGNLSNGLIV-
LSNFWDWVVKRKLSTIDKILLTLAISRITLIW EMY-
ACFKIVYGSSSFIFGMKLQILYFAW-
ILSSHFSLWFATALSIFYLLRIANCSWKIFLY
LKWRLKQVIVGMLLASLVFLPGILM-
QRTLEERPYQYGGNTSEDSMETDFAKFTELILFNM
TIFSVIPFSLALISFLLLIFSLWKHLQK-
MQLSSRGHGDPSTKAHRNALRIMVSFLLLYTS
YFLSLLISWIAQKHHSKLVDIIGI-
ITELMYPSVHSFILILGNSKLKQTSLWILSHLKCRL
KGENILTPSGKPIN

SEQ ID NO:92

Rat T2R08 Nucleotide Sequence

CTGCAGGTTGGTGATCCAGTAATGAG-
CAGCACTGTTATATCTCAGGCTTTCTAAGATCAT
GGAACCTGTCATTCACGTCTTTGC-
CACTCTACTAATACATGTGGAGTTCATTTTTGGGAA
TCTGAGCAATGGATTAATAGTGTTGT-
CAAACTTCTGGGACTGGGTCGTTAAACGAAAACT
TTCCACAATTGATAAAATTCTTCTTA-
CATTGGCAATTTCAAGAATCACTCTCATCTGGGA
AATGTATGCTTGTTTTAAAATTG-
TATATGGTTCATCTTCATTTATATTTGGGATGAAGTT
ACAAATTCTTTATTTTGCCTGGATC-
CTTTCTAGTCACTTCAGCCTCTGGTTTGCCACAGC
TCTCAGCATCTTTTACTTACTCAGAAT-
AGCTAACTGCTCCTGGAAGATCTTCCTGTATCT
GAAATGGAGACTTAAACAAGTGAT-
TGTGGGGATGTTGCTGGCAAGCTTGGT-
GTTCTTGCC TGGAATCCTGATGCAAAGGACTCT-
TGAAGAGAGGCCCTATCAATATGGAGGAAACACAA
G TGAGGATTCCATGGAAACTGACTTTG-
CAAAGTTTACAGAGCTGATTCTTTTCAACATGAC
TATATTCTCTGTAATACCATTTTCATTG-
GCCTTGATTTCTTTTCTCCTGCTAATCTTCTC
TTTGTGGAAACATCTCCAGAAGATG-
CAGCTCAGTTCCAGAGGACATGGAGACCCTAGCAC
CAAGGCCCACAGAAATGCTTTGAGAAT-
TATGGTCTCCTTCCTCTTGCTCTACACTTCATA
TTTCCTGTCTCTTCTTATATCATGGAT-
TGCTCAGAAGCATCACAGTAAACTGGTTGACAT
TATTGGTATTATTACTGAACTCATG-
TATCCTTCAGTCCACTCATTTATCCTGATTCTAGG
AAATTCTAAATTAAAGCAGACT-
TCTCTTTGGATACTGAGTCATTTGAAAT-
GTAGACTGAA AGGAGAGAATATTTTAACTC-
CATCTGGCAAACCAATTAACTAGCTGTTATATATTCT
GTA TTGCAAACAAATCAGTGAGTTAGTGGT-
TCAAGGATTCCATCCTTGACTTATTGTATCATG
GAAGTCATATAGGGAGAGGCTGAA-
CAAGCTATCTTCTGTAAATTGGCAAGGGTTGCATAT
AGTACTGGTACTGGGACACCATCCAAC-
CATAAAACCTTCTAACCATAACCTACCTGACTG
CAAGATATGCTGGGACAATGGTGGCTCA-
GAGATTTTGGGACTGGCCAACCAATGTCTATT
CTTTCTTGAGGCTCACTCAATAAGGAG-
GCCATGCCCAACTCGTCcTGGATGGCCAGGAAC
CAGAATCTCTGATGGsCCAATGATC-
TATGGnAGAACCCAGCATTACTGGGAAAAAAGAAT
AATCACTTTGATGAATGGT-
CAAATATTTCCTAAATATATTCTGATA-
CACTTGTACATCAT TTCTCTTTCCCAATCATCATCA-
CAGGGACTTCTCCCCAGCACCTGATGGGAACAGAT
ACC AAAATCTACAGCCAAATACTAAATGCAG-
GTTGGGGAACTCCACAAAAGACTGGAAGGAAG
TACTGTGAGAGCCAGAGTGGTCCAGAA-
CACTAGGAGAACACAGAACATCGAATTAACTAA
GCAGCACTCATAGGGTTAATG-
TAAAATAAAGCAGCAGTCACATAGACTG-
CACAGGTGTAC TCTAGATCCTCTGCATATATGT-
TGTGGTTGTCAAACTTGGGAGTTTTGTTGGACTAAT
AA CAATGTGAATAAGTAAGTCTCTGACACT-
TATTCCCGCTCTTGGAACCCTTTTCCACATTT
TGTATTGTCTTACCACCTTGATATGAAG-
GTTTCTGAATAGTCCAAAAAAAAAAAAAAAAA
AAAAAAAAAAAAAAAAAAAAAAAAAAA

SEQ ID NO:93

Rat T2R09 Amino Acid Sequence

MLSAAEGILLSIATVEAGLGVLGNTFI-
ALVNCMDWAKNKKLSKIGFLLFGLATSRIFIVW ILIL-
DAYAKLFFPGKYLSKSLTEIISCIW-
MTVNHMTVWFATSLSIFYFLKIANFSHYIFL
WLKRRTDKVFAFLLWCLLISWAISFS-
FTVKVMKSNPKNHGNRTSGTHWEKREFTSNYVLT
NIGVISLLIMTLTACFLLIISLWKH-
SRQMQSNVSGFRDLNTEAHVKAIKFLISFIILFIL
YFIGVAVEIICMFIPENKLLFIFGLT-
TASVYPCCHSVILILTNSQLKQAFVKVLEGLKFS
ENGKDLRAT

SEQ ID NO:94

Rat T2R09 Nucleotide Sequence

GGACACTGCAGCAGATCTGCTATA-
GAATAACAGATACAAACATAGCAACCTG-

CAGAGATG CTCAGTGCAGCAGAAGGCATCCT-TCTTTCCATTGCAACTGTTGAAGCTGGGCTGGGAGT T TTAGGGAACACATTTATCGCCCTGGT-TAACTGCATGGATTGGGCCAAGAACAAGAAGCTC TCTAAGATTGGTTTCCTTCTCTTTGGCT-TAGCAACTTCCAGAATTTTTATTGTATGGATA TTAATTTTAGACGCATATGCAAAGCTAT-TCTTTCCGGGGAAGTATTTGTCTAAGAGTCTG ACT-GAAATCATCTCTTGTATATGGATGACT-GTGAATCACATGACTGTCTGGTTTGCCACC AGCCTCAGCATCTTCTATTTC-CTAAAAATAGCAAATTTTTCCCAC-TATATATTTCTCTGG TTAAAGAGGAGAACT-GATAAAGTATTTGCCTTTCTCTTGTGGTGTTTATTAA TTTCATGG GCAATCTCCTTCTCATTCACTGT-GAAAGTGATGAAGAGCAATCCAAAGAAT-CATGGAAAC AGGACCAGTGGGACACATTGG-GAGAAGAGAGAATTCACAAGTAACTATGTTTTAATC AAT ATTGGAGTCATTTCTCTCTTGATCAT-GACCTTAACTGCATGTTTCTTGTTAATTATTTCA CTTTGGAAACACAGCAGGCAGATG-CAGTCTAATGTTTCAGGATTCAGAGATCTCAACACT GAAGCTCATGTGAAAGCCATAAAATTTT-TAATTTCATTTATCATCCTTTTCATCTTGTAC TTTAT-AGGTGTTGCAGTAGAAATCATCTGCAT-GTTTATCCCAGAAAACAAACTGCTATTT ATTTTTGGTTTGACAACTGCATCCGTC-TATCCCTGCTGTCACTCAGTCATTCTAATTCTA ACAAACAGCCAGCTGAAGCAAGCCTTTG-TAAAGGTACTGGAGGGATTAAAGTTCTCTGAG AACGGAAAAGATCTCAGGGCCACAT-GAGTCTGGAACAGAAATGGGTAGTCTGGAATAATT GTAAGGAAGTCGTAGAAG-GTCTTTTTCATTTGTACAGTGCTCTTAC-CTTGTTTTTGAGGA GATGTAAACTTTTTTATTTT-TATTTTTTATCCTATGTGAATAAGTGTGTGTGTGTGT GTG TGTGTTTATGTGTGTGTGTATATATGTC-TATGTGTGTTTTAGGAGGTTTAAGAGGGAAGA GGGAATAGAGGTATGTTGGTGTTTTTAA-CATGGATATTCACAGGCCAAGGAACTTGTTCT CTC-CTTTTACCTTAGGGTAGTGTCCTTTGTG-GCTGTCACTCTGACAGTCTACACTAGTTG AACTAAGAGCTTTTAGCCAGTTCACT-TGTCTAAACCTCCCTTCTCATGGTAGCAGTGTTC TGATTACAGAATCATGCTGTCACATA-CAGCTTTTTAACAAGGTTCCCATAGACAGAATTC ATGTCAAACGGAATGCACAGCTGT-CACTCTTACCCACCGATCTCTCTTGCCAGCCCATTC CTATTGACTTTAAACTGTAGTAT-TAAACTTTACTGAAATCTTCTGCAAC-CAGTCTGACTA TGTCTCTTGAAATCACATGATATG-GTGGAATTTTAATGCCATGTGAAAATTTGTTTGTTC AGTTAGTTTCCTACTCTGCCAAATCAT-TCTCTTACACTTGGCAGAAAAAAACCATCAACT GTAGACTATTTTGTGTAAAGACTAATA-CAGATAGAATAAGTATCTTAATCAAGATGTCAT TGT-GATTATCCTAATTTCCCCAGAGCACTG-GTTCCCTTTCCCCAGAAAGACTCACAAAGG AACTGAGGCAAACAGTTGTGGTCACTCT-TGATATTTACCAGTTGAAACTGAAGAACAGTG TTTCCTTTCTGTTCAGTTTTACTACTTA-CAGTTACTTTATTTCATCCATTAAATCCCAAA GTGCTTATTAATAGTAGATATTTGAT-GAAGCAACAATGGTTATAAGAGTGGATGTGGATC TATGACAAAGATCTAGAGAAACAGAC-TATTTGTGAAAGATGGATGAAAGCCCTGATGAAA GGATTCTTCATGGTCTTTGACCCCAGG-GAGTTTTGAAATCAAGCAGCCACAGATCAAAGA GAGCTGAGAAGAGGTTCTCCTGAA-GAAAATATCCAAACACATGGTGCCAGC-CAAAGCAGA AAATAGTGGACAATTCAGTCCAG-GACCTGAATGAGGTAGACAATGTCCTGTTAAGGGT TG GAACAAATATATAGATATGGTCAT-TCATATACAGAAACCTACAGGCGTGTTTGAACTCTT GGTTTCTCAGTAATCAATTCT-TAAATCTTTTTTAGAATGGATTTTTTAT-CATCATTCATG ATCTCTCAGCAGAGTCTG-CAGGGGCTAAGAGACACACTAAGAGTATCTGGAGG GGGGAGT GTCTTCCTGCTCTATCAACCCCTAAAGT-CATATATAACAATACAAAATTCCACATTAGTT AAGT-TCTTTTTTTTACATCTTTATTAAAT-TGGGTATTTCTTATTTACATTTCAAATGTGA TTCCCTTTCCTGGTTTCCAGGC-CAATATCCCCCTAACCTCTCCCCTTC-TATGTGGGTATT CCCTCGTGCCGAATTC

SEQ ID NO:95

Rat T2R10 Amino Acid Sequence

MFLHTIKQRDIFTLIIIFFVEIT-MGILGNGFIALVNIVDWIKRRRISSVDKILTTLALTR LIYAWSMLIFILLFILGPH-LIMRSEILTSMGVIWVVNNHFSIWLAT-CLGVFYFLKIANFS NSLFLYLKWRVKKVVLM

SEQ ID NO:96

Rat T2R10 Nucleotide Sequence

CCCGGGCTGCAGGATTCGGCACGAGAAT-GAAAACTTTTGCTCTACTATTTTGCTGTTCTG TGATACCACAGACCATAAAACAATC-GAGCCAAGGGATCAAGAGCTGAAACT-TCAGAAAGT GGGAATCAAATTTCCTTCCTGATAG-GTTAGCTTATGAGAATTCAGCATCTTATTCAACTT CAGAAAATTGGATATAAGATACAGT-GTCTGGATGAAGCCGAATTGATCTATTTGGGGAGA AAAAACGCCAACATTTATAATAAGGTTT-TATGAGACAGTTCCTGGGAAATTTGGATATTT CCTAGTTAGTAATGTGTAAATGGGATTT-TAAAACATGATTATTTTGTATTTTTAACAACC AACATGAGGAGCTTTTTAAATGCCACT-TAGACATTATAAACTGAAGCATGTTCTTACACA CAATAAAGCAACGTGATATTTT-TACTTTGATAATCATATTTTTTGTG-GAAATAACAATGG GAATCTTAGGAAATGGATTCAT-AGCACTAGTGAACATTGTGGACTGGATCAAGAGAA GAA GGATTTCTTCAGTGGATAAGATTCTCAC-TACCTTGGCCCTTACCAGACTCATTTATGCGT GGTCTATGCTCATTTTTATATTGTTAT-TCATACTGGGCCCGCATTTGATTATGAGATCAG AAATACTTACATCAATGGGTGT-TATCTGGGTGGTGAACAATCACTTCAG-CATCTGGCTTG CTACATGCCTCGGTGTCTTT-TATTTTCTCAAGATAGCCAATTTTTCTAACTCTTTGT TTC TTTACCTAAAGTGGAGAGT-TAAAAAAGTGGTTTTAATG

SEQ ID NO:97

Rat T2R11 Amino Acid Sequence

GSGNGFIVSVNGSHWFKSKKISLSDFI-ITSLALFRIFLLWIIFTDSLIIVFSYHAHDSGI RMQLID-VFWTFTTHFSIWLISCLSVFYCLKIATFSHPS FL*LKSR

SEQ ID NO:98

Rat T2R11 Nucleotide Sequence

GGATCCGGAAACGGTTTTATCGTGT-
CAGTCAATGGCAGCCATTGGTTCAAGAGCAAGAAG
ATTTCTTTGTCTGACTTCATCATTAC-
CAGCTTGGCCCTCTTCAGGATCTTTCTGCTGTGG
ATCATCTTTACTGATAGCCTCATAAT-
AGTGTTCTCTTACCACGCCCACGACTCAGGGATA
AGGATGCAACTTATTGATGTTTTCTGGA-
CATTTACAACCCACTTCAGTATTTGGCTTATC TCCT-
GTCTCAGTGTTTTCTACTGCCTGAAAAT-
AGCCACTTTCTCCCACCCCCTCATTCCTG
TAGCTCAAATCTAGA

SEQ ID NO:99

Rat T2R12 Amino Acid Sequence

MLSTVSVFFMSIFVLLCFLGILANGFIV-
LMLSREWLWRGRLLPSDMILLSLGTSRFCQQC
VGLVNSFYYSLHLVEYSRSLARQLISLH-
MDFLNSATFWFGTWLSVLFCIKIANFSHPAFL WLK-
WRFPALVPWLLLGSILVSFIVTLMFF-
WGNHTVYQAFLRRKFSGNTTFKEWNRRLEID
YFMPLKLVTTSIPCSLFLVSILLLINSL-
RRHSQRMQHNAHSLQDPNTQAHSRALKSLISF LVLY-
ALSYVSMVIDATVVISSDNVWYWPWQII-
LYLCMSVHPFILITNNLKFRGTFRQLLL LARGFWVT

SEQ ID NO:100

Rat T2R12 Nucleotide Sequence

GTGTGAGGGACTGTGGGTAGGGGCTGG-
GAGGAGGCCAGGAACCAAGGCAACCAGTGGTGA
CAGGAGGGGCTGAAATGCTATCAACTG-
TATCAGTTTTCTTCATGTCGATCTTTGTTCTGC TCT-
GTTTCCTGGGAATCCTGGCAAACGGCT-
TCATTGTGCTGATGCTGAGCAGGGAATGGC
TATGGCGCGGTAGGCTGCTCCCCTCAGA-
CATGATCCTCCTCAGTTTGGGCACCTCCCGAT TCT-
GCCAGCAGTGCGTTGGGCTGGTGAA-
CAGTTTCTACTATTCCCTCCACCTTGTTGAGT
ACTCCAGGAGCCTTGCCCGTCAACT-
CATTAGTCTTCACATGGACTTCTTGAACTCAGCCA
CTTTCTGGTTTGGCACCTGGCT-
CAGCGTCCTGTTCTGTATCAAGAT-
TGCTAACTTCTCCC ATCCTGCCTTCCTGTGGT-
TGAAGTGGAGATTCCCAGCATTGGTGCCTTGGCTCC
TACTGG GCTCTATCTTGGTGTCCTTCATCG-
TAACTCTGATGTTCTTTGGGGAAACCACACTGTCT
ATCAGGCATTCTTAAG-
GAGAAAGTTTTCTGGGAACACAACCTT-
TAAGGAGTGGAACAGAA GGCTGGAAATAGAC-
TATTTCATGCCTCTGAAACTTGTCACCACGTCAATT
CCTTGCTCTC TTTTTCTAGTCTCAATTTTGCTGT-
TGATCAATTCTCTCAGAAGGCATTCA-
CAAAGAATGC AGCACAATGCTCACAGCTTGCAA-
GACCCCAACACCCAGGCTCACAGCAGAGCCCTGAAGT
CACTCATCTCATTTCTGGTTCTT-
TACGCGCTGTCCTATGTGTCAATGGT-
CATTGACGCTA CAGTTGTCATCTCCTCA-
GATAACGTGTGGTATTGGCCCTGGCAAATTATACTT
TACTTGT GCATGTCCGTACATCCATTTATCCTTAT-
CACTAATAATCTCAAGTTCCGAGGCACCTTCA
GGCAGCTACTCCTGTTGGCCAGGGGAT-
TCTGGGTGACCTAGAAGGTTTGGTCTCTTTATC
TGTACCCTTTGAAGAGACTTAGGT-
GAGGGTGACTTCCCTTGGAAGTGATCTCATCTACAT
GGAAATGTCTTTGTAGGCTGA-
CATGGGGTCATACTATGTGGTTCCTCCT-
TGGGAAAGAGG AGAAGAAAATACAGGGATTCT-
GAGCGTTCTTCCTTATCTTGGGATATTATGAAAATGG
AC ATTCTGAATCCTGAACCAGTATTGATCT-
GAAGTGCAAAGTACAATATGCCTGTTCCCTTC
ATGTCTGCTATCCTCTTGGTACTTATTAATTCCCT

SEQ ID NO:101

Rat T2R13 Amino Acid Sequence

MCGFPLSIQLLTGLVQMYVILIIAVFT-
PGMLGNVFIGLVNYSDWVKNKKITFINFILICL AAS-
RISSVLVVFIDAIILELTPHVYHSYS-
RVKCSDIFWVITDQLSTWLATCLSIFYLLKI
AHFSHPLFLWLKWRLRGVLVGFLLFSLF-
SLIVYFLLLELLSIWGDIYVIPKSNLTLYSET IKT-
LAFQKIIVFDMLYLVPFLVSLASLLLL-
FLSLVKHSQNLDRISTTSEDSRAKIHKKAM
KMLLSFLVLFIIHIFCMQLSRWLFFLFP-
NNRSTNFLLLTLNIFPLSHTFIIILGNSKLRQ RAMRV-
LQHLKSQLQELILSLHRLSRVFTMEIA

SEQ ID NO:102

Rat T2R13 Nucleotide Sequence

GGGATTCAGTTGGATAAGAGAAAAGT-
CAAAACCCTAAGACTAAGAATTTCCTTAAGTAGA
TATCAATTTCTATCCATTGGAAG-
GAGTTTCCAATCACACTGAAATTA-
CAATAAAAAAGGA GCAAGATAACTATGGGAAAG-
GATGATTTTCGGTGGATGTTTGAGAACTGAGCAGCA
AGGC AAATTGATAGATGTGTGGATTC-
CCTCTTTCTATTCAACTGCTTACTGGAT-
TGGTTCAAAT GTACGTGATATTGATAATAGCAGT-
GTTTACACCTGGAATGCTGGGGAATGTGTTCATTGG
ACTGGTAAACTACTCTGACTGGG-
TAAAAAACAAGAAAATCACCTTCAT-
CAACTTCATCCT GATCTGTTTGGCAGCGTCCA-
GAATCAGCTCTGTGTTGGTGGTATTTATTGATGCAAT
CAT CCTAGAACTAACTCCTCATGTCTATCAT-
TCTTACAGTCGAGTGAAATGCTCTGATATATT
CTGGGTTATAACTGACCAGCTGT-
CAACGTGGCTTGCCACCTGCCTCAG-
CATTTTCTACTT ACTCAAAATAGCCCACTTCTC-
CCATCCCCTTTTCCTTTGGTTGAAGTGGAGATTGAG
AGG AGTGCTTGTTGGTTTTCTTC-
TATTTTCTTTGTTCTCATTGATTGTT-
TATTTTCTACTCCT GGAATTACTGTCTATTTGGG-
GAGATATTTATGTGATCCCTAAAAGCAATCTGACTT
TATA TTCAGAAACAATTAAGACCCT-
TGCTTTTCAAAAGATAAT-
TGTTTTTGATATGCTATATTT AGTCCCATTTCTTGT-
GTCCCTAGCCTCATTGCTCCTTTTATTTTTATCCTTG
GTGAAGCA CTCCCAAAACCTTGACAGGATTTC-
TACCACCTCTGAAGATTCCAGAGCCAA-
GATCCACAA GAAGGCCATGAAAATGCTAT-
TATCTTTCCTCGTTCTCTTTATAATTCACATTTTTTGC
AT GCAGTTGTCACGGTGGTTAT-
TCTTTTTGTTTCCAAACAACAGGTCAAC-
TAATTTTCTTTT GTTAACATTAAACATCTTCCCAT-
TATCTCATACATTCATTATCATCCTGGGAAACAGCAA
GCTTCGACAAAGAGCAATGAGGGTCCTG-
CAACATCTTAAAAGCCAACTTCAAGAGTTGAT
CCTCTCCCTTCATAGATTGTCCA-

GAGTCTTCACTATGGAAATAGCT-
TAAAGGGGAGACTT GGAAGGTCACTGGTAACT-
TGTTCTTCCGCTGAGTTCTGTTAAGTAATGCTGGAC
ATATAT GAACTATCCCTAGTGCATACTGATATT

SEQ ID NO:103

Rat T2R14 Amino Acid Sequence

VANIMDWVKRRKLSAVDQLLTVLAIS-
RITLLWSLYILKSTFSMVPNFEVAIPSTRLTNLV WIIS-
NHFN

SEQ ID NO:104

Rat T2R14 Nucleotide Sequence

CTGTGGCAAACATAATGGATTGGGTCAA-
GAGAAGGAAGCTCTCTGCAGTGGATCAGCTCC
TCACTGTGCTGGCCATCTCCAGAAT-
CACTCTGTTGTGGTCATTGTACATACTGAAATCAA
CATTTTCAATGGTGCCAAACTTTGAGG-
TAGCTATACCGTCAACAAGACTAACTAATCTTG
TCTGGATAATTTCTAACCATTTTAAT

SEQ ID NO:105

Mouse T2R01 Amino Acid Sequence

MQHLLKTIFVICHSTLAIILIFELIIG-
ILGNGFMALVHCMDWVKRKKMSLVNKILTALAI
SRIFHLSLLLISLVIFFSYSDIP-
MTSRMTQVSNNVWIIVNHFSIWLSTCLSVLYFLKISN
FSNSFFLYLKWRVEKVVSVTLLVSLLL-
LILNILLINLEISICIKECQRNISCSFSSHYYA
KCHRQVIRLHIIFLSVPVVLSLSTFLL-
LIFSLWTLHQRMQQHVQGGRDARTTAHFKALQT
VIAFFLLYSIFILSVLIQNELLKKNLFV-
VFCEVVYIAFPTFHSYILIVGDMKLRQACLPL
CIIAAEIQTTLCRNFRSLKYFRLCCIF

SEQ ID NO:106

Mouse T2R01 Nucleotide Sequence

AGCTGTGCGTGAGCAAAGCATTTCT-
TGTCTGCCACTTCTGAGCTGTGTGAGGAGACACAT
TATCACGGAAAGAGATTCAGACTCT-
GTCGCTGTCAAACCTGTATGTTTGCTCCTCTTTTA
CTGTGAAGGCAGAGTTACGAAAAAAAT-
GTTATGAGAACCAACTCAGAAATTGACAAAAA
TTTTCTAAATGTCATTTTTAAAAAT-
TATATTTCAAATGGAAATGTGAGCAAATCTTTATA
ACTAATATATAAAATGCAGCATCTTT-
TAAAGACAATATTTGTTATCTGCCATAGCACACT
TGCAATCATTTTAATCTTTGAAT-
TAATAATTGGAATTTTAGGAAATGGGT-
TCATGGCCCT GGTGCACTGTATGGACTGGGTTAA-
GAGAAAGAAAATGTCCTTAGTTAATAAAATCCTCAC
TGCTTTGGCAATCTCCA-
GAATTTTTCATCTCAGTTTATTGCT-
TATAAGTTTAGTCATATT CTTTTCATATTCTGATAT-
TCCTATGACTTCAAGGATGACACAAGTCAGTAATAA
TGTTTG GATTATAGTCAATCATTTCAGTATCTG-
GCTTTCTACATGCCTCAGTGTCCTTTATTTTCT CAA-
GATATC-
CAATTTTTCTAACTCTTTTTTTCTTTATCTAAAGTGG
AGAGTTGAAAAAGT AGTTTCAGTTACACTGTTG-
GTGTCATTGCTCCTCCTGATTT-
TAAATATTTTATTAATTAA CTTGGAAATTAGCATATG-
CATAAAGGAATGTCAAAGAAACATATCATGCAGCTT
CAGTTC TCATTACTATGCAAAGTGTCACAGGCAG-
GTGATAAGGCTTCACATTATTTTCCTGTCTGT
CCCCGTTGTTTTGTCCCTGT-
CAACTTTTCTCCTGCTCATCTTCTCCCT-
GTGGACACTTCA CCAGAGGATGCAGCAGCATGT-
TCAGGGAGGCAGAGATGCCAGAACCACGGCCCAC
TTCAA AGCCCTACAAACTGTGATTGCATTTTTC-
CTACTATATTCCATTTTTATTCTGTCTGTCTT AATA-
CAAATATGAATTACTGAA-
GAAAAATCTTTTCGTTGTATTTTGTGAGGTTGTATA
TA TAGCTTTTCCGACATTCCATTCATATAT-
TCTGATTGTAGGAGACATGAAGCTGAGACAGG
CCTGCCTGCCTCTCTGTATTATCG-
CAGCTGAAATTCAGACTACACTATGTAGAAATTTTA
GATCACTAAAGTACTTTAGATTATGTTG-
TATATTCTAGACAAAAATTAACTGATACAAAT
GTCTTTTGTATTTTTCATTTTAAATATC-
CTTTAATTTTGACTGCATGAAATTGATTTCTG CTTG-
CAATTATCACTGATTAAAACTAT-
TAATAATTTAACTAGTTGTATACAAGG

SEQ ID NO:107

Mouse T2R02 Amino Acid Sequence

MESVLHNFATVLIYVEFIFGNLSNGFIV-
LSNFLDWVIKQKLSLIDKILLTLAISRITLIW EIYAW-
FKSLYDPSSFLIGIEFQIIYFSWV-
LSSHFSLWLATTLSVFYLLRIANCSWQIFLY
LKWRLKQLIVGMLLGSLVFLLGNLMQSM-
LEERFYQYGRNTSVNTMSNDLAMWTELIFFNM
AMFSVIPFTLALISFLLLIFSLWKHLQK-
MQLISRRHRDPSTKAHMNALRIMVSFLLLYTM
HFLSLLISWIAQKHQSELADIIG-
MITELMYPSVHSCILILGNSKLKQTSLCMLRHLRCRL
KGENITIAYSNQITSFCVFCVANKSMR

SEQ ID NO:108

Mouse T2R02 Nucleotide Sequence

CAGCACAGTGAAAAACTCATGGGCCACT-
TGGTCACCCAGGGACAGGCGACGCTGTTATAT
GCCAAGCTTTCTATGAACATGGAATCT-
GTCCTTCACAACTTTGCCACTGTACTAATATAC
GTGGAGTTTATTTTTGGGAATTTGAG-
CAATGGATTCATAGTGTTGTCAAACTTCTTGGAC
TGGGTCATTAAACAAAAGCTTTCCT-
TAATAGATAAAATTCTTCTTACATTGGCAATTTCA
AGAATCACTCTCATCTGGGAAATATAT-
GCTTGGTTTAAAAGTTTATATGATCCATCTTCC
TTTTTAATTGGAATAGAATTTCAAAT-
TATTTATTTTAGCTGGGTCCTTTCTAGTCACTTC
AGCCTCTGGCTTGCCACAACTCT-
CAGCGTCTTTTATTTACTCAGAAT-
AGCTAACTGCTCC TGGCAGATCTTTCTC-
TATTTGAAATGGAGACTTAAACAACTGATTGTGGG
GATGTTGCTG GGAAGCTTGGTGTTCTTGCTTG-
GAAATCTGATGCAAAGCATGCTTGAA-
GAGAGGTTCTAT CAATATGGAAGGAACACAAGT-
GTGAATACCATGAGCAATGACCTTGCAATGTGGAC
CGAG CTGATCTTTTTCAACATGGCTATGT-
TCTCTGTAATACCATTTACATTGGCCTTGATTTCT
TTTCTCCTGCTAATCTTCTCTTTGTG-
GAAACATCTCCAGAAGATGCAGCTCATTTCCAGA
AGACACAGAGACCCTAGCACCAAGGC-
CCACATGAATGCCTTGAGAATTATGGTGTCCTTC
CTCTTGCTCTATACCATGCATTTCCT-

GTCTCTTCTTATATCATGGATTGCTCAAAAGCAT CAGAGTCAACTGGCTGATATTATTGG-TATGATAACTGAACTCATGTATCCTTCAGTCCAT TCATGTATCCTGATTCTAGGAAAT-TCTAAATTAAAGCAGACTTCTCTTTGTATGCTGAGG CATTTGAGATGTAGGCTGAAAG-GAGAGAATATCACAATTGCATATAG-CAACCAAATAACT AGCTTTTGTGTATTCTGTGTTG-CAAACAAATCTATGAGGTAGTTGTTCAAGGAATCCT TC CTTGACTTATTGTATCATGGAAGT-CATATGGGGGAGTCTGAAAGAGCTGTCT-TCTGTAAG CAAGGTTTGTATACAC-TAGTGGGGCTGGGACACCAACCCAAGCACAAAACC TAGCTATAA CCTATCCTGGCTGCAGGATATGCTG-GAACAATGGTGGCTTGGAAATTGTGGGACTGGCAA AGCAATAGCTAGTCTAACTTGAGGC-CCATTCCACAGCAGGAAGCTCATGCCCACCTCTGC CTGGATGGCCAGGAAGCAAAATCT-TGATGGCCCCAAGACCTATGGTAAACT-GAACACTAC TGGAAAAAGAAAGACTCGTGTTAAT-GATCTATCAAATATTTCCTAATGATATTCTGATAA ACTCATATATTAGTCCCTGTCCTAAT-CATCATCACTGGGACTCCTTCCCAGCACCTGATG GGAGCAGATAGAGATCTACATCCAAAT-AGTAAGTGTATCTTGGGGAACTCCACTTAAGAA TAGAAGGAACAATTATGAGAGCCAGAGT-GATCCAGAACACTAGGATCACAGAATCAACTA AGCAGCATGCATAGGGGTTAATG-GAGACTGAAGTGGCAATCACAGAGCCTG-CATAGGTCT ACACTAAGTCCTCTGTGTATATACT-GTGGCTGTTTAGCTTAGGAATTTTGTTGGACTCCT AACAATGGATAAGGAATTC

SEQ ID NO:109

Mouse T2R03 Amino Acid Sequence

MVLTIRAILWVTLITIISLEFIIGILGN-VFIALVNIIDWVKRGKISAVDKTYMALAISRT AFLLSLITGFLVSLLDPALLGMRTMVR-LLTISWMVTNHFSVWFATCLSIFYFLKIANFSN SIFLV-LKWEAKKVVSVTLVVSVIILIMNI-IVINKFTDRLQVNTLQNCSTSNTLKDYGLFL FISTGFTLTPEAVSLTMFLLLIFSL-WRHLKNMCHSATGSRDVSTVAHIKGLQTVVTFLLL YTAFVMSLLSESLNINIQHTNLLSHFLR-SIGVAFPTGHSCVLILGNSKLRQASLSVILWL RYKYKHIENWGP

SEQ ID NO:110

Mouse T2R03 Nucleotide Sequence

CTTTAATAGCAGGGTGTGAATATT-TAAATTTTCTTTCTGCAGCAACTACTGAGGGCTTCA GACTGCTGTATACAGGGCATGAAG-CATCTGGATGAAGTTCAGCTGTGCTGC-CTTTGACAA CAATTTTTTGTGTATGTGTGGAGAA-CATAAACCATTTCATTAGTGAAATTTGGCTTTTGG GTGACATTGTCTATGATAGTTCT-GAAAGTGATTATGTTAAGAATCAGACA-CAGCCGTCTA GAAGATTGTATTAACACATCTTTGG-TAGTTCAGAAGAAATTAGATCATCATGGTGTTGAC AATAAGGGCTATTTTATGGGTAACAT-TGATAACTATTATAAGTCTGGAGTTTATCATAGG AATTTTAGGAAATGTATTCAT-AGCTCTCGTGAACATCATAGACTGGGT-TAAAAGAGGAAA GATCTCTGCAGTGGATAAGAC-CTATATGGCCCTGGCCATCTCCAGGACTGCTTTTTA TT GTCACTAATCACAGGGTTCTTGGTAT-CATTATTGGACCCAGCTTTATTGGGAATGAGAAC GATGGTAAGGCTCCTTACTATTTCCTG-GATGGTGACCAATCATTTCAGTGTCTGGTTTGC AACATGCCTCAGTATCTTTTATTTTCT-CAAGATAGCTAATTTCTCAAATTCTATTTTCCT TGT-TCTCAAATGGGAAGCTAAAAAAGTGG-TATCAGTGACATTGGTGGTATCTGTGATAAT CTTGATCATGAACATTATAGTCATAAA-CAAATTCACTGACAGACTTCAAGTAAACACACT CCAGAACTGTAGTACAAGTAACACTT-TAAAAGATTATGGGCTCTTTTTATTCATTAGCAC TGGGTTTACACTCACCCCATTCGCTGT-GTCTTTGACAATGTTTCTTCTGCTCATCTTCTC CCT-GTGGAGACATCTGAAGAATATGTGTCA-CAGTGCCACAGGCTCCAGAGATGTCAGCAC AGTGGCCCACATAAAAGGCTTGCAAACT-GTGGTAACCTTCCTGTTACTATATACTGCTTT TGT-TATGTCACTTCTTTCA-GAGTCTTTGAATATTAACATTCAACATACAAATCTTC TTTC TCATTTTTTACGGAGTATAGGAG-TAGCTTTTCCCACAGGCCACTCCTGTG-TACTGATTCT TGGAAACAGTAAGCTGAGGCAAGC-CTCTCTTTCTGTGATATTGTGGCTGAGGTATAAGTA CAAACATATAGAGAATTGGGGC-CCCTAAATCATATCAGGGATCCTTTTC-CACATTCTAGA AAAAAATCAGTTAATAAGAACAG-GAATTTAGGAAGGAATCTGAAATTATGAATCTCATA G GCCATGAACCTTCAGACAAAGGAT-TCATTAGAGAGATAGAGAGAGAACATTGTTATCTGT AACTCGACAGGCAACACTGTAGATTAT-GAAAATAAATGTCAGTCTGTAATGGAAAGCAAA ACATGCTATATTTTATTAATTGGTTTTG-GTTTAAGGTCGGGATA

SEQ ID NO:111

Mouse T2R04 Amino Acid Sequence

MLSALESILLSVATSEAMLGVLGNTFIV-LVNYTDWVRNKKLSKINFILTGLAISRIFTIW IITL-DAYTKVFLLTMLMPSSLHECMSYIWVI-INHLSVWFSTSLGIFYFLKIANFSHYIFL WMKRRADKVFVFLIVFLIITWLASF-PLAVKVIKDVKIYQSNTSWLIHLEKSELLINYVFA NMGPISLFIVAIIACFLLTISL-WRHSRQMQSIGSGFRDLNTEAHMKAMKV-LIAFIILFIL YFLGILIETLCLFLTNNKLLFIFGFTL-SAMYPCCHSFILILTSRELKQDTMRALQRLKCC ET

SEQ ID NO:112

Mouse T2R04 Nucleotide Sequence

CTGCAGCAGGTAAATCACACCAGATC-CAGCAGAAGCCTTCTTGGAAATTGGCAGAGATGC TGAGTGCACTGGAAAGCATCCTC-CTTTCTGTTGCCACTAGTGAAGCCAT-GCTGGGAGTTT TAGGGAACACATTTATTGTACTTG-TAAACTACACAGACTGGGTCAGGAATAAGAAACTC T CTAAGATTAACTTTATTCTCACTGGCT-TAGCAATTTCCAGGATTTTTACCATATGGATAA TAACTTTAGATGCATATACAAAG-GTTTTCCTTCTGACTATGCTTATGC-CGAGCAGTCTAC ATGAATGCATGAGTTA-CATATGGGTAATTATTAACCATCTGAGCGTTTGGTTT AGCACCA GCCTCGGCATCTTTTATTTTCTGAAGAT-AGCAAATTTTTCCCACTACATATTTCTCTGGA TGAAGAGAAGAGCT-

GATAAAGTTTTTGTCTTTCTAATTGTAT-TCTTAATTATAACGTGGC TAGCTTCCTTTC-CGCTAGCTGTGAAGGTCATTAAAGATGTTAAAATAT ATCAGAGCAACA CATCCTGGCTGATCCACCTG-GAGAAGAGTGAGTTACTTATAAACTAT-GTTTTTGCCAATA TGGGGCCCATTTCCCTCTTTAT-TGTAGCCATAATTGCTTGTTTCTTGTTAACCATTTCC C TTTGGAGACACAGCAGGCAGATGCAATC-CATTGGATCAGGATTCACAGATCTCAACACAG AAGCTCACATGAAAGCCATGAAAGTTT-TAATTGCATTTATCATCCTCTTTATCTTATATT TTTTGGGTATTCTCATAGAAACATTAT-GCTTGTTTCTTACAAACAATAAACTTCTCTTTA TTTTTGGCTTCACTTTGTCAGCCATG-TATCCCTGTTGCCATTCCTTTATCCTAATTCTAA CAAGCAGGGAGCTGAAGCAAGACACTAT-GAGGGCACTGCAGAGATTAAAATGCTGTGAGA CTTGACAGAGAAATGAATGTTCTGGCA-CAGTTCAGCAGGGAATCCCTGGAGCCCTTTCCA TTCCCACTATGTTCTCACACTGTCTT-TAGTTGAATTGTTAAAAGTTTTTGAAACCTTTGG CAACTGATTGACTGCAGCTACGCCAGTG-TAAGATTTTCATAGTAAGAGCAAACATTGAAA ATAAGACTTCTCAGTCTTATTTCAT-TGAGTTTCTAAAGCATTGACACCCATTCACCAGAA AAACCAAAGGGGAAGAGAGGAGTTTTCA-GACATGTGTGATGAATCTTGATATTTAGGACA TGGAATTGAGGAG-CCAGAGGGATGCTACCGTGTGTCTA-CAGCTTTGTTTGTTAAATAGC TACTTTTCCTTTC-CCAGTTAGTTAAAGTAGATGCTTGGAGTAGTGGTG AAAATCATGGCA GTAGATGGGATCTGTGG-GAAGTGGTTGAGGAAGCAGGCTGTTTCT-GAACGAAGAGACCAG AGGACTGATTGAACTGGT-CATTGTGTATATCAAAAATAGTGATTTCAGATGAAG CCAAGT TGTAGAGCAAAGATATCTGAGGAA-GAATTC

SEQ ID NO:113

Mouse T2R05 Amino Acid Sequence

MLSAAEGILLSIATVEAGLGVLGNTFI-ALVNCMDWAKNNKLSMTGFLLIGLATSRIFIVW LLTLDAYAKLFYPSKYFSSSLIEIISYI-WMTVNHLTVWFATSLSIFYFLKIANFSDCVFL WLKRRTDKAFVFLLGCLLTSWVISFSFV-VKVMKDGKVNHRNRTSEMYWEKRQFTINYVFL NIGVISLFMMTLTACFLLIMSL-WRHSRQMQSGVSGFRDLNTEAHVKAIKF-LISFIILFVL YFIGVSIEIICIFIPENKLLFIFGETTA-SIYPCCHSFILILSNSQLKQAFVKVLQGLKFF

SEQ ID NO:114

Mouse T2R05 Nucleotide Sequence

ATGCTGAGTGCGGCAGAAGGCATCCTC-CTTTCCATTGCAACTGTTGAAGCTGGGCTGGGA GTTTTAGGGAACACATTTATTGCACTGG-TAAACTGCATGGACTGGGCCAAGAACAATAAG CTTTCTATGACTGGCTTCCTTCTCATCG-GCTTAGCAACTTCCAGGATTTTTATTGTGTGG CTAT-TAACTTTAGATGCATATGCAAAGCTAT-TCTATCCAAGTAAGTATTTTTCTAGTAGT CTGATTGAAATCATCTCTTATATATG-GATGACTGTGAATCACCTGACTGTCTGGTTTGCC ACCAGCCTAAGCATCTTCTATTTCCT-GAAGATAGCCAATTTTTCCGACTGTGTATTTCTC TGGTTGAAGAGGAGAACT-GATAAAGCTTTTGTTTTTCTCTTGGGGT-GTTTGCTAACTTCA TGGGTAATCTCCTTCT-CATTTGTTGTGAAGGTGATGAAGGACGGTAAAGTG AATCATAGA AACAGGACCTCGGAGATGTACTGG-GAGAAAAGGCAATTCACTATTAACTACGTTTTCCTC AATATTGGAGTCATTTCTCTCTTTAT-GATGACCTTAACTGCATGTTTCTTGTTAATTATG TCACTTTGGAGACACAGCAGGCAGATG-CAGTCTGGTGTTTCAGGATTCAGAGACCTCAAC ACAGAAGCTCATGTGAAAGCCAT-AAAATTTTTAATTTCATTTATCATCCTTTTCGTCTTG TATTTTATAGGTGTTTCAATAGAAAT-TATCTGCATATTTATACCAGAAAACAAACTGCTA TTTATTTTTGGTTTCACAACTGCATC-CATATATCCTTGCTGTCACTCATTTATTCTAATT CTATCTAACAGCCAGCTAAAGCAAGC-CTTTGTAAAGGTACTGCAAGGATTAAAGTTCTTT TAG

SEQ ID NO:115

Mouse T2R06 Amino Acid Sequence

MLTVAEGILLCFVTSGSVLGVLGNGFIL-HANYINCVRKKFSTAGFILTGLAICRIFVICI IIS-DGYLKLFSPHMVASDAHIIVISYIWVI-INHTSIWFATSLNLFYLLKIANFSHYIFFC LKRRINTVFIFLLGCLFISWSIAF-PQTVKIFNVKKQHRNVSWQVYLYKNEFIVSHILLNL GVIFFFMVAIITCFLLIISLWKHNRKMQ-LYASRFKSLNTEVHVKVMKVLISFIILLILHF IGILI-ETLSFLKYENKLLLILGLIISCMYPCCH-SFILILANSQLKQASLKALKQLKCHKK DKDVRVTW

SEQ ID NO:116

Mouse T2R06 Nucleotide Sequence

TATAGTTGCAGCAGAAGCAACGTTAGG-GATCTGTAGAGATGCTGACTGTAGCAGAAGGAA TCCTCCTTTGTTTTGTAACTAGTGGT-TCAGTCCTGGGAGTTCTAGGAAATGGATTTATCC TGCATGCAAACTACATTAACTGTGTCA-GAAAGAAGTTCTCCACAGCTGGCTTTATTCTCA CAGGCTTGGCTATTTGCAGAATCTTTGT-CATATGTATAATAATCTCTGATGGATATTTAA AAT-TGTTTTCTCCACATATGGTTGCCTCT-GATGCCCACATTATAGTGATTTCTTACATAT GGGTAATTATCAATCATACAAGTATATG-GTTTGCCACCAGCCTCAACCTCTTCTATCTCC TGAAGATAGCAAATTTTTCTCACTA-CATCTTCTTCTGCTTGAAGAGAAGAATCAATACAG TATTTATCTTTCTCCTGGGATGCTTATT-TATATCATGGTCAATTGCTTTCCCACAAACAG TGAAGATATTTAATGTTAAAAAGCAGCA-CAGAAaTGTTTCCTGGCAGGTTTACCTCTATA AGAATGAGTTCATtGTAAGCCACATTCT-TCTCAACCTGGGAGTTATATTCTTCTTTATGG TGGC-TATCATTACATGCTTCCTATTAAT-TATTTCACTTTGGAAACATAACAGAAAGATGC AGTTGTATGCCTCAAGATTCAAAAGCCT-TAACACAGAAGTACATGTGAAAGTCATGAAAG TTTTAATTTCTTTTATTATCCTGT-TAATCTTGCATTTCATAGGGATTTTGATAGAAACAT TGAGCTTTTTAAAATATGAAAATAAACT-GCTACTTATTTTGGGTTTGATAATTTCATGCA TGTATCCTTGCTGTCATTCATTTATC-CTAATTCTAGCAAACAGTCAGCTGAAGCAGGCTT

CTTTGAAGGCACTGAAGCAATTAAAAT-
GCCATAAGAAAGACAAGGACGTCAgAGTGACAT
GGTAGACTTATGGAGAAATGAATGGTCA-
CAAGAAATAGCCTGGTGTGGAGATGTTGATAT
CTCTAAAGACCGTTTCACTTCCAAAT-
TCTTGCAATTATTTAAAAAAAAAAGTCTTGCTGA
TATCATGGAATCATGGGAAATGTTG-
CAATTGTGTTTTGGGGACAGGGTGACCAGTGAAGG
TATGGTTAAGCAGCGAAACACTCATA-
CAGCTCGTTCGTTCTTTTTGTATTTTATTTTGTG
TTGGTGGCCTTCCAAGACATGATTTCTC-
TATGTAAGTTTTGG

SEQ ID NO:117

Mouse T2R07 Amino Acid Sequence

MLNSAEGILLCVVTSEAVLGVLGDTY-
IALFNCMDYAKNKKLSKIGFILIGLAISRIGVVW
IIILQGYIQVFFPHMLTSGNITEYITYI-
WVFLNHLSVWFVTNLNILYFLKIANFSNSVFL
WLKRRVNAVFIFLSGCLLTSWLLCF-
PQMTKILQNSKMHQRNTSWVHQRKNYFLINQSVTN
LGIFFFIIVSLITCFLLIVFLWRHVRQM-
HSDVSGFRDHSTKVHVKAMKFLISFMVFFILH
FVGLSIEVLCFILPQNKLLFITGLTAT-
CLYPCGHSIIVILGNKQLKQASLKALQQLKCCE
TKGNFRVK

SEQ ID NO:118

Mouse T2R07 Nucleotide Sequence

TTCATAATGAAGAGGAGGCAGGGCAAT-
GTTGGTTTCTGTTGTCTGACCAGTGTATTTGAC
AGTGATACTACACATTTGATTGCTAAAT-
GCAAATAGTTCCAAAGGAACAAGTAAATTTTA
TGAAATAGAAGCTTCTATTTGCTTAT-
TAACAAACTGCAAGCAAACATTAGTCTGCACACA
TTTTATAGACAAGCTAAATCTTCAAAAG-
CAATAAAAAAGAGCACCCATAAAGTTCTGACT
CTATCACATGACAATAGGCTTGAAAA-
GATTGTCTATGTAGATAAAGAAGATGGCATAACT
TCTCCATCAAGAAGCCAGTATATGGGA-
CATTCTCCAGCAGATAATTTACAATAGATGCAG
CAGAAGTAACCTTAGAGATCTGTAAA-
GATGCTGAATTCAGCAGAAGGCATCCTCCTTTGT
GTTGTCACTAGTGAGGCTGTGCTCG-
GAGTTTTAGGGGACACATATATTGCACTTTTTAAC
TGCATGGACTATGCTAAGAACAA-
GAAGCTCTCTAAGATCGGTTTCATTCT-
CATTGGCTTG GCGATTTCCAGAATTGGTGTTG-
TATGGATAATAATTTTACAAGGGTATATACAAGTATTT
TTTCCACACATGCTTACCTCTGGAAA-
CATAACTGAATATATTACTTACATATGGGTATTT
CTCAATCACTTAAGTGTCTGGTTTGT-
CACCAACCTCAACATCCTCTACTTTCTAAAGATA
GCTAATTTTTCCAACTCTG-
TATTTCTCTGGCTGAAAAGGAGAGT-
CAATGCAGTTTTTATC TTTCTGTCAGGATGCTTACT-
TACCTCATGGTTACTATGTTTTCCACAAATGACAAA
GATA CTTCAAAATAGTAAAATGCACCA-
GAGAAACACATCTTGGGTCCACCAGCG-
GAAAAATTAC TTTCTTATTAACCAAAGTGTGAC-
CAATCTGGGAATCTTTTTCTTCATTATTGTATCCCTG
ATTACCTGCTTTCTGTTGATTGTTTTC-
CTCTGGAGACATGTCAGACAAATGCACTCAGAT
GTTTCAGGATTCAGAGACCACAGCA-
CAAAAGTACATGTGAAAGCTATGAAATTTCTAATA
TCTTTTATGGTCTTCTTTATTCTG-
CATTTTGTAGGCCTTTCCATAGAAGTGCTATGCTTT
ATTCTGCCACAAAATAAACTGCTCTT-
TATAACTGGTTTGACAGCCACATGCCTCTATCCC
TGCGGTCACTCAATCATCGTAATTTTAG-
GAAATAAGCAGTTAAAGCAAGCCTCTTTGAAG
GCACTGCAGCAACTAAAATGCTGTGAGA-
CAAAAGGAAATTTCAGAGTCAAATAAATGGGT
TTGCAAATAAATAGCTGCCTTGTTCTTc-
CACTGGTTTTTACCCTGTTAGTTGATGTTATG
AAAAGTTCCTGCTATGGTTGATGA-
CATCTCAAGGAATCTATTTTTCTGGTGGCATGTTAA
GTCCACGTGAAGCCTCACTTCATACTGT-
GACTTGACTATGCAAATTCTTTCCACAAAATA
ACCAGATAACATTCAGCCTG-
GAGATAAATTCATTTAAAGGCTTTTATG-
GTGAGGATAAAC AAAAAAAAAAAATCATTTTTCT-
GTGATTCACTGTAACTCCCAGGATGAGTAAAAGAA
AAC AAGACAAATGGTTGTGATCAGCCTTTGT-
GTGTCTAGACAGAGCTAGGGACCAGATGTTGA
TGCTTGTGTGTGGTTTTGAGTTCTTTAA-
GAAGTTATTGCCTCTCTGCCATTCGGTATTCC
TCAGGTGAGAATTC

SEQ ID NO:119

Mouse T2R08 Amino Acid Sequence

MLWELYVFVFAASVFLNFVGIIANLFI-
IVIIIKTWVNSRRIASPDRILFSLAITRFLTLG LFLLNS-
VYIATNTGRSVYFSTFFLLCWK-
FLDANSLWLVTILNSLYCVKITNFQHPVFLLL
KRTISMKTTSLLLACLLISALTTL-
LYYMLSQISRFPEHIIGRNDTSFDLSDGILTLVASL
VLNSLLQFMLNVTFASLLIHSLRRHIQK-
MQRNRTSFWNPQTEAHMGAMRLMICFLVLYIP YSI-
ATLLYLPSYMRKNLRAQAICMIITAAYP-
PGHSVLLIITHHKLKAKAKKIFCFYK

SEQ ID NO:120

Mouse T2R08 Nucleotide Sequence

AAGCTTGTTTGTAATTAGGCATTCCTAA-
GAAAATAAGAACAGGAGTGAAGAAATAGTAAT
TTAATCCTTGAAAGATTTGCATCTCAG-
TAAAAGCAGCTGCCTCTTAGACCAGAAATGGTG
TTTGCCATGCTGGAAAATAAAAAG-
GAGACCTCTTTCCAGGCTGCATCCTGTGTCTGCTTA
CTTATTTCAGTTTGTTTTCATCGGCAC-
CAAACGAGGAAAGATGCTCTGGGAACTGTATGT
ATTTGTGTTTGCTGCCTCGGTTTTTT-
TAAATTTTGTAGGAATCATTGCAAATCTATTTAT TAT-
AGTGATAATTATTAAGACTTGGGTCAA-
CAGTCGCAGAATTGCCTCTCCGGATAGGAT
CCTGTTCAGCTTGGCCATCACTAGATTC-
CTGACTTTGGGGTTGTTTCTACTGAACAGTGT CTA-
CATTGCTACAAATACTGGAAGGTCAGTC-
TACTTTTCCACATTTTTTCTATTGTGTTG
GAAGTTTCTGGATGCAAACAGTCTCTG-
GTTAGTGACCATTCTGAACAGCTTGTATTGTGT
GAAGATTACTAATTTTCAACACCCAGT-
GTTTCTCCTGTTGAAACGGACTATCTCTATGAA
GACCACCAGCCTGCTGTTGGCCTGTCT-
TCTGATTTCAGCCCTCACCACTCTCCTATATTA TAT-
GCTCTCACAGATATCACGTTTTCCTGAA-
CACATAATTGGGAGAAATGACACGTCATT
TGACCTCAGTGATGGTATCTTGACGT-
TAGTAGCCTCTTTGGTCCTGAACTCACTTCTACA

GTTTATGCTCAATGTGACTTTTGCTTC-
CTTGTTAATACATTCCTTGAGAAGACATATACA
GAAGATGCAGAGAAACAGGAC-
CAGCTTTTGGAATCCCCAGACGGAGGCT-
CACATGGGTGC TATGAGGCTGATGATCTGTTTC-
CTCGTGCTCTACATTCCATATTCAATTGCTACCCTGC
T CTATCTTCCTTCCTATATGAGGAA-
GAATCTGAGAGCCCAGGCCATTTGCATGATTATTAC
TGCTGCTTACCCTCCAGGACATTCTGTC-
CTCCTCATTATCACACATCATAAACTGAAAGC
TAAAGCAAAGAAGATTTTCTGTTTCTA-
CAAGTAGCAGAATTTCATTAGTAGTTAACAGCA
TCAATTCATGGTTTGGTTGCATTA-
GAAATGTCTCAGTGATCTAAGGACTTAATTTTGTGA
TCTTGTATCTGGCATCCTGACCCT-
GAGACTAAGTGCTTATATTTGGTCAATACAGCATC
TTTTGGCTAATATTTTAAAGTAAATCA-
CATTCCATAAGAAATTGTTTAAGGGATTTACGT
ATTTTTCATGGCTATCACATTCCTAGA-
CAATGGAAATCACCATACTGTTTCGCTAGCTAC
TGAAGTACCAGGGGAAAGTCCATGAAT-
GAAGGCCACATTGTGATGTTCTTGGTTAGCACA
GATTAGAGAATTTGGCCTCAACTGAGCAAGATATC

SEQ ID NO:121

Mouse T2R09 Amino Acid Sequence

MEHLLKRTFDITENILLIILFIELI-
IGLIGNGFTALVHCMDWVKRKKMSLVNKILTALAT
SRIFLLWFMLVGFPISSLYPYLVTTR-
LMIQFTSTLWTIANHISVWFATCLSVFYFLKIAN
FSNSPFLYLKRRVEKVVSVTLLVSLVLL-
FLNILLLNLFINMCINEYHQINISYIFISYYH LSCQIQV-
LGSHIIFLSVPVVLSLSTFLLLIFSL-
WTLHKRMQQHVQGGRDARTTAHFKALQ
AVIAFLLLYSIFILSLLLQFWIHGL-
RKKPPFIAFCQVVDTAFPSFHSYVLILRDRKLRHA
SLSVLSWLKCRPNYVK

SEQ ID NO:122

Mouse T2R09 Nucleotide Sequence

GAATTCAGAAATCATCAAAAAATCT-
TCAAAACTACATGTTTAAAATAGCACTTCAAATGA
ATACATTTGCAAATCTTTACAACTAATA-
CATAAAATGGAGCATCTTTTGAAGAGAACATT
TGATATCACCGAGAACATACTTCTAAT-
TATTTTATTCATTGAATTAATAATTGGACTTAT
AGGAAACGGATTCACAGCCTTGGTG-
CACTGCATGGACTGGGTTAAGAGAAAAAAAATGTC
ATTAGTTAATAAAATCCTCACCGCTTTG-
GCAACTTCTAGAATTTTCCTGCTCTGGTTCAT
GCTAGTAGGTTTTCCAATTAGCTCACTG-
TACCCATATTTAGTTACTACTAGACTGATGAT
ACAGTTCACTAGTACTCTATGGACTAT-
AGCTAACCATATTAGTGTCTGGTTTGCTACATG CCT-
CAGTGTCTTTTATTTTCTCAAGATAGC-
CAATTTTTCTAATTCTCCTTTTCTCTATCT
AAAGAGGAGAGTTGAAAAAG-
TAGTTTCAGTTACATTACTGGT-
GTCTCTGGTCCTCTTGTT TTTAAATATTTTACTACT-
TAATTTGGAAATTAACATGTGTATAAATGAATATCAT
CAAAT AAACATATCATACATCTTCATTTCTTAT-
TACCATTTAAGTTGTCAAATTCAGGTGTTAGG
AAGTCACATTATTTTCCTGTCTGTC-
CCCGTTGTTTTGTCCCTGTCAACTTTTCTCCTGCT
CATCTTCTCCCTGTGGACACTTCACAA-
GAGGATGCAGCAGCATGTTCAGGGAGGCAGAGA
TGCCAGAACCACGGCCCACTTCAAAGC-
CTTGCAAGCAGTGATTGCCTTTCTCCTACTATA CTC-
CATTTTTATCCTGTCACTGTTACTA-
CAATTTTGGATCCATGGATTAAGGAAGAAACC
TCCTTTCATTGCATTTTGTCAGGTTGTA-
GATACAGCTTTTCCTTCATTCCATTCATATGT
CTTGATTCTGAGAGACAGGAAGCTGAGA-
CACGCCTCTCTCTCTGTGTTGTCGTGGCTGAA ATG-
CAGGCCAAATTATGT-
GAAATAATATTTCTTTGTATTTTCATTTTCAATTTTAA
AATA TTCTTAGAATTTGACTGCATG-
TATTTCATCTTTTATTTGAAACAACCAC-
TAATTAAAGCT ATTACTAATTTAGCAAGTCGTATA-
CAAGGTTATTTTTTAATACACATATCAAAAACTGAC
ATGTTTATGTTCTACAAAAACCT-
GAATATATCAAAATTATATAAATTTTGTATCAACGAT
TAACAATGGAGTTTTTTTATTTATGAC-
CTGTCACGGGACTCCGGTGGAGTCAGCTTGTCA
GATGAAAGTCTGAAAGCTT

Seq Id No:123

Mouse T2R10 Amino Acid Sequence

MFSQIISTSDIFTFTIILFVELVIG-
ILGNGFIALVNIMDWTKRRSISSADQILTALAITR FLY-
VWFMIICILLFMLCPHLL-
TRSEIVTSIGIIWIVNNHFSVWLATCLGVFYFLKIANFS
NSLFLYLKWRVKKVVLMIIQVSMIF-
LILNLLSLSMYDQFSIDVYEGNTSYNLGDSTPFPT
ISLFINSSKVFVITNSSHIFLPINSLFM-
LIPFTVSLVAFLMLIFSLWKHHKKMQVNAKPP
RDASTMAHIKALQTGFSFLLLYAVYLL-
FIVIGMLSLRLIGGKLILLFDHISGIGFPISHS
FVLILGNNKLRQASLSVLHCLRCRSKDMDTMGP

Seq Id No:124

Mouse T2R10 Nucleotide Sequence

GAATTCAACATCTTATTCAACTTCA-
GAAAACTGGATATTAGACACAGTGTCTGGATGAAG
CAGAGGTGATCTCTTTGGGAAAAAAAGC-
CAAGTAGTCATAAAGAATTTATGAAACAATTC
CTGGGATTGTTTATATTTGTTACAAA-
CAAATTTATATGTTTGTTAGTCAGTAATGTATAA
GTGGGATTTTAAAGCATGATTATCT-
TGAATTTTTAACAAAAAACATGTAGTGCTTTTTAA
ATGTAGCAGAAACATTAAAAATTGAAG-
CATGTTCTCACAGATAATAAGCACCAGTGATAT TTT-
TACTTTTACAATAATATTATTTGTG-
GAATTAGTAATAGGAATTTTAGGAAATGGATT
CATAGCACTAGTGAATATCATGGACTG-
GACCAAGAGAAGAAGCATTTCATCAGCGGATCA
GATTCTCACTGCTTTGGCCATTACCA-
GATTTCTCTATGTGTGGTTTATGATCATTTGTAT
ATTGTTATTCATGCTGTGCCCA-
CATTTGCTTACAAGATCAGAAATAGTAA-
CATCAATTGG TATTATTTGGATAGTGAATAAC-
CATTTCAGCGTTTGGCTTGCCACATGCCTCGGTGTC
TT TTATTTTCTGAAGATAGC-
CAATTTTTCTAACTCTTTGTTTCTTTAC-
CTAAAGTGGAGAGT TAAAAAAGTAGTTTTAAT-
GATAATACAGGTATCAATGATTTTCTTGATTTTAAAC
CTGTT ATCTCTAAGCATGTATGATCAGTTCT-
CAATTGATGTTTATGAAGGAAATACATCTTATAA
TTTAGGGGATTCAACCCCATTTCCCA-
CAATTTCCTTATTCATCAATTCATCAAAAGTTTT

CGTAATCACCAACTCATC-
CCATATTTTCTTACCCATCAACTCCCT-
GTTCATGCTCATACC CTTCACAGTGTCCCTGG-
TAGCCTTTCTCATGCTCATCTTCTCACTGTCCAAGCA
TCACAA AAAGATGCAGGTCAATGCCAAACCAC-
CTAGAGATGCCAGCACCATGGCCCACATTAAAGC
CTTGCAAACAGGGTTCTCCTTCCTGCT-
GCTGTATGCAGTATACTTACTTTTTATTGTCAT
AGGAATGTTGAGCCTTAGGTTGATAG-
GAGGAAAATTAATACTTTTATTTGACCACATTTC
TGGAATAGGTTTTCCTATAAGCCACT-
CATTTGTGCTGATTCTGGGAAATAACAAGCTGAG
ACAAGCCAGTCTTTCAGTGTTGCAT-
TGTCTGAGGTGCCGATCCAAAGATATGGACACCAT
GGGTCCATAAAAAATTTCAGAGGTCAT-
TGGGAAACATTTTGAGATCTTATAGGGGAAAAA
GGGTCCATAAAAAATTTCAGAGGTCAT-
TGGGAAACATTTTGAGATCTTATAGGGGAAAAA
GAAAATGTGGGGCTTCAAAGCTGGTAG-
GAGTAATATAGAGAAGGATAGGAG

Seq Id No:125

Mouse T2R11 Amino Acid Sequence

MEHPLRRTFDFSQSILLTILFIELIIG-
LIRNGLMVLVHCIDWVKRKKFHLLIKSSPLWQT SRI-
CLLWFMLIHLLITLLYADLASTRTMMQ-
FASNPWTISNHISIWLATCLGVFYFLKIAN
FSNSTFLYLKWRVQFLLLNILLVKFEIN-
MWINEYHQINIPYSFISYYQXCQIQVLSLHII FLSVP-
FILSLSTFLLLIFSLWTLHQRMQQH-
VQGYRDASTMAHFKALQAVIAFLLIHSIFI
LSLLLQLWKHELRKKPPFVVFCQVAY-
IAFPSSHSYVFILGDRKLRQACLSVLWRLKCRPN
YVG

Seq Id No:126

Mouse T2R11 Nucleotide Sequence

AATAATGTATGTGGAAGAGTTAAG-
TATAAATGTTGTATGAGAATGAACTCAGAAATCATC
AAAAATCTTTAAAACTGCATGT-
TAAAAATCACACTTCAAAT-
GAATATATTTGTAATTCTT TAGAAC-
TAATAAATAAAATGGAGCATCCTTTGAGGAGAACAT
TTGATTTCTCCCAGAGCA TACTTCTAACCATTTTAT-
TCATTGAATTAATAATTGGACTTATAA-
GAAATGGATTAATGG TATTGGTGCACTGCATAGAT-
TGGGTTAAGAGAAAAAAATTTCATTTGTTAATCAAA
TCCT CACCACTTTGGCAAACTTCCA-
GAATTTGTCTGCTCTGGTTCAT-
GCTAATACATCTCCTGA TTACTTTATTGTATGCA-
GATTTAGCTAGTACTAGAACGATGATGCAATTCGCT
AGCAATC CATGGACTATATCTAACCATATCAG-
CATCTGGCTTGCTACATGCCTTGGTGTCTTTTATT
TTCTCAAGATAGCCAATTTTTCTAACTC-
TACTTTTCTCTATCTAAAATGGCGAGTTCAGT
TCCTCTTGTTAAATATTTTACTGGT-
TAAATTTGAGATTAACATGTGGATAAATGAATATC
ATCAAATAAACATACCATACAGCT-
TCATTTCTTATTACCAAATTGTCAAATACAGGTGTT
AAGTCTTCACATTATTTTCCTGTCTGTC-
CCCTTTATTTTGTCCCTGTCAACTTTTCTCCT GCT-
CATCTTCTCCCTGTGGACACTTCACCA-
GAGGATGCAGCAGCATGTTCAAGGATACAG
AGATGCCAGCACAATGGCCCACT-
TCAAAGCCTTGCAAGCAGTGATTGC-

CTTTCTCTTAAT ACACTCCATTTTTATCCTGTCACT-
GTTACTACAACTTTGGAAACATGAATTAAGGAAGA
A ACCTCCTTTTGTTGTATTTTGTCAGGT-
TGCATATATAGCTTTTCCTTCATCCCATTCATA
TGTCTTCATTCTGGGAGACAGAAAGCT-
GAGACAGGCTTGTCTCTCTGTGTTGTGGAGGCT
GAAATGCAGGCCAAATTATGTGG-
GATAAAATCTCTTTGTGCTTTCATTTCCAATTCTTAA
ATATTCTTTGATTTTGACTGCATAAATT

Seq Id No:127

Mouse T2R12 Amino Acid Sequence

GAIVNVDFLIGNVGNGFIVVANIM-
DLVKRRKLSSVDQLLTALAVSRITLLWYLYIMKRTF
LVDPNIGAIMQSTRLTNVIWIISNHFSI-
WLATTLSIFYFLKIANFSNSIFCYLRWRFEKV
ILMALLVSLVLLFIDILVTNMYINIWTDEF

Seq Id No:128

Mouse T2R12 Nucleotide Sequence

TTTTCAGCAGTGACTTTGGGAAGCA-
GAACGTCCTCTTAGAGACAGTGGGTGCTGCTATCC
TAGTTAATGTGGAGCAATAGTTAATGTG-
GATTTCCTAATTGGAAATGTTGGGAATGGATT CAT-
TGTTGTGGCAAACATAATGGACTTGGT-
CAAGAGAAGAAAGCTTTCTTCAGTGGATCA
GCTGCTCACTGCACTGGCCGTCTCCA-
GAATCACTTTGCTGTGGTACCTGTACATAATGAA
ACGAACATTTTTAGTGGATCCAAACAT-
TGGTGCAATTATGCAATCAACAAGACTGACTAA
TGTTATCTGGATAATTTCTAACCATTT-
TAGTATATGGCTGGCCACCACCCTCAGCATCTT
TTATTTTCTCAAGATAG-
CAAATTTTTCTAACTCTATTTTCTGT-
TACCTGAGGTGGAGATT TGAAAAGGT-
GATTTTGATGGCATTGCTGGTGTCCCTGGTCCTCTT
GTTTATAGATATTTT AGTAACAAACATGTACAT-
TAATATTTGGACTGATGAATTC

Seq Id No:129

Mouse T2R13 Amino Acid Sequence

MVAVLQSTLPIIFSMEFIMGTLGNG-
FIFLIVCIDWVQRRKISLVDQIRTALAISRIALIW
LIFLDWWVSVHYPALHETGKMLSTYL-
ISWTVINHCNFWLTANLSILYFLKIANFSNIIFL YLK-
FRSKNVVLVTLLVSLFFLFLNTVI-
IKIFSDVCFDSVQRNVSQIFIMYNHEQICKFLS
FTNPMFTFIPFVMSTVMFSLLIFSL-
WRHLKNMQHTAKGCRDISTTVHIRALQTIIVSVVL
YTIFFLSFFVKVWS-
FVSPERYLIFLFVWALGNAVFSAH-
PFVMILVNRRLRLASLSLIFWL WYRFKNIEV

Seq Id No:130

Mouse T2R13 Nucleotide Sequence

AAGCTTGTTTGTGTTTGGATGAATTC-
TATTTATGTCTATCAATTTAAGATTTTCATATGA
ATCATTAAGAAATCTTGATAGT-
TGTTTGTGAGATATCACTTCTG-
CAATTTTTAAATGAAA TTACACTCATATTTTGAAG-
GAACAATATGTTTTAAAGGAATATATTAACAAATCTT
CAGC AGTTACCTCAGAAGTTTGGGTATTGTTT-

TACAGAAAATGGTGGCAGTTCTACAGAGCACA
CTTCCAATAATTTTCAGTATGGAAT-
TCATAATGGGAACCTTAGGAAATGGATTCATTTTT
CTGATAGTCTGCATAGACTGGGTCCAAA-
GAAGAAAAATCTCTTTAGTGGATCAAATCCGC ACT-
GCTCTGGCAATTAGCA-
GAATCGCTCTAATTTGGTTGATATTCCTAGATTGGTG
GGTG TCTGTTCATTACCCAGCATTACAT-
GAAACTGGTAAGATGTTATCAACATATTTGATTTCC
TGGACGGTGATCAATCATTG-
TAACTTTTGGCTTACTGCAAACTTGAG-
CATCCTTTATTTT CTCAAGATAGCCAACTTTTCTAA-
CATTATTTTTCTTTATCTAAAGTTTAGATCTAAAAAT
GTGGTATTAGTGACCCTGTTAGTGTCTC-
TATTTTTCTTGTTCTTAAATACTGTAATTATA
AAAATATTTTCTGATGTGTGTTTTGAT-
AGTGTTCAAAGAAATGTGTCTCAAATTTTCATA
ATGTATAACCATGAACAAATTTG-
TAAATTTCTTTCCTTTACTAACCCTATGTTCACATTC
ATACCTTTTGTTATGTCCACGGTAAT-
GTTTTCTTTGCTCATCTTCTCCCTGTGGAGACAT
CTGAAGAATATGCAGCACACCGCCAAAG-
GATGCAGAGACATCAGCACCACAGTGCACATC
AGAGCCCTGCAAACCATCATTGTGTCTG-
TAGTGCTATACACTATTTTTTTTTCTATCATTT TTTGT-
TAAAGTTTGGAGTTTTGTGTCACCA-
GAGAGATACCTGATCTTTTTGTTTGTCTGG
GCTCTGGGAAATGCTGTTTTTTTCTGCT-
CACCCATTTGTCATGATTTTGGTAAACAGAAGA
TTGAGATTGGCTTCTCTCTCTCT-
GATTTTTTGGCTCTGGTACAGGTT-
TAAAAATATAGAA GTATAGGGTCCAAAGACCAC-
CAAGGAATCATTTTCCTTATCCTAAAGAAAAATCAG
GAG

Seq Id No:131

Mouse T2R14 Amino Acid Sequence

MLSTMEGVLLSVSTSEAVLCTVGNTFI-
ALVNCMDYNRNKKLSNIGFILTGLAISRICLVL
ILITEAYIKIFYPQLLSPVNIIELISYL-
WIIICQLNVWFATSLSIFYFLKIANFSHYIFV
WLKRRIDLVFFFLIGCLLISWLFSFPV-
VAKMVKDNKMLYINTSWOIHMKKSELIINYVFT
NGGVFLFFMIMLIVCFLLIISLWRHR-
ROMESNKLGFRDLNTEVHVRTIKVLLSFIILFIL
HFMGITINVICLLIPESNLLFMFGLT-
TAFIYPGCHSLILILANSRLKQCSVMILQLLKCC
ENGKELRDT

Seq Id No:132

Mouse T2R14 Nucleotide Sequence

CTGCAGGTATATACCTACCCTGAAGGCT-
TCATCTAGAGTAAACAAAGTAGTCTGTATAGT
CTGCCATTCCTCAGATTCTCCTCAACT-
TCCCACCCTCCAGTGACCTTTCTCCTTTTCTAC
AGTCAAACTATGGACCTCACAACCTGA-
CACTTCTTCAGATGCAAAATATTCTCACAGAGA
CAAGTAAAACATACAAAACAAATACTT-
TAATTTGCCTATTAACAAATGGCAAGAAAAGAT
TCAGGCTTGAACATCCTGTAGA-
CAAGCTAAGGACAGGAGCAACTGAAGG-
GATCTCCATGA AGACCTTTCAGATTTCTAC-
CAAAAGTAATTTTTAACTATATTTAAGTCTTTAAAGA
AAGA AAGTAAAGCCACTCTTTTATTGAACAG-
CAATAGATTGGAATCTTAAACAACTGCAACAGA
AGCCATTTTAAAGATCAACAAAGATGCT-
GAGCACAATGGAAGGTGTCCTCCTTTCAGTTT
CAACTAGTGAGGCTGTGCTGGGCATTG-
TAGGGAACACATTCATTGCACTTGTAAACTGTA
TGGACTATAACAGGAACAA-
GAAGCTCTCTAATATTGGCTTTATTCT-
CACTGGCTTGGCAA TTTCCAGAATTTGCCTTGTGT-
TGATCTTAATCACAGAGGCATACATAAAAATATTCTA
TC CACAGTTGCTGTCTCCTGTCAACATAAT-
TGAGCTCATCAGTTATCTATGGATAATTATCT
GTCAATTGAATGTCTGGTTTGCCAC-
TAGTCTCAGTATTTTTTATTTCCTGAAGATAGCAA
ATTTTTCCCACTACATATTTGTCTGGT-
TAAAAAGAAGAATTGATTTAGTTTTTTTCTTCC
TGATAGGGTGCTTGCTTATCTCATGGC-
TATTTTCTTTCCCAGTTGTTGCGAAGATGGTTA
AAGATAATAAAATGCTGTATATAAACA-
CATCTTGGCAGATCCACATGAAGAAAAGTGAGT
TAATCATTAACTATGTTTTCAC-
CAATGGGGGGAGTATTTTTATTTTTTAT-
GATAATGTTAA TTGTATGTTTCCTGTTAAT-
CATTTCACTTTGGAGACATCGCAGGCAGATGGAATC
AAATA AATTAGGATTCAGAGATCTCAACACA-
GAAGTTCATGTGAGAACAATAAAAGTTTATTGT
CTTTTATTATCCTTTTTATATATTG-
CATTTCATGGGTATTACCATAAATGTAATTTGTCTGT
TAATCCCAGAAAGCAACTTGTTATTCAT-
GTTTGGTTTGACAACTGCATTCATCTATCCCG GCT-
GCCACTCACTTATCCTAATTCTAGCAAA-
CAGTCGGCTGAAGCAGTGCTCTGTAATGA
TACTGCAACTATTAAAGTGCTGT-
GAGAATGGTAAAGAACTCAGAGACACAT-
GACAGTCTG GAACACATGCAATCTGGAATTGT-
CAGTGGAAAAAGTTACTGAAGATCTTTTCACTTGC
AC TATGCTCTTTTATTGATTTGGCATCAT-
TATCAAACACTGTTGGAGCCTTGTGAACTCTTG
TTCAGAGTCTTCTGCCTCTCAAGGAATCACACTCC

Seq Id No:133

Mouse T2R15 Amino Acid Sequence

MCAVLRSILTIIFILEFFIGNLGNGFI-
ALVQCMDLRKRRTFPSADHFLTALAISRLALIW
VLFLDSFLFIQSPLLMTRNTLRLIQTAW-
NISNHFSIWFATSLSIFYLFKIAIFSNYLFFY
LKRRVKRVVLVILLLSMILLFFNI-
FLEIKHIDVWIYGTKRNITNGLSSNSFSEFSRLILI
PSLMFTLVPFGVSLIAFLLLIFSLMKH-
VRKMQYYTKGCKDVRTMAHTTALQTVVAFLLLY
TTFFLSLVVEVSTLEMDESLMLL-
FAKVTIMIFPSIHSCIFILKHNKLRQDLLSVLKWLQY
WCKREKTLDS

Seq Id No:134

Mouse T2R15 Nucleotide Sequence

AATAATAGATTTTTTAATATTCA-
GAATTTTTAAGTAATGTAGTATTGTTAG-
CAGCATAGC TTATAGGAAAAGTTCCAAG-
TAATTTTGATTTTGTAATTCTGATTCCCCCAAATCAA
GTAT CAAGTTTACCTGCACAGACAAGGGAA-
GAAGTGGCAAAATGTGCAAATGAGAGCAACTTTA
TTTGACTGTCAGTACGTTGAAATTCAGT-
GTTTCCTTAATCAGTTATGGATTGACATTTAT GTG-
CACAGAACCTGGAAGAATTTCAGC-
CAAGCTGGAGGTAAAAATCCAAAATTCTGATGA
TAAAACCAAAAGTAAATCACAGG-

TAAATCTTCTTTATTTTTCTTTTTTAATACTGTATAT
GGACATTTTTTAATACAG-
CATATTTTTTTTTTTGAAATTTA-
GAAAAAAACCACTAAGAAAT ATTCACCAATG-
GAATAGACTTTAAAGTCACTTAGAGAATGTGTGCTG
TTCTACGTAGCAT ACTGACAATCATTTTCATTTTG-
GAGTTCTTCATTGGAAATCTGGGGAATG-
GATTCATAGC TCTGGTACAATGCATGGACTTAC-
GAAAGAGAAGAACGTTCCCTTCAGCAGATCATTTC
CT CACTGCTCTGGCCATCTCCAGGCT-
TGCTCTGATATGGGTTTTATTTCTAGATTCATTTCT
GTTTATACAATCCCCATTACTGATGAC-
TAGAAATACATTAAGACTGATTCAGACTGCCTG
GAATATAAGCAATCATTTCAGTATATG-
GTTTGCTACCAGCCTCAGCATCTTTTATCTCTT CAA-
GATAGCCATTTTTTTCTAAC-
TATCTTTTCTTCTACCTGAAGCGGAGAGTTAAAAGG
GT GGTTTTGGTGATACTGCTGCTATCCAT-
GATCCTTTTGTTTTTTAATATATTTTTAGAAAT
CAAACATATTGATGTCTGGATCTATG-
GAACCAAAAGAAACATAACTAATGGTTTGAGTTC
AAACAGTTTTTCAGAGTTTTCCAGGCT-
TATTTTAATTCCAAGTTTAATGTTCACATTAGT
ACCCTTTGGTGTATCCTTGATAGCTTTC-
CTCCTCCTAATCTTTTCCCTTATGAAACATGT AAG-
GAAGATGCAGTACTACACCAAAGGATG-
CAAAGATGTCAGAACCATGGCCCACACCAC
AGCCCTGCAGACTGTGGTTGCCTTCCTC-
CTATTATATACTACTTTCTTTCTGTCTCTAGT TGTG-
GAAGTTTCAACACTTGAAATGGAT-
GAAAGTCTGATGCTTCTGTTTGCAAAAGTTAC
TATAATGATTTTTCCTTCCATCCACTC-
CTGTATTTTCATTTTGAAACATAATAAGTTGAG
ACAGGACTTGCTTTCAGTACTGAAGTG-
GCTACAGTATTGGTGCAAGCGTGAGAAAACCTT
GGATTCATAGACCATTGTATGCATCAC-
CTTGAATATTCTAGAGGGGTGTAGGTTCATATG
AAAGTATTGAATTTTTAAATTTGAGC-
CTTTTGTATATTTTCT

Seq Id No:135

Mouse T2R16 Amino Acid Sequence

MNGVLQVTFIVILSVEFIIGIFGNGFIA-
VVNIKDLVKGRKISSVDQILTALAISRIALLW LILVSW-
WIFVLYPGQWMTDRRVSIMHSIWTTFN-
QSSLWFATSLSIFYFFKIANFSNPIFL
YLKVRLKKVMIGTLIMSLILFCLNIIIM-
NAPENILITEYNVSMSYSLILNNTQLSMLFPF ANTMF-
GFIPFAVSLVTFVLLVFSLWKHQRKMQH-
SAHGCRDASTKAHIRALQTLIASLLLY
SIFFLSHVMKVWSALLLERTLLLLITQ-
VARTAFPSVHSWVLILGNAKMRKASLYVFLWLR
CRHKE

Seq Id No:136

Mouse T2R16 Nucleotide Sequence

TTTATGATGGAAAGAATAAAACCATTAG-
CAAGGCTTAATGGCTTGTTTGGTATTAGACCT GTA-
CATTGTTTATGGAACATGATATG-
GAGCTTTGTTTATTGAATATGCACAATATTTTAG
AAGCATGTTTCAAAGAATCTTAAGTAAT-
TACAATAGAAATTGAAGCATCCAAGTGAAGAT
GAATGGTGTCCTACAGGTTACATTTAT-
AGTCATTTTGAGTGTGGAATTTATAATTGGCAT
CTTTGGCAATGGATTCATAGCGGTGGT-
GAACATAAAGGACTTGGTCAAGGGAAGGAAGAT
CTCTTCAGTGGATCAGATCCTCACT-
GCTCTGGCCATCTCCAGAATTGCACTGCTGTGGTT
AATATTAGTAAGTTGGTGGATATTTGT-
GCTTTACCCAGGACAATGGATGACTGATAGAAG
AGTTAGCATAATGCACAGTATATGGA-
CAACATTCAACCAGAGTAGTCTCTGGTTTGCTAC
AAGTCTCAGCATCTTTTATTTTTTCAA-
GATAGCAAATTTTTCCAACCCTATTTTTCTTTA
TTTAAAGGTCAGACTTAAAAAAGTCAT-
GATAGGGACATTGATAATGTCTTTGATTCTCTT
TTGTTTAAATATTATCATTATGAATG-
CACCTGAGAACATTTTAATCACTGAATATAATGT
ATCTATGTCTTACAGCT-
TGATTTTGAATAACACACAGCTTTCTAT-
GCTGTTTCCATTTGC CAACACCATGTTTGGGT-
TCATACCTTTTGCTGTGTCACTGGTCACTTTTGTCCT
TCTTGT TTTCTCCCTGTGGAAACATCAGAGAAA-
GATGCAACACAGTGCCCATGGATGCAGAGATGC
CAGCACTAAGGCCCACATCAGAGCCTTG-
CAGACATTGATTGCCTCCCTCCTCCTGTATTC
CATTTTCTTCCTGTCTCATGTTATGAAG-
GTTTGGAGTGCTCTGCTTCTGGAGAGGACACT
CCTGCTTTTGATCACACAGGTTGCAA-
GAACAGCTTTTCCGTCAGTGCACTCCTGGGTCCT
GATTCTGGGCAATGCTAAGATGAGAAAG-
GCTTCTCTCTATGTATTCCTGTGGCTGAGGTG CAG-
GCACAAAGAATGAAACCCTACAGTGTA-
CAGACCTGGGGTATATTTATGTGGATGATC
TTACATATCTTAGAGGAAAATGGAT-
TAAAAGAAATTCTCATATTTATAAATTTTTAGGTC
TGAATTACATAAAAATG-
TATATAATATTTTCAAAGTACAAGATAG-
TAGTTTATAACTTAC ATGATAAATACTGTCTATG-
CATCTTCTAGTCTTTGTAGAATATGTAAAAACATGTT

Seq Id No:137

Mouse T2R17 Amino Acid Sequence

MKHFWKILSVISQSTLSVILIVELVIGI-
IGNGFMVLVHCMDWVKKKKMSLVNQILTALSI
SRIFQLCLLFISLVINFSYTDLTTSS-
RMIQVMYNAWILANHFSIWIATCLTVLYFLKIAN
FSNSFFLYLKWRVEKVVSVTLLVSLLL-
LILNILLTNLETDMWTNEYQRNISCSFSSHYYA
KCHRQVLRLHIIFLSVPVVLSLSTFLL-
LIFSLWTHHKRMQQHVQGGRDARTTAHFKALQT
VIAFFLLYSIFILSVLIQIWKYELLKKN-
LFVVFCEVVYIAFPTFHSYILIVGDMKLRQAC LPLCI-
IAAEIQTTLCRNFRSLKYFRLCCIF

Seq Id No:138

Mouse T2R17 Nucleotide Sequence

GAATTCTGGTCTGGCACCCCTGAGCTGT-
GTGAGTAGACACATTATCATGGAAAGAGATTC
AGAATCTGTCACTGTCAAAACTGCAT-
GTTTGCTCCTCTGTTAGTGTGTTGGGGAAAGTTA
AGAAAAATACATTTTATGAGAATCAACT-
CAGAGGTTGTCAGAAATTGTCGAAACAGCATT
TTAAAAATTTACATCTCAACTG-
GATATATGAGCAAGTCTTTATAACT-
GATATATAAAATG AGCACTTTTGGAAGATATTATCT-
GTTATCTCCCAGAGCACACTTTCAGTCATTTTAATC
GTGGAATTAGTAATTGGAATTATAG-
GAAATGGGTTCATGGTCCTGGTCCACTGTATGGAC
TGGGTTAAGAAAAAGAAAATGTC-

CCTAGTTAATCAAATTCTTACTGCTTTGTCAATCTCC AGAATTTTTCAGCTCTGTTTATTGTT-TATAAGTTTAGTAATCAACTTTTCATATACAGAT TTAACTACAAGTTCAAGGATGATA-CAAGTCATGTACAATGCTTGGATTTTAGCCAACCAT TTCAGCATCTGGATTGCTACATGCCT-CACTGTCCTTTATTTTCTAAAGATAGCCAATTTT TCTAACTCTTTTTTTCTT-TATCTAAAGTGGAGAGTTGAAAAAG-TAGTTTCAGTTACACTG TTGGTGTCATTGCTCCTC-CTGATTTTAAATATTTTACTAACTAACTTGGAAACCG ACATG TGGACAAATGAATATCAAAGAAACATAT-CATGCAGCTTCAGTTCTCATTACTATGCAAAG TGT-CACAGGCAGGTGTTAAGGCTTCACAT-TATTTTCCTGTCTGTCCCCGTTGTTTTGTCC CTGTCAACTTTTCTCCTGCTCATCT-TCTCCCTGTGGACACATCACAAGAGGATGCAGCAG CATGTTCAGGGAGGCAGAGATGCCA-GAACCACGGCCCACTTCAAAGCCCTACAAACTGTG ATTGCATTTTTCCTACTATATTC-CATTTTTATTCTGTCTGTCTTAATACAAATTTGGAAA TATGAATTACTGAA-GAAAAATCTTTTCGTTGTATTTTGTGAG-GTTGTATATATAGCTTTT CCGACATTCCAT-TCATATATTCTGATTGTAGGAGACATGAAGCTGAGA CAGGCCTGCCTG CCTCTCTGTATTATCGCAGCT-GAAATTCAGACTACACTATGTA-GAAATTTTAGATCACTA AAGTACTTTAGATTATGT-TGTATATTCTAGACAAAAATTAACTGATACAAATGTC TTTTG TATTTTTCATTTTAAATATCCTT-TAATTTTGACTGCATGAAATTGATTTCT-GCTTGCAAT TATCACTGATTAAAACTATTAATAATT-TAACTAG

Seq Id No:139

Mouse T2R18 Amino Acid Sequence

MVPTQVTIFSIIMYVLESLVIIVQSCT-TVAVLFREWMHFQRLSPVETILISLGISHFCLQ WTSM-LYNFGTYSRPVLLFWKVSVVWEFMNILT-FWLTSWLAVLYCVKVSSFTHPIFLWLRM KILKLVLWLILGALIASCLSIIPSVVKY-HIQMELVTLDNLPKNNSLILRLQQFEWYFSNP LKMIGFGIPFFVFLASIILLTVSLVQH-WVQMKHYSSSNSSLKAQFTVLKSLATFFTFFTS YFLTIVISFIGTVFDKKSWF-WVCEAVIYGLVCIHFTSLMMSN-PALKKALKLQFWSPEPS

Seq Id No:140

Mouse T2R18 Nucleotide Sequence

GCGTGCTTCACAGAGCAGTATACTA-CAAAGCAAATGTCATTGCTGCCATTGTATATTTCT CTAAAGACATTTCACATTTTATCTCCCT-GTCCCATTGTGTGCAGAGCCCACACTTCAATC AAT-CAATTCCTTAATTATAAGCTAT-TGTTTCATTATTTCATTTCCTACGTTTTTTTGCAT TTTTACTAAAACTCCAAAGCAGA-CATTTTCTAATTATAATCCTACATGTAGTTAGAATTT TAAAAATTATATACTATTTTCTTTGCAC-CACTGAGTTCAGTAGGTTTTGAAGGTTTATGC TTAACAATTGAACATTTCATGTTAGAT-TATTCCTGCCTTCCTAATCTTGAATAATTAAAT GTC-CATCCAGGCTTAGAATTCACAGAGTCAA-CAGCTTTCACCTTGATTCTCTCACTATCT ATCAATGACTAGAATCTGTCTGT-

CACTTTTGAAACCGCTAATTAAATAGT-TGGTGCTTAT TTAAAGGGTGCCCCATGCCAA-GAGAAAATGTATTTCTTCTCTAGATGCCTTCGTCCTT TA CAAGTTACATGCTTTACTGATGGTGAAT-TGGTTTTCTTCCAGTTCATCTGGGTTAAGTGA CCTAAGAACCTAGCCATGGAAGGAGAAA-CAGAAGCAAATATTAACGATACAAGAACAAGT TCCAGAACATTGGAAAGTACTTAG-TAAAGGCATTGGAATTAGCAAAAGAAT-AGTAGCGAA GCAAAAAATACTTCATCTCCATTGG-GAGGTCAAGAAAGACTATGCAGTGTTTTTGATGCA ACTTGTCATCTCTGAGTTAGACGAT-TCAGCACACACTTTTGAGATTGAACTTCAACAGGT GGAGCCAGCAGACCTGAGCTTTAGGAAT-GATGGTGGAATTTCCAAGCAAAGACTTCCGTT ACCTTTTTGATGTCCCCTAACAATTCG-GTTGCAATGCTCACACCCCCCAACTGTTGAAAT GCTTGGGAAAAGGGATTCTGAGACTG-GCATTAGTATGTCATTTGACAGAATGGAAACATT GCCCAGGGCATTAATGCACAGTAAAG-GATTCACCTTTTCTAAGTGCTCAAATTTTAAATT TGnATATTTTTAGAAGACATTATT-TAAAAGAAAGGTGGAGAGGATATCCAAA-CAGCACCT TGAGCAGATAAAGAGGTGAAGAA-GAAAAAACAACATGCGTACATGATGGATTTCTCTTT A TGAAAATGATCAAATGATCTTAGGAT-CAAGAATCCACACCTGAATGAGATTTGCTTGTAT CCCTGTGTGAATTTGACCTAACAAG-CAAAGCACAGACAAATGCTGTAGATAGGGAAATGT CTATGTCAAATGTGTGTAAGGAG-GATTTGCATCCACAAAGAAGTGCCCTCT-TATACTGAG AGTGCTAAGAACACATGTC-CGTTTCATATTCGGAAAGTGGTATAGAGCTGTTGAG TCTTT GGCTAGGAAGAGACTTCAGAGTGGAAG-CATGGTGCCAACGCAAGTCACCATCTTCTCCAT CATCATGTATGTGCTTGAGTCCTTAG-TAATAATTGTGCAAAGTTGCACAACGGTTGCAGT GCTATTCAGAGAGTGGATG-CACTTTCAAAGACTGTCACCGGTG-GAGACGATTCTCATCAG CCTGGGCATCTCA-CATTTCTGTCTACAGTGGACATCAATGCTATACAAC TTTGGTACTTA TTCTAGGCCTGTCCTTTTATTTTG-GAAGGTATCAGTCGTCTGGGAGTTCATGAACATTTT GACATTCTGGTTAACCAGTTGGCTTGCT-GTCCTCTACTGTGTCAAGGTCTCTTCCTTCAC TCACCCCATCTTCCTCTGGCTGAGGAT-GAAAATCTTGAAACTGGTTCTCTGGTTGATACT GGGTGCTCTGATAGCTTCTTGTTTGT-CAATCATCCCTTCTGTTGTTAAATATCACATCCA GATGGAATTAGTCACCCTAGATAATT-TACCCAAGAACAATTCTTTGATTCTAAGACTACA ACAGTTTGAATGGTATTTTTCTAATC-CTTTAAAAATGATTGGCTTTGGTATTCCTTTCTT CGTGTTCCTGGCTTCTATCATCTTACT-CACAGTCTCATTGGTCCAACACTGGGTGCAGAT GAAACACTACAGCAGCAGCAACTCCAGC-CTGAAAGCTCAGTTCACTGTTCTGAAGTCTCT TGC-TACCTTCTTCACCTTCTTCACATC-CTATTTTCTGACTATAGTCATCTCCTTTATTGG CACTGTGTTTGATAAGAAATCTTGGT-TCTGGGTCTGCGAAGCTGTCATCTATGGTTTAGT CTGTATTCACTTCACTTCACTGATGAT-GAGCAACCCTGCATTGAAAAAGGCACTGAAGCT GCAGTTCTGGAGCCCAGAGCCTTCCT-GAGGCAGGAAACACAGTTAAGCCTCTAGGGTAAG GAGACTTTGCATTGGCACAGTCCCTAT-AGTGTAATGCAAACTTGAACACAAACTTCATCC

CTTTTCACATCCACAAATGGCTGCATC-
TATACATCATCACCAGTCTTCCCTGTATTCTGA
CCCATTCTCTTCCTGTCCTATCCAT-
AGTCCCCAGGTTGGTTTTGATTTTTCTCATGATCA
CACCAACTCTGCTTAGCTTTTGCCAC-
CACTGTAATAGTAAACATGGGGTGTTCTATATAT
TACAGTCAAAATCATTCTCACATTGT-
TGATTGCCTCACAAATTCATATAAATCCCCCTTC
CTGTCAGGAATTTATTGTCTGCTCACT-
TAATGCTCACCATATATTAAAGCCATTAATTCC
CCCTTCCTACCTTGAGTTTAAGAAG-
GAAAATGTCTTACCATTGCCCACAACCTATTCTGC
TGCTTCTAGACTTTTATGCAAGTGATT-
TATACACACACACACACACACACACACACATAC
AAACAAC

Seq Id No:141

Mouse T2R19 Amino Acid Sequence

MMEGHMLFFLLVVVVQFLTGVLANGLIV-
VVNAIDLIMWKKMAPLDLLLFCLATSRIILQL CIL-
FAQLGLSCLVRHTLFADNVTFVYI-
INELSLWFATWLGVFYCAKIATIPHPLFLWLKM
RISRLVPWLILASVVYVTVTTFIHSRET-
SELPKQIFISFFSKNTTRVRPAHATLLSVFVF GLTLP-
FLIFTVAVLLLLSSLWNHSRQMRTM-
VGTREPSRHALVSAMLSILSFLILYLSHDM
VAVLICTQGLHFGSRTFAFCLLVIG-
MYPSLHSIVLILGNPKLKRNAKTFIVHCKCCHCAR
AWVTSRNPRLSDLPVPATHHSANKTSCSEACIMPS

Seq Id No:142

Mouse T2R19 Nucleotide Sequence

CTGCAGCCTAGAGAACTAATGCATAG-
GAAACTTATATTCCCACCTCCGTGACGTCACTCT
GACAGAAGTGAACTTATATTCCCACCTC-
CGTGACGTCACTCTGACAGAAGTGACTTGTTT
TTGTATGATGCTCCAGGATGCCTCATT-
AGCATTGAGGACAATCATAATTAAGTAAGGCAA
GGCATGAAGGTGGTCCTCACTAGGTAC-
CTGGAGGCTTCTGGTTGCATGATTTACTTGTGA
TGACTCTGACACTTAAGAAGACCT-
GAAAAATGCAAAAGCTGTCATAAGGCA-
CAGTTCGTT TCTATGGTATCTCTTCCTTATTTGACT-
GACATTGAGTTGAGAAGGCAGCACTATAAACAA
ATGGGCCCCACCTTCCTCTTCCAT-
TGTCTTTGGGTTGGCATCATCTCCAAAGGAACCTTG
GTCTAGTTGAAAGAAGCCAGAAATCATA-
CATGGCTGAGACTGTGCATAACTCTATGTATC ATT-
TAAAGAAGTCATTGGTTCTTCTTATTT-
TAAAATGATGGAAGGTCATATGCTCTTCTT
CCTTCTGGTCGTGGTAGTGCAGTTTT-
TAACTGGGGTCTTGGCAAATGGCCTCATTGTGGT
TGTCAATGCCATCGACTTGATCATGTG-
GAAGAAAATGGCCCCACTGGATCTGCTTCTTTT
TTGCCTGGCGACTTCTCGGATCATTCT-
TCAATTGTGTATATTGTTTGCACAGCTGGGTCT ATC-
CTGTTTGGTGAGACACACGTTATTTGCT-
GACAATGTTACCTTTGTCTACATTATAAA
CGAACTGAGTCTCTGGTTTGCCACATG-
GCTTGGTGTTTTCTACTGTGCCAAGATTGCTAC
CATCCCTCACCCACTCTTTCTGTGGAT-
GAAGATGAGGATATCCAGGTTGGTGCCATGGCT
GATCCTGGCATCTGTGGTCTATGTAACT-
GTTACTACTTTCATCCATAGCAGAGAGACTTC
AGAACTTCCTAAGCAAATCTT-
TATAAGCTTTTTTTCTAAAAATA-
CAACTCGGGTCAGACC AGCGCATGCCACAC-
TACTCTCAGTCTTTGTCTTTGGGCTCACACTACCAT
TTCTCATCTT CACTGTTGCTGTTCTGCTCTTGT-
TGTCCTCCCTGTGGAACCACAGCCGGCA-
GATGAGGAC TATGGTGGGAACTAGGGAACCTAG-
CAGACATGCCCTCGTCAGTGCGATGCTCTCCATTCT
GTCATTCCTCATCCTCTATCTCTCCCAT-
GACATGGTAGCTGTTCTGATCTGTACCCAAGG
CCTCCACTTTGGAAGCAGAACCTTTG-
CATTCTGCTTATTGGTTATTGGTATGTACCCCTC
CTTACACTCGATTGTCTTAATTTTAG-
GAAACCCTAAGCTGAAACGAAATGCAAAAACGTT
CATTGTCCATTGTAAGTGTTGTCATTGT-
GCAAGAGCTTGGGTCACCTCAAGGAACCCAAG
ACTCAGCGACTTGCCAGTGCCTGCTACT-
CATCACTCAGCCAACAAGACATCCTGCTCAGA
AGCCTGTATAATGCCATCTTAATTGTC-
CAACCTGAGGCTTAATCATTTCAAAGGGTAAAT
TGATGATCAAAGCCCAACACATGATAT-
GACATCAAGGTCCATATCCCAGTAGTCATGTGG
AAATACCACCTTGCAAAATGATGTCAT-
TGAGAAACCAGGGCAAATGGAGTCTAGGTCTTT
CAGTATGATTTGCTGCAG

Seq Id No:143

Mouse T2R20 Amino Acid Sequence

MNLVEWIVTIIMMTEFLLGNCAN-
VFITIVNFIDCVKRRKISSADRIITAIAIFRIGLLWA
MLTNWHSHVFTPDTDNLQMRVFGGIT-
WAITNHFTTWLGTILSMFYLFKIANFSNSLFLHL
KRKLDNVLLVIFLGSSLFLVATLGMVNI-
KKIAWMSIHEGNVTTKSKLKHVTSITNMLLFS LINI-
VPFGISLNCVLLLIYSLSKHLKNMK-
FYGKGCQDQSTMVHIKALQTVVSFLLLYATY
SSCVIISGWSLQNAPVFLFCVTIGS-
FYPAGHSCILIWGNQKLKQVFLLLLRQMRC

Seq Id No:144

Mouse T2R20 Nucleotide Sequence

CTAGATGGGCTGTTTCATATAATGACTG-
GAACTCCCTACATGCTCCACGTCTTGAGTTCT
AAAATTTCACTAACAAATTTTTGACTGC-
CATAAATAATGAAGGTTTAAAGAAAGAACAAC
ATTTGAAGCAATGGACCAGAATTC-
CTCTTTATTTGACTCTTAGCAAATTGGAATGCAGCA
TCCTTTCAAGAGCAGCACTGAAATATAC-
CAGTCAATGGCAGAGAGTAAAAAAGTATGCAA
TTGGAGACATTATGGTAATATAAATTTC-
CATTAAAAATGAGACTGCATTCACCTATTACA ACA-
CATTGCTATTCTGCTCAACACAGAGT-
TAAAAAGAAACAAGAACTCTTGTATACATTC
AGTTAGTCACAAGTATAATTATGTTCA-
CATATTTTAAAAAAATGAATCATGATCTGTGAA
TTGAGCCTG-
GCTTTTTTTGTCTCTCTCTTTTTAT-
TCTTTTCCTTTAGACAGACACAATGA ATTTGGTA-
GAATGGATTGTTACCATCATAATGATGACAGAATTTC
TCTTAGGAAACTGTG CCAATGTCTTCATAACCAT-
AGTGAACTTCATCGACTGTGTGAA-
GAGAAGAAAGATCTCCT CAGCTGATCGAAT-
TATAACTGCTATTGCCATCTTCAGAATTGGTTTGTTG
TGGGCAATGT TAACGAACTGGCATTCACATGTGTT-
TACTCCAGACACAGACAATTTACAAATGAGAGTTT
TCGGTGGAATTACCTGGGCTATAAC-

CAACCATTTTACCACTTGGCTGGGGACCATACTGA GCATGTTTTATTTATTCAAGATAGC-CAATTTTTCCAACAGTCTATTTCTTCATCTAAAAA GAAAACTTGACAATGTTCTACTTGT-GATTTTCCTGGGATCGTCTCTGTTTTTGGTTGCAT ATCTTGGGATGGTGAACATCAAGAAGAT-TGCTTGGATGAGTATTCATGAAGGAAATGTGA CCA-CAAAGAGCAAACTGAAGCATGTAACAAG-CATCACAAATATGCTTCTCTTCAGCCTGA TAAACATTGTACCATTTGGTATATCACT-GAACTGTGTTCTGCTCTTAATCTATTCCCTGA GTAAACATCTCAAGAATATGAAATTC-TATGGCAAAGGATGTCAAGATCAGAGCACCATGG TCCACATAAAGGCCTTGCAAACTGTG-GTCTCTTTTCTCTTGTTATATGCCACATACTCTT CCT-GTGTCATTATATCAGGTTGGAGTTTG-CAAAATGCACCAGTCTTCCTGTTTTGTGTGA CAATTGGATCCTTCTACCCAGCAGGT-CATTCTTGTATCTTGATTTGGGGAAACCAGAAAC TTAAACAGGTCTTTCTGTTGTTGCTGAG-GCAGATGAGATGCTGACTGAAAAAATGAAAGT CCCCCTGTCTCTAG

Seq Id No:145

Mouse T2R21 Amino Acid Sequence

MGSNVYGILTMVMIAEFVFGNMSNGFIV-LINCIDWVRKGTLSSIGWILLFLAISRMVLIW EMLIT-WIKYMKYSFSFVTGTELRGIMFTWVISN-HFSLWLATILSIFYLLKIASFSKPVFL YLKWREKKVLLIVLLGNLIFLMLNIL-QINKHIEHWMYQYERNITWSSRVSDFAGFSNLVL LEMIVFSVTPFTVALVSFILLIFSL-WKHLQKMHLNSRGERDPSTKAHVNALRIMVSFLLL YATYFISFFLSLIPMAHKTRLGLMF-SITVGLFYPSSHSFILILGHSNLRQASLWVMTYLK CGQKH

Seq Id No:146

Mouse T2R21 Nucleotide Sequence

CTCTTTTGAAGACAATAGTTGTTCTAC-TAGCTATTGATAGCATGTTTACATTTGTCATTT TCAAGTATGTTCAGAAACAAAGCTA-CATATTGTGGGGAGTATATAAAATATGAAAGCTAG CCATTCCCAGGCATCCAAGGATCCCTGT-GTATTAAAAGGCAACAAAGCAGAACCAAATGT TCTGTTTTGGACATGAGCTTCTTCCAAT-TCAACTGCTGAAAAAATTTGGATAACTACATAT AAAACTAAGAACACAGAGTGTCACAGAG-CAGTCTCTGCTCTCCAATTCACCAGGATTAAT ATTGACAGACCCAAAAGATGTCATTTAG-GTAAATTTTGGATGAATCATATTGTTGTCACC TTTGTGCTCTAGAACATAAGCTGATA-GAATCAAATTTTCTTTAGCAGAGACAATGCAAAT TGATATAACAGTGAAA-GAGAATATATCTTTATTTGCATGTTAG-CAAATGACAGCTGGATG CACTTCATGATTTTCTG-CAATCTAGTTCAGTCTTTAGAAGGATATATATATATAT ATATA TATATATATATATATATATATATATATATATATATAAACCTTA GTCTTGAAAGATATCAGAA AGAAGGATTTCACAA-GAATGTACAGAGCCATTAGCAAAATTT-TAATATACTCATCGACAT TAGGTCAGTCACTACAT-AAGAAGGACTTGAATGAAAGCTTATCTTAGTTTTTG AGACTAC AGGGACATTTCACCTTGCCAAAT-GAGAAGCAGTGAGTCTTCTTTGTCTGGA-CATGGGAAG CAATGTGTATGGTATCTTAACTATG-GTTATGATTGCAGAGTTTGTATTTGGAAATATGAG CAATGGATTCATAGTGCTGATAAACTG-CATTGATTGGGTCAGGAAAGGAACTCTTTCTTC CATTGGTTGGATCCTGCTTTTCTTGGC-CATTTCAAGAATGGTGTTGATATGGGAAATGTT AATAACATGGATAAAATATATGAAGTAT-TCATTTTCATTTGTGACTGGAACAGAATTACG GGG-TATCATGTTTACCTGGGTAATTTCCAAT-CACTTCAGTCTCTGGCTTGCCACTATTCT CAGCATCTTTTATTTGCTCAAAATAGC-CAGTTTCTCCAAACCGGTTTTTCTCTATTTGAA GTGGAGAGAGAAGAAAGTGCTTCTGAT-TGTCCTTCTGGGAAATTTGATCTTCTTGATGCT CAACATATTACAAATAAACAAACATATA-GAACACTGGATGTATCAATATGAGAGAAATAT AACTTGGAGTTCTAGAGTGAGT-GACTTTGCAGGGTTTTCAAATCTGGTCT-TATTGGAGAT GATTGTGTTCTCTGTAACACCAT-TCACAGTGGCCCTGGTCTCCTTCATCCTGTTAATCTT CTCCTTGTGGAAACATCTACAGAAAATG-CATCTCAATTCTAGAGGGGAACGAGACCCCAG CACTAAAGCCCATGTGAATGCCT-TGAGAATTATGGTCTCCTTCCTCTTACTCTATGCCAC TTACTTCATATCTTTTTTTCTATCAT-TGATTCCCATGGCACATAAAACACGACTGGGTCT TATGTTTAGCATAACTGTTGGGCTTTTC-TACCCTTCAAGCCACTCATTTATCTTAATTTT GGGA-CATTCTAATTTAAGGCAAGC-CAGTCTTTGGGTGATGACATATCTTAAATGTGGGCA AAAGCATTAGAATTTCACTATTCCAT-AAGGCAGCCAAACCACGTGCTACTAGGTATATGA TACTACTCAGTGGTAAAGCCCTAG-GCAAACATTAACCTTAGAAAATATATAATTTTGTGA CTCTTCTGTATTTGATAAATCACTCA-CATATTTAGAAGAATGCTACAGTAGTGTGATCTT GTACATGATTGTAACAATTCAATTTTAT-TAATATAGTTCAGGCATGATAACATACCCCTG ATAACTGAAAAGTAAGTAGGATGCTA-CATATATATTTAGATCTAGACTTAGGGGCAAAGA GAGACCCAGCTGATAGCTGTGCAATAAA-GATTTTAATTTTCATCCTGTTGTGAGTTATCT GAAATCTATGTCACTGAAGGCATAAG-CAAGATTTTCACACACTGAAACAATCTCTTATGC TTTCTTATATTGTTTTAAAAGTAAATTA-GAAAATTTAAATAAACTTAATGGCAATTGAAA TTA-CAAAAGCTAAACACATGTGGTTATTA-GAAATTAGACTGTATGTAGGTCCTAGGGGAT GGCTTAGTAAAGTGCTTTGTTGCAAGCT-TCAGGATATGATTCTAAATCCCTAGATTCAAT TAAAAACCTGGCATAAATAGCCAATG-TAAAATTTGTCTGTAAAATGTAACCAGTGCTAAG AGTACCAAGACAACAAAATGTTTACTTT-TAAAACCATTTATTGATATTCTTTTAAAAATA GGTATGTATTTTACTATTTAAATAA-GATTTTGTCAAAAGCTAGTCTTGACACCTTAGGTA AACATAGGAAGGCAACAAGTTTGAAGT-CAGCTACTGGGGACAGTGCTGCTAGCAGCTGAC AGAGGCCACTGCTGACTACAGCAGAT-CATTTACAGGTTCAGCACTAG

Seq Id No:147

Mouse T2R22 Amino Acid Sequence

MSSLLEIFFVIISVVEFIIGTLGNGFIV-LINSTSWFKNQKISVIDFILTWLAISRMCVLW TTIA-GASLRKFYKTLSYSKNFKFCFDIIWTGS-

NYLCIACTTCISVFYLFKIANFSNSIFF WIKQRIHAVLLAIVLGTLMYFIL-FLIFMKMIANNFIYKWTKLEQNTTFPVLDTLSGFLVY HSLYNGILIFFFIVSLTSFLLLIFSLW-SHLRRMKLQGIHTKDISTEAHIKAMKTMMSFLL FFI-IYYISNIMLIVASSILDNVVAQIFSYN-LIFLYLSVHPFLLVLWNSKLKWTFQHVLRK LVCHCGGYS

Seq Id No:148

Mouse T2R22 Nucleotide Sequence

AAATGAATAATTTCATGCAAAGGATAC-CATTAGAATATGATCACTATTTAAATTTTAGCA AATACATATTCAAATACCAGCACAAT-GTTTCAAATTTAAAATATAAACATTATAAAACCC AGCAGAGAACAAAATGATAGCCT-TGATAATTGTTGGTTTGCTCAA-GAAAAATGGGTGTAT ACTTTAACATTTAATTGG-GAACTCAGTTGAGAGCATACATTTAGGGTTTTACAG AGGTAT TCATTGCCCATTTAAGATTTGGATTCA-CACATCTACATCAATGTGGCTGTAATCCATTTT CCCATGATGAAATAAGGTAGAGACTGC-CTATTAAACGACATGTCGAGCCTACTGGAGATT TTCTTTGTGATCATTTCGGTTGTAGAAT-TCATAATAGGAACTTTGGGAAATGGATTTATT GTC-CTGATAAACAGTACTTCTTGGTTCAA-GAATCAGAAAATCTCTGTAATTGATTTCATT CTTACTTGGTTGGCCATCTCCAGAATGT-GTGTTCTATGGACAACAATTGCTGGTGCCTCT CTCAGGAAATTCTACAAGACGTTAAGT-TACTCTAAGAATTTCAAATTTTGTTTTGACATT ATCTGGACAGGATCCAACTATTTATG-CATAGCCTGTACAACGTGCATCAGTGTCTTCTAC TTGTTCAAGATTGCCAACTTTTCTAAT-TCCATTTTCTTCTGGATTAAACAGAGAATTCAT GCAGTACTTCTGGCTATTGTCCTAGGCA-CACTCATGTATTTCATTTTATTTCTCATTTTT ATGAAAATGATAGCTAATAATTTTATC-TACAAATGGACAAAATTGGAACAAAACACAACA TTCCCTGTTTTAGATACTCTAAGTG-GTTTCTTAGTCTACCATAGCCTCTACAATGGGATT CTCATTTTCTTTTTTATAGTGTCTCT-GACCTCATTTCTTCTTTTAATCTTCTCTTTATGG AGCCACCTTAGGAGGATGAAACTA-CAGGGCATACATACCAAAGACATAAGCA-CAGAAGCA CACATAAAAGCTATGAAAACTATGAT-GTCATTCCTTTTGTTCTTCATCATATATTATATT AGCAACATTATGCTTATTGTG-GCAAGCTCCATTCTTGACAATGTGGTTG-CACAAATTTTC TCTTATAACCTAATATTTCTGTATT-TATCTFTTCATCCTTTTCTTCTGGTTTTATGGAAC AGCAAATTGAAATGGACATTCCAGCATG-TATTGAGAAAGCTGGTGTGTCATTGTGGAGGT TAT-TCTTGATTTCAGTAAATACACT-CAATATAACTGATGGATTTCTAAGGTAAGAAAAAT GGAACAAGGAATAAAGAG-GAGAAATATATTCCTTTTCAGATCATCT-GCTCTGTCATTCTG TCCTTAGCATGCTATTAAGAAT-TGTTGACTAAATCCAGTCATTTTTAACATGAGGAAA GG ATGTTTCAATCCAACTTAGAGAGGGTA-CAAAATAGTCCTAGGAGGCAG

Seq Id No:149

Mouse T2R23 Nucleotide Sequence

MFSQKINYSHLFTFSITLYVEIVT-GILGHGFIALVNIMDWVKRRRISSVDQILTALALTR FIYVLSMLICILLFMLCPHLPRRSEML-SAMGIFWVVNSHFSIWLTTCLGVFYFLKIANFS NSFF-LYLKWRVKKVILIIILASLIFLTL-HILSLGIYDQFSIAAYVGNMSYSLTDLTQFSS TFLFSNSSNVFLITNSSHVFLPINSLFM-LIPFTVSLVAFLMLIFSLWKHHKKMQVNAKQP RDVSTMAHIKALQTVFSFLLLYAIYLL-FLIIGILNLGLMEKIVILIFDHISGAVFPISHS FVLILGN-SKLRQASLSVLPCLRCQSKDMDTMGL

Seq Id No:150

T2R23 Nucleotide Sequence

AATTTTCAGCAACCAATATGTAGACT-GCTTAAATGCATCAGAAACATTATAAATTGAAGC ATGTTTTCACAGAAAATAAACTACAGC-CATTTGTTTACTTTTTCAATCACCTTGTATGTG GAAATAGTAACGGGAATCTTAGGACATG-GATTCATAGCATTAGTGAACATCATGGACTGG GTCAAAAGAAGAAGGATCTCTTCAGTG-GATCAGATTCTCACTGCTTTGGCCCTTACCAGA TTCATTTATGTCTTGTCTATGCT-GATTTGCATATTGTTATTCATGCTGTGCCCACATTTG CCTAGGAGATCAGAAATGCTTTCAG-CAATGGGTATTTTCTGGGTAGTCAACAGCCATTTT AGCATCTGGCTTACTACATGCCTCGGT-GTCTTTTATTTTCTCAAGATAGCCAATTTTTCT AACTCTTTTTTTCTTTATCTAAAGTG-GAGAGTTAAAAAAGTGATTTTAATAATAATCCTG GCATCACTGATTTTCTTGACTTTACA-CATTTTATCTTTAGGGATATATGATCAGTTCTCA ATTGCTGCTTATGTAGGAAATATGTCT-TATAGTTTGACAGATTTAACACAATTTTCCAGT ACTTTCTTATTCTCCAACTCATCCAAT-GTTTTCTTAATCACCAACTCATCCCATGTTTTC TTACCCATCAACTCCCTGTTCATGCT-CATACCCTTCACAGTGTCCCTGGTAGCCTTTCTC ATGCTCATCTTCTCACTGTGGAAGCAT-CACAAAAAGATGCAGGTCAATGCCAAACAACCT AGAGATGTCAGTACTATGGCCCACAT-TAAAGCCTTGCAAACTGTGTTCTCCTTCCTGCTG CTGTATGCCATATACTTACTTTTCCT-TATCATAGGAATTTTGAACCTTGGATTGATGGAG AAAATAGTGATACTGATATTTGACCA-CATTTCTGGAGCAGTTTTTCCTATAAGCCACTCA TTTGTACTGATTCTGGGAAACAG-TAAGCTGAGACAAGCCAGTCTTTCTGT-GTTGCCTTGT CTAAGGTGCCAGTCCAAAGATATG-GACACCATGGGTCTCTAGTAAATTCCAGAGTACATT TTGTAAAAATCTTGAGGATGATCAGT-TCATAGAAAAAAGTTACCTTATGGGGGAAAATAA AAAGTGGGGCTTCAATCCTGGGAG-TAATAATAVAVAGGAGGGTAGGACAG-CATGAAGGAG ACTAGCACTATATAAGTGGTCT-CATACAGGATATGGGAAAGGAAAGATTTATGCAATA AA GAGGGAGATCATATTGGAGGATGAGGAG-GCATTACATATGTAAAATGACTATAAGAATGG AAT-CATGCTAATCTAAAAAAATCTGTAATG-CATTTCATTCAGACTATATACATATATGCC TATATATGGATATATGGGGATATATAT-TCTATACATATTTTAAAAGAACCTTTCTTATAT

Seq Id No:151

Mouse T2R24 Amino Acid Sequence

MVPVLHSLSTIILIAEFVWGNLSNGLIV-LKNCIDWINKKELSTVDQILIVLAISRISLIW ETLII-

WVKDQLISSITIEELKIIVFSFILSSHF-
SLWLATALSIFYLFRIPNCYWQIFLYL
KWRIKQLIVHMLLGSLVFLVANMIQI-
TITLEERFYQYGGNTSVNSMETEFSILIELMLFN
MTMFSIIPFSLALISFLLLIFSL-
WKHLQKMPLNSRGDRDPSATAHRNAL-
RILVSFLLLYT IYFLSLLISWVAQKNQSELVHIIC-
MITSLVYPSFHSYILILGNYKLKQTSLWVMRQLGCR
MKRQNTPTT

Seq Id No:152

Mouse T2R24 Nucleotide Sequence

CAAAGAGGAGAAATATTTAGCTACA-
CAGTGTACCACATACAAGCCGTTCAATCAGTATAA
GGGGAGCAGTCATATA-
GAATTTGGGCTTTCTTTCTTTTAATATG-
GTACCTGTTCTGCACA GTCTCTCCACCATCATAC-
TAATTGCAGAGTTTGTTTGGGGAAATTTGAGCAATG
GTTTGA TAGTGTTGAAGAACTGCATTGACTGGAT-
CAATAAAAAAGAGCTCTCCACAGTTGATCAAA
TACTCATTGTCTTGGCAATTTCAA-
GAATTAGTCTCATCTGGGAAACACTAATTATATGGG
TTAAAGATCAACTAATTTCATCTATTAC-
TATTGAAGAATTAAAAATAATTGTGTTCAGCT
TTATACTATCTAGCCACTTCAGTCTCTG-
GCTTGCTACAGCTCTCAGCATCTTCTATTTAT TCA-
GAATACCTAATTGCTACTGGCA-
GATCTTTCTCTACTTGAAATGGAGAATAAAGCAAC
TGATTGTCCACATGCTTCTGGGAAGCT-
TGGTGTTCTTGGTTGCAAATATGATACAGATAA
CCATCACTCTTGAAGAGAGGTTCTAT-
CAATATGGAGGAAATACAAGTGTAAATTCCATGG
AGACTGAGTTCTCAATTTTGATAGAGCT-
GATGTTATTTAACATGACTATGTTCTCCATTA TAC-
CATTTTCATTGGCCTTAATTTCTTTTCT-
TCTGCTAATCTTCTCTTTATGGAAACATC
TCCAGAAGATGCCACTCAATTCTAGAG-
GAGATAGAGACCCTAGTGCTACGGCCCACAGAA
ATGCCTTGAGAATTTTGGTCTCCTTC-
CTCTTGCTCTATACTATATATTTCCTGTCTCTTC
TTATATCATGGGTTGCTCAGAAGAAT-
CAAAGTGAACTGGTTCACATTATTTGTATGATAA
CTTCACTCGTGTATCCTTCATTCCACT-
CATATATCCTGATTCTGGGAAATTATAAATTAA
AGCAGACCTCTCTTTGGGTAATGAG-
GCAGCTGGGATGTAGGATGAAAAGACAGAATACAC
CAACTACATAAGGCAGCCAAACAGTC-
TATTGGGTTTTAGATAACAAATCTAAATCTATGA
GGAAGTAGTTCAATAACATTTTTCCCCT-
TGACATGGAGTAGCAGGGTTTTTTTTTATTAG
ATATTTTCTTTACTTACATTTCAAATGC-
TATCCCGAAAATTCCCTGTACCCTCTCCCTGT CCT-
GTTCCCCTACCCACCCACTCCCACTTCT-
TGGCCCTGGCATTCCCCTGGAGTATCAGT
TTTTTATTAGTCAAACTATCTCACTGAC-
TAAGGGTCATAAAACAAGTTATTTTAACACTA
ATTTCAATTAAATCAAAGGTAAAGTGT-
CAGCACATGCCTTTAATCACACAATTCCATCAA
ATTCAGCACTCAGGAGAGGGT-
GATCTCTCTGAATTCCAGCACACRGGCG-
GCCGRRACTAG TGGATCCGAGCTCGGTAC-
CAAGCTT

Seq Id No:153

Mouse T2R25 Amino Acid Sequence

MMGIAIDILWAAIIIVQFIIGNIANGFI-
ALVNIIDWVKRRKISLMDKIITALAISRIYLL WST-
FLITLTSSLDPDIKMAVKIIRISNNTWI-
IANHFSIWFATCLSIFYFLKIANFSNYIF
LYLRWRFKKVVSVTLLISLIFLLLNILL-
MNMHIDIWSDKSKRNLSFSVRSNNCTQFPRLV
LLINTMFTSIPFTVSLLAFLLLIFSL-
WRHLKTMQYYAKGSEDTTTAAHIKALHMVVAFLL
FYTVFFLSLAIQYWTSGSQENNNLFYAT-
IVITFPSVHSCILILRNSQLRQASLLVLWWLL CKSKD-
VRMLVP

Seq Id No:154

Mouse T2R25 Nucleotide Sequence

AAAACTATTCGAATTGAACACAGTAAC-
CAATTCTTCAGCGGACTTACACAAATCAAGCTA
TTATCTTATGGATGATGGGTATTGC-
CATAGATATCTTATGGGCAGCTATTATCATTGTGC
AATTCATAATTGGGAATATTGCAAATG-
GATTCATAGCATTGGTGAACATCATAGACTGGG
TGAAGAGAAGAAAAATCTCTTTAATG-
GATAAGATCATTACTGCTTTGGCAATCTCTAGGA
TTTATCTGCTGTGGTCTACATTCTTAAT-
TACACTAACATCTTCACTGGATCCAGATATTA
AAATGGCTGTGAAAATCATTAGAATAAG-
CAATAACACCTGGATTATTGCAAATCATTTCA
GCATTTGGTTTGCTACATGTCTCAG-
CATCTTTTATTTTCTCAAGATAGCCAATTTTTCTA
ACTATATTTTTCTCTACTTAAGGTG-
GAGATTTAAGAAGGTGGTTTCAGTGACATTGCTAA
TCTCTCTTATCTTCCTGCTTT-
TAAATATTTTACTGATGAACATGCATAT-
TGATATCTGGA GTGATAAGTCCAAAAGAAAC-
CTTTCTTTTAGTGTCAGATCAAATAATTGCACTCAGT
TTC CCAGACTTGTCCTTTTAATCAACACAAT-
GTTCACATCAATCCCCTTCACTGTGTCCCTGT
TGGCTTTTCTGCTTCTCATCTTCTCCCT-
GTGGAGACACCTGAAAACCATGCAATACTATG
CTAAAGGCTCCGAAGACACCACCA-
CAGCTGCACATATAAAGGCCTTGCA-
CATGGTAGTGG CCTTTCTCCTGTTCTACA-
CAGTTTTCTTTTTGTCTCTTGCCATACAATATTGGAC
CTCTG GGTCTCAAGAGAATAACAACCTGTTT-
TATGCCACAATTGTAATTACTTTCCCTTCAGTCC
ATTCATGTATCCTGATTCTGAGAAA-
CAGCCAGCTGAGGCAGGCATCTCTGTTGGTGCTGT
GGTGGCTGCTGTGCAAGTCCAAAGATG-
TACGGATGTTGGTTCCCTGAAATACTCTGTCAA
TGCTCTTTAGTAGTGAAGAAGAAAAT-
AGCTTAGTTAAGGAAATTCTTGTTCATTACCGAA
GTATACTTTCAAGTTTATGTATC

Seq Id No:155

Mouse T2R26 Amino Acid Sequence

MLPTLSVFFMLTFVLLCFLGILANGFIV-
LMLSREWLLRGRLLPSDMILFSLGTSRFFQQC
VGLVNSFYYFLHLVEYSGSLARQLISLH-
WDFLNSATFWFCTWLSVLFCIKIANFSHPAFL WFK-
WRFPALVPWFLLGSILVSVIVTLLFF-
WGNHTIYQAFLRRKFTGNTTFKEWNRRLEID
YFMPLKVVTMSIPCSLFLVSILLLISSL-
RRHSLRMQHNTHSLQDPNVQAHSRALKSLISF
FLLYAVSFVSMIIDATVFISSDNVWYWP-
WQUILYFCMSVHPFILITNNLRFRGTFRQLLL LARGF-
WVA

Seq Id No:156

Mouse T2R26 Nucleotide Sequence

GAATTCTAGACAAGGAAAGACACACAC-
TAAATGACTTTACTTGTGGGACCTAAAATAACC

AAAATAAGTCAAAATCACAGTGATGT-
TACTAGGGATCTAGGATAAGGGAATGAAGAGAAA
GATGTTGGTCATAGAGTACAAAAAT-
TCAGCTAAGAACTCAGTCCTGGAGGCTGAATGTAT
AGCTGTGTGACAGACAGCAGCTAGCCAT-
ACCAGAGTATACACTTGCCTCTTGCTGAAAGA GTA-
GATCTTATGTGTCCTTGTCACACAT-
AAAAGTAATTGAAAAAGTAACTCTCTGAGATG
ACAGATACGTTAAAATGGTTT-
TACTTTTCAACCTGCTCCAGTAGGGGTC-
CCTTTAATGTT TGTGCTAGTAGATGGGGGACTCT-
CAAGTATCTTTGTGGTAGACAAATCTAAGGTGGCCT
T CATGAATACCAACCCAGACTTTTGT-
GACTTTGTGATCCCCCACTTTTGAAGTGGATAAGA
GCTGTGACTTGAGTCTAATCAAAG-
GAGTCCAACGTGTTGTTTATTCTGTAACAGTGCTTT
GTGTTTCTAGTTAATAACACAGGCAAA-
GAAGGCTAGGGTGACATTCCTAGGATTGTGTTA
TTTCTATCTTGCTCATGCCTCCCTCT-
GCTGGTCTAATGAAATAAGTCAGTGGCCATATTT
AAATATGACTACGTGGCAAATACTGAT-
GATAGCCTGTGTGTTCCAACAAATATCCAGTAG
GAGACCTAGGCATTCAGTCCTGCAGCCA-
CAAGGAAATAGGTTCTTTCACTGGAAAAAGAG
CAGTTTAGATGGTTATAAATTACT-
TAATCCATAGAAGCCATAGGGGCTTTATGTAGAGAT
TTGGGTAGAGAGGTAGACCTAGATAT-
TGACTTAGGAGTGGCTATTCCTGAGTGGGGGTAG
ATATATGGCAGGGAAACTCAGATAA-
GAAAGACTTCTTTAGTGTCACGATTTTTCCTAGGT
ATCTCCTTGTGCCAGATATCTATGCGTC-
TATGTACCTACCTACCTACCTACCTACCTACC TAC-
CTACCTACCTACTGACACCTAATAGGAA-
GAGGCAAGTGGTCACAACCTGCAATGATG
GGATAAGAATGATGGAACTCAGTTAC-
CAAGATTAAAATACCTTCCCCACTGATGTTATTG
CAAGCATGGCAGCATGTAGGCAAAATCA-
GAGAAGGCAAATCATGAGCAGCTGCTGCCCCA
TGGTACCCGAGCCCGGGAAATATTTG-
CATCATATCTGAGCCAAAAGCACACCTTTTATCT
ACTGCCTGAGCATTTTTCACATTGAAGT-
TCTGGCTCACATGCAGAATCCAACCATTTATC
TCCTGTCTCCAGAAGGGAGTGTCAGG-
GACTGTGGGTAGGGGCAGGGAGGAGGCCAGGAAC
CAAGGCAATCAGTGGTGACAGGAGGAGG-
GACTGAAATGCTACCAACATTATCAGTTTTCT TCAT-
GTTGACCTTTGTTCTGCTCTGTTTC-
CTGGGGATCCTGGCCAACGGCTTCATTGTGC
TGATGCTGAGCAGGGAATGGCTACT-
GCGTGGTAGGCTGCTCCCCTCGGACATGATCCTCT
TCAGTTTGGGCACCTCCCGATTCTTC-
CAGCAGTGTGTGGGATTGGTCAACAGTTTCTATT
ACTTCCTCCATCTGGTTGAGTACTCCGG-
GAGCCTTGCCCGGCAGCTCATTAGTCTTCACT
GGGACTTCTTGAACTCAGCCACTTTCTG-
GTTTTGTACCTGGCTCAGCGTCCTGTTCTGTA
TCAAGATTGCTAACTTCTCCCATCCTGC-
CTTCCTGTGGTTGAAGTGGAGATTCCCAGCGT
TGGTGCCCTGGTTCTTGTTGGGCTC-
TATCTTGGTGTCCGTCATTGTAACTCTGCTGTTCT
TTTGGGGAAACCACACTATATATCAG-
GCATTCTTAAGGAGAAAGTTTACTGGGAACACAA
CCTTTAAGGAGTGGAACAGAAGGCTG-
GAAATAGACTATTTCATGCCTCTGAAAGTTGTCA
CCATGTCAATTCCTTGT-
TCTCTTTTTCTGGTCTCAATTTTGCTGT-
TGATCAGTTCTCTCA GAAGGCATTCGCTAAGAATG-
CAGCACAATACCCACAGCTTGCAAGACCCCAACGT
CCAGG CTCACAGCAGAGCCCTGAAGTCACT-
CATCTCATTCCTGGTTCTTTATGCGGTGTCCTTTG
TGTCCATGATCATTGATGCTACAGTCT-
TCATCTCCTCAGATAATGTGTGGTATTGGCCCT
GGCAAATTATACTTTACTTTTGCAT-
GTCTGTACATCCATTTATCCTCATCACCAATAATC
TCAGGTTCCGCGGCACCTTCAGGCAGC-
TACTCCTGTTGGCCAGGGGATTCTGGGTGGCCT
AGAAGGCTTGGTCTCTTTATCTAGAGC-
CTTTGAAGAGACTCAGGTGAGGGTAACTTCACT
TGGAAGTGAGCTCATCTACGTGGAAAT-
GTCTTTGTAGGCAGGCATGGGGTCATACTGTGA
GGTTCCTCATTGGGAAAGAGGAGAA-
GAAAATACAGAGTGTCCTTCCTTACCTTAGGATAT
TATGAAAGTGGAAATTCCGAATCCTG-
GACCAGTATTGATCTAAGTGCAAAGTACAATATG
TCCTGTTCCTTTCATGTCTGTTTTC-
CTTTTGTTACTGATTCATTCTCTAGGGAATAGTCT
TGATCAACTGAATCATCTCATCTGGCTG-
GCCACTGGGGAGGTAAAAGAACTTTGTGTCAC
TGCTGCATTGGGATATACATGGGTGG-
GAAGCAAGTGTCCCTGAGGCAGAGTAGCACTCAG
TATGAGAACCTCAAAGAGCAGGTGGCT-
GTGCATGCAGGGGCTGGGGCAAGGAGTCCTGAT
CACTCTTCACTGTATGGGGAT-
TATTTGTCTCTTGCCAAAATTTG-
GAGACTTTGGCTTTAG TTTTGTGAAGATGACTG-
GAAAAATTCTTAATGCTACCCTGTATCATTTCTCAAT
AATATT TTCCTTTTCCTGCCTTTAATTTTCTC-
CTATCTGCAGCGCCCCTTGCTTGTTATCCGTAAA
TAAATAAATAAATAAATAAATAAGC-
CCAATCCTCATTTTCCTGTCTTTGGGAACCCTTTT
ACTTCCCCAGGTATACGCTACAAAGC-
CACTTCTGCATTGAATAAACATTATCTTTCATTC
AGAAAAAGACTTAAGAATCTCACCTTTA-
CAAAAAAAAAAAAAAAAGAATCTCACTTATTT
TATATTCAAATTCCATTTTTAAAAA-
GAAAAGCACAGCATTAATTTTTCTAAATACTGTTT
ATAAAAATAACTTGCTCTAAGAATTATA-
CAAATGTTTTGAAAGGTAACTTTGGAAAAAAA
GTGTGATTAGACATGGATGTTTGTAAGA-
CAGAACAAAGAGCTCTTGGAAGTCCATGGCAG
CTCATTGGTCTTGCCTTCAGTAGAGCCT-
GTCTGAATCCTGTAACCTCTTATGCCCTTTTG
TAGCTTTTCTGCAGATC

Seq Id No:157

Mouse T2R27 Nucleotide Sequence

GAATTCGCCCTTGCGGGATCCGGGAACG-
GATTCATAGCACTGGTAAACTTCATGGGCTGG
ATGAAGAATAGGAAGATTGCCTCCAT-
TGATTTAATCCTCACAAGTCTGGCCATATCCAGA
ATTTGTCTATTGTGCGTAATACTATTA-
GATTGTTTTATATTGGTGCTATATCCAGATGTC TAT-
GCCACTGGTAAAGAAATGAGAATCAT-
TGACTTCTTCTGGACACTAACCAATCACTTA
AGTATCTGGTTTGCAACCTGCCTCAG-
CATTTACTATTTCTTCAAGATAGGTAATTTCTTT
CACCCACTTTTCCTATGCCTCAAGTCTA-
GACGCCAAGGGC

Seq Id No:158

Mouse T2R28 Amino Acid

GREWLRYGRLLPLDMILISLGASRF-
CLQLVGTVHNFYYSAQKVEYSGGLGRQFFHLHWHF
LNSATFWFCSWLSVLFCVKIAN

Seq Id No:159

Mouse T2R28 Nucleotide Sequence

GAATTCGCCCTTGCGGGATCCGG-GAACGGGTTTATTGTGCTGGT-GCTGGGCAGGGAGTGG CTGCGATATGGCAGGT-TGCTGCCCTTGGATATGATCCTCATTAGCTTGGGTGC CTCCCGC TTCTGCCTGCAGTTGGTTGGGACGGTG-CACAACTTCTACTACTCTGCCCAGAAGGTCGAG TACTCTGGGGGTCTCGGCCGACAGTTCT-TCCATCTACACTGGCACTTCCTGAACTCAGCC ACCTTCTGGTTTTGCAGCTGGCTCAGT-GTCCTGTTCTGTGTGAAGATTGCTAACATCACA CACTCCACCTTCCTGTGTCTCAAGTCTA-GACGCCAAGGGCG

Seq Id No:160

Mouse T2R29 Amino Acid Sequence

MDGIVQNMFTFIVIVEIIIGWIGNGFI-ALVNCIHWYKRRKISALNQILTALAFSRIYLLL TVFTVIAVSTLYTHVLVTRRVVKLINF-HLLFSNHFSMWLAACLGLYYFLKIAHFPNSIFV YLK-MRINQVVSGTLLMSLGLLFLNTLLINSY-IDTKIDDYREHLLYDFTSNNTASFYRVIL VINNCIFTSIPFTLSQSTFLLLIFSLW-RHYKKMQQHAQRCRDVLADAHIRVLQTMVTYVL LCAIFFLSLSMQILRSELLKNILYVRF-CEIVAAVFPSGHSCVLICRDTNLRGTFLSVLSW LKQRFTSWIPNINCRSSCIF

Seq Id No:161

Mouse T2R29 Nucleotide Sequence

AGCTTGATATTTCCTATTTGTTACTGCA-CAGAGTTTTTTTTAAAAATTGAGTTTGTTATG TGGATTCAATACTCAGATAGAGCTCTT-TAATTTTTTTACAGTGACCTCATGAATCATAAC TTGCCTTACAGACAATGGATGGAATCG-TACAGAACATGTTTACATTCATTGTAATTGTGG AAATAATAATAGGATGGATTGGAAATG-GATTCATAGCTCTGGTGAACTGCATACACTGGT ACAAGAGAAGAAAGATCTCTGCACT-GAATCAAATACTCACAGCCTTGGCTTTCTCCAGAA TCTACCTTCTTTTAACAGTATTCACTGT-TATAGCAGTGTCTACGCTATACACACACGTGT TGG-TAACTAGAAGAGTGGTAAAACTGAT-TAATTTCCATTTGCTTTTCAGCAATCATTTTA GCATGTGGCTTGCTGCATGCCTTGGC-CTTTATTATTTTCTTAAAATAGCTACATTTCCTA ACTCTATTTTTGTTTACTTAAAGAT-GAGAATTAACCAGGTGGTTTCAGGGACTTTGCTCA TGTCTTTGGGCCTCTTGTTTCTAAA-CACTCTGCTGATAAACTCATACATTGATACCAAGA TAGATGACTACAGAGAACATCTACTG-TATGATTTCACTTCGAATAATACTGCTTCATTTT ACAGGGTTATTTTAGTCATTAACAACTG-TATTTTCACATCTATACCCTTTACACTTTCCC AGTC-CACTTTTCTCCTGCTCATCTTCTCCCT-GTGGAGACATTACAAGAAGATGCAACAGC ATGCACAAAGATGCAGAGATGTCCTTG-CAGATGCCCACATCAGAGTCTTGCAAACCATGG TCACCTATGTCCTACTCTGTGC-CATTTTCTTTCTGTCTCTTTCCATG-CAAATTTTGAGGA GTGAGTTGTTGAAGAACAT-TCTTTACGTTAGGTTCTGCGAGATTGTTGCAGCAGT TTTTC CTTCAGGACACTCCTGTGTCTTAATCTG-TAGAGACACAAACCTGAGAGGGACCTTTCTTT CTGTGCTATCGTGGCTGAAGCAGAGGTT-TACATCATGGATTCCTAACATAAATTGCAGAT CATCTTGCATATTCTAAAAGAAACTGAG

Seq Id No:162

Mouse T2R30 Amino Acid Sequence

MTYETDTTLMLVAVGEALVGILGNAFI-ALVNFMGWMKNRKIASIDLILSSVAMSRICLQC IILL-DCIILVQYPDTYNRGKEMRTVDFFWTLT-NHLSVWFATCLSIFYLFKIANFFHPLFL WIKWRIDKLILRTLLACVIISLCFS-LPVTENLSDDFRRCVKTKERINSTLRCKVNKAGHA SVKVNLNLVMLFPFSVSLVSFLLLILSL-WRHTRQIQLSVTGYKDPSTTAHVKAMKAVISF LALFVVYCLAFLIATSSYFMPESELAVI-WGELIALIYPSSHSFILILGSSKLKQASVRVL CRVKT-MLKGKKY

Seq Id No:163

Mouse T2R30 Nucleotide Sequence

AAAAATGTTCATTGTTTATCTAAAAT-TCAAATTTAACTGAGTGCCCTACATTTTTATTTA TTCAATCTAGTAGCTGTACTGAGGT-TATTAGTGTGATTTCTGAAGCCCAAATTTGTAAAA CTTAGCCTCAGATAAACAGCTTGAGAC-CATGGAAAGTAATTTGGTAAATTTGCATCTTAG CAAATAGTAGCTCAGCCTAAATTAACT-GTGTGTAGAAAAGAATGACCTGCGGAGAAGATA AATGGACATACAATATCCAGGCTAAG-GATTGCCAAACACACTGTTTTTAAGACTAATTGA GATTTAGATAAACTATCTACAGTCT-TCATGTATAATTCTCATCTTCATCACAAGACAGAC TTCAACTTAAGGAGGTAAAGACAAGGA-CAGCGAACCCTAAACAGCCAAGTGTAGAAACCA AACTGCATCAAATCAGCCAGAAACTAAT-TGGATACTTCTCTACTTTAAAATGACATACGA AACAGATACTACCTTAATGCTTGTAGCT-GTTGGTGAGGCCTTAGTAGGGATTTAGGAAA TGCATTCATTGCACTGGTAAACT-TCATGGGCTGGATGAAGAATAGGAAGAT-TGCCTCTAT TGATTTAATCCTCTCAAGTGTGGCCAT-GTCCAGAATTTGTCTACAGTGTATAATCCTATT AGATTGTATTATATTGGTGCAGTATCCA-GACACCTACAACAGAGGTAAAGAAATGAGGAC CGTTGACTTCTTCTGGACACTTACCAAC-CATTTAAGTGTCTGGTTTGCCACCTGCCTCAG CATTTTCTATTTATTCAAGATAG-CAAACTTCTTCCACCCTCTTTTCCTCTG-GATAAAGTG GAGAATTGACAAGCTAATTCTCA-GAACTCTACTGGCATGTGTGATTATCTCCCTGTGTTT TAGCCTCCCAGTCACTGAAAATCTGAGT-GATGATTTCAGACGTTGTGTTAAGACAAAGGA GAGAATAAACTCTACTTTGAGATG-CAAAGTAAATAAAGCTGGACATGCCTCT-GTCAAGGT AAATCTCAACTTGGTCATGCTGTTC-CCCTTTTCTGTGTCTCTGGTCTCCTTTCTCCTCTT GATCCTCTCCCTGTGGAGACACACCAG-GCAGATACAACTCAGTGTAACAGGGTACAAAGA TCCCAGCACAACAGCTCATGTGAAAGC-CATGAAAGCAGTAATTTCCTTCCTGGCCCTGTT TGTTGTCTACTGCCTAGCCTTTCTCAT-AGCCACCTCCAGCTACTTTATGCCAGAGAGTGA ATTAGCTGTAAATATGGGGTGAGCTGAT-

AGCTCTAATCTATCCTTCAAGCCATTCATTTAT CCT-
CATCCTGGGGAGTAGTAAACTAAAA-
CAAGCATCTGTGAGGGTGCTTTGTAGAGTAAA
GACCATGTTAAAGGGAAAAAAATATTAG-
CATCATGAGCATATCTGAAGAAAAACTATCAC
TTTCTAAGAGAAAGGAAGACACGATCAT-
TATCCGTCCTTTTCACATGAATATTGATTTCA
TGCAGTGACATCCTCTTAACAAACT-
TAAATTGAACCTTGAGAAATCTCATATACAGCAAC
TTTGCATGTCTCTATCTCT-
GCTTTTTCTCTCCTTTTCAATATGAGT-
TGACATAAAAAATA ATTTTCAGAACAAATTATAA-
CAGAAGAAAGGGCATTTTCATAATCAGTTCTGAATC
ACTC CTCCAAATGCAAAGCTGCCTGACAAAT-
TCAAAACAATTGTAACAGCATCTCACTGTCGTT
TGCATTCTTTGGAAAAGCAGGTG-
GTTTGTTCTTGGAGCCTGGCTTA-
GAGTTTTCTTCTTA GACCATTGAATTATGTTCAT-
GATTGGAGAAGAGTCAAGTACCAAGTAACAATTTT
TATTG TGAAGATGGGTGTTCATCATGT-
GATTTTGGCTGGCCTGGAACTTGTTATG-
TAGACTAGTC TGTCATCAAACACACAAAGATCT-
GCCTGCCTCACCTGCCAGTTCTAGGATTCAAGGAAT
G CACCACCACAGCTTGTTCAAGTGACAAT-
TCTTACAAATGTTTTAGAAATAAATAATATAC
TAGAAATTAACACTGAATGTAAGTGCT-
GTTTAGGTATAAATTATGATTAAATGTTATAGT
TAGAAAATTATTTAAGATTATAGAT-
CAGTGATGAAAATATTCTAGAATAAGTTTTATGAA
GAAACTTTTATAAAGAAACTG-
GAAAAAAATCTCTTGATTGCATAT-
TGAAACAAATTTCTC CAAAAAGAACACCTA-
CAAATTTGCTCTAGACATCTAGACTGTATCAAACAG
TGAATATGA AAATATCATAACAGGATATAGCCTT-
TAGTATTGAAGACAGGTTCATCTATATTAAACCTG
CATACATACCTAAAAGACTAAGT-
CAATATCCCACAAACATATTTGCACTATCATGTCTAT
TGAAACACTATTCATAG-
TAGCTAAAATATGGCACAAAACTAGA-
CATTCATCAATAGATGA ATCAATAAAGCAAATGTA-
CATACACAAGATGAAATTGTATTCAGGCATAAAGAA
GAATGC AGTCATGTCATTAGCAAAAACATAAACA-
GAATTGGAGGTCATTGTGATAATTGAAATAAA CCA-
GACCTGGAAAAAACAAAACCTGTG-
TAATTTTTCTGAAGTAGAGAATATACTCTTGGA
TGGATAGATGGGTACTGTTATAG-
TATAAAATGTGTGTGTGTGTGTGTGTGTGT-
GTGTGTGTG TATTTCATGAAAGCAAGAATGGGACT-
GCTTAGAGAAAGAAAAGGACAAACAGGTGAAGGG
GTGAAAGAAAAAGGCAATGACAAGGAG-
TAATGATATGAGCAAAGTACCATTATTAAACAT
GTFACAATATTATATAGAAACACAT-
GATTTTGTGTGCCTACCAAAACTGGATAATAATTT
TTAAAATGTATCTATTAAAAGGAAA-
GAAAAGAAAGTGCAAGCCCAGGAAAGG-
GAGAAAAG GAAACAATGAGAGAGAAATG-
GAAAATGGTGAGAAGTGAAGAGAACAAAAAGAAA
TGGAGT AAGTGTGGCCAGGAATGAAGGATCT-
CAGCTATAGTTATCCCAGTACGGTAATACAAATCT
GTGACTCCAGCACTTGACAAGGCT-
GAGAGATGTGAGAGAGGGCCAGTTAA-
CAACCAGTCT GGGCTTATTCCAAGAGATAAGAA-
GATTGGGGGAAAGTATGTAGAAGGGTTTGGAGGGA
AG AGAGAGAAGAGGGAAATGATGTAATGAT-
AGTACAAATCAAAAGTTATTTTTTCTAAAAAA
GCAATGGGACAGGAAACCAACCTAA-
CAAGTAAAGGTGCTTGGTTCACAAGAC-
CAGCAACC TGAGTGCATCCTTGCTAGAATGAAAT-
TGGCCTTACTCTGGAAAGCTTACTTCCTCAGTGT
ATTCATTGTTAAAATTCATGTG-
GAGATTTTAAAGAAAAAAG-
GAAAAAAAAAGTTAAATGG TAGATTTGTGTAGGG-
GAATATTCCCCTAATTAATTGATTAGATAATAAAGAT
GACAAGCA AATTGCTGTGCAAAAAGGAAGA-
CAAGGTCTAAGAGGGGAAGAGGGGA-
CACGGGAGGAAAA AAAACGGCCCTTTTTAAAG-
CAAGGTGGGGAGTGAGGGAAGCGAGATGTAGACA
GGGAACT GTTAGACCTGGTGGCAGCTTCTGCCAC-
CTGAAGATTTTCAACATAGTATAGTTCATGAGT
TTAGGAAGATATGTTCCCTGCCCAGCG-
GTTGTATCATCTGTTGATTTTAAACTAAGATTG
TCTGGTGTTTTCATTTGCGGAGACT-
CAAGTAGACCAAAGGGAAAGAATGAATTC

Seq Id No:164

Mouse T2R31 Amino Acid Sequence

MYMILVRAVFITGMLGNMFIGLANCSD-
WVKNQKITFINFIMVCLAASRISSVLMLFIDAT IQE-
LAPHFYYSYRLVKCSDIFWVITDQLSTW-
LATCLSIFYLFKVAHISHPLFLWLKWRLR
GVLVVFLVFSLFLLISYFLLLETLPI-
WGDIYVTLKNNLTLFSGTIKTTAFQKIIVFDIIY LVP-
FLVSLASLLLLFLSLVKHSRSLDLISTT-
SEDSRTKIHKKAMKMLVSFLILFIIHIFF
MQLARWLLFLFPMSRPINFILTLNIFAL-
THSFILILGNSNLRQRAMRILQHLKSQLQELI LSL-
HRFSSLY

Seq Id No:165

Mouse T2R31 Nucleotide Sequence

CTGCAGCTTTCTAGAAATCTCACCA-
GAATGTCTTTGTGCAGCTTTAATAGTTCCTGGTTA
TACCTTGTCACATTATAAGCTAAGA-
CATCTTTGGTGCCACAATATACTCTCACTAATCAG
AGAGATTAGACAGAAAAATAAGTTTCT-
TAACAACTGTTTTAGATAGGGTCATGAAATGAC
ATAAAACACCAATGCTAAGGCAATCCAT-
TATGTTTTCTCATGAGGAGCCCATATGTACAC
TTGAGTGTGTCTTATTATTTCCCTGAGT-
GATTTTGTAATTTTATTAAACACTTAACTGTG
ATTCATACTAGTTAGTTCTGAAAT-
TCTTTTCTTCATCAAAGCCATTAATCCTGGGGTTTT
TTAAATGGAGAACCCCAAAACAAAGT-
GAAATGTTGTGTGTGGAGCAGGCTGTCTTCCCAC
ACACTACCATGAGATGCTCATTCTG-
TAATTGTTCCCCGGAATAGGAAATGCCCTGAATTC
AGGCACACAAGAGCTAGTCTGTGCAC-
CATGTCTGGTTCTTGCATTAATACCCACTTTTGT
CACGAAGCTTCATTGATTCGCATCTTCA-
GAAGCTGGTATCATTATTAGTTTCTTTCCTCA GGT-
GACTCTGGnCCAAAATATTAnGGCGC-
CCTTTAAAAAAGTAAAACTACAAAATTTCTT
TATAATTTTCTTTAAGTTTGT-
TATAATATAGCATGACCTACACACACA-
CACACACACACA CACACACACACACACACA-
CAAGTATGCCTCTCCTTTCCTTCTAAAATCTCACTT
AAAGC AATTGTTTAGCTGTCTTCGAAGTCTA-
GACTGCCACTGTCGTGCTTCTAGCCAAAACAAAT
GCAACACATAAAATGATAGAGCT-
CAAAACTTAGGAATCTATTTAACTGT-
GAAGATCACGC AAGCAAACCTGAGAAACCTCTA-
GAAGGAAACCACAGCAAATCACTGGAGAGAAGGT

GTTA ATCTAGTAAGAATAGTTTTTATTTTGGG-
TATCCTTTTGTAGATTGGTTAGTTCATCCAAA ATC-
CAACTTGTTAGTTCTTCATAAATTG-
TAAGTGTCTCCAACATCAAAGCACCACTTCTC
TCTTTTCCCCTGTATGAAGATGCTT-
TAAGTACAGAGTTACTCTTTTTCTGTACTGACAGT
AATTTAAAAAAATTGTTCACTCAT-
TCTTTTTTGGTGTTGTTATTCTGTGTTCCTCAATGT
TATCTTTTTTTTTTCAAAACTTTCTTT-
TATAAAAAGTCATACACATAGCAAATGCAGTGC
ATGTTTATGGAATCCATAACTAACTTAT-
TGAGACTTCTCCTAGTACTTTCTTTGAACAGT
AACAAAGATATCTGCTTCTACAGAGTG-
CAGTGTTTCAGGTGAGGAGGAACATATTATACA
AATCAGTGAAAAAAAAATCTGAT-
TCAAATTTGTATTTTAATATATTTGACTTTATCACTT
CAGATATTACATCAATGG-
GAATTTTGAAGGCACACAAGTGATGAT-
GTGGGCATAGAGACT GTCTGTACTAGAATT-
TAATATTTCTTTTAAATATCTTTAAATAAAAATATGAT
GCTGTAT TCATAAACAGATCTTTATAGATTAAG-
TATGAGATTAAAGTTGGAAAAACAAAAGACAAAA
ACCTAGGACTAAGAATTTCCTTAAGTAT-
GTGTGAATATCAACCTAATGGAGGAAGTTTCC AAT-
CAAAGCTGAAATTACAGTAAAAAGGAG-
GAAGATAAATATGGAAAAGGATGATTTTCT
GTGGAAGTTTGTTTGAGAACTGATCCAC-
GAGACAAATTGCTAGAAGTGTGGATTCCCTTT TAC-
TATTCAACTGCTTATAGGACTGGAT-
CAAATGTATATGATACTGGTAAGAGCAGTATT
GAACCAGAAAATCACCTTCATCAACT-
TCATCATGGTCTGTTTGGCAGCTTCCAGAATCAG
CTCTGTGCTGATGTTATTTATTGATG-
CAACCATACAAGAACTAGCGCCTCATTTCTATTA
TTCTTACCGTCTAGTAAAATGCTCT-
GATATATTCTGGGTTATAACTGATCAACTATCAAC
ATGGCTTGCCACCTGCCTGAGCATATTC-
TACTTATTCAAAGTAGCCCACATTTCCCATCC
CCTTTTCCTCTGGTTGAAGTGGAGAT-
TGAGAGGTGTGCTTGTTGTTTTTCTTGTATTTTC
TTTGTTCTTATTGATTTCTTATTTTC-
TACTGCTTGAAACACTTCCTATTTGGGGAGATAT
TTATGTAACCCTTAAAAACAATCTGAC-
CTTATTTTCAGGTACAATTAAGACCACTGCTTT
TCAAAAGATAAT-
TGTTTTTGATATAAATATATTTAGTC-
CCATTTCTTGTGTCCCTAGCATC ATTGCTCCTTT-
TATTTTTGTCCTTGGTGAAACACTCCCGAAGCCTTG
ACCTGATTTCTAC CACTTCTGAAGATTCCAGAAC-
CAAGATTCATAAGAAGGCCATGAAAAT-
GCTGGTGTCTTT CCTCATTCTCTTTATAATTCA-
CATTTTTTTCATGCAGTTAGCACGGTGGTTATTATTT
TT GTTTCCAATGAGCAGGCCAAT-
TAATTTCATCTTAACAT-
TAAATATCTTTGCCTTAACTC
A CTCATTTATTCTCATCCTGGGAAATAG-
CAATCTTCGACAGAGAGCAATGAGGATCCTGCA
ACATCTTAAAAGCCAGCTTCAAGAGCT-
GATCCTCTCCCTTCATAGATTCTCCAGTCTTTA CTA-
GAGGAACAGCTTAACAGGGAGACTTG-
GAAGGTCACTGGCAAATTATTCTTCTTTGAT
TTCTTTTAAGTACTGCTGAACATATAT-
GAACTGTCCCCAGAGCATAGTGCTATCTTATGA
GAAGGATATCATCTCACAGTCTGGT-
TATAAAACACAAACCAATCTTTTTATAATTTCTTT
ACAGCATTGCTAATAAAAGACTTG-
TAGTCTCAAATATTTTAAAGAGAATAATTAATTTA
TAGGCAAAAGGTATGAAATTACAATTCA-
CAGGGAAGGTTCATGACTCCTTAGATATTAAA
GTTAATTGTAAGCCACAATAGGCAGAA-
GATGAGCAAAATGTTGATAGGAGATAAATAAAA
TCTAAAGTTACGGAGAAAAAAAACAT-
CAACTTGCCTTTTAGATTACTTTAAAGCTCTCTC
TCTCGCTCTCTCTCTCTGTATCTACT-
TACTTTATATATACAAATGTTTTGTCTGCATGTA
TTTCTTTGCACCATATAAATGTCTAAG-
TATCCAGAAnGTCAGCAGAGGGCATCAAATTCT
CTGGAAAGAGAGTTACAAATTGCT-
GTGGGTAACACTGGGTGCTGGGAAC-
TAACCTGAGTC CTCTGCCACAGCAACTGCTCTTC-
CCTGCTGAGTCATGTTTTAAGTCTCCACAACTTAAA
C TCATTGTTGATGTGGTCATTGCATAAT-
GATGAATTTACATTCTAAGGTTTGTATCATAGG TAG-
GAGGGCTGGTTTTAATCATATTCTAAT-
GTTCTTATACAAACCCAGGTTTTGTAAGAG
ACTGTATTCTATCATGAGACTCTTTC-
CCCACACCGCCAATGTAACATTTTTATTAATTTT
GAGGGGAATTTTATACAGTGTACCCT-
GATCACCCTTGCTTCCCACTCCTTGCAGGTCTAC
CCTCCCACCATTGCTCAATC-
CCCCCTAAAAGAGAGAGAAACAAACCAT-
GTCCAATTTGTG TTGGACACATACTCAGTGGAA-
CATGGCCAAACCCCTAGTGAGCAGTTCCTTAAAGA
AAAC TAAGCTGCCTCCCCACCACTACCACCAT-
AGGGCATTAACTGTGAAGAGCTACACTTTAGC
TATTTTATCACCAATTTAAAAGACT-
GTCTTCAATAGCTTCCTCTATGGACTGTTTCTGGT
TTTAGTGGGACAGGGAGAAGGGGTCAA-
GAGGTTGTCACAGAAACTTTTGATGTCTCTTAT
TCTCAGTTAAAGTCCACTGCAAAA-
GAAGTCTGCTGGCTCTAATAAAGCTTG-
CAACAGCAT GGGCCAGTGACATCATCAT-
GATTTCTGGCAACAATATGGACCACAAATATCATGG
CTCAG GTGGCATTACGGACCACAGACATCAA-
CATGGTCTCTGGCAGCAAGAACCAGAATCTTTTG
AGGAGGCTTCATTCAGAAAAT-
GAATTTTTCTTCATCCCAGATATACT-
GATGTTGCTCAAT CAGAGTATTAGTATGGT-
TGGGCACCATATTTGGGGACAGGACCTTCAATATTT
CCAGGCT GCTGTGTAACACATTATCTTTAGTGT-
CAGGTGCCCTTAGTGTCAGGACATGACCATCATG
TATGCGCCTGTGGGCAGAAATA-
CATCTTTGTACTTTCTTACACCTAG-
CAGGGTGAGTAGC AGGAGCAGCGGCATTAATACT-
TCCATACCTCTGGGCAGCCTATCAGGTATCATCTAG
GCA AGGTAAGCCCAGTAGTGGCCCAAGGCTC-
CTGGTGTCTACTTGGCAACAACATGCTCCTTT
GTCTGCACTGCCATATCTATGGCTGGT-
TCTCCATCCCTAGTTCTGCTTCTCTCAGGTTTT
ATACGACTCTATTCCACATTC-
TATTTTTCCAGTTCCATGAAACCAGT-
GTTTAAAAGTATC ATCCCATAAGACCGGCCTTT-
TAAAGGTTATTCTGGAGATATTGCAGCGTCTGCAG

Seq Id No:166

T2R Family Consensus Sequence 1

E(F/A) (I/V/L) (V/L)G(I/V) (L/V)GN(G/T)FI(V/A) LVNC(I/M)DW

Seq Id No:167

T2R Family Consensus Sequence 2

(D/G) (F/L) (I/L)L(T/I) (G/A/S)LAISRI(C/G/F)L

Seq Id No:168

T2R Family Consensus Sequence 3

NH(L/F)(S/T/N)(L/I/V)W(F/L)(A/T)T(C/S/N)L(S/N/G)(I/V)

SEQ ID NO:169

T2R Family Consensus Sequence 4

FY(F/C)LKIA(N/S)FS(H/N)(P/S)(L/I/V)FL(W/Y)LK

SEQ ID NO:170

T2R Family Consensus Sequence 5

LLI(I/F/V)SLW(K/R)H(S/T)(K/R)(Q/K)(M/I)(Q/K)

SEQ ID NO:171

T2R Family Consensus Sequence 6

HS(F/L)(I/V)LI(L/M)(G/S/T)N(P/S/N)KL(K/R)(Q/R)

hT2R51 Full-Length cDNA (BAC AC011654)
(SEQ ID NO: 172)

ATGTTGACTCTAACTCGCATCCGCACT-
GTGTCCTATGAAGTCAGGAGTACATTTCTGTTCA
TTTCAGTCCTGGAGTTTG-
CAGTGGGGTTTCTGACCAATGCCT-
TCGTTTTCTTGGTGAATTTT TGGGATGTAGTGAA-
GAGGCAGGCACTGAGCAACAGTGATTGTGTGCTGC
TGTGTCTCAGC ATCAGCCGGCTTTTCCTGCATG-
GACTGCTGTTCCTGAGTGCTATCCAGCT-
TACCCACTTCCA GAAGTTGAGTGAACCACTGAAC-
CACAGCTACCAAGCCATCATCATGCTATGGATGATT
GCA AACCAAGCCAACCTCTGGCTTGCTGCCT-
GCCTCAGCCTGCTTTACTGCTCCAAGCTCATCC
GTTTCTCTCACACCTTCCTGATCTGCT-
TGGCAAGCTGGGTCTCCAGGAAGATCTCCCAGAT
GCTCCTGGGTATTATTCTTTGCTCCTG-
CATCTGCACTGTCCTCTGTGTTTGGTGCTTTTTTA
GCAGACCTCACTTCACAGTCACAACTGT-
GCTATTCATGAATAACAATACAAGGCTCAACTG
GCAGATTAAAGATCTCAATTTATTTTAT-
TCCTTTCTCTTCTGCTATCTGTGGTCTGTGCCTC
CTTTCCTATTGTTTCTGGTTTCTTCTGG-
GATGCTGACTGTCTCCCTGGGAAGGCACATGAGG
ACAATGAAGGTCTATACCA-
GAAACTCTCGTGACCCCAGCCTGGAGGC-
CCACATTAAAGCCC TCAAGTCTCTTGTCTC-
CTTTTTCTGCTTCTTTGTGATATCATCCTGTGTTGCC
TTCATCTCTG TGCCCCTACTGATTCTGTGGCGCGA-
CAAAATAGGGGTGATGGTTTGTGTTGG-
GATAATGGC AGCTTGTCCCTCTGGGCATGCAGC-
CATCCTGATCTCAGGCAATGCCAAGTTGAGGAGAG
CT GTGATGACCATTCTGCTCTGGGCTCA-
GAGCAGCCTGAAGGTAAGAGCCGACCACAAGGCA
GATTCCCGGACACTGTGCTGA hT2R51 Conceptual Translation (BAC AC011654)
(SEQ ID NO: 173)

MLTLTRIRTVSYEVRSTFLFISVLE-
FAVGFLTNAFVFLVNFWDVVKRQALSNS-
DCVLLCLSISRL FLHGLLFLSAIQLTHFQKLSEPLNH-
SYQAIIMLWMIANQANLWLAACLSLLYCSKLIRFSHT
FLI CLASWVSRKISQMLLGIILCSCICTVL-
CVWCFFSRPHFTVTTVLFMNNNTRLNW-
QIKDLNLFYS FLFCYLWSVPPFLLFLVSSGMLTVS-
LGRHMRTMKVYTRNSRDPSLEAHIKALKSLVSFFCF
FVIS SCVAFISVPLLILWRDKIGVMVCVGI-
MAACPSGHAAILISGNAKLRRAVMTILL-
WAQSSLKVRA DHKADSRTLC hT2R54 Full-Length cDNA (BAC AC024156)
(SEQ ID NO: 174)

ATGACTAAACTCTGCGATCCTGCA-
GAAAGTGAATTGTCGCCATTTCTCAT-
CACCTTAATTTT AGCAGTTTTACTTGCTGAATACCT-
CATTGGTATCATTGCAAATGGTTTCATCATGGCTATA
C ATGCAGCTGAATGGGTTCAAAATAAG-
GCAGTTTCCACAAGTGGCAGGATCCTGGTTTTCCT
GAGTGTATCCAGAATAGCTCTCCAAAGC-
CTCATGATGTTAGAAATTACCATCAGCTCAACC
TCCCTAAGTTTTTATTCTGAAGACGCTG-
TATATTATGCATTCAAAATAAGTTTTATATTCTT
AAATTTTTGTAGCCTGTGGTTTGCTGC-
CTGGCTCAGTTTCTTCTACTTTGTGAAGATTGCCA
ATTTCTCCTACCCCCTTTTCCTCAAACT-
GAGGTGGAGAATTACTGGATTGATACCCTGGCTT
CTGTGGCTGTCCGTGTTTATTTCCT-
TCAGTCACAGCATGTTCTGCATCAA-
CATCTGCACTGT GTATTGTAACAATTCTTTC-
CCTATCCACTCCTCCAACTCCACTAAGAAAACATAC
TTGTCTG AGATCAATGTGGTCGGTCTGGCTTTTT-
TAACCTGGGGATTGTGACTCCTCTGATCATG
TTCATCCTGACAGCCACCCTGCTGATC-
CTCTCTCTCAAGAGACACACCCTACACATGGGAA
GCAATGCCACAGGGTCCAACGACCCCAG-
CATGGAGGCTCACATGGGGGCCATCAAAGCTA
TCAGCTACTTTCTCATTCTCTA-
CATTTTCAATGCAGTTGCTCTGTTTATC-
TACCTGTCCAAC ATGTTTGACATCAACAGTCTGTG-
GAATAATTTGTGCCAGATCATCATGGCTGCCTACCC
TG CCAGCCACTCAATTCTACTGATTCAA-
GATAACCCTGGGCTGAGAAGAGCCTG-
GAAGCGGCT TCAGCTTCGACTTCATCTTTAC-
CCAAAAGAGTGGACTCTGTGA hT2R54 Conceptual Translation (BAC AC024156)
(SEQ ID NO: 175)

MTKLCDPAESELSPFLITLILAVLLAEY-
LIGIIANGFIMAIHAAEWVQNKAVSTSGRILVFLSVSRI
ALQSLMMLEITISSTSLSFYSE-
DAVYYAFKISFIFLNFCSLWFAAWLS-
FFYFVKIANFSYPLFLKL RWRITGLIPWLLWLSVFISF-
SHSMFCINICTVYCNNSFPIHSSNSTKKTYLSEINVVG
LAFFFNLGI VTPLIMFILTATLLILSLKRHTLHMG-
SNATGSNDPSMEAHMGAIKAISYFLILY-
IFNAVALFIYLS NMFDINSLWNNLCQIIMAAYPASH-
SILLIQDNPGLRRAWKRLQLRLHLYPKEWTL hT2R55 Full-Length cDNA (BAC AC024156)
(SEQ ID NO: 176)

ATGGCAACGGTGAACACAGATGCCACA-
GATAAAGACATATCCAAGTTCAAGGTCACCTTC
ACTTTGGTGGTCTCCGGAATAGAGTG-
CATCACTGGCATCCTTGGGAGTGGCTTCATCACGG
CCATCTATGGGGCTGAGTGGGC-
CAGGGGCAAAACACTCCCCACTGGTGAC-
CGCATTATGTT GATGCTGAGCTTTTCCAGGCTCT-
TGCTACAGATTTGGATGATGCTGGAGAACATTTTCA
GT CTGCTATTCCGAATTGTTTATAAC-
CAAAACTCAGTGTATATCCTCT-
TCAAAGTCATCACTGT CTTTCTGAACCATTC-
CAATCTCTGGTTTGCTGCCTGGCTCAAAGTCTTCTA
TGTCTTAGAA TTGCAAACTTCAATCATCCTTTGT-
TCTTCCTGATGAAGAGGAAAATCATAGT-
GCTGATGCC TTGGCTTCTCAGGCTGTCAGTGTTG-
GTTTCCTTAAGCTTCAGCTTTCCTCTCTCGAGAGAT
G TCTTCAATGTGTATGTGAATAGCTCCAT-
TCCTATCCCCTCCTCCAACTCCACGGAG
AAGAA GTACTTCTCTGAGACCAATATGGTCAAC-
CTGGTATTTTTCTATAACATGGGGATCTTCGTTC

CTCTGATCATGTTCATCCTGGCAGCCAC-CCTGCTGATCCTCTCTCTCAAGAGACACACCCTACACATGGGAAGCAATGCCACAGGGTC-CAGGGACCCCAGCATGAAGGCTCACATAGGGGCCATCAAAGCCACCAGCTACTTTCTCATC-CTCTACATTTTCAATGCAATTGCTCTATTTCTTTCCACGTCCAACATCTTTGACACTTACAGT-TCCTGGAATATTTTGTGCAAGATCATCATGGCTGCCTACCCTGCCGGCCACTCAGTA-CAACTGATCTTGGGCAACCCTGGGCT-GAGAAGAGCCT GGAAGCGGTTTCAGCACCAAGT-TCCTCTTTACCTAAAAGGGCAGACTCTGTGA hT2R55 Conceptual Translation (BAC AC024156)
(SEQ ID NO: 177)

MATVNTDATDKDISKFKVTFTLVVS-GIECITGILGSGFITAIYGAEWARGK-TLPTGDRIMLMLSF SRLLLQIWMMLENIFSLL-FRIVYNQNSVYILFKVITVFLNHSNLWFAAWLKVFYCLRIANFNHP LFFLMKRRKIIVLMPWLLRLSVLVSLSF-SFPLSRDVFNVYVNSSIPIPSSN-STEKKYFSETNMVNLV FFYNMGIFVPLIMFILAATL-LILSLKRHTLHMGSNATGSRDPSMKAHIGAIKATSYFLILYIFNAI ALFLSTSNIFDTYSSWNILCKIIMAAY-PAGHSVQLILGNPGLRRAWKRFQHQVPLYLKGQTL hT2R61 Full-Length cDNA (BAC AC018630)
(SEQ ID NO: 178)

ATGATAACTTTTCTACCCAT-CATTTTTTCCAGTCTGGTAGTGGTTA-CATTTGTTATTGGAAA TTTTGCTAATGGCTTCATAG-CACTGGTAAATTCCATTGAGTGGTTCAAGAGACAAAAGATC TCCTTTGCTGACCAAATTCTCACT-GCTCTGGCGGTCTCCAGAGTTG-GTTTGCTCTGGGTATT ATTATTAAACTGGTAT-TCAACTGTGTTGAATCCAGCTTTTAATAGTGTAGAAGTAAGAACT ACTGCTTATAATATCTGGGCAGTGAT-CAACCAATTTCAGCAACTGGCTTGCTACTACCCTCAGCATATTTTATTTGCTCAAGATTGC-CAATTTCTCCAACTTTATTTTTCT-TCACTTAAAGAGG AGAGTTAAGAGTGTCATTCTG-GTGATGTTGTTGGGGCCTTTGCTATTTTGGCTTGTCATCT TTTTGTGATAAACATGAATGAGATTGT-GCGGACAAAAGAATTTGAAGGAAACATGACTTGGAAGATCAAATTGAAGAGTGCAATG-TACTTTTCAAATATGACTGTAACCATGGTAGCAAACTTAGTACCCTTCACTCTGACCCTAC-TATCTTTTATGCTGTTAATCTGTTCTTTGTGTAAACATCTCAAGAAGATGCAGCTCCATGG-TAAAGGATCTCAAGATCCCAGCACCAAGGTCCACATAAAAGCTTTGCAAACTGTGATCTCCT-TCCTCTTGTTATGTGCCATTTACTTTCTGTCCATAATGATATCAGTTTGGAGTTTTG-GAAGTCTGGAAAACAAACCTGTCTTCAT-GTTCTGCAAAG CTATTAGATTCAGCTATCCT-TCAATCCACCCATTCATCCTGATTTGGGGAAACAAGAAGCT AAAGCAGACTTTTCTTTCAGTTTTTTG-GCAAATGAGGTACTGGGTGAAAGGAGAGAAGACTTCATCTCCATAG hT2R61 Conceptual Translation (BAC AC018630)
(SEQ ID NO: 179)

MITFLPIIFSSLVVVTFVIGNFANGFI-ALVNSIEWFKRQKISFADQILTALAVS-RVGLLWVLLLNW YSTVLNPAFNSVEVRTTAYNI-WAVINHFSNWLATTLSIFYLLKIANFSNFIFLHLKRRVKSVILV MLLGPLLFLACHLFINMNEIVRTKEFEG-NMTWKIKLKSAMYFSNMTVTMVANLVPFTLTLLSFMLLICSLCKHLKKMQLHGKGSQDPST-KVHIKALQTVISFLLLCAIYFLSIMISVWSFGSLENKPVFMFCKAIRFSYPSIHPFILI-WGNKKLKQTFLSVFWQMRYWVKGEKTSSP hT2R63 Full-Length cDNA (BAC AC018630)
(SEQ ID NO: 180)

ATGATGAGTTTTCTACACAT-TGTTTTTTCCATTCTAGTAGTGGTTG-CATTTATTCTTGGAAA TTTTGCCAATGGCTTTATAG-CACTGATAAATTTCATTGCCTGGGTCAAGAGACAAAAGATC TCCTCAGCTGATCAAATTATTGCT-GCTCTGGCAGTCTCCAGAGTTG-GTTTGCTCTGGGTAA TATTATTACATTGGTAT-TCAACTGTGTTGAATCCAACTTCATCTAATTTAAAAGTAATAATT TTTATTTCTAATGCCTGGGCAGTAAC-CAATCATTTCAGCATCTGGCTTGCTACTAGCCTCAGCATATTTTATTTGCTCAAGATCGT-CAATTTCTCCAGACTTATTTTTCAT-CACTTAAAAAGGA AGGCTAAGAGTGTAGTTCTG-GTGATAGTGTTGGGGTCTTTGTTCTTTTTGGTTTGTCACCTT GTGATGAAACACACGTATATAAATGT-GTGGACAGAAGAATGTGAAGGAAACGTAACTTGGAAGATCAAACTGAGGAATGCAATGCAC-CTTTCCAACTTGACTGTAGCCATGCTAGCAAACTTGATACCATTCACTCTGACCCT-GATATCTTTTCTGCTGTTAATC-TACTCTCTGTGTAAACAT CTGAAGAAGATG-CAGCTCCATGGCAAAGGATCTCAAGATCCCAGCACCAAGATCCACATA AAAGCTCTGCAAACTGTGAC-CTCCTTCCTCATATTACTTGCCATT-TACTTTCTGTGTCTAAT CATATCGTTTTGGAATTT-TAAGATGCGACCAAAAGAAATTGTCTTAATGCTTTGCCAAGCT TTTGGAATCATATATCCATCATTCCACT-CATTCATTCTGATTTGGGGGAACAAGACGCTAAAGCAGACCTTTCTTTCAGTTTTGTG-GCAGGTGACTTGCTGGGCAAAAGGACA-GAACCAGTC AACTCCATAG hT2R63 Conceptual Translation (BAC AC018630)
(SEQ ID NO: 181)

MMSFLHIVFSILVVVAFILGNFANGFIA-LINFIAWVKRQKISSADQIIAALAVSRVGLLWVILLHWYSTVLNPTSSNLKVIIFISNAWAVT-NHFSIWLATSLSIFYLLKIVNFSRLIF-HHLKRKAKSVVLV IVLGSLFFLVCHLVMKHTYIN-VWTEECEGNVTWKIKLRNAMHLSNLTVAMLANLIPFTLTLISF LLLIYSLCKHLKKMQLHGKGSQDPSTKI-HIKALQTVTSFLILLAIYFLCLIISFWNFKMRPKEIVLMLCQAFGIIYPSFHSFILIWGNK-TLKQTFSLSVLWQVTCWAQKGQNQSTP hT2R64 Full-Length cDNA (BAC AC018630)
(SEQ ID NO: 182)

ATGACAACTTTTATACCCAT-CATTTTTTCCAGTGTGGTAGTGGTTC-TATTTGTTATTGGAAA TTTTGCTAATGGCTTCATAG-CATTGGTAAATTCCATTGAGCGGGTCAAGAGACAAAAGATC TCTTTTGCTGACCAGATTCTCACT-GCTCTGGCGGTCTCCAGAGTTG-GTTTGCTCTGGGTATT ATTATTAAATTGGTAT-TCAACTGTGTTTAATCCAGCTTTTTATAGTGTAGAAGTAAGAACT ACTGCTTATAATGTCTGGGCAGTAAC-CGGCCATTTCAGCAACTGGCTTGCTACTAGCCTCA

GCATATTTTATTTGCTCAAGATTGC-CAATTTCTCCAACCTTATTTTTCT-TCACTTAAAGAGG AGAGTTAAGAGTGTCATTCTG-GTGATGCTGTTGGGGCCTTTACTATTTTTGGCTTGTC AAC TTTTTGTGATAAACATGAAAGAGATTG-TACGGACAAAAGAATATGAAGGAAACTTGACTT GGAAGATCAAATTGAGGAGTGCAGTG-TACCTTTCAGATGCGACTGTAACCACGCTAGGAA ACTTAGTGCCCTTCACTCTGACCCTGC-TATGTTTTTTGCTGTTAATCTGTTCTCTGTGTAAA CATCTCAAGAAGATGCAGCTCCATGG-TAAAGGATCTCAAGATCCCAGCACCAAGGTCCAC ATAAAAGCTTTGCAAACTGT-GATCTTTTCCTCTTGTTATGTGCCGTT-TACTTTCTGTCCAT AATGATATCAGTTTG-GAGTTTTGGGAGTCTGGAAAACAAACCTGTCTTCA TGTTCTGCAAA GCTATTAGATTCAGCTATCCT-TCAATCCACCCATTCATCCTGATTTGGG-GAAACAAGAAGC TAAAGCA-GACTTTTCTTTCAGTTTTGCGGCAAGTGAGGTACT GGGTGAAAGGAGAGAAGC CTTCATCTCCATAG hT2R64 Conceptual Translation (BAC AC018630)
(SEQ ID NO: 183)

MTTFIPIIFSSVVVVLFVIGNFANGFI-ALVNSIERVKRQKISFADQILTALAVS-RVGLLWVLLLNW YSTVFNPAFYSVEVRTTAYNV-WAVTGHFSNWLATSLSIFYLLKIANFSNLIFLHLKRRV KSVIL VMLLGPLLFLACQLFVINMKEIVRT-KEYEGNLTWKIKLRSAVYLSDATVT-TLGNLVPFTLTLLC FLLLICSLCKHLKKMQLHGKG-SQDPSTKVHIKALQTVIFFLLLCAVYFLSIMISVWSFG SLENKP VFMFCKAIRFSYPSIHPFILI-WGNKKLKQTFLSVLRQVRYWVKGEKPSSP hT2R65 Full-Length cDNA (BAC AC018630)
(SEQ ID NO: 184)

ATGATGTGTTTTCTGCTCATCATTTCAT-CAATTCTGGTAGTGTTTGCATTTGTTCTTGGAAA TGTTGCCAATGGCTTCATAGCCCTAG-TAAATGTCATTGACTGGGTTAACACACGAAAGATC TCCTCAGCTGAGCAAATTCTCACT-GCTCTGGTGGTCTCCAGAATTGGTT-TACTCTGGGTCAT GTTATTCCTTTGGTATGCAACT-GTGTTTAATTCTGCTTTATATGGTTTAGAAGTAAGAA TTG TTGCTTCTAATGCCTGGGCTGTAAC-GAACCATTTCAGCATGTGGCTTGCT-GCTAGCCTCAG CATATTTGTTTGCTCAAGATTGC-CAATTTCTCCAACCTTATTTCTCTCCACCTAAAGAA GA GAATTAAGAGTGTTGTTCTGGTGATACT-GTTGGGGCCCTTGGTATTTCTGATTTGTAATCTT GCTGTGATAACCATGGATGAGAGAGT-GTGGACAAAAGAATATGAAGGAAATGTGACTTGG AAGATCAAATTGAGGAATGCAATACAC-CTTTCAAGCTTGACTGTAACTACTCTAGCAAACC TCATACCCTTTACTCTGAGCCTAATAT-GTTTTCTGCTGTTAATCTGTTCTCTTTGTAAACAT CTCAAGAAGATGCGGCTCCATAGCAAAG-GATCTCAAGATCCCAGCACCAAGGTCCATATA AAAGCTTTGCAAACTGTGACCTCCTTC-CTCATGTTATTTGCCATTTACTTTCTGTGTATAAT CACATCCAACTTGGAATCTTAGGACA-CAGCAGAGCAAACTTGTACTCCT-GCTTTGCCAAACT GTTGCAATCATGTATCCTTCAT-TCCACTCATTCATCCTGATTATGGGAAGTAGGAAGC TAA AACAGACCTTTCTTTCAGTTTTGTGGCA-GATGACACGCTGA hT2R65 Conceptual Translation (BAC AC018630)
(SEQ ID NO: 185)

MMCFLLIISSILVVFAFVLGNVANGFI-ALVNVIDWVNTRKISSAEQILTALVVS-RIGLLWVMLFL WYATVFNSALYGLEVRIVASNA-WAVTNHFSMWLAASLSIFCLLKIANFSNLISLHLKKRI KSVV LVILLGPLVFLICNLAVITMDERVWT-KEYEGNVTWKIKLRNAIHLSSLTVT-TLANLIPFTLSLICF LLLICSLCKHLKKMRLHSKG-SQDPSTKVHIKALQTVTSFLMLFAIYFLCIITSTWNLR TQQSKLV LLLCQTVAIMYPSFHSFILIMG-SRKLKQTFLSVLWQMTR hT2R67 Full-Length cDNA (BAC AC018630)
(SEQ ID NO: 186)

ATGATAACTTTTCTATA-CATTTTTTTTTCAATTCTAATAATG-GTTTTATTTGTTCTCGGAAA CTTTGCCAATGGCT-TCATAGCACTGGTAAATTTCATTGACTGGGTGAAGA GAAAAGATC TCCTCAGCTGACCAAATTCTCACT-GCTCTGGCGGTCTCCAGAATTG-GTTTGCTCTGGGCATT ATTATTAAATTGGTATT-TAACTGTGTTGAATCCAGCTTTTTATAGTGTAGAATT AAGAATT ACTTCTTATAATGCCTGGGTTGTAAC-CAACCATTTCAGCATGTGGCTTGTCTGCTAACCTCA GCATATTTTATTTGCTCAAGATTGC-CAATTTCTCCAACCTTCTTTTTCT-TCATTTAAAGAGG AGAGTTAGGAGTGTCATTCTG-GTGATACTGTTGGGGACTTTGATATTTTTGGTTTGTC ATC TTCTTGTGGCAAACATGGATGAGAGTAT-GTGGGCAGAAGAATATGAAGGAAACATGACTG GGAAGATGAAATTGAGGAATACAGTA-CATCTTTCATATTTGACTGTAACTACCCTATGGAG CTTCATACCCTTTACTCTGTCCCT-GATATCTTTTCTGATGCTAATCTGT-TCTCTGTGTAAAC ATCTCAAGAAGATGCAGCTC-CATGGAGAAGGATCGCAAGATCTCAGCACCAAGGT CCACA TAAAAGCTTTGCAAACTCTGATCTCCT-TCCTCTTGTTATGTGCCATTTTCTTTCTATTCCTA ATCGTTTCGGTTTGGAGTCCTAGGAG-GCTGCGGAATGACCCGGTTGTCATGGTTAGCAAGG CTGTTGGAAACATATATCTTGCATTC-GACTCATTCATCCTAATTTGGAGAACCAAGAAGCT AAAACACACCTTTCTTTTGATTTTGTGT-CAGATTAGGTGCTGA hT2R67 Conceptual Translation (BAC AC018630)
(SEQ ID NO: 187)

MITFLYIFFSILIMVLFVLGNFANGFI-ALVNFIDWVKRKKISSADQILTALAVS-RIGLLWALLLNW YLTVLNPAFYSVELRITSYNAWV-VTNHFSMWLAANLSIFYLLKIANFSNLLFLHLKRRVR SVIL VILLGTLIFLVCHLLVANMDESM-WAEEYEGNMTGKMKLRNTVHLSYLTVT-TLWSFIPFTLSLIS FLMLICSLCKHLKKMQLHGEG-SQDLSTKVHIKALQTLISFLLLCAIFFLFLIVSVWSPRR LRNDP VVMVSKAVGNIYLAFDSFILIWRT-KKLKHTFLLILCQIRC hT2R71 Full-Length cDNA (BAC AC073264)
(SEQ ID NO: 188)

ATGCAAGCAGCACTGACGGCCTTCT-TCGTGTTGCTCTTTAGCCTGCTGAGTCTTCTGGGGA TTGCAGCGAATGGCTTCATTGTGCTGGT-GCTGGGCAGGGAGTGGCTGCGATATGGCAGGT

TGCTGCCCTTGGATATGATCCTCATT-
AGCTTGGGTGCCTCCCGCTTCTGCCTG-
CAGTTGGTT GGGACGGTGCACAACTTCTAC-
TACTCTGCCCAGAAGGTCGAGTACTCTGGGGGTCT
CGGCC GACAGTTCTTCCATCTACACTGGCACT-
TCCTGAACTCAGCCACCTTCTGGTTTTGCAGCTGG
CTCAGTGTCCTGTTCTGTGTGAAGAT-
TGCTAACATCACACACTCCACCTTCCTGTGGCTGA
AGTGGAGGTTCCCAGGGTGGGTGCCCTG-
GCTCCTGTTGGGCTCTGTCCTGATCTCCTTCAT CAT-
AACCCTGCTGTTTTTTTGGGTGAACTAC-
CCTGTATATCAAGAATTTTTAATTAGAAAAT
TTTCTGGGAACATGACCTACAAGTG-
GAATACAAGGATAGAAACATACTATTTCCCATCCCT
GAAACTGGTCATCTGGTCAATTC-
CTTTTTCTGTTTTTCTGGTCTCAATTAT-
GCTGTTAATTA ATTCTCTGAGGAGGCATACTCA-
GAGAATGCAGCACAACGGGCACAGCCTGCAGGAC
CCCA GCACCCAGGCTCACACCAGAGCTCT-
GAAGTCCCTCATCTCCTTCCTCATTCTTTATGCTCTG
TCCTTTCTGTCCCTGATCATTGATGCCG-
CAAAATTTATCTCCATGCAGAACGACTTTTACTG
GCCATGGCAAATTGCAGTCTACCTGTG-
CATATCTGTCCATCCCTTCATCCTCATCTTCAGCA
ACCTCAAGCTTCGAAGCGTGTTCTCG-
CAGCTCCTGTTGTTGGCAAGGGGCTTCTGGGTGGC
CTAG hT2R71 Conceptual Translation (BAC AC073264) (SEQ ID NO: 189)

MQAALTAFFVLLFSLLSLLGIAANGFIV-
LVLGREWLRYGRLLPLDMILISLGASRFCLQLVGTVH
NFYYSAQKVEYSGGLGRQFFHLHWHFLN-
SATFWFCWLSVLFCVKIANITHSTFLWLKWRFPG
WVPWLLLGSVLISFIITLLFF-
WVNYPVYQEFLIRKFSGNMTYKWNTRI-
ETYYFPSLKLVIWSIPFS VFLVSIMLLINSLRRHTQRM-
QHNGHSLQDPSTQAHTRALKSLISFLILYALSFLSLIID
AAKFISM QNDFYWPWQIAVYLCISVHPFILIFSN-
LKLRSVFSQLLLLARGFWVA hT2R75 Full-Length cDNA (SEQ ID NO: 190)

ATGATAACTTTTCTGCCCAT-
CATTTTTTCCATTCTAATAGTGGTTA-
CATTTGTGATTGGAAA TTTTGCTAATGGCTTCATAG-
CATTGGTAAATTCCATTGAGTGGTTCAAGAGACAAA
AGATC TCTTTTGCTGACCAAATTCTCACT-
GCTCTGGCAGTCTCCAGAGTTGGTT-
TACTCTGGGTATT AGTATTAAATTGGTATGCAACT-
GAGTTGAATCCAGCTTTTAACAGTATAGAAGTAAGA
ATT ACTGCTTACAATGTCTGGGCAGTAAT-
CAACCATTTCAGCAACTGGCTTGCTACTAGCCTCA
GCATATTTTATTTGCTCAAGATTGC-
CAATTTCTCCAACCTTATTTTTCT-
TCACTTAAAGAGG AGAGTTAAGAGTGTTGTTCTG-
GTGATACTATTGGGGCCTTTGCTATTTTTGGTTTGTC
ATCT TTTTGTGATAAACATGAATCAGAT-
TATATGGACAAAAGAATATGAAGGAAA-
CATGACTTG GAAGATCAAACTGAGGAGTGCAATG-
TACCTTTCAAATACAACGGTAACCATCCTAGCAAA
CTTAGTTCCCTTCACTCTGACCCT-
GATATCTTTTCTGCTGTTAATCTGT-
TCTCTGTGTAAAC ATCTCAAAAAGATGCAGCTC-
CATGGCAAAGGATCTCAAGATCCCAGCATGAAGGT
CCACA TAAAAGCTTTGCAAACTGTGACCTCCT-
TCCTCTTGTTATGTGCCATTTACTTTCTGTCCATA
ATCATGTCAGTTTG-
GAGTTTTGAGAGTCTGGAAAACAAACCT-
GTCTTCATGTTCTGCCAAG CTATTGCATTCAGC-
TATCCTTCAACCCACCCATTCATCCTGATTTGGGGA
AACAAGAAGCT AAAGCA-
GACTTTTCTTTCAGTTTTGTGGCATGT-
GAGGTACTGGGTGAAAGGAGAGAAGCCT TCATCT-
TCATAG hT2R59 Conceptual Translation cDNA (SEQ ID NO: 191)

MITFLPIIFSILIVVTFVIGNFANGFI-
ALVNSIEWFKRQKISFADQILTALAVS-
RVGLLWVLVLNW YATELNPAFNSIEVRITAYNVWAV-
INHFSNWLATSLSIFYLLKIANFSNLIFLHLKRRVKSV
VLVI LLGPLLFLVCHLFVINMNQIIWTKEYEG-
NMTWKIKLRSAMYLSNTTVTILANLVPFTLTLISFLL
LICSLCKHLKKMQLHGKG-
SQDPSMKVHIKALQTVTSFLLICAIY-
FLSIIMSVWSFESLENKPVF MFCEAIAFSYPSTHPFILI-
WGNKKLKQTFLSVLWHVRYWVKGEKPSSS hT2R59 Pseudogene (BAC AC018630) (SEQ ID NO: 192)

ATGGTATATTTTCTGCTCATCATTTTAT-
CAATTCTGGTAGTGTTTGCATTTGTTCTTGGAAA
TTTTTCCAATGGCTTCATAGCTCTAG-
TAAATGTCATTGACTGGGTTAAGACACGAAAGATC
TCCTCAGCTGACCAAATCCTCACT-
GCTCTGGTGGTCTCCAGAATTGGTT-
TACTCTGGGTCAT ATTATTACATTGGTATGCAAAT-
GTGTTTAATTCAGCTTTATATAGTTCAGAAGTAGGA
GCT GTTGCTTCTAATATCTCAGCAATAAT-
CAACCAATTTCAGCATCTGGCTTGCT-
GCTAGCCTCAG CATATTTTATTTGCTCAAGATTGC-
CAATTTCTCCAACCTTATTTTTCTCCACCTAAAGAA
GA GAATTAGGAGTGTTGTTCTGGTGATACT-
GTTGGGTCCCTTGGTATTTTTGATTTGTAATCTT
GCTGTGATAACCATGGATGACAGTGT-
GTGGACAAAAGAATATGAAGGAAATGTGACTTGG
AAGATCAAATTGAGGAATGCAATACAC-
CTTTCAAACTTGACTGTAAGCACACTAGCAAACC
TCATACCCTTCATTCTGACCCTAATAT-
GTTTTCTGCTGTTAATCTGTTCTCTGCATAAACAT
CTCAAGAAGATGCAGCTCCATGGCAAAG-
GATCTCAAGATCTCAGCACCAAGGTCCACATA
AAAGCTTTGCAAACTGTGATCTCCTTC-
CTCATGTTATATGCCATTTACTTTCTGTATCTAAT
CACATTAACCTGGAATCTTTGAACACAG-
CAGAACAAACTTGTATTCCTGCTTTGCCAAACT
CTTGGAATCATGTATCCTTCATTCCACT-
CATTCTTCCTGATTATGGGAAGCAGGAAACTAA
AACAGACGTTTCTTTCAGTTTTATGT-
CAGGTCACATGCTTAGTGAAAGGACAGCAACCCTC
AACTCCATAG hT2R69 Pseudogene (BAC AC018630) (SEQ ID NO: 193)

ATGATATGTTTTCTGCTCATCATTTTAT-
CAATTCTGGTAGTGTTTGCATTTGTTCTTGGAAA
TGTTGCCAATGGCTTCATAGCTCTAG-
TAGGTGTCCTTGAGTGGGTTAAGACACAAAAGATC
TCATCAGCTGACCAAATTTCTCACT-
GCTCTGGTGGTGTCCAGAGTTGGTT-
TACTCTGGGTC ATATTATTACATTGGTATGCAACT-
GTGTTTAATTTGGCTTCACATAGATTAGAAGTAAGA
A TTTTTGGTTCTAATGTCTCAGCAATAAC-

CAAGCATTTCAGCATCTGGGTGTTACTAGCCTCA GCATATTTCATTTGCTCAAGACTGC-CAATTTCTCCAACCTTATTTTTCTCCAC-CTAAAGAAA AGGATTAAGAATGTTGGTTTGGTGAT-GCTGTTGGGGCCCTTGGTATTTTTCATTTGTAATC TTGCTCTGATAACCACGGGTGAGAGTGT-GTGGACAAAAGAATATGAAGGAAATTTGTCTT GGATGATCAAATTGAGGAATGCAATA-CAGCTTTCAAACTTGACTGTAACCATGCCAGCAA ACGTCACACCCTGCACTCTGACAC-TAATATCTTTTCTGCTGTTAATCTAT-TCTCCATGTAAA CATGTCAAGAAGATGCAGCTC-CATGGCAAAGGATCTCAACATCTCAGCACCAAGGT GCAC ATAAAAGCTTTGCAAACTGTGATCTCCT-TCCTTATGTTATTTGCCATTTACTTTCTGTGTCT AAT-CACATCAACTTGGAATCCTAGGACTCAG-CAGAGCAAACTTGTATTCCTGCTTTACCAA ACTCTTGGATTCATGTATCTTTTGTTC-CACTCATTCATCCTGACTATGGGAAGTAGGAAGCC AAAACAGACCTTTCTTTCAGCTTTGTGA mT2R33 Full-Length cDNA (BAC AC020619)
(SEQ ID NO: 194)

ATGACCTCCCCTTTCCCAGCTATTTAT-CACATGGTCATCATGACAGCAGAGTTTCTCATCGG GACTACAGTGAATGGATTCCTTATCAT-TGTGAACTGCTATGACTTGTTCAAGAGCCGAACG TTCCTGATCCTGCAGACCCTCTTGATGT-GCACAGGGCTGTCCAGACTCGGTCTGCAGATAA TGCTCATGACCCAAAGCTTCTTCTCTGT-GTTCTTTCCATACTCTTATGAGGAAAATATTTAT AGTTCAGATATAATGTTCGTCTGGATGT-TCTTCAGCTCGATTGGCCTCTGGTTTGCCACATG TCTCTCTGTCTTTTACTGCCTCAA-GATTTCAGGCTTCACTCCACCCTG-GTTTCTTTGGCTGA AATTCAGAATTTCAAAGCT-CATATTTTGGCTGCTTCTGGGCAGCTTGCTGGCCTC TCTGGG CACTGCAACTGTGTGCATCGAGGTAG-GTTTCCCTTTAATTGAGGATGGCTATGTCCTGAGA AACGCAGGACTAAATGATAGTAATGC-CAAGCTAGTGAGAAATAATGACTTGCTCCTCATC AACCTGATCCTCCTGCTTCCCCTGTCT-GTGTTTGTGATGTGCACCTCTATGTTATTTGTTTC TCTTTACAAGCACATGCACTGGATG-CAAAGCGAATCTCACAAGCTGTCAAGT-GCCAGAACC GAAGCTCATATAAATGCATTAAAGA-CAGTGACAACATTCTTTTGTTTCTTTGTTTCTTACTT TGCTGCCTTCATGGCAAATATGACATT-TAGAATTCCATACAGAAGTCATCAGTTCTTCGTG GTGAAGGAAATCATGGCAGCATATC-CCGCCGGCCACTCTGTCATAATCGTCTTGAGTAACT CTAAGTTCAAAGACTTATTCAGGAGAAT-GATCTGTCTACAGAAGGAAGAGTGA mT2R33 Conceptual Translation (BAC AC020619)
(SEQ ID NO: 195)

MTSPFPAIYHMVIMTAEFLIGTTVNG-FLIIVNCYDLFKSRTFLILQTLLMCT-GLSRLGLQIMLMT QSFFSVFFPYSYEENIYSSDIM-FVWMFFSSIGLWFATCLSVFYCLKISGFTPPWFLWLKF RISKLIF WLLLGSLLASLGTATVCIEVGF-PLIEDGYVLRNAGLNDSNAKLVRNNDLL-LINLILLLPLSVFVM CTSMLFVSLYKHMHWM-QSESHLKSSARTEAHINALKTVTTFFCFFVSYFAAFM ANMTFRIPYR SHQFFVVKEIMAAYPAGHSVIIVLSN-SKFKDLFRRMICLQKEE

SEQ ID NO: 196

Amino Acid Sequence rT1R3

MPGLAILGLSLAAFLELGMGSS-LCLSQQFKAQGDYILGGLFPLGTTEE-ATLNQRTQPNGI LCTRFSPLGLFLAMAMKMAVEEIN-NGSALLPGLRLGYDLFDTCSEPVVTMKPSLMFMAKV GSQSIAAYCNYTQYQPRVLAVIGPHSSE-LALITGKFFSFFLMPQVSYSASMDRLSDRETF PSF-FRTVPSDRVQLQAVVTLLQNFSWN-WVAALGSDDDYGREGLSIFSGLANSRGICIAHE GLVPQHDTSGQQLGKVVDVLRQVN-QSKVQVVVLFASARAVYSLFSYSILHDLSPKVWVAS ESWLTSDLVMTLPNIARVGTVLGFLQR-GALLPEFSHYVETRLALAADPTFCASLKAELDL EERVMGPRCSQCDYIMLQNLSSGLMQNL-SAGQLHHGIFATYAAVYSVAQALHNTLQCNVS HCHTSEPVQPWQLLENMYNMSFRA-RDLTLQFDAKGSVDMEYDLKMWVWQSPT-PVLHTVGT FNGTLQLQHSKMYWPGNQVPVSQCS-RQCKDGQVRRVKGFHSCCYDCVDCKAGSYRKHPDD FTCTPCGKDQWSPEKSTTCLPRRPK-FLAWGEPAVLSLLLLLCLVLGLTLAALGLFVHYWD SPLVQASGGSLFCFGLICLGLFCLSVLL-FPGRPRSASCLAQQPMAHLPLTGCLSTLFLQA AEIFVESELPLSWANWLCSYLRGP-WAWLVVLLATLVEAALCAWYLMAFPPEV-VTDWQVLP TEVLEHCRMRSWVSLGLVHITNAV-LAFLCFLGTFLVQSQPGRYNRARGLTFAMLAYFIIW VSFVPLLANVQVAYQPAVQMGAILFCAL-GILATFHLPKCYVLLWLPELNTQEFFLGRSPK EAS-DGNSGSSEATRGHSE

SEQ ID NO: 197

Amino Acid Sequence hT1R1

MLLCTARLVGLQLLISCCWAFACHST-ESSPDFTLPGDYLLAGLFPLHSGCLQVRHRPEVT LCDRSCSFNEHGYHLFQAMRLGV-EEINNSTALLPNITLGYQLYDVCSDSANVYATLRVLS LPGQHHIELQGDLLHYSPTVLAVIGPD-STNRAATTAALLSPFLVPMISYAASSETLSVKR QYPS-FLRTIPNDKYQVETMVLLLQKFGWTWIS-LVGSSDDYGQLGVQALENQATGQGICIA FKDIMPFSAQVGDERMQCLMRHLAQA-GATVVVVFSSRQLARVFFESVVLTNLTGKVWVAS EAWALSRHITGVPGIQRIGMV-LGVAIQKRAVPGLKAFEEAYARAD-KKAPRPCHKGSWCSS NQLCRECQAFMAHTMP-KLKAFSMSSAYNAYRAVYAVAHGLHQLLGCASGACS RGRVYPWQ LLEQIHKVHFLLHKDTVAFNDRND-PLSSYNIIAWDWNGPKWTFTVLGSSTWSPVQLNINE TKIQWHGKDNQVPKSVCSSDCLEGHQRV-VTGFHHCCFECVPCGAGTFLNKSDLYRCQPCG KEE-WAPEGSQTCFPRTVVFLALREHTSWVL-LAANTLLLLLLLGTAGLFAWHLDTPVVRSA GGRLCFLMLGSLAAGSGSLYGFFGEPTR-PACLLRQALFALGFTIFLSCLTVRSFQLIIIF KFST-KVPTFYHAWVQNHGAGLFVMISSAAQL-LICLTWLVVWTPLPAREYQRFPHLVMLEC TETNSLGFILAFLYNGLLSISAFAC-SYLGKDLPENYNEAKCVTFSLLFNFVSWIAFFTTA SVYDGKYLPAANMMAGLSSLSSGFGGY-FLPKCYVILCRPDLNSTEHFQASIQDYTRRCGS T

SEQ ID NO: 198

Amino Acid Sequence hT1R2

MGPRAKTICSLFFLLWVLAEPAENSD-FYLPGDYLLGGLFSLHANMKGIVHLNFLQVPMCK

EYEVKVIGYNLMQAMRFAVEEINNDSS-
LLPGVLLGYEIVDVCYISNNVQPVLYFLAHEDN
LLPIQEDYSNYISRVVAVIGPDNSES-
VMTVANFLSLFLLPQITYSAISDELRDKVRFPAL LRT-
TPSADHHVEAMVQLMLHFRWNWIIV-
LVSSDTYGRDNGQLLGERVARRDICIAFQETL
PTLQPNQNMTSEERQRLVTIVD-
KLQQSTARVVVVFSPDLTLYHFFNEVL-
RQNFTGAVWIA SESWAIDPVLHNLTELGHLGTFLGI-
TIQSVPIPGFSEFREWGPQAGPPPLSRTSQSYTCN
QECDNCLNATLSFNTILRLSGERVVYS-
VYSAVYAVAHALHSLLGCDKSTCTKRVVYPWQL
LEEIWKVNFTLLDHQIFFDPQGD-
VALHLEIVQWQWDRSQNPFQSVASYY-
PLQRQLKNIQD ISWHTVNNTIPMSMCSKRCQS-
GQKKKPVGIHVCCFECIDCLPGTFLNHTEDEYECQAC
PN NEWSYGSETSCFKRQLVFLEWHEAPTIA-
VALLAALGFLSTLAILVIFWRHFQTPIVRSAG GPMC-
FLMLTLLLVAYMVVPVYVGPPKVST-
CLCRQALFPLCFTICISCIAVRSFQIVCAFK
MASRFPRAYSYWVRYQGPYVSMAFITV-
LKMVIVVIGMLATGLSPTTRTDPDDPKITIVSC
NPNYRNSLLFNTSLDLLLSVVGFS-
FAYMGKELPTNYNEAKFITLSMTFYFTSSVSLCTFM
SAYSGVLVTIVDLLVTVLNLLAISLGYF-
GPKCYMILFYPERNTPAYFNSMIQGYTMRRD

SEQ ID NO: 199

Amino Acid Sequence hT1R3

MLGPAVLGLSLWALLHPGTGA-
PLCLSQQLRMKGDYVLGGLFPLGEAEEA-
GLRSRTRPSSP VCTRFSSNGLLWALAMKMAVEEINN-
KSDLLPGLRLGYDLFDTCSEPVVAMKPSLMFLAKA
GSRDIAAYCNYTQYQPRVLAVIGPHSSE-
LAMVTGKFFSFELMPQVSYGASMELLSARETF PSF-
FRTVPSDRVQLTAAAELLQEFGWN-
WVAALGSDDEYGRQGLSIFSALAAARGICIAHE
GLVPLPRADDSRLGKVQDVLHQVNQSS-
VQVVLLFASVHAAHALFNYSISSRLSPKVWVAS
EAWLTSDLVMGLPGMAQMGTVLGFLQR-
GAQLHEFPQYVKTHLALATDPAFCSALGEREQG
LEEDVVGQRCPQCDCITLQNVSAGLNH-
HQTFSVYAAVYSVAQALHNTLQCNASGCPAQDP
VKPWQLLENMYNLTFHVGGLPLRFDSS-
GNVDMEYDLKLWVWQGSVPRLHDVGRFNGSLRT
ERLKIRWHTSDNQKPVSRCSRQC-
QEGQVRRVKGFHSCCYDCVDCEAGSYR-
QNPDDIACTF CGQDEWSPERSTRCFRRRSR-
FLAWGEPAVLLLLLLLSLALGLVLAALGLFVHHRDSP
LVQ ASGGPLACFGLVCLGLVCLSVLLF-
PGQPSPARCLAQQPLSHLPLTGCLSTLFLQAAEIFV
ESELPLSWADRLSGCLRGPWAWLVVL-
LAMLVEVALCTWYLVAFPPEVVTDWHMLPTEALV
HCRTRSWVSFGLAHATNATLAFLCFLGT-
FLVRSQPGRYNRARGLTFAMLAYFITWVSFVP LLAN-
VQVVLRPAVQMGALLLCVLGILAAFHL-
PRCYLLMRQPGLNTPEFFLGGGPGDAQGQ
NDGNTGNQGKHE

SEQ ID NO: 200

Nucleic Acid Sequence hT1R1

ATGCTGCTCTGCACGGCTCGCCTGGTCG-
GCCTGCAGCTTCTCATTTCCTGCTGCTGGGCC
TTTGCCTGCCATAGCACGGAGTCTTCTC-
CTGACTTCACCCTCCCCGGAGATTACCTCCTG
GCAGGCCTGTTCCCTCTCCATTCTGGCT-
GTCTGCAGGTGAGGCACAGACCCGAGGTGACC
CTGTGTGACAGGTCTTGTAGCTTCAAT-
GAGCATGGCTACCACCTCTTCCAGGCTATGCGG
CTTGGGGTTGAGGAGATAAACAACTC-
CACGGCCCTGCTGCCCAACATCACCCTGGGGTAC
CAGCTGTATGATGTGTGTTCTGACTCT-
GCCAATGTGTATGCCACGCTGAGAGTGCTCTCC
CTGCCAGGGCAACACCACATAGAGCTC-
CAAGGAGACCTTCTCCACTATTCCCCTACGGTG
CTGGCAGTGATTGGGCCTGACAGCAC-
CAACCGTGCTGCCACCACAGCCGCCCTGCTGAGC
CCTTTCCTGGTGCCCATGATTAGCTAT-
GCGGCCAGCAGCGAGACGCTCAGCGTGAAGCGG
CAGTATCCCTCTTTCCTGCGCACCATC-
CCCAATGACAAGTACCAGGTGGAGACCATGGTG
CTGCTGCTGCAGAAGTTCGGGTGGAC-
CTGGATCTCTCTGGTTGGCAGCAGTGACGACTAT
GGGCAGCTAGGGGTGCAGGCACTG-
GAGAACCAGGCCACTGGTCAGGGGATCT-
GCATTGCT TTCAAGGACATCATGCCCTTCTCTGC-
CCAGGTGGGCGATGAGAGGATGCAGTGCCTCATG
CGCCACCTGGCCCAGGCCGGGGCCAC-
CGTCGTGGTTGTTTTTTCCAGCCGGCAGTTGGCC
AGGGTGTTTTTCGAGTCCGTGGTGCT-
GACCAACCTGACTGGCAAGGTGTGGGTCGCCTCA
GAAGCCTGGGCCCTCTCCAGGCACAT-
CACTGGGGTGCCCGGGATCCAGCGCATTGGGATG
GTGCTGGGCGTGGCCATCCAGAA-
GAGGGCTGTCCCTGGCCTGAAG-
GCGTTTGAAGAAGCC TATGCCCGGGCAGACAA-
GAAGGCCCCTAGGCCTTGCCACAAGGGCTCCTGGT
GCAGCAGC AATCAGCTCTGCAGAGAATGC-
CAAGCTTTCATGGCACACACGATGC-
CCAAGCTCAAAGCC TTCTCCATGAGTTCTGCCTA-
CAACGCATACCGGGCTGTGTATGCGGTGGCCCATG
GCCTC CACCAGCTCCTGGGCTGTGCCTCTG-
GAGCTTGTTCCAGGGGCCGAGTCTACCCCTGGCAG
CTTTTGGAGCAGATCCACAAGGTG-
CATTTCCTTCTACACAAGGACACTGTGGCGTTTAAT
GACAACAGAGATCCCCTCAGTAGC-
TATAACATAATTGCCTGGGACTGGAATG-
GACCCAAG TGGACCTTCACGGTCCTCGGTTCCTC-
CACATGGTCTCCAGTTCAGCTAAACATAAATGAG
ACCAAAATCCAGTGGCACGGAAAGGA-
CAACCAGGTGCCTAAGTCTGTGTGTTCCAGCGAC
TGTCTTGAAGGGCACCAGCGAGTGGT-
TACGGGTTTCCATCACTGCTGCTTTGAGTGTGTG
CCCTGTGGGGCTGGGACCTTCCTCAA-
CAAGAGTGACCTCTACAGATGCCAGCCTTGTGGG
AAAGAAGAGTGGGCACCTGAGGGAAGC-
CAGACCTGCTTCCCGCGCACTGTGGTGTTTTTG
GCTTTGCGTGAGCACACCTCTTGGGT-
GCTGCTGGCAGCTAACACGCTGCTGCTGCTGCTG
CTGCTTGGGACTGCTGGCCTGTTTGC-
CTGGCACCTAGACACCCCTGTGGTGAGGTCAGCA
GGGGGCCGCCTGTGCTTTCTTAT-
GCTGGGCTCCCTGGCAGCAGGTAGTG-
GCAGCCTCTAT GGCTTCTTTGGGGAACCCACAAG-
GCCTGCGTGCTTGCTACGCCAGGCCCTCTTTGCCCT
T GGTTTCACCATCTTCCTGTCCTGCCTGA-
CAGTTCGCTCATTCCAACTAATCATCATCTTC
AAGTTTTCCACCAAGGTACCTACATTC-
TACCACGCCTGGGTCCAAAACCACGGTGCTGGC
CTGTTTGTGATGATCAGCTCAGCGGC-
CCAGCTGCTTATCTGTCTAACTTGGCTGGTGGTG
TGGACCCCACTGCCTGCTAGGGAATAC-

CAGCGCTTCCCCCATCTGGTGATGCTTGAGTGC
ACAGAGACCAACTCCCTGGGCTTCAT-
ACTGGCCTTCCTCTACAATGGCCTCCTCTCCATC
AGTGCCTTTGCCTGCAGCTACCTGGG-
TAAGGACTTGCCAGAGAACTACAACGAGGCCAAA
TGTGTCACCTTCAGCCTGCTCTTCAACT-
TCGTGTCCTGGATCGCCTTCTTCACCACGGCC
AGCGTCTACGACGGCAAGTACCTGCCT-
GCGGCCAACATGATGGCTGGGCTGAGCAGCCTG
AGCAGCGGCTTCGGTGGGTATTTTCTGC-
CTAAGTGCTACGTGATCCTCTGCCGCCCAGAC
CTCAACAGCACAGAGCACTTCCAGGC-
CTCCATTCAGGACTACACGAGGCGCTGCGGCTCC
ACCTGA

SEQ ID NO: 201

Nucleic Acid Sequence hT1R3

ATGCTGGGCCCTGCTGTCCTGGGCCT-
CAGCCTCTGGGCTCTCCTGCACCCTGGGACGGGG
GCCCCATTGTGCCTGTCACAGCAACT-
TAGGATGAAGGGGGACTACGTGCTGGGGGGGCTG
TTCCCCCTGGGCGAGGCCGAGGAGGCTG-
GCCTCCGCAGCCGGACACGGCCCAGCAGCCCT
GTGTGCACCAGGTTCTCCTCAAACGGC-
CTGCTCTGGGCACTGGCCATGAAAATGGCCGTG
GAGGAGATCAACAACAAGTCGGATCT-
GCTGCCCGGGCTGCGCCTGGGCTACGACCTCTTT
GATACGTGCTCGGAGCCTGTGGTGGC-
CATGAAGCCCAGCCTCATGTTCCTGGCCAAGGCA
GGCAGCCGCGACATCGCCGCCTACTG-
CAACTACACGCAGTACCAGCCCCGTGTGCTGGCT
GTCATCGGGCCCCACTCGTCA-
GAGCTCGCCATGGTCACCGGCAAGTTCT-
TCAGCTTCTTC CTCATGCCCCAggtcagCTACGGT-
GCTAGCATGGAGCTGCTGAGCGCCCGGGAGACCTT
C CCCTCCTTCTTCCGCACCGTGCCCAGC-
GACCGTGTGCAGCTGACGGCCGCCGCGGAGCTG
CTGCAGGAGTTCGGCTGGAACTGGGTG-
GCCGCCCTGGGCAGCGACGACGAGTACGGCCGG
CAGGGCCTGAGCATCTTCTCGGCCCTG-
GCCGCGGCACGCGGCATCTGCATCGCGCACGAG
GGCCTGGTGCCGCTGCCCCGTGCCGAT-
GACTCGCGGCTGGGGAAGGTGCAGGACGTCCTG
CACCAGGTGAACCAGAGCAGCGTGCAG-
GTGGTGCTGCTGTTCGCCTCCGTGCACGCCGCC
CACGCCCTCTTCAACTACAGCATCAG-
CAGCAGGCTCTCGCCCAAGGTGTGGGTGGCCAGC
GAGGCCTGGCTGACCTCTGACCTGGT-
CATGGGGCTGCCCGGCATGGCCCAGATGGGCACG
GTGCTTGGCTTCCTCCAGAGGGGTGC-
CCAGCTGCACGAGTTCCCCCAGTACGTGAAGACG
CACCTGGCCCTGGCCACCGACCCGGCCT-
TCTGCTCTGCCCTGGGCGAGAGGGAGCAGGGT
CTGGAGGAGGACGTGGTGGGCCAGCGCT-
GCCCGCAGTGTGACTGCATCACGCTGCAGAAC
GTGAGCGCAGGGCTAAATCACCACCA-
GACGTTCTCTGTCTACGCAGCTGTGTATAGCGTG
GCCCAGGCCCTGCACAACACTCTTCAGT-
GCAACGCCTCAGGCTGCCCCGCGCAGGACCCC
GTGAAGCCCTGGCAGCTCCTGGAGAA-
CATGTACAACCTGACCTTCCACGTGGGCGGGCTG
CCGCTGCGGTTCGACAGCAGCG-
GAAACGTGGACATGGAGTACGACCT-
GAAGCTGTGGGTG TGGCAGGGCTCAGTGCCCAG-
GCTCCACGACGTGGGCAGGTTCAACGGCAGCCTCA
GGACA GAGCGCCTGAAGATCCGCTGGCA-
CACGTCTGACAACCAGAAGCCCGTGTC-
CCGGTGCTCG CGGCAGTGCCAGGAGGGCCAGGT-
GCGCCGGGTCAAGGGGTTCCACTCCTGCTGCTACG
AC TGTGTGGACTGCGAGGCGGGCAGCTAC-
CGGCAAAACCCAGACGACATCGCCTGCACCTTT
TGTGGCCAGGATGAGTGGTCCCCGGAGC-
GAAGCACACGCTGCTTCCGCCGCAGGTCTCGG
TTCCTGGCATGGGGCGAGCCGGCTGT-
GCTGCTGCTGCTCCTGCTGCTGAGCCTGGCGCTG
GGCCTTGTGCTGGCTGCTTTGGGGCTGT-
TCGTTCACCATCGGGACAGCCCACTGGTTCAG
GCCTCGGGGGGGCCCCTGGCCTGCTTTG-
GCCTGGTGTGCCTGGGCCTGGTCTGCCTCAGC
GTCCTCCTGTTCCCTGGCCAGCCCAGC-
CCTGCCCGATGCCTGGCCCAGCAGCCCTTGTCC
CACCTCCCGCTCACGGGCTGCCTGAGCA-
CACTCTTCCTGCAGGCGGCCGAGATCTTCGTG
GAGTCAGAACTGCCTCTGAGCTGGGCA-
GACCGGCTGAGTGGCTGCCTGCGGGGGCCCTGG
GCCTGGCTGGTGGTGCTGCTGGCCAT-
GCTGGTGGAGGTCGCACTGTGCACCTGGTACCTG
GTGGCCTTCCCGCCGGAGGTGGTGACG-
GACTGGCACATGCTGCCCACGGAGGCGCTGGTG
CACTGCCGCACACGCTCCTGGGTCAGCT-
TCGGCCTAGCGCACGCCACCAATGCCACGCTG
GCCTTTCTCTGCTTCCTGGGCACTTTC-
CTGGTGCGGAGCCAGCCGGGCTGCTACAACCGT
GCCCGTGGCCTCACCTTTGCCATGCTG-
GCCTACTTCATCACCTGGGTCTCCTTTGTGCCC
CTCCTGGCCAATGTGCAGGTGGTCCT-
CAGGCCCGCCGTGCAGATGGGCGCCCTCCTGCTC
TGTGTCCTGGGCATCCTGGCTGCCTTC-
CACCTGCCCAGGTGTTACCTGCTCATGCGGCAG
CCAGGGCTCAACACCCCCGAGTTCTTC-
CTGGGAGGGGGCCCTGGGGATGCCCAAGGCCAG
AATGACGGGAACACAGGAAATCAGGG-
GAAACATGAGTGA

SEQ ID NO: 202

Nucleic Acid Sequence hT1R2

ATGGGGCCCAGGGCAAAGACCATCT-
GCTCCCTGTTCTTCCTCCTATGGGTCCTGGCTGAG
CCGGCTGAGAACTCGGACTTCTACCTGC-
CTGGGGATTACCTCCTGGGTGGCCTCTTCTCC CTC-
CATGCCAACATGAAGGGCATTGTTCAC-
CTTAACTTCCTGCAGGTGCCCATGTGCAAG
GAGTATGAAGTGAAGGTGATAGGCTA-
CAACCTCATGCAGGCCATGCGCTTCGCGGTGGAG
GAGATCAACAATGACAGCAGCCTGCTGC-
CTGGTGTGCTGCTGGGCTATGAGATCGTGGAT
GTGTGCTACATCTCCAACAATGTCCAGC-
CGGTGCTCTACTTCCTGGCACACGAGGACAAC
CTCCTTCCCATCCAAGAGGACTACAG-
TAACTACATTTCCCGTGTGGTGGCTGTCATTGGC
CCTGACAACTCCGAGTCTGTCATGACT-
GTGGCCAACTTCCTCTCCCTATTTCTCCTTCCA
CAGATCACCTACAGCGCCATCAGCGAT-
GAGCTGCGAGACAAGGTGCGCTTCCCGGCTTTG
CTGCGTACCACACCCAGCGCCGACCAC-
CACGTCGAGGCCATGGTGCAGCTGATGCTGCAC
TTCCGCTGGAACTGGATCATTGTGCTG-
GTGAGCAGCGACACCTATGGCCGCGACAATGGC
AGCTGCTTGGCGAGCGCGTGGCCCG-
GCGCGACATCTGCATCGCCTTCCAGGAGACGCTGC
CCACACTGCAGCCCAACCAGAACAT-
GACGTCAGAGGAGCGCCAGCGCCTGGT-

GACCATTG TGGACAAGCTGCAGCAGAGCA-
CAGCGCGCGTCGTGGTCGTGTTCTCGCCCGACCTG
ACCC TGTACCACTTCTTCAATGAGGTGCT-
GCGCCAGAACTTCACGGGCGCCGTGTGGATCGCCT
CCGAGTCCTGGGCCATCGACCCGGTCCT-
GCACAACCTCACGGAGCTGGGCCACTTGGGCA
CCTTCCTGGGCATCACCATCCAGAGCGT-
GCCCATCCCGGGCTTCAGTGAGTTCCGCGAGT
GGGGCCCACAGGCTGGGCCGCCACCCCT-
CAGCAGGACCAGCCAGAGCTATACCTGCAACC
AGGAGTGCGACAACTGCCTGAACGCCAC-
CTTGTCCTTCAACACCATTCTCAGGCTCTCTG
GGGAGCGTGTCGTCTACAGCGTG-
TACTCTGCGGTCTATGCTGTGGCCCAT-
GCCCTGCACA GCCTCCTCGGCTGTGACAAAAG-
CACCTGCACCAAGAGGGTGGTCTACCCCTGGCAGC
TGC TTGAGGAGATCTGGAAGGTCAACT-
TCACTCTCCTGGACCACCAAATCTTCTTCGACCCGC
AAGGGGACGTGGCTCTGCACTTGGAGAT-
TGTCCAGTGGCAATGGGACCGGAGCCAGAATC
CCTTCCAGAGCGTCGCCTCCTACTAC-
CCCCTGCAGCGACAGCTGAAGAACATCCAAGACA
TCTCCTGGCACACCGTCAACAACAC-
GATCCCTATGTCCATGTGTTCCAAGAGGTGCCAGT
CAGGGCAAAAGAAGAAGCCT-
GTGGGCATCCACGTCTGCTGCTTCGAGT-
GCATCGACTGCC TTCCCGGCACCTTCCTCAACCA-
CACTGAAGATGAATATGAATGCCAGGCCTGCCCGA
ATA ACGAGTGGTCCTACCAGAGTGAGACCTC-
CTGCTTCAAGCGGCAGCTGGTCTTCCTGGAAT
GGCATGAGGCACCCACCATCGCTGTGGC-
CCTGCTGGCCGCCCTGGGCTTCCTCAGCACCC
TGGCCATCCTGGTGATATTCTGGAG-
GCACTTCCAGACACCCATAGTTCGCTCGGCTGGGG
GCCCCATGTGCTTCCTGATGCTGACACT-
GCTGCTGGTGGCATACATGGTGGTCCCGGTGT
ACGTGGGGCCGCCCAAGGTCTCCACCT-
GCCTCTGCCGCCAGGCCCTCTTTCCCCTCTGCT
TCACAATTTGCATCTCCTGTATCGCCGT-
GCGTTCTTTCCAGATCGTCTGCGCCTTCAAGA
TGGCCAGCCGCTTCCCACGCGCCTA-
CAGCTACTGGGTCCGCTACCAGGGGCCCTACGTCT
CTATGGCATTTATCACGGTACT-
CAAAATGGTCATTGTGGTAATTGGCAT-
GCTGGCCACGG GCCTCAGTCCCACCACCCGTACT-
GACCCCGATGACCCCAAGATCACAATTGTCTCCTGT
A ACCCCAACTACCGCAACAGCCTGCTGT-
TCAACACCAGCCTGGACCTGCTGCTCTCAGTGG
TGGGTTTCAGCTTCGCCTA-
CATGGGCAAAGAGCTGCCCACCAACTA-
CAACGAGGCCAAGT TCATCACCCTCAGCATGAC-
CTTCTATTTCACCTCATCCGTCTCCCTCTGCACCTTC
ATGT CTGCCTACAGCGGGGTGCTGGTCAC-
CATCGTGGACCTCTTGGTCACTGTGCTCAACCTCC
TGGCCATCAGCCTGGGCTACTTCGGC-
CCCAAGTGCTACATGATCCTCTTCTACCCGGAGC
GCAACACGCCCGCCTACTTCAACAGCAT-
GATCCAGGGCTACACCATGAGGAGGGACTAG

SEQ ID NO: 203

Nucleic Acid Sequence rT1R3

ATGCCGGGTTTGGCTATCTTGGGCCT-
CAGTCTGGCTGCTTTCCTGGAGCTTGGGATGGGG
TCCTCTTTGTGTCTGTCACAGCAAT-
TCAAGGCACAAGGGGACTATATATTGGGTGGACTA
TTTCCCCTGGGCACAACTGAGGAGGC-
CACTCTCAACCAGAGAACACAGCCCAACGGCATC
CTATGTACCAGGTTCTCGCCCCTTG-
GTTTGTTCCTGGCCATGGCTATGAAGATGGCTGTA
GAGGAGATCAACAATGGATCTGCCT-
TGCTCCCTGGGCTGCGACTGGGCTATGACCTGTTT
GACACATGCTCAGAGCCAGTGGTCAC-
CATGAAGCCCAGCCTCATGTTCATGGCCAAGGTG
GGAAGTCAAAGCATTGCTGCCTACTG-
CAACTACACACAGTACCAACCCCGTGTGCTGGCT
GTCATTGGTCCCCACTCATCAGAGCT-
TGCCCTCATTACAGGCAAGTTCTTCAGCTTCTTC
CTCATGCCACAGGTCAGCTATAGTGC-
CAGCATGGATCGGCTAAGTGACCGGGAAACATTT
CCATCCTTCTTCCGCACAGTGCCCAGT-
GACCGGGTGCAGCTGCAGGCCGTTGTGACACTG
TTGCAGAATTTCAGCTGGAACTGGGTG-
GCTGCCTTAGGTAGTGATGATGACTATGGCCGG
GAAGGTCTGAGCATCTTTTCTGGTCTG-
GCCAACTCACGAGGTATCTGCATTGCACACGAG
GGCCTGGTGCCACAACATGACACTAGTG-
GCCAACAATTGGGCAAGGTGGTGGATGTGCTA
CGCCAAGTGAACCAAAGCAAAGTACAG-
GTGGTGGTGCTGTTTGCATCTGCCCGTGCTGTC
TACTCCCTTTTTAGCTACAGCATCCT-
TCATGACCTCTCACCCAAGGTATGGGTGGCCAGT
GAGTCCTGGCTGACCTCTGACCTGGT-
CATGACACTTCCCAATATTGCCCGTGTGGGCACT
GTTCTTGGGTTTCTGCAGCGCGGTGC-
CCTACTGCCTGAATTTTCCCATTATGTGGAGACT
CGCCTTGCCCTAGCTGCTGACCCAACAT-
TCTGTGCCTCCCTGAAAGCTGAGTTGGATCTG
GAGGAGCGCGTGATGGGGCCACGCTGT-
TCACAATGTGACTACATCATGCTACAGAACCTG
TCATCTGGGCTGATGCAGAACCTAT-
CAGCTGGGCAGTTGCACCACCAAATATTTGCAACC
TATGCAGCTGTGTACAGTGTGGCTCAG-
GCCCTTCACAACACCCTGCAGTGCAATGTCTCA
CATTGCCACACATCAGAGCCTGTTCAAC-
CCTGGCAGCTCCTGGAGAACATGTACAATATG
AGTTTCCGTGCTCGAGACTTGACACTG-
CAGTTTGATGCCAAAGGGAGTGTAGACATGGAA
TATGACCTGAAGATGTGGGTGTGGCA-
GAGCCCTACACCTGTACTACATACTGTAGGCACC
TTCAACGGCACCCTTCAGCTGCAG-
CACTCGAAAATGTATTGGCCAGGCAAC-
CAGGTGCCA GTCTCCCAGTGCTCCCGGCAGTG-
CAAAGATGGCCAGGTGCGCAGAGTAAAGGGCTTT
CAT TCCTGCTGCTATGACTGTGTGGACTG-
CAAGGCAGGGAGCTACCGGAAGCATCCAGATGAC
TTCACCTGTACTCCATGTGGCAAGGAT-
CAGTGGTCCCCAGAAAAAAGCACAACCTGCTTA
CCTCGCAGGCCCAAGTTTCTGGCT-
TGGGGGGAGCCAGCTGTGCTGTCACT-
TCTCCTGCTG CTTTGCCTGGTGCTGGGCCTGA-
CACTGGCTGCCCTGGGGCTCTTTGTCCACTACTGG
GAC AGCCCTCTTGTTCAGGCCTCAGGTGGGT-
CACTGTTCTGCTTTGGCCTGATCTGCCTAGGC
CTCTTCTGCCTCAGTGTCCTTCTGTTC-
CCAGGACGACCACGCTCTGCCAGCTGCCTTGCC
CAACAACCAATGGCTCACCTCCCTCTCA-
CAGGCTGCCTGAGCACACTCTTCCTGCAAGCA
GCCGAGATCTTTGTGGAGTCTGAGCTGC-
CACTGAGTTGGGCAAACTGGCTCTGCAGCTAC
CTTCGGGGCCCCTGGGCTTGGCTGGTGG-
TACTGCTGGCCACTCTTGTGGAGGCTGCACTA TGT-
GCCTGGTACTTGATGGCTTTCCCTCCA-
GAGGTGGTGACAGATTGGCAGGTGCTGCCC

ACGGAGGTACTGGAACACTGCCGCAT-GCGTTCCTGGGTCAGCCTGGGCTTGGTGCACATCACCAATGCAGTGTTAGCTTTCCTCT-GCTTTCTGGGCACTTTCCTGGTACAGAGCCAGCCTGGTCGCTATAACCGTGCCCGTGGCCT-CACCTTCGCCATGCTAGCTTATTTCATCATCTGGGTCTCTTTTGTGCCCCTCCTGGCTAAT-GTGCAGGTGGCCTACCAGCCAGCTGTGCAGATGGGTGCTATCTTATTCTGTGC-CCTGGGCATCCTGGCCACCTTCCACCT-GCCCAAATGCTAT GTACTTCTGTGGCTGCCA-GAGCTCAACACCCAGGAGTTCTTCCTGGGAAGGAGCCCCAAG GAAGCATCAGATGGGAATAGTGGTAG-TAGTGAGGCAACTCGGGGACACAGTGAATGA

Also, the following conceptual translations, which correspond to the C-termini of two orthologous pairs of fish T1Rs, are derived from unpublished genomic sequence fragments and provided Fugu T1RA was derived from accession ‘scaffold 164’; Fugu T1RB was derived from accession LPC61711; Tetradon T1RA was derived from accession AL226735; Tetradon T1RB was derived from accession AL222381. Ambiguities in the conceptual translations (‘X’) result from ambiguities in database sequences.

SEQ ID NO: 204

T1RA Fugu

PSPFRDIVSYPDKIILGCFMNLKTSSVS-FVLLLLLCLLCFIFSYMGKDLPKNYNEAKAITFCLLLLILTWIIFTTASLLYQGKYIH-SLNALAVLSSIYSFLLWYFLPKCYIIIFQPQKNT QKY-FQGLIQDYTKTISQ

SEQ ID NO: 205

T1RA Tetradon

FAVNYNTPVVRSAGGPMCFLILG-CLSLCSISVFFYFERPTEAFCILRFMPFLLFYAVCLACFAVRSFQIVIIFKIAAKFPRVHSWW-MKYHGQWLVISMTFVLQAVVIVIGFSSNPPLPYXXFVSYPDKIILGCDVNLNMASTSF-FLLLLLCILCFTFSYMGKDLPKNYNEAKAITFCLLLLILTWIIFATAFMLYHGKYIHTLNALAV-LSSAYCFLLWYFLPKCYIIIFQPHKNTQKYFQ LS

SEQ ID NO: 206

T1RB Fugu

KKQGPEVDIFIVSVTILCISVLGVAVG-PPEPSQDLDFYMDSIVLECSNTLSPGSFIELCY VCV-LSVLCFFFSYMGKDLPANYNEAKCVTFS-LMVYMISWISFFTVYLISRGPFTVAAYVCATLVSVLAFFGGYFLPKIYIIVLK-PQMNTTAHFQNCIQMYTMSKQ

SEQ ID NO: 207

T1RB Tetradon

APKSSQRXLRRTRLXLEWDHPMSVALLF-FLVCCLLMTSSSAVILLLNINTPVAKSAGGXT CXLK-LAALTAAAMSSXCHFGQPS-PLASKLKQPQFTFSFTVCLACNRCALATGHLHFXIRVALPPAYNXWAKNHGPXATIFIASAAIL-CVLCLRVAVGPPQPSQBLBFXTNSIXLXXSNTL SPGS-FVELCNVSLLSAVCFVFSXMGK-BLPANYNEAKCVTFSLMVNXISWISFFTVY

What is claimed is:

1. A method for identifying a compound that modulates the activity of a T1R or T2R taste receptor by a Gi protein signaling pathway comprising:

i. providing a eukaryotic cell that expresses at least one functional T1R or T2R taste receptor and a Gi protein that couples thereto;

ii. contacting said eukaryotic cell with at least one compound that putatively modulates the activity of said T1R or T2R;

iii. assaying the effect of said putative modulatory compound on at least one of of MAPK activation, cAMP accumulation or adenylyl cyclase activity in said eukaryotic cell;

iv. identifying whether said at least one putative modulatory compound modulates the activity of such functional T1R or T2R expressed by said eukaryotic cell by a $G_i$ protein signaling pathway based on its effect on at least one of MAPK activity, cAMP accumulation or adenylyl cyclase activity.

2. The method of claim 1 wherein said eukaryotic cell is selected from the group consisting of insect cells, amphibian cells, yeast cells, worm cells and mammalian cells.

3. The method of claim 1 wherein said eukaryotic cell is selected from the group consisting of HEK-293 cells, CHO cells, mouse macrophages, HeLa cells and BHK cells.

4. The method of claim 1 which is a high throughput screening assay.

5. The method of claim 1 wherein the assay step (iii) detects activation of MAPK.

6. The method of claim 5 wherein MAPK activation is detected using a ligand that specifically binds MAPK.

7. The method of claim 5 wherein said ligand is a monoclonal or polyclonal antibody that specifically binds activated (phosphorylated) MAPK.

8. The method of claim 7 wherein said monoclonal antibody specifically binds phosphorylated p44/42 MAP Kinase (ERK1 or ERK2).

9. The method of claim 1 wherein said assay step (iii) detects whether said putative modulatory compounds results in a decrease in cAMP accumulation.

10. The method of claim 9 wherein cAMP accumulation is detected using a ligand that specifically binds cAMP.

11. The method of claim 9 wherein cAMP levels are detected by a chemiluminescent, radiological or fluorescent immunoassay technique.

12. The method of claim 9 wherein cAMP accumulation is induced prior to contacting the eukuryotic cell with a putative T1R or T2R modulatory compound.

13. The method of claim 12 wherein cAMP accumulation is induced by addition of forskolin.

14. The method of claim 1 wherein said assay step (iii) detects whether said putative modulator inhibits adenylyl cyclase activity.

15. The method of claim 1 wherein said eukaryotic cell stably expresses said at least one T1R or T2R.

16. The method of claim 1 wherein said eukaryotic cell transiently expresses said at least one T1R or T2R.

17. The method of claim 1 wherein said eukaryotic cell stably express a $G_i$ protein that functionally couples to said T1R or T2R.

18. The method of claim 17 wherein said $G_i$ protein is selected from the group consisting of $G\alpha_{i-1}$ $G\alpha_{i-2}$, $G\alpha_{i-3}$, $G\alpha_{0-1}$, $G\alpha_{0-2}$, and $G\alpha_{\alpha 2}$, or variant or a chimera thereof that couples to said at least one T1R or T2R.

19. The method of claim 17 wherein said eukaryotic cell is transfected with a DNA that encodes said $G_i$ protein.

20. The method of claim 17 wherein said eukaryotic cell endogenously expresses said $G_i$ protein.

21. The method of claim 5 wherein MAPK activation is detected by use of a proximity assay.

22. The method of claim 10 wherein cAMP accumulation is detected by an immunoassay.

23. A method for identifying a compound that modulates the effect of another compound on T1R or T2R activity by a Gi protein signaling pathway comprising the following steps:

i. obtaining a eukaryotic cell that expresses at least one T1R or T2R receptor and a Gi protein that functionally couples to said T1R or T2R;

ii. contacting said eukaryotic cell with at least one compound that modulates the activity of said T1R or T2R;

iii. further contacting said eukaryotic cell with at least one compound that putatively modulates the effect of said compound in (ii) on T1R or T2R activity;

iv. determining whether said at least one putative modulatory compound in (iii) modulates the effect of said compound (ii) on T1R or T2R activity on a $G_i$ protein signaling pathway by measuring the effect of said putative modulator compound (iii) on at least one of MAPK activity, cAMP accumulation, or adenylyl cyclase activity.

24. The method of claim 23 wherein said eukaryotic cell expresses a functional T1R1/T1R3 umami taste receptor and the compound in (ii) is monosodium glutamate, L-aspartate or L-glutamate.

25. The method of claim 23 wherein said eukaryotic cell expresses a functional T1R2/T1R3 sweet taste receptor and the compound in (ii) is a natural or artificial sweetener.

26. The method of claim 25 wherein said sweetener is selected from the group consisting of saccharin, glucose, sucrose, sorbitol, xylose, dextran, aspartame, monellin, cyclamate, fructose, and treholose.

27. The method of claim 23 wherein said eukaryotic cell expresses a functional T2R bitter taste receptor and the compound in (ii) is a bitter compound that activates said T2R.

28. The method of claim 27 wherein said bitter compound is selected from the group consisting of quinine, denatonium, lidocaine, cycloheximide, strychnine, salicin, and phenylthiocarbamide.

29. The method of claim 28 wherein said T2R is selected from the group consisting of mT2R5, rT2R9, TAS2R10, TAS2R16, and TAS2R38.

30. The method of claim 26 wherein said eukaryotic cell endogenously expresses a $G_i$ protein that couples to said T1R or T2R.

31. The method of claim 30 wherein said $G_i$ protein selected is selected from $G_{\alpha i\text{-}1}$, $G_{\alpha i\text{-}2}$, $G_{\alpha i\text{-}3}$, $G_{\alpha 0\text{-}1}$, $G_{\alpha 0\text{-}2}$ and $G_{\alpha z}$ or a variant or chimera thereof that functionally couples to said T1R or T2R.

32. The method of claim 31 wherein said $G_i$ protein is a member of the $G\alpha_{i1\text{-}3}$ subfamily.

33. The method of claim 23 which is used to identify a compound that blocks bitter taste associated with a particular T2R activator.

34. The method of claim 23 which is used to identify a compound that blocks or enhances umami taste elicited by a compound that activates the T1R1/T1R3 (umami) taste receptor.

35. The method of claim 34 wherein said compound is a glutamate containing compound.

36. The method of claim 25 wherein said compound is monosodium glutamate.

37. The method of claim 23 which is used to identify a compound that blocks or enhances sweet taste elicited by a compound that activates the T1R2/T1R3 (sweet) taste receptor.

38. The method of claim 37 wherein said compound is an artificial or natural sweetener.

39. The method of claim 38 wherein said sweetener compound is selected from the group consisting of saccharin, xylitol, sucrose, glucose, cyclamate, monellin, dextran, glucose, xorbitol, fructose, and D- or L-tryptophan.

40. The method of claim 33 wherein the bitter compound that activates said T2R is selected from the group consisting of guinine, denatonium benzoate, lidocaine, and cycloheximide.

41. The method of claim 23 wherein in step (iv), the effect of said putative modulator of said compound is detected based on its effect on MAPK activity.

42. The method of claim 41 wherein MAPK activity is detected by immunoassay.

43. The method of claim 42 wherein said immunoassay uses an antibody that specifically binds an activated form of MAPK.

44. The method of claim 1 wherein said T1R is selected from the group consisting of rat, mice and human T1R3.

45. The method of claim 44 wherein said T1R is selected from the group consisting of mouse, human and rat T1R1, mouse, human and rat T1R2 and mouse, human and rat T1R3.

46. The method of claim 1 wherein the eukaryotic cell co-expresses T1R1 and T1R3 or co-expresses T1R2 and T1R3.

47. The method of claim 1 wherein in step (iii) MAPK is assayed by use of a phosphospecific antibody cell-based ELISA (PACE).

48. The method of claim 1 wherein the eukaryotic cells are cultured in multi-well plates.

49. The method of claim 1 wherein said eukaryotic cells are adhered to a substrate.

50. The method of claim 1 wherein said eukaryotic cells are in suspension.

51. The method of claim 1 wherein the effect of said modulator compound on MAPK activation, cAMP accumulation or adenylyl cyclase activity is concentration (dose) dependent.

52. An assay kit for the identification of a modulator of a T1R or T2R, wherein said modulator modulates a $G_i$ protein signaling pathway, that comprises:

i. a eukaryotic cell that stably or transiently expresses at least one T1R or T2R and a Gi protein that couples functionally thereto;

ii. a ligand or reagent that provides for the detection of an activated form of MAPK, cAMP or adenylyl cyclase.

53. The assay kit of claim 52 wherein the eukaryotic cell is a yeast, mammalian, insect, amphibian or worm cell.

54. The assay kit of claim 53 wherein the eukaryotic cell is an HEK-293, BHK, CHO, Xenopus oocyte or HeLa cell.

55. The assay kit of claim 37 wherein said ligand or reagent is attached to a detectable label.

56. The assay kit of claim 52 wherein said label is a detectable label is an enzyme, fluorophore, chemiluminescent compound, or radionuclide.

* * * * *